(12) United States Patent
Alcazar Vaca et al.

(10) Patent No.: US 11,225,478 B2
(45) Date of Patent: Jan. 18, 2022

(54) P2X7 MODULATORS

(71) Applicant: Janssen Pharmaceutica NV, Beerse (BE)

(72) Inventors: Manuel Jesus Alcazar Vaca, Toledo (ES); Jose Ignacio Andres Gil, Madrid (ES); Christa C. Chrovian, La Jolla, CA (US); Heather R. Coate, San Diego, CA (US); Meri De angelis, Munich (DE); Curt A. Dvorak, Poway, CA (US); Christine F. Gelin, San Diego, CA (US); Michael A. Letavic, San Diego, CA (US); Brad M. Savall, San Diego, CA (US); Akinola Soyode-Johnson, San Diego, CA (US); Brice M. Stenne, San Diego, CA (US); Devin M. Swanson, Carlsbad, CA (US)

(73) Assignee: JANSSEN PHARMACEUTICA NV, Beerse (BE)

( * ) Notice: Subject to any disclaimer, the term of this patent is extended or adjusted under 35 U.S.C. 154(b) by 0 days.

(21) Appl. No.: 16/911,428

(22) Filed: Jun. 25, 2020

(65) Prior Publication Data
US 2020/0325138 A1 Oct. 15, 2020

Related U.S. Application Data

(63) Continuation of application No. 16/196,140, filed on Nov. 20, 2018, now Pat. No. 10,703,749, which is a continuation of application No. 15/258,320, filed on Sep. 7, 2016, now Pat. No. 10,150,765, which is a continuation of application No. 14/714,714, filed on May 18, 2015, now Pat. No. 9,464,084, which is a continuation of application No. 14/212,669, filed on Mar. 14, 2014, now Pat. No. 9,066,946.

(60) Provisional application No. 61/786,260, filed on Mar. 14, 2013.

(51) Int. Cl.
C07D 471/04 (2006.01)
A61K 31/497 (2006.01)
C07F 7/08 (2006.01)
C07D 401/14 (2006.01)

(52) U.S. Cl.
CPC .......... *C07D 471/04* (2013.01); *A61K 31/497* (2013.01); *C07F 7/0812* (2013.01); *C07B 2200/07* (2013.01); *C07D 401/14* (2013.01); *Y02A 50/30* (2018.01)

(58) Field of Classification Search
CPC .................................................. C07D 471/04
USPC ......................................................... 514/63
See application file for complete search history.

(56) References Cited

U.S. PATENT DOCUMENTS

| | | | |
|---|---|---|---|
| 4,812,462 | A | 3/1989 | Blankley et al. |
| 4,816,463 | A | 3/1989 | Blankley et al. |
| 5,338,744 | A | 8/1994 | Dudley et al. |
| 8,431,704 | B2 | 4/2013 | Love et al. |
| 8,871,760 | B2 | 10/2014 | Brotherton-Pleiss et al. |
| 8,933,236 | B2 | 1/2015 | Chowdhury et al. |
| 8,987,249 | B2 | 3/2015 | Anderskewitz et al. |
| 9,056,874 | B2 | 6/2015 | Adams et al. |
| 9,066,946 | B2 | 6/2015 | Alcazar Vaca et al. |
| 9,156,824 | B2 | 10/2015 | Dally et al. |
| 9,181,271 | B2 | 11/2015 | Li et al. |

(Continued)

FOREIGN PATENT DOCUMENTS

| | | |
|---|---|---|
| CN | 1823066 | 8/2006 |
| CN | 101778850 | 7/2010 |

(Continued)

OTHER PUBLICATIONS

U.S. Appl. No. 15/258,320, filed Sep. 7, 2016, Janssen Pharmaceutica NV.

(Continued)

*Primary Examiner* — Taofiq A Solola
(74) *Attorney, Agent, or Firm* — Fay Kaplun & Marcin, LLP

(57) ABSTRACT

The present invention is directed to compounds of Formulas (I, IIa and IIb):

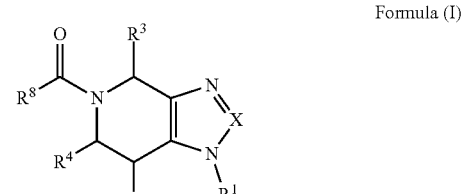

Formula (I)

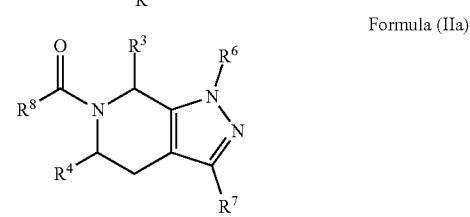

Formula (IIa)

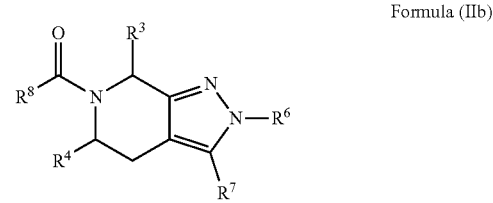

Formula (IIb)

The invention also relates to pharmaceutical compositions comprising compounds of Formulas (I, IIa and IIb). Meth- (Continued)

ods of making and using the compounds of Formulas (I, IIa and IIb) are also within the scope of the invention.

46 Claims, 2 Drawing Sheets

(56) References Cited

U.S. PATENT DOCUMENTS

| | | | |
|---|---|---|---|
| 9,233,974 | B2 | 1/2016 | Link et al. |
| 9,242,969 | B2 | 1/2016 | Barsanti et al. |
| 9,273,047 | B2 | 3/2016 | Hunt et al. |
| 9,273,947 | B2 | 3/2016 | Kim et al. |
| 9,290,476 | B2 | 3/2016 | Leonard et al. |
| 9,375,418 | B2 | 6/2016 | Schmidt et al. |
| 9,434,715 | B2 | 9/2016 | Conza et al. |
| 9,447,045 | B2 | 9/2016 | Chen et al. |
| 9,464,084 | B2 | 10/2016 | Alcazar Vaca et al. |
| 9,532,992 | B2 | 1/2017 | Kuntz et al. |
| 9,561,228 | B2 | 2/2017 | Haq et al. |
| 9,617,272 | B2 | 4/2017 | Kumar et al. |
| 9,637,456 | B2 | 5/2017 | Amans et al. |
| 10,112,937 | B2 | 10/2018 | Alcazar Vaca et al. |
| 10,150,765 | B2 | 12/2018 | Alcazar Vaca et al. |
| 2005/0096345 | A1 | 5/2005 | Thompson et al. |
| 2006/0217448 | A1 | 9/2006 | Kelly et al. |
| 2006/0293337 | A1 | 12/2006 | Evans et al. |
| 2008/0275052 | A1 | 11/2008 | Dhar et al. |
| 2010/0144758 | A1 | 6/2010 | Dillon et al. |
| 2011/0252717 | A1 | 10/2011 | Garf Fernandez |
| 2011/0294790 | A1 | 12/2011 | Mantegani et al. |
| 2012/0190680 | A1 | 7/2012 | Bakthavatchalam et al. |
| 2014/0213554 | A1 | 7/2014 | Wu et al. |
| 2014/0251902 | A1 | 9/2014 | Solheim et al. |
| 2014/0275015 | A1 | 9/2014 | Alcazar Vaca et al. |
| 2014/0275056 | A1 | 9/2014 | Letavic et al. |
| 2014/0275096 | A1 | 9/2014 | Ameriks et al. |
| 2014/0275120 | A1 | 9/2014 | Alcazar Vaca et al. |
| 2015/0029190 | A1 | 1/2015 | Ishida et al. |
| 2015/0322062 | A1 | 11/2015 | Alcazar Vaca et al. |
| 2016/0016962 | A1 | 1/2016 | Ameriks et al. |
| 2016/0024082 | A1 | 1/2016 | Alcazar Vaca et al. |
| 2016/0039809 | A1 | 2/2016 | Alcazar Vaca et al. |
| 2016/0039836 | A1 | 2/2016 | Letavic et al. |
| 2016/0046596 | A1 | 2/2016 | Banerjee et al. |
| 2017/0081342 | A1 | 3/2017 | Cheung et al. |

FOREIGN PATENT DOCUMENTS

| | | | |
|---|---|---|---|
| FR | 2857363 | | 1/2005 |
| JP | 2012-525351 | | 10/2012 |
| JP | 2013-505220 | A1 | 2/2013 |
| WO | 2004/013144 | A1 | 2/2004 |
| WO | WO 2004/014374 | | 2/2004 |
| WO | WO 2006023750 | | 3/2006 |
| WO | WO 2006/080884 | | 8/2006 |
| WO | WO 2006/110516 | | 10/2006 |
| WO | WO 2009/002423 | | 12/2008 |
| WO | WO 2009/023623 | | 2/2009 |
| WO | WO 2009/023623 | A1 | 2/2009 |
| WO | 2009/095253 | A1 | 8/2009 |
| WO | WO 2010/125101 | | 11/2010 |
| WO | WO 2010/125102 | | 11/2010 |
| WO | 2011/050202 | A1 | 4/2011 |
| WO | 2011/103715 | A1 | 9/2011 |
| WO | WO 2011/121137 | | 10/2011 |
| WO | WO 2011/121137 | A1 | 10/2011 |
| WO | WO 2012/040048 | | 3/2012 |
| WO | 2012/145581 | A1 | 10/2012 |
| WO | WO 2014/152589 | | 9/2014 |
| WO | WO 2014/152589 | A1 | 9/2014 |
| WO | WO 2014/152621 | | 9/2014 |
| WO | WO 2014/152621 | A1 | 9/2014 |
| WO | WO 2014/154897 | | 10/2014 |
| WO | WO 2014/154897 | A1 | 10/2014 |
| WO | WO 2016/039977 | | 3/2016 |
| WO | WO 2016/039983 | | 3/2016 |
| WO | 2020/065613 | A1 | 4/2020 |
| WO | 2021/064569 | A1 | 4/2021 |

OTHER PUBLICATIONS

U.S. Appl. No. 62/049,727, filed Sep. 12, 2014, Janssen Pharmaceutica NV.

U.S. Appl. No. 62/049,687, filed Sep. 12, 2014, Janssen Pharmaceutica NV.

Arbeloa et al "P2X7 Receptor Blockade Prevents ATP Excitotoxicity in Neurons and Reduces Brain Damage After Ischemia" Neurobiology of Disease 2012 vol. 45 pp. 954-961.

Avignone et al "Status Epilepticus Induces a Particular Microglial Activation State Characterized by Enhanced Purinergic Signalling" The Journal of Neuroscience 2008 vol. 28(37) pp. 9133-9144.

Bagshawe et al "Antibody-Directed Enzyme Prodrug Therapy: A Review" Drug Development Research 1995 vol. 34 pp. 220-230.

Bartlett et al., "The P2X7 Receptor Channel: Recent Developments and the Use of P2X7 Antagonists in Models of Disease", Pharmacol. Rev. vol. 66, pp. 638-675, 2014.

Basso et al "Behavioral Profile of P2X7 Receptor Knockout Mice in Animal Models of Depression and Anxiety: Relevance of Neuropsychiatric Disorders" Behavioral Brain Research 2009 vol. 198 pp. 83-90.

Bennet, et al. (Editor), "Part XIV Oncology", Cecil Textbook of Medicine, vol. 1, $20^{th}$ Edition, pp. 1004-1010 (1996).

Berge et al "Pharmaceutical Salts" Journal of Pharmaceutical Sciences, 1997, vol. 66(1) pp. 1-19.

Bertolini et al "A New Rational Hypothesis for the Pharmacophore of the Active Metabolite of Leflunomide, A Potent Immunosuppresive Drug" J Med Chem 1997 vol. 40 pp. 2011-2016.

Bodor et al "Novel Approaches to the Design of Safer Drugs: Soft Drugs and Site-Specific Chemical Delivery Systems" Advances in Drug Research 1984 vol. 13 pp. 224-331.

Bourzac et al "Glucose Transporter 2 Expression is Down Regulated Following P2X7 Activation in Enterocytes" J Cell Physiol 2013 vol. 228 pp. 120-129.

Bundgaard "Design of Prodrugs—(Contents)", Elsevier Science Publishers B.V. (Biomedical Division), 1985.

Capouron et al "Immune System to Brain Signaling: Neuropsychopharmacological Implications" Pharmacology & Therapeutics 2011 vol. 130 pp. 226-238.

Chessel et al "Disruption of the P2X7 Purinoreceptor Gene Abolishes Chronic Inflammatory and Neuropathic Pain" Pain 2005 vol. 114 pp. 386-396.

Chu et al "Inhibitionof P2XY Receptor Ameliorates Transient Global Cerebral Ischemia/Reperfusion Injury via Modulating Inflammatory Responses in the Rat Hippocampus" Journal of Neuroinflammation 2012 9:69.

Van Nostrand's Encyclopedia of Chemistry 2005 $5^{th}$ Ed. p. 261 Considine G D. Ed.

Dantzer et al "Cytokine, Sickness Behavior, and Depression" Immunol Allergy Clin N AM 2009 vol. 29 pp. 247-264.

Diaz-Hernandez et al "Altered P2X7-Receptor Level and Function in Mouse Models of Huntington's Disease and Therapeutic Efficacy of Antagonist Administration" FASEB J. 2009 vol. 23(6) pp. 1893-1906.

Diaz-Hernandez et al "In Vivo P2X7 Inhibition Reduces Amyloid Plaques in Alzheimer's Disease Through GXK3β and Secretases" Neurobiology of Aging 2012 vol. 33 pp. 1816-1828.

Donnelly-Roberts et al "[$^3$H]A-804598 ([$^3$H]2-Cyano-1-[ (1S)-1-Phenylethyl]-3-Quinolin-5-Ylguanidine) is a Novel, Potent, and Selective Antagonist Radioligand for P2X7 Receptors" Neuropharmacology 2009 vol. 56 pp. 223-229.

Dermer, "Another Anniversarty Fo the War on Cancer", Bio/Technology, vol. 11: pp. 320 (March 1994).

Duan et al "P2X7 Receptors: Properties and Relevance to CNX Function" GLIA 2006 vol. 54 pp. 738-746.

(56) References Cited

OTHER PUBLICATIONS

Engel et al "Seizure Suppression and Neuroprotection by Targeting the Purinergic P2X7 Receptor During Status Epilepticus in Mice" FASEB J 2012 vol. 26 pp. 1616-1628.
Ferrari et al "The P2X7 Receptor: A Key Player in IL-1 Processing and Release" J Immunol 2006 vol. 176 pp. 3877-3883.
Fleisher et al "Improved Oreal Drug Delivery: Solubility Limitations Overcome by the Use of Prodrugs" Advanced Drug Delivery Reviews 1996 vol. 19 pp. 115-130.
Freshney et al., Culture of Animal Cells, Manual of Basic Technique, 1983, pp. 1-6, Chapter 1.
Friedle et al "Recent Patents on Novel P2X7 Receptor Antagonists and Their Potential for Reducing Central Nervous System Inflammation" Recent Patents on CNS Drug Discovery 2010 vol. 5 pp. 35-45.
Furlan-Freguia et al "P2X7 Receptor Signaling Contributes to Tissue Factor-Dependent Thrombosis in Mice" J Clin Invest 2011 vol. 121(7) pp. 2932-2944.
Golub et al., "Molecular Classification of Cancer: Class Discovery and Class Prediction by Gene Expression Monitoring", Science, 1999, pp. 531-537, vol. 286.
Grygorowicz et al "Temporal Expression of P2X7 Purinergic Receptor During the Course of Experimental Autoimmune Encephalomyelitis" Neurochemistry International 2010 vol. 57 pp. 823-829.
Guile et al., "Antagonists of the $P2X_7$ Receptor. From Lead Identification to Drug Development", Journal of Medicinal Chemistry, May 28, 2009, vol. 52, No. 10, pp. 3123-3141.
Gunosewoyo and Kassiou, "PX2 Purinergic Receptor Ligands: Recently Patented Compounds", Brain and Mind Research Institute, 2010, pp. 625-646.
Simone, Part XIV—Oncology, Textbook of Medicine, 1996 $20^{th}$ edition pp. 1004-1010. vol. 1.
Delarasse et al "The Purinergic Receptor P2X7 Triggers α-Secretase-Dependent Processing of the Amyloid Precursor Protein" Journal of Biological Chemistry 2011 vol. 286(4) pp. 2596-2606.
Keating et al "P2X7 Receptor-Dependent Intestinal Afferent Hypersensitivity in a Mouse Model of Postinfectious Irritable Bowel Syndrome" The Journal of Immunology 2011 vol. 187 pp. 1467-1474.
Kim et al "Blockade of P2X7 Receptor Prevents Astroglial Death in the Dentate Gyrus Following Pilocarpine-Induced Status Epilepticus" Neurol Res 2009 vol. 31 pp. 982-988.
Larsen and Bundgaard "A Textbook of Drug Design and Development—(Index)", 1992, 18 Pgs., Harwood Academic Publishers.
Rudolph et al., "Novel Methyl Substituted 1-(5,6-Dihydro-[1,2,4]Triazolo[4,3-A]Pyrazin-7(8H)-YL)Methanones Are P2X7 Antagonists", Bioorganic & Medicinal Chemistry Letters, vol. 25, No. 16, Aug. 1, 2015 (Aug. 1, 2015), p. 3157-3163.
Marcellino et al "On the Role of P2X7 Receptors in Dopamine Nerve Cell Degeneration in a Rat Model of Parkinson's Disease: Studies With the P2X7 Receptor Antagonist A-438079" J Neural Transm 2010 vol. 117 pp. 681-687.
Martins et al "The Role of P2X7 Purinergic Receptors in Inflammatory and Nociceptive Changes Accompanying Cyclophosphamde-Induced Haemorrhagic Cystitis in Mice" Br J Pharmacol 2012 vol. 165 pp. 183-196.
Muller et al "A Potential Role for P2X7R in Allergic Airway Inflammation in Mice and Humans" Am J Respir Cell Mol Biol 2011 vol. 44 pp. 456-464.
Oyanguren-Desez et al "Gain-of-Function of P2X7 Receptor Gene Variants in Multiple Sclerosis" Cell Calcium 2011 vol. 50 pp. 468-472.
Parvathenani et al "P2X7 Mediates Superoxide Production in Primary Microglia and is Up-Regulated in a Transgenic Mouse Model of Alzheimer's Disease" J Biol Chem 2003 vol. 278(15) pp. 13309-13317.
Paulekuhn et al "Trends in Active Pharmaceutical Ingredient Salt Selection Based on Analysis of Athe Orange Book Database" J Med Chem 2007 vol. 30 pp. 6665-6672.
Robinson et al "Discovery of the Hemifumarate and ($_{α-L}$ Alanyloxy)Methyl Ether as Prodrugs of an Antirheumatic Oxindole: Prodrugs for the Enolic OH Group" J Med Chem 1996 vol. 39 pp. 10-18.
Romagnoli et al "The P2X7 Receptor as a Therapeutic Agent" Expert Opin Ther Targets 2008 vol. 12(5) pp. 647-661.
Sanz et al "Activation of Microglia by Amyloid β Requires P2X7 Receptor Expression" J Immunol 2009 vol. 182 pp. 4378-4385.
Shan et al "Prodrug Strategies Based on Intramolecular Cyclization Reactions" J Pharm Sci 1977 vol. 86(7) pp. 765-767.
Sharp et al "P2X7 Deficiency Suppresses Development of Experimental Autoimmune Encephalomyelitis" J Neuroinflammation 2008 vol. 5 :33.
Skarper et al "The P2X7 Purinergic Receptor: From Physiology to Neurological Disorders" FASEB J 2009 vol. 24 pp. 337-345.
Solini et al "Enhanced P2X7 Activity in Human Fibroblasts From Diabetic Patients—A Possible Pathogenic Mechanism for Vascular Damage in Diabetes" Artherioscler Thromb Vasc Biol 2004 vol. 24 pp. 1240-1245.
Stahl and Wermuth, "Handbook of Pharmaceutical Salts—(Index)", International Union of Pure and Applied Chemistry (IUPAC), 2002, 3 Pgs.
Suprenant et al "Signaling At Purinergic P2X Receptors" Annu Rev Physiol 2009 vol. 71 pp. 333-359.
Ji et al "P2X7 Deficiency Attenuates Hypertension and Renal Injury in Deoxycorticosterone Acetate-Salt Hypertension" Am J Physiol Renal Physiol 2012 vol. 303 pp. F1207-F1215.
Stephen M. Berge, et al., "*Pharmaceutical Salts*", Journal of Pharmaceutical Sciences, vol. 66, No. 1, 1977, pp. 1-19.
PCT International Search Report dated Jul. 1, 2014 for International Application No. PCT/US2014/027522.
Arulkumaran, N., et al. "A Potential Therapeutic Role for P2X7 Receptor (P2X7R) Antagonists in the Treatment of Inflammatory Diseases", Expert Opinion on Investigative Drugs, vol. 20(7), pp. 897-915 (2011).
Hudson, Derek, "Methodological Implications of Simultaneous Solid-Phase Peptide Synthesis. 1. Comparison of Different Coupling Procedures", J. Organic Chemistry, vol. 53, pp. 617-624 (1988).
Killeen, M. E., et al., "Signaling Through Purinergic Receptors for ATP Induces Human Cutaneous Innate and Adaptive Th17 Responses: Implications in the Pathogenesis of Psoriasis", J. Immunology, vol. 190(8), pp. 4324-4336 (2013).
Skaper, S., et al., "The P2X7 Purinergic Receptor: From Physiology to Neurological Disorders", FASEB Journal, vol. 24, pp. 337-345 (2010).
Thiboutot, D., J. "Inflammasome Activation by Propionibacterium Acnes: The Study of IL-1 In Acne Continues to Unfold", Investigative Dermatology, vol. 134, pp. 595-597 (2014).
Vergani, A., et al., "Long-Term Heart Transplant Survival by Targeting the Ionotropic Purinergic Receptor P2X7", Circulation, vol. 127, pp. 463-475 (2013).
Vergani, A., et al., "Effect of the Purinergic Inhibitor Oxidized ATP in a Model of Islet Allograft Rejection", Diabetes, vol. 62, pp. 1665-1675 (2013).
Thomas A. Godwin (Gastrointestinal Diseases) http://edcenter.med.cornell.edu/CUMC_PathNotes/Gastrointestinal/Gastrointestinal.html (2003).
Dyatkin et al "Determination of the Absolute Configuration of a Key Tricyclic Component of a Novel Vasopressing Receptor Antagonist by Use of Vibrational Circular Dichroism" Chirality 2002 vol. 14 pp. 215-219.
Rudolph et al., "Novel Methyl Substituted 1-(5,6-Dihydro-[1,2,4]Triazolo[4,3-A]Pyrazine-7(8H)-YL)Methanones Are P2X7 Antagonists", Bioorganic & Medicinal Chemistry Letters, vol. 25, No. 16, Aug. 1, 2015 (Aug. 1, 2015), p. 3157-3162.
Hackam and Redelmeier, Translation of Research Evidence ffrom Animals to Humans:, JAMA, 2006, vol. 296, No. 14, 1731-1732.
Database Chemcats Enamine Screening Library Database Accession 2035772210 Jan. 17, 2008.
Jordan, Tamoxifen: A Most Unlikely Pioneering Medicine:, Nature Reviews, 2003, vol. 2, 205-213.

(56) References Cited

OTHER PUBLICATIONS

Database Chemcats Ukrorgsynthesis Screeing Collection Accession 2033253463 Mar. 6, 2007.
Database Chemcats Ryan Scientific Screening Library Database Accession 2042676574 Jan. 25, 2008.
Database Chemcats Ambinter Stock Screeing Collection Database Accession 2046454718 Feb. 13, 2008.
Database Chemcats Ryan Scientific Screening Library Database Accession 2043876860 Jan. 25, 2008.
Database Chemcats Ryan Scientific Screening Library Database Accession 2042637020 Jan. 25, 2008.
Database Chemcats Ryan Scientific Screening Library Database Accession 2042634059 Jan. 25, 2008.
Database Chemcats Ambinter Stock Screening Collection Database Accession 2040548370 Feb. 13, 2008.
Database Chemcats Ambinter Stock Screening Collection Database Accession 2040381923 Feb. 13, 2008.
Database Chemcats Ambinter Stock Screening Collection Database Accession 2040033692 Feb. 13, 2008.
Database Chemcats Aurora Screening Library Database Accession 2037938546 Sep. 6, 2007.
European Search Report for corresponding EP Application 08154909.9 dated Jun. 20, 2008.
European Search Report for corresponding EP 16176059.0-1462 dated Sep. 21, 2016.
PCT ISR dated Oct. 15, 2015 for International Application No. PCT/US2015/046852.
Government of Pakistan Intellectual Property Organization the Patent Office Karachi, Mailed Apr. 28, 2016.
U.S. Appl. No. 14/714,714, Notice of Allowance, dated Aug. 15, 2016.
U.S. Appl. No. 14/775,432, Restriction Requirement, Office Action dated Aug. 25, 2016.
Singapore Search Report corresponding to Application No. 11201507259U dated May 5, 2016.
China Application No. 201480027363.2 First Office Action dated May 5, 2016.
PCT ISR dated Jul. 31, 2009 for International Application No. PCT/US2009/041249.
U.S. Appl. No. 14/775,436, Notice of Allowance, dated Oct. 14, 2016.
U.S. Appl. No. 14/775,436, Notice of Allowance, dated Nov. 8, 2016.
PCT ISR dated Oct. 15, 2015 for International Application No. PCT/US2015/046710.
U.S. Appl. No. 14/775,424. Non-Final Rejection Office Action, dated Jul. 22, 2016.
U.S. Appl. No. 14/775,424. Restriction Requirement Office Action, dated Apr. 26, 2016.
U.S. Appl. No. 14/775,436, Non-Final Rejection Office Action, dated Jul. 27, 2016.
U.S. Appl. No. 14/775,436, Restriction Requirement Office Action, dated Apr. 27, 2016.
U.S. Appl. No. 14/775,424, Notice of Allowance dated Nov. 18, 2016.
Brazil Search Report for BR112015023142-0 dated Oct. 17, 2019.
English translation of Brazil Search Report for BR112015023142-0 dated Oct. 17, 2019.
Alekseev, et al., "Use of the Graebe-Ullmann reaction in the synthesis of 8-methyl-γ-carboline and isomeric aromatic aza-γ-carbolines", Chemistry of Heterocyclic Compounds, 2012, vol. 48, No. 8, pp. 1235-1250.
Carroll et al., "Synthesis and Pharmacological Characterization of Nicotinic Acetylcholine Receptor Properties of (+)- and (-)-Pyrido-[3,4-b]homotropanes", Journal of Medicinal Chemistry, vol. 49, No. 11, 2006, pp. 3244-3250.
Greene et al., Chapter 7 Protection for the Amino Group, Protective Groups in Organic Synthesis, Third Edition, John Wiley & Sons, 1999, pp. 518-525, 579-580, and 620-621.
Nikitenko et al., "Selective Hydrolysis of Ethyl 5,6-Dihydro-4H-pyrrolo[1,2-b]pyrazole-2-carboxylate and Ethyl 5,6-Dihydro-4H-pyrrolo[1,2-b]pyrazole-3-carboxylate as a Key Step in the Large-Scale Synthesis of Bicyclic Heteroaryl Carboxyaldehydes", Organic Process Research & Development, vol. 10, No. 4, 2006, pp. 712-716.

P2X7 MODULATORS

CROSS REFERENCE TO RELATED APPLICATIONS

This application is a continuation of U.S. application Ser. No. 16/196,140 filed on Nov. 20, 2018, which is a continuation of U.S. application Ser. No. 15/258,320, now U.S. Pat. No. 10,150,765, filed on Sep. 7, 2016, which is a continuation of U.S. application Ser. No. 14/714,714, now U.S. Pat. No. 9,464,084, filed on May 18, 2015, which is a continuation of U.S. application Ser. No. 14/212,669, now U.S. Pat. No. 9,066,946, filed on Mar. 14, 2014, which claims priority to U.S. Application No. 61/786,260 filed on Mar. 14, 2013. The contents of each application of which is incorporated herein by reference in its entirety.

FIELD OF THE INVENTION

The present invention is related compounds having P2X7 modulating properties, pharmaceutical compositions comprising these compounds, chemical processes for preparing these compounds and their use in the treatment of diseases associated with P2X7 receptor activity in animals, in particular humans.

BACKGROUND OF THE INVENTION

The P2X7 receptor is a ligand-gated ion channel and is present on a variety of cell types, largely those known to be involved in the inflammatory and/or immune process, specifically, macrophages and monocytes in the periphery and predominantly in glial cells (microglia and astrocytes) of the CNS. (Duan and Neary, *Glia* 2006, 54, 738-746; Skaper et al., *FASEB J* 2009, 24, 337-345; Surprenant and North, *Annu. Rev. Physiol.* 2009, 71, 333-359). Activation of the P2X7 receptor by extracellular nucleotides, in particular adenosine triphosphate, leads to the release of proinflammatory cytokines IL-1β and IL-18 (Muller, et. al. *Am. J. Respir. Cell Mol. Biol.* 2011, 44, 456-464), giant cell formation (macrophages/microglial cells), degranulation (mast cells) and L-selectin shedding (lymphocytes) (Ferrari et al., *J. Immunol.* 2006, 176, 3877-3883; Surprenant and North, *Annu. Rev. Physiol.* 2009, 71, 333-359). P2X7 receptors are also located on antigen-presenting cells (keratinocytes, salivary acinar cells (parotid cells)), hepatocytes, erythrocytes, erythroleukaemic cells, monocytes, fibroblasts, bone marrow cells, neurones, and renal mesangial cells.

The importance of P2X7 in the nervous system arises primarily from experiments using P2X7 knock out mice. These mice demonstrate the role of P2X7 in the development and maintenance of pain as these mice were protected from the development of both adjuvant-induced inflammatory pain and partial nerve ligation induced neuropathic pain (Chessell et al., *Pain* 2005, 114, 386-396). In addition P2X7 knock out mice also exhibit an anti-depressant phenotype based on reduced immobility in forced swim and tail suspension tests (Basso et al., *Behav. Brain Res.* 2009, 198, 83-90.). Moreover, the P2X7 pathway is linked to the release of the proinflammatory cytokine, IL-1β, which has been linked to precipitation of mood disorders in humans (Dantzer, *Immunol. Allergy Clin. North Am.* 2009, 29, 247-264; Capuron and Miller, *Pharmacol. Ther.* 2011, 130, 226-238). In addition, in murine models of Alzheimer's disease, P2X7 was upregulated around amyloid plaques indicating a role of this target in such pathology as well (Parvathenani et al., *J. Biol. Chem.* 2003, 278, 13309-13317).

In view of the clinical importance of P2X7, the identification of compounds that modulate P2X7 receptor function represents an attractive avenue into the development of new therapeutic agents. Such compounds are provided herein.

SUMMARY OF THE INVENTION

The invention is directed to the general and preferred embodiments defined, respectively, by the independent and dependent claims appended hereto, which are incorporated by reference herein. One aspect of this invention concerns compounds of Formula (I):

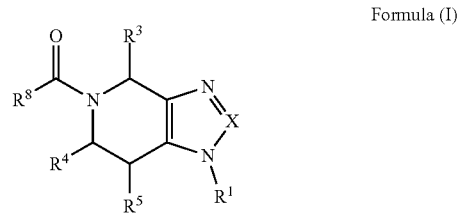

Formula (I)

wherein:
R$^1$ is (a) phenyl, optionally substituted with zero to four groups selected from: halo, C$_1$-C$_4$alkyl, alkoxy, perhaloalkyl or perhaloalkoxy; or
(b) heteroaryl, selected from the group consisting of:

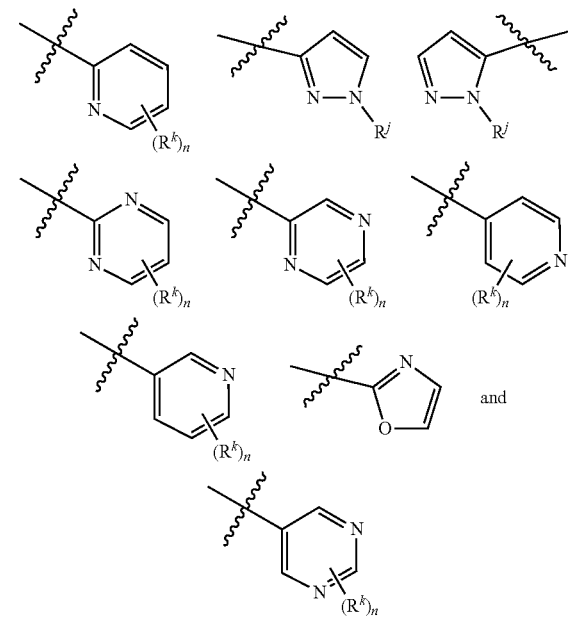

and wherein R$^k$ is selected from: H, halo, C$_1$-C$_3$alkyl or alkoxy;
R$^j$ is selected from H, C$_1$-C$_3$alkyl optionally substituted with halo, OH or alkoxy; and
n is an integer from 0-3;
X is N or CR$^2$;
R$^2$ is H, perhaloalkyl or C$_1$-C$_3$ lower alkyl;
R$^3$ is H, perhaloalkyl, C$_1$-C$_4$ alkyl, alkalkoxy, CH$_2$R$^i$, —C(O)R$^e$ or phenyl, optionally substituted with zero to two groups selected from the group consisting of: halo, $C_1$-$C_3$alkyl, alkoxy, perhaloalkyl and perhaloalkoxy;
$R^j$ is OH, $OC_1$-$C_3$ alkyl, $NC_3H_6$, $N(C_1$-$C_3$alkyl$)_2$ or halo;
$R^e$ is OH, $OC_1$-$C_3$ alkyl, $N(C_1$-$C_3$alkyl$)_2$, or $NC_3H_6$;
$R^4$ and $R^5$ are independently H or $C_1$-$C_3$ alkyl;
$R^8$ is phenyl or pyridyl, optionally substituted with zero to four $R^m$ substituents wherein $R^m$ is selected from the group consisting of: halo, $C_1$-$C_3$alkyl, alkoxy, perhaloalkyl and perhaloalkoxy; or
$R^8$ is selected from the group consisting of:

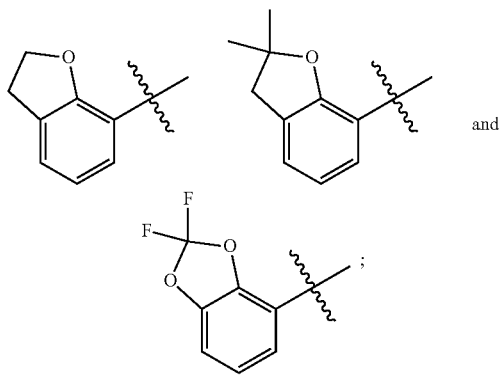

and pharmaceutically acceptable salts of compounds of Formula (I).

Another aspect of this invention concerns compounds of Formula (IIa and IIb):

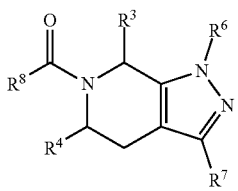

Formula (IIa)

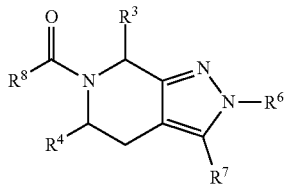

Formula (IIb)

wherein:
$R^3$, $R^4$ and $R^6$ are independently H or $C_1$-$C_3$ alkyl;
$R^8$ is phenyl or pyridyl, optionally substituted with zero to three $R^m$ substituents wherein $R^m$ is selected from the group consisting of: halo, $C_1$-$C_3$alkyl and perhaloalkyl;
$R^7$ is (a) phenyl, optionally substituted with zero to two groups selected from halo or $C_1$-$C_3$alkyl; or
(b) heteroaryl, selected from the group consisting of:

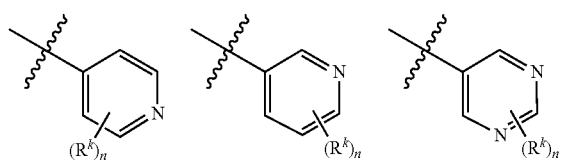

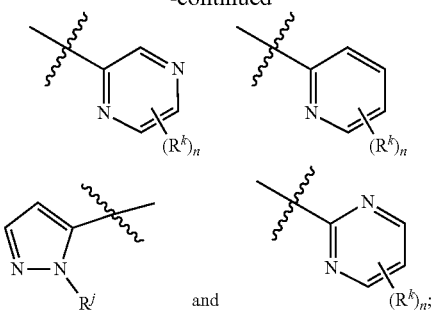

wherein $R^k$ is selected from halo or $C_1$-$C_3$alkyl;
$R^j$ is selected from H or $C_1$-$C_3$alkyl wherein $C_1$-$C_3$alkyl is optionally substituted with halo or alkoxy; and
n is an integer from 0-3; and
pharmaceutically acceptable salts of compounds of Formulas (I, IIa and IIb).

Further embodiments are provided by pharmaceutically acceptable salts of compounds of Formula (I IIa and IIb), pharmaceutically acceptable prodrugs of compounds of Formulas (I, IIa and IIb), and pharmaceutically active metabolites of compounds of Formulas (I, IIa and IIb).

In certain embodiments, the compounds of Formulas (I, IIa and IIb) are compounds selected from those species described or exemplified in the detailed description below.

In a further aspect, the invention relates to pharmaceutical compositions for treating a disease, disorder, or medical condition mediated by P2X7 receptor activity, comprising a therapeutically effective amount of at least one compound selected from compounds of Formulas (I, IIa and IIb), pharmaceutically acceptable salts of compounds of Formulas (I, IIa and IIb), pharmaceutically acceptable prodrugs of compounds of Formulas (I, IIa and IIb), and pharmaceutically active metabolites of Formulas (I, IIa and IIb).

Pharmaceutical compositions according to the invention may further comprise one or more pharmaceutically acceptable excipients.

In another aspect, the chemical embodiments of the present invention are useful as P2X7 receptor modulators. Thus, the invention is directed to a method for modulating P2X7 receptor activity, including when such receptor is in a subject, comprising exposing P2X7 receptor to a therapeutically effective amount of at least one compound selected from compounds of Formulas (I, IIa and IIb), pharmaceutically acceptable salts of compounds of Formulas (I, IIa and IIb), pharmaceutically acceptable prodrugs of compounds of Formulas (I, IIa and IIb), and pharmaceutically active metabolites of compounds of Formulas (I, IIa and IIb).

In another aspect, the invention is directed to a method of treating a subject suffering from or diagnosed with a disease, disorder, or medical condition mediated by P2X7 receptor activity, comprising administering to the subject in need of such treatment a therapeutically effective amount of at least one compound selected from compounds of Formulas (I, IIa and IIb), pharmaceutically acceptable salts of compounds of Formulas (I, IIa and IIb), pharmaceutically acceptable prodrugs of compounds of Formulas (I, IIa and IIb), and pharmaceutically active metabolites of compounds of Formulas (I, IIa and IIb). Additional embodiments of methods of treatment are set forth in the detailed description.

In another aspect, method of studying isotopically labeled compounds in metabolic studies (preferably with $^{14}$C), reaction kinetic studies (with, for example $^2$H or $^3$H), detection or imaging techniques [such as positron emission tomography (PET) or single-photon emission computed tomography (SPECT)] including drug or substrate tissue distribution assays, or in radioactive treatment of patients. For example, an $^{18}$F or $^{11}$C labeled compound may be particularly preferred for PET or SPECT studies.

An object of the present invention is to overcome or ameliorate at least one of the disadvantages of the conventional methodologies and/or prior art, or to provide a useful alternative thereto.

Additional embodiments, features, and advantages of the invention will be apparent from the following detailed description and through practice of the invention.

Additional embodiments of this invention include methods of making compounds of Formulas (I, IIa and IIb), pharmaceutically acceptable salts of compounds of Formulas (I, IIa and IIb), pharmaceutically acceptable prodrugs of compounds of Formulas (I, IIa and IIb), and pharmaceutically active metabolites of Formulas (I, IIa and IIb).

DETAILED DESCRIPTION OF THE INVENTION

Figure 1:
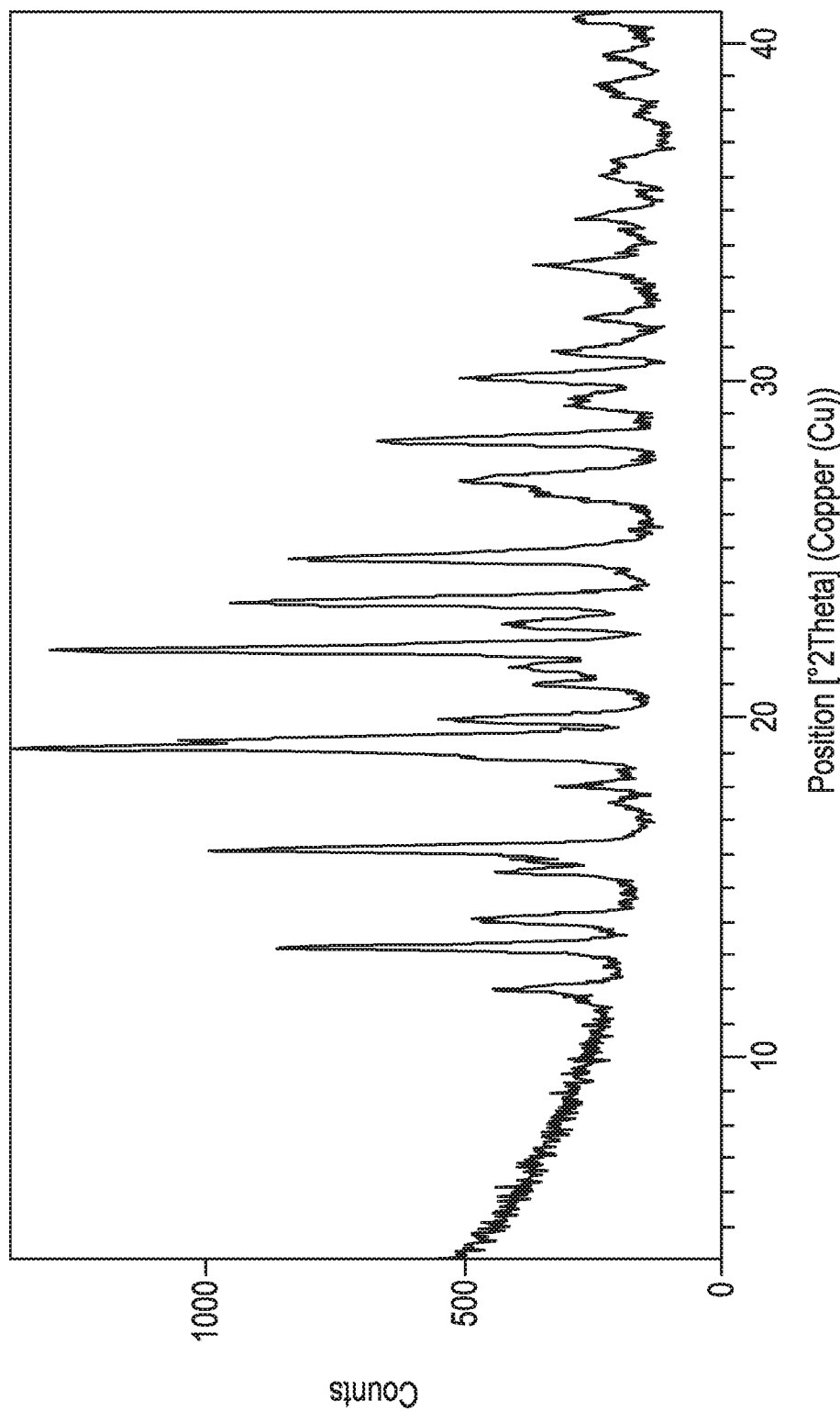
FIG. 1. Powder X-Ray Diffraction Pattern for (R)-(2-chloro-3-(trifluoromethyl)phenyl)(1-(5-fluoropyrimidin-2-yl)-4-methyl-6,7-dihydro-1H-[1,2,3]triazolo[4,5-c]pyridin-5(4H)-yl)methanone (Examples 158 and 344)
Figure 2:
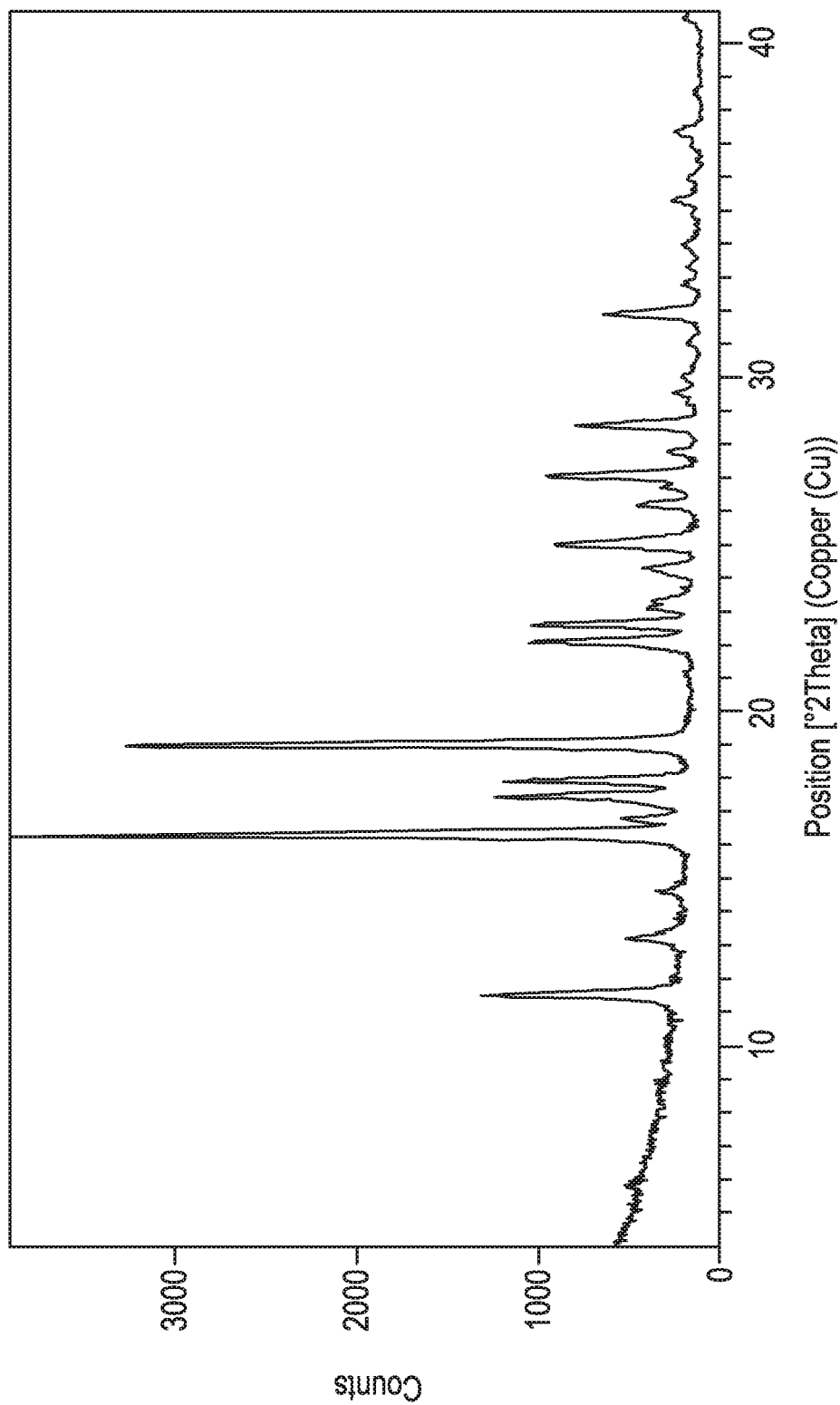
FIG. 2. Powder X-Ray Diffraction Pattern for (S)-(3-fluoro-2-(trifluoromethyl)pyridin-4-yl)(1-(5-fluoropyrimidin-2-yl)-6-methyl-6,7-dihydro-1H-[1,2,3]triazolo[4,5-c]pyridin-5(4H)-yl)methanone (Example 228)

A compound of Formula (I):

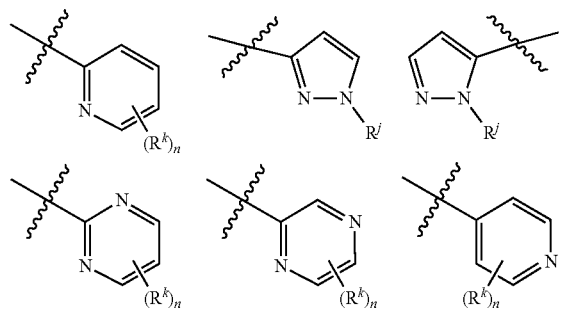

Formula (I)

wherein:
R$^1$ is (a) phenyl, optionally substituted with zero to four groups selected from the group consisting of: halo, C$_1$-C$_4$alkyl, alkoxy, perhaloalkyl and perhaloalkoxy; or
(b) heteroaryl, selected from the group consisting of:

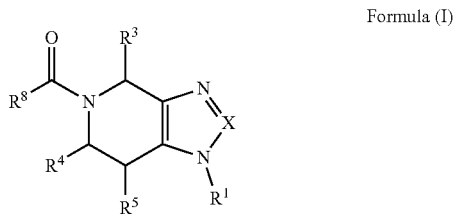

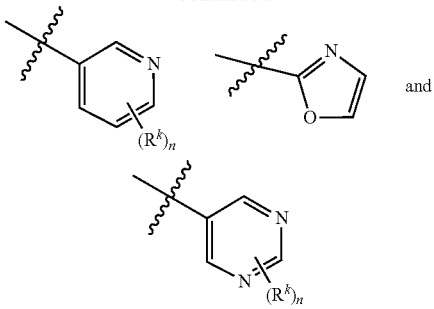

wherein R$^k$ is selected from: H, halo, C$_1$-C$_3$alkyl or alkoxy;
R$^j$ is selected from H, C$_1$-C$_3$alkyl; wherein C$_1$-C$_3$alkyl is optionally substituted with halo, OH or alkoxy; and
n is an integer from 0-3;
X is N or CR$^2$;
R$^2$ is H, perhaloalkyl or C$_1$-C$_3$ lower alkyl;
R$^3$ is H, perhaloalkyl, C$_1$-C$_4$ alkyl, alkalkoxy, CH$_2$R$^i$, —C(O)R$^e$ or phenyl; wherein phenyl is optionally substituted with zero to two groups selected from the group consisting of: halo, C$_1$-C$_3$alkyl, alkoxy, perhaloalkyl and perhaloalkoxy;
R$^i$ is OH, OC$_1$-C$_3$ alkyl, NC$_3$H$_6$, N(C$_1$-C$_3$alkyl)$_2$ or halo;
R$^e$ is OH, OC$_1$-C$_3$ alkyl, N(C$_1$-C$_3$alkyl)$_2$, or NC$_3$H$_6$;
R$^4$ and R$^5$ are independently H or C$_1$-C$_3$ alkyl; and
R$^8$ is phenyl or pyridyl, optionally substituted with zero to four R$^m$ substituents wherein R$^m$ is selected from the group consisting of: halo, C$_1$-C$_3$alkyl, alkoxy, perhaloalkyl and perhaloalkoxy; or
R$^8$ is selected from the group consisting of:

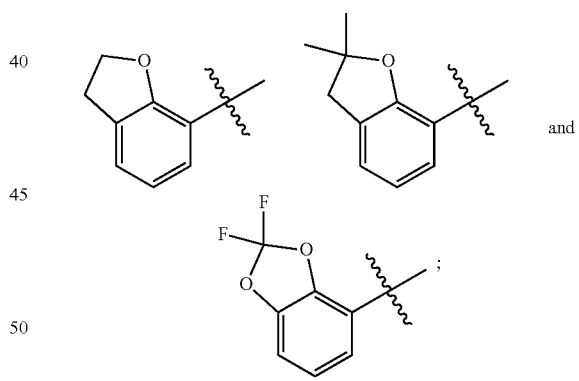

and
pharmaceutically acceptable salts of compounds of Formula (I).

An additional embodiment of the invention is a compound of Formula (I) wherein, R$^1$ is phenyl, optionally substituted with zero to four groups selected from: halo, C$_1$-C$_3$alkyl, alkoxy, perhaloalkyl or perhaloalkoxy.

An additional embodiment of the invention is a compound of Formula (I) wherein, R$^1$ is phenyl, optionally substituted with one to three groups selected from: halo, C$_1$-C$_3$alkyl, alkoxy, perhaloalkyl or perhaloalkoxy.

An additional embodiment of the invention is a compound of Formula (I) wherein, R$^1$ is phenyl, optionally substituted with one to two groups selected from: halo or perhaloalkyl.

An additional embodiment of the invention is a compound of Formula (I) wherein, R¹ is heteroaryl, selected from the group consisting of:

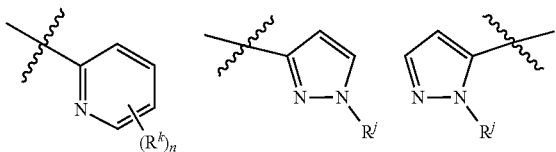

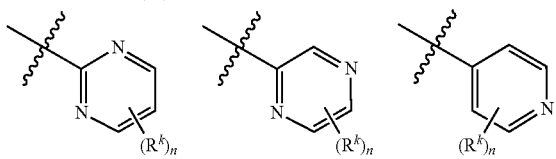

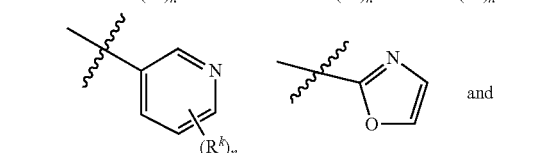 and

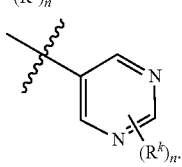

An additional embodiment of the invention is a compound of Formula (I) wherein, R¹ is heteroaryl, selected from the group consisting of:

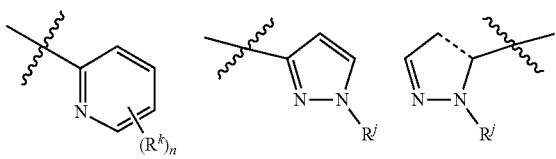

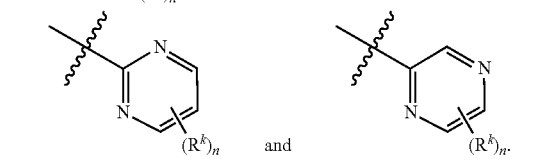

An additional embodiment of the invention is a compound of Formula (I) wherein, R¹ is heteroaryl, selected from the group consisting of:

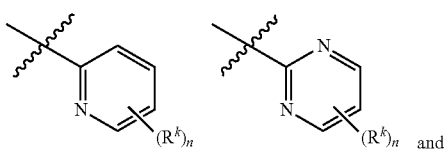 and

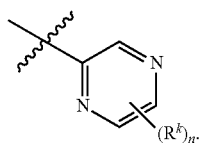

An additional embodiment of the invention is a compound of Formula (I) wherein, R¹ is:

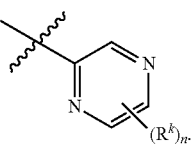

An additional embodiment of the invention is a compound of Formula (I) wherein, R¹ is

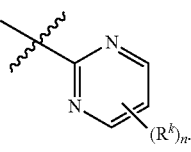

An additional embodiment of the invention is a compound of Formula (I) wherein, R¹ is

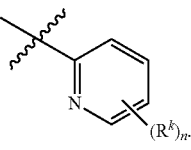

An additional embodiment of the invention is a compound of Formula (I) wherein, R¹ is:

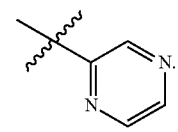

An additional embodiment of the invention is a compound of Formula (I) wherein, R¹ is:

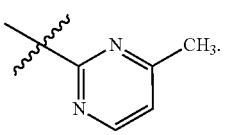 [SMILES: *c1nccc(C)n1]

An additional embodiment of the invention is a compound of Formula (I) wherein, R¹ is:

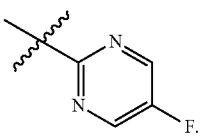 [SMILES: *c1ncc(F)cn1]

An additional embodiment of the invention is a compound of Formula (I) wherein, $R^1$ is:

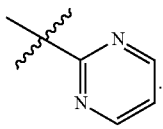 [SMILES: *c1ncccn1]

An additional embodiment of the invention is a compound of Formula (I) wherein, $R^1$ is:

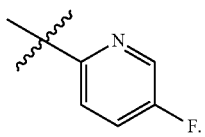 [SMILES: *c1ccc(F)cn1]

An additional embodiment of the invention is a compound of Formula (I) wherein, X is N.

An additional embodiment of the invention is a compound of Formula (I) wherein, X is $CR^2$.

An additional embodiment of the invention is a compound of Formula (I) wherein, X is $CR^2$ and $R^2$ is H, perhaloalkyl or $C_1$-$C_3$ lower alkyl.

An additional embodiment of the invention is a compound of Formula (I) wherein, X is $CR^2$ and $R^2$ is H or $C_1$-$C_3$ lower alkyl.

An additional embodiment of the invention is a compound of Formula (I) wherein, X is $CR^2$ and $R^2$ is H.

An additional embodiment of the invention is a compound of Formula (I) wherein, $R^3$ is phenyl, optionally substituted with halo, $C_1$-$C_3$alkyl, alkoxy, perhaloalkyl or perhaloalkoxy.

An additional embodiment of the invention is a compound of Formula (I) wherein, $R^3$ is phenyl, optionally substituted with halo, $C_1$-$C_3$alkyl, alkoxy or perhaloalkyl.

An additional embodiment of the invention is a compound of Formula (I) wherein, $R^3$ is phenyl, optionally substituted with halo.

An additional embodiment of the invention is a compound of Formula (I) wherein, $R^3$ is H, perhaloalkyl or $C_1$-$C_4$ alkyl.

An additional embodiment of the invention is a compound of Formula (I) wherein, $R^3$ is H or $C_1$-$C_4$ alkyl.

An additional embodiment of the invention is a compound of Formula (I) wherein, $R^3$ is H.

An additional embodiment of the invention is a compound of Formula (I) wherein, $R^3$ is $C_1$-$C_4$ alkyl.

An additional embodiment of the invention is a compound of Formula (I) wherein, $R^3$ is $C_1$-$C_3$ alkyl.

An additional embodiment of the invention is a compound of Formula (I) wherein, $R^3$ is $C_1$-$C_2$ alkyl.

An additional embodiment of the invention is a compound of Formula (I) wherein, $R^3$ is $CH_3$.

An additional embodiment of the invention is a compound of Formula (I) wherein, $R^4$ and $R^5$ are H.

An additional embodiment of the invention is a compound of Formula (I) wherein, $R^4$ and $R^5$ are $C_1$-$C_3$ alkyl.

An additional embodiment of the invention is a compound of Formula (I) wherein, $R^4$ is H and $R^5$ is $C_1$-$C_3$ alkyl.

An additional embodiment of the invention is a compound of Formula (I) wherein, $R^4$ is $C_1$-$C_3$ alkyl and $R^5$ is H.

An additional embodiment of the invention is a compound of Formula (I) wherein, $R^4$ and $R^5$ are $CH_3$.

An additional embodiment of the invention is a compound of Formula (I) wherein, $R^4$ is H and $R^5$ is $CH_3$.

An additional embodiment of the invention is a compound of Formula (I) wherein, $R^4$ is $CH_3$ and $R^5$ is H.

An additional embodiment of the invention is a compound of Formula (I) wherein, $R^8$ is phenyl optionally substituted with zero to four $R'''$ substituents wherein $R'''$ is selected from the group consisting of: halo, $C_1$-$C_3$alkyl, alkoxy, perhaloalkyl and perhaloalkoxy.

An additional embodiment of the invention is a compound of Formula (I) wherein, $R^8$ is phenyl optionally substituted with two to four $R'''$ substituents wherein $R'''$ is selected from the group consisting of: halo, $C_1$-$C_3$alkyl, alkoxy, perhaloalkyl and perhaloalkoxy.

An additional embodiment of the invention is a compound of Formula (I) wherein, $R^8$ is phenyl and $R'''$ is selected from the group consisting of: halo, $C_1$-$C_3$alkyl and perhaloalkyl.

An additional embodiment of the invention is a compound of Formula (I) wherein, $R^8$ is phenyl and $R'''$ is halo in the ortho position and $R'''$ is perhaloalkyl in the meta position.

An additional embodiment of the invention is a compound of Formula (I) wherein, $R^8$ is phenyl and $R'''$ is C in the ortho position and $R'''$ is $CF_3$ in the meta position.

An additional embodiment of the invention is a compound of Formula (I) wherein, X is N, $R^3$ is $CH_3$, $R^4$ and $R^5$ are H, $R^8$ is phenyl, $R'''$ is C in the ortho position, $R'''$ is $CF_3$ in the meta position and $R^1$ is:

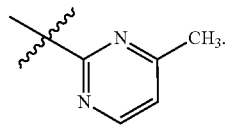

An additional embodiment of the invention is a compound of Formula (I) wherein, X is N, $R^3$ is $CH_3$, $R^4$ and $R^5$ are H, $R^8$ is phenyl, $R'''$ is C in the ortho position, $R'''$ is $CF_3$ in the meta position and $R^1$ is:

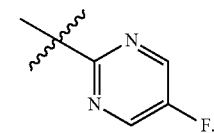 [SMILES: *c1ncc(F)cn1]

An additional embodiment of the invention is a compound of Formula (I) wherein, X is N, $R^3$ is $CH_3$, $R^4$ and $R^5$ are H, $R^8$ is phenyl, $R'''$ is C in the ortho position, $R'''$ is $CF_3$ in the meta position and $R^1$ is:

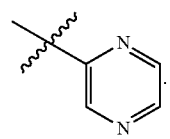 [SMILES: *c1cnccn1]

An additional embodiment of the invention is a compound of Formula (I) wherein, X is N, $R^3$ is $CH_3$, $R^4$ and $R^5$ are H, $R^8$ is phenyl, $R'''$ is C in the ortho position, $R'''$ is $CF_3$ in the meta position and $R^1$ is:

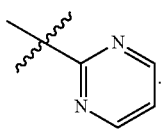 [SMILES: *c1ncccn1]

An additional embodiment of the invention is a compound of Formula (I) wherein, X is $CR^2$, $R^3$ is $CH_3$, $R^2$, $R^4$ and $R^5$ are H, $R^8$ is phenyl, $R^m$ is C in the ortho position, $R^m$ is $CF_3$ in the meta position and $R^1$ is:

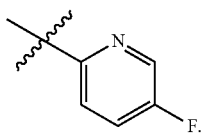 [SMILES: *c1ccc(F)cn1]

Another aspect of the invention is compounds of Formula IIa or IIb:

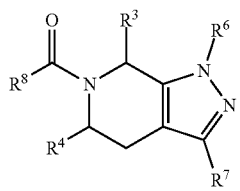

Formula (IIa)

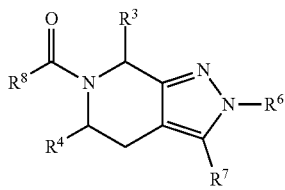

Formula (IIb)

wherein:

$R^3$, $R^4$ and $R^6$ are independently H or $C_1$-$C_3$ alkyl;

$R^8$ is phenyl or pyridyl; optionally substituted with zero to three $R^m$ substituents wherein $R^m$ is selected from the group consisting of: halo, $C_1$-$C_3$alkyl and perhaloalkyl; and $R^7$ is (a) phenyl, optionally substituted with zero to two groups selected from halo or $C_1$-$C_3$alkyl, or (b) heteroaryl, selected from the group consisting of:

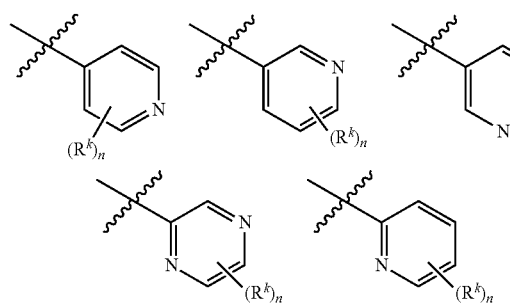

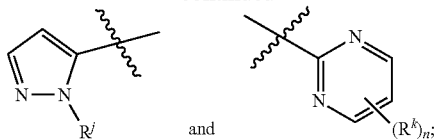

wherein $R^k$ is selected from halo or $C_1$-$C_3$alkyl;

$R^j$ is selected from H or $C_1$-$C_3$alkyl; wherein $C_1$-$C_3$alkyl is optionally substituted with halo or alkoxy; and n is an integer from 0-3; and pharmaceutically acceptable salts of compounds of Formula (I).

An additional embodiment of the invention are compounds of Formula IIa and IIb wherein, $R^8$ is phenyl optionally substituted with two to four $R^m$ substituents wherein $R^m$ is selected from the group consisting of: halo, $C_1$-$C_3$alkyl, alkoxy, perhaloalkyl and perhaloalkoxy.

An additional embodiment of the invention are compounds of Formula IIa and IIb wherein, $R^8$ is phenyl and $R^m$ is selected from the group consisting of: halo, $C_1$-$C_3$alkyl and perhaloalkyl.

An additional embodiment of the invention are compounds of Formula IIa and IIb wherein, $R^8$ is phenyl, $R^m$ is halo in the ortho position and $R^m$ is perhaloalkyl in the meta position.

An additional embodiment of the invention are compounds of Formula IIa and IIb wherein, $R^8$ is phenyl, $R^m$ is C in the ortho position and $R^m$ is $CF_3$ in the meta position.

An additional embodiment of the invention are compounds of Formula IIa and IIb wherein, $R^3$ is H and $R^4$ is $CH_3$.

An additional embodiment of the invention are compounds of Formula IIa and IIb wherein, $R^3$ is $CH_3$ and $R^4$ is H.

An additional embodiment of the invention are compounds of Formula IIa and IIb wherein, $R^7$ is (a) phenyl, optionally substituted with zero to two groups selected from: halo or $C_1$-$C_3$alkyl, An additional embodiment of the invention are compounds of Formula IIa and IIb wherein, $R^7$ is heteroaryl, selected from the group consisting of:

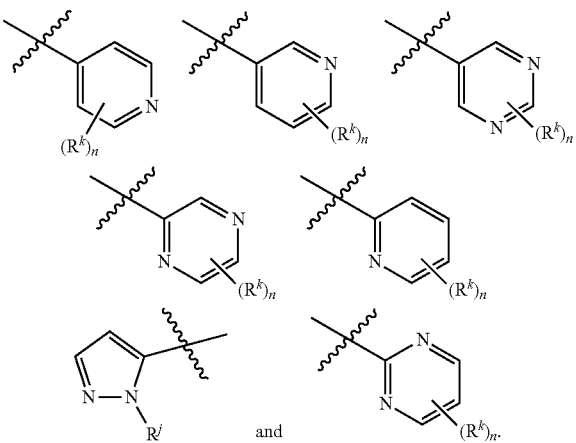

An additional embodiment of the invention is a compound selected from the group consisting of those presented in Table 1:

TABLE 1

Compounds of Formulas (I, IIa and IIb)

(2-Chloro-3-(trifluoromethyl)phenyl)(1-(pyridin-2-yl)-6,7-dihydro-1H-imidazo[4,5-c]pyridin-5(4H)-yl)methanone
(2-Chloro-3-(trifluoromethyl)phenyl)(1-phenyl-6,7-dihydro-1H-imidazo[4,5-c]pyridin-5(4H)-yl)methanone
(2,3-Dichlorophenyl)(1-phenyl-6,7-dihydro-1H-imidazo[4,5-c]pyridin-5(4H)-yl)methanone
(2,3-Dichlorophenyl)(1-(pyridin-2-yl)-6,7-dihydro-1H-imidazo[4,5-c]pyridin-5(4H)-yl)methanone
(1-(1H-Pyrazol-5-yl)-6,7-dihydro-1H-imidazo[4,5-c]pyridin-5(4H)-yl)(2-chloro-3-(trifluoromethyl)phenyl)methanone
(2-Chloro-3-(trifluoromethyl)phenyl)(1-(pyrazin-2-yl)-6,7-dihydro-1H-imidazo[4,5-c]pyridin-5(4H)-yl)methanone
(2-Chloro-3-(trifluoromethyl)phenyl)(1-(3,5-difluorophenyl)-6,7-dihydro-1H-imidazo[4,5-c]pyridin-5(4H)-yl)methanone
(2-Chloro-3-(trifluoromethyl)phenyl)(3-(pyridin-2-yl)-6,7-dihydro-3H-imidazo[4,5-c]pyridin-5(4H)-yl)methanone
(2,3-Dichlorophenyl)(3-(pyridin-2-yl)-6,7-dihydro-3H-imidazo[4,5-c]pyridin-5(4H)-yl)methanone
(2-Chloro-3-(trifluoromethyl)phenyl)(3-(pyrazin-2-yl)-6,7-dihydro-3H-imidazo[4,5-c]pyridin-5(4H)-yl)methanone
(2-Chloro-3-(trifluoromethyl)phenyl)(1-(5-fluoropyridin-2-yl)-4-methyl-6,7-dihydro-1H-imidazo[4,5-c]pyridin-5(4H)-yl)methanone
(2-Chloro-3-(trifluoromethyl)phenyl)(4-methyl-1-phenyl-6,7-dihydro-1H-imidazo[4,5-c]pyridin-5(4H)-yl)methanone
(2-Chloro-3-(trifluoromethyl)phenyl)(4-methyl-1-phenyl-6,7-dihydro-1H-imidazo[4,5-c]pyridin-5(4H)-yl)methanone
(2-Fluoro-3-(trifluoromethyl)phenyl)(4-methyl-1-(pyrazin-2-yl)-6,7-dihydro-1H-imidazo[4,5-c]pyridin-5(4H)-yl)methanone
(2-Chloro-3-(trifluoromethyl)phenyl)(4-ethyl-1-(pyrazin-2-yl)-6,7-dihydro-1H-imidazo[4,5-c]pyridin-5(4H)-yl)methanone
(2-Chloro-3-(trifluoromethyl)phenyl)(4-isopropyl-1-(pyrazin-2-yl)-6,7-dihydro-1H-imidazo[4,5-c]pyridin-5(4H)-yl)methanone
(2-Chloro-3-(trifluoromethyl)phenyl)(4-methyl-1-(pyridin-2-yl)-6,7-dihydro-1H-imidazo[4,5-c]pyridin-5(4H)-yl)methanone
(2-Chloro-3-(trifluoromethyl)phenyl)(1-(4-fluorophenyl)-4-methyl-6,7-dihydro-1H-imidazo[4,5-c]pyridin-5(4H)-yl)methanone
(2-Fluoro-3-(trifluoromethyl)phenyl)(4-methyl-1-(pyridin-2-yl)-6,7-dihydro-1H-imidazo[4,5-c]pyridin-5(4H)-yl)methanone
(2-Fluoro-3-(trifluoromethyl)phenyl)(1-(4-fluorophenyl)-4-methyl-6,7-dihydro-1H-imidazo[4,5-c]pyridin-5(4H)-yl)methanone
(2-Chloro-3-(trifluoromethyl)phenyl)(1-(3-fluoropyridin-2-yl)-4-methyl-6,7-dihydro-1H-imidazo[4,5-c]pyridin-5(4H)-yl)methanone
(2-Chloro-3-(trifluoromethyl)phenyl)(1-(5-fluoropyrimidin-2-yl)-4-methyl-6,7-dihydro-1H-imidazo[4,5-c]pyridin-5(4H)-yl)methanone
(2-Chloro-3-(trifluoromethyl)phenyl)(4-methyl-1-(pyrimidin-2-yl)-6,7-dihydro-1H-imidazo[4,5-c]pyridin-5(4H)-yl)methanone
Ethyl 5-(2-chloro-3-(trifluoromethyl)benzoyl)-1-(pyridin-2-yl)-4,5,6,7-tetrahydro-1H-imidazo[4,5-c]pyridine-4-carboxylate
Ethyl 5-(2,3-dichlorobenzoyl)-1-(pyridin-2-yl)-4,5,6,7-tetrahydro-1H-imidazo[4,5-c]pyridine-4-carboxylate
Ethyl 5-(2-chloro-3-(trifluoromethyl)benzoyl)-1-phenyl-4,5,6,7-tetrahydro-1H-imidazo[4,5-c]pyridine-4-carboxylate
Ethyl 5-(2,3-dichlorobenzoyl)-1-phenyl-4,5,6,7-tetrahydro-1H-imidazo[4,5-c]pyridine-4-carboxylate
Ethyl 5-{[2-chloro-3-(trifluoromethyl)phenyl]carbonyl}-1-pyrazin-2-yl-4,5,6,7-tetrahydro-1H-imidazo[4,5-c]pyridine-4-carboxylate
Ethyl 5-[(2,3-dichlorophenyl)carbonyl]-1-pyrazin-2-yl-4,5,6,7-tetrahydro-1H-imidazo[4,5-c]pyridine-4-carboxylate
(5-{[2-Chloro-3-(trifluoromethyl)phenyl]carbonyl}-1-phenyl-4,5,6,7-tetrahydro-1H-imidazo[4,5-c]pyridin-4-yl)methanol
1-(5-{[2-Chloro-3-(trifluoromethyl)phenyl]carbonyl}-1-pyridin-2-yl-4,5,6,7-tetrahydro-1H-imidazo[4,5-c]pyridin-4-yl)-N,N-dimethylmethanamine
(2-Chloro-3-(trifluoromethyl)phenyl)(4-(fluoromethyl)-1-(pyridin-2-yl)-6,7-dihydro-1H-imidazo[4,5-c]pyridin-5(4H)-yl)methanone
5-{[2-Chloro-3-(trifluoromethyl)phenyl]carbonyl}-1-pyridin-2-yl-4,5,6,7-tetrahydro-1H-imidazo[4,5-c]pyridine-4-carboxylic acid
5-{[2-Chloro-3-(trifluoromethyl)phenyl]carbonyl}-N,N-dimethyl-1-pyridin-2-yl-4,5,6,7-tetrahydro-1H-imidazo[4,5-c]pyridine-4-carboxamide
4-(Azetidin-1-ylcarbonyl)-5-{[2-chloro-3-(trifluoromethyl)phenyl]carbonyl}-1-pyridin-2-yl-4,5,6,7-tetrahydro-1H-imidazo[4,5-c]pyridine
(5-{[2-Chloro-3-(trifluoromethyl)phenyl]carbonyl}-1-phenyl-4,5,6,7-tetrahydro-1H-imidazo[4,5-c]pyridin-4-yl)methyl 2-chloro-3-(trifluoromethyl)benzoate
(2-Chloro-3-(trifluoromethyl)phenyl)(2-methyl-1-phenyl-6,7-dihydro-1H-imidazo[4,5-c]pyridin-5(4H)-yl)methanone
(2-Chloro-3-(trifluoromethyl)phenyl)(1-phenyl-2-(trifluoromethyl)-6,7-dihydro-1H-imidazo[4,5-c]pyridin-5(4H)-yl)methanone
5-{[2-Chloro-3-(trifluoromethyl)phenyl]carbonyl}-4-(trifluoromethyl)-4,5,6,7-tetrahydro-1H-imidazo[4,5-c]pyridine
(R)-(2-chloro-3-(trifluoromethyl)phenyl)(1-(5-fluoropyridin-2-yl)-4-methyl-6,7-dihydro-1H-imidazo[4,5-c]pyridin-5(4H)-yl)methanone
(4S*)-5-{[2-Fluoro-3-(trifluoromethyl)phenyl]carbonyl}-4-methyl-1-pyridin-2-yl-4,5,6,7-tetrahydro-1H-imidazo[4,5-c]pyridine
(4R*)-5-{[2-Fluoro-3-(trifluoromethyl)phenyl]carbonyl}-4-methyl-1-pyridin-2-yl-4,5,6,7-tetrahydro-1H-imidazo[4,5-c]pyridine
(4S*)-5-{[2-Chloro-3-(trifluoromethyl)phenyl]carbonyl}-4-methyl-1-pyridin-2-yl-4,5,6,7-tetrahydro-1H-imidazo[4,5-c]pyridine
(4R*)-5-{[2-Chloro-3-(trifluoromethyl)phenyl]carbonyl}-4-methyl-1-pyridin-2-yl-4,5,6,7-tetrahydro-1H-imidazo[4,5-c]pyridine
(4S*)-5-{[2-Chloro-3-(trifluoromethyl)phenyl]carbonyl}-4-methyl-1-pyridin-2-yl-4,5,6,7-tetrahydro-1H-imidazo[4,5-c]pyridine
(4R*)-5-{[2-Chloro-3-(trifluoromethyl)phenyl]carbonyl}-1-(4-fluorophenyl)-4-methyl-4,5,6,7-tetrahydro-1H-imidazo[4,5-c]pyridine
(4S)-5-{[2-Chloro-3-(trifluoromethyl)phenyl]carbonyl}-1-(4-fluorophenyl)-4-methyl-4,5,6,7-tetrahydro-1H-imidazo[4,5-c]pyridine
5-{[2-Chloro-3-(trifluoromethyl)phenyl]carbonyl}-4,5,6,7-tetrahydro-3H-imidazo[4,5-c]pyridine
5-{[2-Chloro-3-(trifluoromethyl)phenyl]carbonyl}-1-phenyl-4,5-dihydro-1H-imidazo[4,5-c]pyridine
5-[(2,2-Difluoro-1,3-benzodioxol-4-yl)carbonyl]-1-phenyl-4,5,6,7-tetrahydro-1H-imidazo[4,5-c]pyridine
5-(2,3-Dihydro-1-benzofuran-7-ylcarbonyl)-1-phenyl-4,5,6,7-tetrahydro-1H-imidazo[4,5-c]pyridine
5-[(2,2-Dimethyl-2,3-dihydro-1-benzofuran-7-yl)carbonyl]-1-phenyl-4,5,6,7-tetrahydro-1H-imidazo[4,5-c]pyridine
5-{[2-Chloro-3-(trifluoromethyl)phenyl]carbonyl}-4,4-dimethyl-1-phenyl-4,5,6,7-tetrahydro-1H-imidazo[4,5-c]pyridine
5-{[2-Chloro-3-(trifluoromethyl)phenyl]carbonyl}-1-pyrazin-2-yl-4,5-dihydro-1H-imidazo[4,5-c]pyridine
5-{[2-Chloro-3-(trifluoromethyl)phenyl]carbonyl}-4-ethyl-1-pyrazin-2-yl-4,5-dihydro-1H-imidazo[4,5-c]pyridine
5-{[2-Chloro-3-(trifluoromethyl)phenyl]carbonyl}-4-methyl-1-pyrazin-2-yl-4,5-dihydro-1H-imidazo[4,5-c]pyridine
5-{[2-Fluoro-3-(trifluoromethyl)phenyl]carbonyl}-1-phenyl-2-(trifluoromethyl)-4,5,6,7-tetrahydro-1H-imidazo[4,5-c]pyridine
5-[(2,3-Dichlorophenyl)carbonyl]-1-phenyl-2-(trifluoromethyl)-4,5,6,7-tetrahydro-1H-imidazo[4,5-c]pyridine
5-{[2-Fluoro-3-(trifluoromethyl)phenyl]carbonyl}-1-(1H-pyrazol-5-yl)-4,5,6,7-tetrahydro-1H-imidazo[4,5-c]pyridine
5-[(2,3-Dichlorophenyl)carbonyl]-1-(1H-pyrazol-5-yl)-4,5,6,7-tetrahydro-1H-imidazo[4,5-c]pyridine
5-{[2-Chloro-3-(trifluoromethyl)phenyl]carbonyl}-1-phenyl-4,5,6,7-tetrahydro-1H-[1,2,3]triazolo[4,5-c]pyridine
5-[(2,3-Dichlorophenyl)carbonyl]-1-phenyl-4,5,6,7-tetrahydro-1H-[1,2,3]triazolo[4,5-c]pyridine
5-{[2-Chloro-3-(trifluoromethyl)phenyl]carbonyl}-1-pyridin-2-yl-4,5,6,7-tetrahydro-1H-[1,2,3]triazolo[4,5-c]pyridine
5-{[2-Chloro-3-(trifluoromethyl)phenyl]carbonyl}-1-(5-fluoropyrimidin-2-yl)-4,5,6,7-tetrahydro-1H-[1,2,3]triazolo[4,5-c]pyridine
5-{[2-Chloro-3-(trifluoromethyl)phenyl]carbonyl}-1-pyrimidin-2-yl-4,5,6,7-tetrahydro-1H-[1,2,3]triazolo[4,5-c]pyridine
{[2-Fluoro-3-(trifluoromethyl)phenyl]carbonyl}-1-pyrimidin-2-yl-4,5,6,7-tetrahydro-1H-[1,2,3]triazolo[4,5-c]pyridine
5-[(2,3-Dichlorophenyl)carbonyl]-1-pyrimidin-2-yl-4,5,6,7-tetrahydro-1H-[1,2,3]triazolo[4,5-c]pyridine
5-{[2-Chloro-3-(trifluoromethyl)phenyl]carbonyl}-1-(1H-pyrazol-5-yl)-4,5,6,7-tetrahydro-1H-[1,2,3]triazolo[4,5-c]pyridine
5-{[2-Fluoro-3-(trifluoromethyl)phenyl]carbonyl}-1-pyrazin-2-yl-4,5,6,7-tetrahydro-1H-[1,2,3]triazolo[4,5-c]pyridine
5-[(2,3-Dichlorophenyl)carbonyl]-1-pyrazin-2-yl-4,5,6,7-tetrahydro-1H-[1,2,3]triazolo[4,5-c]pyridine
5-{[2-Chloro-3-(trifluoromethyl)phenyl]carbonyl}-1-(5-fluoropyridin-2-yl)-4-methyl-4,5,6,7-tetrahydro-1H-[1,2,3]triazolo[4,5-c]pyridine
5-{[2-Chloro-3-(trifluoromethyl)phenyl]carbonyl}-4-methyl-1-pyrazin-2-yl-4,5-dihydro-1H-[1,2,3]triazolo[4,5-c]pyridine
5-{[2-Chloro-3-(trifluoromethyl)phenyl]carbonyl}-4-methyl-1-pyrazin-2-yl-4,5,6,7-tetrahydro-1H-[1,2,3]triazolo[4,5-c]pyridine
(4R*)-5-{[2-Chloro-3-(trifluoromethyl)phenyl]carbonyl}-4-methyl-1-pyrazin-2-yl-4,5,6,7-tetrahydro-1H-[1,2,3]triazolo[4,5-c]pyridine
(4S*)-5-{[2-Chloro-3-(trifluoromethyl)phenyl]carbonyl}-4-methyl-1-pyrazin-2-yl-4,5,6,7-tetrahydro-1H-[1,2,3]triazolo[4,5-c]pyridine
5-{[2-Chloro-3-(trifluoromethyl)phenyl]carbonyl}-4-phenyl-1-pyrazin-2-yl-4,5-dihydro-1H-[1,2,3]triazolo[4,5-c]pyridine TABLE 1-continued Compounds of Formulas (I, IIa and IIb)

5-{[2-Chloro-3-(trifluoromethyl)phenyl]carbonyl}-4-phenyl-1-pyrazin-2-yl-4,5,6,7-tetrahydro-1H-[1,2,3]triazolo[4,5-c]pyridine
5-{[2-Chloro-3-(trifluoromethyl)phenyl]carbonyl}-4-phenyl-4,5,6,7-tetrahydro-1H-[1,2,3]triazolo[4,5-c]pyridine
5-{[2-Chloro-3-(trifluoromethyl)phenyl]carbonyl}-4-methyl-1-pyrimidin-2-yl-4,5-dihydro-1H-[1,2,3]triazolo[4,5-c]pyridine
5-{[2-Chloro-3-(trifluoromethyl)phenyl]carbonyl}-4-methyl-1-pyrimidin-2-yl-4,5,6,7-tetrahydro-1H-[1,2,3]triazolo[4,5-c]pyridine
5-{[2-Chloro-3-(trifluoromethyl)phenyl]carbonyl}-1-(4-fluorophenyl)-4-methyl-4,5-dihydro-1H-[1,2,3]triazolo[4,5-c]pyridine
5-{[2-Chloro-3-(trifluoromethyl)phenyl]carbonyl}-1-(3-fluoropyridin-2-yl)-4-methyl-4,5-dihydro-1H-[1,2,3]triazolo[4,5-c]pyridine
5-{[2-Chloro-3-(trifluoromethyl)phenyl]carbonyl}-1-(4-fluorophenyl)-4-methyl-4,5,6,7-tetrahydro-1H-[1,2,3]triazolo[4,5-c]pyridine
5-{[2-Chloro-3-(trifluoromethyl)phenyl]carbonyl}-1-(3-fluoropyridin-2-yl)-4-methyl-4,5,6,7-tetrahydro-1H-[1,2,3]triazolo[4,5-c]pyridine
5-{[2-Chloro-3-(trifluoromethyl)phenyl]carbonyl}-4-methyl-1-(1H-pyrazol-3-yl)-4,5,6,7-tetrahydro-1H-[1,2,3]triazolo[4,5-c]pyridine
5-{[2-Chloro-3-(trifluoromethyl)phenyl]carbonyl}-4-methyl-1-(1H-pyrazol-3-yl)-4,5-dihydro-1H-[1,2,3]triazolo[4,5-c]pyridine
(4S*)-5-{[2-Chloro-3-(trifluoromethyl)phenyl]carbonyl}-4-methyl-1-pyrimidin-2-yl-4,5,6,7-tetrahydro-1H-[1,2,3]triazolo[4,5-c]pyridine
(4R*)-5-{[2-Chloro-3-(trifluoromethyl)phenyl]carbonyl}-4-methyl-1-pyrimidin-2-yl-4,5,6,7-tetrahydro-1H-[1,2,3]triazolo[4,5-c]pyridine
5-{[2-Chloro-3-(trifluoromethyl)phenyl]carbonyl}-1-pyrazin-2-yl-4,5-dihydro-1H-[1,2,3]triazolo[4,5-c]pyridine
5-{[2-Chloro-3-(trifluoromethyl)phenyl]carbonyl}-1-pyridin-2-yl-4,5-dihydro-1H-[1,2,3]triazolo[4,5-c]pyridine
5-{[2-Chloro-3-(trifluoromethyl)phenyl]carbonyl}-1-pyrazin-2-yl-4,5,6,7-tetrahydro-1H-[1,2,3]triazolo[4,5-c]pyridine
92: 6-{[2-Chloro-3-(trifluoromethyl)phenyl]carbonyl}-2-methyl-3-pyridin-2-yl-4,5,6,7-tetrahydro-2H-pyrazolo[3,4-c]pyridine
6-{[2-Chloro-3-(trifluoromethyl)phenyl]carbonyl}-3-pyridin-2-yl-4,5,6,7-tetrahydro-2H-pyrazolo[3,4-c]pyridine. TFA salt
6-{[2-Chloro-3-(trifluoromethyl)phenyl]carbonyl}-3-(5-fluoropyridin-2-yl)-4,5,6,7-tetrahydro-2H-pyrazolo[3,4-c]pyridine
6-{[2-Chloro-3-(trifluoromethyl)phenyl]carbonyl}-3-(5-fluoropyridin-3-yl)-4,5,6,7-tetrahydro-2H-pyrazolo[3,4-c]pyridine
6-{[2-Chloro-3-(trifluoromethyl)phenyl]carbonyl}-3-pyridin-3-yl-4,5,6,7-tetrahydro-2H-pyrazolo[3,4-c]pyridine
6-{[2-Chloro-3-(trifluoromethyl)phenyl]carbonyl}-3-pyrazin-2-yl-4,5,6,7-tetrahydro-2H-pyrazolo[3,4-c]pyridine
98: 6-{[2-Chloro-3-(trifluoromethyl)phenyl]carbonyl}-3-pyrimidin-2-yl-4,5,6,7-tetrahydro-2H-pyrazolo[3,4-c]pyridine
(2-Chloro-3-(trifluoromethyl)phenyl)(3-phenyl-4,5-dihydro-1H-pyrazolo[3,4-c]pyridin-6(7H)-yl)methanone
6-[(2,3-Dichlorophenyl)carbonyl]-3-phenyl-4,5,6,7-tetrahydro-1H-pyrazolo[3,4-c]pyridine
6-[(2,3-Dichlorophenyl)carbonyl]-1-methyl-3-phenyl-4,5,6,7-tetrahydro-1H-pyrazolo[3,4-c]pyridine and 6-[(2,3-dichlorophenyl)carbonyl]-2-methyl-3-phenyl-4,5,6,7-tetrahydro-2H-pyrazolo[3,4-c]pyridine (1:1)
6-[(2,3-Dichlorophenyl)carbonyl]-2-methyl-3-phenyl-4,5,6,7-tetrahydro-2H-pyrazolo[3,4-c]pyridine
6-[(2,3-Dichlorophenyl)carbonyl]-1-methyl-3-phenyl-4,5,6,7-tetrahydro-1H-pyrazolo[3,4-c]pyridine
6-[(2,3-Dichloropyridin-4-yl)carbonyl]-3-phenyl-4,5,6,7-tetrahydro-1H-pyrazolo[3,4-c]pyridine
6-{[2-Chloro-3-(trifluoromethyl)phenyl]carbonyl}-3-(4-fluorophenyl)-2-methyl-4,5,6,7-tetrahydro-2H-pyrazolo[3,4-c]pyridine
6-{[2-Chloro-3-(trifluoromethyl)phenyl]carbonyl}-3-(4-fluorophenyl)-1-methyl-4,5,6,7-tetrahydro-1H-pyrazolo[3,4-c]pyridine
6-{[2-Chloro-3-(trifluoromethyl)phenyl]carbonyl}-2-methyl-3-pyridin-3-yl-4,5,6,7-tetrahydro-2H-pyrazolo[3,4-c]pyridine
6-{[2-Chloro-3-(trifluoromethyl)phenyl]carbonyl}-1-methyl-3-pyridin-3-yl-4,5,6,7-tetrahydro-1H-pyrazolo[3,4-c]pyridine
6-[(2,3-Dichlorophenyl)carbonyl]-3-(4-fluorophenyl)-1-methyl-4,5,6,7-tetrahydro-1H-pyrazolo[3,4-c]pyridine
6-{[2-Chloro-3-(trifluoromethyl)phenyl]carbonyl}-3-(4-fluorophenyl)-4,5,6,7-tetrahydro-2H-pyrazolo[3,4-c]pyridine
6-[(2,3-Dichlorophenyl)carbonyl]-2-methyl-3-pyridin-3-yl-4,5,6,7-tetrahydro-2H-pyrazolo[3,4-c]pyridine
6-[(2,3-Dichlorophenyl)carbonyl]-2-methyl-3-pyridin-3-yl-4,5,6,7-tetrahydro-2H-pyrazolo[3,4-c]pyridine
6-{[2-Chloro-3-(trifluoromethyl)phenyl]carbonyl}-2-methyl-3-pyrimidin-5-yl-4,5,6,7-tetrahydro-2H-pyrazolo[3,4-c]pyridine
6-[(2,3-Dichlorophenyl)carbonyl]-3-(4-fluorophenyl)-4,5,6,7-tetrahydro-2H-pyrazolo[3,4-c]pyridine
6-[(2,3-Dichlorophenyl)carbonyl]-3-pyridin-4-yl-4,5,6,7-tetrahydro-2H-pyrazolo[3,4-c]pyridine
5-{[2-Chloro-3-(trifluoromethyl)phenyl]carbonyl}-6-methyl-1-pyridin-2-yl-4,5,6,7-tetrahydro-1H-[1,2,3]triazolo[4,5-c]pyridine
(2-Chloro-4-fluorophenyl)(1-(pyridin-2-yl)-6,7-dihydro-1H-[1,2,3]triazolo[4,5-c]pyridin-5(4H)-yl)methanone
5-{[2-Chloro-3-(trifluoromethyl)phenyl]carbonyl}-(S*)-6-methyl-1-pyridin-2-yl-4,5,6,7-tetrahydro-1H-[1,2,3]triazolo[4,5-c]pyridine
5-{[2-Chloro-3-(trifluoromethyl)phenyl]carbonyl}-(R*)-6-methyl-1-pyridin-2-yl-4,5,6,7-tetrahydro-1H-[1,2,3]triazolo[4,5-c]pyridine
5-[(2,3-Dichlorophenyl)carbonyl]-6-methyl-1-pyridin-2-yl-4,5,6,7-tetrahydro-1H-[1,2,3]triazolo[4,5-c]pyridine
5-[(2,3-Dichloro-4-fluorophenyl)carbonyl]-6-methyl-1-pyridin-2-yl-4,5,6,7-tetrahydro-1H-[1,2,3]triazolo[4,5-c]pyridine
5-{[2-Chloro-3-(trifluoromethyl)phenyl]carbonyl}-1-(3-fluoropyridin-2-yl)-6-methyl-4,5,6,7-tetrahydro-1H-[1,2,3]triazolo[4,5-c]pyridine
(2-Fluoro-3-(trifluoromethyl)phenyl)(1-(pyridin-2-yl)-6,7-dihydro-1H-[1,2,3]triazolo[4,5-c]pyridin-5(4H)-yl)methanone
(2-Fluoro-3-(trifluoromethyl)phenyl)(1-(2-methoxyphenyl)-6,7-dihydro-1H-[1,2,3]triazolo[4,5-c]pyridin-5(4H)-yl)methanone
(2-Chloro-3-(trifluoromethyl)phenyl)(1-(2-methoxyphenyl)-6,7-dihydro-1H-[1,2,3]triazolo[4,5-c]pyridin-5(4H)-yl)methanone
(2-Chloro-3-(trifluoromethyl)phenyl)(1-(2-(2-fluoroethoxy)phenyl)-6,7-dihydro-1H-[1,2,3]triazolo[4,5-c]pyridin-5(4H)-yl)methanone
(2-Chloro-3-(trifluoromethyl)phenyl)(1-(1-methyl-1H-pyrazol-3-yl)-6,7-dihydro-1H-[1,2,3]triazolo[4,5-c]pyridin-5(4H)-yl)methanone
(2-Chloro-3-(trifluoromethyl)phenyl)(1-(1-methyl-1H-pyrazol-5-yl)-6,7-dihydro-1H-[1,2,3]triazolo[4,5-c]pyridin-5(4H)-yl)methanone
(4-Chloro-2-fluorophenyl)(1-(pyridin-2-yl)-6,7-dihydro-1H-[1,2,3]triazolo[4,5-c]pyridin-5(4H)-yl)methanone
(2,3-Dichloro-4-fluorophenyl)(1-(pyridin-2-yl)-6,7-dihydro-1H-[1,2,3]triazolo[4,5-c]pyridin-5(4H)-yl)methanone
(2-Chloro-3-(trifluoromethyl)phenyl)(1-(4-fluoropyridin-2-yl)-6,7-dihydro-1H-[1,2,3]triazolo[4,5-c]pyridin-5(4H)-yl)methanone
(3,4-Difluoro-2-methylphenyl)(1-(pyridin-2-yl)-6,7-dihydro-1H-[1,2,3]triazolo-[4,5-c]pyridin-5(4H)-yl)methanone
(R*)-(2-Chloro-3-(trifluoromethyl)phenyl)(4-methyl-1-(1H-pyrazol-5-yl)-6,7-dihydro-1H-[1,2,3]triazolo[4,5-c]pyridin-5(4H)-yl)methanone
(S*)-(2-Chloro-3-(trifluoromethyl)phenyl)(4-methyl-1-(1H-pyrazol-5-yl)-6,7-dihydro-1H-[1,2,3]triazolo[4,5-c]pyridin-5(4H)-yl)methanone
(2-Chloro-3-(trifluoromethyl)phenyl)(1-(6-fluoropyridin-2-yl)-6,7-dihydro-1H-[1,2,3]triazolo[4,5-c]pyridin-5(4H)-yl)methanone
(2-Chloro-3-(trifluoromethyl)phenyl)(1-(4-methoxypyridin-2-yl)-6,7-dihydro-1H-[1,2,3]triazolo[4,5-c]pyridin-5(4H)-yl)methanone
(2-Chloro-3-(trifluoromethyl)phenyl)(1-(6-fluoropyridin-2-yl)-4-methyl-6,7-dihydro-1H-[1,2,3]triazolo[4,5-c]pyridin-5(4H)-yl)methanone
(2-Chloro-3-(trifluoromethyl)phenyl)(1-(4-fluoropyridin-2-yl)-4-methyl-6,7-dihydro-1H-[1,2,3]triazolo[4,5-c]pyridin-5(4H)-yl)methanone
(2,3-dichloro-4-fluorophenyl)(4-methyl-1-(pyridin-2-yl)-6,7-dihydro-1H-[1,2,3]triazolo[4,5-c]pyridin-5(4H)-yl)methanone
(2,3-dichloro-4-fluorophenyl)(4-methyl-1-(pyrazin-2-yl)-6,7-dihydro-1H-[1,2,3]triazolo[4,5-c]pyridin-5(4H)-yl)methanone
(R*)-(2,3-Dichloro-4-fluorophenyl)(4-methyl-1-(pyridin-2-yl)-6,7-dihydro-1H-[1,2,3]triazolo[4,5-c]pyridin-5(4H)-yl)methanone
(S*)-(2,3-Dichloro-4-fluorophenyl)(4-methyl-1-(pyridin-2-yl)-6,7-dihydro-1H-[1,2,3]triazolo[4,5-c]pyridin-5(4H)-yl)methanone
(R*)-(2,3-Dichloro-4-fluorophenyl)(4-methyl-1-(pyrazin-2-yl)-6,7-dihydro-1H-[1,2,3]triazolo[4,5-c]pyridin-5(4H)-yl)methanone
(S*)-(2,3-Dichloro-4-fluorophenyl)(4-methyl-1-(pyrazin-2-yl)-6,7-dihydro-1H-[1,2,3]triazolo[4,5-c]pyridin-5(4H)-yl)methanone
(2-Chloro-3-(trifluoromethyl)phenyl)(1-(5-methoxypyridin-2-yl)-4-methyl-6,7-dihydro-1H-[1,2,3]triazolo[4,5-c]pyridin-5(4H)-yl)methanone
(R*)-(2-chloro-3-(trifluoromethyl)phenyl)(1-(6-fluoropyridin-2-yl)-4-methyl-6,7-dihydro-1H-[1,2,3]triazolo[4,5-c]pyridin-5(4H)-yl)methanone
(S*)-(2-Chloro-3-(trifluoromethyl)phenyl)(1-(6-fluoropyridin-2-yl)-4-methyl-6,7-dihydro-1H-[1,2,3]triazolo[4,5-c]pyridin-5(4H)-yl)methanone
(R*)-(2-Chloro-3-(trifluoromethyl)phenyl)(1-(4-fluoropyridin-2-yl)-4-methyl-6,7-dihydro-1H-[1,2,3]triazolo[4,5-c]pyridin-5(4H)-yl)methanone
(S*)-(2-Chloro-3-(trifluoromethyl)phenyl)(1-(4-fluoropyridin-2-yl)-4-methyl-6,7-dihydro-1H-[1,2,3]triazolo[4,5-c]pyridin-5(4H)-yl)methanone
(2-Chloro-3-(trifluoromethyl)phenyl)(1-(4-methoxypyridin-2-yl)-4-

TABLE 1-continued

Compounds of Formulas (I, IIa and IIb)

methyl-6,7-dihydro-1H-[1,2,3]triazolo[4,5-c]pyridin-5(4H)-yl)methanone
(R*)-(2-Chloro-3-(trifluoromethyl)phenyl)(1-(4-methoxypyridin-2-yl)-4-methyl-6,7-dihydro-1H-[1,2,3]triazolo[4,5-c]pyridin-5(4H)-yl)methanone
(S*)-(2-Chloro-3-(trifluoromethyl)phenyl)(1-(4-methoxypyridin-2-yl)-4-methyl-6,7-dihydro-1H-[1,2,3]triazolo[4,5-c]pyridin-5(4H)-yl)methanone
(2-Chloro-3-(trifluoromethyl)phenyl)(1-(5-fluoropyrimidin-2-yl)-4-methyl-6,7-dihydro-1H-[1,2,3]triazolo[4,5-c]pyridin-5(4H)-yl)methanone
(6-methyl-1-(1H-pyrazol-3-yl)-6,7-dihydro-1H-[1,2,3]triazolo[4,5-c]pyridin-5(4H)-yl)(2-methyl-3-(trifluoromethyl)phenyl)methanone
(S)-(4-chloro-2-fluorophenyl)(1-(5-fluoropyrimidin-2-yl)-6-methyl-6,7-dihydro-1H-[1,2,3]triazolo[4,5-c]pyridin-5(4H)-yl)methanone
(S)-(4-chloro-2-fluorophenyl)(1-(5-fluoropyrimidin-2-yl)-6-methyl-6,7-dihydro-1H-[1,2,3]triazolo[4,5-c]pyridin-5(4H)-yl)methanone
(S*)-(2-Chloro-3-(trifluoromethyl)phenyl)(1-(5-fluoropyrimidin-2-yl)-4-methyl-6,7-dihydro-1H-[1,2,3]triazolo[4,5-c]pyridin-5(4H)-yl)methanone
(R*)-(2-Chloro-3-(trifluoromethyl)phenyl)(1-(5-fluoropyrimidin-2-yl)-4-methyl-6,7-dihydro-1H-[1,2,3]triazolo[4,5-c]pyridin-5(4H)-yl)methanone
(2-chloro-3-(trifluoromethyl)phenyl)(1-(3,5-dimethylpyridin-2-yl)-4-methyl-6,7-dihydro-1H-[1,2,3]triazolo[4,5-c]pyridin-5(4H)-yl)methanone
(2,3-dichlorophenyl)(1-(3,5-dimethylpyridin-2-yl)-4-methyl-6,7-dihydro-1H-[1,2,3]triazolo[4,5-c]pyridin-5(4H)-yl)methanone
(2,3-Dichlorophenyl)(1-(3-fluoropyridin-2-yl)-6-methyl-6,7-dihydro-1H-[1,2,3]triazolo[4,5-c]pyridin-5(4H)-yl)methanone
(2-Chloro-3-(trifluoromethyl)phenyl)(1-(1-(2-fluoroethyl)-1H-pyrazol-3-yl)-4-methyl-6,7-dihydro-1H-[1,2,3]triazolo[4,5-c]pyridin-5(4H)-yl)methanone
(2-Chloro-3-(trifluoromethyl)phenyl)(4-methyl-1-(1-methyl-1H-pyrazol-3-yl)-6,7-dihydro-1H-[1,2,3]triazolo[4,5-c]pyridin-5(4H)-yl)methanone
(S)-(3-chloro-2-(trifluoromethyl)pyridin-4-yl)(1-(5-fluoropyrimidin-2-yl)-4-methyl-6,7-dihydro-1H-[1,2,3]triazolo[4,5-c]pyridin-5(4H)-yl)methanone
(6R*)-5-[(2,3-Dichlorophenyl)carbonyl]-1-(3-fluoropyridin-2-yl)-6-methyl-4,5,6,7-tetrahydro-1H-[1,2,3]triazolo[4,5-c]pyridine
(6S*)-5-[(2,3-Dichlorophenyl)carbonyl]-1-(3-fluoropyridin-2-yl)-6-methyl-4,5,6,7-tetrahydro-1H-[1,2,3]triazolo[4,5-c]pyridine
(6R*)-5-{[2-Chloro-3-(trifluoromethyl)phenyl]carbonyl}-1-(3-fluoropyridin-2-yl)-6-methyl-4,5,6,7-tetrahydro-1H-[1,2,3]triazolo[4,5-c]pyridine
(6S*)-5-{[2-Chloro-3-(trifluoromethyl)phenyl]carbonyl}-1-(3-fluoropyridin-2-yl)-6-methyl-4,5,6,7-tetrahydro-1H-[1,2,3]triazolo[4,5-c]pyridine
(R*)-(2-Chloro-3-(trifluoromethyl)phenyl)(4-methyl-1-(1-methyl-1H-pyrazol-3-yl)-6,7-dihydro-1H-[1,2,3]triazolo[4,5-c]pyridin-5(4H)-yl)methanone
(S*)-(2-Chloro-3-(trifluoromethyl)phenyl)(4-methyl-1-(1-methyl-1H-pyrazol-3-yl)-6,7-dihydro-1H-[1,2,3]triazolo[4,5-c]pyridin-5(4H)-yl)methanone
(R*)-(2-Chloro-3-(trifluoromethyl)phenyl)(1-(1-(2-fluoroethyl)-1H-pyrazol-3-yl)-4-methyl-6,7-dihydro-1H-[1,2,3]triazolo[4,5-c]pyridin-5(4H)-yl)methanone
(S*)-(2-Chloro-3-(trifluoromethyl)phenyl)(1-(1-(2-fluoroethyl)-1H-pyrazol-3-yl)-4-methyl-6,7-dihydro-1H-[1,2,3]triazolo[4,5-c]pyridin-5(4H)-yl)methanone
5-[(2,3-Dichlorophenyl)carbonyl]-1-(4-fluoropyridin-2-yl)-6-methyl-4,5,6,7-tetrahydro-1H-[1,2,3]triazolo[4,5-c]pyridine
(2,3-Dichlorophenyl)(1-(5-fluoropyrimidin-2-yl)-4-methyl-6,7-dihydro-1H-[1,2,3]triazolo[4,5-c]pyridin-5(4H)-yl)methanone
(2-fluoro-3-(trifluoromethyl)phenyl)(1-(5-fluoropyrimidin-2-yl)-4-methyl-6,7-dihydro-1H-[1,2,3]triazolo[4,5-c]pyridin-5(4H)-yl)methanone
(2-Chloro-3-(trifluoromethyl)phenyl)(1-(4-fluoropyridin-2-yl)-6-methyl-6,7-dihydro-1H-[1,2,3]triazolo[4,5-c]pyridin-5(4H)-yl)methanone
(2-Chloro-3-(trifluoromethyl)phenyl)(4-methyl-1-(pyrimidin-5-yl)-6,7-dihydro-1H-[1,2,3]triazolo[4,5-c]pyridin-5(4H)-yl)methanone
(S)-(2-fluoro-3-(trifluoromethyl)phenyl)(1-(5-fluoropyrimidin-2-yl)-4-methyl-6,7-dihydro-1H-[1,2,3]triazolo[4,5-c]pyridin-5(4H)-yl)methanone
(2,3-dichlorophenyl)(1-(4,6-dimethylpyrimidin-2-yl)-4-methyl-6,7-dihydro-1H-[1,2,3]triazolo[4,5-c]pyridin-5(4H)-yl)methanone
(2,3-dichlorophenyl)(4-methyl-1-(6-methylpyrazin-2-yl)-6,7-dihydro-1H-[1,2,3]triazolo[4,5-c]pyridin-5(4H)-yl)methanone
(R)-(2-chloro-3-(trifluoromethyl)phenyl)(1-(4,6-dimethylpyrimidin-2-yl)-4-methyl-6,7-dihydro-1H-[1,2,3]triazolo[4,5-c]pyridin-5(4H)-yl)methanone
(S)-(2-chloro-3-(trifluoromethyl)phenyl)(1-(4,6-dimethylpyrimidin-2-yl)-4-methyl-6,7-dihydro-1H-[1,2,3]triazolo[4,5-c]pyridin-5(4H)-yl)methanone
(R)-(3-chloro-2-(trifluoromethyl)pyridin-4-yl)(1-(5-fluoropyrimidin-2-yl)-6-methyl-6,7-dihydro-1H-[1,2,3]triazolo[4,5-c]pyridin-5(4H)-yl)methanone
(2-Chloro-3-(trifluoromethyl)phenyl)(2-ethyl-4-methyl-1-phenyl-6,7-dihydro-1H-imidazo[4,5-c]pyridin-5(4H)-yl)methanone
(R)-(2-chloro-3-(trifluoromethyl)phenyl)(4-methyl-1-(4-methylpyridin-2-yl)-6,7-dihydro-1H-[1,2,3]triazolo[4,5-c]pyridin-5(4H)-yl)methanone
(S)-(2-chloro-3-(trifluoromethyl)phenyl)(4-methyl-1-(4-methylpyridin-2-yl)-6,7-dihydro-1H-[1,2,3]triazolo[4,5-c]pyridin-5(4H)-yl)methanone
(S)-(1-(5-fluoropyrimidin-2-yl)-6-methyl-6,7-dihydro-1H-[1,2,3]triazolo[4,5-c]pyridin-5(4H)-yl)(3-methyl-2-(trifluoromethyl)pyridin-4-yl)methanone
(R)-(4-methyl-1-(pyrimidin-2-yl)-6,7-dihydro-1H-[1,2,3]triazolo[4,5-c]pyridin-5(4H)-yl)(2-methyl-3-(trifluoromethyl)phenyl)methanone
(2-fluoro-3-(trifluoromethyl)phenyl)(6-methyl-1-(1H-pyrazol-3-yl)-6,7-dihydro-1H-[1,2,3]triazolo[4,5-c]pyridin-5(4H)-yl)methanone
(R)-(2-fluoro-3-(trifluoromethyl)phenyl)(1-(5-fluoropyrimidin-2-yl)-4-methyl-6,7-dihydro-1H-[1,2,3]triazolo[4,5-c]pyridin-5(4H)-yl)methanone
(S*)-(2,3-Dichlorophenyl)(4-methyl-1-(pyridin-2-yl)-6,7-dihydro-1H-imidazo[4,5-c]pyridin-5(4H)-yl)methanone
(R*)-(2,3-Dichlorophenyl)(4-methyl-1-(pyridin-2-yl)-6,7-dihydro-1H-imidazo[4,5-c]pyridin-5(4H)-yl)methanone
(R*)-(2-Chloro-3-(trifluoromethyl)phenyl)(1-(5-fluoropyrimidin-2-yl)-4-methyl-6,7-dihydro-1H-imidazo[4,5-c]pyridin-5(4H)-yl)methanone
(S*)-(2-Chloro-3-(trifluoromethyl)phenyl)(1-(5-fluoropyrimidin-2-yl)-4-methyl-6,7-dihydro-1H-imidazo[4,5-c]pyridin-5(4H)-yl)methanone
(6R*)-5-[(2,3-Dichlorophenyl)carbonyl]-1-(4-fluoropyridin-2-yl)-6-methyl-4,5,6,7-tetrahydro-1H-[1,2,3]triazolo[4,5-c]pyridine
(6S*)-5-[(2,3-Dichlorophenyl)carbonyl]-1-(4-fluoropyridin-2-yl)-6-methyl-4,5,6,7-tetrahydro-1H-[1,2,3]triazolo[4,5-c]pyridine
(S)-(4-methyl-1-(pyrimidin-2-yl)-6,7-dihydro-1H-[1,2,3]triazolo[4,5-c]pyridin-5(4H)-yl)(2-methyl-3-(trifluoromethyl)phenyl)methanone
(6R*)-5-{[2-Chloro-3-(trifluoromethyl)phenyl]carbonyl}-1-(4-fluoropyridin-2-yl)-6-methyl-4,5,6,7-tetrahydro-1H-[1,2,3]triazolo[4,5-c]pyridine
(6S*)-5-{[2-Chloro-3-(trifluoromethyl)phenyl]carbonyl}-1-(4-fluoropyridin-2-yl)-6-methyl-4,5,6,7-tetrahydro-1H-[1,2,3]triazolo[4,5-c]pyridine
5-{[2-Chloro-3-(trifluoromethyl)phenyl]carbonyl}-1-(5-fluoropyrimidin-2-yl)-6-methyl-4,5,6,7-tetrahydro-1H-[1,2,3]triazolo[4,5-c]pyridine
(6R*)-5-{[2-Chloro-3-(trifluoromethyl)phenyl]carbonyl}-1-(5-fluoropyrimidin-2-yl)-6-methyl-4,5,6,7-tetrahydro-1H-[1,2,3]triazolo[4,5-c]pyridine
(6S*)-5-{[2-Chloro-3-(trifluoromethyl)phenyl]carbonyl}-1-(5-fluoropyrimidin-2-yl)-6-methyl-4,5,6,7-tetrahydro-1H-[1,2,3]triazolo[4,5-c]pyridine
5-[(2,3-Dichlorophenyl)carbonyl]-1-(5-fluoropyrimidin-2-yl)-6-methyl-4,5,6,7-tetrahydro-1H-[1,2,3]triazolo[4,5-c]pyridine
(6R*)-5-[(2,3-Dichlorophenyl)carbonyl]-1-(5-fluoropyrimidin-2-yl)-6-methyl-4,5,6,7-tetrahydro-1H-[1,2,3]triazolo[4,5-c]pyridine
(6S*)-5-[(2,3-Dichlorophenyl)carbonyl]-1-(5-fluoropyrimidin-2-yl)-6-methyl-4,5,6,7-tetrahydro-1H-[1,2,3]triazolo[4,5-c]pyridine
1-(5-Fluoropyrimidin-2-yl)-6-methyl-5-{[2-methyl-3-(trifluoromethyl)phenyl]carbonyl}-4,5,6,7-tetrahydro-1H-[1,2,3]triazolo[4,5-c]pyridine
(6R*)-1-(5-Fluoropyrimidin-2-yl)-6-methyl-5-{[2-methyl-3-(trifluoromethyl)phenyl]carbonyl}-4,5,6,7-tetrahydro-1H-[1,2,3]triazolo[4,5-c]pyridine
(6S*)-1-(5-Fluoropyrimidin-2-yl)-6-methyl-5-{[2-methyl-3-(trifluoromethyl)phenyl]carbonyl}-4,5,6,7-tetrahydro-1H-[1,2,3]triazolo[4,5-c]pyridine
5-{[2-Chloro-3-(trifluoromethyl)phenyl]carbonyl}-6-methyl-1-pyrazin-2-yl-4,5,6,7-tetrahydro-1H-[1,2,3]triazolo[4,5-c]pyridine
(2-chloro-3-(trifluoromethyl)phenyl)(6-methyl-1-(1H-pyrazol-3-yl)-6,7-dihydro-1H-[1,2,3]triazolo[4,5-c]pyridin-5(4H)-yl)methanone
(6R*)-5-{[2-Chloro-3-(trifluoromethyl)phenyl]carbonyl}-6-methyl-1-pyrazin-2-yl-4,5,6,7-tetrahydro-1H-[1,2,3]triazolo[4,5-c]pyridine
(6S*)-5-{[2-Chloro-3-(trifluoromethyl)phenyl]carbonyl}-6-methyl-1-pyrazin-2-yl-4,5,6,7-tetrahydro-1H-[1,2,3]triazolo[4,5-c]pyridine

TABLE 1-continued

Compounds of Formulas (I, IIa and IIb)

5-[(2,3-Dichloro-4-fluorophenyl)carbonyl]-1-(5-fluoropyrimidin-2-yl)-6-methyl-4,5,6,7-tetrahydro-1H-[1,2,3]triazolo[4,5-c]pyridine
(6R*)-5-[(2,3-Dichloro-4-fluorophenyl)carbonyl]-1-(5-fluoropyrimidin-2-yl)-6-methyl-4,5,6,7-tetrahydro-1H-[1,2,3]triazolo[4,5-c]pyridine
(6S*)-5-[(2,3-Dichloro-4-fluorophenyl)carbonyl]-1-(5-fluoropyrimidin-2-yl)-6-methyl-4,5,6,7-tetrahydro-1H-[1,2,3]triazolo[4,5-c]pyridine
5-[(2,4-Dichloro-3-fluorophenyl)carbonyl]-1-(5-fluoropyrimidin-2-yl)-6-methyl-4,5,6,7-tetrahydro-1H-[1,2,3]triazolo[4,5-c]pyridine
(6R*)-5-[(2,4-Dichloro-3-fluorophenyl)carbonyl]-1-(5-fluoropyrimidin-2-yl)-6-methyl-4,5,6,7-tetrahydro-1H-[1,2,3]triazolo[4,5-c]pyridine
(6S*)-5-[(2,4-Dichloro-3-fluorophenyl)carbonyl]-1-(5-fluoropyrimidin-2-yl)-6-methyl-4,5,6,7-tetrahydro-1H-[1,2,3]triazolo[4,5-c]pyridine
(6R)-1-(5-Fluoropyrimidin-2-yl)-5-{[2-fluoro-3-(trifluoromethyl)phenyl]carbonyl}-6-methyl-4,5,6,7-tetrahydro-1H-[1,2,3]triazolo[4,5-c]pyridine
(6S)-1-(5-Fluoropyrimidin-2-yl)-5-{[2-fluoro-3-(trifluoromethyl)phenyl]carbonyl}-6-methyl-4,5,6,7-tetrahydro-1H-[1,2,3]triazolo[4,5-c]pyridine
(6R*)-5-{[2-Chloro-3-(trifluoromethyl)phenyl]carbonyl}-6-methyl-1-pyrimidin-2-yl-4,5,6,7-tetrahydro-1H-[1,2,3]triazolo[4,5-c]pyridine
(6S*)-5-{[2-Chloro-3-(trifluoromethyl)phenyl]carbonyl}-6-methyl-1-pyrimidin-2-yl-4,5,6,7-tetrahydro-1H-[1,2,3]triazolo[4,5-c]pyridine
(R)-(2-chloro-3-(trifluoromethyl)phenyl)(3-(5-fluoropyrimidin-2-yl)-7-methyl-4,5-dihydro-2H-pyrazolo[3,4-c]pyridin-6(7H)-yl)methanone
(S)-(2-chloro-3-(trifluoromethyl)phenyl)(3-(5-fluoropyrimidin-2-yl)-7-methyl-4,5-dihydro-2H-pyrazolo[3,4-c]pyridin-6(7H)-yl)methanone
(2,3-dichlorophenyl)(4-methyl-1-(4-methylpyrimidin-2-yl)-6,7-dihydro-1H-[1,2,3]triazolo[4,5-c]pyridin-5(4H)-yl)methanone
(R)-(2-chloro-3-(trifluoromethyl)phenyl)(4-methyl-1-(6-methylpyridin-2-yl)-6,7-dihydro-1H-[1,2,3]triazolo[4,5-c]pyridin-5(4H)-yl)methanone
(S)-(2-chloro-3-(trifluoromethyl)phenyl)(4-methyl-1-(6-methylpyridin-2-yl)-6,7-dihydro-1H-[1,2,3]triazolo[4,5-c]pyridin-5(4H)-yl)methanone
(S)-(3-fluoro-2-(trifluoromethyl)pyridin-4-yl)(1-(5-fluoropyrimidin-2-yl)-6-methyl-6,7-dihydro-1H-[1,2,3]triazolo[4,5-c]pyridin-5(4H)-yl)methanone
(S)-(3-fluoro-2-(trifluoromethyl)pyridin-4-yl)(1-(5-fluoropyrimidin-2-yl)-4-methyl-6,7-dihydro-1H-[1,2,3]triazolo[4,5-c]pyridin-5(4H)-yl)methanone
(2-chloro-3-(trifluoromethyl)phenyl)(1-(5-fluoro-4-methylpyrimidin-2-yl)-4-methyl-6,7-dihydro-1H-[1,2,3]triazolo[4,5-c]pyridin-5(4H)-yl)methanone
(2,3-dichlorophenyl)(1-(4,6-dimethylpyridin-2-yl)-4-methyl-6,7-dihydro-1H-[1,2,3]triazolo[4,5-c]pyridin-5(4H)-yl)methanone
(S)-(2-fluoro-5-(trifluoromethyl)phenyl)(1-(5-fluoropyrimidin-2-yl)-6-methyl-6,7-dihydro-1H-[1,2,3]triazolo[4,5-c]pyridin-5(4H)-yl)methanone
(2,3-dichlorophenyl)(4-methyl-1-(6-methylpyridin-2-yl)-6,7-dihydro-1H-[1,2,3]triazolo[4,5-c]pyridin-5(4H)-yl)methanone
(4R*)-(2-Chloro-3-(trifluoromethyl)phenyl)((4R)-4-methyl-1-(6-methyl-1,6-dihydropyrimidin-2-yl)-6,7-dihydro-1H-[1,2,3]triazolo[4,5-c]pyridin-5(4H)-yl)methanone
(4R)-(2-Chloro-3-(trifluoromethyl)phenyl)(4-methyl-1-(4-methylpyrimidin-2-yl)-6,7-dihydro-1H-[1,2,3]triazolo[4,5-c]pyridin-5(4H)-yl)methanone
(2-Chloro-3-(trifluoromethyl)phenyl)(4-methyl-1-(pyrimidin-5-yl)-1H-[1,2,3]triazolo[4,5-c]pyridin-5(4H)-yl)methanone
(2,3-dichlorophenyl)(4-methyl-1-(4-methylpyridin-2-yl)-6,7-dihydro-1H-[1,2,3]triazolo[4,5-c]pyridin-5(4H)-yl)methanone
(2-Chloro-3-(trifluoromethyl)phenyl)(1-(4-fluorophenyl)-4,7-dimethyl-6,7-dihydro-1H-[1,2,3]triazolo[4,5-c]pyridin-5(4H)-yl)methanone
(S)-(2-chloro-3-(trifluoromethyl)phenyl)(4-methyl-1-(5-methylpyridin-2-yl)-6,7-dihydro-1H-[1,2,3]triazolo[4,5-c]pyridin-5(4H)-yl)methanone
(2-Chloro-3-(trifluoromethyl)phenyl)(4,6-dimethyl-1-phenyl-6,7-dihydro-1H-[1,2,3]triazolo[4,5-c]pyridin-5(4H)-yl)methanone
(2-Chloro-3-(trifluoromethyl)phenyl)(4,7-dimethyl-1-phenyl-6,7-dihydro-1H-[1,2,3]triazolo[4,5-c]pyridin-5(4H)-yl)methanone
(2,3-Dichlorophenyl)(1-(4-fluorophenyl)-4,6-dimethyl-6,7-dihydro-1H-[1,2,3]triazolo[4,5-c]pyridin-5(4H)-yl)methanone
(2-Chloro-3-(trifluoromethyl)phenyl)(1-(4-fluorophenyl)-4,6-dimethyl-6,7-dihydro-1H-[1,2,3]triazolo[4,5-c]pyridin-5(4H)-yl)methanone
(2,3-Dichlorophenyl)(7-methyl-1-phenyl-6,7-dihydro-1H-[1,2,3]triazolo[4,5-c]pyridin-5(4H)-yl)methanone
(2-Chloro-3-(trifluoromethyl)phenyl)(7-methyl-1-phenyl-6,7-dihydro-1H-[1,2,3]triazolo[4,5-c]pyridin-5(4H)-yl)methanone
(2-Chloro-3-(trifluoromethyl)phenyl)(1-(4-fluorophenyl)-7-methyl-6,7-dihydro-1H-[1,2,3]triazolo[4,5-c]pyridin-5(4H)-yl)methanone
(2,3-Dichlorophenyl)(1-(4-fluorophenyl)-7-methyl-6,7-dihydro-1H-[1,2,3]triazolo[4,5-c]pyridin-5(4H)-yl)methanone
(R*)-(2-Chloro-3-(trifluoromethyl)phenyl)(1-(1-(2-methoxyethyl)-1H-pyrazol-3-yl)-4-methyl-6,7-dihydro-1H-[1,2,3]triazolo[4,5-c]pyridin-5(4H)-yl)methanone
(S*)-(2-Chloro-3-(trifluoromethyl)phenyl)(1-(1-(2-methoxyethyl)-1H-pyrazol-3-yl)-4-methyl-6,7-dihydro-1H-[1,2,3]triazolo[4,5-c]pyridin-5(4H)-yl)methanone
(2-Chloro-3-(trifluoromethyl)phenyl)(4-methyl-1-(oxazol-2-yl)-6,7-dihydro-1H-[1,2,3]triazolo[4,5-c]pyridin-5(4H)-yl)methanone
(2-Chloro-3-(trifluoromethyl)phenyl)(4-methyl-1-(6-methylpyrazin-2-yl)-6,7-dihydro-1H-[1,2,3]triazolo[4,5-c]pyridin-5(4H)-yl)methanone
(2-Chloro-3-(trifluoromethyl)phenyl)(4-methyl-1-(4-methylpyrimidin-2-yl)-6,7-dihydro-1H-[1,2,3]triazolo[4,5-c]pyridin-5(4H)-yl)methanone
(2-Chloro-3-(trifluoromethyl)phenyl)(1-(4,6-dimethylpyrimidin-2-yl)-4-methyl-6,7-dihydro-1H-[1,2,3]triazolo[4,5-c]pyridin-5(4H)-yl)methanone
(2-Chloro-3-(trifluoromethyl)phenyl)(1-(3-ethylpyridin-2-yl)-4-methyl-6,7-dihydro-1H-[1,2,3]triazolo[4,5-c]pyridin-5(4H)-yl)methanone
(R)-(2-chloro-3-(trifluoromethyl)phenyl)(4-methyl-1-(5-methylpyridin-2-yl)-6,7-dihydro-1H-[1,2,3]triazolo[4,5-c]pyridin-5(4H)-yl)methanone
(2-chloro-4-fluorophenyl)(1-(5-fluoropyridin-2-yl)-4-methyl-6,7-dihydro-1H-imidazo[4,5-c]pyridin-5(4H)-yl)methanone
(2,4-dichlorophenyl)(1-(pyrimidin-2-yl)-6,7-dihydro-1H-[1,2,3]triazolo[4,5-c]pyridin-5(4H)-yl)methanone
(2-Chloro-3-(trifluoromethyl)phenyl)(1-(3-ethoxypyridin-2-yl)-4-methyl-6,7-dihydro-1H-[1,2,3]triazolo[4,5-c]pyridin-5(4H)-yl)methanone
(2-Chloro-3-(trifluoromethyl)phenyl)(4-methyl-1-(3-methylpyridin-2-yl)-6,7-dihydro-1H-[1,2,3]triazolo[4,5-c]pyridin-5(4H)-yl)methanone
(2-Chloro-3-(trifluoromethyl)phenyl)(1-(3-methoxypyridin-2-yl)-4-methyl-6,7-dihydro-1H-[1,2,3]triazolo[4,5-c]pyridin-5(4H)-yl)methanone
(2,3-dichloro-4-fluorophenyl)(1-(5-fluoropyridin-2-yl)-4-methyl-6,7-dihydro-1H-imidazo[4,5-c]pyridin-5(4H)-yl)methanone
(2-fluoro-3-(trifluoromethyl)phenyl)(1-(5-fluoropyridin-2-yl)-4-methyl-6,7-dihydro-1H-imidazo[4,5-c]pyridin-5(4H)-yl)methanone
(1-(5-fluoropyridin-2-yl)-4-methyl-6,7-dihydro-1H-imidazo[4,5-c]pyridin-5(4H)-yl)(2-methyl-3-(trifluoromethyl)phenyl)methanone
(2-fluorophenyl)(1-(5-fluoropyridin-2-yl)-4-methyl-6,7-dihydro-1H-imidazo[4,5-c]pyridin-5(4H)-yl)methanone
(4-(tert-butyl)phenyl)(1-(5-fluoropyridin-2-yl)-4-methyl-6,7-dihydro-1H-imidazo[4,5-c]pyridin-5(4H)-yl)methanone
(2-chloro-3-(trifluoromethyl)phenyl)(1,5-dimethyl-3-(1-methyl-1H-pyrazol-5-yl)-4,5-dihydro-1H-pyrazolo[3,4-c]pyridin-6(7H)-yl)methanone
(2-chloro-3-(trifluoromethyl)phenyl)(5-methyl-3-(1H-pyrazol-5-yl)-4,5-dihydro-1H-pyrazolo[3,4-c]pyridin-6(7H)-yl)methanone
(2,4-dichlorophenyl)(5-methyl-3-(1H-pyrazol-5-yl)-4,5-dihydro-1H-pyrazolo[3,4-c]pyridin-6(7H)-yl)methanone
(2-fluoro-3-(trifluoromethyl)phenyl)(4-methyl-1-(4-methylpyrimidin-2-yl)-6,7-dihydro-1H-[1,2,3]triazolo[4,5-c]pyridin-5(4H)-yl)methanone
(S)-(2-fluoro-3-(trifluoromethyl)phenyl)(4-methyl-1-(pyrimidin-2-yl)-6,7-dihydro-1H-[1,2,3]triazolo[4,5-c]pyridin-5(4H)-yl)methanone
(R)-(2-fluoro-3-(trifluoromethyl)phenyl)(4-methyl-1-(pyrimidin-2-yl)-6,7-dihydro-1H-[1,2,3]triazolo[4,5-c]pyridin-5(4H)-yl)methanone
(4-chloro-2-fluorophenyl)(1-(pyrazin-2-yl)-6,7-dihydro-1H-[1,2,3]triazolo[4,5-c]pyridin-5(4H)-yl)methanone
(2-fluoro-3-(trifluoromethyl)phenyl)(4-methyl-1-(pyrazin-2-yl)-6,7-dihydro-1H-[1,2,3]triazolo[4,5-c]pyridin-5(4H)-yl)methanone
(4-chloro-2-fluorophenyl)(4-methyl-1-(pyrazin-2-yl)-6,7-dihydro-1H-[1,2,3]triazolo[4,5-c]pyridin-5(4H)-yl)methanone
(4-chloro-2-fluorophenyl)(4-methyl-1-(pyrimidin-2-yl)-6,7-dihydro-1H-[1,2,3]triazolo[4,5-c]pyridin-5(4H)-yl)methanone
(2-methyl-3-(trifluoromethyl)phenyl)(1-(pyrazin-2-yl)-6,7-dihydro-1H-[1,2,3]triazolo[4,5-c]pyridin-5(4H)-yl)methanone
(2,4-dichlorophenyl)(1-(pyrazin-2-yl)-6,7-dihydro-1H-[1,2,3]triazolo[4,5-c]pyridin-5(4H)-yl)methanone
(4-methyl-1-(pyrazin-2-yl)-6,7-dihydro-1H-[1,2,3]triazolo[4,5-c]pyridin-5(4H)-yl)(2-methyl-3-(trifluoromethyl)phenyl)methanone
(2,4-dichlorophenyl)(4-methyl-1-(pyrazin-2-yl)-6,7-dihydro-1H-[1,2,3]triazolo[4,5-c]pyridin-5(4H)-yl)methanone
(4-chloro-2-fluorophenyl)(1-(pyrimidin-2-yl)-6,7-dihydro-1H-[1,2,3]triazolo[4,5-c]pyridin-5(4H)-yl)methanone
(2-methyl-3-(trifluoromethyl)phenyl)(1-(pyrimidin-2-yl)-6,7-dihydro-1H-[1,2,3]triazolo[4,5-c]pyridin-5(4H)-yl)methanone
(4-methyl-1-(pyrimidin-2-yl)-6,7-dihydro-1H-[1,2,3]triazolo[4,5-c]pyridin-5(4H)-yl)(2-methyl-3-(trifluoromethyl)phenyl)methanone
(2,4-dichlorophenyl)(4-methyl-1-(pyrimidin-2-yl)-6,7-dihydro-1H-[1,2,3]triazolo[4,5-c]pyridin-5(4H)-yl)methanone TABLE 1-continued Compounds of Formulas (I, IIa and IIb)

(2-chloro-3-(trifluoromethyl)phenyl)((4R,6R)-1-(4-fluorophenyl)-4,6-dimethyl-6,7-dihydro-1H-[1,2,3]triazolo[4,5-c]pyridin-5(4H)-yl)methanone
(2-chloro-3-(trifluoromethyl)phenyl)((4S,6S)-1-(4-fluorophenyl)-4,6-dimethyl-6,7-dihydro-1H-[1,2,3]triazolo[4,5-c]pyridin-5(4H)-yl)methanone
2-chloro-3-(trifluoromethyl)phenyl)((4S,6R)-1-(4-fluorophenyl)-4,6-dimethyl-6,7-dihydro-1H-[1,2,3]triazolo[4,5-c]pyridin-5(4H)-yl)methanone
(2-chloro-3-(trifluoromethyl)phenyl)((4R,6S)-1-(4-fluorophenyl)-4,6-dimethyl-6,7-dihydro-1H-[1,2,3]triazolo[4,5-c]pyridin-5(4H)-yl)methanone
(S)-(2-chloro-3-(trifluoromethyl)phenyl)(6-methyl-1-phenyl-6,7-dihydro-1H-[1,2,3]triazolo[4,5-c]pyridin-5(4H)-yl)methanone
(2-chloro-3-(trifluoromethyl)phenyl)(4-methyl-3-phenyl-6,7-dihydro-3H-[1,2,3]triazolo[4,5-c]pyridin-5(4H)-yl)methanone
(2-chloro-3-(trifluoromethyl)phenyl)(6-methyl-1-phenyl-6,7-dihydro-1H-[1,2,3]triazolo[4,5-c]pyridin-5(4H)-yl)methanone
(R)-(2-chloro-3-(trifluoromethyl)phenyl)(4-methyl-1-(3-methylpyridin-2-yl)-6,7-dihydro-1H-[1,2,3]triazolo[4,5-c]pyridin-5(4H)-yl)methanone
(S)-(2-chloro-3-(trifluoromethyl)phenyl)(4-methyl-1-(3-methylpyridin-2-yl)-6,7-dihydro-1H-[1,2,3]triazolo[4,5-c]pyridin-5(4H)-yl)methanone
(2-chloro-3-(trifluoromethyl)phenyl)(4-methyl-1-(3-propoxypyridin-2-yl)-6,7-dihydro-1H-[1,2,3]triazolo[4,5-c]pyridin-5(4H)-yl)methanone
(R)-(2-chloro-3-(trifluoromethyl)phenyl)(1-(4-ethylpyrimidin-2-yl)-4-methyl-6,7-dihydro-1H-[1,2,3]triazolo[4,5-c]pyridin-5(4H)-yl)methanone
(1-(3-ethylpyridin-2-yl)-4-methyl-6,7-dihydro-1H-[1,2,3]triazolo[4,5-c]pyridin-5(4H)-yl)(3-(trifluoromethyl)phenyl)methanone
(2-chloro-3-(trifluoromethyl)phenyl)((4R,6R)-4,6-dimethyl-1-(1H-pyrazol-5-yl)-6,7-dihydro-1H-[1,2,3]triazolo[4,5-c]pyridin-5(4H)-yl)methanone
(2-chloro-3-(trifluoromethyl)phenyl)((4S,6R)-4,6-dimethyl-1-(1H-pyrazol-5-yl)-6,7-dihydro-1H-[1,2,3]triazolo[4,5-c]pyridin-5(4H)-yl)methanone
(2-chloro-3-(trifluoromethyl)phenyl)(4,6-dimethyl-1-(1H-pyrazol-5-yl)-6,7-dihydro-1H-[1,2,3]triazolo[4,5-c]pyridin-5(4H)-yl)methanone
(2-chloro-3-(trifluoromethyl)phenyl)(4-methyl-1-(4-methylpyridin-2-yl)-6,7-dihydro-1H-[1,2,3]triazolo[4,5-c]pyridin-5(4H)-yl)methanone
(2-chloro-3-(trifluoromethyl)phenyl)(1-(4,6-dimethylpyridin-2-yl)-4-methyl-6,7-dihydro-1H-[1,2,3]triazolo[4,5-c]pyridin-5(4H)-yl)methanone
(2-chloro-3-(trifluoromethyl)phenyl)(4-methyl-1-(5-methylpyridin-2-yl)-6,7-dihydro-1H-[1,2,3]triazolo[4,5-c]pyridin-5(4H)-yl)methanone
(2-chloro-3-(trifluoromethyl)phenyl)(4-methyl-1-(6-methylpyridin-2-yl)-6,7-dihydro-1H-[1,2,3]triazolo[4,5-c]pyridin-5(4H)-yl)methanone
(2-chloro-3-(trifluoromethyl)phenyl)(3-(5-fluoropyrimidin-2-yl)-7-methyl-2-((2-(trimethylsilyl)ethoxy)methyl)-4,5-dihydro-2H-pyrazolo[3,4-c]pyridin-6(7H)-yl)methanone
(S)-(1-(5-fluoropyrimidin-2-yl)-6-methyl-6,7-dihydro-1H-[1,2,3]triazolo[4,5-c]pyridin-5(4H)-yl)(3-(trifluoromethyl)phenyl)methanone
(R)-(2-chloro-3-(trifluoromethyl)phenyl)(1-(5-fluoro-4-methylpyrimidin-2-yl)-4-methyl-6,7-dihydro-1H-[1,2,3]triazolo[4,5-c]pyridin-5(4H)-yl)methanone
(S)-(2-chloro-3-(trifluoromethyl)phenyl)(1-(5-fluoro-4-methylpyrimidin-2-yl)-4-methyl-6,7-dihydro-1H-[1,2,3]triazolo[4,5-c]pyridin-5(4H)-yl)methanone
(S)-(3-fluoro-5-(trifluoromethyl)phenyl)(1-(5-fluoropyrimidin-2-yl)-6-methyl-6,7-dihydro-1H-[1,2,3]triazolo[4,5-c]pyridin-5(4H)-yl)methanone
(2-chloro-3-(trifluoromethyl)phenyl)(7-methyl-3-(trifluoromethyl)-4,5-dihydro-1H-pyrazolo[3,4-c]pyridin-6(7H)-yl)methanone
(2-chloro-3-(trifluoromethyl)phenyl)((4S,6R)-4,6-dimethyl-1-(1H-pyrazol-5-yl)-6,7-dihydro-1H-[1,2,3]triazolo[4,5-c]pyridin-5(4H)-yl)methanone
(2-chloro-3-(trifluoromethyl)phenyl)((4R,6S)-4,6-dimethyl-1-(1H-pyrazol-5-yl)-6,7-dihydro-1H-[1,2,3]triazolo[4,5-c]pyridin-5(4H)-yl)methanone
(2-fluoro-3-(trifluoromethyl)phenyl)(1-(5-fluoropyrimidin-2-yl)-6-methyl-6,7-dihydro-1H-[1,2,3]triazolo[4,5-c]pyridin-5(4H)-yl)methanone
(1-(5-fluoropyridin-2-yl)-6,7-dihydro-1H-imidazo[4,5-c]pyridin-5(4H)-yl)(2-methyl-3-(trifluoromethyl)phenyl)methanone
(2,4-dichlorophenyl)(1-(5-fluoropyridin-2-yl)-6,7-dihydro-1H-imidazo[4,5-c]pyridin-5(4H)-yl)methanone
(2-fluoro-3-(trifluoromethyl)phenyl)(1-(5-fluoropyridin-2-yl)-6,7-dihydro-1H-imidazo[4,5-c]pyridin-5(4H)-yl)methanone
(2-chloro-3-(trifluoromethyl)phenyl)(1-(5-fluoropyridin-2-yl)-6,7-dihydro-1H-imidazo[4,5-c]pyridin-5(4H)-yl)methanone
(R)-(2-chloro-3-(trifluoromethyl)phenyl)(1-(3-ethoxypyridin-2-yl)-4-methyl-6,7-dihydro-1H-[1,2,3]triazolo[4,5-c]pyridin-5(4H)-yl)methanone
(S)-(2-chloro-3-(trifluoromethyl)phenyl)(1-(3-ethoxypyridin-2-yl)-4-methyl-6,7-dihydro-1H-[1,2,3]triazolo[4,5-c]pyridin-5(4H)-yl)methanone
(S)-(2-chloro-3-(trifluoromethyl)phenyl)(1-(1-(2-hydroxyethyl)-1H-pyrazol-3-yl)-4-methyl-6,7-dihydro-1H-[1,2,3]triazolo[4,5-c]pyridin-5(4H)-yl)methanone
(2-chloro-3-(trifluoromethyl)phenyl)((4S,6S)-4,6-dimethyl-1-(1H-pyrazol-5-yl)-6,7-dihydro-1H-[1,2,3]triazolo[4,5-c]pyridin-5(4H)-yl)methanone
(2-chloro-3-(trifluoromethyl)phenyl)((4R,6R)-4,6-dimethyl-1-(1H-pyrazol-5-yl)-6,7-dihydro-1H-[1,2,3]triazolo[4,5-c]pyridin-5(4H)-yl)methanone
(2-chloro-3-(trifluoromethyl)phenyl)(1-(5-fluoropyridin-2-yl)-4-methyl-1H-imidazo[4,5-c]pyridin-5(4H)-yl)methanone
322: (3-phenyl-4,5-dihydro-1H-pyrazolo[3,4-c]pyridin-6(7H)-yl)(2-(trifluoromethyl)pyridin-3-yl)methanone
(2-chloro-4-fluorophenyl)(3-phenyl-4,5-dihydro-1H-pyrazolo[3,4-c]pyridin-6(7H)-yl)methanone
(2,6-dichlorophenyl)(3-phenyl-4,5-dihydro-1H-pyrazolo[3,4-c]pyridin-6(7H)-yl)methanone
(2-chloro-6-fluorophenyl)(3-phenyl-4,5-dihydro-1H-pyrazolo[3,4-c]pyridin-6(7H)-yl)methanone
(2,3-dichlorophenyl)(3-(4-fluorophenyl)-2-methyl-4,5-dihydro-2H-pyrazolo[3,4-c]pyridin-6(7H)-yl)methanone
(2-chloro-3-(trifluoromethyl)phenyl)(2-methyl-3-(pyridin-4-yl)-4,5-dihydro-2H-pyrazolo[3,4-c]pyridin-6(7H)-yl)methanone
(2,3-dichlorophenyl)(2-methyl-3-(pyridin-4-yl)-4,5-dihydro-2H-pyrazolo[3,4-c]pyridin-6(7H)-yl)methanone
(2,3-dichlorophenyl)(2-methyl-3-(pyrimidin-5-yl)-4,5-dihydro-2H-pyrazolo[3,4-c]pyridin-6(7H)-yl)methanone
(2,3-dichlorophenyl)(3-(pyrimidin-5-yl)-4,5-dihydro-2H-pyrazolo[3,4-c]pyridin-6(7H)-yl)methanone
(2,3-dichlorophenyl)(2-methyl-1-phenyl-6,7-dihydro-1H-imidazo[4,5-c]pyridin-5(4H)-yl)methanone
(2,3-dichlorophenyl)(2-ethyl-1-phenyl-6,7-dihydro-1H-imidazo[4,5-c]pyridin-5(4H)-yl)methanone
(S)-(2-chloro-3-(trifluoromethyl)phenyl)(4-methyl-1-(pyrimidin-5-yl)-6,7-dihydro-1H-[1,2,3]triazolo[4,5-c]pyridin-5(4H)-yl)methanone
(R)-(2-chloro-3-(trifluoromethyl)phenyl)(4-methyl-1-(pyrimidin-5-yl)-6,7-dihydro-1H-[1,2,3]triazolo[4,5-c]pyridin-5(4H)-yl)methanone
(2,3-dichlorophenyl)(8-methyl-3-(pyrazin-2-yl)-5,6-dihydroimidazo[1,2-a]pyrazin-7(8H)-yl)methanone
(2,3-dichlorophenyl)(4-methyl-1-(5-methylpyridin-2-yl)-6,7-dihydro-1H-[1,2,3]triazolo[4,5-c]pyridin-5(4H)-yl)methanone
(R*)-(3-chloro-4-(trifluoromethyl)pyridin-2-yl)(1-(5-fluoropyrimidin-2-yl)-4-methyl-6,7-dihydro-1H-[1,2,3]triazolo[4,5-c]pyridin-5(4H)-yl)methanone
(R*)-(4-chloro-5-(trifluoromethyl)pyridin-3-yl)(1-(5-fluoropyrimidin-2-yl)-4-methyl-6,7-dihydro-1H-[1,2,3]triazolo[4,5-c]pyridin-5(4H)-yl)methanone
(R*)-(3-chloro-2-(trifluoromethyl)pyridin-4-yl)(1-(5-fluoropyrimidin-2-yl)-4-methyl-6,7-dihydro-1H-[1,2,3]triazolo[4,5-c]pyridin-5(4H)-yl)methanone
(R*)-(3-chloro-4-(trifluoromethyl)pyridin-2-yl)(4-methyl-1-(pyrazin-2-yl)-6,7-dihydro-1H-[1,2,3]triazolo[4,5-c]pyridin-5(4H)-yl)methanone
(R*)-(4-chloro-5-(trifluoromethyl)pyridin-3-yl)(4-methyl-1-(pyrazin-2-yl)-6,7-dihydro-1H-[1,2,3]triazolo[4,5-c]pyridin-5(4H)-yl)methanone
(R*)-(3-chloro-2-(trifluoromethyl)pyridin-4-yl)(4-methyl-1-(pyrazin-2-yl)-6,7-dihydro-1H-[1,2,3]triazolo[4,5-c]pyridin-5(4H)-yl)methanone An additional embodiment of the invention is a pharmaceutical composition, comprising:

(a) a therapeutically effective amount of at least one compound selected from compounds Formula I:

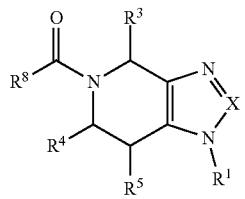

Formula (I)

wherein;
R¹ is (a) phenyl, optionally substituted with zero to four groups selected from the group consisting of: halo, $C_1$-$C_4$alkyl, alkoxy, perhaloalkyl and perhaloalkoxy; or
(b) heteroaryl, selected from the group consisting of:

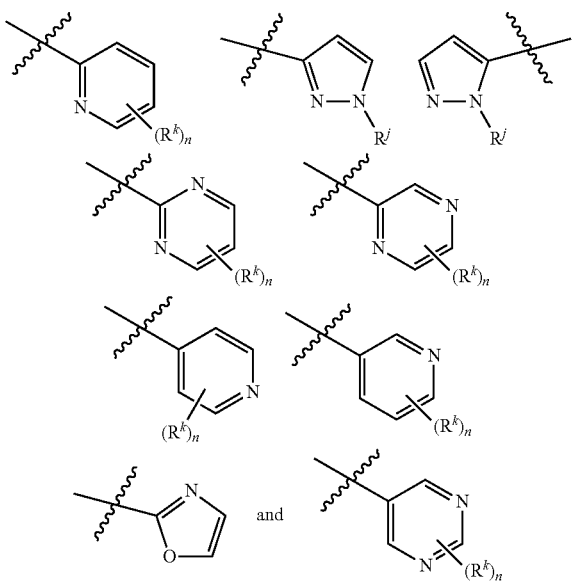

wherein $R^k$ is selected from the group consisting of: H, halo, $C_1$-$C_3$alkyl and alkoxy;
$R^j$ is selected from the group consisting of: H, $C_1$-$C_3$alkyl optionally substituted with halo, OH and alkoxy; and
n is an integer from 0-3;
X is N or $CR^2$;
$R^2$ is H, perhaloalkyl or $C_1$-$C_3$ lower alkyl;
$R^3$ is H, perhaloalkyl, $C_1$-$C_4$ alkyl, alkalkoxy, $CH_2R$, $-C(O)R^e$ or phenyl, optionally substituted with zero to two groups selected from:
halo, $C_1$-$C_3$alkyl, alkoxy, perhaloalkyl and perhaloalkoxy;
$R^i$ is OH, $OC_1$-$C_3$ alkyl, $NC_3H_6$, $N(C_1$-$C_3$alkyl$)_2$ or halo;
$R^e$ is OH, $OC_1$-$C_3$ alkyl, $N(C_1$-$C_3$alkyl$)_2$, $NC_3H_6$;
$R^4$ and $R^5$ are independently H or $C_1$-$C_3$ alkyl; and
$R^8$ is phenyl or pyridyl, optionally substituted with zero to four $R^m$ substituents wherein $R^m$ is selected from the group consisting of: halo, $C_1$-$C_3$alkyl, alkoxy, perhaloalkyl and perhaloalkoxy; or $R^8$ is selected from the group consisting of:

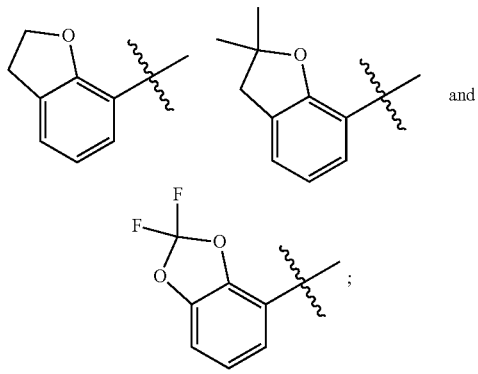

and
pharmaceutically acceptable salts of compounds of Formula (I); and
(b) at least one pharmaceutically acceptable excipient.

An additional embodiment of the invention is a pharmaceutical composition, comprising:
(a) a therapeutically effective amount of at least one compound selected from compounds of Formula (IIa and IIb):

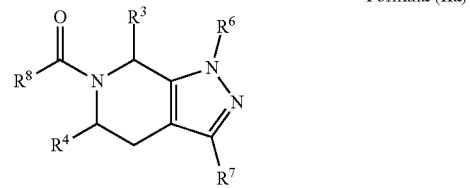

Formula (IIa)

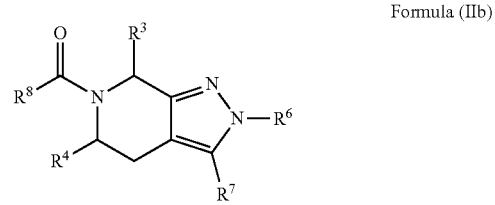

Formula (IIb)

wherein:
$R^3$, $R^4$ and $R^6$ are independently H or $C_1$-$C_3$ alkyl;
$R^8$ is phenyl or pyridyl, optionally substituted with zero to three $R^m$ substituents wherein $R^m$ is selected from the group consisting of: halo, $C_1$-$C_3$alkyl and perhaloalkyl;
$R^7$ is (a) phenyl, optionally substituted with zero to two groups selected from halo or $C_1$-$C_3$alkyl; or
(b) heteroaryl, selected from the group consisting of:

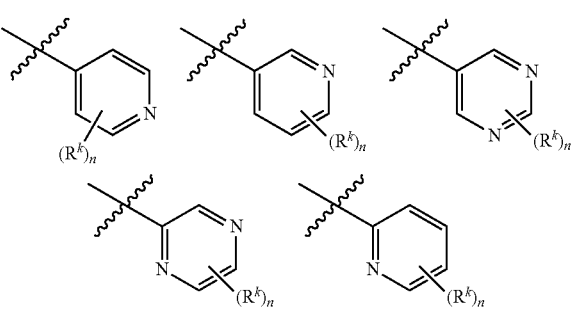

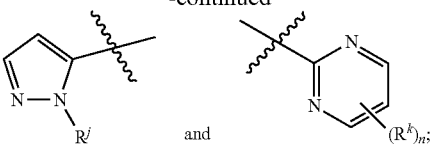

wherein $R^k$ is selected from halo or $C_1$-$C_3$alkyl;
$R^j$ is selected from H or $C_1$-$C_3$alkyl wherein $C_1$-$C_3$alkyl is optionally substituted with halo or alkoxy;
n is an integer from 0-3; and
pharmaceutically acceptable salts of compounds of Formula (IIa and IIb); and
(b) at least one pharmaceutically acceptable excipient.

An additional embodiment of the invention is a pharmaceutical composition comprising a therapeutically effective amount of at least one compound in Table 1 and at least one pharmaceutically acceptable excipient.

An additional embodiment of the invention is a method of treating a subject suffering from or diagnosed with a disease, disorder, or medical condition mediated by P2X7 receptor activity, comprising administering to a subject in need of such treatment a therapeutically effective amount of at least one compound selected from compounds of Formula (I):

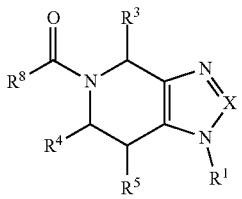

Formula (I)

wherein:
$R^1$ is (a) phenyl, optionally substituted with zero to four groups selected from the group consisting of: halo, $C_1$-$C_4$alkyl, alkoxy, perhaloalkyl and perhaloalkoxy; or
(b) heteroaryl, selected from the group consisting of:

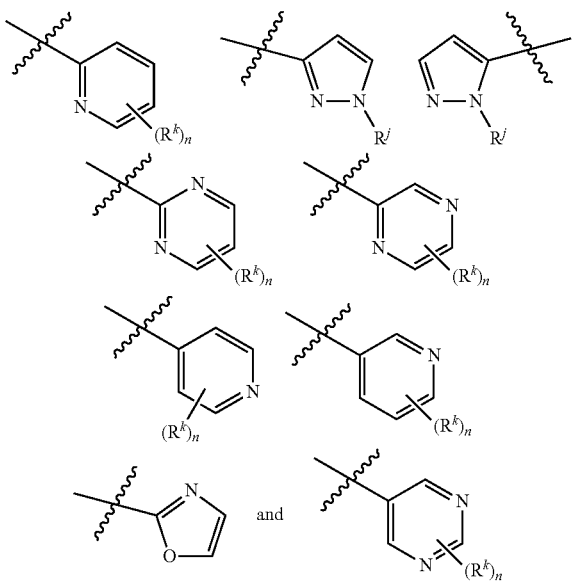

wherein $R^k$ is selected from the group consisting of: H, halo, $C_1$-$C_3$alkyl and alkoxy;
$R^j$ is selected from the group consisting of: H, $C_1$-$C_3$alkyl optionally substituted with halo, OH and alkoxy; and
n is 0-3;
X is N or $CR^2$;
$R^2$ is H, perhaloalkyl or $C_1$-$C_3$ lower alkyl;
$R^3$ is H, perhaloalkyl, $C_1$-$C_4$ alkyl, alkalkoxy, $CH_2R$, —C(O)$R^e$ or phenyl, optionally substituted with zero to two groups selected from the group consisting of: halo, $C_1$-$C_3$alkyl, alkoxy, perhaloalkyl and perhaloalkoxy;
$R^i$ is OH, $OC_1$-$C_3$ alkyl, $NC_3H_6$, $N(C_1$-$C_3$alkyl$)_2$ or halo;
$R^e$ is OH, $OC_1$-$C_3$ alkyl, $N(C_1$-$C_3$alkyl$)_2$, or $NC_3H_6$;
$R^4$ and $R^5$ are independently H or $C_1$-$C_3$ alkyl; and
$R^8$ is phenyl or pyridyl, optionally substituted with zero to four $R^m$ substituents wherein $R^m$ is selected from the group consisting of: halo, $C_1$-$C_3$alkyl, alkoxy, perhaloalkyl and perhaloalkoxy; or
$R^8$ is selected from the group consisting of

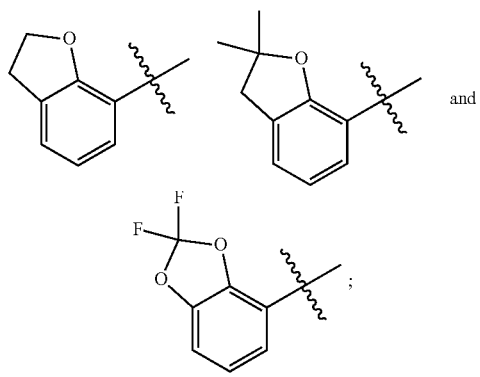

and
pharmaceutically acceptable salts of compounds of Formula (I)

An additional embodiment of the invention is a method of treating a subject suffering from or diagnosed with a disease, disorder, or medical condition mediated by P2X7 receptor activity, comprising administering to a subject in need of such treatment a therapeutically effective amount of at least one compound selected from compounds of Formula (IIa and IIb):

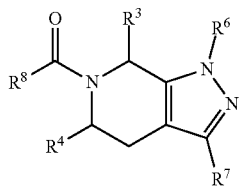

Formula (IIa)

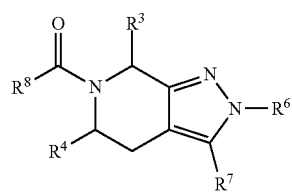

Formula (IIb)

wherein:

$R^3$, $R^4$ and $R^6$ are independently H or $C_1$-$C_3$ alkyl;

$R^8$ is phenyl or pyridyl, optionally substituted with zero to three $R^m$ substituents wherein $R^m$ is selected from the group consisting of: halo, $C_1$-$C_3$alkyl and perhaloalkyl;

$R^7$ is (a) phenyl, optionally substituted with zero to two groups selected from halo or $C_1$-$C_3$alkyl; or (b) heteroaryl, selected from the group consisting of:

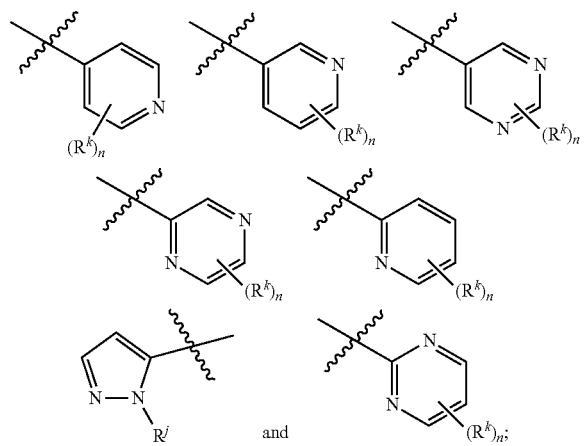

wherein $R^k$ is selected from: halo or $C_1$-$C_3$alkyl;

$R^j$ is selected from H or $C_1$-$C_3$alkyl wherein $C_1$-$C_3$alkyl is optionally substituted with halo or alkoxy; and n is an integer from 0-3; and pharmaceutically acceptable salts of compounds of Formula (IIa and IIb).

In preferred embodiments of the inventive method, the disease, disorder, or medical condition is selected from: diseases of the autoimmune and inflammatory system such as: rheumatoid arthritis, osteoarthritis, psoriasis, septic shock, allergic dermatitis, asthma, allergic asthma, mild to severe asthma, steroid resistant asthma, idiopathic pulmonary fibrosis, allergic rhinitis, chronic obstructive pulmonary disease and airway hyper-responsiveness; diseases of the nervous and neuro-immune system such as acute and chronic pain states of neuropathic pain, inflammatory pain, spontaneous pain (diabetic neuropathy, postherpetic neuralgia, low back pain, chemotherapy-induced neuropathic pain, fibromyalgia) (Romagnoli, R, et. al., *Expert Opin. Ther. Targets*, 2008, 12(5), 647-661), and diseases involved with and without neuroinflammation of the CNS such as mood disorders (major depression, major depressive disorder, treatment resistant depression, bipolar disorder, anxious depression, anxiety) (Friedle, S A, et. al., *Recent Patents on CNS Drug Discovery*, 2010, 5, 35-45, Romagnoli, R, et. al., *Expert Opin. Ther. Targets*, 2008, 12(5), 647-661), cognition, sleep disorders, multiple sclerosis (Sharp A J, et. al., J Neuroinflammation. 2008 Aug. 8; 5:33, Oyanguren-Desez O, et. al., *Cell Calcium*. 2011 November; 50(5):468-72, Grygorowicz T, et. al., *Neurochem Int*. 2010 December; 57(7):823-9), epileptic seizures (Engel T, et. al., *FASEB J.* 2012 April; 26(4):1616-28, Kim J E, et. al. *Neurol Res*. 2009 November; 31(9):982-8, Avignone E, et. al., *J Neurosci.* 2008 Sep. 10; 28(37):9133-44), Parkinson's disease (Marcellino D, et. al., *J Neural Transm.* 2010 June; 117(6):681-7), schizophrenia, Alzheimer's disease (Diaz-Hernandez J I, et. al., *Neurobiol Aging.* 2012 August; 33(8):1816-28, Delarasse C, *J Biol Chem.* 2011 Jan. 28; 286(4):2596-606, Sanz J M, et. al., *J Immunol.* 2009 Apr. 1; 182(7):4378-85), Huntington's disease (Diaz-Hernández M, et. Al., *FASEB J.* 2009 June; 23(6):1893-906), autism, spinal cord injury and cerebral ischemia/traumatic brain injury (Chu K, et. al., *J Neuroinflammation.* 2012 Apr. 18; 9:69, Arbeloa J, et. al, *Neurobiol Dis.* 2012 March; 45(3):954-61).

P2X7 antagonism may also be beneficial in several stress-related disorders. In addition, P2X7 intervention may be beneficial in diseases of the cardiovascular, metabolic, gastrointestinal and urogenital systems such as diabetes (*Arterioscler Thromb Vasc Biol.* 2004 July; 24(7):1240-5), thrombosis (Furlan-Freguia C, et. al., *J Clin Invest.* 2011 July; 121(7):2932-44), irritable bowel syndrome, Crohn's disease, ischemic heart disease, hypertension (Ji X, et. al., *Am J Physiol Renal Physiol.* 2012 October; 303(8):F1207-15), myocardial infarction, and lower urinary tract dysfunction such as incontinence. P2X7 antagonism may also present a novel therapeutic strategy for skeletal disorders, namely osteoporosis/osteopetrosis and may also modulate secretory function of exocrine glands. It is also hypothesized that blocking P2X7 may also be beneficial in glaucoma, interstitial cystitis (Martins J P, et. al., *Br J Pharmacol.* 2012 January; 165(1):183-96) and lower urinary tract syndrome (*Br J Pharmacol.* 2012 January; 165(1):183-96), IBD/IBS (*J Immunol.* 2011 Aug. 1; 187(3):1467-74. Epub 2011 Jun. 22), Sleep, RA/OA, Cough/COPD/asthma, cardiovascular disease, GN, ureteric obstruction, diabetes mellitus, hypertension, sepsis, ischaemia, Amyotrophic Lateral Sclerosis, Chaga's Disease, Chlamydia, Neuroblastoma, Tuberculosis, Polycystic Kidney Disease, and migraine.

An additional embodiment of the invention is a method of treating a subject suffering from or diagnosed with a disease, disorder, or medical condition mediated by P2X7 receptor activity, wherein the disease, disorder, or medical condition is selected from the group consisting of: rheumatoid arthritis, osteoarthritis, psoriasis, septic shock, allergic dermatitis, asthma, allergic asthma, mild to severe asthma, steroid resistant asthma, idiopathic pulmonary fibrosis, allergic rhinitis, chronic obstructive pulmonary disease and airway hyper-responsiveness; diseases of the nervous and neuro-immune system such as acute and chronic pain states of neuropathic pain, inflammatory pain, spontaneous pain (diabetic neuropathy, postherpetic neuralgia, low back pain, chemotherapy-induced neuropathic pain, fibromyalgia); diseases involved with and without neuroinflammation of the central nervous system such as mood disorders (major depression, major depressive disorder, treatment resistant depression, bipolar disorder, anxious depression, anxiety), cognition, sleep disorders, multiple sclerosis, epileptic seizures, Parkinson's disease, schizophrenia, Alzheimer's disease, Huntington's disease, autism, spinal cord injury and cerebral ischemia/traumatic brain injury, stress-related disorders; diseases of the cardiovascular, metabolic, gastrointestinal and urogenital systems such as diabetes, diabetes mellitus, thrombosis, irritable bowel syndrome, irritable bowel syndrome, Crohn's disease, ischemic heart disease, ischaemia, hypertension, cardiovascular disease, myocardial infarction, and lower urinary tract dysfunction such as incontinence, lower urinary tract syndrome, Polycystic Kidney Disease, Glomerulonephritis, skeletal disorders, namely osteoporosis/osteopetrosis: and glaucoma, interstitial cystitis, cough, ureteric obstruction, sepsis, Amyotrophic Lateral Sclerosis, Chaga's Disease, chlamydia, neuroblastoma, Tuberculosis, and migraine.

An additional embodiment of the invention is a method of treating a subject suffering from or diagnosed with a disease, disorder, or medical condition mediated by P2X7 receptor activity wherein the disease, disorder or medical condition is treatment resistant depression.

Additional embodiments, features, and advantages of the invention will be apparent from the following detailed description and through practice of the invention.

The invention may be more fully appreciated by reference to the following description, including the following glossary of terms and the concluding examples.

For the sake of brevity, the disclosures of the publications, including patents, cited in this specification are herein incorporated by reference.

As used herein, the terms "including", "containing" and "comprising" are used herein in their open, non-limiting sense.

The term "alkyl" refers to a straight- or branched-chain alkyl group having from 1 to 12 carbon atoms in the chain. Examples of alkyl groups include methyl (Me, which also may be structurally depicted by the symbol, "/"), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples. The term $C_1$-$C_3$ alkyl as used here refers to a straight- or branched-chain alkyl group having from 1 to 3 carbon atoms in the chain. The term $C_1$-$C_4$ alkyl as used here refers to a straight- or branched-chain alkyl group having from 1 to 4 carbon atoms in the chain.

The term "alkoxy" includes a straight chain or branched alkyl group with a terminal oxygen linking the alkyl group to the rest of the molecule. Alkoxy includes methoxy, ethoxy, propoxy, isopropoxy, butoxy, t-butoxy, pentoxy and so on.

The term "alkalkoxy" refers to the group alkyl-O-alkyl, where alkyl is defined above. Such groups include methylenemethoxy (—CH$_2$OCH$_3$) and ethylenemethoxy (—CH$_2$CH$_2$OCH$_3$).

The term "cycloalkyl" refers to a saturated carbocycle having from 3 to 6 ring atoms per carbocycle. Illustrative examples of cycloalkyl groups include the following entities, in the form of properly bonded moieties:

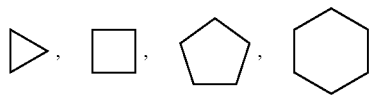

The term "$C_3$-$C_4$ cycloalkyl" as used here refers to a saturated carbocycle having from 3 to 4 ring atoms.

A "heterocycloalkyl" refers to a monocyclic ring structure that is saturated and has from 4 to 6 ring atoms per ring structure selected from carbon atoms and one nitrogen atom. Illustrative entities, in the form of properly bonded moieties, include:

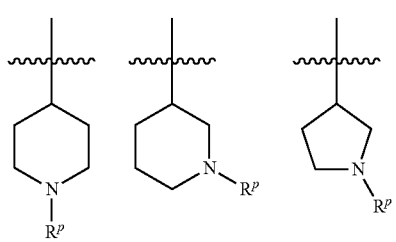

The term "aryl" refers to a monocyclic, aromatic carbocycle (ring structure having ring atoms that are all carbon) having 6 atoms per ring. (Carbon atoms in the aryl groups are sp$^2$ hybridized.)

The term "phenyl" represents the following moiety:

The term "heteroaryl" refers to a monocyclic or fused bicyclic heterocycle (ring structure having ring atoms selected from carbon atoms and up to four heteroatoms selected from nitrogen, oxygen, and sulfur) having from 3 to 9 ring atoms per heterocycle. Illustrative examples of heteroaryl groups include the following entities in the form of properly bonded moieties:

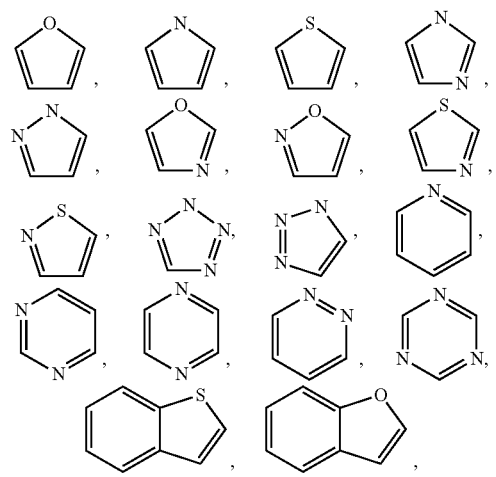

Those skilled in the art will recognize that the species of heteroaryl, cycloalkyl, aryl and heterocycloalkyl groups listed or illustrated above are not exhaustive, and that additional species within the scope of these defined terms may also be selected.

The term "cyano" refers to the group —CN.

The term "halo" represents chloro, fluoro, bromo or iodo.

The term "perhaloalkyl" refers to a straight- or branched-chain alkyl group having from 1 to 4 carbon atoms in the chain optionally substituting hydrogens with halogens. Examples of perhaloalkyl groups include trifluoromethyl (CF$_3$), difluoromethyl (CF$_2$H), monofluoromethyl (CH$_2$F), pentafluoroethyl (CF$_2$CF$_3$), tetrafluoroethyl (CHFCF$_3$), monofluoroethyl (CH$_2$CH$_2$F), trifluoroethyl (CH$_2$CF$_3$), tetrafluorotrifluoromethylethyl (—CF(CF$_3$)$_2$), and groups that in light of the ordinary skill in the art and the teachings provided herein would be considered equivalent to any one of the foregoing examples.

The term "perhaloalkoxy" refers to a straight- or branched-chain alkoxy group having from 1 to 4 carbon atoms in the chain optionally substituting hydrogens with halogens. Examples of perhaloalkoxy groups include trifluoromethoxy (OCF$_3$), difluoromethoxy (OCF$_2$H), monofluoromethoxy (OCH$_2$F), momofluoroethoxy (OCH$_2$CH$_2$F), pentafluoroethoxy (OCF$_2$CF$_3$), tetrafluoroethoxy (OCHFCF$_3$), trifluoroethoxy (OCH$_2$CF$_3$), tetrafluorotrifluoromethylethoxy (—OCF(CF$_3$)$_2$), and groups that in light of the ordinary skill in the art and the teachings provided herein would be considered equivalent to any one of the foregoing examples.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system. In cases where a specified moiety or group is not expressly noted as being optionally substituted or substituted with any specified substituent, it is understood that such a moiety or group is intended to be unsubstituted.

The terms "para", "meta", and "ortho" have the meanings as understood in the art. Thus, for example, a fully substituted phenyl group has substituents at both "ortho" (o) positions adjacent to the point of attachment of the phenyl ring, both "meta" (m) positions, and the one "para" (p) position across from the point of attachment. To further clarify the position of substituents on the phenyl ring, the 2 different ortho positions will be designated as ortho and ortho' and the 2 different meta positions as meta and meta' as illustrated below.

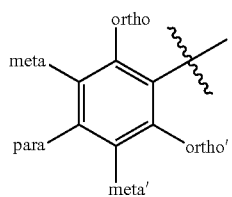

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

The terms "buffered" solution or "buffer" solution are used herein interchangeably according to their standard meaning. Buffered solutions are used to control the pH of a medium, and their choice, use, and function is known to those of ordinary skill in the art. See, for example, G. D. Considine, ed., Van Nostrand's Encyclopedia of Chemistry, p. 261, $5^{th}$ ed. (2005), describing, inter alia, buffer solutions and how the concentrations of the buffer constituents relate to the pH of the buffer. For example, a buffered solution is obtained by adding $MgSO_4$ and $NaHCO_3$ to a solution in a 10:1 w/w ratio to maintain the pH of the solution at about 7.5.

Any formula given herein is intended to represent compounds having structures depicted by the structural formula as well as certain variations or forms. In particular, compounds of any formula given herein may have asymmetric centers and therefore exist in different enantiomeric forms. All optical isomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers, or as atropisomers.

It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers."

Stereoisomers that are not mirror images of one another are termed "diastereomers" and those that are non-superimposable mirror images of each other are termed "enantiomers." When a compound has an asymmetric center, for example, it is bonded to four different groups, and a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture."

"Tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenyl nitromethane, that are likewise formed by treatment with acid or base.

Tautomeric forms may be relevant to the attainment of the optimal chemical reactivity and biological activity of a compound of interest.

Compounds of the invention may also exist as "rotamers," that is, conformational isomers that occur when the rotation leading to different conformations is hindered, resulting a rotational energy barrier to be overcome to convert from one conformational isomer to another.

The compounds of this invention may possess one or more asymmetric centers; such compounds can therefore be produced as individual (R)- or (S)-stereoisomers or as mixtures thereof.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

Certain examples contain chemical structures that are depicted as an absolute enantiomer but are intended to indicate enatiopure material that is of unknown configuration. In these cases (R*) or (S*) is used in the name to indicate that the absolute stereochemistry of the corresponding stereocenter is unknown. Thus, a compound designated as (R*) refers to an enantiopure compound with an absolute configuration of either (R) or (S). In cases where the absolute stereochemistry has been confirmed, the structures are named using (R) and (S).

The symbols ▬ and ◄▬ are used as meaning the same spatial arrangement in chemical structures shown herein. Analogously, the symbols ⦀⦀⦀ and ┅┅┅ are used as meaning the same spatial arrangement in chemical structures shown herein.

Additionally, any formula given herein is intended to refer also to hydrates, solvates, and polymorphs of such compounds, and mixtures thereof, even if such forms are not listed explicitly. Certain compounds of Formula (I, IIa and IIb) or pharmaceutically acceptable salts of compounds of Formula (I, IIa and IIb) may be obtained as solvates. Solvates include those formed from the interaction or complexation of compounds of the invention with one or more solvents, either in solution or as a solid or crystalline form. In some embodiments, the solvent is water and then the solvates are hydrates. In addition, certain crystalline forms of compounds of Formula (I, IIa and IIb) or pharmaceutically acceptable salts of compounds of Formula (I, IIa and IIb) may be obtained as co-crystals. In certain embodiments of the invention, compounds of Formula (I, IIa and IIb) were obtained in a crystalline form. In other embodiments, crystalline forms of compounds of Formula (I, IIa and IIb) were cubic in nature. In other embodiments, pharmaceutically acceptable salts of compounds of Formula (I, IIa and IIb) were obtained in a crystalline form. In still other embodiments, compounds of Formula (I, IIa and IIb) were obtained in one of several polymorphic forms, as a mixture of crystalline forms, as a polymorphic form, or as an amorphous form. In other embodiments, compounds of Formula (I, IIa and IIb) convert in solution between one or more crystalline forms and/or polymorphic forms.

Reference to a compound herein stands for a reference to any one of: (a) the actually recited form of such compound, and (b) any of the forms of such compound in the medium in which the compound is being considered when named. For example, reference herein to a compound such as R—COOH, encompasses reference to any one of, for example, R—COOH$_{(s)}$, R—COOH$_{(sol)}$, and R—COO$^-_{(sol)}$. In this example, R—COOH$_{(s)}$ refers to the solid compound, as it could be for example in a tablet or some other solid pharmaceutical composition or preparation; R—COOH$_{(sol)}$ refers to the undissociated form of the compound in a solvent; and R—COO$^-_{(sol)}$ refers to the dissociated form of the compound in a solvent, such as the dissociated form of the compound in an aqueous environment, whether such dissociated form derives from R—COOH, from a salt thereof, or from any other entity that yields R—COO$^-$ upon dissociation in the medium being considered. In another example, an expression such as "exposing an entity to compound of formula R—COOH" refers to the exposure of such entity to the form, or forms, of the compound R—COOH that exists, or exist, in the medium in which such exposure takes place. In still another example, an expression such as "reacting an entity with a compound of formula R—COOH" refers to the reacting of (a) such entity in the chemically relevant form, or forms, of such entity that exists, or exist, in the medium in which such reacting takes place, with (b) the chemically relevant form, or forms, of the compound R—COOH that exists, or exist, in the medium in which such reacting takes place. In this regard, if such entity is for example in an aqueous environment, it is understood that the compound R—OOH is in such same medium, and therefore the entity is being exposed to species such as R—COOH$_{(aq)}$ and/or R—COO$^-_{(aq)}$, where the subscript "(aq)" stands for "aqueous" according to its conventional meaning in chemistry and biochemistry. A carboxylic acid functional group has been chosen in these nomenclature examples; this choice is not intended, however, as a limitation but it is merely an illustration. It is understood that analogous examples can be provided in terms of other functional groups, including but not limited to hydroxyl, basic nitrogen members, such as those in amines, and any other group that interacts or transforms according to known manners in the medium that contains the compound. Such interactions and transformations include, but are not limited to, dissociation, association, tautomerism, solvolysis, including hydrolysis, solvation, including hydration, protonation, and deprotonation. No further examples in this regard are provided herein because these interactions and transformations in a given medium are known by any one of ordinary skill in the art.

In another example, a zwitterionic compound is encompassed herein by referring to a compound that is known to form a zwitterion, even if it is not explicitly named in its zwitterionic form. Terms such as zwitterion, zwitterions, and their synonyms zwitterionic compound(s) are standard IUPAC-endorsed names that are well known and part of standard sets of defined scientific names. In this regard, the name zwitterion is assigned the name identification CHEBI: 27369 by the Chemical Entities of Biological Interest (ChEBI) dictionary of molecular entities. As generally well known, a zwitterion or zwitterionic compound is a neutral compound that has formal unit charges of opposite sign. Sometimes these compounds are referred to by the term "inner salts". Other sources refer to these compounds as "dipolar ions", although the latter term is regarded by still other sources as a misnomer. As a specific example, aminoethanoic acid (the amino acid glycine) has the formula H$_2$NCH$_2$COOH, and it exists in some media (in this case in neutral media) in the form of the zwitterion $^+$H$_3$NCH$_2$COO$^-$. Zwitterions, zwitterionic compounds, inner salts and dipolar ions in the known and well established meanings of these terms are within the scope of this invention, as would in any case be so appreciated by those of ordinary skill in the art. Because there is no need to name each and every embodiment that would be recognized by those of ordinary skill in the art, no structures of the zwitterionic compounds that are associated with the compounds of this invention are given explicitly herein. They are, however, part of the embodiments of this invention. No further examples in this regard are provided herein because the interactions and transformations in a given medium that lead to the various forms of a given compound are known by any one of ordinary skill in the art.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorus, fluorine, and chlorine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F, $^{36}$Cl, $^{125}$I, respectively. Such isotopically labeled compounds are useful in metabolic studies (preferably with $^{14}$C), reaction kinetic studies (with, for example $^2$H or $^3$H), detection or imaging techniques [such as positron emission tomography (PET) or single-photon emission computed tomography (SPECT)] including drug or substrate tissue distribution assays, or in radioactive treatment of patients. In particular, an $^{18}$F or $^{11}$C labeled compound may be particularly preferred for PET or SPECT studies. Further, substitution with heavier isotopes such as deuterium (i.e., $^2$H) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the same choice of the species for the variable appearing elsewhere. In other words, where a variable appears more than once, the choice of the species from a specified list is independent of the choice of the species for the same variable elsewhere in the formula, unless stated otherwise.

According to the foregoing interpretive considerations on assignments and nomenclature, it is understood that explicit reference herein to a set implies, where chemically meaningful and unless indicated otherwise, independent reference to embodiments of such set, and reference to each and every one of the possible embodiments of subsets of the set referred to explicitly.

The invention includes also pharmaceutically acceptable salts of the compounds of Formula (I, IIa and IIb), preferably of those described above and of the specific compounds exemplified herein, and methods of treatment using such salts.

The term "pharmaceutically acceptable" means approved or approvable by a regulatory agency of Federal or a state government or the corresponding agency in countries other than the United States, or that is listed in the U. S. Pharmcopoeia or other generally recognized pharmacopoeia for use in animals, and more particularly, in humans.

A "pharmaceutically acceptable salt" is intended to mean a salt of a free acid or base of compounds represented by Formula (I, IIa and IIb) that are non-toxic, biologically tolerable, or otherwise biologically suitable for administration to the subject. It should possess the desired pharmacological activity of the parent compound. See, generally, G. S. Paulekuhn, et al., "Trends in Active Pharmaceutical Ingredient Salt Selection based on Analysis of the Orange Book Database", *J. Med. Chem.*, 2007, 50:6665-72, S. M. Berge, et al., "Pharmaceutical Salts", *J Pharm Sci.*, 1977, 66:1-19, and *Handbook of Pharmaceutical Salts, Properties, Selection, and Use*, Stahl and Wermuth, Eds., Wiley-VCH and VHCA, Zurich, 2002. Examples of pharmaceutically acceptable salts are those that are pharmacologically effective and suitable for contact with the tissues of patients without undue toxicity, irritation, or allergic response. A compound of Formula (I, IIa or IIb) may possess a sufficiently acidic group, a sufficiently basic group, or both types of functional groups, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

When the compounds of Formula (I, IIa and IIb) contain a basic nitrogen, the desired pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid, glutaric acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

The invention may be more fully appreciated by reference to the following description, including the following glossary of terms and the concluding examples. For the sake of brevity, the disclosures of the publications, including patents, cited in this specification are herein incorporated by reference.

As used herein, the terms "including", "containing" and "comprising" are used herein in their open, non-limiting sense.

is an acid, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as N-methyl-D-glucamine, lysine, choline, glycine and arginine, ammonia, carbonates, bicarbonates, primary, secondary, and tertiary amines, and cyclic amines, such as tromethamine, benzylamines, pyrrolidines, piperidine, morpholine, and piperazine, and inorganic salts derived from sodium, calcium, potassium, magnesium, manganese, iron, copper, zinc, aluminum, and lithium.

The invention also relates to pharmaceutically acceptable prodrugs of the compounds of Formula (I, IIa and IIb), and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula (I, IIa or IIb)). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "Design of Prodrugs", ed. H. Bundgaard, Elsevier, 1985.

Exemplary prodrugs include compounds having an amino acid residue, or a polypeptide chain of two or more (e.g., two, three or four) amino acid residues, covalently joined through an amide or ester bond to a free amino, hydroxy, or carboxylic acid group of a compound of Formula (I, IIa or IIb). Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs may be produced, for instance, by derivatizing free carboxyl groups of structures of Formula (I, IIa and IIb) as amides or alkyl esters. Examples of amides include those derived from ammonia, primary $C_{1-6}$alkyl amines and secondary di($C_{1-6}$alkyl) amines. Secondary amines include 5- or 6-membered heterocycloalkyl or heteroaryl ring moieties. Examples of amides include those that are derived from ammonia, $C_{1-3}$alkyl primary amines, and di($C_{1-2}$alkyl)amines. Examples of esters of the invention include $C_{1-7}$alkyl, $C_{5-7}$cycloalkyl, phenyl, and phenyl($C_{1-6}$alkyl) esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in Fleisher et al., *Adv. Drug Delivery Rev.* 1996, 19, 115-130. Carbamate derivatives of hydroxy and amino groups may also yield prodrugs. Carbonate derivatives, sulfonate esters, and sulfate esters of hydroxy groups may also provide prodrugs. Derivatization of hydroxy groups as (acyloxy)methyl and (acyloxy)ethyl ethers, wherein the acyl group may be an alkyl ester, optionally substituted with one or more ether, amine, or carboxylic acid functionalities, or where the acyl group is an amino acid ester as described above, is also useful to yield prodrugs. Prodrugs of this type may be prepared as described in Robinson et al., *J Med Chem.* 1996, 39 (1), 10-18. Free amines can also be derivatized as amides, sulfonamides or phosphonamides. All of these prodrug moieties may incorporate groups including ether, amine, and carboxylic acid functionalities.

The present invention also relates to pharmaceutically active metabolites of the compounds of Formula (I, IIa and IIb), which may also be used in the methods of the invention. A "pharmaceutically active metabolite" means a pharmacologically active product of metabolism in the body of a compound of Formula (I, IIa or IIb) or salt thereof. Prodrugs and active metabolites of a compound may be determined using routine techniques known or available in the art. See, e.g., Bertolini, et al., *J Med Chem.* 1997, 40, 2011-2016; Shan, et al., *J Pharm Sci.* 1997, 86 (7), 765-767; Bagshawe, *Drug Dev Res.* 1995, 34, 220-230; Bodor, *Adv Drug Res.* 1984, 13, 224-331; Bundgaard, *Design of Prodrugs* (Elsevier Press, 1985); and Larsen, *Design and Application of Prodrugs, Drug Design and Development* (Krogsgaard-Larsen, et al., eds., Harwood Academic Publishers, 1991).

The compounds of Formula (I, IIa and IIb) and their pharmaceutically acceptable salts, pharmaceutically acceptable prodrugs, and pharmaceutically active metabolites of the present invention are useful as modulators of the P2X7 receptor in the methods of the invention. As such modulators, the compounds may act as antagonists, agonists, or inverse agonists. The term "modulators" include both inhibitors and activators, where "inhibitors" refer to compounds that decrease, prevent, inactivate, desensitize or down-regulate the P2X7 receptor expression or activity, and "activators" are compounds that increase, activate, facilitate, sensitize, or up-regulate P2X7 receptor expression or activity.

The term "treat", "treatment" or "treating" as used herein is intended to refer to administration of an active agent or composition of the invention to a subject for the purpose of affecting a therapeutic or prophylactic benefit through modulation of P2X7 receptor activity. Treating includes reversing, ameliorating, alleviating, inhibiting the progress of, lessening the severity of, or preventing a disease, disorder, or condition, or one or more symptoms of such disease, disorder or condition mediated through modulation of P2X7 receptor activity. The term "subject" refers to a mammalian patient in need of such treatment, such as a human.

Accordingly, the invention relates to methods of using the compounds described herein to treat subjects diagnosed with or suffering from a disease, disorder, or condition mediated by P2X7 receptor activity, such as: rheumatoid arthritis, osteoarthritis, psoriasis, septic shock, allergic dermatitis, asthma, allergic asthma, mild to severe asthma, steroid resistant asthma, idiopathic pulmonary fibrosis, allergic rhinitis, chronic obstructive pulmonary disease (COPD) and airway hyper-responsiveness; diseases of the nervous and neuro-immune system such as acute and chronic pain states of neuropathic pain, inflammatory pain, spontaneous pain (diabetic neuropathy, postherpetic neuralgia, low back pain, chemotherapy-induced neuropathic pain, fibromyalgia); diseases involved with and without neuroinflammation of the CNS such as mood disorders (major depression, major depressive disorder, treatment resistant depression, bipolar disorder, anxious depression, anxiety), cognition, sleep disorders, multiple sclerosis, epileptic seizures, Parkinson's disease, schizophrenia, Alzheimer's disease, Huntington's disease, autism, spinal cord injury and cerebral ischemia/traumatic brain injury, stress-related disorders; diseases of the cardiovascular, metabolic, gastrointestinal and urogenital systems such as diabetes, diabetes mellitus, thrombosis, irritable bowel syndrome, IBD, Crohn's disease, ischemic heart disease, ischaemia, hypertension, cardiovascular disease, myocardial infarction, and lower urinary tract dysfunction such as incontinence, lower urinary tract syndrome, Polycystic Kidney Disease, Glomerulonephritis, (GN); skeletal disorders, namely osteoporosis/osteopetrosis: and glaucoma, interstitial cystitis, cough, ureteric obstruction, sepsis, Amyotrophic Lateral Sclerosis, Chaga's Disease, chlamydia, neuroblastoma, Tuberculosis, and migraine.

In treatment methods according to the invention, a therapeutically effective amount of a pharmaceutical agent according to the invention is administered to a subject suffering from or diagnosed as having such a disease, disorder, or condition. An "effective amount" or "therapeutically effective amount" means an amount or dose sufficient to generally bring about the desired therapeutic or prophylactic benefit in patients in need of such treatment for the designated disease, disorder, or condition. Therapeutically effective amounts or doses of the compounds of the present invention may be ascertained by routine methods such as modeling, dose escalation studies or clinical trials, and by taking into consideration routine factors, e.g., the mode or route of administration or drug delivery, the pharmacokinetics of the compound, the severity and course of the disease, disorder, or condition, the subject's previous or ongoing therapy, the subject's health status and response to drugs, and the judgment of the treating physician. An example of a dose is in the range of from about 0.001 to about 200 mg of compound per kg of subject's body weight per day, preferably about 0.05 to 100 mg/kg/day, or about 1 to 35 mg/kg/day, in single or divided dosage units (e.g., BID, TID, QID). For a 70-kg human, an illustrative range for a suitable dosage amount is from about 0.05 to about 7 g/day, or about 0.2 to about 2.5 g/day.

Once improvement of the patient's disease, disorder, or condition has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

In addition, the active agents of the invention may be used in combination with additional active ingredients in the treatment of the above conditions. The additional active ingredients may be coadministered separately with an active agent of compounds of Table 1 or included with such an agent in a pharmaceutical composition according to the invention. In an exemplary embodiment, additional active ingredients are those that are known or discovered to be therapeutically effective in the treatment of conditions, disorders, or diseases mediated by P2X7 activity, such as another P2X7 modulator or a compound active against another target associated with the particular condition, disorder, or disease. The combination may serve to increase efficacy (e.g., by including in the combination a compound potentiating the potency or effectiveness of an active agent according to the invention), decrease one or more side effects, or decrease the required dose of the active agent according to the invention.

The active agents of the invention are used, alone or in combination with one or more additional active ingredients, to formulate pharmaceutical compositions of the invention. A pharmaceutical composition of the invention comprises: (a) a therapeutically effective amount of at least one active agent in accordance with the invention; and (b) a pharmaceutically acceptable excipient.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith. Examples of excipients include calcium carbonate, calcium phosphate, various sugars and types of starch, cellulose derivatives, gelatin, vegetable oils, and polyethylene glycols.

Delivery forms of the pharmaceutical compositions containing one or more dosage units of the active agents may be prepared using suitable pharmaceutical excipients and compounding techniques known or that become available to those skilled in the art. The compositions may be administered in the inventive methods by a suitable route of delivery, e.g., oral, parenteral, rectal, topical, or ocular routes, or by inhalation.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration.

For oral administration, the compounds of the invention can be provided in the form of tablets or capsules, or as a solution, emulsion, or suspension. To prepare the oral compositions, the compounds may be formulated to yield a dosage of, e.g., from about 0.05 to about 100 mg/kg daily, or from about 0.05 to about 35 mg/kg daily, or from about 0.1 to about 10 mg/kg daily. For example, a total daily dosage of about 5 mg to 5 g daily may be accomplished by dosing once, twice, three, or four times per day.

Oral tablets may include a compound according to the invention mixed with pharmaceutically acceptable excipients such as inert diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are suitable disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, compounds of the invention may be mixed with a solid, semisolid, or liquid diluent. Soft gelatin capsules may be prepared by mixing the compound of the invention with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions or syrups or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The active agents of this invention may also be administered by non-oral routes. For example, the compositions may be formulated for rectal administration as a suppository. For parenteral use, including intravenous, intramuscular, intraperitoneal, or subcutaneous routes, the compounds of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms will be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses may range from about 1 to 1000 µg/kg/minute of compound, admixed with a pharmaceutical carrier over a period ranging from several minutes to several days.

For topical administration, the compounds may be mixed with a pharmaceutical carrier at a concentration of about 0.1% to about 10% of drug to vehicle. Another mode of administering the compounds of the invention may utilize a patch formulation to affect transdermal delivery.

procedures to prepare embodiments of the invention. Variables presented in the schemes are intended to refer to the synthesis described in that scheme.

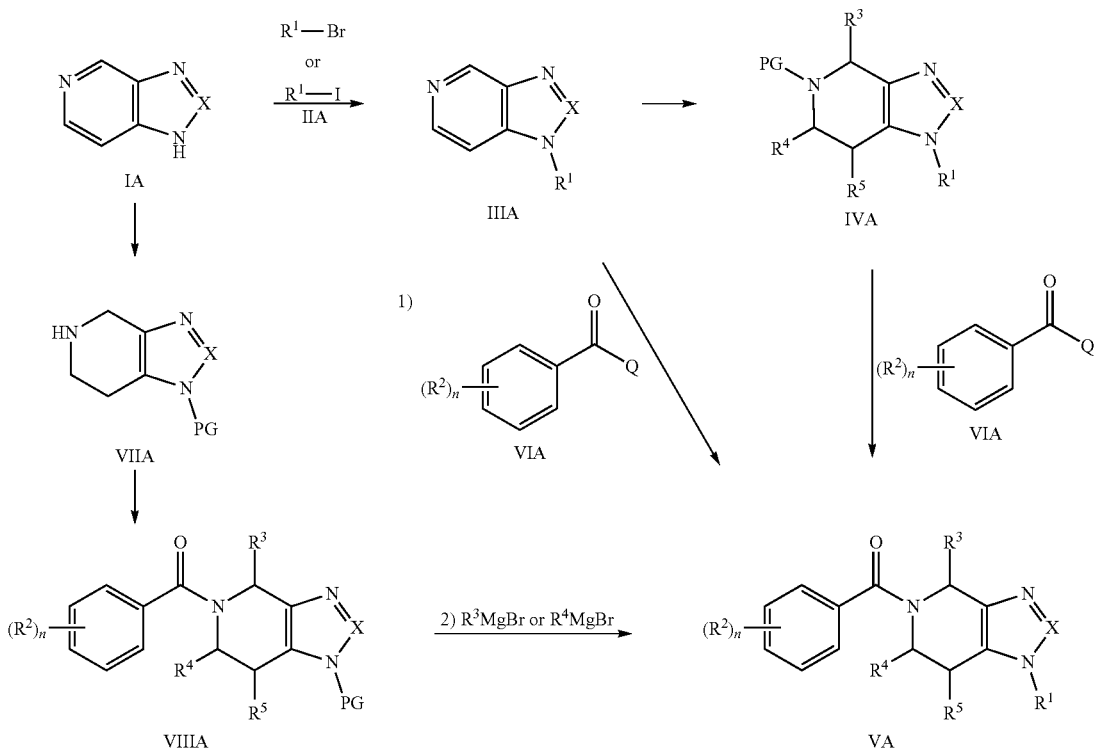

Scheme 1

Compounds of the invention may alternatively be administered in methods of this invention by inhalation, via the nasal or oral routes, e.g., in a spray formulation also containing a suitable carrier.

EXAMPLES

Exemplary compounds useful in methods of the invention will now be described by reference to the illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I, IIa and IIb). Reactions may be performed between the melting point and the reflux temperature of the solvent, and preferably between 0° C. and the reflux temperature of the solvent. Reactions may be heated employing conventional heating or microwave heating. Reactions may also be conducted in sealed pressure vessels above the normal reflux temperature of the solvent.

Synthetic procedures described in the Schemes below are meant to describe the synthesis of intermediates and general The group PG represents a protecting group. One skilled in the art will select the appropriate protecting group compatible with the desired reactions. The protecting groups may be removed at a convenient subsequent stage using methods known from the art.

Alternatively, it may be necessary to employ, in the place of the ultimately desired substituent, a suitable group that may be carried through the reaction scheme and replaced as appropriate with the desired substituent. Such compounds, precursors, or prodrugs are also within the scope of the invention. Examples of preferred protecting groups include; carbamates, benzyl and substituted benzyl groups. Especially preferred protecting groups are; tert-butyloxycarbonyl, 2,2,2-trichloroethoxycarbonyl, alpha-chloroethoxycarbonyl, benzyl, 4-nitrobenzyl and diphenylmethyl.

Heterocycle IA is converted to compound IIIA through coupling with aryl halide IIA using copper oxide, 8-hydroxyquiniolone or 4,7dimeththoxy[1,10]-phenanthroline, CsCO₃ in a solvent such as DMSO or butyronitrile. This reaction is heated overnight at 110° C. or heated in a microwave reactor for 1 hour at 140° C.

Compound IIIA is converted to amine IVA where PG=H by initial treatment with an alkylating agent such as benzyl bromide in a solvent such as DCM or DMF, followed by reduction with a reducing agent such as NaBH₄ in a solvent such as MeOH, EtOH or isopropanol. Final treatment with chloroethylchloroformate provides amine IVA where PG=H.

Compound IIIA is also converted to compound VA by initial treatment with acid chloride VIA, where Q=Cl in a solvent such as DCM or DMF. Subsequent treatment with a Grignard reagent such as $R^3$MgBr or $R^4$MgBr followed by reduction with hydrogen gas and a metal catalyst such as Pd/C or Pt/C provides VA. If however one does not perform this final reduction, the partially reduced compound, the 4,5-dihydro-[4,5,c]pyridine (compound not shown) is obtained.

Compound IIIA is also converted to compound IVA by passing a solution of IIIA through a $PtO_2$ catalyst cartridge on a H-Cube hydrogenation apparatus at 70 bar and at 1 mL/min.

Compound IVA, where PG=H is converted to compound VA by treatment with compound VIA, where Q=OH using amide coupling conditions such as HATU, DIPEA in a solvent such as DCM or DMF.

One of ordinary skill in the art will also realize that when $R^1$ is a 3-pyrazolo or a 5-pyrazolo group, the N1 nitrogen may be unsubstituted, substituted or may be protected with a protecting group. This nitrogen may be subjected to standard conditions to convert it from one of the above mentioned states to another.

Scheme 2

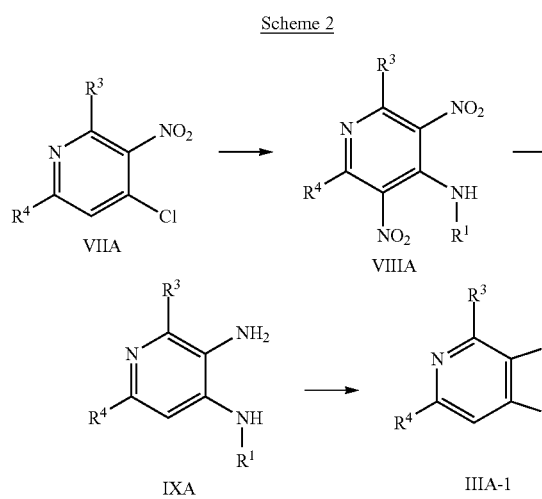

Alternatively IIIA, for example IIIA-1 as shown in Scheme 2, is prepared through a series of steps commencing with the addition of Pd(OAc)$_2$ to BINAP in toluene, followed by the addition of the following reagents: a chloronitropyridine (VIIA), an amino compound such as an aminopyridine ($R^1$—NH$_2$) and a base such as $K_2CO_3$, NaH or NaOtBu in a solvent such as toluene, THF or DMSO. Heating for approximately 2 hours at 110° C. in a sealed vessel provides compound VIIIA.

Reduction of VIIIA using catalytic hydrogenation conditions of hydrogen gas and a metal catalyst such as 10% Pd/C in a solvent such as MeOH or EtOH provides diamine compound IXA. Alternatively this reduction is carried out using Zn in HOAC or using a combination of Pd/C in a solvent such as $NH_3$ in MeOH. Triazole IIIA-1 is then formed by treatment of diamine IXA in THF and HOAc with t-butylnitrite or isoamyl nitrite at 100° C. for 90 minutes.

Scheme 3

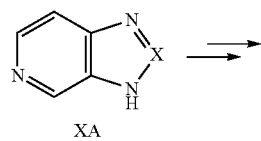

XA

-continued

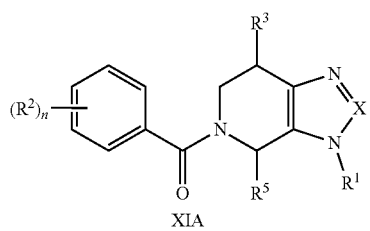

XIA

Through a series of steps analogous to those shown in Scheme I, compound XA is converted to analog XIA.

Scheme 4

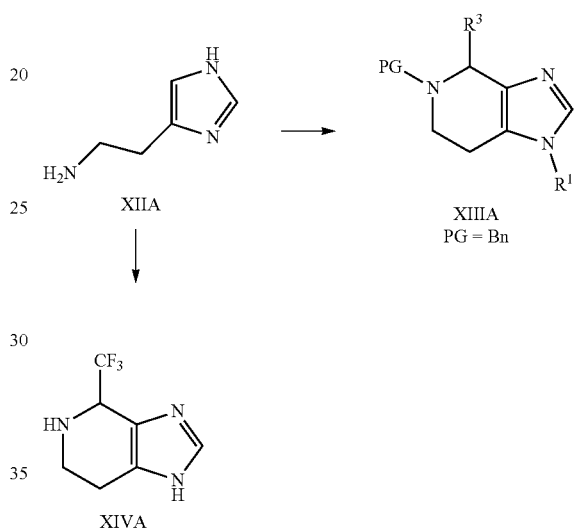

Compound XIIIA is prepared by treatment of a mixture of compound XIIA, histamine, and benzaldehyde in a solvent such as MeOH or EtOH, with a reducing agent such as NaBH$_4$ to provide N-benzyl-2-(1H-imidazol-5-yl) ethanamine (compound not shown). To this compound in water at 0° C., is added KOH followed by acetaldehyde. After approximately six hours at 80° C. followed by treatment with acid, compound XIIIA, PG=Bn, is isolated. Trifluoromethyl derivative XIVA is also prepared from compound XIIA. To a solution of compound XIIA in a solvent such as water at a temperature of about 0° C., is added a base such as KOH along with trifluoroacetaldehyde. After heating at a temperature of approximately 80° C. for approximately 6 hours and acidification, compound XIVA is isolated.

Scheme 5

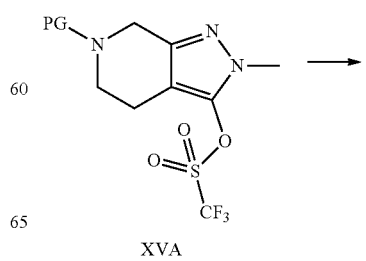

XVA

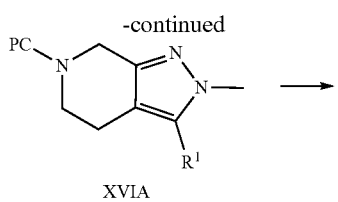

XVIA

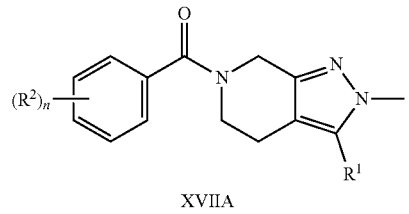

XVIIA

Compound XVA is prepared from 1-tert-butyl 4-ethyl 3-oxopiperidine-1,4-dicarboxylate upon the addition of methyl hydrazine in EtOH. Heating to approximately 80° C. overnight followed by treatment with and diisopropylethylamine and N-phenyltrifluoromethanesulfonate in DCM provides compound XVA where PG=BOC. This compound is then converted to compound XVIA by addition of the appropriate boronic acid pinacol ester, cesium carbonate, copper chloride, palladium acetate and 1,1'-bis(diphenylphosphino)ferrocene in DMF. Compound XVIA is then converted to pyrazole compound XVIIA through standard removal of the nitrogen protecting group (PG) and coupling to compound VIA as described in Scheme 1.

protected as its THP ether upon treatment with 3,4-dihydropyran and para-toluenesulfonic acid. The THP ethers, are represented here as a compound XXA, a mixture of regioisomers and are transformed into compound XXIA using the same conditions described in Scheme 5 for the conversion of XVA to XVIA, followed by THP deprotection using TFA in DCM.

Scheme 7

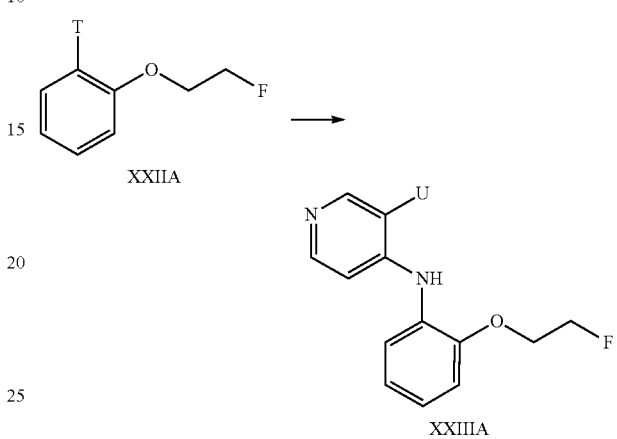

Compound XXIIA, where T=Br is prepared via the reaction of 2-bromophenol and a base such as NaH in a solvent Scheme 6

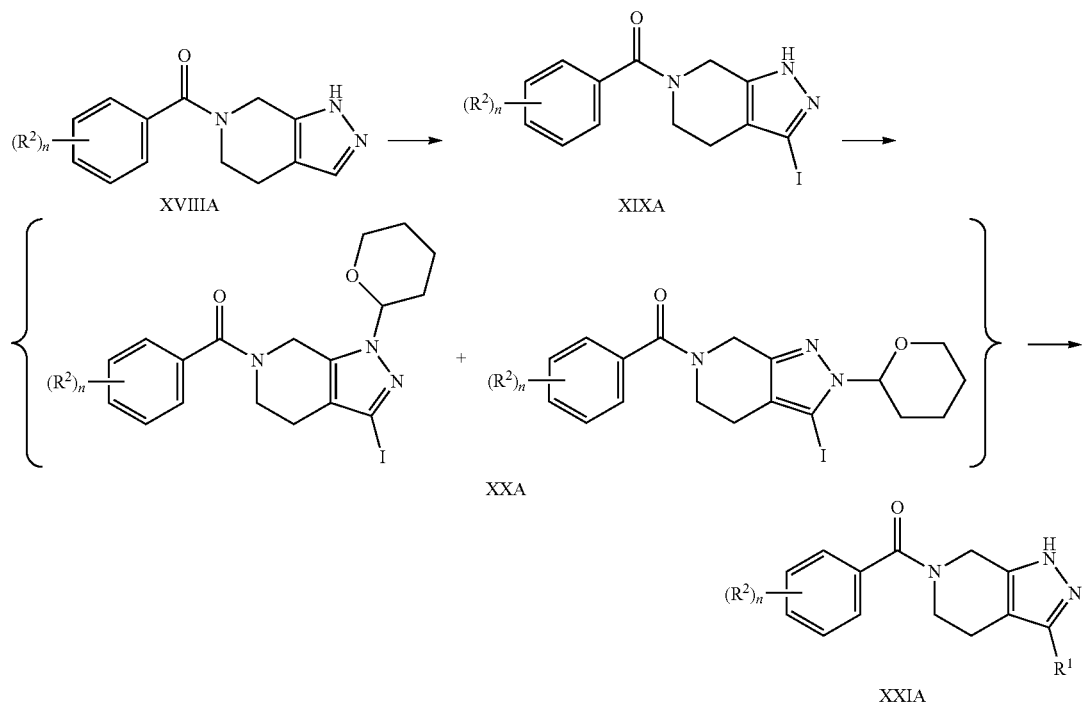

Compound XVIIIA is prepared from commercially available 4,5,6,7-tetrahydro-1H-pyrazolo[3,4-c]pyridine and compound VIA as described in Scheme 1. This compound is then converted to iodo compound XIXA upon treatment with N-iodosuccinimide in DMF. This pyrazole is then such as THF, followed by treatment with 1-bromo-2-fluoroethane. This compound is then converted to 2-(2-fluoroethoxy)aniline, compound XXIIA, where T=NH$_2$, by treatment of the bromo compound, XXIIA, T=Br, with benzophenone imine, NaOtBu, BINAP, Pd$_2$(dba)$_3$, in a solvent such as toluene at 120 C for approximately 3 hours. This compound is then converted to compound XXIIIA, where U=NO$_2$, using conditions analogous to those described in Scheme 2 for the conversion of VIIA to VIIIA. Subsequently XXIIIA, where U=NO$_2$ is converted to XXIIIA, where U=NH$_2$ as described in Scheme 2 for the conversion of VIIIA to IXA.

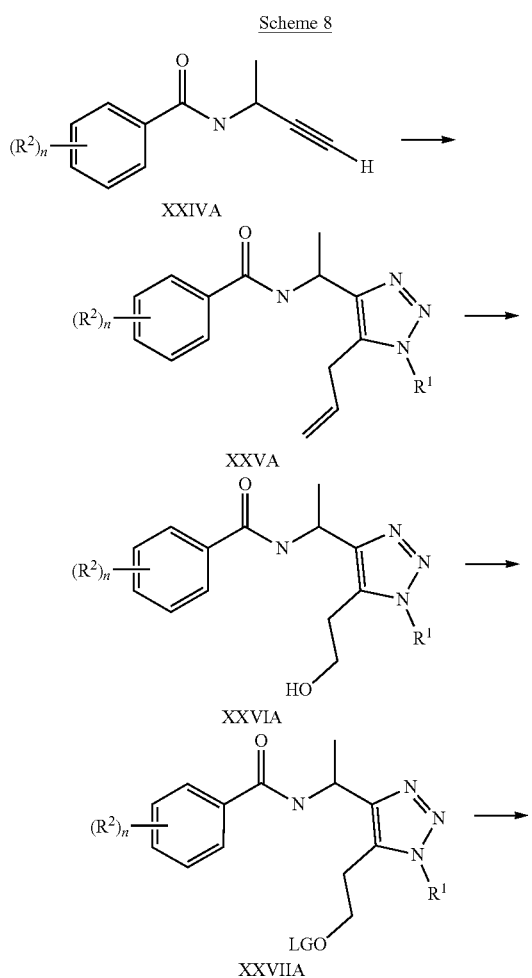

Scheme 8

Compound XXIVA is made from the reaction of but-2-yn-2-amine and compound VIA where Q is Cl in the presence of a base such as TEA and in a solvent such as THF. Alternatively compound VIA, where Q is OH is used employing the conditions described in Scheme I for the conversion of compound IVA, where PG is H, to compound VA.

Compound XXVA is prepared by the reaction of compound XXIVA, an azide source such as tetrazolo[1,5-a]pyrimidine, an alkylating agent such as such allyl bromide, (E)-1-bromobut-2-ene, 3-bromo-2-methylprop-1-ene, 1-bromo-3-methylbut-2-ene, (E)-(3-bromoprop-1-en-1-yl)benzene, ethyl 2-(bromomethyl)acrylate, or 3-bromocyclohex-1-ene, a base such as Cs$_2$CO$_3$, TEA or Hunig's base, a copper (I) salt, such as CuI or CuBr, used in either stochiometric amounts or sub-stochiometric amounts, at a temperature between −78° C. and rt, in a solvent such as THF, DCM, 2-Me-THF, CH$_3$CN, EtOAc or DMF.

Compound XXVIA is prepared via an ozonolysis of compound XXVA in a solvent such as MeOH at a temperature of about −78° C., followed by reduction with a reducing agent such as NaBH$_4$.

Compound XXVIIA is prepared by conversion of the hydroxyl group of compound XXVIA to a leaving group (designated LG), by treatment with an agent such as tosyl chloride or mesyl chloride, in the presence of a base such as TEA, with a catalyst such as diemethylaminopyridine.

Compound XXVIIA is then converted to compound VA upon treatment with a base such as NaH in a solvent such as THF, with heating to a temperature of about 60° C. for approximately 3 hours.

In obtaining the compounds described in the examples below and the corresponding analytical data, the following experimental and analytical protocols were followed unless otherwise indicated.

Unless otherwise stated, reaction mixtures were magnetically stirred at room temperature (rt) under a nitrogen atmosphere. Where solutions were "dried," they were generally dried over a drying agent such as Na$_2$SO$_4$ or MgSO$_4$. Where mixtures, solutions, and extracts were "concentrated", they were typically concentrated on a rotary evaporator under reduced pressure. Reactions under microwave irradiation conditions were carried out in a Biotage Initiator or CEM Discover instrument. Hydrogenations on the H-cube were run by passing solvent containing reactant through a catalyst cartridge on an H-Cube hydrogenation apparatus at a pressure of 15 to 100 bar and a flow rate of 1 to 30 ml/min.

Normal-phase silica gel column chromatography (sgc) was performed on silica gel (SiO$_2$) using prepackaged cartridges, eluting with 2 M NH$_3$/MeOH in CH$_2$Cl$_2$ unless otherwise indicated.

Preparative reverse-phase high performance liquid chromatography (HPLC) was performed on a Agilent HPLC with an Xterra Prep RP$_{18}$ (5 m, 30×100 mm, or 50×150 mm) column, and a gradient of 10 to 99% acetonitrile/water (20 mM NH$_4$OH) over 12 to 18 min, and a flow rate of 30 or 80 mL/min, unless otherwise indicated.

Preparative supercritical fluid high performance liquid chromatography (SFC) was performed either on a JASCO preparative SFC system, an APS 1010 system from Berger instruments, or a SFC-PICLAB-PREP 200 (PIC SOLUTION, Avignon, France). The separations were conducted between at 100-150 bar with a flow rate ranging from 40-60 mL/min. The columns used were heated to 35-40° C.

Mass spectra (MS) were obtained on an Agilent series 1100 MSD using electrospray ionization (ESI) in positive mode unless otherwise indicated. Calculated (calcd.) mass corresponds to the exact mass.

Nuclear magnetic resonance (NMR) spectra were obtained on Bruker model DRX spectrometers. The format of the $^1$H NMR data below is: chemical shift in ppm downfield of the tetramethylsilane reference (multiplicity, coupling constant J in Hz, integration).

Chemical names were generated using ChemDraw Ultra 6.0.2 (CambridgeSoft Corp., Cambridge, Mass.) or ACD/Name Version 9 (Advanced Chemistry Development, Toronto, Ontario, Canada).

Abbreviations and acronyms used herein include the following:

| Term | Acronym/Abbreviation |
|---|---|
| High-pressure liquid chromatography | HPLC |
| Diisopropylethylamine | DIPEA, Hunig's base |
| Tetrahydrofuran | THF |
| tert-Butylcarbamoyl | boc |
| Dichloromethane | DCM |
| Dichlorethane | DCE |
| Trifluoroacetic acid | TFA |
| Acetic Acid | HOAc |
| N,N-Dimethylformamide | DMF |
| Methanol | MeOH |
| Ethanol | EtOH |
| Acetonitrile | ACN, MeCN |
| Ethyl Acetate | EtOAc, or EA |
| Triethylamine | TEA |
| 2-(1H-9-Azobenzotriazole-1-yl)-1,1,3,3-tetramethylaminium hexafluorophosphate | HATU |
| Benzotriazol-1-yloxytris(dimethylamino)-phosphonium hexafluorophosphate | BOP |
| Acetic acid | HOAc |
| 2-methyltetrahydrofuran | 2-Me-THF |
| Methyl magnesium bromide | MeMgBr |
| Ethyl magnesium bromide | EtMgBr |
| Isopropyl magnesium bromide | i-PrMgBr |
| Dimethyl sulfoxide | DMSO |
| Supercritical Fluid Chromatography | SFC |
| Diethyl 1,4-dihydro-2,6-dimethyl-3,5-pyridinecarboxylate | Hantzsch Ester |
| Tetrahydropyran | THP |
| 2,2'-bis(diphenylphosphino)-1,1'-binaphthyl | BINAP |
| Sodium tert-butoxide | NaOtBu |
| Tris(dibenzylideneacetone(dipalladium (0) | $Pd_2(dba)_3$ |
| 4,5-bis(diphenylphosphino)-9,9-dimethylxanthene | Xantphos |

Intermediate 1: 1-(5-Fluoropyridin-2-yl)-1H-imidazo[4,5-c]pyridine

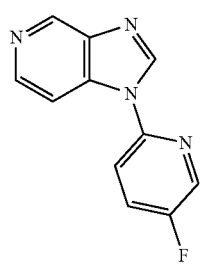 [SMILES: Fc1ccc(-n2cnc3cnccc32)nc1]

A solution of 5-azabenzimidazole (1.00 g, 8.40 mmol), 2-bromo-5-fluoropyridine (1.48 g, 8.40 mmol), copper (I) oxide (0.13 g, 0.84 mmol), 8-hydroxyquinoline (0.24 g, 1.68 mmol), and $Cs_2CO_3$ (5.47 g, 16.8 mmol) in DMSO (4 mL) was irradiated in a microwave apparatus for 1 hour at 140° C. The reaction was diluted with $H_2O$ (100 mL) and extracted with EtOAc (75 mL×3). The organic layers were combined, dried ($Na_2SO_4$), and concentrated. Chromatography of the resulting residue ($SiO_2$; MeOH ($NH_3$):DCM) gave the title compound (0.45 g, 25%). MS (ESI): mass calculated for $C_{11}H_7FN_4$, 214.07; m/z found 215.1 $[M+H]^+$.

Intermediate 2: 1-Phenyl-1H-imidazo[4,5-c]pyridine

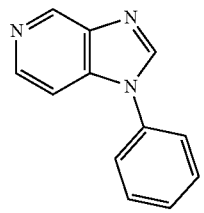 [SMILES: c1ccc(-n2cnc3cnccc32)cc1]

Intermediate 2 was prepared in a manner analogous to Intermediate 1, substituting 2-bromobenzene for 2-bromo-5-fluoropyridine. MS (ESI): mass calculated for $C_{12}H_9N_3$, 197.07; m/z found 198.1 $[M+H]^+$.

Intermediate 3: 1-(Pyridin-2-yl)-1H-imidazo[4,5-c]pyridine

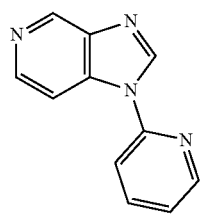 [SMILES: c1ccc(-n2cnc3cnccc32)nc1]

Intermediate 3 was prepared in a manner analogous to Intermediate 1, substituting 2-bromopyridine for 2-bromo-5-fluoropyridine. MS (ESI): mass calculated for $C_{11}H_8N_4$, 196.07; m/z found 197.1 $[M+H]^+$.

Intermediate 4: 1-(Pyrazin-2-yl)-1H-imidazo[4,5-c]pyridine

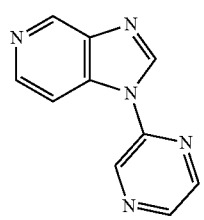 [SMILES: c1cnc(-n2cnc3cnccc32)cn1]

Intermediate 4 was prepared in a manner analogous to Intermediate 1, substituting 2-bromopyrazine for 2-bromo-5-fluoropyridine. MS (ESI): mass calculated for $C_{10}H_7N_5$, 198.07; m/z found 199.1 $[M+H]^+$.

Intermediate 5: 1-(Pyrimidin-2-yl)-1H-imidazo[4,5-c]pyridine

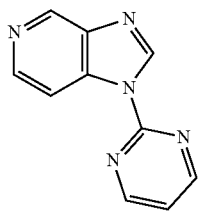 [SMILES: c1cnc(-n2cnc3cnccc32)nc1]

Intermediate 5 was prepared in a manner analogous to Intermediate 1, substituting 2-bromopyrimidine for 2-bromo-5-fluoropyridine. MS (ESI): mass calculated for $C_{10}H_7N_5$, 198.07; m/z found 199.1 [M+H]$^+$.

Intermediate 6: 1-(5-Fluoropyrimidin-2-yl)-1H-imidazo[4,5-c]pyridine

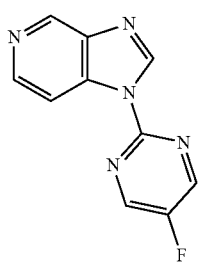 [SMILES: Fc1cnc(-n2cnc3cnccc32)nc1]

Intermediate 6 was prepared in a manner analogous to Intermediate 1, substituting 2-bromo-5-fluoropyrimidine for 2-bromo-5-fluoropyridine. MS (ESI): mass calculated for $C_{10}H_6FN_5$, 215.06; m/z found 216.1 [M+H]$^+$.

Intermediate 7: 1-(4-Fluorophenyl)-1H-imidazo[4,5-c]pyridine

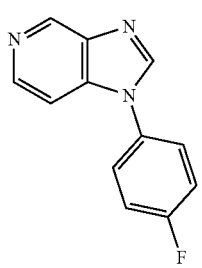 [SMILES: Fc1ccc(-n2cnc3cnccc32)cc1]

Intermediate 7 was prepared in a manner analogous to Intermediate 1, substituting 1-bromo-4-fluorobenzene for 2-bromo-5-fluoropyridine. MS (ESI): mass calculated for $C_{12}H_6FN_3$, 213.07; m/z found 214.1 [M+H]$^+$.

Intermediate 8: 1-(3-Fluoropyridin-2-yl)-1H-imidazo[4,5-c]pyridine

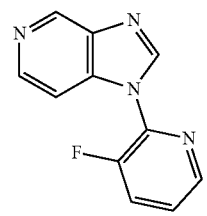 [SMILES: Fc1cccnc1-n1cnc2cnccc21]

Intermediate 8 was prepared in a manner analogous to Intermediate 1, substituting 2-bromo-3-fluoropyridine for 2-bromo-5-fluoropyridine. MS (ESI): mass calculated for $C_{11}H_7FN_4$, 214.07; m/z found 215.1 [M+H]$^+$.

Intermediate 9: 1-(3,5-Difluorophenyl)-1H-imidazo[4,5-c]pyridine

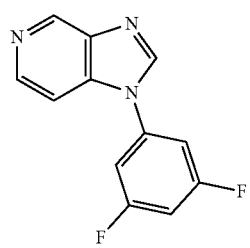 [SMILES: Fc1cc(F)cc(-n2cnc3cnccc32)c1]

Intermediate 9 was prepared in a manner analogous to Intermediate 1, substituting bromo-3,5-difluorobenzene for 2-bromo-5-fluoropyridine. MS (ESI): mass calculated for $C_{11}H_7FN_3$, 231.06; m/z found 232.1 [M+H]$^+$.

Intermediate 10: 3-(Pyridin-2-yl)-3H-imidazo[4,5-c]pyridine

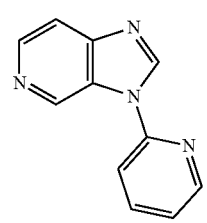 [SMILES: c1ccc(-n2cnc3ccncc32)nc1]

Intermediate 10 was prepared in a manner analogous to Intermediate 1, substituting 2-bromopyridine for 2-bromo-5-fluoropyridine. MS (ESI): mass calculated for $C_{11}H_7N_4$, 196.07; m/z found 197.1 [M+H]$^+$.

Intermediate 11: 5-Benzyl-4-methyl-4,5,6,7-tetra-hydro-1H-imidazo[4,5-c]pyridine

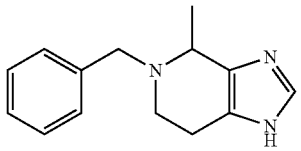 [SMILES: CC1c2nc[nH]c2CCN1Cc1ccccc1]

Step A. N-Benzyl-2-(1H-imidazol-5-yl)ethanamine.

A solution of histamine (free base) (1.00 g, 9.0 mmol) and benzaldehyde (0.91 mL, 9.0 mmol) in MeOH (25 mL) was stirred at rt for 30 min. To this solution was slowly added NaBH$_4$ (0.21 g, 5.4 mmol). The reaction was let stir for 3 h, quenched with a minimal amount of H$_2$O and concentrated. The residue was dissolved in EtOH and filtered through Celite©. The solvent was concentrated to give the title product (1.50 g, 83%). MS (ESI): mass calculated for C$_{12}$H$_{15}$N$_3$, 201.1; m/z found 202.2 [M+H]$^+$.

Step B. 5-Benzyl-4-methyl-4,5,6,7-tetrahydro-1H-imidazo[4,5-c]pyridine

A suspension of N-benzyl-2-(1H-imidazol-5-yl)ethanamine (0.20 g, 1.0 mmol) in H$_2$O (5 mL) was cooled in an ice bath. To this suspension was added solid KOH (85%) (0.112 g, 2.0 mmol) followed by acetaldehyde (0.11 mL, 2.0 mmol). The reaction was allowed to warm to rt and heated to 80° C. After 6 h, the reaction was cooled to rt, acidified using 6N HCl, and concentrated. The resulting residue was dissolved in hot EtOH and filtered through Celite©. The solvent was evaporated to give the title product as the HCl salt. The salt was then treated with 3N NaOH and extracted with EtOAc (50 mL×3). The organic layers were combined, dried (Na$_2$SO$_4$), and concentrated. Chromatography of the resulting residue (SiO$_2$; MeOH (NH$_3$):DCM) gave the title compound (0.09 g, 40%). $^1$H NMR (500 MHz, CDCl$_3$) δ 7.47 (s, 1H), 7.37 (t, J=9.2 Hz, 2H), 7.32 (t, J=7.5 Hz, 2H), 7.28-7.23 (m, 1H), 3.94 (d, J=13.6 Hz, 1H), 3.81-3.68 (m, 1H), 3.59 (t, J=19.1 Hz, 1H), 3.12-2.99 (m, 1H), 2.74-2.47 (m, 3H), 1.44 (d, J=6.5 Hz, 3H). MS (ESI): mass calculated for C$_{14}$H$_{17}$N$_3$, 227.1; m/z found 228.2 [M+H]$^+$.

Intermediate 12: 2-Chloro-3-(trifluoromethyl)benzoyl chloride

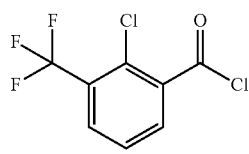 [SMILES: O=C(Cl)c1cccc(C(F)(F)F)c1Cl]

To a suspension of 2-chloro-3-(trifluoromethyl)benzoic acid (15 g, 67 mmol) and catalytic DMF (0.06 mL, 0.67 mmol) in DCM (150 mL) was added oxalyl chloride (6.8 mL, 80 mmol) dropwise. The reaction was let stir (vigorous bubbling) for 4 h and concentrated to an oily solid which became solid after overnight drying on high vacuum.

Intermediate 13: 2-Fluoro-3-(trifluoromethyl)benzoyl chloride

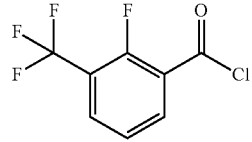

Intermediate 13 was prepared in a similar manner as Intermediate 12 substituting 2-fluoro-3-(trifluoromethyl)benzoic acid for 2-chloro-3-(trifluoromethyl)benzoic acid.

Intermediate 14: 2,3-Dichlorobenzoyl Chloride

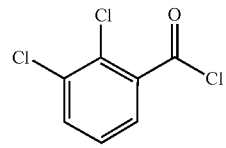

Intermediate 14 was prepared in a similar manner as Intermediate 12 substituting 2,3-dichlorobenzoic acid for 2-chloro-3-(trifluoromethyl)benzoic acid.

Example 1. (2-Chloro-3-(trifluoromethyl)phenyl)(1-(pyridin-2-yl)-6,7-dihydro-1H-imidazo[4,5-c]pyridin-5(4H)-yl)methanone

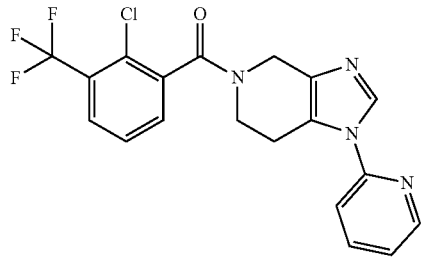 [SMILES: O=C(c1cccc(C(F)(F)F)c1Cl)N1CCc2c(ncn2-c2ccccn2)C1]

Step A. 5-Benzyl-1-(pyridin-2-yl)-4,5,6,7-tetrahydro-1H-imidazo[4,5-c]pyridine To a solution of Intermediate 3 (0.20 g, 1.02 mmol) in DCM (25 mL) was added benzyl bromide (0.12 g, 1.02 mmol). The reaction was let stir for 4 h then concentrated. The resulting solid was dissolved in MeOH (10 mL) and NaBH$_4$ (0.05 g, 1.4 mmol) was added slowly. After 5 h, the reaction was quenched with a small amount of water and concentrated.

Chromatography of the resulting residue (SiO$_2$; MeOH (NH$_3$):DCM) gave the title compound (0.20 mg, 68%). $^1$H NMR (500 MHz, CDCl$_3$) δ 8.76-8.66 (m, 1H), 8.55-8.39 (m, 2H), 8.14-8.03 (m, 1H), 7.32 (ddt, J=22.0, 11.6, 7.5 Hz, 6H), 3.89 (s, 1H), 3.78 (d, J=5.4 Hz, 2H), 3.63 (s, 1H), 2.99 (t, J=5.5 Hz, 1H), 2.83 (tt, J=26.6, 5.6 Hz, 3H). MS (ESI): mass calculated for C$_{18}$H$_{18}$N$_4$, 290.2; m/z found 291.2 [M+H]$^+$.

Step B. 1-(Pyridin-2-yl)-4,5,6,7-tetrahydro-1H-imidazo[4,5-c]pyridine

To a solution of 5-benzyl-1-(pyridin-2-yl)-4,5,6,7-tetrahydro-1H-imidazo[4,5-c]pyridine (0.13 g, 0.45 mmol) in DCE (5 mL) was added 1-chloroethyl chloroformate (0.10 mL, 0.90 mmol). The reaction was allowed to stir for 15 min then heated at reflux for 4 h. The reaction was let cool, concentrated, dissolved in MeOH and heated again at 60° C. for 1 h. The reaction was concentrated and the product was used in the next step without further purification (0.075 g, 83%). MS (ESI): mass calculated for $C_{11}H_{12}N_4$, 200.1; m/z found 201.2 [M+H]$^+$.

Step C. (2-Chloro-3-(trifluoromethyl)phenyl)(1-(pyridin-2-yl)-6,7-dihydro-1H-imidazo[4,5-c]pyridin-5(4H)-yl)methanone A solution of 1-(pyridin-2-yl)-4,5,6,7-tetrahydro-1H-imidazo[4,5-c]pyridine (0.050 g, 0.25 mmol), 2-chloro-3-trifluoromethyl benzoic acid (0.056 g, 0.25 mmol), HATU (0.10 g, 0.26 mmol, and DIPEA (0.09 mL, 0.50 mmol) in DMF (2 mL) was stirred for 30 min. The reaction was diluted with EtOAc (15 mL) and washed with H$_2$O (3×10 mL). The organic layers were combined, dried (Na$_2$SO$_4$), and concentrated. Chromatography of the resulting residue (SiO$_2$; MeOH (NH$_3$):DCM) gave the title compound (22 mg, 22%). $^1$H NMR (400 MHz, CDCl$_3$) δ 8.52 (dd, J=4.9, 1.8 Hz, 1H), 8.02 (d, J=18.1 Hz, 1H), 7.92-7.71 (m, 2H), 7.58-7.40 (m, 2H), 7.37-7.28 (m, 2H), 5.12-4.78 (m, 1H), 4.51-4.19 (m, 2H), 3.97 (ddd, J=13.4, 12.7, 9.9 Hz, 1H), 3.61-3.45 (m, 1H), 3.27-2.82 (m, 2H). MS (ESI): mass calculated for $C_{19}H_{14}CF_3N_4O$, 406.1; m/z found 407.1 [M+H]$^+$.

Example 2. (2-Chloro-3-(trifluoromethyl)phenyl)(1-phenyl-6,7-dihydro-1H-imidazo[4,5-c]pyridin-5(4H)-yl)methanone

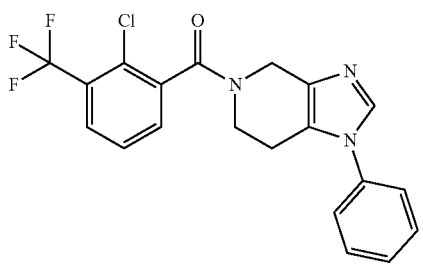 [SMILES: O=C(c1cccc(C(F)(F)F)c1Cl)N1CCc2c(ncn2-c2ccccc2)C1]

Example 2 was made in a manner analogous with Example 1 substituting Intermediate 2 for Intermediate 3 in Step A.

MS (ESI): mass calcd. for $C_{20}H_{15}ClF_3N_3O$, 405.1; m/z found, 406.3 [M+H]$^+$. $^1$H NMR (400 MHz, CDCl$_3$) δ 7.79-7.74 (m, 1H), 7.68 (s, 0.4H), 7.60 (s, 0.6H), 7.56-7.39 (m, 5H), 7.34-7.28 (m, 2H), 4.99-4.90 (m, 1H), 4.45-4.27 (m, 2H), 3.93 (ddd, J=12.8, 7.2, 5.2 Hz, 1H), 3.60-3.45 (m, 1H), 2.76-2.55 (m, 1H).

Example 3. (2,3-Dichlorophenyl)(1-phenyl-6,7-dihydro-1H-imidazo[4,5-c]pyridin-5(4H)-yl)methanone

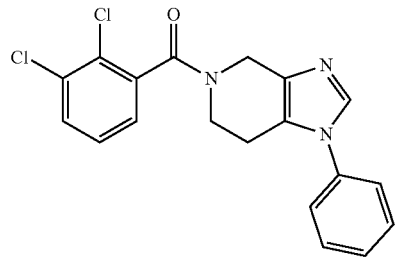 [SMILES: O=C(c1cccc(Cl)c1Cl)N1CCc2c(ncn2-c2ccccc2)C1]

Example 3 was made in a manner analogous with Example 1 substituting 2,3-dichlorobenzoic acid for 2-chloro-3-trifluoromethyl benzoic acid in Step C and substituting Intermediate 2 for Intermediate 3 in Step A.

MS (ESI): mass calcd. for $C_{19}H_{15}Cl_2N_3O$, 371.1; m/z found, 372.2 [M+H]$^+$. $^1$H NMR (400 MHz, CDCl$_3$) δ 7.67 (s, 0.4H), 7.60 (s, 0.6H), 7.56-7.39 (m, 4H), 7.33-7.20 (m, 4H), 4.96-4.90 (m, 1H), 4.46-4.20 (m, 2H), 4.03-3.92 (m, 1H), 3.60-3.43 (m, 1H), 2.67 (ddd, J=20.9, 15.5, 6.8 Hz, 1H).

Example 4. (2,3-Dichlorophenyl)(1-(pyridin-2-yl)-6,7-dihydro-1H-imidazo[4,5-c]pyridin-5(4H)-yl)methanone

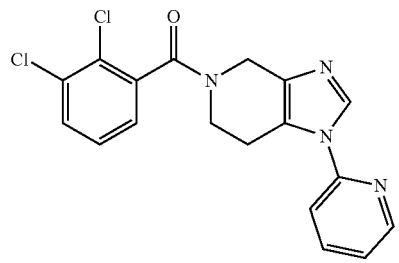 [SMILES: O=C(c1cccc(Cl)c1Cl)N1CCc2c(ncn2-c2ccccn2)C1]

Example 4 was made in a manner analogous with Example 1 substituting 2,3-dichlorobenzoic acid for 2-chloro-3-trifluoromethyl benzoic acid in Step C. MS (ESI): mass calculated for $C_{18}H_{14}Cl_2N_4O$, 406.1; m/z found 407.1 [M+H]$^+$.

Example 5. (1-(1H-Pyrazol-5-yl)-6,7-dihydro-1H-imidazo[4,5-c]pyridin-5(4H)-yl)(2-chloro-3-(trifluoromethyl)phenyl)methanone

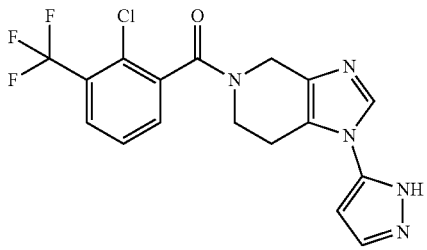 [SMILES: O=C(c1cccc(C(F)(F)F)c1Cl)N1CCc2c(ncn2-c2ccn[nH]2)C1]

Example 5 was made in a manner analogous to Example 1 substituting 1-(1H-pyrazol-5-yl)-1H-imidazo[4,5-c]pyridine for Intermediate 3 in Example 1 Step A.

MS (ESI): mass calcd. for $C_{17}H_{13}ClF_3N_5O$, 395.0; m/z found, 396.1 [M+H]$^+$. $^1$H NMR (400 MHz, CDCl$_3$) δ 11.98-11.66 (m, 1H), 7.91 (s, 1H), 7.81 (s, 1H), 7.76 (ddd, J=7.8, 3.8, 1.7 Hz, 1H), 7.62-7.55 (m, 1H), 7.55-7.41 (m, 3H), 6.28 (dd, J=9.6, 2.5 Hz, 1H), 5.09-4.78 (m, 1H), 4.46-4.24 (m, 2H), 4.03 (ddd, J=12.7, 6.9, 5.3 Hz, 1H), 3.62-3.50 (m, 1H), 3.17-3.02 (m, 2H), 2.98-2.76 (m, 1H).

Example 6. (2-Chloro-3-(trifluoromethyl)phenyl)(1-(pyrazin-2-yl)-6,7-dihydro-1H-imidazo[4,5-c]pyridin-5(4H)-yl)methanone

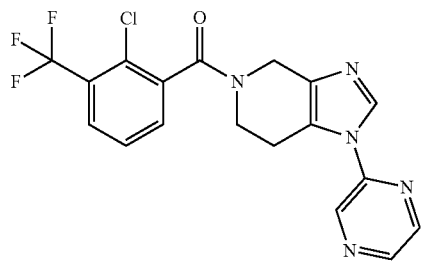 [SMILES: O=C(c1cccc(C(F)(F)F)c1Cl)N1CCc2c(ncn2-c2cnccn2)C1]

Example 6 was made in a manner analogous to Example 1 substituting Intermediate 4 for Intermediate 3 in Step A. MS (ESI): mass calcd. for $C_{18}H_{13}CF_3N_5O$, 407.1; m/z found, 408.2 [M+H]$^+$.

Example 7. (2-Chloro-3-(trifluoromethyl)phenyl)(1-(3,5-difluorophenyl)-6,7-dihydro-1H-imidazo[4,5-c]pyridin-5(4H)-yl)methanone

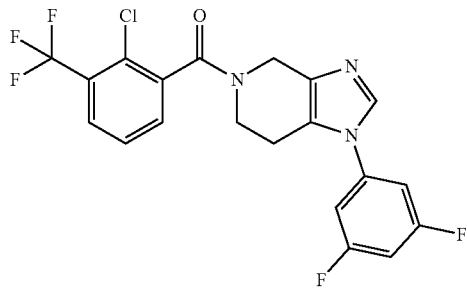 [SMILES: O=C(c1cccc(C(F)(F)F)c1Cl)N1CCc2c(ncn2-c2cc(F)cc(F)c2)C1]

Example 7 was made in a manner analogous to Example 1 substituting Intermediate 9 for Intermediate 3 in Step A. $^1$H NMR (500 MHz, CDCl$_3$) δ 7.83-7.75 (m, 1H), 7.52-7.46 (m, 4H), 6.96-6.90 (m, 2H), 4.885.07-4.71 (m, 3H), 3.58 3.59-3.57 (m, 3H). MS (ESI): mass calculated for $C_{20}H_{13}ClF_5N_3O$, 441.07; m/z found 442.2 [M+H]$^+$.

Example 8. (2-Chloro-3-(trifluoromethyl)phenyl)(3-(pyridin-2-yl)-6,7-dihydro-3H-imidazo[4,5-c]pyridin-5(4H)-yl)methanone

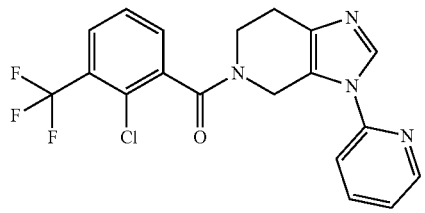 [SMILES: O=C(c1cccc(C(F)(F)F)c1Cl)N1CCc2ncn(-c3ccccn3)c2C1]

Example 8 was made in a manner analogous to Example 1 substituting Intermediate 10 for Intermediate 3 in Step A. $^1$H NMR (500 MHz, CDCl$_3$) δ 8.54 (dd, J=4.8, 1.0 Hz, 1H), 8.04-7.74 (m, 3H), 7.53-7.26 (m, 4H), 5.53-5.01 (m, 2H), 3.67-3.48 (m, 2H), 3.00-2.61 (m, 2H). MS (ESI): mass calculated for $C_{19}H_{14}ClF_3N_4O$, 406.08; m/z found 407.1 [M+H]$^+$.

Example 9. (2,3-Dichlorophenyl)(3-(pyridin-2-yl)-6,7-dihydro-3H-imidazo[4,5-c]pyridin-5(4H)-yl)methanone

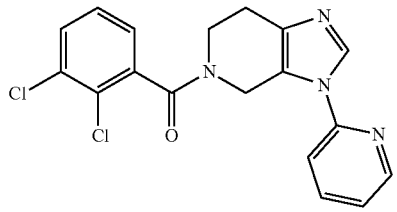 [SMILES: O=C(c1cccc(Cl)c1Cl)N1CCc2ncn(-c3ccccn3)c2C1]

Example 9 was made in a manner analogous to Example 1 substituting 2,3-dichlorobenzoic acid for 2-chloro-3-trifluoromethyl benzoic acid in Step C. $^1$H NMR (500 MHz, CDCl$_3$) δ 8.59-8.49 (m, 1H), 8.05-7.84 (m, 2H), 7.57-7.18 (m, 5H), 5.41-5.05 (m, 2H), 3.67-3.53 (m, 2H), 2.99-2.64 (m, 2H). MS (ESI): mass calculated for $C_{18}H_{14}Cl_2N_4O$, 372.05; m/z found 373.1 [M+H]$^+$.

Example 10. (2-Chloro-3-(trifluoromethyl)phenyl)(3-(pyrazin-2-yl)-6,7-dihydro-3H-imidazo[4,5-c]pyridin-5(4H)-yl)methanone

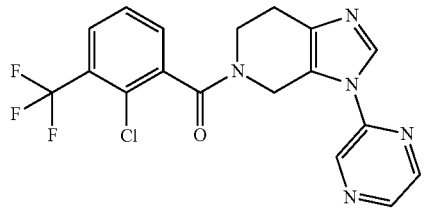 [SMILES: O=C(c1cccc(C(F)(F)F)c1Cl)N1CCc2ncn(-c3cnccn3)c2C1]

Example 10 was made in a manner analogous to Example 1 substituting Intermediate 10 for Intermediate 3 in Step A. MS (ESI): mass calcd. for $C_{18}H_{13}ClF_3N_5O$, 407.1; m/z found, 408.2 [M+H]$^+$.

Example 11. (2-Chloro-3-(trifluoromethyl)phenyl)(1-(5-fluoropyridin-2-yl)-4-methyl-6,7-dihydro-1H-imidazo[4,5-c]pyridin-5(4H)-yl)methanone

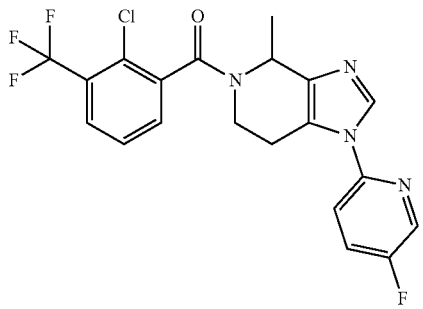 [SMILES: CC1c2ncn(-c3ccc(F)cn3)c2CCN1C(=O)c1cccc(C(F)(F)F)c1Cl]

Step A. (2-Chloro-3-(trifluoromethyl)phenyl)(1-(5-fluoropyridin-2-yl)-4-methyl-1H-imidazo[4,5-c]pyridin-5(4H)-yl)methanone To a solution of Intermediate 1 (0.70 g, 3.27 mmol) in THF (20 mL) was added Intermediate 12 (0.87 g, 3.60 mmol) dropwise. The reaction was allowed to stir for 1 h then cooled to −78° C. To the cooled solution was added 3M MeMgBr in Et$_2$O (1.31 mL, 3.92 mmoL) and the reaction was let come to room temperature. The mixture was then quenched with 1N NaOH (50 mL) and extracted with EtOAc (3×30 mL). The organic layers were combined, dried (Na$_2$SO$_4$), and concentrated. Chromatography of the resulting residue (SiO$_2$; MeOH (NH$_3$):DCM) gave the title compound (770 mg, 54%). $^1$H NMR (400 MHz, CDCl$_3$) δ 8.43-8.34 (m, 1H), 7.92-7.73 (m, 2H), 7.70-7.33 (m, 4H), 6.08 (dtd, J=19.7, 11.7, 8.0 Hz, 3H), 1.54 (t, J=7.0 Hz, 3H). MS (ESI): mass calculated for C$_{20}$H$_{13}$CF$_4$N$_4$O, 436.07; m/z found 437.1 [M+H]$^+$.

Step B. (2-Chloro-3-(trifluoromethyl)phenyl)(1-(5-fluoropyridin-2-yl)-4-methyl-6,7-dihydro-1H-imidazo[4,5-c]pyridin-5(4H)-yl)methanone To a solution of (2-chloro-3-(trifluoromethyl)phenyl)(1-(5-fluoropyridin-2-yl)-4-methyl-1H-imidazo[4,5-c]pyridin-5(4H)-yl)methanone (0.80 g, 1.83 mmol) in degassed EtOH (25 mL) was added 10% palladium on carbon (0.20 mg, 0.19 mmol). The reaction was placed under an atmosphere of hydrogen and let stir for 48 h. The reaction was diluted with DCM and filtered through a pad of Celite©. The solvent was concentrated and chromatography of the resulting residue (SiO$_2$; MeOH (NH$_3$):DCM) gave the title compound (500 mg, 62%). $^1$H NMR (500 MHz, CDCl$_3$) δ 8.45-8.30 (m, 1H), 7.94 (dd, J=18.2, 10.7 Hz, 1H), 7.76 (d, J=5.7 Hz, 1H), 7.67-7.43 (m, 3H), 7.43-7.30 (m, 1H), 5.81 (dd, J=13.3, 6.7 Hz, 1H), 5.07 (d, J=5.6 Hz, 1H), 4.52 (d, J=6.7 Hz, 1H), 3.61-3.31 (m, 1H), 3.08-2.69 (m, 1H), 1.63-145 (m, 3H).

MS (ESI): mass calculated for C$_{20}$H$_{15}$ClF$_4$N$_4$O, 438.08; m/z found 439.1 [M+H]$^+$.

Example 12. (2-Chloro-3-(trifluoromethyl)phenyl)(4-methyl-1-phenyl-6,7-dihydro-1H-imidazo[4,5-c]pyridin-5(4H)-yl)methanone

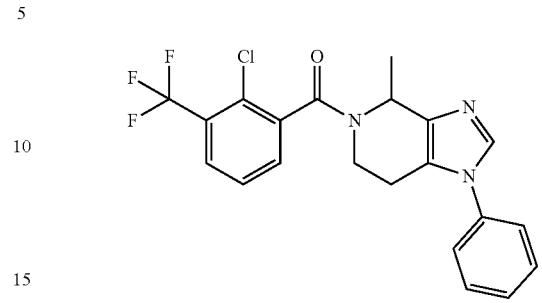

Example 12 was prepared in an analogous way as Example 11 substituting Intermediate 2 for Intermediate 1 in Step A. $^1$H NMR (500 MHz, CDCl$_3$) δ 7.76 (dd, J=5.1, 2.0 Hz, 1H), 7.65 (d, J=15.1 Hz, 1H), 7.59-7.39 (m, 5H), 7.35-7.28 (m, 2H), 5.83 (dd, J=13.5, 6.7 Hz, 1H), 5.07 (dd, J=12.3, 10.6 Hz, 1H), 4.19-3.99 (m, 1H), 3.61-2.93 (m, 1H), 2.75-2.35 (m, 1H), 1.99-1.90 (m, 3H). MS (ESI): mass calculated for C$_{21}$H$_{17}$CF$_3$N$_3$O, 419.08; m/z found 420.1 [M+H]$^+$.

Example 13. (2-Chloro-3-(trifluoromethyl)phenyl)(4-methyl-1-phenyl-6,7-dihydro-1H-imidazo[4,5-c]pyridin-5(4H)-yl)methanone

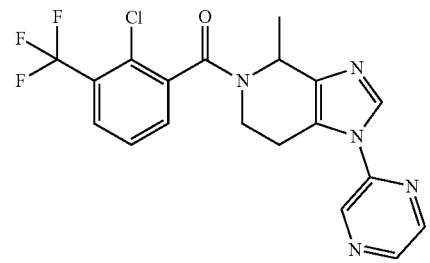 [SMILES: CC1c2ncn(-c3cnccn3)c2CCN1C(=O)c1cccc(C(F)(F)F)c1Cl]

Example 13 was prepared in an analogous way as Example 11 substituting Intermediate 4 for Intermediate 1 in Step A.

MS (ESI): mass calcd. for C$_{19}$H$_{15}$ClF$_3$N$_5$O, 421.1; m/z found, 422.1 [M+H]$^+$.

Example 14. (2-Fluoro-3-(trifluoromethyl)phenyl)(4-methyl-1-(pyrazin-2-yl)-6,7-dihydro-1H-imidazo[4,5-c]pyridin-5(4H)-yl)methanone

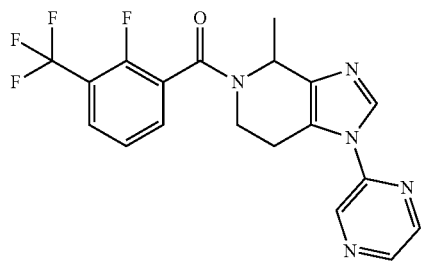 [SMILES: CC1c2ncn(-c3cnccn3)c2CCN1C(=O)c1cccc(C(F)(F)F)c1F]

Example 14 was prepared in an analogous way as Example 11 substituting Intermediate 13 for Intermediate 12 in Step A. MS (ESI): mass calculated for $C_{19}H_{15}F_4N_5O$, 405.12; m/z found 406.1 $[M+H]^+$.

Example 15. (2-Chloro-3-(trifluoromethyl)phenyl) (4-ethyl-1-(pyrazin-2-yl)-6,7-dihydro-1H-imidazo[4,5-c]pyridin-5(4H)-yl)methanone

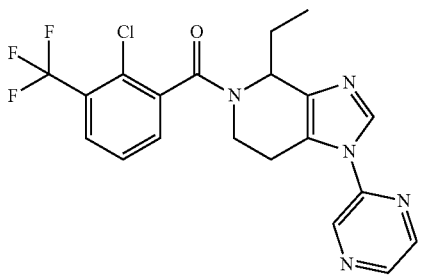 [SMILES: CCC1c2ncn(-c3cnccn3)c2CCN1C(=O)c1cccc(C(F)(F)F)c1Cl]

Example 15 was prepared in an analogous way as Example 11 substituting EtMgBr for MeMgBr and substituting Intermediate 4 for Intermediate 1 in Step A. MS (ESI): mass calculated for $C_{20}H_{17}CF_3N_5O$, 435.11; m/z found 436.1 $[M+H]^+$.

Example 16. (2-Chloro-3-(trifluoromethyl)phenyl) (4-isopropyl-1-(pyrazin-2-yl)-6,7-dihydro-1H-imidazo[4,5-c]pyridin-5(4H)-yl)methanone

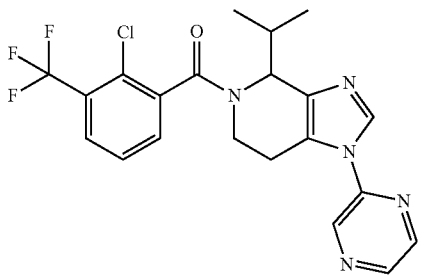 [SMILES: CC(C)C1c2ncn(-c3cnccn3)c2CCN1C(=O)c1cccc(C(F)(F)F)c1Cl]

Example 16 was prepared in an analogous way as Example 11 substituting iPrMgBr for MeMgBr and Intermediate 14 for Intermediate 1 in Step A. MS (ESI): mass calculated for $C_{21}H_{19}ClF_3N_5O$, 449.11; m/z found 450.1 $[M+H]^+$.

Example 17. (2-Chloro-3-(trifluoromethyl)phenyl) (4-methyl-1-(pyridin-2-yl)-6,7-dihydro-1H-imidazo[4,5-c]pyridin-5(4H)-yl)methanone

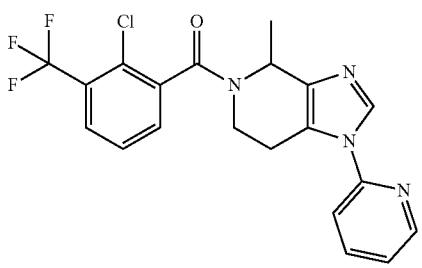

Example 17 was prepared in an analogous way as Example 11 substituting Intermediate 3 for Intermediate 1 in Step A. $^1$H NMR (500 MHz, CDCl$_3$) δ 8.58-8.44 (m, 1H), 7.99 (dt, J=10.8, 8.7 Hz, 1H), 7.93-7.80 (m, 1H), 7.80-7.72 (m, 1H), 7.59-7.43 (m, 2H), 7.41-7.24 (m, 2H), 5.91-5.72 (m, 1H), 5.20-4.58 (m, 1H), 3.63-3.29 (m, 1H), 3.29-2.76 (m, 2H), 1.74-1.60 (m, 3H). MS (ESI): mass calculated for $C_{20}H_{16}CF_3N_4O$, 420.1; m/z found 421.1 $[M+H]^+$.

Example 18. (2-Chloro-3-(trifluoromethyl)phenyl) (1-(4-fluorophenyl)-4-methyl-6,7-dihydro-1H-imidazo[4,5-c]pyridin-5(4H)-yl)methanone

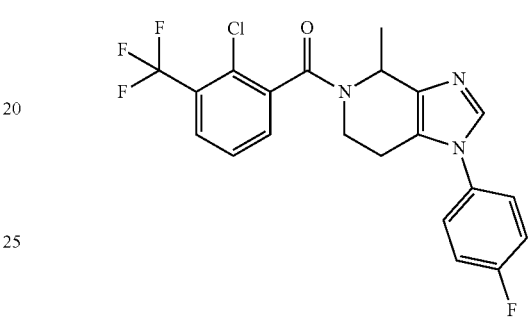

Example 18 was prepared in an analogous way as Example 11 substituting Intermediate 7 for Intermediate 1 in Step A. $^1$H NMR (500 MHz, CDCl$_3$) δ 7.79-7.73 (m, 1H), 7.62 (d, J=1.3 Hz, 1H), 7.58-7.35 (m, 2H), 7.33-7.25 (m, 2H), 7.25-7.15 (m, 2H), 5.94-5.47 (m, 1H), 5.07-4.59 (m, 1H), 4.10-3.73 (m, 1H), 3.59-2.81 (m, 1H), 2.74-2.23 (m, 1H), 1.69-1.50 (m, 3H). MS (ESI): mass calculated for $C_{21}H_{16}ClF_4N_3O$, 437.1; m/z found 438.1 $[M+H]^+$.

Example 19. (2-Fluoro-3-(trifluoromethyl)phenyl) (4-methyl-1-(pyridin-2-yl)-6,7-dihydro-1H-imidazo[4,5-c]pyridin-5(4H)-yl)methanone

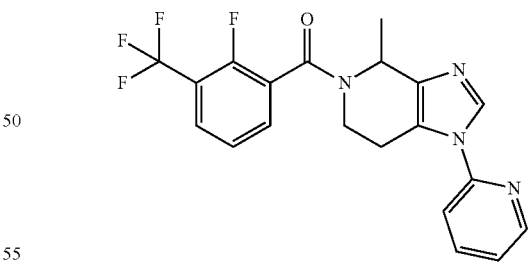

Example 19 was prepared in an analogous way as Example 11 substituting Intermediate 3 for Intermediate 1 and Intermediate 13 for Intermediate 12 in Step A. $^1$H NMR (500 M, CDCl$_3$) δ 8.53 (dd, J=12.7, 11.7 Hz, 1H), 8.03-7.99 (m, 1H), 7.92-7.80 (m, 1H), 7.70-7.60 (m, 2H), 7.40-7.27 (m, 3H), 5.78 (s, 1H), 5.10-4.56 (m, 1H), 3.75-3.31 (m, 1H), 3.31-2.76 (m, 2H), 1.83-1.38 (m, 3H). MS (ESI): mass calculated for $C_{20}H_{16}F_4N_4O$, 404.13; m/z found 405.2 $[M+H]^+$.

Example 20. (2-Fluoro-3-(trifluoromethyl)phenyl)(1-(4-fluorophenyl)-4-methyl-6,7-dihydro-1H-imidazo[4,5-c]pyridin-5(4H)-yl)methanone

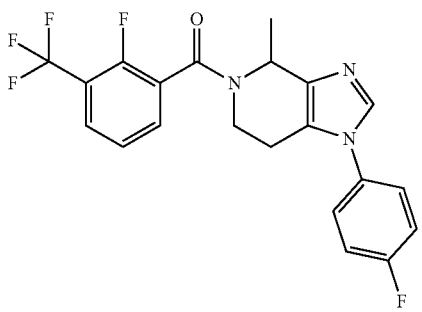 [SMILES: CC1c2ncn(-c3ccc(F)cc3)c2CCN1C(=O)c1cccc(C(F)(F)F)c1F]

Example 20 was prepared in manner analogous to that described in Example 11 substituting Intermediate 7 for Intermediate 1 and Intermediate 13 for Intermediate 12 in Step A. $^1$H NMR (500 MHz, CDCl$_3$) δ 7.70-7.66 (m, 1H), 7.60-7.55 (m, 2H), 7.39-7.25 (m, 3H), 7.25-7.14 (m, 2H), 5.73 (br s, 1H), 5.16-4.53 (m, 1H), 3.48 (d, J=7.7 Hz, 1H), 2.99-2.89 (m, 1H), 2.67-2.09 (m, 1H), 1.65-1.50 (m, 3H). MS (ESI): mass calculated for C$_{21}$H$_{16}$F$_5$N$_3$O, 421.12; m/z found 422.2 [M+H]$^+$.

Example 21. (2-Chloro-3-(trifluoromethyl)phenyl)(1-(3-fluoropyridin-2-yl)-4-methyl-6,7-dihydro-1H-imidazo[4,5-c]pyridin-5(4H)-yl)methanone

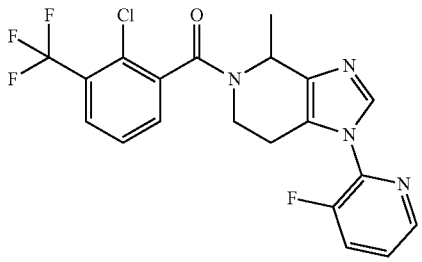 [SMILES: CC1c2ncn(-c3ncccc3F)c2CCN1C(=O)c1cccc(C(F)(F)F)c1Cl]

Example 21 was prepared in a manner analogous to that as described for Example 11 substituting Intermediate 8 for Intermediate 1 in Step A. $^1$H NMR (500 MHz, CDCl$_3$) δ 8.43-8.28 (m, 1H), 7.96-7.92 (m, 1H), 7.81-7.61 (m, 2H), 7.59-7.29 (m, 3H), 5.82 (dt, J=12.9, 6.5 Hz, 1H), 5.06 (dd, J=13.5, 6.7 Hz, 1H), 4.76-4.37 (m, 1H), 3.63-2.62 (m, 2H), 1.86-1.55 (m, 3H). MS (ESI): mass calculated for C$_{20}$H$_{15}$ClF$_4$N$_4$O, 438.09; m/z found 439.2 [M+H]$^+$.

Example 22. (2-Chloro-3-(trifluoromethyl)phenyl)(1-(5-fluoropyrimidin-2-yl)-4-methyl-6,7-dihydro-1H-imidazo[4,5-c]pyridin-5(4H)-yl)methanone

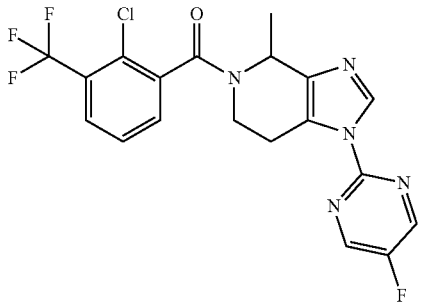

Example 22 was prepared in manner analogous to that described in Example 11 substituting Intermediate 6 for Intermediate 1 in Step A. $^1$H NMR (500 MHz, CDCl$_3$) δ 8.61-8.38 (m, 3H), 7.82-7.70 (m, 1H), 7.58-7.32 (m, 2H), 5.90-5.60 (m, 1H), 5.19-4.54 (m, 1H), 3.66-2.82 (m, 3H), 1.81-1.29 (m, 3H). MS (ESI): mass calculated for C$_{19}$H$_{14}$ClF$_4$N$_5$O, 439.12; m/z found 440.2 [M+H]$^+$.

Example 23. (2-Chloro-3-(trifluoromethyl)phenyl)(4-methyl-1-(pyrimidin-2-yl)-6,7-dihydro-1H-imidazo[4,5-c]pyridin-5(4H)-yl)methanone

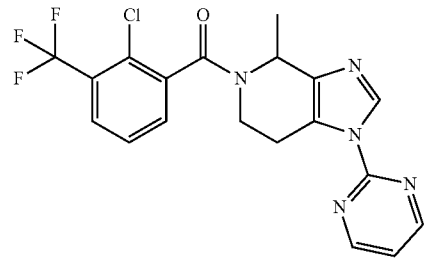 [SMILES: CC1c2ncn(-c3ncccn3)c2CCN1C(=O)c1cccc(C(F)(F)F)c1Cl]

Example 23 was prepared in manner analogous to that described in Example 11 substituting Intermediate 5 for Intermediate 1 in Step A. $^1$H NMR (500 MHz, CDCl$_3$) δ 8.75-8.49 (m, 3H), 7.76 (dt, J=9.6, 4.8 Hz, 1H), 7.59-7.42 (m, 2H), 7.21 (ddd, J=17.7, 8.0, 4.8 Hz, 1H), 5.91-5.67 (m, 1H), 5.16-4.55 (m, 1H), 3.60-2.87 (m, 3H), 1.72-1.56 (m, 3H). MS (ESI): mass calculated for C$_{19}$H$_{15}$ClF$_3$N$_5$O, 421.09; m/z found 422.2 [M+H]$^+$.

Example 24. Ethyl 5-(2-chloro-3-(trifluoromethyl)benzoyl)-1-(pyridin-2-yl)-4,5,6,7-tetrahydro-1H-imidazo[4,5-c]pyridine-4-carboxylate

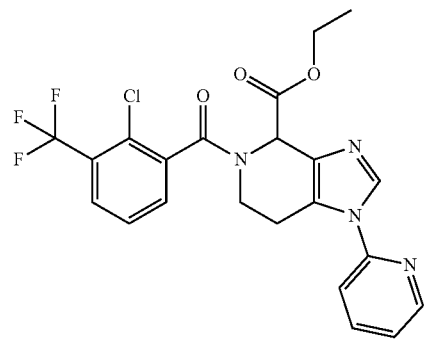 [SMILES: CCOC(=O)C1c2ncn(-c3ccccn3)c2CCN1C(=O)c1cccc(C(F)(F)F)c1Cl]

Step A. 5-tert-Butyl 4-ethyl 6,7-dihydro-1H-imidazo[4,5-c]pyridine-4,5(4H)-dicarboxylate To a solution of ethyl 4,5,6,7-tetrahydro-1H-imidazo[4,5-c]pyridine-4-carboxylate dihydrochloride. (1.00 g, 3.73 mmol) and Et$_3$N (1.04 mL, 7.46 mmol) in DCM (100 mL) was added di-tert-butyl dicarbonate (0.90 g, 4.11 mmol). The reaction was let stir for 4 h and concentrated. Chromatography of the resulting residue (SiO$_2$; MeOH (NH$_3$); DCM) gave the title compound (0.80 mg, 72%). MS (ESI): mass calculated for C$_{14}$H$_{21}$N$_3$O$_4$, 295.2; m/z found 296.2 [M+H]$^+$.

Step B. 5-tert-Butyl 4-ethyl 1-(pyridin-2-yl)-6,7-dihydro-1H-imidazo[4,5-c]pyridine-4,5(4H)-dicarboxylate A solution of 5-tert-butyl 4-ethyl 6,7-dihydro-1H-imidazo[4,5-c]pyridine-4,5(4H)-dicarboxylate (0.50 g, 1.69 mmol), 2-bromo-pyridine (0.27 g, 1.69 mmol), copper (I) oxide (0.03 g, 0.17 mmol), 8-hydroxyquinoline (0.05 g, 0.34 mmol), and Cs$_2$CO$_3$ (1.10 g, 3.39 mmol) in DMSO (2 mL) was irradiated in a microwave apparatus for 1 hour at 140° C. The reaction was diluted with H$_2$O (100 mL) and extracted with EtOAc (75 mL×3). The organic layers were combined, dried (Na$_2$SO$_4$), and concentrated. Chromatography of the resulting residue (SiO$_2$; MeOH (NH$_3$):DCM) gave the title compound (0.25 g, 40%). MS (ESI): mass calculated for C$_{19}$H$_{24}$N$_4$O$_4$, 372.2; m/z found 273.2 [M+H—BOC]$^+$.

Step C. Ethyl 1-(pyridin-2-yl)-4,5,6,7-tetrahydro-1H-imidazo[4,5-c]pyridine-4-carboxylate To a solution of 5-tert-butyl 4-ethyl 1-(pyridin-2-yl)-6,7-dihydro-1H-imidazo[4,5-c]pyridine-4,5(4H)-dicarboxylate (0.20 g, 0.54 mmol) in DCM (25 mL) was added 1N HCl in ether (1.08 mL, 1.08 mmol). The reaction was let stir for 14 h and concentrated to give the desired product as the HCl salt (0.12 g, 72%). MS (ESI): mass calculated for C$_{14}$H$_{16}$N$_4$O$_2$, 272.1; m/z found 273.2 [M+H]$^+$.

Step D. Ethyl 5-(2-chloro-3-(trifluoromethyl)benzoyl)-1-(pyridin-2-yl)-4,5,6,7-tetrahydro-1H-imidazo[4,5-c]pyridine-4-carboxylate A mixture of ethyl 1-(pyridin-2-yl)-4,5,6,7-tetrahydro-1H-imidazo[4,5-c]pyridine-4-carboxylate hydrochloride (0.050 g, 0.18 mmol), 2-chloro-3-trifluoromethyl benzoic acid (0.045 g, 0.20 mmol), HATU (0.077 g, 0.20 mmol), and DIPEA (0.035 mL, 0.20 mmol) in DMF (2 mL) was stirred for 30 min. The reaction was diluted with EtOAc (15 mL) and washed with H$_2$O (3×10 mL). The organic layers were combined, dried (Na$_2$SO$_4$), and concentrated. Chromatography of the resulting residue (SiO$_2$; MeOH (NH$_3$):DCM) gave the title compound (26 mg, 30%). $^1$H NMR (500 MHz, CDCl$_3$) δ 8.58-8.45 (m, 1H), 8.10-7.98 (m, 1H), 7.94-7.82 (m, 1H), 7.82-7.72 (m, 1H), 7.63 (dd, J=7.6, 1.3 Hz, 1H), 7.55-7.28 (m, 3H), 6.23 (dd, J=12.3, 6.3 Hz, 1H), 5.25-5.00 (m, 1H), 4.48-4.06 (m, 2H), 4.01-3.60 (m, 3H), 3.50-2.85 (m, 3H). MS (ESI): mass calculated for C$_{22}$H$_{18}$ClF$_3$N$_4$O$_3$, 478.1; m/z found 479.2 [M+H]$^+$.

Example 25. Ethyl 5-(2,3-dichlorobenzoyl)-1-(pyridin-2-yl)-4,5,6,7-tetrahydro-1H-imidazo[4,5-c]pyridine-4-carboxylate Example 25 was prepared in manner analogous to that described in Example 24 substituting 2,3-dichlorobenzoic acid for 2-chloro-3-trifluoromethyl benzoic acid in Step D. $^1$H NMR (500 MHz, CDCl$_3$) δ 8.58-8.46 (m, 1H), 8.03-7.82 (m, 3H), 7.61-7.43 (m, 1H), 7.43-7.18 (m, 3H), 6.24-6.12 (m, 1H), 5.23-4.99 (m, 1H), 4.44-4.03 (m, 1H), 4.00-3.67 (m, 2H), 3.51-3.00 (m, 2H) 1.35-1.25 (m, 3H). MS (ESI): mass calculated for C$_{21}$H$_{18}$Cl$_2$N$_4$O, 444.1; m/z found 445.2 [M+H]$^+$.

Example 26. Ethyl 5-(2-chloro-3-(trifluoromethyl)benzoyl)-1-phenyl-4,5,6,7-tetrahydro-1H-imidazo[4,5-c]pyridine-4-carboxylate

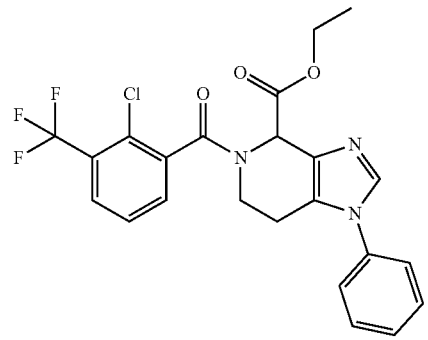

Example 26 was prepared in manner analogous to that described in Example 24 substituting bromobenzene for 2-bromo-pyridine in Step B. $^1$H NMR (500 MHz, CDCl$_3$) δ 7.77 (t, J=7.4 Hz, 1H), 7.70 (s, 1H), 7.62 (dd, J=11.1, 3.1 Hz, 1H), 7.57-7.38 (m, 4H), 7.37-7.27 (m, 2H), 6.23 (s, 1H), 5.26-4.97 (m, 1H), 4.50-3.38 (m, 2H), 3.10-2.90 (m, 1H), 2.77-2.42 (m, 2H), 1.38 (ddd, J=18.6, 13.6, 6.4 Hz, 3H). MS (ESI): mass calculated for C$_{23}$H$_{19}$CF$_3$N$_3$O$_3$, 477.1; m/z found 478.2 [M+H]$^+$.

Example 27. Ethyl 5-(2,3-dichlorobenzoyl)-1-phenyl-4,5,6,7-tetrahydro-1H-imidazo[4,5-c]pyridine-4-carboxylate

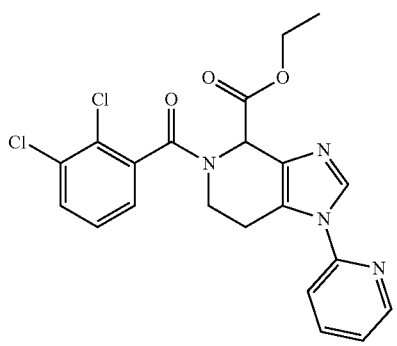 [SMILES: CCOC(=O)C1c2ncn(-c3ccccn3)c2CCN1C(=O)c1cccc(Cl)c1Cl]

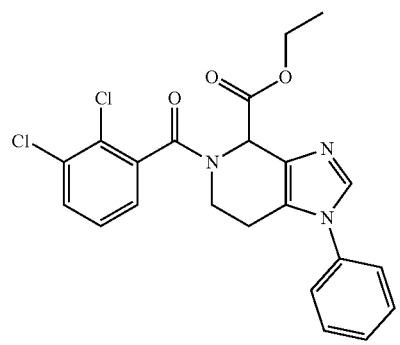 [SMILES: CCOC(=O)C1c2ncn(-c3ccccc3)c2CCN1C(=O)c1cccc(Cl)c1Cl]

Example 27 was prepared in manner analogous to that described in Example 24 substituting bromobenzene for 2-bromo-pyridine in Step B and 2,3-dichlorobenzoic acid for 2-chloro-3-trifluoromethylbenzoic acid in Step D. $^1$H NMR (500 MHz, CDCl$_3$) δ 7.68-7.63 (m, 1H), 7.56-7.38 (m, 4H), 7.38-7.24 (m, 4H), 5.37-4.99 (m, 1H), 4.47-3.60 (m, 3H), 3.07-2.41 (m, 2H), 2.11-1.13 (m, 4H). MS (ESI): mass calculated for $C_{22}H_{19}Cl_2N_3O_3$, 443.1; m/z found 444.1 $[M+H]^+$.

Example 28: Ethyl 5-{[2-chloro-3-(trifluoromethyl) phenyl]carbonyl}-1-pyrazin-2-yl-4,5,6,7-tetrahydro-1H-imidazo[4,5-c]pyridine-4-carboxylate

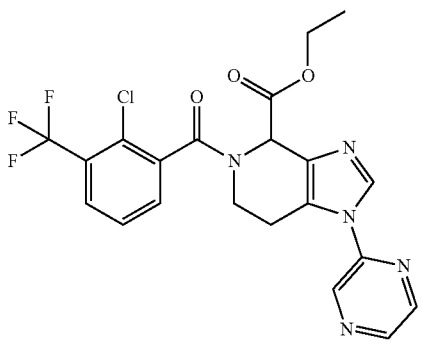 [SMILES: CCOC(=O)C1c2ncn(-c3cnccn3)c2CCN1C(=O)c1cccc(C(F)(F)F)c1Cl]

Example 28 was prepared in manner analogous to that described in Example 24 substituting 2-bromopyrazine for 2-bromo-pyridine in Step B. $^1$H NMR (500 MHz, CDCl$_3$) δ 8.83-8.42 (m, 2H), 8.24-8.00 (m, 1H), 7.84-7.36 (m, 3H), 6.49-6.17 (m, 1H), 4.48-3.47 (m, 4H), 3.52-2.66 (m, 2H), 1.86-1.13 (m, 4H). MS (ESI): mass calculated for $C_{21}H_{17}ClF_3N_5O_3$, 479.1; m/z found 480.1 $[M+H]^+$.

Example 29. Ethyl 5-[(2,3-dichlorophenyl)carbonyl]-1-pyrazin-2-yl-4,5,6,7-tetrahydro-1H-imidazo[4,5-c]pyridine-4-carboxylate

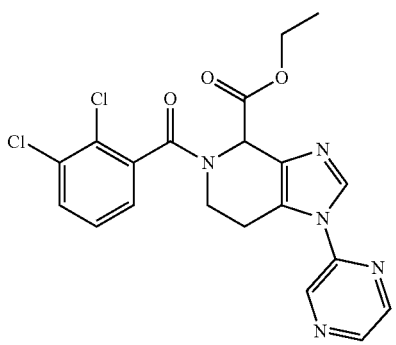 [SMILES: CCOC(=O)C1c2ncn(-c3cnccn3)c2CCN1C(=O)c1cccc(Cl)c1Cl]

Example 29 was prepared in manner analogous to that described in Example 24 substituting 2-bromopyrazine for 2-bromo-pyridine in Step B and 2,3-dichlorobenzoic acid for 2-chloro-3-trifluoromethylbenzoic acid in Step D. $^1$H NMR (500 MHz, CDCl$_3$) δ 8.84-8.42 (m, 2H), 8.18-8.02 (m, 1H), 7.84-7.39 (m, 3H), 6.44-6.16 (m, 1H), 4.51-3.60 (m, 4H), 3.55-2.69 (m, 2H), 1.89-1.18 (m, 4H). MS (ESI): mass calculated for $C_{20}H_{17}Cl_2N_5O_3$, 445.1; m/z found 446.1 $[M+H]^+$.

Example 30. (5-{[2-Chloro-3-(trifluoromethyl)phenyl]carbonyl}-1-phenyl-4,5,6,7-tetrahydro-1H-imidazo[4,5-c]pyridin-4-yl)methanol

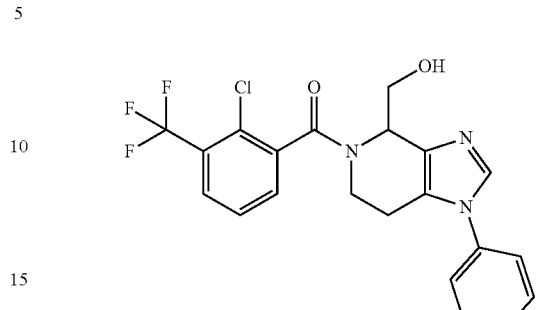

To a solution of Example 26 (0.10 g, 0.21 mmol) in THF (10 mL) at −78° C. was added lithium borohydride (0.02 g, 1.08 mmol). After 14 h the reaction was quenched with 1 N NaOH and extracted with DCM (3×25 mL). The organic layers were combined, dried (Na$_2$SO$_4$), and concentrated. Chromatography of the resulting residue (SiO$_2$; MeOH (NH$_3$):DCM) gave the title compound (0.07 g, 76%). MS (ESI): mass calculated for $C_{21}H_{17}ClF_3N_3O_2$, 435.1; m/z found 436.1 $[M+H]^+$.

Example 31. 1-(5-{[2-Chloro-3-(trifluoromethyl)phenyl]carbonyl}-1-pyridin-2-yl-4,5,6,7-tetrahydro-1H-imidazo[4,5-c]pyridin-4-yl)-N,N-dimethylmethanamine

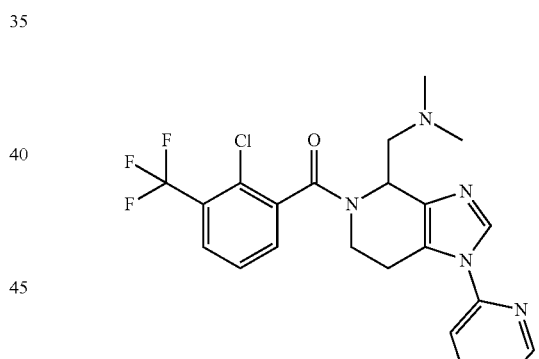

Step A. (5-(2-chloro-3-(trifluoromethyl)benzoyl)-1-(pyridin-2-yl)-4,5,6,7-tetrahydro-1H-imidazo[4,5-c]pyridin-4-yl)methyl sulfochloridate A solution of (2-chloro-3-(trifluoromethyl)phenyl)(4-(hydroxymethyl)-1-(pyridin-2-yl)-6,7-dihydro-1H-imidazo[4,5-c]pyridin-5(4H)-yl)methanone-0.10 g, 0.23 mmol), methane sulfonyl chloride (0.27 mg, 0.23 mmol), and Et$_3$N (0.32 mL, 0.23 mmol) in DCM (10 mL) was stirred for 1 h. The reaction was diluted with H$_2$O and extracted with DCM (3×10 mL). The organic layers were combined, dried (Na$_2$SO$_4$), and concentrated. Chromatography of the resulting residue (SiO$_2$; MeOH (NH$_3$):DCM) gave the title compound (0.04 g, 30%). MS (ESI): mass calculated for $C_{21}H_1ClF_3N_4O_4S$, 514.1; m/z found 515.1 $[M+H]^+$.

Step B. 1-(5-{[2-Chloro-3-(trifluoromethyl)phenyl]carbonyl}-1-pyridin-2-yl-4,5,6,7-tetrahydro-1H-imidazo[4,5-c]pyridin-4-yl)-N,N-dimethylmethanamine A solution of (5-(2-chloro-3-(trifluoromethyl)benzoyl)-1-(pyridin-2-yl)-4,5,6,7-tetrahydro-1H-imidazo[4,5-c]pyridin-4-yl)methyl sulfochloridate (0.05 g, 0.097 mmol), dimethylamine hydrochloride (0.016 g, 0.19 mmol), and Na$_2$CO$_3$ (0.021 g, 0.19 mmol) in CH$_3$CN was irradiated in a microwave at 100° C. for 1 h. The reaction was allowed to cool and concentrated.

Chromatography of the resulting residue (SiO$_2$; MeOH (NH$_3$):DCM) gave the title compound (0.02 g, 44%). $^1$H NMR (500 MHz, CDCl$_3$) δ 8.54-8.51 (m, 1H), 8.10-7.62 (m, 4H), 7.58-7.28 (m, 3H), 5.30 (s, 1H), 4.00-3.42 (m, 2H), 3.35-2.77 (m, 2H), 2.77-2.40 (m, 2H), 2.09-2.03 (m, 6H). MS (ESI): mass calculated for C$_{22}$H$_{21}$ClF$_3$N$_5$O, 463.1; m/z found, m/z found 464.2 [M+H]$^+$.

Example 32. (2-Chloro-3-(trifluoromethyl)phenyl)(4-(fluoromethyl)-1-(pyridin-2-yl)-6,7-dihydro-1H-imidazo[4,5-c]pyridin-5(4H)-yl)methanone

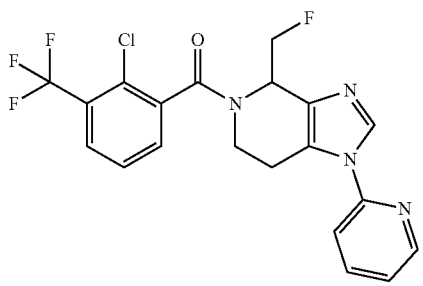 [SMILES: O=C(c1cccc(C(F)(F)F)c1Cl)N1CCc2c(ncn2-c2ccccn2)C1CF]

MS (ESI): mass calculated for C$_{20}$H$_{15}$ClF$_4$N$_4$O, 438.09; m/z found 439.1 [M+H]$^+$.

Example 33. 5-{[2-Chloro-3-(trifluoromethyl)phenyl]carbonyl}-1-pyridin-2-yl-4,5,6,7-tetrahydro-1H-imidazo[4,5-c]pyridine-4-carboxylic acid

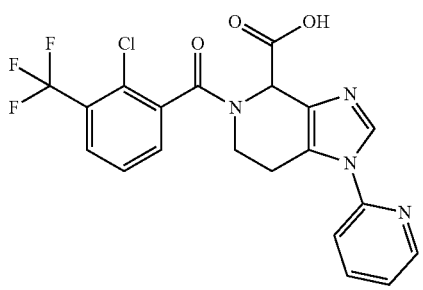 [SMILES: O=C(O)C1c2ncn(-c3ccccn3)c2CCN1C(=O)c1cccc(C(F)(F)F)c1Cl]

A solution of Example 24 (0.10 g, 0.21 mmol) and KOH (0.012 g, 0.21 mmol) in EtOH (5 mL) was heated at 80° C. After 4 h, the reaction was concentrated to give the title product as the potassium salt (0.07 g, 70%). MS (ESI): mass calculated for C$_{20}$H$_{14}$CF$_3$N$_4$O$_3$, 450.07; m/z found, 451.1 [M+H]$^+$.

Example 34. 5-{[2-Chloro-3-(trifluoromethyl)phenyl]carbonyl}-N,N-dimethyl-1-pyridin-2-yl-4,5,6,7-tetrahydro-1H-imidazo[4,5-c]pyridine-4-carboxamide

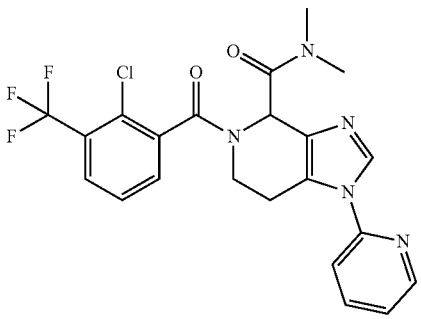 [SMILES: CN(C)C(=O)C1c2ncn(-c3ccccn3)c2CCN1C(=O)c1cccc(C(F)(F)F)c1Cl]

A solution of 5-{[2-chloro-3-(trifluoromethyl)phenyl]carbonyl}-1-pyridin-2-yl-4,5,6,7-tetrahydro-1H-imidazo[4,5-c]pyridine-4-carboxylic acid (0.05 g, 0.10 mmol), dimethylamine hydrochloride (0.01 g, 0.10 mmol), HATU (0.04 g, 0.11 mmol), and DIPEA (0.05 mL, 0.26 mmol) in DMF (2 mL) was stirred for 30 min. The reaction was diluted with EtOAc (15 mL) and washed with H$_2$O (3×10 mL). The organic layers were combined, dried (Na$_2$SO$_4$), and concentrated. Chromatography of the resulting residue (SiO$_2$; MeOH (NH$_3$):DCM) gave the title compound (26 mg, 53%). $^1$H NMR (500 MHz, CDCl$_3$) δ 8.60-8.35 (m, 1H), 8.09-7.69 (m, 3H), 7.65-7.27 (m, 4H), 6.64-6.46 (m, 1H), 4.17 (tt, J=19.0, 5.6 Hz, 1H), 3.72-3.53 (m, 3H), 3.33-2.85 (m, 6H). MS (ESI): mass calculated for C$_{22}$H$_{19}$CF$_3$N$_5$O$_2$, 477.12; m/z found, 478.1 [M+H]$^+$.

Example 35. 4-(Azetidin-1-ylcarbonyl)-5-{[2-chloro-3-(trifluoromethyl)phenyl]carbonyl}-1-pyridin-2-yl-4,5,6,7-tetrahydro-1H-imidazo[4,5-c]pyridine

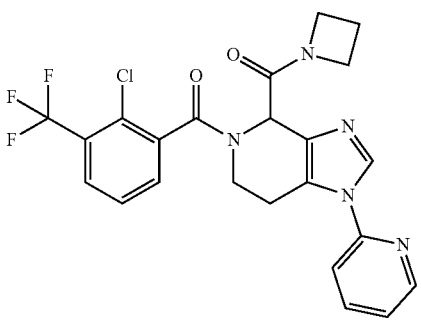 [SMILES: O=C(C1c2ncn(-c3ccccn3)c2CCN1C(=O)c1cccc(C(F)(F)F)c1Cl)N1CCC1]

Example 35 was prepared in a manner analogous to Example 34 substituting azetidine hydrochloride for dimethylamine hydrochloride. MS (ESI): mass calculated for C$_{23}$H$_{19}$CF$_3$N$_5$O$_2$, 489.118; m/z found, 490.2 [M+H]$^+$.

Intermediate 233. (1-phenyl-4,5,6,7-tetrahydro-1H-imidazo[4,5-c]pyridin-4-yl)methanol

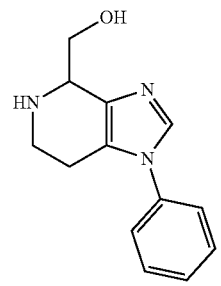 [SMILES: OCC1NCCc2c1ncn2-c1ccccc1]

Step A. 5-tert-butyl 4-ethyl 1-phenyl-6,7-dihydro-1H-imidazo[4,5-c]pyridine-4,5(4H)-dicarboxylate A solution of 5-tert-butyl 4-ethyl 6,7-dihydro-1H-imidazo[4,5-c]pyridine-4,5(4H)-dicarboxylate (0.65 g, 2.20 mmol), iodobenzene (0.45 g, 2.20 mmol), copper (I) oxide (0.03 g, 0.22 mmol), 8-hydroxyquinoline (0.06 g, 0.44 mmol), and $Cs_2CO_3$ (1.40 g, 4.40 mmol) in DMSO (2 mL) was irradiated in a microwave apparatus for 1 hour at 140° C. The reaction was diluted with $H_2O$ (100 mL) and extracted with EtOAc (75 mL×3). The organic layers were combined, dried ($Na_2SO_4$), and concentrated. Chromatography of the resulting residue ($SiO_2$; MeOH ($NH_3$):DCM) gave the title compound (0.41 g, 50%). MS (ESI): mass calculated for $C_{20}H_{25}N_3O_4$, 371.2; m/z found 272.2 [M+H—BOC]*.

Step B. ethyl 1-phenyl-4,5,6,7-tetrahydro-1H-imidazo[4,5-c]pyridine-4-carboxylate To a solution of 5-tert-butyl 4-ethyl 1-phenyl-6,7-dihydro-1H-imidazo[4,5-c]pyridine-4,5(4H)-dicarboxylate (0.40 g, 1.07 mmol) in DCM (25 mL) was added 1N HCl in ether (1.2 mL, 1.20 mmol). The reaction was allowed to stir for 14 h and concentrated to give the desired product as the HCl salt (0.320 g, 96%). MS (ESI): mass calculated for $C_{15}H_{17}N_3O_2$, 271.13; m/z found 272.2 [M+H]⁺.

Step C. (1-phenyl-4,5,6,7-tetrahydro-1H-imidazo[4,5-c]pyridin-4-yl)methanol To a solution of ethyl 1-phenyl-4,5,6,7-tetrahydro-1H-imidazo[4,5-c]pyridine-4-carboxylate (0.10 g, 0.37 mmol) in THF (10 mL) at −78° C. was added $LiAlH_4$ (1M in THF) (1.1 mL, 1.10 mmol). After 14 h the reaction was quenched with 1 N NaOH, Rochelle's salt, and extracted with DCM (3×25 mL). The organic layers were combined, dried ($Na_2SO_4$), and concentrated.

Chromatography of the resulting residue ($SiO_2$; MeOH ($NH_3$):DCM) gave the title compound (0.06 g, 71%). MS (ESI): mass calculated for $C_{13}H_{15}N_3O$, 229.12; m/z found 230.1 [M+H]⁺.

Intermediate XXX. 5-tert-butyl 4-ethyl 1-(pyridin-2-yl)-6,7-dihydro-1H-imidazo[4,5-c]pyridine-4,5(4H)-dicarboxylate

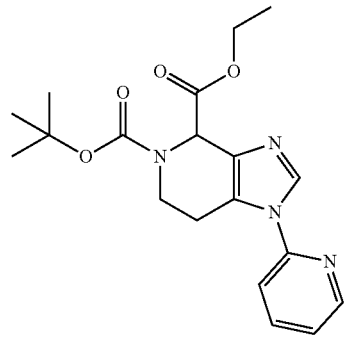 [SMILES: CCOC(=O)C1c2ncn(-c3ccccn3)c2CCN1C(=O)OC(C)(C)C]

Intermediate XXX was prepared in a similar manner as Intermediate 233 substituting 2-bromopyridine in Step A. MS (ESI): mass calculated for $C_{19}H_{24}N_4O_4$, 372.18; m/z found 373.2 [M+H]⁺.

Example 36. (5-{[2-Chloro-3-(trifluoromethyl)phenyl]carbonyl}-1-phenyl-4,5,6,7-tetrahydro-1H-imidazo[4,5-c]pyridin-4-yl)methyl 2-chloro-3-(trifluoromethyl)benzoate

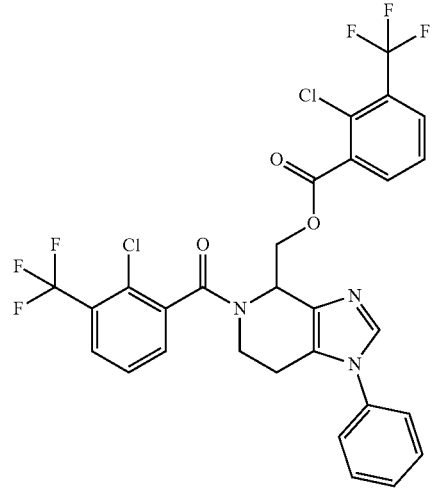 [SMILES: O=C(OCC1c2ncn(-c3ccccc3)c2CCN1C(=O)c1cccc(C(F)(F)F)c1Cl)c1cccc(C(F)(F)F)c1Cl]

A solution of Intermediate 233. (0.050 g, 0.22 mmol), 2-chloro-3-trifluoromethyl benzoic acid (0.054 g, 0.24 mmol), HATU (0.091 g, 0.24 mmol), and DIPEA (0.04 mL, 0.24 mmol) in DMF (2 mL) was stirred for 30 min. The reaction was diluted with EtOAc (15 mL) and washed with $H_2O$ (3×10 mL). The organic layers were combined, dried ($Na_2SO_4$), and concentrated.

Chromatography of the resulting residue ($SiO_2$; MeOH ($NH_3$):DCM) gave the title compound (30 mg, 21%). MS (ESI): mass calculated for $C_{29}H_{19}C_2F_6N_3O_3$, 641.07; m/z found, 642.1 [M+H]⁺.

Example 37. (2-Chloro-3-(trifluoromethyl)phenyl)(2-methyl-1-phenyl-6,7-dihydro-1H-imidazo[4,5-c]pyridin-5(4H)-yl)methanone

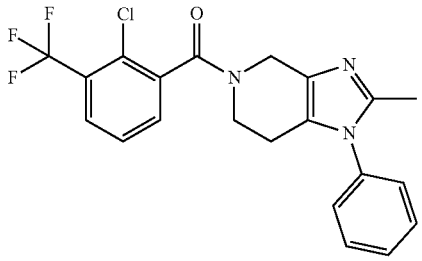 [SMILES: Cc1nc2c(n1-c1ccccc1)CCN(C(=O)c1cccc(C(F)(F)F)c1Cl)C2]

Step 1: 2-methyl-1-phenyl-1H-imidazo[4,5-c]pyridine

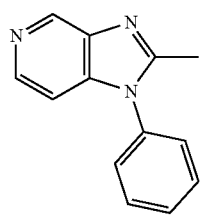 [SMILES: Cc1nc2cnccc2n1-c1ccccc1]

To a solution of N₄-phenylpyridine-3,4-diamine (8.08 g, 43.7 mmol) and p-toluenesulfonic acid (0.379 g, 2.2 mmol) was added trimethyl orthoformate (83 mL, 655 mmol). The solution was heated to 80° C. for 4 h after which time it was cooled to rt and concentrated. Flash chromatography (1:1 petroleum ether:ethyl acetate) provided the product as a pale yellow solid (4.7 g, 75%).

Step 2: 2-methyl-1-phenyl-4,5,6,7-tetrahydro-1H-imidazo[4,5-c]pyridine

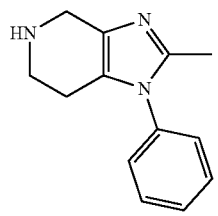 [SMILES: Cc1nc2c(n1-c1ccccc1)CCNC2]

To a solution of 2-methyl-1-phenyl-1H-imidazo[4,5-c]pyridine (1.05 g, 5 mmol) in CH₂Cl₂ (5 mL) was added benzyl bromide (3.0 mL, 25 mmol). The solution stirred at rt for 4 h after which time it was concentrated to dryness. The residue was dissolved in MeOH (10 mL) and to it 20% Pd(OH)₂/C (0.24 g) was added. The reaction was stirred under an atmosphere of hydrogen for 3 h at rt. The mixture was filtered and the filtrate was concentrated under reduced pressure to a white solid (0.60 g, 56% over 2 steps).

Step 3: (2-Chloro-3-(trifluoromethyl)phenyl)(2-methyl-1-phenyl-6,7-dihydro-1H-imidazo[4,5-c]pyridin-5(4H)-yl)methanone

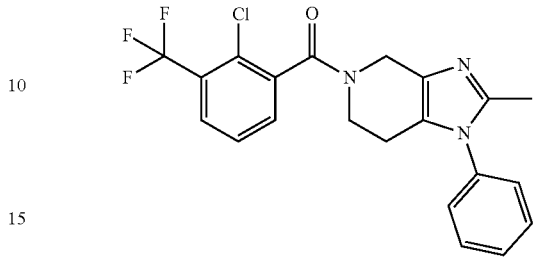

To a solution of 2-methyl-1-phenyl-4,5,6,7-tetrahydro-1H-imidazo[4,5-c]pyridine (114 mg, 0.51 mmol), 2-chloro-3-trifluoromethylcarboxylic acid (90 mg, 0.42 mmol) and HATU (319 mg, 0.84 mmol) in DCM (15 mL) was added NEt₃ (0.16 mL, 1.26 mmol). The mixture was stirred at rt overnight after which time the reaction was concentrated under reduced pressure and purified by basic HPLC to provide the product as a white solid (100 mg, 55%). $^1$H NMR (400 MHz, DMSO-$d_6$) δ 8.03-7.89 (m, 1H), 7.80-7.54 (m, 7H), 5.06-4.27 (m, 2H), 4.14-3.38 (m, 2H), 2.63-2.32 (m, 5H). MS (ESI): mass calculated for $C_{21}H_{17}ClF_3N_3O$, 419.10; m/z found, 420.0 [M+H]$^+$.

Example 38. (2-Chloro-3-(trifluoromethyl)phenyl)(1-phenyl-2-(trifluoromethyl)-6,7-dihydro-1H-imidazo[4,5-c]pyridin-5(4H)-yl)methanone

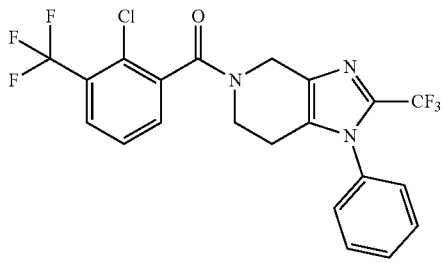 [SMILES: O=C(c1cccc(C(F)(F)F)c1Cl)N1CCc2c(nc(C(F)(F)F)n2-c2ccccc2)C1]

Step A: 1-phenyl-2-(trifluoromethyl)-4,5,6,7-tetrahydro-1H-imidazo[4,5-c]pyridine 1-phenyl-2-(trifluoromethyl)-4,5,6,7-tetrahydro-1H-imidazo[4,5-c]pyridine. The title compound was made in a manner analogous to Example 61 step 2 substituting 1-phenyl-2-(trifluoromethyl)-1H-imidazo[4,5-c]pyridine for 1-phenyl-1H-[1,2,3]triazolo[4,5-c]pyridine.

Step B: (2-Chloro-3-(trifluoromethyl)phenyl)(1-phenyl-2-(trifluoromethyl)-6,7-dihydro-1H-imidazo[4,5-c]pyridin-5(4H)-yl)methanone was made in manner analogous to Example 65 using 1-phenyl-2-(trifluoromethyl)-4,5,6,7-tetrahydro-1H-imidazo[4,5-c]pyridine. MS (ESI): mass calcd. for $C_{21}H_{14}ClF_6N_3O$, 473.1; m/z found, 474.1 [M+H]$^+$. $^1$H NMR (400 MHz, CDCl₃) δ 7.59-7.40 (ddd, J=3.8, 2.6, 1.1 Hz, 3H), 7.32-7.27 (dd, J=6.7, 3.0 Hz, 2H), 4.02-3.90 (t, J=1.6 Hz, 2H), 3.18-3.06 (t, J=5.7 Hz, 2H), 2.46-2.30 (ddt, J=7.0, 5.6, 1.3 Hz, 2H).

Example 39. 5-{[2-Chloro-3-(trifluoromethyl)phenyl]carbonyl}-4-(trifluoromethyl)-4,5,6,7-tetrahydro-1H-imidazo[4,5-c]pyridine

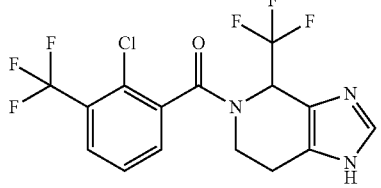

Step A. 4-(trifluoromethyl)-4,5,6,7-tetrahydro-1H-imidazo[4,5-c]pyridine hydrochloride A suspension of histamine dihydrochloride (1.0 g, 5.3 mmol) in $H_2O$ (20 mL) was cooled in an ice bath. To this suspension was added solid KOH (85%) (0.9 g, 16 mmol) followed by trifluoroacetaldehyde hydrate (0.5 g, 5.3 mmol). The reaction was allowed to warm to rt and heated to 80° C. After 6 h, the reaction was cooled to rt, acidified using 6N HCl, and concentrated. The resulting residue was dissolved in hot EtOH and filtered through Celite©. The solvent was evaporated to give the product as the HCl salt. This was purified by dissolving in minimal water and loading on silica ($SiO_2$; MeOH ($NH_3$):DCM) to give the title compound (0.6 g, 45%).

Step B. (2-Chloro-3-(trifluoromethyl)phenyl)(4-(trifluoromethyl)-6,7-dihydro-1H-imidazo[4,5-c]pyridin-5(4H)-yl)methanone A solution of 4-(trifluoromethyl)-4,5,6,7-tetrahydro-1H-imidazo[4,5-c]pyridine hydrochloride (0.10 g, 0.44 mmol), 2-chloro-3-trifluoromethyl benzoic acid (0.10 g, 0.44 mmol), HATU (0.18 g, 0.48 mmol, and DIPEA (0.19 mL, 1.1 mmol) in DMF (2 mL) was stirred for 30 min. The reaction was diluted with EtOAc (15 mL) and washed with $H_2O$ (3×10 mL). The organic layers were combined, dried ($Na_2SO_4$), and concentrated. Chromatography of the resulting residue ($SiO_2$; MeOH ($NH_3$):DCM) gave the title compound (0.06 g, 34%). $^1H$ NMR (500 MHz, $CDCl_3$) δ 8.02-7.94 (m, 1H), 7.80-7.58 (m, 1H), 7.51-7.39 (m, 1H), 6.60-6.50 (m, 1H), 4.42 (q, J=7.6 Hz, 1H), 2.95 (s, 4H). MS (ESI): mass calculated for $C_{15}H_{10}ClF_6N_3O$, 397.042; m/z found 398.1 $[M+H]^+$.

Example 40. (R*)-(2-chloro-3-(trifluoromethyl)phenyl)(1-(5-fluoropyridin-2-yl)-4-methyl-6,7-dihydro-1H-imidazo[4,5-c]pyridin-5(4H)-yl)methanone

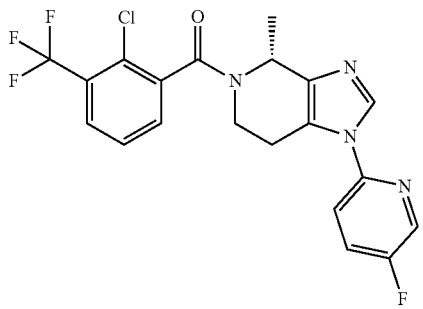 [SMILES: C[C@@H]1c2ncn(-c3ccc(F)cn3)c2CCN1C(=O)c1cccc(C(F)(F)F)c1Cl]

The title compound, absolute configuration unknown, was obtained as a single enantiomer by Chiral SFC purification of Example 11 performed using CHIRALCEL OD-H (5 μm, 250×20 mm) and a mobile phase of 70% $CO_2$, 30% EtOH. The enantiomeric purity was confirmed by analytical SFC using a CHIRALCEL OD-H (250×4.6 mm) and a mobile phase of 70% $CO_2$, 30% EtOH over 7 minutes. (100% single enantiomer, 2.29 min retention time). MS (ESI): mass calculated for $C_{20}H_{15}ClF_4N_4O$, 438.1; m/z found, 439.3 $[M+H]^+$.

Example 41. (4S*)-5-{[2-Fluoro-3-(trifluoromethyl)phenyl]carbonyl}-4-methyl-1-pyridin-2-yl-4,5,6,7-tetrahydro-1H-imidazo[4,5-c]pyridine

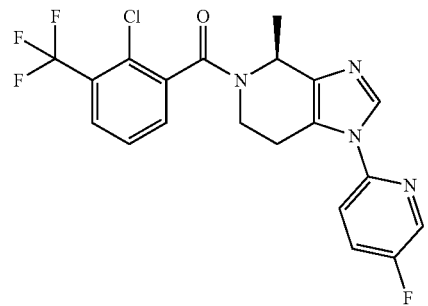 [SMILES: C[C@H]1c2ncn(-c3ccc(F)cn3)c2CCN1C(=O)c1cccc(C(F)(F)F)c1Cl]

The title compound, absolute configuration unknown, was obtained as a single enantiomer by Chiral SFC purification of Example 11 performed using CHIRALCEL OD-H (5 μm, 250×20 mm) and a mobile phase of 70% $CO_2$, 30% EtOH. The enantiomeric purity was confirmed by analytical SFC using a CHIRALCEL OD-H (250×4.6 mm) and a mobile phase of 70% $CO_2$, 30% EtOH over 7 minutes. (100% single enantiomer, 2.81 min retention time). MS (ESI): mass calculated for $C_{20}H_{15}ClF_4N_4O$, 438.1; m/z found, 439.3$[M+H]^+$.

Example 42. (4R*)-5-{[2-Fluoro-3-(trifluoromethyl)phenyl]carbonyl}-4-methyl-1-pyridin-2-yl-4,5,6,7-tetrahydro-1H-imidazo[4,5-c]pyridine

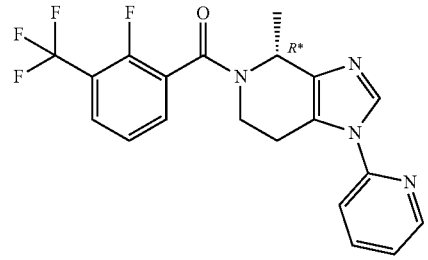 [SMILES: C[C@@H]1c2ncn(-c3ccccn3)c2CCN1C(=O)c1cccc(C(F)(F)F)c1F]

Example 42 was prepared in a manner analogous to example 40 using example 19 as starting material. Purification by LC Gilson prep system-stationary phase Lux 5 um Amylose-2, 30 mm×250 nm; mobile phase 20% EtOH+ 0.2% TEA, 80% hexanes. $^1H$ NMR (500 MHz, $CDCl_3$) δ 8.60-8.45 (m, 1H), 7.99 (t, J=17.2 Hz, 1H), 7.91-7.79 (m, 1H), 7.75-7.46 (m, 2H), 7.42-7.28 (m, 3H), 5.79 (s, 1H), 5.09-4.59 (m, 1H), 3.73-3.37 (m, 1H), 3.37-2.84 (m, 2H), Example 43. (4S*)-5-{[2-Fluoro-3-(trifluoromethyl)phenyl]carbonyl}-4-methyl-1-pyridin-2-yl-4,5,6,7-tetrahydro-1H-imidazo[4,5-c]pyridine

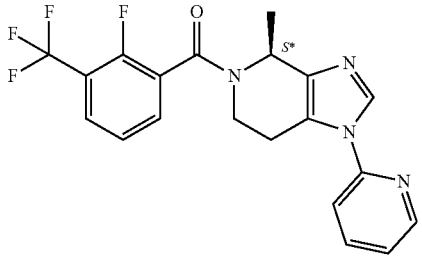 [SMILES: C[C@H]1c2ncn(-c3ccccn3)c2CCN1C(=O)c1cccc(C(F)(F)F)c1F]

Example 43 was prepared in a manner analogous to example 40 using example 19 as starting material. Purification by LC Gilson prep system-stationary phase Lux Sum Amylose-2, 30 mm×250 mm; mobile phase 20% EtOH+0.2% TEA, 80% hexanes. $^1$H NMR (500 MHz, CDCl$_3$) δ 8.59-8.46 (m, 1H), 8.03-7.99 (m, 1H), 7.93-7.81 (m, 1H), 7.74-7.48 (m, 2H), 7.42-7.28 (m, 3H), 5.78 (s, 1H), 5.14-4.53 (m, 1H), 3.76-3.34 (m, 1H), 3.31-2.82 (m, 2H), 1.68-1.33 (m, 3H). MS (ESI): mass calculated for C$_{20}$H$_{16}$F$_4$N$_4$O, 404.126; m/z found, 405.2 [M+H]$^+$.

Example 44. (4R*)-5-{[2-Chloro-3-(trifluoromethyl)phenyl]carbonyl}-4-methyl-1-pyridin-2-yl-4,5,6,7-tetrahydro-1H-imidazo[4,5-c]pyridine

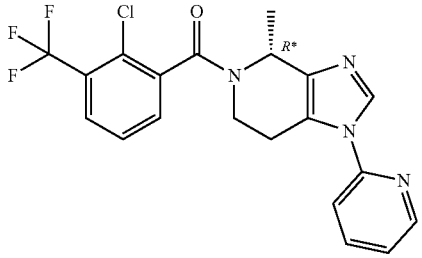

Example 44 was prepared in a manner analogous to example 40 using Example 17 as starting material. Purification by SFC JASCO prep system-stationary phase Chiralpak OD 5 um, 21 mm×250 mm; mobile phase 10% IPA+0.2% IPamine, 90% CO$_2$. $^1$H NMR (600 MHz, CDCl$_3$) δ 8.59-8.45 (m, 1H), 8.04-7.98 (m, 1H), 7.88-7.84 (m, 1H), 7.76 (dd, J=6.3, 4.7 Hz, 1H), 7.58-7.28 (m, 4H), 5.86-5.79 (m, 1H), 4.58 (d, J=6.5 Hz, 1H), 4.12-3.92 (m, 1H), 3.34-2.80 (m, 2H), 1.69-1.44 (m, 3H). (ESI): mass calculated for C$_{20}$H$_{16}$ClF$_3$N$_4$O, 420.10; m/z found, 421.1 [M+H]$^+$.

Example 45. (4S*)-5-{[2-Chloro-3-(trifluoromethyl)phenyl]carbonyl}-4-methyl-1-pyridin-2-yl-4,5,6,7-tetrahydro-1H-imidazo[4,5-c]pyridine

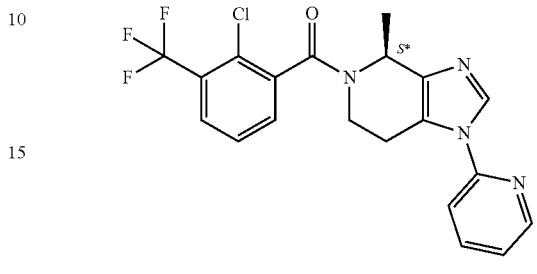

Example 45 was prepared in a manner analogous to example 40 using Example 17 as starting material. Purification by SFC JASCO prep system-stationary phase Chiralpak OD 5um, 21 mm×250 mm; mobile phase 10% IPA+0.2% IPamine, 90% CO$_2$. $^1$H NMR (600 MHz, CDCl$_3$) δ 8.59-8.45 (m, 1H), 8.03-7.98 (m 1H), 7.91-7.81 (m, 1H), 7.81-7.72 (m, 1H), 7.59-7.28 (m, 4H), 5.90-5.74 (m, 1H), 5.07 (dd, J=11.3, 4.4 Hz, 1H), 4.78-4.45 (m, 1H), 4.03 (dt, J=12.2, 6.1 Hz, 1H), 3.62-2.79 (m, 4H). MS (ESI): mass calculated for C$_{20}$H$_{16}$CF$_3$N$_4$O, 420.10; m/z found, 421.1 [M+H]$^+$.

Example 46. (4R*)-5-{[2-Chloro-3-(trifluoromethyl)phenyl]carbonyl}-1-(4-fluorophenyl)-4-methyl-4,5,6,7-tetrahydro-1H-imidazo[4,5-c]pyridine

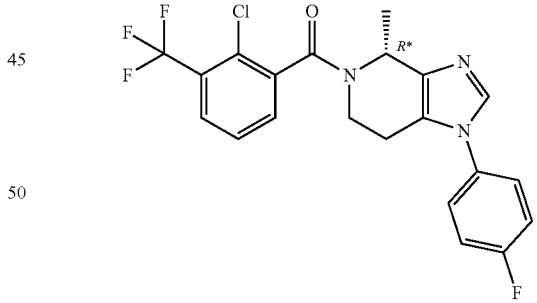

Example 46 was prepared in a manner analogous to Example 40 using Example 18 as starting material. Purification by LC Gilson prep system-stationary phase Chiralpak AD-H 5 um, 21 mm×250 mm; mobile phase 10% EtOH+0.2% TEA, 90% hexanes. $^1$H NMR (500 MHz, CDCl$_3$) δ 7.76 (dd, J=5.1, 3.2 Hz, 1H), 7.62 (s, 1H), 7.58-7.36 (m, 2H), 7.33-7.24 (m, 2H), 7.24-7.14 (m, 2H), 5.89-5.78 (m, 1H), 5.07 (dt, J=12.3, 6.0 Hz, 1H), 4.77-4.39 (m, 1H), 3.62-2.86 (m, 1H), 2.77-2.28 (m, 1H), 1.80-1.10 (m, 3H). MS (ESI): mass calculated for C$_{21}$H$_{16}$ClF$_4$N$_3$O, 437.10; m/z found, 438.1 [M+H]$^+$.

Example 47. (4S)-5-{[2-Chloro-3-(trifluoromethyl)phenyl]carbonyl}-1-(4-fluorophenyl)-4-methyl-4,5,6,7-tetrahydro-1H-imidazo[4,5-c]pyridine

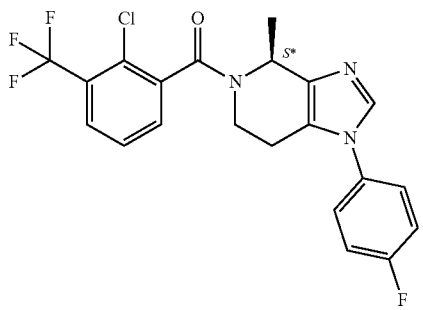 [SMILES: C[C@H]1c2ncn(-c3ccc(F)cc3)c2CCN1C(=O)c1cccc(C(F)(F)F)c1Cl]

Example 47 was prepare in a manner analogous to Example 40 using Example 18 as starting material. Purification by LC Gilson prep system-stationary phase Chiralpak AD-H 5um, 21 mm×250 mm; mobile phase 10% EtOH+0.2% TEA, 90% hexanes. MS (ESI): mass calculated for C$_{21}$H$_{16}$ClF$_4$N$_3$O, 437.10; m/z found, 438.1 [M+H]$^+$.

Example 48: 5-{[2-Chloro-3-(trifluoromethyl)phenyl]carbonyl}-4,5,6,7-tetrahydro-3H-imidazo[4,5-c]pyridine

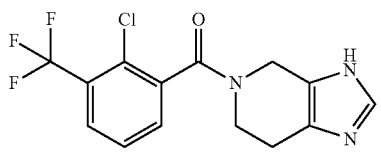 [SMILES: O=C(c1cccc(C(F)(F)F)c1Cl)N1CCc2nc[nH]c2C1]

The title compound was prepared in a manner analogous to Example 1, Step C substituting 4,5,6,7-tetrahydro-3H-imidazo[4,5-c]pyridine for 1-(pyridin-2-yl)-4,5,6,7-tetrahydro-1H-imidazo[4,5-c]pyridine. MS (ESI): mass calcd. for C$_{14}$H$_{11}$ClF$_3$N$_3$O, 329.0; m/z found, 330.2 [M+H]$^+$. $^1$H NMR (500 MHz, CDCl$_3$) δ 7.79-7.73 (m, 1H), 7.57 (s, 0.5H), 7.53-7.39 (m, 2.5H), 5.02-4.71 (m, 1H), 4.39-4.19 (m, 1.5H), 3.99 (dt, J=12.6, 6.0 Hz, 0.5H), 3.60-3.47 (m, 1H), 2.84 (td, J=5.3, 2.6 Hz, 1H), 2.77-2.58 (m, 1H).

Example 49: 5-{[2-Chloro-3-(trifluoromethyl)phenyl]carbonyl}-1-phenyl-4,5-dihydro-1H-imidazo[4,5-c]pyridine Step A: 1-phenyl-4,5-dihydro-1H-imidazo[4,5-c]pyridine

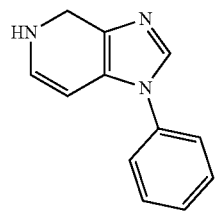 [SMILES: C1=Cc2c(ncn2-c2ccccc2)CN1]

A solution of Intermediate 2 (196 mg, 1.00 mmol) in AcOH (25 ml) was passed through a Pt$_2$O catalyst cartridge on an H-Cube hydrogenation apparatus at a pressure of 80 bar and a flow rate of 1 ml/min at 100° C. The reaction was looped through the apparatus for 5 h. The crude reaction mixture was concentrated and purified on 16 g SiO$_2$ column with 0-10% NH$_3$/MeOH CH$_2$Cl$_2$ to give the desired compound (35 mg, 17%). MS (ESI): mass calcd. for C$_{12}$H$_{11}$N$_3$, 197.1; m/z found, 198.2 [M+H]$^+$.

Step B: 5-{[2-Chloro-3-(trifluoromethyl)phenyl]carbonyl}-1-phenyl-4,5-dihydro-1H-imidazo[4,5-c]pyridine

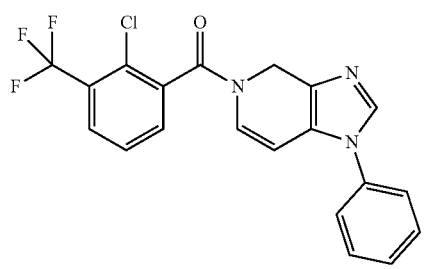 [SMILES: O=C(c1cccc(C(F)(F)F)c1Cl)N1C=Cc2c(ncn2-c2ccccc2)C1]

To a solution of the product of Example 49, Step A (5.5 mg, 0.028 mmol) in DCM (3 mL) was added TEA (11 L, 0.084 mmol), 2-chloro-3-(trifluoromethyl)benzoic acid (7 mg, 0.031 mmol) and HATU (13 mg, 0.033 mmol). The reaction was stirred at room temperature overnight. The crude reaction mixture was concentrated and purified on 4 g SiO$_2$ column with 0-3% NH$_3$/MeOH CH$_2$Cl$_2$ to give the desired compound (9.9 mg, 87%). MS (ESI): mass calcd. for C$_{20}$H$_{13}$CF$_3$N$_3$O, 403.1; m/z found, 404.3 [M+H]$^+$. $^1$H NMR (400 MHz, CDCl$_3$) δ 9.06 (s, 1H), 8.09 (m 1H), 7.94-7.84 (m, 1H), 7.76-7.53 (m, 2H), 7.53-7.39 (m, 2H), 7.39-7.22 (m, 4H), 6.96-6.86 (m, 1H), 6.73 (s, 1H), 5.95 (q, J=7.0 Hz, 1H), 5.54 (s, 1H), 3.22 (q, J=7.3 Hz, 2H), 1.37 (t, J=7.3 Hz, 3H).

Example 50: 5-[(2,2-Difluoro-1,3-benzodioxol-4-yl)carbonyl]-1-phenyl-4,5,6,7-tetrahydro-1H-imidazo[4,5-c]pyridine Step A: 1-phenyl-4,5,6,7-tetrahydro-1H-imidazo[4,5-c]pyridine

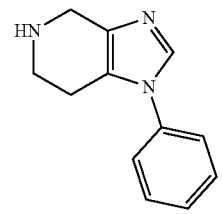 [SMILES: c1ccc(-n2cnc3c2CCNC3)cc1]

A solution of Intermediate 2 (111 mg, 0.569 mmol) in AcOH (15 ml) was passed through a Rh/C catalyst cartridge on an H-Cube hydrogenation apparatus at a pressure of 80 bar and a flow rate of 1 ml/min at 100° C. The reaction was looped through the apparatus for 2 h. The crude reaction mixture was concentrated and purified on 12 g SiO$_2$ column with 0-10% NH$_3$/MeOH CH$_2$Cl$_2$ to give the desired compound (90 mg, 80%). MS (ESI): mass calcd. for C$_{12}$H$_{13}$N$_3$, 199.3; m/z found, 200.2 [M+H]$^+$.

Step B: 5-[(2,2-Difluoro-1,3-benzodioxol-4-yl)carbonyl]-1-phenyl-4,5,6,7-tetrahydro-1H-imidazo[4,5-c]pyridine

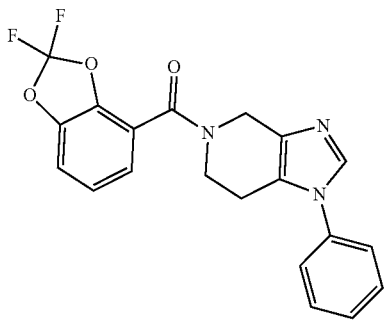 [SMILES: O=C(c1cccc2c1OC(F)(F)O2)N1CCc2c(ncn2-c2ccccc2)C1]

To a solution of the product of Example 50, Step A (28 mg, 0.141 mmol) and TEA (23 µL, 0.169 mmol) in CHCl$_3$ (1 mL) cooled to 0° C. was added 2,2-difluoro-1,3-benzodioxole-4-carbonyl chloride (34 mg, 0.155 mmol). The reaction was warmed to room temperature and stirred overnight. The crude reaction mixture purified on 12 g SiO$_2$ column with 0-4% NH$_3$/MeOH CH$_2$Cl$_2$ to give the desired compound (43 mg, 80%). MS (ESI): mass calcd. for C$_{20}$H$_{15}$F$_2$N$_3$O$_3$, 383.1; m/z found, 384.0 [M+H]$^+$. $^1$H NMR (400 MHz, CDCl$_3$) δ 7.71-7.39 (m, 4H), 7.36-7.09 (m, 5H), 4.88 (s, 1H), 4.58 (t, J=1.6 Hz, 2H), 4.08 (t, J=5.9 Hz, 2H), 3.66 (t, J=5.6 Hz, 1H), 2.86-2.74 (m, 3H).

Example 51: 5-(2,3-Dihydro-1-benzofuran-7-ylcarbonyl)-1-phenyl-4,5,6,7-tetrahydro-1H-imidazo[4,5-c]pyridine

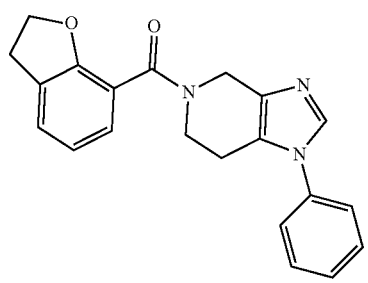 [SMILES: O=C(c1cccc2c1OCC2)N1CCc2c(ncn2-c2ccccc2)C1]

The title compound was prepared in a manner analogous to Example 50 substituting 2,3-dihydro-1-benzofuran-7-carbonyl chloride for 2,2-difluoro-1,3-benzodioxole-4-carbonyl chloride. MS (ESI): mass calcd. for C$_{21}$H$_{19}$N$_3$O$_2$, 345.1; m/z found, 346.3 [M+H]$^+$.

Example 52: 5-[(2,2-Dimethyl-2,3-dihydro-1-benzofuran-7-yl)carbonyl]-1-phenyl-4,5,6,7-tetrahydro-1H-imidazo[4,5-c]pyridine

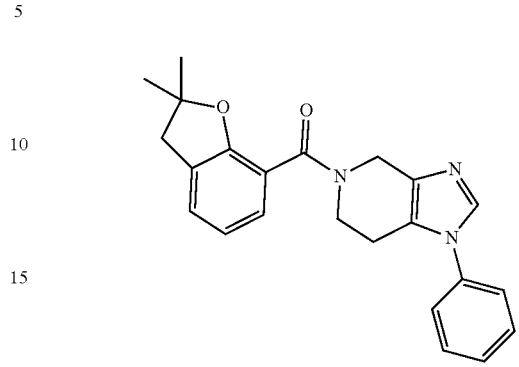

The title compound was prepared in a manner analogous to Example 50 substituting 2,2-dimethyl-2,3-dihydro-1-benzofuran-7-carbonyl chloride for 2,2-difluoro-1,3-benzodioxole-4-carbonyl chloride. MS (ESI): mass calcd. for C$_{23}$H$_{23}$N$_3$O$_2$, 373.2; m/z found, 374.3 [M+H]$^+$.

Example 53: 5-{[2-Chloro-3-(trifluoromethyl)phenyl]carbonyl}-4,4-dimethyl-1-phenyl-4,5,6,7-tetrahydro-1H-imidazo[4,5-c]pyridine Step A: 4,4-dimethyl-4,5,6,7-tetrahydro-1H-imidazo[4,5-c]pyridine

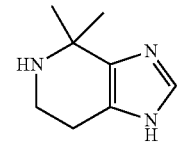

A solution of histamine (500 mg, 4.5 mmol) and acetone (3.3 mL, 45 mmol) in AcOH (3 mL) was heated at 100° C. overnight. The crude reaction mixture was concentrated and purified on 16 g SiO$_2$ column with 0-80% NH$_3$/MeOH CH$_2$Cl$_2$ to give the desired compound (543 mg, 80%). MS (ESI): mass calcd. for CH$_{13}$N$_3$, 151.1; m/z found, 152.2 [M+H]$^+$. $^1$H NMR (400 MHz, CDCl$_3$) δ 7.44 (s, 1H), 3.16 (t, J=5.7 Hz, 2H), 2.61 (t, J=5.7 Hz, 2H), 1.43 (s, 6H).

Step B: 4,4-dimethyl-1-phenyl-4,5,6,7-tetrahydro-1H-imidazo[4,5-c]pyridine

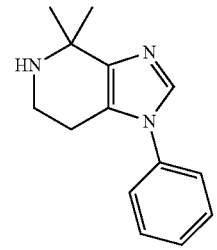 [SMILES: CC1(C)NCCc2c1ncn2-c1ccccc1]

The title compound was prepared in a manner analogous to Intermediate 15, Step 1 substituting the product of Example 53, Step A for 1H-[1,2,3]-triazolo-[4,5-C]-pyridine. MS (ESI): mass calcd. for C H$_{17}$N$_3$, 227.1; m/z found, 228.1 [M+H]$^+$.

Step C: 5-{[2-Chloro-3-(trifluoromethyl)phenyl]carbonyl}-4,4-dimethyl-1-phenyl-4,5,6,7-tetrahydro-1H-imidazo[4,5-c]pyridine

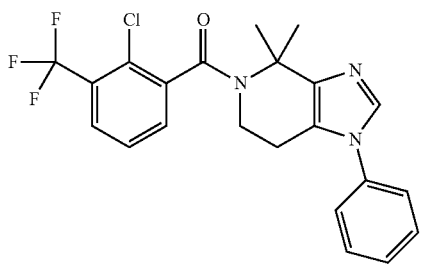 [SMILES: CC1(C)c2ncn(-c3ccccc3)c2CCN1C(=O)c1cccc(C(F)(F)F)c1Cl]

To a solution of the product of Example 53, Step B (59 mg, 0.26 mmol) in DCM (2 mL) was added Intermediate 12 (63 mg, 0.26 mmol) and K$_2$CO$_3$ (89 mg, 0.65 mmol). The resulting suspension was stirred at room temperature for 2 h. The crude reaction mixture was filtered and concentrated and then purified on 12 g SiO$_2$ column with 0-4% NH$_3$/MeOH CH$_2$Cl$_2$ to give the desired compound (55 mg, 48%). MS (ESI): mass calcd. for C$_{22}$H$_{19}$ClF$_3$N$_3$O, 433.1; m/z found, 434.1 [M+H]$^+$. $^1$H NMR (400 MHz, CDCl$_3$) δ 7.72 (dd, J=7.8, 1.4 Hz, 1H), 7.67 (s, 1H), 7.54-7.37 (m, 5H), 7.30 (dd, J=5.3, 3.3 Hz, 2H), 3.53-3.38 (m, 2H), 2.72-2.54 (m, 2H), 2.01 (d, J=6.3 Hz, 6H).

Example 54: 5-{[2-Chloro-3-(trifluoromethyl)phenyl]carbonyl}-1-pyrazin-2-yl-4,5-dihydro-1H-imidazo[4,5-c]pyridine

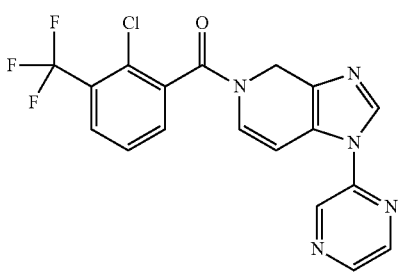 [SMILES: O=C(c1cccc(C(F)(F)F)c1Cl)N1C=Cc2c(ncn2-c2cnccn2)C1]

The title compound was prepared in a manner analogous to Example 11 substituting Intermediate 4 for 1-pyrazin-2-yl-1H-[1,2,3]triazolo[4,5-c]pyridine. MS (ESI): mass calcd. for C$_{18}$H$_{11}$ClF$_3$N$_5$O, 405.1; m/z found, 406.1 [M+H]$^+$.

Example 55: 5-{[2-Chloro-3-(trifluoromethyl)phenyl]carbonyl}-4-ethyl-1-pyrazin-2-yl-4,5-dihydro-1H-imidazo[4,5-c]pyridine

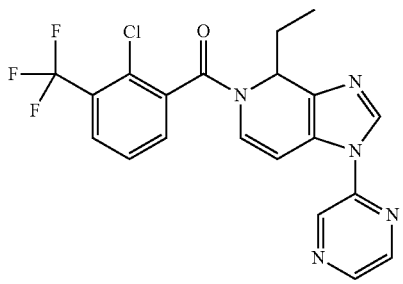 [SMILES: CCC1c2ncn(-c3cnccn3)c2C=CN1C(=O)c1cccc(C(F)(F)F)c1Cl]

The title compound was prepared in a manner analogous to Example 11 substituting Intermediate 4 for 1-pyrazin-2-yl-1H-[1,2,3]triazolo[4,5-c]pyridine and EtMgBr for MeMgBr. MS (ESI): mass calcd. for C$_{20}$H$_{15}$ClF$_3$N$_5$O, 433.1; m/z found, 434.2 [M+H]$^+$.

Example 56: 5-{[2-Chloro-3-(trifluoromethyl)phenyl]carbonyl}-4-methyl-1-pyrazin-2-yl-4,5-dihydro-1H-imidazo[4,5-c]pyridine

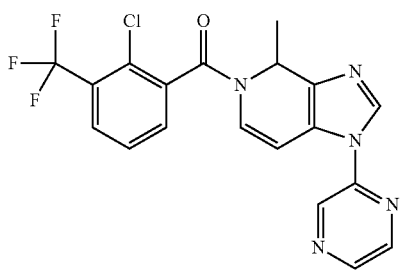 [SMILES: CC1c2ncn(-c3cnccn3)c2C=CN1C(=O)c1cccc(C(F)(F)F)c1Cl]

The title compound was prepared in a manner analogous to Example 11 substituting Intermediate 4 for 1-pyrazin-2-yl-1H-[1,2,3]triazolo[4,5-c]pyridine. MS (ESI): mass calcd. for C$_{19}$H$_{13}$ClF$_3$N$_5$O, 419.1; m/z found, 420.0 [M+H]$^+$.

Example 57: 5-{[2-Fluoro-3-(trifluoromethyl)phenyl]carbonyl}-1-phenyl-2-(trifluoromethyl)-4,5,6,7-tetrahydro-1H-imidazo[4,5-c]pyridine

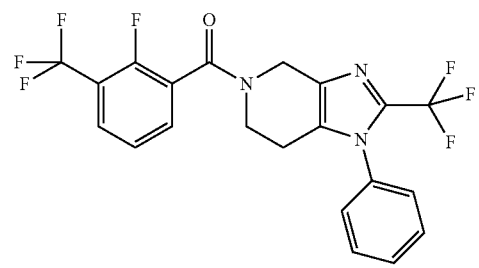 [SMILES: O=C(c1cccc(C(F)(F)F)c1F)N1CCc2c(nc(C(F)(F)F)n2-c2ccccc2)C1]

MS (ESI): mass calcd. for C$_{21}$H$_{14}$F$_7$N$_3$O, 457.1; m/z found, 458.1 [M+H]$^+$.

Example 58: 5-[(2,3-Dichlorophenyl)carbonyl]-1-phenyl-2-(trifluoromethyl)-4,5,6,7-tetrahydro-1H-imidazo[4,5-c]pyridine

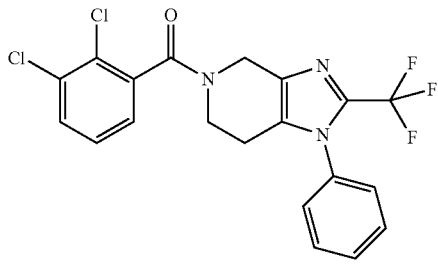 [SMILES: O=C(c1cccc(Cl)c1Cl)N1CCc2c(nc(C(F)(F)F)n2-c2ccccc2)C1]

MS (ESI): mass calcd. for $C_{20}H_{14}Cl_2F_3N_3O$, 439.0; m/z found, 440.1 [M+H]⁺. ¹H NMR (400 MHz, CDCl₃) δ 7.62-7.44 (m, 3H), 7.37-7.17 (m, 3H), 5.04-4.83 (m, 1H), 4.49-4.26 (m, 1H), 4.22 (dt, J=13.1, 5.5 Hz, 1H), 3.99 (dt, J=13.2, 6.0 Hz, 1H), 3.61-3.44 (m, 1H), 2.59 (td, J=6.0, 1.6 Hz, 1H), 2.54-2.42 (m, 1H), 2.42-2.29 (m, 1H)

Example 59: 5-{[2-Fluoro-3-(trifluoromethyl)phenyl]carbonyl}-1-(1H-pyrazol-5-yl)-4,5,6,7-tetrahydro-1H-imidazo[4,5-c]pyridine

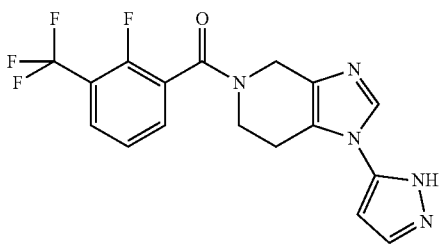 [SMILES: O=C(c1cccc(C(F)(F)F)c1F)N1CCc2c(ncn2-c2ccn[nH]2)C1]

Example 59 was prepared in analogy to Example 5. MS (ESI): mass calcd. for $C_{17}H_{13}F_4N_5O$, 379.1; m/z found, 380.1 [M+H]⁺. ¹H NMR (400 MHz, CDCl₃) δ 11.74 (s, 1H), 7.91 (s, 1H), 7.81 (s, 1H), 7.75-7.56 (m, 3H), 7.34 (dt, J=10.9, 7.8 Hz, 1H), 6.30 (d, J=2.4 Hz, 1H), 4.90 (s, 1H), 4.48 (s, 2H), 3.83 (s, 1H), 3.63 (s, 1H), 3.20 (q, J=7.3 Hz, 1H), 3.06 (s, 1H), 2.90 (s, 1H), 1.34 (t, J=7.3 Hz, 1H).

Example 60: 5-[(2,3-Dichlorophenyl)carbonyl]-1-(1H-pyrazol-5-yl)-4,5,6,7-tetrahydro-1H-imidazo[4,5-c]pyridine

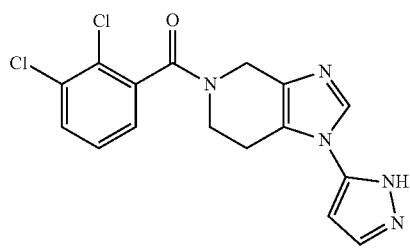 [SMILES: O=C(c1cccc(Cl)c1Cl)N1CCc2c(ncn2-c2ccn[nH]2)C1]

Example 60 was prepared in analogy to Example 5. MS (ESI): mass calcd. for $C_{16}H_{13}Cl_2N_5O$, 361.0; m/z found, 362.1 [M+H]⁺. ¹H NMR (400 MHz, CDCl₃) δ 12.18-11.79 (m, 1H), 7.98-7.85 (s, 0.4H), 7.88-7.76 (s, 0.6H), 7.62-7.53 (m, 1H), 7.54-7.47 (ddd, J=7.9, 3.6, 1.7 Hz, 1H), 7.33-7.17 (m, 3H), 6.32-6.23 (dd, J=10.6, 2.4 Hz, 1H), 5.05-4.78 (ddt, J=68.4, 16.2, 1.7 Hz, 1H), 4.47-4.28 (m, 1H), 4.28-4.20 (m, 1H), 4.13-4.02 (dt, J=12.5, 5.9 Hz, 1H), 3.60-3.49 (td, J=6.2, 5.6, 3.8 Hz, 1H), 3.15-2.99 (dt, J=7.5, 4.1 Hz, 1H), 2.97-2.73 (m, 1H).

Example 61: 5-{[2-Chloro-3-(trifluoromethyl)phenyl]carbonyl}-1-phenyl-4,5,6,7-tetrahydro-1H-[1,2,3]triazolo[4,5-c]pyridine

Step 1 Intermediate 15: 1-Phenyl-1H-[1,2,3]triazolo[4,5-c]pyridine

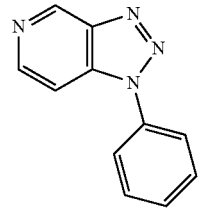 [SMILES: c1ccc(-n2nnc3cnccc32)cc1]

A solution of 1H-[1,2,3]-triazolo-[4,5-C]-pyridine (200 mg, 1.7 mmol), iodobenzene (407 mg, 2.0 mmol), Cs₂CO₃, (1.08 g, 3.3 mmol), copper (I) oxide (17 mg, 0.12 mmol), 4,7-dimethoxy-[1,10]-phenanthroline (84 mg, 0.35 mmol), PEG 400 (0.3 ml) were combined in butyronitrile (3 ml) and heated to 110° C. overnight. The reaction was diluted with CHCl₃, filtered through Celite© and then concentrated and purified on 16 g SiO₂ with 0-3.5% NH₃/MeOH in CH₂Cl₂ to give 52 mg (16%) of 1-phenyl-1H-[1,2,3]triazolo[4,5-c]pyridine. MS (ESI): mass calcd. for $C_{11}H_8N_4$, 196.1; m/z found, 197.1 [M+H]⁺. ¹H NMR δ (400 MHz, CDCl₃) δ 9.58 (s, 1H), 8.66 (d, J=5.8 Hz, 1H), 7.83-7.75 (m, 2H), 7.72-7.62 (m, 3H), 7.62-7.52 (m, 1H).

Step 2 Intermediate 16: 1-Phenyl-4,5,6,7-tetrahydro-1H-[1,2,3]triazolo[4,5-c]pyridine

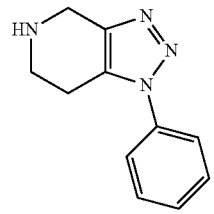 [SMILES: c1ccc(-n2nnc3c2CCNC3)cc1]

A solution of 1-phenyl-1H-[1,2,3]triazolo[4,5-c]pyridine (61 mg, 0.31 mmol) in MeOH (15 ml) was passed through a PtO₂ catalyst cartridge on an H-Cube hydrogenation apparatus at a pressure of 70 bar and a flow rate of 1 ml/min. The reaction was concentrated and the crude reaction mixture purified on 12 g SiO₂ column with 0-8% NH₃/MeOH CH₂Cl₂ to give 35 mg (56%) of 1-phenyl-4,5,6,7-tetrahydro-1H-[1,2,3]triazolo[4,5-c]pyridine. MS (ESI): mass calcd. for $C_{11}H_{12}N_4$, 200.2; m/z found, 201.2 [M+H]⁺. ¹H NMR (400 MHz, CDCl₃) δ 7.99 (dt, J=8.0, 1.1 Hz, 2H), 7.61-7.50 (m, 2H), 7.48-7.41 (m, 2H), 7.33-7.27 (m, 1H), 4.14-4.07 (m, 2H), 3.20 (t, J=5.9 Hz, 2H), 2.88 (t, J=5.9 Hz, 2H).

Step 3 Example 61: 5-{[2-Chloro-3-(trifluoromethyl)phenyl]carbonyl}-1-phenyl-4,5,6,7-tetrahydro-1H-[1,2,3]triazolo[4,5-c]pyridine

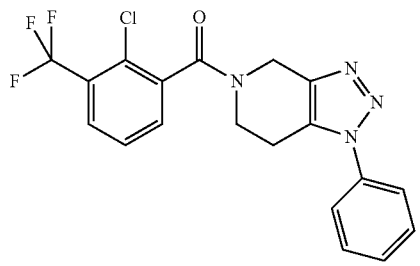 [SMILES: O=C(c1cccc(C(F)(F)F)c1Cl)N1CCc2c(nnn2-c2ccccc2)C1]

A solution of 1-phenyl-4,5,6,7-tetrahydro-1H-[1,2,3]triazolo[4,5-c]pyridine (17 mg, 0.085 mmol) and 2-chloro-3-(triflouromethyl) benzoic acid (21 mg, 0.093 mmol) in DCM (8 mL) was treated with Et$_3$N (35 µL, 0.25 mmol) followed by HATU (38 mg, 0.1 mmol). The reaction was stirred overnight, then concentrated to minimum volume and purified on 16 g SiO$_2$ with 0-3.5% NH$_3$ in MeOH/CH$_2$Cl$_2$ to give 32 mg (91%) of 5-{[2-chloro-3-(trifluoromethyl)phenyl]carbonyl}-1-phenyl-4,5,6,7-tetrahydro-1H-[1,2,3]triazolo[4,5-c]pyridine. MS (ESI): mass calcd. for C$_{19}$H$_{14}$ClF$_3$N$_4$O, 406.1; m/z found, 407.1 [M+H]$^+$. $^1$H NMR (400 MHz, CDCl$_3$): δ 7.84-7.75 (m, 1H), 7.62-7.43 (m, 7H), 5.11 (q, J=16.5 Hz, 1H), 4.64-4.45 (m, 1H), 4.32 (dt, J=13.2, 5.4 Hz, 0.5H), 4.05-3.95 (m, 0.5H), 3.65-3.48 (m, 1H), 3.04 (t, J=5.9 Hz, 1H), 3.01-2.76 (m, 1H).

Example 62: 5-[(2,3-Dichlorophenyl)carbonyl]-1-phenyl-4,5,6,7-tetrahydro-1H-[1,2,3]triazolo[4,5-c]pyridine

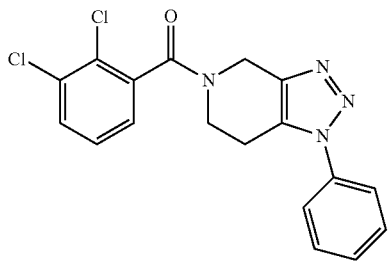 [SMILES: O=C(c1cccc(Cl)c1Cl)N1CCc2c(nnn2-c2ccccc2)C1]

A solution of 1-phenyl-4,5,6,7-tetrahydro-1H-[1,2,3]triazolo[4,5-c]pyridine (17 mg, 0.085 mmol) and 2,3-dichlorobenzoic acid (18 mg, 0.093 mmol) in DCM (8 ml) was treated with Et$_3$N (35 µL, 0.25 mmol) followed by HATU (38 mg, 0.1 mmol). The reaction was stirred overnight, then concentrated to minimum volume and purified on 16 g SiO$_2$ with 0-3.5% NH$_3$ in MeOH/CH$_2$Cl$_2$ to give 24 mg (75%) of 5-[(2,3-dichlorophenyl)carbonyl]-1-phenyl-4,5,6,7-tetrahydro-1H-[1,2,3]triazolo[4,5-c]pyridine. MS (ESI): mass calcd. for C$_{18}$H$_{14}$Cl$_2$N$_4$O, 372.0; m/z found, 373.2 [M+H]$^+$. $^1$H NMR (400 MHz, CDCl$_3$) δ 7.63-7.42 (m, 5H), 7.38-7.17 (m, 2H), 5.23-4.88 (m, 1H), 4.54 (q, J=15.7 Hz, 1H), 4.23 (dt, J=13.2, 5.5 Hz, 1.0H), 4.10-4.00 (m, 1.0H), 3.65-3.48 (m, 1H), 3.03 (t, J=5.7 Hz, 1H), 3.00-2.74 (m, 1H).

Example 63: 5-{[2-Chloro-3-(trifluoromethyl)phenyl]carbonyl}-1-pyridin-2-yl-4,5,6,7-tetrahydro-1H-[1,2,3]triazolo[4,5-c]pyridine Step 1 Intermediate 17: N-(3-Nitropyridin-4-yl)pyridin-2-amine

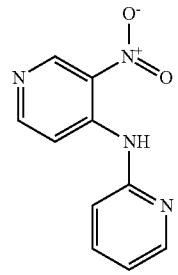 [SMILES: O=[N+]([O-])c1cnccc1Nc1ccccn1]

Pd(OAc)$_2$ (9.5 mg, 0.042 mmol) and BINAP (26 mg, 0.042 mmol) were combined in toluene (1 ml) and stirred at rt for 10 minutes. This mixture was then added to a sealed vessel which contained 4-chloro-3-nitropyridine (172 mg 1.0 mmol), 2-aminopyridine (100 mg, 1.0 mmol), and K$_2$CO$_3$ (160 mg, 1.2 mmol) in toluene (2 ml). The reaction was heated to 110° C. for 2 h. The reaction was filtered while hot and the filter cake washed with EtOAc. The combined filtrates were concentrated and purified on 16 g SiO$_2$ with 0-40% EtOAc/hexanes. MS (ESI): mass calcd. for C$_{10}$H$_8$N$_4$O$_2$, 216.0; m/z found, 217.1 [M+H]$^+$. $^1$H NMR (400 MHz, CDCl$_3$) δ 10.39 (s, 1H), 9.35 (s, 1H), 8.81 (d, J=6.2 Hz, 1H), 8.50 (d, J=6.1 Hz, 1H), 8.44 (dd, J=5.0, 1.2 Hz, 1H), 7.74 (ddd, J=8.2, 7.4, 1.9 Hz, 1H), 7.09 (ddd, J=7.4, 5.0, 0.9 Hz, 1H), 7.02 (t, J=7.8 Hz, 1H).

Step 2 Intermediate 18: N-4-Pyridin-2-ylpyridine-3,4-diamine

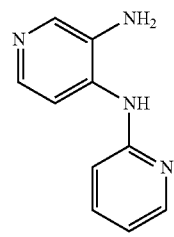

A solution of N-(3-Nitropyridin-4-yl)pyridin-2-amine (195 mg, 0.9 mmol) in EtOH (15 ml) was treated with 10% Pd/C (10 mg) and then put under an atmosphere of H$_2$ and stirred for 4 h. The reaction was filtered through Celite© and concentrated to pale yellow solid. MS (ESI): mass calcd. for C$_{10}$H$_{10}$N$_4$, 186.1; m/z found, 187.1 [M+H]$^+$. $^1$H NMR (400 MHz, CDCl$_3$): δ 8.28 (ddd, J=5.0, 1.9, 0.9 Hz, 1H), 8.15 (s, 1H), 8.06 (d, J=5.4 Hz, 1H), 7.58 (ddd, J=8.3, 7.3, 1.9 Hz, 1H), 7.54 (d, J=5.4 Hz, 1H), 6.90-6.81 (m, 2H), 6.58 (s, 1H), 3.52 (s, 2H).

Step 3 Intermediate 19: 1-Pyridin-2-yl-1H-[1,2,3]-triazolo[4,5-c]pyridine

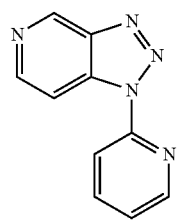 [SMILES: c1ccc(-n2nnc3cnccc32)nc1]

N-4-Pyridin-2-ylpyridine-3,4-diamine (100 mg, 0.54 mmol) in THF (5 ml) and HOAc (0.034 ml, 0.59 mmol) was treated with t-butyl nitrite (0.11 ml, 0.81 mmol) and heated to 100° C. for 90 min. The reaction was cooled to 23° C. and a solid precipitated. The reaction mixture was warmed to dissolve the solid, filtered and the filtrate was partially concentrated. A solid was isolated (55 mg, 52%) then filtrate concentrated to provide a additional crop of product (57 mg, 54%). MS (ESI): mass calcd. for $C_{10}H_7N_5$, 197.1; m/z found, 198.1 [M+H]$^+$. $^1$H NMR (400 MHz, CDCl$_3$) δ 9.55 (d, J=1.0 Hz, 1H), 8.70 (d, J=5.8 Hz, 1H), 8.65 (ddd, J=4.9, 1.8, 0.8 Hz, 1H), 8.55 (dd, J=5.8, 1.2 Hz, 1H), 8.33 (dt, J=8.3, 0.9 Hz, 1H), 8.00 (ddd, J=8.3, 7.5, 1.9 Hz, 1H), 7.39 (ddd, J=7.4, 4.9, 1.0 Hz, 1H).

Step 4 Intermediate 20: 1-(Pyridin-2-yl)-4,5,6,7-tetrahydro-1H-[1,2,3]triazolo[4,5-c]pyridine

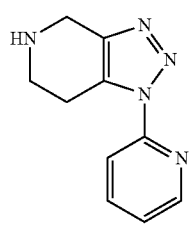 [SMILES: c1ccc(-n2nnc3c2CCNC3)nc1]

1-Pyridin-2-yl-1H-[1,2,3]-triazolo[4,5-c]pyridine (23 mg, 0.12 mmol) in HOAc (14 mL) was hydrogenated at 50 bar using Rh/C as catalyst on the H-cube apparatus with a flow rate of 1 ml/min and looped with product recycling for 2 hrs. Reaction was concentrated then partially purified on 12 g SiO$_2$ with 0-10% NH$_3$ MeOH/CH$_2$Cl$_2$. Used without further purification in next reaction. MS (ESI): mass calcd. for $C_{10}H_{11}N_5$, 201.2; m/z found, 202.2 [M+H]$^+$. $^1$H NMR (400 MHz, CDCl$_3$): δ 8.49 (ddd, J=4.9, 2.0, 0.9 Hz, 1H), 8.18-8.10 (m, 1H), 7.90 (ddd, J=8.3, 7.4, 1.9 Hz, 1H), 7.36-7.27 (m, 1H), 4.12 (t, J=1.4 Hz, 2H), 3.31-3.12 (m, 4H).

Step 5 Example 63: 5-{[2-Chloro-3-(trifluoromethyl)phenyl]carbonyl}-1-pyridin-2-yl-4,5,6,7-tetrahydro-1H-[1,2,3]triazolo[4,5-c]pyridine

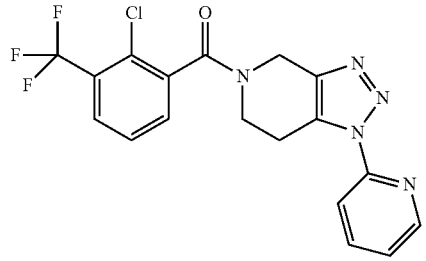 [SMILES: O=C(c1cccc(C(F)(F)F)c1Cl)N1CCc2c(nnn2-c2ccccn2)C1]

A solution of 1-(pyridin-2-yl)-4,5,6,7-tetrahydro-1H-[1,2,3]triazolo[4,5-c]pyridine (13 mg, 0.065 mmol) in THF (1 mL) was treated with 2-chloro-3-(trifluoromethyl)benzoyl chloride (19 mg, 0.078 mmol) followed by Et$_3$N (0.013 mL, 0.097 mmol). After 5 min the reaction was diluted with CH$_2$Cl$_2$ and the organic portion washed with NaHCO$_3$. The organic portion was then dried over Na$_2$SO$_4$, concentrated and purified on 4 g SiO$_2$ to yield 20 mg (75%) of: 5-{[2-Chloro-3-(trifluoromethyl) phenyl]carbonyl}-1-pyridin-2-yl-4,5,6,7-tetrahydro-1H-[1,2,3]triazolo[4,5-c]pyridine. MS (ESI): mass calcd. for $C_{18}H_{13}ClF_3N_5O$, 407.1; m/z found, 408.1 [M+H]$^+$. $^1$H NMR (400 MHz, CDCl$_3$) δ 8.49 (dddd, J=32.1, 4.9, 1.8, 0.8 Hz, 1H), 8.17 (ddt, J=17.3, 8.3, 1.0 Hz, 1H), 7.93 (ddt, J=8.4, 7.5, 1.7 Hz, 1H), 7.79 (ddd, J=6.6, 4.4, 2.2 Hz, 1H), 7.57-7.42 (m, 2H), 7.35 (dddd, J=12.3, 7.5, 4.9, 1.0 Hz, 1H), 5.25-4.96 (m, 1H), 4.35 (dt, J=13.3, 5.4 Hz, 1H), 4.11-3.95 (m, 1H), 3.61-3.53 (m, 1H), 3.51-3.44 (m, 1H), 3.36 (s, 1H).

Intermediates 21-30 were made in manner analogous to Intermediate 17 substituting the appropriate aryl or heteroaryl amine for N-(3-Nitropyridin-4-yl)pyridin-2-amine and the appropriate halo-nitro pyridine for 4-chloro-3-nitropyridine in the synthesis of Intermediate 17.

Intermediate 21: N-(3-Nitropyridin-4-yl)pyrazin-2-amine

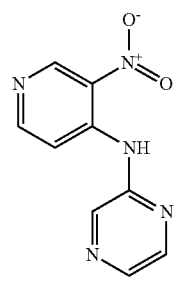 [SMILES: O=[N+]([O-])c1cnccc1Nc1cnccn1]

MS (ESI): mass calcd. for $C_9H_7N_5O_2$, 217.1; m/z found, 218.1 [M+H]$^+$. $^1$H NMR (400 MHz, CDCl$_3$): δ 10.57 (s, 1H), 9.40 (s, 1H), 8.84 (d, J=6.1 Hz, 1H), 8.59 (d, J=6.1 Hz, 1H), 8.45 (d, J=1.3 Hz, 1H), 8.38-8.30 (m, 2H).

Intermediate 22:
N-(4-Fluorophenyl)-3-nitropyridin-4-amine

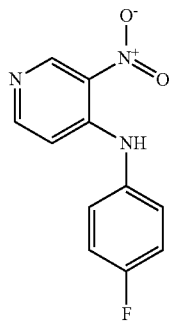 [SMILES: O=[N+]([O-])c1cnccc1Nc1ccc(F)cc1]

MS (ESI): mass calcd. for $C_{11}H_8FN_3O_2$, 233.0; m/z found, M/Z=234.1 [M+H]$^+$, $^1$H NMR (400 MHz, DMSO-d$_6$): 9.79 (s, 1H), 9.08 (s, 1H), 8.22 (d, J=6.1 Hz, 1H), 7.50-7.23 (m, 4H), 6.77 (d, J=6.1 Hz, 1H).

Intermediate 23: 3-Nitro-N-phenylpyridin-4-amine

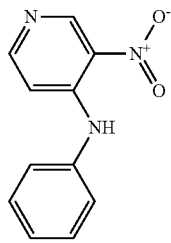 [SMILES: O=[N+]([O-])c1cnccc1Nc1ccccc1]

MS (ESI): mass calcd. for $C_{11}H_9N_3O_2$, 215.1; m/z found, M/Z=216.1 [M+H]$^+$, $^1$H NMR (400 MHz, CDCl$_3$): δ 9.66 (s, 1H), 9.26 (s, 1H), 8.23 (d, J=6.1 Hz, 1H), 7.48 (t, J=7.6 Hz, 2H), 7.34 (t, J=7.4 Hz, 1H), 7.28 (d, J=7.7 Hz, 2H), 6.93 (d, J=6.2 Hz, 1H).

Intermediate 24:
N-(3-Nitropyridin-4-yl)pyridin-3-amine

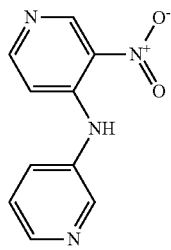 [SMILES: O=[N+]([O-])c1cnccc1Nc1cccnc1]

MS (ESI): mass calcd. for $C_{10}H_8N_4O_2$, 216.1; m/z found, M/Z=217.1 [M+H]$^+$, $^1$H NMR (400 MHz, DMSO-d$_6$): δ 9.87 (s, 1H), 9.11 (s, 1H), 8.58 (d, J=2.5 Hz, 1H), 8.51 (dd, J=4.7, 1.3 Hz, 1H), 8.26 (d, J=6.1 Hz, 1H), 7.82 (d, J=8.4 Hz, 1H), 7.50 (dd, J=8.1, 4.7 Hz, 1H), 6.86 (d, J=6.1 Hz, 1H)

Intermediate 25:
3-Fluoro-N-(3-nitropyridin-4-yl)pyridin-2-amine

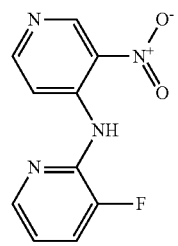 [SMILES: O=[N+]([O-])c1cnccc1Nc1ncccc1F]

MS (ESI): mass calcd. for $C_{10}H_7FN_4O_2$, 234.1; m/z found, M/Z=235.1 [M+H]$^+$, $^1$H NMR (400 MHz, CDCl$_3$): δ 10.78 (s, 1H), 9.40 (s, 1H), 9.09 (d, J=6.1 Hz, 1H), 8.57 (d, J=6.2 Hz, 1H), 8.22 (d, J=4.4 Hz, 1H), 7.51 (t, J=9.2 Hz, 1H), 7.10 (dd, J=8.1, 3.6 Hz, 1H).

Intermediate 26:
3-Nitro-N-1H-pyrazol-5-ylpyridin-4-amine

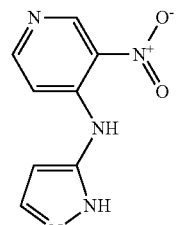

MS (ESI): mass calcd. for $C_8H_7N_5O_2$, 205.1; m/z found, M/Z=206.1 [M+H]$^+$, $^1$H NMR (400 MHz, DMSO-d$_6$): δ 12.74 (s, 1H), 9.88 (s, 1H), 9.10 (s, 1H), 8.37-8.35 (m, 1H), 7.80 (d, J=6.3 Hz, 2H), 6.31 (s, 1H).

Intermediate 27:
N-(3-Nitropyridin-4-yl)pyrimidin-2-amine

MS (ESI): mass calcd. for $C_9H_7N_5O_2$, 217.1; m/z found, M/Z=218.1 [M+H]$^+$, $^1$H NMR (400 MHz, CD$_3$OD): δ 9.65-9.62 (m, 2H), 8.84 (d, J=4.9 Hz, 2H), 8.73-8.67 (m, 1H), 7.39 (t, J=4.9 Hz, 1H).

Intermediate 28: N-(2-Chloro-6-methyl-3-nitropyridin-4-yl)-5-fluoropyrimidin-2-amine

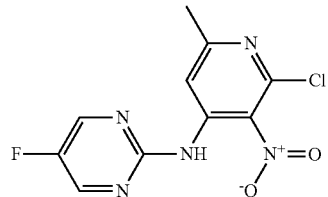

MS (ESI): mass calcd. for $C_{10}H_7ClFN_5O_2$, 283.1; m/z found, M/Z=284.1 [M+H]$^+$, $^1$H NMR (400 MHz, DMSO-d$_6$): δ 10.47 (s, 1H), 8.69 (s, 2H), 7.83 (s, 1H), 2.46 (s, 3H).

Intermediate 29: 5-Fluoro-N-(3-nitropyridin-4-yl)pyrimidin-2-amine

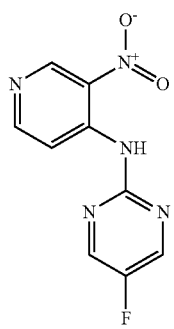 [SMILES: O=[N+]([O-])c1cnccc1Nc1ncc(F)cn1]

MS (ESI): mass calcd. for $C_9H_6FN_5O_2$, 235.1; m/z found, 236.1 [M+H]$^+$. $^1$H NMR (400 MHz, CDCl$_3$) δ 10.84-10.79 (s, 1H), 9.44-9.35 (s, 1H), 9.00-8.92 (d, J=6.1 Hz, 1H), 8.65-8.58 (dd, J=6.1, 0.7 Hz, 1H), 8.55-8.47 (s, 2H).

Intermediate 30: 5-Fluoro-N-(2-methyl-3-nitropyridin-4-yl)pyridin-2-amine

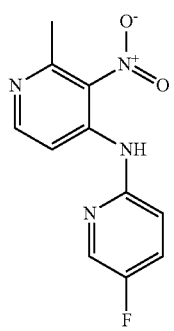

MS (ESI): mass calcd. for $C_{11}H_9FN_4O_2$, 248.071; m/z found, 249.1 [M+H]$^+$.

Intermediates 32-39 were made in a manner analogous to Intermediate 18 substituting Intermediates 21-30 for N-(3-Nitropyridin-4-yl)pyridin-2-amine in the synthesis of Intermediate 18.

Intermediate 32: N-4-Pyrazin-2-ylpyridine-3,4-diamine

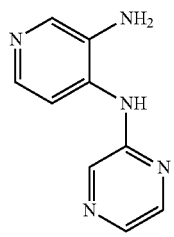

MS (ESI): mass calcd. for $C_9H_9N_5$, 187.1; m/z found, 188.1 [M+H]$^+$. H NMR (400 MHz, CDCl$_3$) δ 8.27 (d, J=1.4 Hz, 1H), 8.20 (t, J=2.1 Hz, 2H), 8.13 (d, J=5.4 Hz, 1H), 8.11 (d, J=2.7 Hz, 1H), 7.73 (d, J=5.4 Hz, 1H), 6.75 (s, 1H).

Intermediate 33: N-4-Pyridin-3-ylpyridine-3,4-diamine

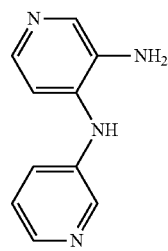 [SMILES: Nc1cnccc1Nc1cccnc1]

MS (ESI): mass calcd. for $C_{10}H_{10}N_4$, 186.1; m/z found, M/Z=187.1 [M+H]$^+$, $^1$H NMR (400 MHz, DMSO-d$_6$): δ 8.34 (d, J=2.5 Hz, 1H), 8.11 (dd, J=4.6, 1.2 Hz, 1H), 7.92 (s, 1H), 7.71 (s, 1H), 7.65 (d, J=5.3 Hz, 1H), 7.45-7.41 (m, 1H), 7.27 (dd, J=8.2, 4.6 Hz, 1H), 6.90 (d, J=5.3 Hz, 1H), 4.94 (s, 2H).

Intermediate 34: N-4-(4-Fluorophenyl)pyridine-3,4-diamine

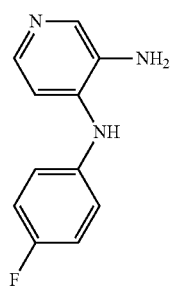 [SMILES: Nc1cnccc1Nc1ccc(F)cc1]

MS (ESI): mass calcd. for $C_{11}H_{10}FN_3$, 203.1; m/z found, M/Z=204.1 [M+H]$^+$, $^1$H NMR (400 MHz, DMSO-d$_6$): δ 7.85 (s, 1H), 7.60 (d, J=5.3 Hz, 1H), 7.44 (s, 1H), 7.19-7.05 (m, 4H), 6.78 (d, J=5.3 Hz, 1H), 4.83 (s, 2H).

Intermediate 35:
N-4-(3-Fluoropyridin-2-yl)pyridine-3,4-diamine

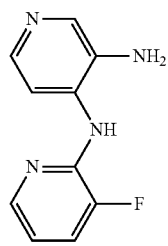 [SMILES: Nc1cnccc1Nc1ncccc1F]

MS (ESI): mass calcd. for $C_{10}H_9FN_4$, 204.1; m/z found, M/Z=205.2 [M+H]$^+$, $^1$H NMR (400 MHz, CD$_3$OD): δ 8.08-7.96 (m, 2H), 7.83 (q, J=5.5 Hz, 2H), 7.49 (ddd, J=11.2, 8.0, 1.4 Hz, 1H), 6.89 (ddd, J=8.3, 4.9, 3.6 Hz, 1H).

Intermediate 36:
N-4-1H-Pyrazol-5-ylpyridine-3,4-diamine

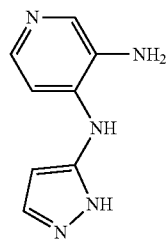 [SMILES: Nc1cnccc1Nc1ccn[nH]1]

MS (ESI): mass calcd. for $C_8H_9N_5$, 175.1; m/z found, M/Z=176.2 [M+H]$^+$, $^1$H NMR (400 MHz, DMSO-d$_6$): δ 12.41 (s, 1H), 8.63 (s, 1H), 7.81-7.63 (m, 4H), 6.10 (s, 1H), 5.45 (s, 2H).

Intermediate 37:
N-4-Pyrimidin-2-ylpyridine-3,4-diamine

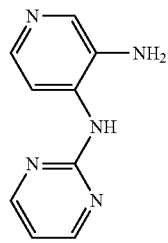 [SMILES: Nc1cnccc1Nc1ncccn1]

MS (ESI): mass calcd. for $C_9H_9N_5$, 187.1; m/z found, M/Z=188.2 [M+H]$^+$, $^1$H NMR (400 MHz, DMSO-d$_6$): δ 8.76 (s, 1H), 8.50 (d, J=4.8 Hz, 2H), 7.96 (s, 1H), 7.85 (d, J=5.4 Hz, 1H), 7.73 (d, J=5.3 Hz, 1H), 6.90 (t, J=4.8 Hz, 1H), 5.15 (s, 2H).

Intermediate 38:
N-4-(5-Fluoropyrimidin-2-yl)pyridine-3,4-diamine

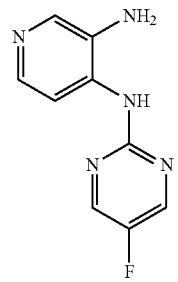 [SMILES: Nc1cnccc1Nc1ncc(F)cn1]

MS (ESI): mass calcd. for $C_9H_8FN_5$, 205.1; m/z found, 206.1 [M+H]$^+$. H NMR (400 MHz, CDCl$_3$) δ 8.37 (d, J=0.6 Hz, 2H), 8.21-8.12 (m, 2H), 8.01 (d, J=5.5 Hz, 1H), 7.40 (s, 1H), 3.43-3.38 (s, 2H).

Intermediate 39: N-4-(5-Fluoropyridin-2-yl)-2-methylpyridine-3,4-diamine

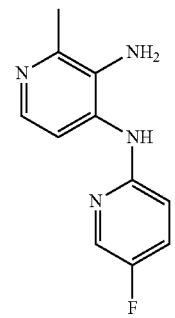 [SMILES: Cc1nccc(Nc2ccc(F)cn2)c1N]

MS (ESI): mass calcd. for $C_{11}H_{11}FN_4$, 218.1; m/z found, 219.1 [M+H]$^+$. $^1$H NMR (400 MHz, CDCl$_3$) δ 7.96 (d, J=5.4 Hz, 1H), 7.38-7.24 (m, 3H), 6.80-6.72 (m, 1H), 6.48 (s, 1H), 3.54-3.47 (m, 2H), 2.49 (s, 3H).

Intermediates 40-47 were made in a manner analogous to Intermediate 19 substituting Intermediates 32-39 for N-4-Pyridin-2-ylpyridine-3,4-diamine in the synthesis of Intermediate 19.

Intermediate 40: 1-Pyrazin-2-yl-1H-[1,2,3]triazolo[4,5-c]pyridine

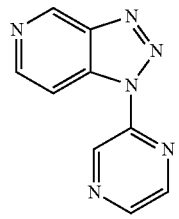 [SMILES: c1cnc(-n2nnc3cnccc32)cn1]

MS (ESI): mass calcd. for $C_9H_6N_6$, 198.1; m/z found, 199.1 [M+H]$^+$. $^1$H NMR (400 MHz, CDCl$_3$) δ 9.70 (d, J=1.2

Hz, 1H), 9.59 (d, J=1.1 Hz, 1H), 8.75 (d, J=5.8 Hz, 1H), 8.71 (d, J=2.5 Hz, 1H), 8.62 (dd, J=2.6, 1.5 Hz, 1H), 8.45 (dd, J=5.8, 1.2 Hz, 1H).

Intermediate 41: 1-Pyridin-3-yl-1H-[1,2,3]triazolo[4,5-c]pyridine

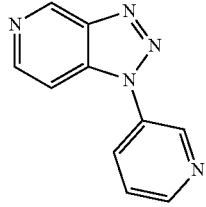 [SMILES: c1cncc(-n2nnc3cnccc32)c1]

MS (ESI): mass calcd. for $C_{10}H_7N_5$, 197.1; m/z found, M/Z=198.1 [M+H]$^+$, $^1$H NMR (400 MHz, DMSO-d$_6$): δ 9.61 (s, 1H), 9.14 (d, J=1.9 Hz, 1H), 8.80 (d, J=4.7 Hz, 1H), 8.68 (d, J=5.9 Hz, 1H), 8.43-8.31 (m, 1H), 8.06 (d, J=5.9 Hz, 1H), 7.75 (dd, J=8.2, 4.8 Hz, 1H).

Intermediate 42: 1-(4-Fluorophenyl)-1H-[1,2,3]triazolo[4,5-c]pyridine

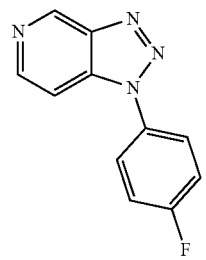 [SMILES: Fc1ccc(-n2nnc3cnccc32)cc1]

MS (ESI): mass calcd. for $C_{11}H_7FN_4$, 214.1; m/z found, M/Z=215.1 [M+H]$^+$, $^1$H NMR (400 MHz, DMSO-d$_6$): 9.60 (s, 1H), 8.66 (d, J=5.9 Hz, 1H), 7.98 (d, J=4.8 Hz, 1H), 7.95 (d, J=4.9 Hz, 2H), 7.56 (t, J=8.8 Hz, 2H).

Intermediate 43: 1-(3-Fluoropyridin-2-yl)-1H-[1,2,3]triazolo[4,5-c]pyridine

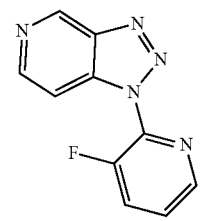 [SMILES: Fc1cccnc1-n1nnc2cnccc21]

MS (ESI): mass calcd. for $C_{10}H_6FN_5$, 215.1; m/z found, M/Z=216.1 [M+H]$^+$, $^1$H NMR (400 MHz, CD$_3$OD): δ 9.50 (d, J=1.1 Hz, 1H), 8.63 (d, J=5.9 Hz, 1H), 8.54 (dd, J=3.6, 1.1 Hz, 1H), 8.13 (dd, J=5.9, 1.0 Hz, 1H), 8.10-7.99 (m, 1H), 7.70-7.64 (m, 1H).

Intermediate 44: 1-Pyrimidin-2-yl-1H-[1,2,3]triazolo[4,5-c]pyridine

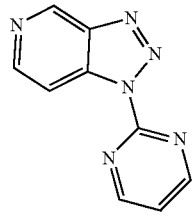 [SMILES: c1cnc(-n2nnc3cnccc32)nc1]

MS (ESI): mass calcd. for $C_9H_6N_6$, 198.1; m/z found, M/Z=199.1 [M+H]$^+$, $^1$H NMR (400 MHz, CD$_3$OD): δ 10.10 (s, 1H), 9.17-9.07 (m, 3H), 8.92 (d, J=6.7 Hz, 1H), 7.74 (t, J=4.9 Hz, 1H).

Intermediate 45: 1-(3-Fluoropyridin-2-yl)-6-methyl-1H-[1,2,3]triazolo[4,5-c]pyridine

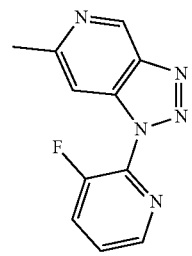 [SMILES: Cc1cc2c(cn1)nnn2-c1ncccc1F]

MS (ESI): mass calcd. for $C_{11}H_8FN_5$, 229.1; m/z found, M/Z=230.2 [M+H]$^+$, $^1$H NMR (400 MHz, DMSO-d$_6$): δ 9.48 (s, 1H), 8.59 (d, J=4.6 Hz, 1H), 8.29-8.17 (m, 1H), 7.89 (s, 1H), 7.81-7.72 (m, 1H), 2.67 (s, 3H).

Intermediate 46: 1-(5-Fluoropyrimidin-2-yl)-1H-[1,2,3]triazolo[4,5-c]pyridine

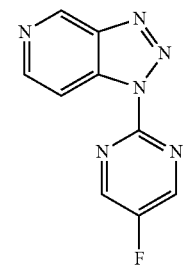 [SMILES: Fc1cnc(-n2nnc3cnccc32)nc1]

MS (ESI): mass calcd. for $C_9H_5FN_6$, 216.1; m/z found, 217.1 [M+H]$^+$. $^1$H NMR (400 MHz, CDCl$_3$) δ 9.59 (d, J=1.2 Hz, 1H), 8.85 (s, 2H), 8.78 (d, J=5.8 Hz, 1H), 8.42 (dd, J=5.8, 1.2 Hz, 1H).

Intermediate 47: 1-(5-Fluoropyridin-2-yl)-4-methyl-1H-[1,2,3]triazolo[4,5-c]pyridine

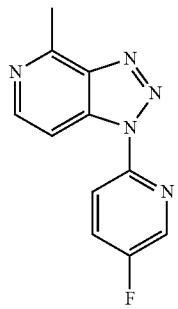 [SMILES: Cc1nccc2c1nnn2-c1ccc(F)cn1]

MS (ESI): mass calcd. for $C_{11}H_8FN_5$, 229.1; m/z found, 230.1 [M+H]$^+$. $^1$H NMR (400 MHz, CDCl$_3$) δ 8.56 (d, J=5.9 Hz, 1H), 8.49 (dd, J=3.0, 0.6 Hz, 1H), 8.34 (ddd, J=9.1, 3.8, 0.7 Hz, 1H), 8.27 (dd, J=5.9, 0.8 Hz, 1H), 7.73 (ddd, J=9.0, 7.4, 2.9 Hz, 1H), 3.10 (s, 3H).

Intermediate 48: 1-(1H-Pyrazol-5-yl)-1H-[1,2,3]triazolo[4,5-c]pyridine

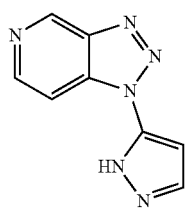 [SMILES: c1cc2c(cn1)nnn2-c1ccn[nH]1]

MS (ESI): mass calcd. for $C_8H_6N_6$, 186.1; m/z found, M/Z=187.1 [M+H]$^+$, $^1$H NMR (400 MHz, DMSO): δ 13.42 (s, 1H), 9.57 (s, 1H), 8.67 (d, J=5.8 Hz, 1H), 8.12 (d, J=5.8 Hz, 1H), 8.06 (d, J=2.0 Hz, 1H), 6.88 (d, J=1.8 Hz, 1H).

Intermediate 49: tert-Butyl 3-(1H-[1,2,3]triazolo[4,5-c]pyridin-1-yl)-1H-pyrazole-1-carboxylate

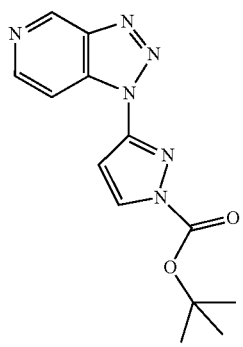 [SMILES: CC(C)(C)OC(=O)n1ccc(-n2nnc3cnccc32)n1]

A solution of 1-(1H-pyrazol-5-yl)-1H-[1,2,3]triazolo[4,5-c]pyridine (1.3 g, 7.0 mmol) in DCM (40 ml) was treated with di-tert-butyl-dicarbonate (1.7 g, 7.7 mmol) and stirred overnight. The reaction mixture was concentrated and purified on 40 g SiO$_2$ with 0-70% EtOAc/hexanes. MS (ESI): mass calcd. for $C_{13}H_{14}N_6O_2$, 286.2; m/z found, 287.1 [M+H]$^+$. $^1$H NMR (400 MHz, CDCl$_3$) δ 9.55 (d, J=1.2 Hz, 1H), 8.74 (d, J=5.8 Hz, 1H), 8.32 (dd, J=5.8, 1.2 Hz, 1H), 8.24 (d, J=2.9 Hz, 1H), 7.10 (d, J=2.9 Hz, 1H), 1.72 (s, 9H).

Intermediate 50: 1-Pyrimidin-2-yl-4,5,6,7-tetrahydro-1H-[1,2,3]triazolo[4,5-c]pyridine

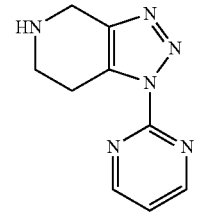 [SMILES: c1cnc(-n2nnc3c2CCNC3)nc1]

The title compound was prepared in a manner analogous to Intermediate 20 substituting Intermediate 44 for 1-Pyridin-2-yl-1H-[1,2,3]-triazolo[4,5-c]pyridine and PtO$_2$ for Rh/C. MS (ESI): mass calcd. for $C_9H_{10}N_6$, 202.2; m/z found, 203.1 [M+H]$^+$. $^1$H NMR (400 MHz, DMSO): δ 9.17 (s, 2H), 9.04 (d, J=4.9 Hz, 2H), 7.72 (t, J=4.9 Hz, 1H), 4.46 (t, J=1.3 Hz, 2H), 3.49 (t, J=6.0 Hz, 2H), 3.38 (s, 2H).

Intermediate 51: 1-(5-Fluoropyrimidin-2-yl)-4,5,6,7-tetrahydro-1H-[1,2,3]-triazolo[4,5-c]pyridine

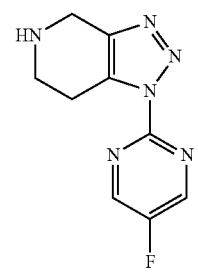 [SMILES: Fc1cnc(-n2nnc3c2CCNC3)nc1]

The title compound was prepared in a manner analogous to Intermediate 20 substituting Intermediate 46 for 1-Pyridin-2-yl-1H-[1,2,3]-triazolo[4,5-c]pyridine and PtO$_2$ for Rh/C. MS (ESI): mass calcd. for $C_9H_9N_6$, 220.2; m/z found, 221.1 [M+H]$^+$. $^1$H NMR (400 MHz, CDCl$_3$): δ 8.73 (s, 2H), 4.13 (t, J=1.4 Hz, 2H), 3.23-3.11 (m, 2H).

Intermediate 52: 1-(5-Fluoropyridin-2-yl)-4-methyl-4,5,6,7-tetrahydro-1H-[1,2,3]triazolo[4,5-c]pyridine

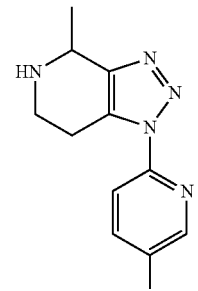

The title compound was prepared in a manner analogous to Intermediate 20 substituting Intermediate 47 for 1-Pyridin-2-yl-1H-[1,2,3]-triazolo[4,5-c]pyridine. MS (ESI): mass calcd. for $C_{11}H_{12}FN_5$, 233.2; m/z found, 234.1 [M+H]$^+$.

Example 64: 5-{[2-Chloro-3-(trifluoromethyl)phenyl]carbonyl}-1-(5-fluoropyrimidin-2-yl)-4,5,6,7-tetrahydro-1H-[1,2,3]triazolo[4,5-c]pyridine

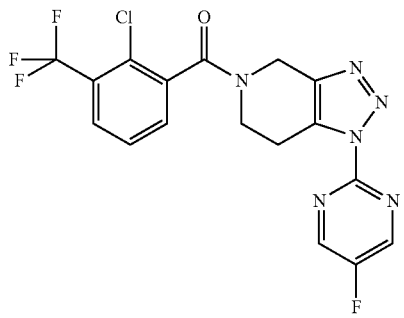 [SMILES: O=C(c1cccc(C(F)(F)F)c1Cl)N1CCc2c(nnn2-c2ncc(F)cn2)C1]

The title compound was prepared in a manner analogous to Example 63, Step 5 substituting Intermediate 51 for 1-(pyridin-2-yl)-4,5,6,7-tetrahydro-1H-[1,2,3]triazolo[4,5-c]pyridine. MS (ESI): mass calcd. for $C_{17}H_{11}ClF_4N_6O$, 426.1; m/z found, 427.1 [M+H]$^+$. $^1$H NMR (400 MHz, CDCl$_3$) δ 8.74 (d, J=15.8 Hz, 2H), 7.84-7.75 (m, 1H), 7.57-7.43 (m, 2H), 5.20-5.02 (m, 1H), 4.64-4.42 (m, 1H), 4.36-4.26 (m, 0.5H), 4.14-4.02 (m, 0.5H), 3.67-3.13 (m, 3H).

Example 65: 5-{[2-Chloro-3-(trifluoromethyl)phenyl]carbonyl}-1-pyrimidin-2-yl-4,5,6,7-tetrahydro-1H-[1,2,3]triazolo[4,5-c]pyridine

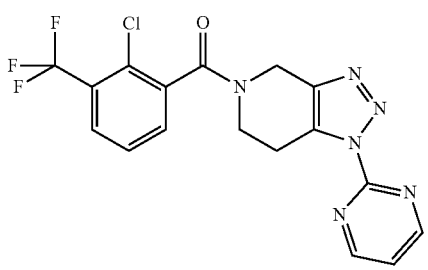 [SMILES: O=C(c1cccc(C(F)(F)F)c1Cl)N1CCc2c(nnn2-c2ncccn2)C1]

A solution of 1-pyrimidin-2-yl-4,5,6,7-tetrahydro-1H-[1,2,3]triazolo[4,5-c]pyridine (97 mg, 0.48 mmol), 2-chloro-3-(trifluoromethyl)-benzoic acid (118 mg, 0.53 mmol) and Et$_3$N (0.1 ml, 0.72 mmol) in DMF (2.5 ml), was treated with HATU (219 mg, 0.58 mmol) and stirred for 3 h. The reaction mixture was then concentrated and purified on silica gel with 0-4% NH$_3$ MeOH/CH$_2$Cl$_2$, followed by 50-100% EA/hexanes. MS (ESI): mass calcd. for $C_{17}H_{12}CF_3N_6O$, 408.1; m/z found, 409.1 [M+H]$^+$. $^1$H NMR (400 MHz, CDCl$_3$) δ 8.94-8.88 (d, J=4.8 Hz, 1H), 8.88-8.82 (d, J=4.8 Hz, 1H), 7.84-7.72 (m, 1H), 7.59-7.46 (m, 2H), 7.47-7.39 (dt, J=11.5, 4.8 Hz, 1H), 5.24-5.01 (m, 1H), 4.65-4.46 (m, 1H), 4.38-4.26 (dt, J=13.4, 5.5 Hz, 0.5H), 4.13-4.00 (ddd, J=13.4, 6.9, 5.4 Hz, 0.5H), 3.68-3.50 (m, 1H), 3.50-3.43 (dt, J=6.9, 4.8 Hz, 1H), 3.43-3.16 (m, 1H).

Example 66: 5-{[2-Fluoro-3-(trifluoromethyl)phenyl]carbonyl}-1-pyrimidin-2-yl-4,5,6,7-tetrahydro-1H-[1,2,3]triazolo[4,5-c]pyridine

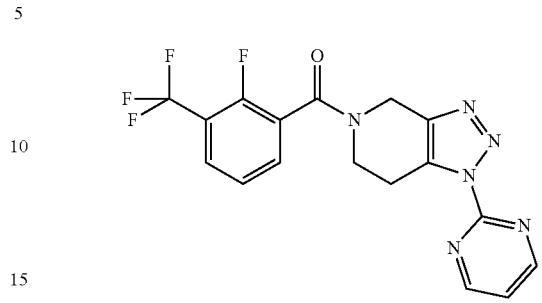

The title compound was prepared in a manner analogous to Example 65 substituting 2-fluoro-3-(trifluoromethyl)-benzoic acid for 2-chloro-3-(trifluoromethyl)-benzoic acid. MS (ESI): mass calcd. for $C_{17}H_{12}F_4N_6O$, 392.1; m/z found, 393.1 [M+H]$^+$.

Example 67: 5-[(2,3-Dichlorophenyl)carbonyl]-1-pyrimidin-2-yl-4,5,6,7-tetrahydro-1H-[1,2,3]triazolo[4,5-c]pyridine

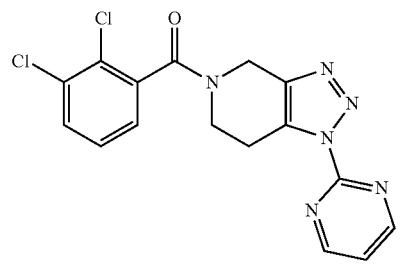 [SMILES: O=C(c1cccc(Cl)c1Cl)N1CCc2c(nnn2-c2ncccn2)C1]

The title compound was prepared in a manner analogous to Example 65 substituting 2, 3 dichlorobenzoic acid for 2-chloro-3-(trifluoromethyl)-benzoic acid. MS (ESI): mass calcd. for $C_{16}H_{12}C_2N_6O$, 374.0; m/z found, 375.1 [M+H]$^+$. $^1$H NMR (400 MHz, CDCl$_3$) δ 8.88 (dd, J=15.2, 4.8 Hz, 1H), 7.54 (ddd, J=8.0, 5.7, 1.6 Hz, 1H), 7.42 (dt, J=10.9, 4.8 Hz, 1H), 7.36-7.17 (m, 3H), 5.20-5.01 (m, 1H), 4.63-4.44 (m, 1H), 4.27-4.03 (m, 1H), 3.68-3.51 (m, 1H), 3.50-3.12 (m, 1H), 3.42-3.16 (m, 1H).

Example 68: 5-{[2-Chloro-3-(trifluoromethyl)phenyl]carbonyl}-1-(1H-pyrazol-5-yl)-4,5,6,7-tetrahydro-1H-[1,2,3]triazolo[4,5-c]pyridine Step A: 1-(1H-pyrazol-5-yl)-4,5,6,7-tetrahydro-1H-[1,2,3]triazolo[4,5-c]pyridine

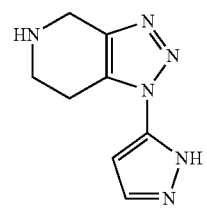

The title compound was prepared in a manner analogous to Intermediate 20 substituting Intermediate 48 for 1-Pyridin-2-yl-1H-[1,2,3]-triazolo[4,5-c]pyridine and PtO$_2$ for Rh/C. MS (ESI): mass calcd. for C$_8$H$_{10}$N$_6$, 190.1; m/z found, 191.1 [M+H]$^+$. $^1$H NMR (400 MHz, MeOD) δ 7.79 (d, J=2.5 Hz, 1H), 6.67 (d, J=2.5 Hz, 1H), 3.98 (t, J=1.2 Hz, 2H), 3.15-2.96 (m, 4H).

Step B: 5-{[2-Chloro-3-(trifluoromethyl)phenyl]carbonyl}-1-(1H-pyrazol-5-yl)-4,5,6,7-tetrahydro-1H-[1,2,3]triazolo[4,5-c]pyridine

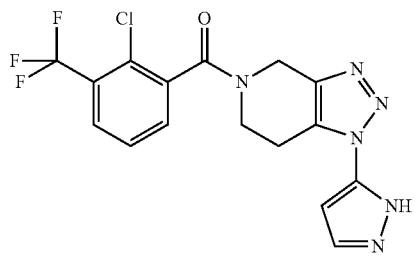 [SMILES: O=C(c1cccc(C(F)(F)F)c1Cl)N1CCc2c(nnn2-c2ccn[nH]2)C1]

The title compound was prepared in a manner analogous to Example 65 substituting the product of Example 68, Step A for 1-pyrimidin-2-yl-4,5,6,7-tetrahydro-1H-[1,2,3]triazolo[4,5-c]pyridine. MS (ESI): mass calcd. for C$_{16}$H$_{12}$ClF$_3$N$_6$O, 396.1; m/z found, 397.1 [M+H]$^+$.

Example 69: 5-{[2-Fluoro-3-(trifluoromethyl)phenyl]carbonyl}-1-pyrazin-2-yl-4,5,6,7-tetrahydro-1H-[1,2,3]triazolo[4,5-c]pyridine

Step A: 1-(pyrazin-2-yl)-4,5,6,7-tetrahydro-1H-[1,2,3]triazolo[4,5-c]pyridine

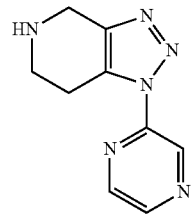 [SMILES: c1cnc(-n2nnc3c2CCNC3)cn1]

The title compound was prepared in a manner analogous to Intermediate 20 substituting Intermediate 40 for 1-Pyridin-2-yl-1H-[1,2,3]-triazolo[4,5-c]pyridine and PtO$_2$ for Rh/C. MS (ESI): mass calcd. for C$_9$H$_{10}$N$_6$, 202.1; m/z found, 203.1 [M+H]$^+$. $^1$H NMR (400 MHz, CDCl$_3$) δ 9.50 (d, J=1.4 Hz, 1H), 8.62 (d, J=2.5 Hz, 1H), 8.47 (dd, J=2.6, 1.5 Hz, 1H), 4.13 (d, J=1.4 Hz, 2H), 3.24-3.13 (m, 4H).

Step B: 5-{[2-Fluoro-3-(trifluoromethyl)phenyl]carbonyl}-1-pyrazin-2-yl-4,5,6,7-tetrahydro-1H-[1,2,3]triazolo[4,5-c]pyridine

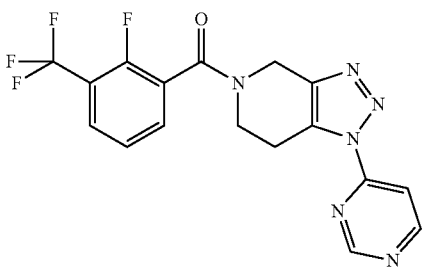 [SMILES: O=C(c1cccc(C(F)(F)F)c1F)N1CCc2c(nnn2-c2ccncn2)C1]

The title compound was prepared in a manner analogous to Example 65 substituting the product of Example 69, Step A for 1-pyrimidin-2-yl-4,5,6,7-tetrahydro-1H-[1,2,3]triazolo[4,5-c]pyridine, 2-fluoro-3-(trifluoromethyl)benzoic acid for 2-chloro-3-(trifluoromethyl)-benzoic acid and DCM for DMF. MS (ESI): mass calcd. for C$_{17}$H$_{12}$F$_4$N$_6$O, 392.1; m/z found, 393.1 [M+H]$^+$. $^1$H NMR (400 MHz, CDCl$_3$) δ 9.52 (dd, J=15.7, 1.4 Hz, 1H), 8.66 (dd, J=7.3, 2.5 Hz, 1H), 8.52-8.45 (m, 1H), 7.80-7.71 (m, 1H), 7.72-7.58 (m, 1H), 7.38 (dt, J=14.9, 7.7 Hz, 1H), 5.09 (s, 1H), 4.67 (s, 1H), 3.67 (s, 1H), 3.43 (t, J=5.8 Hz, 1H), 3.33 (s, 1H), 1.88-1.71 (s, 1H).

Example 70: 5-[(2,3-Dichlorophenyl)carbonyl]-1-pyrazin-2-yl-4,5,6,7-tetrahydro-1H-[1,2,3]triazolo[4,5-c]pyridine

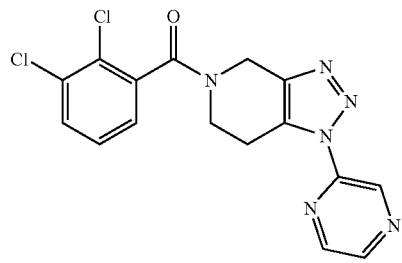 [SMILES: O=C(c1cccc(Cl)c1Cl)N1CCc2c(nnn2-c2cnccn2)C1]

The title compound was prepared in a manner analogous to Example 65 substituting 2,3-dichlorobenzoic acid for 2-chloro-3-(trifluoromethyl)-benzoic acid and DCM for DMF. MS (ESI): mass calcd. for C$_{16}$H$_{12}$Cl$_2$N$_6$O, 374.0; m/z found, 375.1 [M+H]$^+$. $^1$H NMR (400 MHz, CDCl$_3$) δ 9.52 (ddd, J=11.3, 1.4, 0.5 Hz, 1H), 8.66 (ddd, J=10.9, 2.6, 0.5 Hz, 1H), 8.52-8.41 (m, 1H), 7.55 (ddd, J=8.0, 3.1, 1.5 Hz, 1H), 7.38-7.17 (m, 2H), 5.19-5.01 (m, 1H), 4.64-4.40 (m, 1H), 4.28-4.00 (m, 1H), 3.69-3.50 (m, 1H), 3.43 (d, J=1.5 Hz, 1H).

Example 71: 5-{[2-Chloro-3-(trifluoromethyl)phenyl]carbonyl}-1-(5-fluoropyridin-2-yl)-4-methyl-4,5,6,7-tetrahydro-1H-[1,2,3]triazolo[4,5-c]pyridine

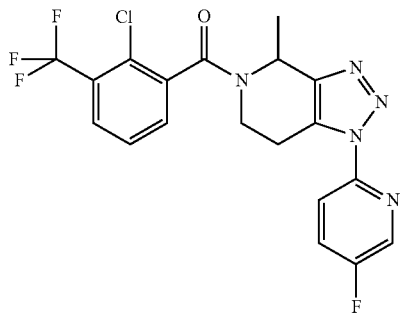 [SMILES: CC1c2nnn(-c3ccc(F)cn3)c2CCN1C(=O)c1cccc(C(F)(F)F)c1Cl]

The title compound was prepared in a manner analogous to Example 63, Step 5 substituting Intermediate 52 for 1-(pyridin-2-yl)-4,5,6,7-tetrahydro-1H-[1,2,3]triazolo[4,5-c]pyridine and DCM for THF. MS (ESI): mass calcd. for $C_{19}H_{14}CF_4N_5O$, 439.1; m/z found, 440.1 [M+H]$^+$.

Example 72: 5-{[2-Chloro-3-(trifluoromethyl)phenyl]carbonyl}-4-methyl-1-pyrazin-2-yl-4,5-dihydro-1H-[1,2,3]triazolo[4,5-c]pyridine

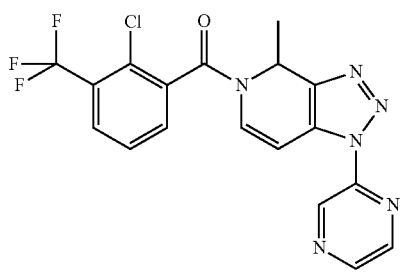 [SMILES: CC1c2nnn(-c3cnccn3)c2C=CN1C(=O)c1cccc(C(F)(F)F)c1Cl]

A suspension of 1-pyrazin-2-yl-1H-[1,2,3]triazolo[4,5-c]pyridine (100 mg, 0.5 mmol) in THF (2.5 mL) was treated with 2-chloro-3-(trifluoromethyl)benzoyl chloride (135 mg, 0.56 mmol) and the reaction stirred for 10 min at 23° C. The reaction was cooled to –50° C. and treated with MeMgBr (3.0 M solution in Et$_2$O, 0.18 mL, 0.56 mmol), and reaction slowly warmed to 23° C. over 30 minutes. Saturated NaHCO$_3$ solution was added to the reaction mixture, which was then extracted with EtOAc and purified on 16 g SiO$_2$ with 0-50% ethyl acetate/hexanes to provide 174 mg (82%) of 5-{[2-chloro-3-(trifluoromethyl)phenyl]carbonyl}-4-methyl-1-pyrazin-2-yl-4,5-dihydro-1H-[1,2,3]triazolo[4,5-c]pyridine. MS (ESI): mass calcd. for $C_{18}H_{12}ClF_3N_6O$, 420.1; m/z found, 421.1 [M+H]$^+$. $^1$H NMR (400 MHz, CDCl$_3$) δ 9.64-9.45 (t, J=1.8 Hz, 1H), 8.75-8.58 (d, J=2.6 Hz, 1H), 8.51-8.38 (ddd, J=6.8, 2.6, 1.5 Hz, 1H), 7.95-7.78 (dt, J=4.5, 1.8 Hz, 1H), 7.70-7.38 (m, 2H), 6.69-6.54 (m, 1H), 6.44-6.22 (m, 2H), 1.70-1.50 (m, 4H).

Example 73: 5-{[2-Chloro-3-(trifluoromethyl)phenyl]carbonyl}-4-methyl-1-pyrazin-2-yl-4,5,6,7-tetrahydro-1H-[1,2,3]triazolo[4,5-c]pyridine

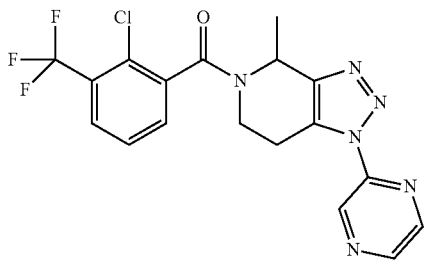 [SMILES: CC1c2nnn(-c3cnccn3)c2CCN1C(=O)c1cccc(C(F)(F)F)c1Cl]

A suspension of the 5-{[2-chloro-3-(trifluoromethyl)phenyl]carbonyl}-4-methyl-1-pyrazin-2-yl-4,5-dihydro-1H-[1,2,3]triazolo[4,5-c]pyridine (150 mg, 0.36 mmol) in MeOH (3.0 mL) and THF (1.0 mL) was treated with 10% Pd/C (30 mg), put under an atmosphere of H$_2$ and stirred overnight. The reaction was filtered through Celite© and purified on 12 g SiO$_2$ with 0-70% EA/DCM. MS (ESI): mass calcd. for $C_8H_{14}ClF_3N_6O$, 422.1; m/z found, 423.1 [M+H]$^+$.

Example 74: (4R*)-5-{[2-Chloro-3-(trifluoromethyl)phenyl]carbonyl}-4-methyl-1-pyrazin-2-yl-4,5,6,7-tetrahydro-1H-[1,2,3]triazolo[4,5-c]pyridine

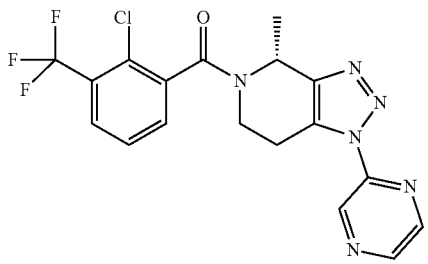 [SMILES: C[C@@H]1c2nnn(-c3cnccn3)c2CCN1C(=O)c1cccc(C(F)(F)F)c1Cl]

The title compound, absolute configuration unknown, was obtained as a single enantiomer by Chiral SFC purification of Example 73 performed using CHIRALPAK AD-H (5 μm, 250×20 mm) and a mobile phase of 75% CO$_2$, 25% EtOH. The enantiomeric purity was confirmed by analytical SFC using a CHIRALPAK AD-H (250×4.6 mm) and a mobile phase of 70% CO$_2$, 30% EtOH containing 0.3% iPrNH$_2$ over 7 minutes. (100% single enantiomer, 2.57 min retention time). MS (ESI): mass calcd. for $C_{18}H_{14}CF_3N_6O$, 422.1; m/z found, 423.1 [M+H]$^+$.

Example 75: (4S*)-5-{[2-Chloro-3-(trifluoromethyl)phenyl]carbonyl}-4-methyl-1-pyrazin-2-yl-4,5,6,7-tetrahydro-1H-[1,2,3]triazolo[4,5-c]pyridine

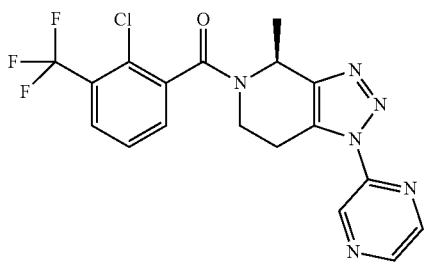 [SMILES: C[C@H]1c2nnn(-c3cnccn3)c2CCN1C(=O)c1cccc(C(F)(F)F)c1Cl]

The title compound, absolute configuration unknown, was obtained as a single enantiomer by Chiral SFC purification of Example 73 performed using CHIRALPAK AD-H (5 μm, 250×20 mm) and a mobile phase of 75% CO$_2$, 25% EtOH. The enantiomeric purity was confirmed by analytical SFC using a CHIRALPAK AD-H (250×4.6 mm) and a mobile phase of 70% CO$_2$, 30% EtOH containing 0.3% iPrNH$_2$ over 7 minutes. (100% single enantiomer, 3.30 min retention time). MS (ESI): mass calcd. for C$_{18}$H$_{14}$CF$_3$N$_6$O, 422.1; m/z found, 423.1 [M+H]$^+$.

Examples 76-88 were made in a manner analogous to Example 72 & 73 substituting the appropriate Grignard reagent for MeMgBr.

Example 76: 5-{[2-Chloro-3-(trifluoromethyl)phenyl]carbonyl}-4-phenyl-1-pyrazin-2-yl-4,5-dihydro-1H-[1,2,3]triazolo[4,5-c]pyridine

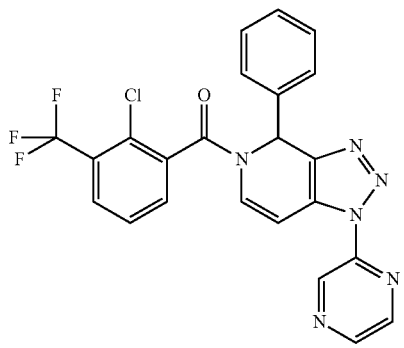 [SMILES: O=C(c1cccc(C(F)(F)F)c1Cl)N1C=Cc2c(nnn2-c2cnccn2)C1c1ccccc1]

The title compound was prepared in a manner analogous to Example 72 substituting PhMgBr for MeMgBr. MS (ESI): mass calcd. for C$_{23}$H$_{14}$ClF$_3$N$_6$O, 482.1; m/z found, 483.1 [M+H]$^+$.

Example 77: 5-{[2-Chloro-3-(trifluoromethyl)phenyl]carbonyl}-4-phenyl-1-pyrazin-2-yl-4,5,6,7-tetrahydro-1H-[1,2,3]triazolo[4,5-c]pyridine

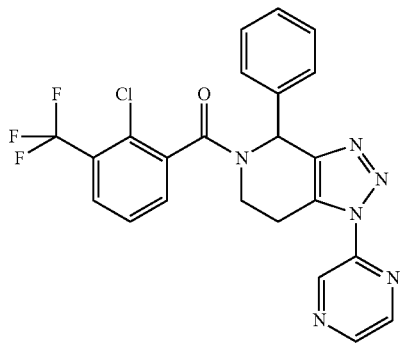 [SMILES: O=C(c1cccc(C(F)(F)F)c1Cl)N1CCc2c(nnn2-c2cnccn2)C1c1ccccc1]

The title compound was prepared in a manner analogous to Example 73 substituting Example 76 for 5-{[2-chloro-3-(trifluoromethyl)phenyl]carbonyl}-4-methyl-1-pyrazin-2-yl-4,5-dihydro-1H-[1,2,3]triazolo[4,5-c]pyridine. MS (ESI): mass calcd. for C$_{23}$H$_{16}$ClF$_3$N$_6$O, 484.1; m/z found, 485.2 [M+H]$^+$.

Example 78: 5-{[2-Chloro-3-(trifluoromethyl)phenyl]carbonyl}-4-phenyl-4,5,6,7-tetrahydro-1H-[1,2,3]triazolo[4,5-c]pyridine

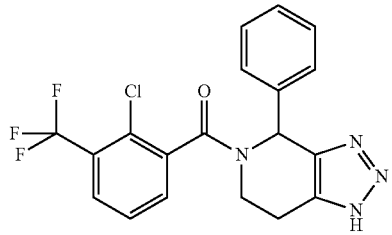 [SMILES: O=C(c1cccc(C(F)(F)F)c1Cl)N1CCc2[nH]nnc2C1c1ccccc1]

The title compound was obtained as a byproduct of the reaction carried out to generate Example 77. MS (ESI): mass calcd. for C$_{19}$H$_{14}$ClF$_3$N$_4$O, 406.1; m/z found, 407.1 [M+H]$^+$.

Example 79: 5-{[2-Chloro-3-(trifluoromethyl)phenyl]carbonyl}-4-methyl-1-pyrimidin-2-yl-4,5-dihydro-1H-[1,2,3]triazolo[4,5-c]pyridine

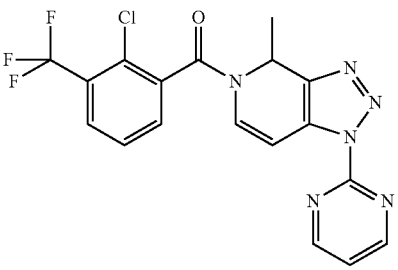

The title compound was prepared in a manner analogous to Example 72 substituting Intermediate 44 for 1-pyrazin-2-yl-1H-[1,2,3]triazolo[4,5-c]pyridine. MS (ESI): mass calcd. for C$_{18}$H$_{12}$CF$_3$N$_6$O, 420.1; m/z found, 421.1 [M+H]$^+$.

Example 80: 5-{[2-Chloro-3-(trifluoromethyl)phenyl]carbonyl}-4-methyl-1-pyrimidin-2-yl-4,5,6,7-tetrahydro-1H-[1,2,3]triazolo[4,5-c]pyridine

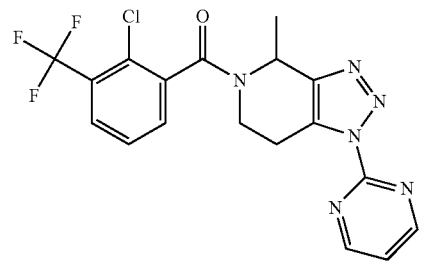

The title compound was prepared in a manner analogous to Example 73 substituting Example 79 for 5-{[2-chloro-3-(trifluoromethyl)phenyl]carbonyl}-4-methyl-1-pyrazin-2-yl-4,5-dihydro-1H-[1,2,3]triazolo[4,5-c]pyridine. MS (ESI): mass calcd. for C$_{18}$H$_{14}$CF$_3$N$_6$O, 422.1; m/z found, 423.1 [M+H]$^+$.

Example 81: 5-{[2-Chloro-3-(trifluoromethyl)phenyl]carbonyl}-1-(4-fluorophenyl)-4-methyl-4,5-dihydro-1H-[1,2,3]triazolo[4,5-c]pyridine

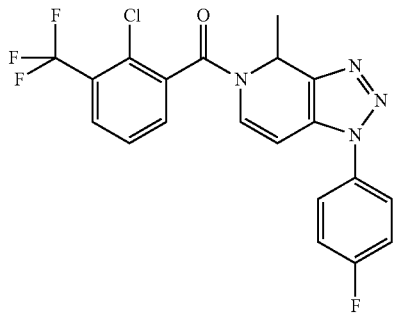 [SMILES: CC1c2nnn(-c3ccc(F)cc3)c2C=CN1C(=O)c1cccc(C(F)(F)F)c1Cl]

The title compound was prepared in a manner analogous to Example 72 substituting Intermediate 42 for 1-pyrazin-2-yl-1H-[1,2,3]triazolo[4,5-c]pyridine. MS (ESI): mass calcd. for $C_{20}H_{13}ClF_4N_4O$, 436.1; m/z found, 437.1 [M+H]$^+$. $^1$H NMR (400 MHz, CDCl$_3$) δ 7.83 (ddd, J=7.3, 4.6, 1.6 Hz, 1H), 7.69-7.41 (m, 3H), 7.32-7.19 (m, 3H), 6.39-6.20 (m, 2H), 5.79-5.70 (m, 1H), 1.67-1.54 (m, 3H).

Example 82: 5-{[2-Chloro-3-(trifluoromethyl)phenyl]carbonyl}-1-(3-fluoropyridin-2-yl)-4-methyl-4,5-dihydro-1H-[1,2,3]triazolo[4,5-c]pyridine

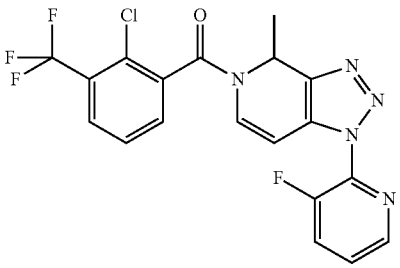 [SMILES: CC1c2nnn(-c3ncccc3F)c2C=CN1C(=O)c1cccc(C(F)(F)F)c1Cl]

The title compound was prepared in a manner analogous to Example 72 substituting Intermediate 43 for 1-pyrazin-2-yl-1H-[1,2,3]triazolo[4,5-c]pyridine. MS (ESI): mass calcd. for $C_{19}H_{12}ClF_4N_5O$, 437.1; m/z found, 438.1 [M+H]$^+$.

Example 83: 5-{[2-Chloro-3-(trifluoromethyl)phenyl]carbonyl}-1-(4-fluorophenyl)-4-methyl-4,5,6,7-tetrahydro-1H-[1,2,3]triazolo[4,5-c]pyridine

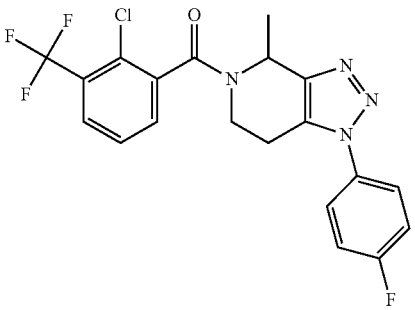 [SMILES: CC1c2nnn(-c3ccc(F)cc3)c2CCN1C(=O)c1cccc(C(F)(F)F)c1Cl]

The title compound was prepared in a manner analogous to Example 73 substituting Example 81 for 5-{[2-chloro-3-(trifluoromethyl)phenyl]carbonyl}-4-methyl-1-pyrazin-2-yl-4,5-dihydro-1H-[1,2,3]triazolo[4,5-c]pyridine. MS (ESI): mass calcd. for $C_{20}H_5ClF_4N_4O$, 438.1; m/z found, 439.1 [M+H]$^+$.

Example 84: 5-{[2-Chloro-3-(trifluoromethyl)phenyl]carbonyl}-1-(3-fluoropyridin-2-yl)-4-methyl-4,5,6,7-tetrahydro-1H-[1,2,3]triazolo[4,5-c]pyridine

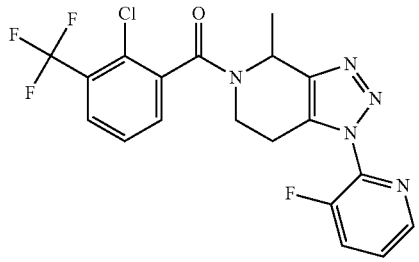 [SMILES: CC1c2nnn(-c3ncccc3F)c2CCN1C(=O)c1cccc(C(F)(F)F)c1Cl]

The title compound was prepared in a manner analogous to Example 73 substituting Example 82 for 5-{[2-chloro-3-(trifluoromethyl)phenyl]carbonyl}-4-methyl-1-pyrazin-2-yl-4,5-dihydro-1H-[1,2,3]triazolo[4,5-c]pyridine. MS (ESI): mass calcd. for $C_{19}H_{14}ClF_4N_5O$, 439.0; m/z found, 440.1 [M+H]$^+$.

Example 85: 5-{[2-Chloro-3-(trifluoromethyl)phenyl]carbonyl}-4-methyl-1-(1H-pyrazol-3-yl)-4,5,6,7-tetrahydro-1H-[1,2,3]triazolo[4,5-c]pyridine

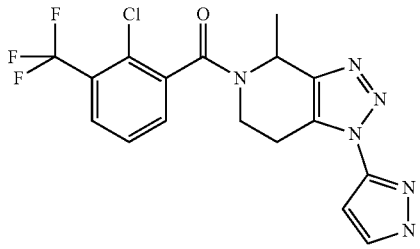

A solution of Intermediate 232 (480 mg, 0.94 mmol) in formic acid 4.0 ml) was treated with 6.0 N HCl (0.31 ml, 1.9 mmol) and stirred for 16 h. The following was performed three times: MeOH was added and rotovapped to the crude reaction mixture to give the desired product. The enantiomers were separated by chiral SFC on (CHIRALPAK AD-H 5 μm 250×20 mm). Mobile phase (70% CO$_2$, 30% EtOH) to give Examples 133 and 134. MS (ESI) mass calcd. $C_{22}H_{22}ClF_3N_6O_3$, 410.09; m/z found, 411.1 [M+H]$^+$. MS (ESI): mass calcd. for $C_{17}H_{14}CF_3N_6O$, 410.1; m/z found, 411.1 [M+H]$^+$.

Example 86: 5-{[2-Chloro-3-(trifluoromethyl)phenyl]carbonyl}-4-methyl-1-(1H-pyrazol-3-yl)-4,5-dihydro-1H-[1,2,3]triazolo[4,5-c]pyridine

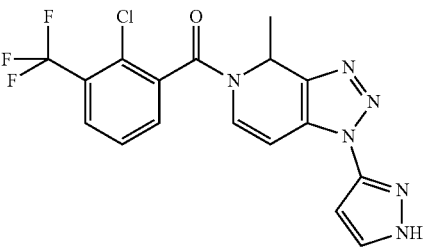 [SMILES: CC1c2nnn(-c3cc[nH]n3)c2C=CN1C(=O)c1cccc(C(F)(F)F)c1Cl]

The title compound was prepared in a manner analogous to Example 61 step 3. MS (ESI): mass calcd. for $C_{17}H_{12}ClF_3N_6O$, 408.1; m/z found, 409.1 [M+H]$^+$.

Example 87: (4S*)-5-{[2-Chloro-3-(trifluoromethyl)phenyl]carbonyl}-4-methyl-1-pyrimidin-2-yl-4,5,6,7-tetrahydro-1H-[1,2,3]triazolo[4,5-c]pyridine

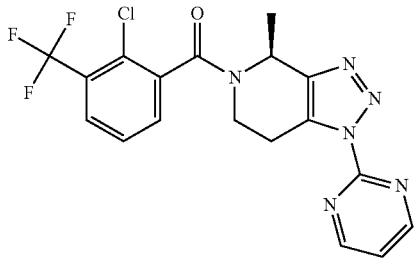

The title compound, absolute configuration unknown, was obtained as a single enantiomer by Chiral SFC purification of Example 80 performed using CHIRALPAK AD-H (5 μm, 250×20 mm) and a mobile phase of 70% $CO_2$, 30% EtOH. The enantiomeric purity was confirmed by analytical SFC using a CHIRALPAK AD (250×4.6 mm) and a mobile phase of 70% $CO_2$, 30% EtOH containing 0.3% iPrNH$_2$ over 7 minutes. (100% single enantiomer, 2.85 min retention time. MS (ESI): mass calcd. for $C_{18}H_{14}ClF_3N_6O$, 422.1; m/z found, 422.8 [M+H]$^+$.

Example 88: (4R*)-5-{[2-Chloro-3-(trifluoromethyl)phenyl]carbonyl}-4-methyl-1-pyrimidin-2-yl-4,5,6,7-tetrahydro-1H-[1,2,3]triazolo[4,5-c]pyridine

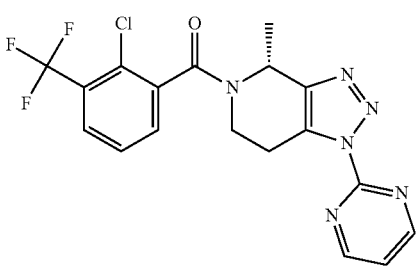 [SMILES: C[C@@H]1c2nnn(-c3ncccn3)c2CCN1C(=O)c1cccc(C(F)(F)F)c1Cl]

The title compound, absolute configuration unknown, was obtained as a single enantiomer by Chiral SFC purification of Example 80 performed using CHIRALPAK AD-H (5 μm, 250×20 mm) and a mobile phase of 70% $CO_2$, 30% EtOH. The enantiomeric purity was confirmed by analytical SFC using a CHIRALPAK AD (250×4.6 mm) and a mobile phase of 70% $CO_2$, 30% EtOH containing 0.3% iPrNH$_2$ over 7 minutes. (100% single enantiomer, 3.57 min retention time. MS (ESI): mass calcd. for $C_{18}H_{14}ClF_3N_6O$, 422.1; m/z found, 422.8 [M+H]$^+$.

Example 89: 5-{[2-Chloro-3-(trifluoromethyl)phenyl]carbonyl}-1-pyrazin-2-yl-4,5-dihydro-1H-[1,2,3]triazolo[4,5-c]pyridine

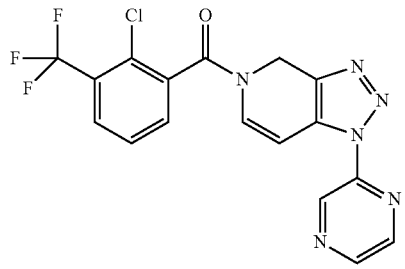 [SMILES: O=C(c1cccc(C(F)(F)F)c1Cl)N1C=Cc2c(nnn2-c2cnccn2)C1]

A solution of 1-pyrazin-2-yl-1H-[1,2,3]triazolo[4,5-c]pyridine (Intermediate 40) (50 mg, 0.25 mmol) in THF (2.0 mL) was treated with 2-chloro-3-(trifluoromethyl)benzoyl chloride (67 mg, 0.28 mmol) and stirred for 5 minutes. The reaction was treated with Hantzsch Ester (269 mg, 1.0 mmol) and heated to 80° C. in sealed tube for 90 min. Reaction was concentrated and purified on 16 g SiO$_2$ with 0-50% EtOAc/hexanes to yield 87 mg (85% yield) MS (ESI): mass calcd. for $C_{17}H_{10}ClF_3N_6O$, 406.1; m/z found, 407.1 [M+H]$^+$.

Example 90: 5-{[2-Chloro-3-(trifluoromethyl)phenyl]carbonyl}-1-pyridin-2-yl-4,5-dihydro-1H-[1,2,3]triazolo[4,5-c]pyridine

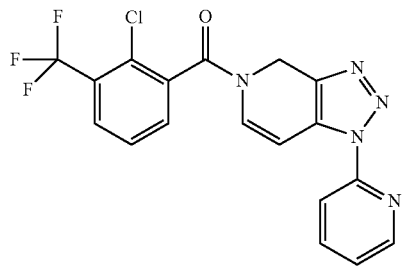 [SMILES: O=C(c1cccc(C(F)(F)F)c1Cl)N1C=Cc2c(nnn2-c2ccccn2)C1]

The title compound was prepared in a manner analogous to Example 89 substituting Intermediate 19 for Intermediate 40. MS (ESI): mass calcd. for $C_{18}H_{11}ClF_3N_5O$, 405.1; m/z found, 406.1 [M+H]$^+$.

Example 91: 5-{[2-Chloro-3-(trifluoromethyl)phenyl]carbonyl}-1-pyrazin-2-yl-4,5,6,7-tetrahydro-1H-[1,2,3]triazolo[4,5-c]pyridine

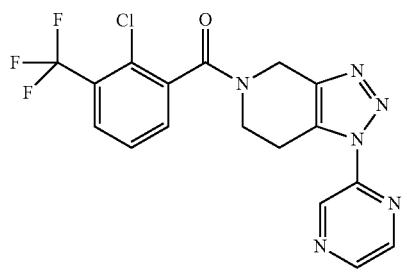 [SMILES: O=C(c1cccc(C(F)(F)F)c1Cl)N1CCc2c(nnn2-c2cnccn2)C1]

The title compound was prepared in a manner analogous to Example 73 substituting Example 89 for 5-{[2-chloro-3-(trifluoromethyl)phenyl]carbonyl}-4-methyl-1-pyrazin-2-yl-4,5-dihydro-1H-[1,2,3]triazolo[4,5-c]pyridine. MS (ESI): mass calcd. for $C_{17}H_{12}CF_3N_6O$, 408.1; m/z found, 409.1 [M+H]⁺.

Example 92: 6-{[2-Chloro-3-(trifluoromethyl)phenyl]carbonyl}-2-methyl-3-pyridin-2-yl-4,5,6,7-tetrahydro-2H-pyrazolo[3,4-c]pyridine

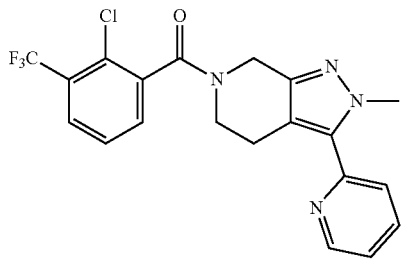 [SMILES: Cn1nc2c(c1-c1ccccn1)CCN(C(=O)c1cccc(C(F)(F)F)c1Cl)C2]

Intermediate 53: tert-Butyl 2-methyl-3-(((trifluoromethyl)sulfonyl)oxy)-4,5-dihydro-2H-pyrazolo[3,4-c]pyridine-6(7H)-carboxylate

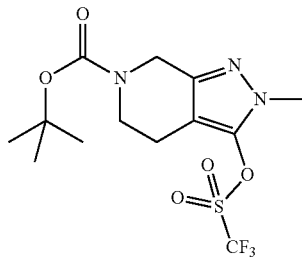 [SMILES: Cn1nc2c(c1OS(=O)(=O)C(F)(F)F)CCN(C(=O)OC(C)(C)C)C2]

Step A: tert-Butyl 2-methyl-3-(((trifluoromethyl)sulfonyl)oxy)-4,5-dihydro-2H-pyrazolo[3,4-c]pyridine-6(7H)-carboxylate To a solution of 1-tert-butyl 4-ethyl 3-oxopiperidine-1,4-dicarboxylate (5.0 g, 18.4 mmol) in ethanol (10 mL) was added methylhydrazine (1.07 mL, 20.3 mmol). The solution was allowed to stir overnight at 80° C. under an atmosphere of nitrogen. The reaction was cooled to rt and concentrated in vacuo. The residue was dissolved in 40 mL $CH_2Cl_2$ and diisopropylethylamine (3.5 mL, 20.3 mmol) and N-phenyltrifluoromethanesulfonate (7.32 g, 20.3 mmol) were added. The solution was allowed to stir overnight. The reaction was concentrated and the residue was purified by chromatography on silica gel (0-30% ethyl acetate/hexanes) to provide the desired product as a colorless oil (4.67 g, 79%). MS (ESI) mass calcd. $C_{13}H_{18}F_3N_3O_5S$, 385.1; m/z found, 386.2 [M+H]⁺. ¹H NMR (500 MHz, CDCl₃) δ 4.53-4.45 (m, 2H), 3.77 (s, 2H), 3.69 (s, 1H), 3.66-3.57 (m, 2H), 2.60-2.54 (m, 2H), 1.49 (s, 3H), 1.48 (s, 6H).

Intermediate 54: tert-Butyl 2-methyl-3-(pyridin-2-yl)-4,5-dihydro-2H-pyrazolo[3,4-c]pyridine-6(7H)-carboxylate

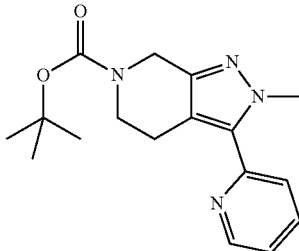 [SMILES: Cn1nc2c(c1-c1ccccn1)CCN(C(=O)OC(C)(C)C)C2]

Step B: tert-Butyl 2-methyl-3-(pyridin-2-yl)-4,5-dihydro-2H-pyrazolo[3,4-c]pyridine-6(7H)-carboxylate To a solution of tert-butyl 2-methyl-3-(((trifluoromethyl)sulfonyl)oxy)-4,5-dihydro-2H-pyrazolo[3,4-c]pyridine-6(7H)-carboxylate (1.0 g, 2.60 mmol) in DMF (25 mL) was added pyridine-2-boronic acid pinacol ester (1.33 g, 6.49 mmol), cesium carbonate (3.42 g, 10.38 mmol), copper chloride (257 mg, 0.259 mmol), palladium acetate (29 mg, 0.130 mmol) and 1,1'-bis(diphenylphosphino)ferrocene (145 mg, 0.259 mmol). The reaction was stirred at 100° C. overnight under an atmosphere of $N_2$. The reaction was poured into ice water and extracted with $CH_2Cl_2$ three times. The combined organic layers were dried over anhydrous $MgSO_4$, filtered and evaporated. Chromatography on silica gel (0-100% ethyl acetate/hexanes) provided the desired product (145 mg, 17%). MS (ESI) mass calcd. $C_{17}H_{22}N_4O_2$, 314.2; m/z found, 315.2 [M+H]⁺. ¹H NMR (500 MHz, CDCl₃) δ 8.73-8.70 (m, 0.5H), 7.80-7.76 (m, 0.5H), 7.40-7.35 (m, 2H), 7.31-7.24 (m, 1H), 4.66-4.44 (m, 2H), 4.07 (s, 2H), 3.84 (s, 1H), 3.70-3.56 (m, 2H), 2.73-2.55 (m, 2H), 1.54-1.42 (m, 9H).

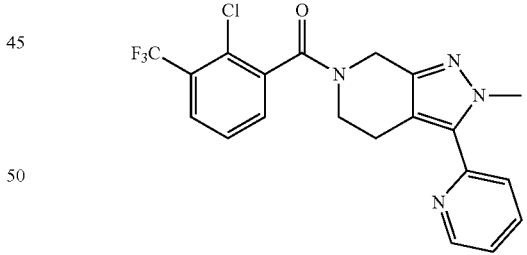

Step C: 6-{[2-Chloro-3-(trifluoromethyl)phenyl]carbonyl}-2-methyl-3-pyridin-2-yl-4,5,6,7-tetrahydro-2H-pyrazolo[3,4-c]pyridine To a solution of tert-butyl 2-methyl-3-(pyridin-2-yl)-4,5-dihydro-2H-pyrazolo[3,4-c]pyridine-6(7H)-carboxylate (135 mg, 0.429 mmol) in $CH_2Cl_2$ (5 mL) was added 4 M HCl in dioxane (0.43 mL, 1.72 mmol). The reaction was allowed to stir at rt for 1 h, then 1 mL MeOH was added and the reaction was stirred overnight. The reaction was concentrated to a yellow gum. It was combined with 2-chloro-3-(trifluoromethyl)benzoic acid (155 mg, 0.690 mmol), BOP (305 mg, 0.690 mmol) and triethylamine (0.37 mL, 2.65 mmol). After stirring overnight at rt, the reaction was filtered and purified by HPLC (Agilent prep system, Waters XBridge C18 5 μm 50×100 mm column, 5-99% MeOH/20 nM NH$_4$OH over 18 min at 80 mL/min). The desired product was isolated as a white solid (56 mg, 31%). MS (ESI) mass calcd. C$_{20}$H$_{16}$ClF$_3$N$_4$O, 420.1; m/z found, 421.1 [M+H]$^+$. $^1$H NMR (500 MHz, CDCl$_3$) δ 8.75-8.69 (m, 1H), 7.85-7.72 (m, 2H), 7.54-7.34 (m, 3H), 7.31-7.25 (m, 1H), 5.09 (d, J=16.6 Hz, 0.5H), 4.90 (d, J=16.6 Hz, 0.5H), 4.46 (d, J=15.8 Hz, 0.5H), 4.36 (d, J=15.8 Hz, 0.5H), 4.24 (dt, J=12.8, 5.4 Hz, 0.5H), 4.10 (s, 1H), 4.04 (s, 2H), 3.92-3.87 (m, 0.5H), 3.52-3.41 (m, 1H), 2.94-2.82 (m, 1H), 2.80-2.61 (m, 1H).

Example 93: 6-{[2-Chloro-3-(trifluoromethyl)phenyl]carbonyl}-3-pyridin-2-yl-4,5,6,7-tetrahydro-2H-pyrazolo[3,4-c]pyridine. TFA salt

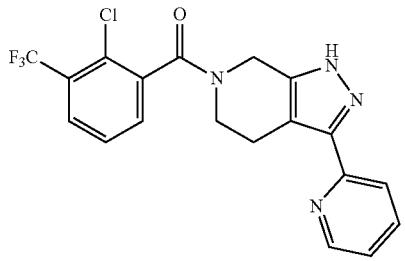 [SMILES: O=C(c1cccc(C(F)(F)F)c1Cl)N1CCc2c(-c3ccccn3)n[nH]c2C1]

To a vial containing 6-{[2-Chloro-3-(trifluoromethyl)phenyl]carbonyl}-2-methyl-3-pyridin-2-yl-4,5,6,7-tetrahydro-2H-pyrazolo[3,4-c]pyridine (17 mg, 0.040 mmol) was added pyridinium chloride (215 mg, 1.86 mmol). The vial was flushed with N$_2$ and heated to 170° C. for 30 min. To the reaction was added EtOAc and 1 M NaOH. The layers were separated and the water layer was extracted with EtOAc three times. The combined organic layers were concentrated in vacuo and the residue was purified by acidic HPLC. The product was isolated as orange oil (8 mg, 38%). MS (ESI) mass calcd. C$_{19}$H$_{14}$ClF$_3$N$_4$O, 406.1; m/z found, 407.1 [M+H]$^+$. $^1$H NMR (500 MHz, MeOD) δ 8.70-8.66 (m, 1H), 8.41-8.34 (m, 1H), 8.05 (dd, J=13.1, 8.2 Hz, 1H), 7.93 (td, J=7.7, 1.8 Hz, 1H), 7.79-7.61 (m, 3H), 5.10-5.06 (m, 0.7H), 4.97-4.93 (m, 0.7H), 4.48 (s, 0.7H), 4.32-2.27 (m, 0.3H), 4.04-3.97 (m, 0.3H), 3.66-3.54 (m, 1.3H), 3.14-3.09 (m, 0.7H), 3.04-2.88 (m, 1.3H).

Example 94: 6-{[2-Chloro-3-(trifluoromethyl)phenyl]carbonyl}-3-(5-fluoropyridin-2-yl)-4,5,6,7-tetrahydro-2H-pyrazolo[3,4-c]pyridine

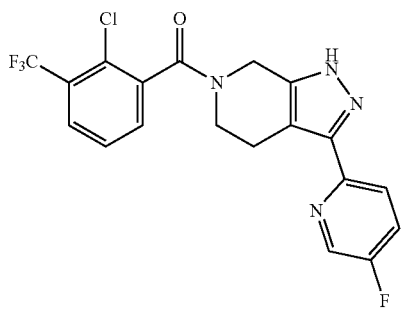 [SMILES: O=C(c1cccc(C(F)(F)F)c1Cl)N1CCc2c(-c3ccc(F)cn3)n[nH]c2C1]

Intermediate 55: 6-{[2-Chloro-3-(trifluoromethyl)phenyl]carbonyl}-3-(5-fluoropyridin-2-yl)-4,5,6,7-tetrahydro-2H-pyrazolo[3,4-c]pyridine

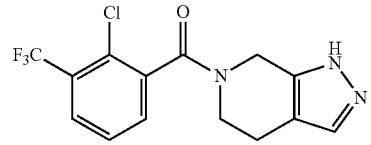 [SMILES: O=C(c1cccc(C(F)(F)F)c1Cl)N1CCc2cn[nH]c2C1]

Step A: 6-{[2-Chloro-3-(trifluoromethyl)phenyl]carbonyl}-4,5,6,7-tetrahydro-1H-pyrazolo[3,4-c]pyridine To a solution of 4,5,6,7-tetrahydro-1H-pyrazolo[3,4-c]pyridine (1.01 g, 5.15 mmol) in DMF (17 mL) was added 2-chloro-3-(trifluoromethyl)benzoic acid (2.31 g, 10.30 mmol), Hunig's base (3.55 mL, 20.60 mmol) and HATU (2.31 g, 10.30 mmol). The solution was allowed to stir for 30 min at rt then poured into ice water (300 mL). The resulting solid was collected by suction filtration and allowed to air dry. The solid was purified by chromatography on silica gel (0-100% ethyl acetate/hexanes). The product fractions were concentrated to a white solid which was dissolved in ethanol (20 mL) and 1M NaOH (20 mL) and stirred at 80° C. for 1 h. Water (50 mL) and CH$_2$Cl$_2$ (50 mL) were added. The layers were separated and the water layer was extracted two times with CH$_2$Cl$_2$. The organic layers were combined, dried over anhydrous MgSO$_4$, filtered and concentrated to an oil (1.37 g, 81%). MS (ESI) mass calcd. C$_{14}$H$_{11}$ClF$_3$N$_3$O, 329.1; m/z found, 330.1 [M+H]$^+$. $^1$H NMR (500 MHz, CDCl$_3$) δ 7.79-7.73 (m, 1H), 7.52-7.41 (m, 2H), 7.37 (br s, 1H), 5.11 (d, J=16.6 Hz, 0.5H), 4.85 (d, J=16.6 Hz, 0.5H), 4.46 (d, J=15.9 Hz, 0.5H), 4.36 (d, J=15.9 Hz, 0.5H), 4.22-4.18 (m, 0.5H), 3.94-3.88 (m, 0.5H), 3.49-3.44 (m, 1H), 2.85-2.80 (m, 1H), 2.75-2.65 (m, 1H), 2.62-2.54 (m, 1H).

Intermediate 56: 6-{[2-Chloro-3-(trifluoromethyl)phenyl]carbonyl}-3-iodo-4,5,6,7-tetrahydro-1H-pyrazolo[3,4-c]pyridine

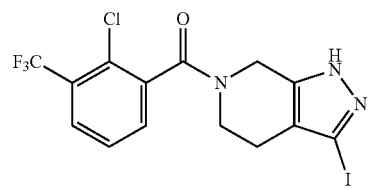 [SMILES: O=C(c1cccc(C(F)(F)F)c1Cl)N1CCc2c(I)n[nH]c2C1]

Step B: 6-{[2-Chloro-3-(trifluoromethyl)phenyl]carbonyl}-3-iodo-4,5,6,7-tetrahydro-1H-pyrazolo[3,4-c]pyridine To a solution of 6-{[2-Chloro-3-(trifluoromethyl)phenyl]carbonyl}-4,5,6,7-tetrahydro-1H-pyrazolo[3,4-c]pyridine (63 mg, 0.191 mmol) in DMF (1 mL) was added N-iodosuccinimide (47 mg, 0.210 mmol). The reaction was allowed to stir for 2 h at rt then poured into ice water (10 mL). The product was extracted with EtOAc three times. The organic layers were combined, dried over anhydrous MgSO$_4$, filtered and concentrated. Chromatography on silica gel (0-50% ethyl acetate/hexanes) provided the desired product (48 mg, 55%). MS (ESI) mass calcd. C$_{14}$H$_{10}$ClF$_3$IN$_3$O, 454.95; m/z found, 455.9 [M+H]$^+$. $^1$H NMR (500 MHz, CDCl$_3$) δ 8.27 (br s, 1H), 7.81-7.74 (m, 1H), 7.52-7.43 (m, 2H), 5.13 (d, J=16.7 Hz, 0.6H), 4.82 (d, J=16.7 Hz, 0.6H), 4.47 (d, J=16.0 Hz, 0.4H), 4.37 (d, J=16.0 Hz, 0.4H), 4.27-4.19 (m, 0.4H), 3.95-3.85 (m, 0.4H), 3.45-3.50 (m, 1.2H), 2.62-2.66 (m, 0.8H), 2.51 (m, 0.6H), 2.46-2.37 (m, 0.6H).

Intermediate 57: 6-{[2-Chloro-3-(trifluoromethyl)phenyl]carbonyl}-3-iodo-1-(tetrahydro-2H-pyran-2-yl)-4,5,6,7-tetrahydro-1H-pyrazolo[3,4-c]pyridine

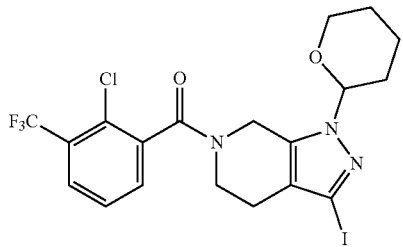

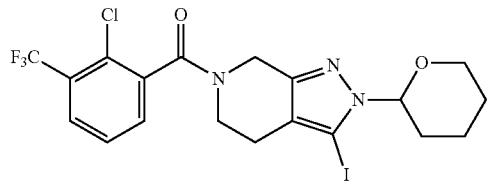

Step C: 6-{[2-Chloro-3-(trifluoromethyl)phenyl]carbonyl}-3-iodo-1-(tetrahydro-2H-pyran-2-yl)-4,5,6,7-tetrahydro-1H-pyrazolo[3,4-c]pyridine/6-{[2-Chloro-3-(trifluoromethyl)phenyl]carbonyl}-3-iodo-2-(tetrahydro-2H-pyran-2-yl)-4,5,6,7-tetrahydro-1H-pyrazolo[3,4-c]pyridine To a solution of 6-{[2-Chloro-3-(trifluoromethyl)phenyl]carbonyl}-3-iodo-4,5,6,7-tetrahydro-1H-pyrazolo[3,4-c]pyridine (40 mg, 0.09 mmol) in dichloroethane (1 mL) was added 3,4-dihydropyran (24 mL, 0.26 mmol) and para-toluenesulfonic acid (2 mg, 0.009 mmol). After stirring for 4 h at rt the reaction was diluted with CH$_2$Cl$_2$ and washed with aqueous saturated sodium bicarbonate. The organic layer was dried over anhydrous MgSO$_4$, filtered and concentrated. Chromatography on silica gel (0-50% ethyl acetate/hexanes) provided the desired product as a mixture of regioisomers (45 mg, 95%). MS (ESI) mass calcd. C$_{19}$H$_{18}$ClF$_3$IN$_3$O$_2$, 539.0; m/z found, 540.0 [M+H]$^+$.

Example 94: 6-{[2-Chloro-3-(trifluoromethyl)phenyl]carbonyl}-3-(5-fluoropyridin-2-yl)-4,5,6,7-tetrahydro-2H-pyrazolo[3,4-c]pyridine

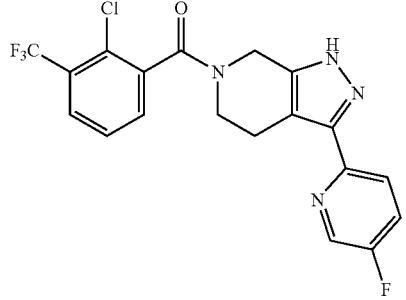

To a solution of 6-{[2-Chloro-3-(trifluoromethyl)phenyl]carbonyl}-3-iodo-1-(tetrahydro-2H-pyran-2-yl)-4,5,6,7-tetrahydro-1H-pyrazolo[3,4-c]pyridine (a mixture of regioisomers) (81 mg, 0.15 mmol) in DMF (1 mL) was added 5-fluoropyridine-2-boronic acid pinacol ester (84 mg, 0.38 mmol), cesium carbonate (198 mg, 0.600 mmol), copper chloride (15 mg, 0.15 mmol), palladium acetate (2 mg, 0.008 mmol) and 1,1'-bis(diphenylphosphino)ferrocene (8 mg, 0.150 mmol). The reaction was stirred at 85° C. overnight under an atmosphere of N$_2$. The reaction was diluted with water and aqueous sodium carbonate (5%) and extracted with EtOAc three times. The organic layers were combined, dried over anhydrous MgSO$_4$, filtered and concentrated. The residue was purified by HPLC (Agilent prep system, Waters XBridge, C18, 5 μm, 30×100 mm column, 5-99% MeOH/20 nM NH$_4$OH over 18 min at 30 mL/min). The product fractions were concentrated in vacuo and then dissolved in CH$_2$Cl$_2$ (1 mL). (THP deprotection) To the solution, triethylsilane (0.011 mL, 0.0737 mmol) and TFA (0.236 mL, 0.059 mmol) were added. The reaction was stirred at rt for 1 h then concentrated in vacuo. Chromatography on silica gel (0-100% ethyl acetate/hexanes) provided the desired product as a colorless oil (4 mg, 6%). MS (ESI) mass calcd. C$_{19}$H$_{13}$ClF$_4$N$_4$O, 424.1; m/z found, 425.1 [M+H]$^+$. $^1$H NMR (500 MHz, CDCl$_3$) δ 8.50-8.47 (m, 1H), 7.81-7.74 (m, 1H), 7.56-7.42 (m, 4H), 5.13 (d, J=16.5 Hz, 0.5H), 4.93 (d, J=16.5 Hz, 0.5H), 4.51 (d, J=15.8 Hz, 0.5H), 4.40 (d, J=15.9 Hz, 0.5H), 4.34-4.25 (m, 0.5H), 4.07-3.98 (m, 0.5H), 3.61-3.49 (m, 1H), 3.08-3.03 (m, 1H), 3.01-2.94 (m, 0.5H), 2.88-2.78 (m, 0.5H).

Example 95: 6-{[2-Chloro-3-(trifluoromethyl)phenyl]carbonyl}-3-(5-fluoropyridin-3-yl)-4,5,6,7-tetrahydro-2H-pyrazolo[3,4-c]pyridine

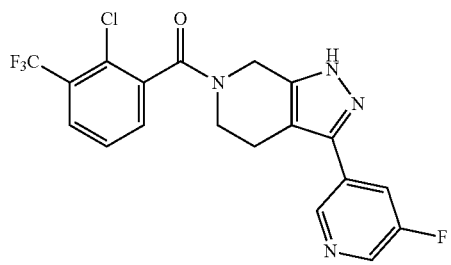 [SMILES: O=C(c1cccc(C(F)(F)F)c1Cl)N1CCc2c(-c3cncc(F)c3)n[nH]c2C1]

To a solution of 6-{[2-Chloro-3-(trifluoromethyl)phenyl]carbonyl}-3-iodo-1-(tetrahydro-2H-pyran-2-yl)-4,5,6,7-tetrahydro-1H-pyrazolo[3,4-c]pyridine (90 mg, 0.167 mmol) in 1,4-dioxane (1 mL) was added 5-fluoropyridine-3-boronic acid (70 mg, 0.50 mmol), potassium phosphate (106 mg, 0.50 mmol), [1,1'-bis(diphenylphosphino)ferrocene]dichloropalladium(II) (18 mg, 0.025 mmol) and 1,1'-bis(diphenylphosphino)ferrocene (6 mg, 0.010 mmol). The reaction was stirred at 100° C. overnight under an atmosphere of $N_2$. The reaction was filtered through Celite© and the Celite© was washed with EtOAc. The solvent was concentrated and the residue was purified by HPLC (Agilent prep system, Waters XBridge, C18, 5 μm, 30×100 mm column, 5-99% MeOH/20 mM $NH_4OH$ over 18 min at 30 mL/min) followed by THP deprotection as described in Example 94 to provide the desired product (30 mg, 42%). MS (ESI) mass calcd. $C_{19}H_{13}ClF_4N_4O$, 424.1; m/z found, 425.1 [M+H]$^+$. $^1$H NMR (500 MHz, CDCl$_3$) δ 8.73-8.64 (d, J=6.1 Hz, 1H), 8.48-8.39 (m, 1H), 7.83-7.74 (m, 1H), 7.72-7.60 (m, 1H), 7.56-7.44 (m, 2H), 5.15 (d, J=16.6 Hz, 0.7H), 4.88 (d, J=16.6 Hz, 0.7H), 4.50 (d, J=15.9 Hz, 0.3H), 4.39 (d, J=15.9 Hz, 0.3H), 4.25 (dt, J=12.8, 5.5 Hz, 0.3H), 4.04-3.95 (m, 0.3H), 3.54 (t, J=5.7 Hz, 1.4H), 2.99 (t, J=5.7 Hz, 0.7H), 2.92-2.73 (m, 1.3H).

Example 96: 6-{[2-Chloro-3-(trifluoromethyl)phenyl]carbonyl}-3-pyridin-3-yl-4,5,6,7-tetrahydro-2H-pyrazolo[3,4-c]pyridine

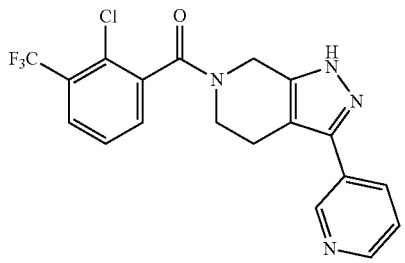

This compound was prepared in a manner analogous to Example 95. MS (ESI) mass calcd. $C_{19}H_{14}CF_3N_4O$, 406.1; m/z found 407.1 [M+H]$^+$. $^1$H NMR (500 MHz, CDCl$_3$) δ 8.87-8.83 (m, 1H), 8.64-8.57 (m, 1H), 7.94-7.84 (m, 1H), 7.82-7.75 (m, 1H), 7.56-7.34 (m, 3H), 5.15 (d, J=16.6 Hz, 0.6H), 4.89 (d, J=16.6 Hz, 0.6H), 4.51 (d, J=15.9 Hz, 0.4H), 4.40 (d, J=15.9 Hz, 0.4H), 4.27 (dt, J=13.0, 5.4 Hz, 0.4H), 4.01-3.91 (m, 0.4H), 3.53 (t, J=5.8 Hz, 1.2H), 2.98 (t, J=5.8 Hz, 0.8H), 2.91-2.71 (m, 1.2H).

Example 97: 6-{[2-Chloro-3-(trifluoromethyl)phenyl]carbonyl}-3-pyrazin-2-yl-4,5,6,7-tetrahydro-2H-pyrazolo[3,4-c]pyridine

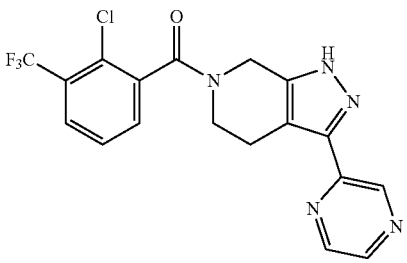

To a solution of 6-{[2-Chloro-3-(trifluoromethyl)phenyl]carbonyl}-3-iodo-4,5,6,7-tetrahydro-1H-pyrazolo[3,4-c]pyridine (Intermediate 57) (47 mg, 0.103 mmol) in 1,4-dioxane (1 mL) was added 2-tributylstannylpyrazine (0.041 mL, 0.124 mmol), lithium chloride (4 mg, 0.103 mmol) and tetrakis(triphenylphosphine)palladium(0) (119 mg, 0.103 mmol). The reaction was allowed to stir overnight at 110° C. and an additional 3 h in a microwave reactor at 170° C. The reaction was diluted with water and EtOAc and 50% potassium fluoride on Celite© (1 g) was added. After stirring for 1 h, the solution was filtered and the layers in the filtrate were separated. The organic layer was concentrated in vacuo and the residue was purified by HPLC (Agilent prep system, Waters XBridge, C18, 5 μm, 30×100 mm column, 5-99% MeOH/20 mM $NH_4OH$ over 18 min at 30 mL/min) to give the desired product. (3 mg, 8%). MS (ESI) mass calcd. $C_{18}H_{13}CF_3N_5O$, 407.1; m/z found 408.1 [M+H]$^+$. $^1$H NMR (500 MHz, CDCl$_3$) δ 8.88 (br s, 1H), 8.60-8.50 (m, 2H), 7.82-7.75 (m, 1H), 7.57-7.41 (m, 3H), 5.20-5.13 (m, 0.5H), 4.95-4.87 (m, 0.5H), 4.52 (d, J=15.7 Hz, 0.5H), 4.41 (d, J=15.8 Hz, 0.5H), 4.34-4.27 (m, 0.5H), 4.10-3.97 (m, 0.5H), 3.60-3.53 (m, 1H), 3.16-3.12 (m, 1H), 2.98 (m, 1H).

Example 98: 6-{[2-Chloro-3-(trifluoromethyl)phenyl]carbonyl}-3-pyrimidin-2-yl-4,5,6,7-tetrahydro-2H-pyrazolo[3,4-c]pyridine

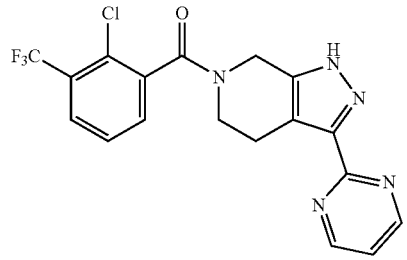

This compound was prepared in a manner analogous to Example 97 substituting copper iodide in place of lithium chloride. MS (ESI) mass calcd. $C_{18}H_{13}ClF_3N_5O$, 407.08; m/z found 408.2 [M+H]$^+$. $^1$H NMR (500 MHz, CDCl$_3$) δ 11.13 (br s, 1H), 8.76 (dd, J=14.9, 4.9 Hz, 2H), 7.77 (dd, J=11.3, 8.1 Hz, 1H), 7.57-7.41 (m, 2H), 7.22-7.17 (m, 1H), 5.19 (d, J=16.4 Hz, 0.5H), 4.90 (d, J=15.7 Hz, 0.5H), 4.51 (d, J=15.7 Hz, 0.5H), 4.41 (d, J=15.8 Hz, 0.5H), 4.32-4.22 (m, 0.5H), 4.01-3.94 (m, 0.5H), 3.57-3.46 (m, 1H), 3.32-3.09 (m, 1.5H), 3.04-2.92 (m, 0.5H).

Intermediate 58: 3-phenyl-4,5,6,7-tetrahydro-1H-pyrazolo[3,4-c]pyridine

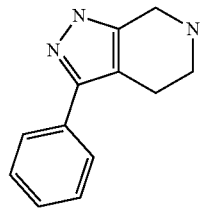

Step A: tert-Butyl 3-oxo-2,3,4,5-tetrahydro-1H-pyrazolo[3,4-c]pyridine-6(7H)-carboxylate To a solution of 1-tert-butyl 4-ethyl 3-oxopiperidine-1,4-dicarboxylate (5.0 g, 18.43 mmol) in ethanol (10 mL) was added hydrazine monohydrate (1.04 g, 20.27 mmol) via syringe. The resulting solution was heated to 80° C. and stirred overnight. A white precipitate formed after stirring overnight. The reaction was cooled to rt and solvent was decanted from the reaction mixture, the solids were dried under vacuum to provide the desired product (3.8 g, 86%). MS (ESI) mass calcd. $C_{11}H_{17}N_3O_3$, 239.2; m/z found, 240.2 [M+H]$^+$. $^1$H NMR (500 MHz, MeOD) δ 4.40 (s, 2H), 3.67-3.54 (m, 2H), 2.40 (t, J=5.6 Hz, 2H), 1.48 (s, 9H).

Step B: tert-Butyl 3-(((trifluoromethyl)sulfonyl)oxy)-4,5-dihydro-1H-pyrazolo[3,4-c]pyridine-6(7H)-carboxylate tert-Butyl 3-oxo-2,3,4,5-tetrahydro-1H-pyrazolo[3,4-c]pyridine-6(7H)-carboxylate (3.8 g, 15.88 mmol) was dissolved in 60 mL of $CH_2Cl_2$ and diisopropylethylamine (6.0 mL, 34.93 mmol) and N-phenyltrifluoromethanesulfonate (6.3 g, 17.46 mmol) were added. The solution was allowed to stir at rt for 2 hours. The reaction was concentrated and the residue was purified by chromatography on silica gel (0-30% ethyl acetate/hexanes) to provide the desired product (2.38 g, 40%). MS (ESI) mass calcd. $C_{12}H_{16}F_3N_3O_5S$, 371.3; m/z found, 372.2 [M+H]$^+$. $^1$H NMR (500 MHz, CDCl$_3$) δ 4.56 (s, 2H), 3.66 (s, 2H), 2.59 (t, J=5.5 Hz, 2H), 1.48 (d, J=10.8 Hz, 9H).

Step C: tert-Butyl 3-(((trifluoromethyl)sulfonyl)oxy)-1-((2-(trimethylsilyl)ethoxy)methyl)-4,5-dihydro-1H-pyrazolo[3,4-c]pyridine-6(7H)-carboxylate tert-Butyl 3-(((trifluoromethyl)sulfonyl)oxy)-4,5-dihydro-1H-pyrazolo[3,4-c]pyridine-6(7H)-carboxylate (2.09 g, 5.63 mmol) was dissolved in THF (30 mL), and NaH (60%) (292.64 mg, 7.32 mmol) was added. The resulting solution was allowed to stir for 1 hour. 2-(Trimethylsilyl)ethoxymethyl chloride (1.32 mL, 7.32 mmol) was then added and the reaction mixture was stirred overnight at rt. The reaction was then cooled to 0° C. and quenched with NH$_4$Cl. Upon quenching a white precipitate formed and was re-dissolved with the addition of water. The reaction mixture was extracted with EtOAc, dried and concentrated. The residue was purified by chromatography on silica gel (0-20% ethyl acetate/hexanes) to provide the desired product (590 mg, 21%). The product was not UV active but stained in KMnO$_4$. MS (ESI) mass calcd. $C_{18}H_{30}F_3N_3O_6SSi$, 501.6; m/z found, 502.2 [M+H]$^+$. $^1$H NMR (500 MHz, CDCl$_3$) δ 5.30 (s, 2H), 4.59 (s, 2H), 3.70-3.62 (m, 2H), 3.60-3.52 (m, 2H), 2.60 (t, J=5.2 Hz, 2H), 1.51 (s, 9H), 0.94-0.87 (m, 11H).

Step D: tert-Butyl 3-phenyl-1-((2-(trimethylsilyl)ethoxy)methyl)-4,5-dihydro-1H-pyrazolo[3,4-c]pyridine-6(7H)-carboxylate To a solution of tert-butyl 3-(((trifluoromethyl)sulfonyl)oxy)-1-((2-(trimethylsilyl)ethoxy)methyl)-4,5-dihydro-1H-pyrazolo[3,4-c]pyridine-6(7H)-carboxylate (440 mg, 0.88 mmol) in 1, 4-dioxane (9 mL) was added phenylboronic acid (331 mg, 2.63 mmol), potassium phosphate (559 mg, 2.63 mmol), 1,1'-bis(diphenylphosphino)ferrocene-dichloropalladium (II) (32 mg, 0.05 mmol) and 1,1'-bis(diphenylphosphino)ferrocene (10 mg, 0.02 mmol). The reaction was stirred at 160° C. for 1 hour in a microwave reactor. The reaction was cooled to rt and filtered through Celite© and rinsed with ethyl acetate. The combined organic layers were dried over anhydrous MgSO$_4$, filtered and concentrated. The residue was purified via chromatography on silica gel (0-25% ethyl acetate/hexanes) to provide the desired product (298 mg, 79%). MS (ESI) mass calcd. $C_{23}H_{35}N_3O_3Si$, 429.7; m/z found, 430.2 [M+H]$^+$.

Step E: 3-Phenyl-4,5,6,7-tetrahydro-1H-pyrazolo[3,4-c]pyridine tert-Butyl 3-phenyl-1-((2-(trimethylsilyl)ethoxy)methyl)-4,5-dihydro-1H-pyrazolo[3,4-c]pyridine-6(7H)-carboxylate (298 mg, 0.69 mmol) was dissolved in DCM (8 mL) with TFA (0.5 mL, 6.98 mmol) and was allowed to stir under N$_2$ pressure at rt overnight. Solvent was removed and the residue partitioned between 2M Na$_2$CO$_3$ and DCM, then extracted with DCM three times. The combined organic layers were dried over Na$_2$SO$_4$ and concentrated. The resulting product was used as is in the next step.

Intermediate 59: 3-(4-Fluorophenyl)-2-methyl-4,5,6,7-tetrahydro-2H-pyrazolo[3,4-c]pyridine HCl and 3-(4-fluorophenyl)-1-methyl-4,5,6,7-tetrahydro-1H-pyrazolo[3,4-c]pyridine HCl

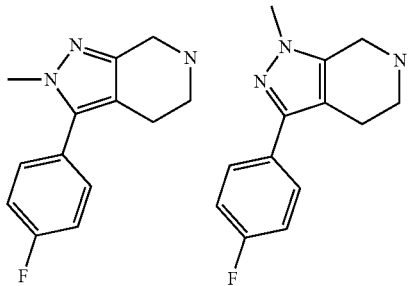

To a 1:1 mixture of tert-butyl 2-methyl-3-(((trifluoromethyl)sulfonyl)oxy)-4,5-dihydro-2H-pyrazolo[3,4-c]pyridine-6(7H)-carboxylate and tert-butyl 3-methyl-3-(((trifluoromethyl)sulfonyl)oxy)-4,5-dihydro-2H-pyrazolo[3,4-c]pyridine-6(7H)-carboxylate (1.0 g, 2.60 mmol) in 1, 4-dioxane (9 mL) was added 4-fluorophenylboronic acid (1.09 g, 7.79 mmol), potassium phosphate (1.65 g, 7.79 mmol), 1,1'-bis(diphenylphosphino)ferrocene-dichloropalladium (II) (287 mg, 0.4 mmol) and 1,1'-bis(diphenylphosphino)ferrocene (87 mg, 0.15 mmol). The reaction was stirred at 160° C. for 1 hour in a microwave reactor. The reaction was cooled to rt and filtered through Celite© and rinsed with ethyl acetate. The combined organic layers were dried over anhydrous MgSO$_4$, filtered and concentrated. The residue was purified via chromatography on silica gel (0-50% ethyl acetate/hexanes) to provide the desired product as a mixture of regio-isomers (520 mg, 60%). The product was then converted the analogous HCl salt with 4M HCl in dioxane. MS (ESI) mass calcd. $C_{18}H_{22}FN_3O_2$ 331.4; m/z found, 332.2 [M+H]$^+$. $^1$H NMR (400 MHz, CDCl$_3$) δ 7.35-7.25 (m, 2H), 7.23-7.12 (m, 2H), 4.57 (s, 2H), 3.79 (s, 3H), 3.64 (s, 2H), 2.54 (s, 2H), 1.50 (d, J=9.9 Hz, 9H).

Intermediate 60: 2-Methyl-3-(pyridin-3-yl)-4,5,6,7-tetrahydro-2H-pyrazolo[3,4-c]pyridine HCl and 1-methyl-3-(pyridin-3-yl)-4,5,6,7-tetrahydro-1H-pyrazolo[3,4-c]pyridine HCl

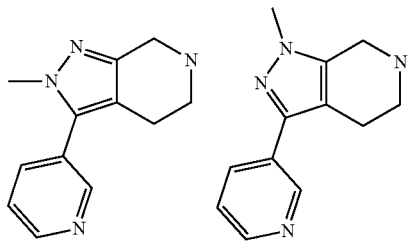

Prepared in manner analogous to that described for Intermediate 59 using pyridine-3-boronic acid to afford the desired product as a mixture of regio-isomers (417 mg, 98%) which was purified via chromatography on silica gel (0-30% ethyl acetate/hexanes). The product was then converted the analogous HCl salt with 4M HCl in dioxane. MS (ESI) mass calcd. $C_{17}H_{22}N_4O_2$ 314.4; m/z found, 315.2 [M+H]$^+$. $^1$H NMR (500 MHz, CDCl$_3$) δ 8.66 (dd, J=4.8, 1.7 Hz, 1H), 8.63 (dd, J=2.2, 0.7 Hz, 1H), 7.70-7.62 (m, 1H), 7.47-7.39 (m, 1H), 4.63-4.53 (m, 2H), 3.85-3.80 (m, 3H), 3.70-3.65 (m, 2H), 2.71-2.65 (m, 2H), 1.52-1.48 (m, 9H).

Intermediate 61: 2-Methyl-3-(pyrimidin-5-yl)-4,5,6,7-tetrahydro-2H-pyrazolo[3,4-c]pyridine HCl and 1-methyl-3-(pyrimidin-5-yl)-4,5,6,7-tetrahydro-1H-pyrazolo[3,4-c]pyridine HCl

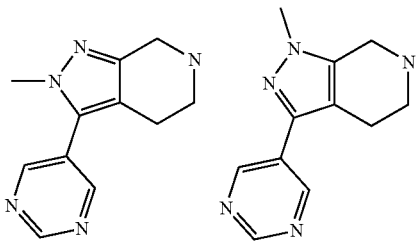

Prepared in manner analogous to that described for Intermediate 59 using pyrimidine-5-boronic acid to afford the desired product as a mixture of regio-isomers (407 mg, 99%) which was purified via chromatography on silica gel (0-30% 2M NH$_3$/methanol in DCM). The product was then converted the analogous HCl salt with 4M HCl in dioxane. MS (ESI) mass calcd. $C_{16}H_{21}N_5O_2$ 315.4; m/z found, 316.2 [M+H]$^+$.

Example 99: (2-Chloro-3-(trifluoromethyl)phenyl)(3-phenyl-4,5-dihydro-1H-pyrazolo[3,4-c]pyridin-6(7H)-yl)methanone

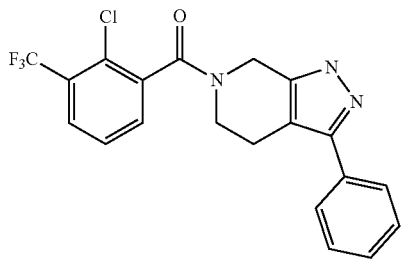

To a solution of Intermediate 58 (433 mg, 1.38 mmol) in DCM (5 mL) was added 2-chloro-3-(trifluoromethyl)benzoic acid (310.3 mg, 1.38 mmol), triethylamine (1.15 mL, 8.29 mmol) and BOP (611.03 mg, 1.38 mmol). The solution was allowed to stir overnight. Following dilution with water, the mixture was extracted with DCM three times. The combined organic layers were dried over Na$_2$SO$_4$ and conc. The resulting residue was purified by basic HPLC (0-99% acetonitrile). (356 mg, 56%). MS (ESI): mass calcd. for $C_{20}H_{15}CF_3N_3O$, 405.81; m/z found, 406.2 [M+H]$^+$. $^1$H NMR (CDCl$_3$): 7.76 (ddd, J=12.1, 7.8, 1.4 Hz, 1H), 7.56-7.33 (m, 7H), 5.17-4.97 (m, 1H), 4.52-4.33 (m, 1H), 4.28 (dt, J=12.9, 5.4 Hz, 1H), 3.99-3.83 (m, 1H), 3.54-3.41 (m, 1H), 2.97 (t, J=5.8 Hz, 1H), 2.79-2.68 (m, 1H).

Example 100: 6-[(2,3-Dichlorophenyl)carbonyl]-3-phenyl-4,5,6,7-tetrahydro-1H-pyrazolo[3,4-c]pyridine

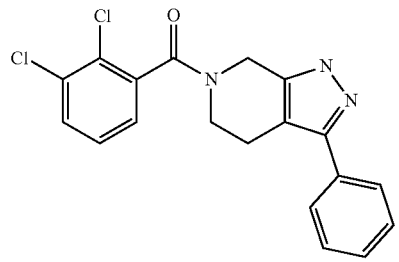

Prepared in manner analogous to that described for Example 99 using 2,3-dichlorobenzoic acid instead of 2-chloro-3-(trifluoromethyl)benzoic acid to afford the desired product. MS (ESI): mass calcd. for $C_{19}H_{15}Cl_2N_3O$, 372.26; m/z found, 373.2 [M+H]$^+$. $^1$H NMR (CDCl$_3$): 7.59-7.55-7.20 (m, 8H), 5.17-4.86 (m, 1H), 4.55-4.34 (m, 1H), 4.26-3.89 (m, 1H), 3.56-3.45 (m, 1H), 3.03-2.93 (m, 1H), 2.91-2.68 (m, 2H).

Example 101: 6-[(2,3-Dichlorophenyl)carbonyl]-1-methyl-3-phenyl-4,5,6,7-tetrahydro-1H-pyrazolo[3,4-c]pyridine-6-[(2,3-dichlorophenyl)carbonyl]-2-methyl-3-phenyl-4,5,6,7-tetrahydro-2H-pyrazolo[3,4-c]pyridine (1:1)

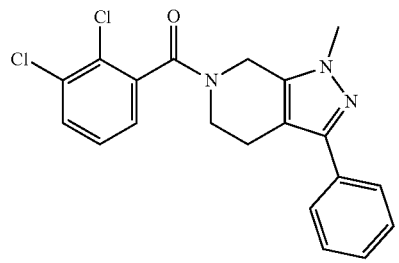

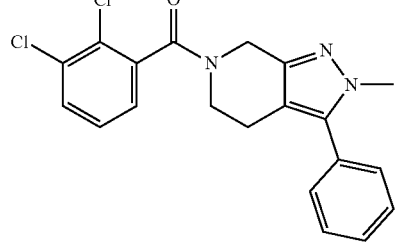

To a solution of 6-[(2,3-Dichlorophenyl)carbonyl]-3-phenyl-4,5,6,7-tetrahydro-1H-pyrazolo[3,4-c]pyridine (35 mg, 0.09 mmol) in DMF (0.5 mL) was added NaH (60%) (5 mg, 0.1 mmol). The reaction was allowed to stir at rt for 1 hr then iodomethane (0.005 mL, 0.09 mmol) was added. The reaction mixture was allowed to stir for 2 hours. After aqueous workup, the resulting mixture was extracted with ethyl acetate. The combined organic layers were dried and concentrated into a yellow residue which was purified via Basic HPLC (0-99% acetonitrile/water (NH$_4$OH)) to afford the desired product 924 mg, 33%). MS (ESI): mass calcd. for C$_{20}$H$_{17}$Cl$_2$N$_3$O, 386.28; m/z found, 387.2 [M+H]$^+$.

Example 102: 6-[(2,3-Dichlorophenyl)carbonyl]-2-methyl-3-phenyl-4,5,6,7-tetrahydro-2H-pyrazolo[3,4-c]pyridine

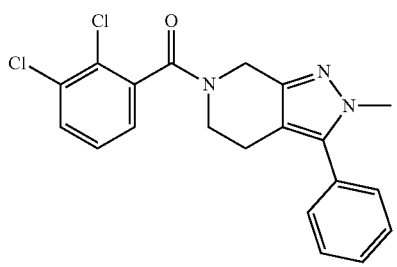

The desired product was obtained from SFC separation of Example 101. MS (ESI): mass calcd. for C$_{20}$H$_{17}$Cl$_2$N$_3$O, 386.28; m/z found, 387.2 [M+H]$^+$. $^1$H NMR (500 MHz, CDCl$_3$) δ 7.52-7.20 (m, 8H), 5.14-4.76 (m, 1H), 4.57-4.19 (m, 1H), 4.19-3.86 (m, 1H), 3.84-2.78 (m, 3H), 3.46-3.40 (m, 1H), 2.72 (t, J=5.8 Hz, 1H), 2.65-2.46 (m, 1H).

Example 103: 6-[(2,3-Dichlorophenyl)carbonyl]-1-methyl-3-phenyl-4,5,6,7-tetrahydro-1H-pyrazolo[3,4-c]pyridine

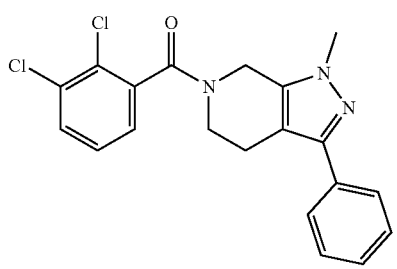

The desired product was obtained SFC separation of Example 101. MS (ESI): mass calcd. for C$_{20}$H$_{17}$Cl$_2$N$_3$O, 386.28; m/z found, 387.2 [M+H]$^+$. $^1$H NMR (500 MHz, CDCl$_3$) δ 7.70-7.62 (m, 2H), 7.58-7.52 (m, 1H), 7.45-7.36 (m, 2H), 7.35-7.27 (m, 2H), 7.27-7.21 (m, 1H), 5.03 (d, J=16.4 Hz, 1H), 4.80 (d, J=16.4 Hz, 1H), 3.76 (s, 3H), 3.51-3.45 (m, 2H), 2.89-2.81 (m, 1H), 2.79-2.70 (m, 1H).

Example 104: 6-[(2,3-Dichloropyridin-4-yl)carbonyl]-3-phenyl-4,5,6,7-tetrahydro-1H-pyrazolo[3,4-c]pyridine

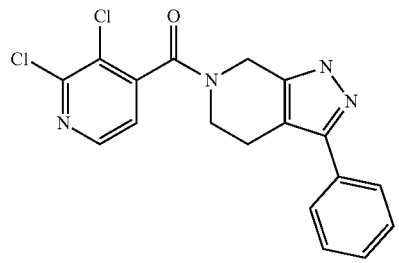 [SMILES: O=C(c1ccnc(Cl)c1Cl)N1CCc2c(-c3ccccc3)n[nH]c2C1]

Prepared in an analogous manner to Example 99 using 2,3-dichloropyridine-4-carboxylic acid to afford the desired product MS (ESI): mass calcd. for C$_{18}$H$_{14}$Cl$_2$N$_4$O, 373.24; m/z found, 374.2 [M+H]$^+$. $^1$H NMR (500 MHz, CDCl$_3$) δ 8.38 (dd, J=18.2, 4.8 Hz, 1H), 7.52-7.36 (m, 5H), 7.24-7.19 (m, 1H), 5.01-4.95 (m, 1H), 4.46-4.37 (m, 1H), 4.23-3.90 (m, 1H), 3.57-3.39 (m, 1H), 2.97 (t, J=5.8 Hz, 1H), 2.91-2.72 (m, 1H).

Example 105: 6-{[2-Chloro-3-(trifluoromethyl)phenyl]carbonyl}-3-(4-fluorophenyl)-2-methyl-4,5,6,7-tetrahydro-2H-pyrazolo[3,4-c]pyridine

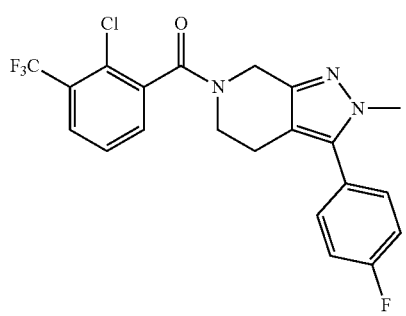 [SMILES: Cn1nc2c(c1-c1ccc(F)cc1)CCN(C(=O)c1cccc(C(F)(F)F)c1Cl)C2]

To a solution of Intermediate 59 (200 mg, 0.74 mmol) in DCM (5 mL) was added 2-chloro-3-(trifluoromethyl)benzoic acid (167 mg, 0.74 mmol), Triethylamine (0.62 mL, 4.48 mmol) and BOP (611.03 mg, 1.38 mmol). The solution was allowed to stir overnight. The reaction was then given an aqueous workup and extracted with DCM three times. The combined organic layers were dried over Na$_2$SO$_4$ and concentrated. The resulting mixture of regioisomers was purified by basic HPLC (0-99% acetonitrile) then by SFC to obtain the desired product (31 mg, 9%) MS (ESI): mass calcd. for C$_{21}$H$_{16}$ClF$_4$N$_3$O, 437.83; m/z found, 438.2 [M+H]$^+$. $^1$H NMR (500 MHz, CDCl$_3$) δ 7.75 (d, J=7.8 Hz, 1H), 7.53-7.48 (m, 1H), 7.45 (dd, J=14.5, 7.3 Hz, 1H), 7.35-7.27 (m, 2H), 7.22-7.13 (m, 2H), 5.01-4.95 (m, 1H), 4.45-4.38 (m, 1H), 4.27-3.84 (m, 1H), 3.78 (m, 3H), 3.50-3.37 (m, 1H), 2.74-2.66 (m, 1H), 2.62-2.43 (m, 1H).

Example 106: 6-{[2-Chloro-3-(trifluoromethyl)phenyl]carbonyl}-3-(4-fluorophenyl)-1-methyl-4,5,6,7-tetrahydro-1H-pyrazolo[3,4-c]pyridine

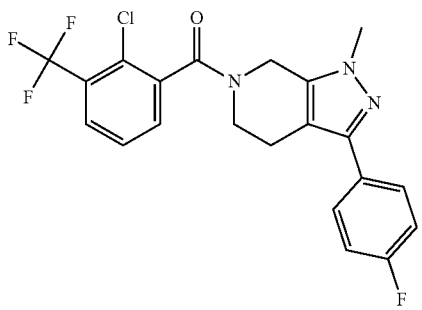 [SMILES: Cn1nc(-c2ccc(F)cc2)c2c1CN(C(=O)c1cccc(C(F)(F)F)c1Cl)CC2]

The desired product (2.6 mg, 1%) was obtained via SFC separation of Example 105. MS (ESI): mass calcd. for $C_{21}H_{16}ClF_4N_3O$, 437.83; m/z found, 438.2 [M+H]$^+$. $^1$H NMR (500 MHz, CDCl$_3$) δ 7.80 (dd, J=7.3, 2.0 Hz, 1H), 7.64-7.59 (m, 2H), 7.55-7.46 (m, 2H), 7.13-7.04 (m, 2H), 5.06 (d, J=16.4 Hz, 1H), 4.80 (d, J=16.4 Hz, 1H), 3.87 (s, 3H), 3.48 (t, J=5.7 Hz, 2H), 2.95-2.67 (m, 2H).

Example 107: 6-{[2-Chloro-3-(trifluoromethyl)phenyl]carbonyl}-2-methyl-3-pyridin-3-yl-4,5,6,7-tetrahydro-2H-pyrazolo[3,4-c]pyridine

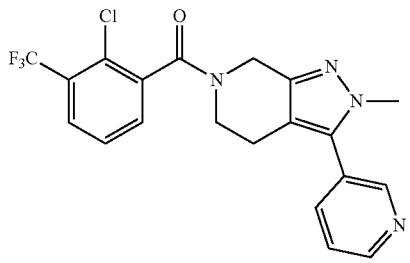

Prepared in an analogous manner to Example 105 using intermediate 60. The resulting mixture of regioisomers was purified by basic HPLC (0-99% acetonitrile), then by SFC to obtain the desired product (60.4 mg, 24%) MS (ESI): mass calcd. for $C_{20}H_{16}ClF_3N_4O$, 420.82; m/z found, 421.2 [M+H]$^+$. $^1$H NMR (500 MHz, CDCl$_3$) δ 8.78-8.54 (m, 2H), 7.75 (t, J=11.2 Hz, 1H), 7.68 (dd, J=9.5, 7.9 Hz, 1H), 7.51 (d, J=7.6 Hz, 1H), 7.45 (dt, J=14.6, 7.4 Hz, 2H), 5.02-4.96 (m, 1H), 4.44-4.37 (m, 1H), 4.26-3.88 (m, 1H), 3.86-3.80 (m, 3H), 3.49-3.41 (m, 1H), 2.77-2.70 (m, 1H), 2.66-2.46 (m, 1H).

Example 108: 6-{[2-Chloro-3-(trifluoromethyl)phenyl]carbonyl}-1-methyl-3-pyridin-3-yl-4,5,6,7-tetrahydro-1H-pyrazolo[3,4-c]pyridine

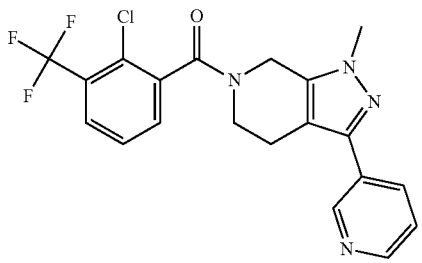 [SMILES: Cn1nc(-c2cccnc2)c2c1CN(C(=O)c1cccc(C(F)(F)F)c1Cl)CC2]

The desired product (33.6 mg, 13%) was obtained via SFC separation of Example 107. MS (ESI): mass calcd. for $C_{20}H_{16}ClF_3N_4O$, 420.82; m/z found, 421.2 [M+H]$^+$. $^1$H NMR (500 MHz, CDCl$_3$) δ 8.93-8.87 (m, 1H), 8.55 (dd, J=11.6, 4.4 Hz, 1H), 8.01 (dt, J=8.0, 1.9 Hz, 1H), 7.80 (dt, J=9.2, 4.5 Hz, 1H), 7.56-7.48 (m, 2H), 7.38-7.30 (m, 1H), 5.09 (d, J=16.5 Hz, 1H), 4.80 (d, J=16.5 Hz, 1H), 3.90 (s, 3H), 3.53-3.48 (m, 2H), 3.03-2.67 (m, 2H).

Example 109: 6-[(2,3-Dichlorophenyl)carbonyl]-3-(4-fluorophenyl)-1-methyl-4,5,6,7-tetrahydro-1H-pyrazolo[3,4-c]pyridine

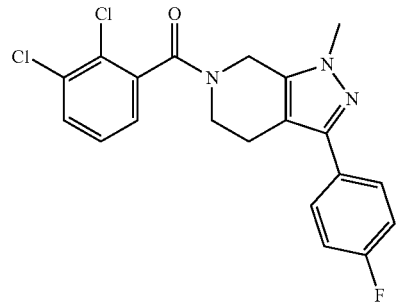

Prepared in an analogous manner to Example 90 using 2,3-dichlorobenzoic acid instead of 2-chloro-3-(trifluoromethyl)benzoic acid and Intermediate 59 instead of Intermediate 58 to afford the desired product. MS (ESI): mass calcd. for $C_{20}H_{16}Cl_2FN_3O$, 404.27; m/z found, 405.2 [M+H]$^+$. $^1$H NMR (500 MHz, CDCl$_3$) δ 7.68-7.59 (m, 2H), 7.55 (dd, J=8.0, 1.5 Hz, 1H), 7.31 (td, J=7.8, 2.4 Hz, 1H), 7.25-7.22 (m, 1H), 7.13-7.05 (m, 2H), 5.01 (d, J=16.4 Hz, 1H), 4.80 (d, J=16.5 Hz, 1H), 3.86 (s, 3H), 3.48 (t, J=5.7 Hz, 2H), 2.96-2.66 (m, 2H).

Example 110: 6-{[2-Chloro-3-(trifluoromethyl)phenyl]carbonyl}-3-(4-fluorophenyl)-4,5,6,7-tetrahydro-2H-pyrazolo[3,4-c]pyridine

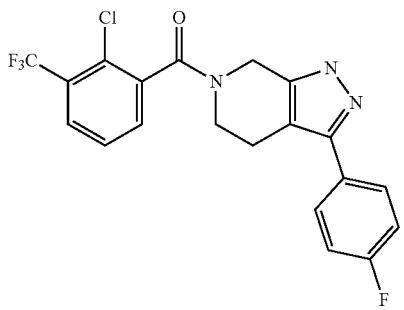

To a vial containing 6-{[2-Chloro-3-(trifluoromethyl)phenyl]carbonyl}-3-(4-fluorophenyl)-2-methyl-4,5,6,7-tetrahydro-2H-pyrazolo[3,4-c]pyridine (50 mg, 0.11 mmol) was added pyridinium chloride (270 mg, 2.30 mmol). The vial was flushed with N$_2$ and heated to 170° C. for 30 min in a microwave reactor. To the reaction was added EtOAc and 1M NaOH. The layers were separated and the water layer was extracted with EtOAc three times. The combined organic layers were concentrated in vacuo and the residue was purified by HPLC (Gilson prep system, inertsil ODS-3, C18, 3 μm 30×100 mm column at 45° C., gradient of 5-70% MeCN/water with 0.05% TFA over 7 min, flow rate of 80 mL/min). The product was isolated as orange oil (9 mg, 19%) MS (ESI): mass calcd. for $C_{20}H_{14}CF_4N_3O$, 423.8; m/z found, 424.2 [M+H]$^+$. $^1$H NMR (500 MHz, CDCl$_3$) δ 7.82-7.69 (m, 1H), 7.58-7.38 (m, 4H), 7.18-7.13 (m, 2H), 5.01 (m, 1H), 4.48-4.39 (m, 1H), 4.30-3.87 (m, 1H), 3.60-3.40 (m, 1H), 2.94 (t, J=5.8 Hz, 1H), 2.86-2.65 (m, 1H).

Example 111: 6-[(2,3-Dichlorophenyl)carbonyl]-2-methyl-3-pyridin-3-yl-4,5,6,7-tetrahydro-2H-pyrazolo[3,4-c]pyridine

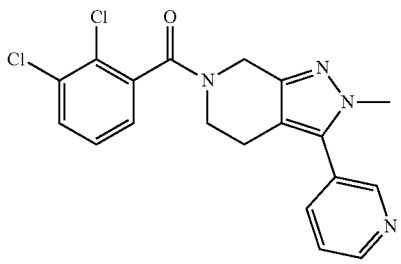 [SMILES: Cn1nc2c(c1-c1cccnc1)CCN(C(=O)c1cccc(Cl)c1Cl)C2]

Prepared in an analogous manner to Example 107 using 2,3-dichlorobenzoic acid to afford the desired product (52.6 mg 22%) MS (ESI): mass calcd. for $C_{19}H_{16}C_{12}N_4O$, 387.27; m/z found, 388.2 [M+H]$^+$. $^1$H NMR (500 MHz, CDCl$_3$) δ 8.67 (ddd, J=11.6, 4.8, 1.5 Hz, 1H), 8.63 (dd, J=11.8, 1.8 Hz, 1H), 7.67 (ddt, J=9.6, 8.0, 1.9 Hz, 1H), 7.51 (dt, J=7.9, 1.6 Hz, 1H), 7.44 (ddd, J=12.8, 7.8, 4.9 Hz, 1H), 7.29 (dd, J=11.0, 4.4 Hz, 1H), 7.24 (t, J=7.6 Hz, 1H), 5.14-4.82 (m, 1H), 4.58-4.20 (m, 1H), 4.17-3.90 (m, 1H), 3.88-3.79 (m, 3H), 3.52-3.39 (m, 1H), 2.73 (t, J=5.8 Hz, 1H), 2.66-2.46 (m, 1H).

Example 112: 6-[(2,3-Dichlorophenyl)carbonyl]-2-methyl-3-pyridin-3-yl-4,5,6,7-tetrahydro-2H-pyrazolo[3,4-c]pyridine

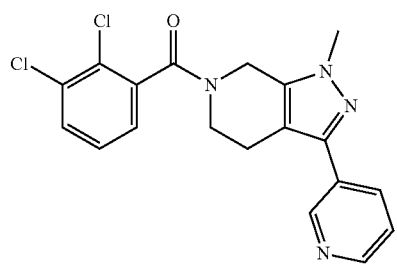 [SMILES: Cn1nc(-c2cccnc2)c2c1CN(C(=O)c1cccc(Cl)c1Cl)CC2]

Prepared in an analogous manner to Example 107 using 2,3-dichlorobenzoic acid to afford the desired product (31.2 mg 13%) via SFC separation. MS (ESI): mass calcd. for $C_{19}H_{16}C_{12}N_4O$, 387.27; m/z found, 388.2 [M+H]$^+$. $^1$H NMR (500 MHz, CDCl$_3$) δ 8.88 (s, 1H), 8.54 (s, 1H), 8.02 (d, J=8.0 Hz, 1H), 7.58-7.53 (m, 1H), 7.37-7.29 (m, 2H), 7.26-7.22 (m, 1H), 5.05 (d, J=16.5 Hz, 1H), 4.81 (d, J=16.5 Hz, 1H), 3.89 (s, 3H), 3.55-3.49 (m, 3H), 2.99-2.70 (m, 2H).

Example 113: 6-{[2-Chloro-3-(trifluoromethyl)phenyl]carbonyl}-2-methyl-3-pyrimidin-5-yl-4,5,6,7-tetrahydro-2H-pyrazolo[3,4-c]pyridine

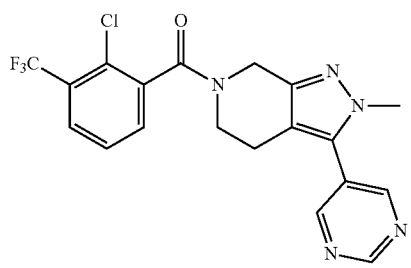 [SMILES: Cn1nc2c(c1-c1cncnc1)CCN(C(=O)c1cccc(C(F)(F)F)c1Cl)C2]

Step A: 6-{[2-Chloro-3-(trifluoromethyl)phenyl]carbonyl}-2-methyl-3-pyrimidin-5-yl-4,5,6,7-tetrahydro-2H-pyrazolo[3,4-c]pyridine Prepared in an analogous manner to Example 105 using intermediate 61. The resulting residue was purified by basic HPLC (0-99% acetonitrile) and then via SFC to obtain the desired product. MS (ESI): mass calcd. for $C_{19}H_{15}ClF_3NO$, 421.81; m/z found, 422.2 [M+H]$^+$.

Example 114: 6-[(2,3-Dichlorophenyl)carbonyl]-3-(4-fluorophenyl)-4,5,6,7-tetrahydro-2H-pyrazolo[3,4-c]pyridine

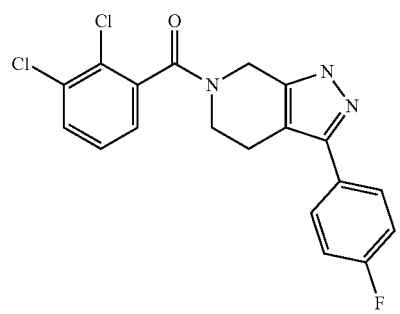

Prepared in an analogous manner to Example 110 using 6-[(2,3-Dichlorophenyl)carbonyl]-3-(4-fluorophenyl)-1-methyl-4,5,6,7-tetrahydro-1H-pyrazolo[3,4-c]pyridine to afford the desired product (22.1 mg 10%) MS (ESI): mass calcd. for $C_{19}H_{14}Cl_2FN_3O$, 390.25; m/z found, 391.2[M+H]$^+$. $^1$H NMR (500 MHz, CDCl$_3$) δ 7.59-7.42 (m, 3H), 7.33-7.21 (m, 2H), 7.18-7.08 (m, 2H), 5.15-4.77 (m, 1H), 4.58-4.33 (m 1H), 4.27-3.88 (m, 1H), 3.57-3.42 (m, 1H), 2.92 (t, J=5.8 Hz, 1H), 2.86-2.64 (m, 1H).

Example 115: 6-[(2,3-Dichlorophenyl)carbonyl]-3-pyridin-4-yl-4,5,6,7-tetrahydro-2H-pyrazolo[3,4-c]pyridine

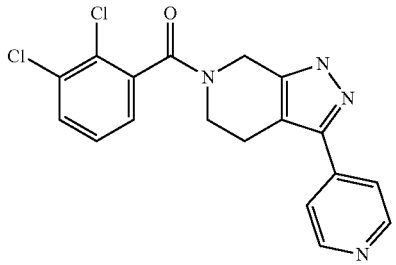

Prepared in an analogous manner to Example 110 using 6-{[2-Chloro-3-(trifluoromethyl)phenyl]carbonyl}-1-methyl-3-pyridin-3-yl-4,5,6,7-tetrahydro-1H-pyrazolo[3,4-c]pyridine to afford the desired product (52.6 mg 22%) MS (ESI): mass calcd. for $C_{18}H_{14}C_2N_4O$, 373.24; m/z found, 374.2 [M+H]$^+$. $^1$H NMR (500 MHz, CDCl$_3$) δ 8.67 (dd, J=21.7, 5.3 Hz, 2H), 7.59-7.45 (m, 2H), 7.35-7.19 (m, 3H), 5.18-4.80 (m, 1H), 4.62-4.27 (m 1H), 4.23-3.96 (m, 1H), 3.60-3.49 (m, 1H), 3.05-2.98 (m, 1H), 2.95-2.75 (m, 1H).

Example 116: 5-{[2-Chloro-3-(trifluoromethyl)phenyl]carbonyl}-6-methyl-1-pyridin-2-yl-4,5,6,7-tetrahydro-1H-[1,2,3]triazolo[4,5-c]pyridine

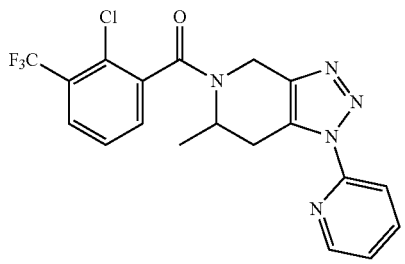

Intermediate 62: N-(2-Chloro-6-methyl-3-nitropyridin-4-yl)pyridin-2-amine

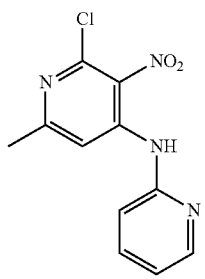 [SMILES: Cc1cc(Nc2ccccn2)c([N+](=O)[O-])c(Cl)n1]

Step A: N-(2-Chloro-6-methyl-3-nitropyridin-4-yl)pyridin-2-amine

To a solution of 2-aminopyridine (361 mg, 3.72 mmol) in THF (30 mL) was added 60% sodium hydride (164 mg, 4.09 mmol). After stirring for 2 h at rt, 2,4-dichloro-6-methyl-3-nitropyridine (864 mg, 4.09 mmol) was added. After stirring 3.5 h additional at rt, sat. NH$_4$C$_1$ solution (30 mL) was added. The organic layer was separated and the water layer was extracted with CH$_2$Cl$_2$ two times. The combined organic layers were dried over anhydrous MgSO$_4$, filtered and concentrated. Chromatography on silica gel (0-30% ethyl acetate/hexanes) provided the desired product (366 mg, 37%). MS (ESI) mass calcd. $C_{11}H_{19}ClN_4O_2$, 264.04; m/z found, 265.1 [M+H]$^+$. $^1$H NMR (500 MHz, CDCl$_3$) δ 8.51 (br s, 1H), 8.39 (ddd, J=5.0, 1.9, 0.7, 1H), 8.32 (s, 1H), 7.71 (ddd, J=8.2, 7.4, 1.9, 1H), 7.07 (ddd, J=7.4, 5.0, 0.9, 1H), 6.93 (dt, J=8.2, 0.8, 1H), 2.53 (s, 3H).

Intermediate 62b: 6-Methyl-N$^4$-(pyridin-2-yl)pyridine-3,4-diamine

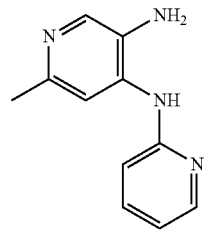

Step B: 6-Methyl-N$^4$-(pyridin-2-yl)pyridine-3,4-diamine

To a solution of N-(2-chloro-6-methyl-3-nitropyridin-4-yl)pyridin-2-amine (860 mg, 3.25 mmol) in methanol (30 mL) was added zinc powder (2.12 g, 32.49 mmol) and acetic acid (0.93 mL, 16.25 mmol). The reaction was heated to reflux and stirred for 2 h after which time 4M HCl in dioxane was added (4.0 mL, 16.0 mmol). After stirring at reflux overnight, the zinc was filtered off and the filtrate was concentrated. The residue was dissolved in CH$_2$Cl$_2$ (100 mL) and IPA (10 mL) and 5% Na$_2$CO$_3$ (aq) was added until pH 11 was obtained. The organic layer was separated. Solid NaCl was added to the water layer to saturate it and then it was extracted with 20% IPA/CH$_2$Cl$_2$ three times. The organic layers were combined, dried over anhydrous MgSO$_4$, filtered and concentrated to an oil (550 mg, 85%). MS (ESI) mass calcd. $C_{11}H_{12}N_4$, 200.11; m/z found, 201.1 [M+H]$^+$.

Intermediate 63: 6-Methyl-1-(pyridin-2-yl)-1H-[1,2,3]triazolo[4,5-c]pyridine

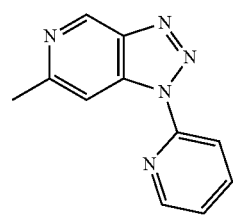 [SMILES: Cc1cc2c(cn1)nnn2-c1ccccn1]

Step C: 6-Methyl-1-(pyridin-2-yl)-1H-[1,2,3]triazolo[4,5-c]pyridine. To a solution of 6-methyl-N$^4$-(pyridin-2-yl)pyridine-3,4-diamine (550 mg, 2.7 mmol) in THF (30 mL)

was added acetic acid (0.17 mL, 6.49 mmol) and tert-butyl nitrite (0.54 mL, 4.12 mmol). The reaction was then heated to reflux and stirred overnight. The reaction was concentrated and the residue was purified by chromatography on silica gel (0-10% [2M NH$_3$ in MeOH]/CH$_2$Cl$_2$) to give the desired product as a yellow gum (408 mg, 70%). MS (ESI) mass calcd. C$_{11}$H$_9$N$_5$, 211.09; m/z found, 212.1 [M+H]$^+$. $^1$H NMR (500 MHz, CDCl$_3$) δ 9.44 (d, J=0.9, 1H), 8.67-8.62 (m, 1H), 8.37 (s, 1H), 8.31-8.23 m, 1H), 8.01-7.96 (m, 1H), 7.41-7.35 (m, 1H), 2.80 (s, 3H).

Intermediate 64: 6-Methyl-1-(pyridin-2-yl)-4,5,6,7-tetrahydro-1H-[1,2,3]triazolo[4,5-c]pyridine

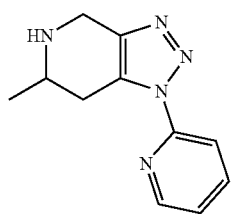 [SMILES: CC1Cc2c(nnn2-c2ccccn2)CN1]

Step D: 6-Methyl-1-(pyridin-2-yl)-4,5,6,7-tetrahydro-1H-[1,2,3]triazolo[4,5-c]pyridine. A solution of 6-methyl-1-(pyridin-2-yl)-1H-[1,2,3]triazolo[4,5-c]pyridine (530 mg, 1.932 mmol) in acetic acid (100 mL) was passed through a Rh/C cartridge using an HCube® hydrogenation apparatus at 90 bar, 90° C. and 1 mL/min. The acetic acid was concentrated and to the residue was added 1N NaOH until pH 12 was obtained. The water layer was extracted with 20% IPA/CH$_2$Cl$_2$ three times. The organic layers were combined, dried over anhydrous MgSO$_4$, filtered and concentrated to a light brown solid (243 mg, 58%). MS (ESI) mass calcd. C$_{11}$H$_{13}$N$_5$, 215.12; m/z found, 216.1 [M+H]$^+$. $^1$H NMR (600 MHz, MeOD) δ 8.57 (ddd, J=4.9, 1.8, 0.9 Hz, 1H), 8.11-8.03 (m, 2H), 7.47 (ddd, J=7.2, 4.9, 1.2 Hz, 1H), 4.13-3.97 (m, 2H), 3.35-3.40 (m, 1H), 3.09-3.02 (m, 1H), 2.86-2.79 (m, 1H), 1.34 (d, J=6.4 Hz, 3H).

Step E: 5-{[2-Chloro-3-(trifluoromethyl)phenyl]carbonyl}-6-methyl-1-pyridin-2-yl-4,5,6,7-tetrahydro-1H-[1,2,3]triazolo[4,5-c]pyridine Step E was carried out from 6-methyl-1-(pyridin-2-yl)-4,5,6,7-tetrahydro-1H-[1,2,3]triazolo[4,5-c]pyridine using the conditions described in Example 65. MS (ESI) mass calcd. C$_{19}$H$_{15}$ClF$_3$N$_5$O, 421.09; m/z found, 422.1 [M+H]$^+$.

Example 117: (2-Chloro-4-fluorophenyl)(1-(pyridin-2-yl)-6,7-dihydro-1H-[1,2,3]triazolo[4,5-c]pyridin-5 (4H)-yl)methanone

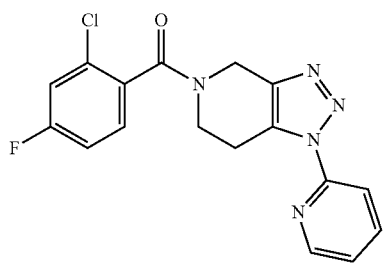

The title compound was prepared in a manner analogous to Example 61 substituting Intermediate 20 for 1-phenyl-4,5,6,7-tetrahydro-1H-[1,2,3]triazolo[4,5-c]pyridine and 2-chloro-4-fluorobenzoic acid for 2,3-dichlorobenzoic acid. MS (ESI) mass calcd. C$_{17}$H$_{13}$ClFN$_5$O, 357.1; m/z found, 358.0 [M+H]$^+$.

Example 118: 5-{[2-Chloro-3-(trifluoromethyl)phenyl]carbonyl}(S*)-6-methyl-1-pyridin-2-yl-4,5,6,7-tetrahydro-1H-[1,2,3]triazolo[4,5-c]pyridine

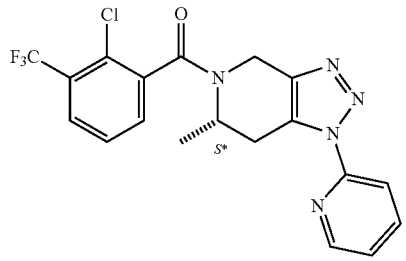

Example 118 and Example 119 were prepared by separation of the enantiomers of Example 116 using a (Chiralcel OD-H column). MS (ESI) mass calcd. C$_{19}$H$_{15}$ClF$_3$N$_5$O, 421.09; m/z found, 422.1 [M+H]$^+$.

Example 119: 5-{[2-Chloro-3-(trifluoromethyl)phenyl]carbonyl}-(R*)-6-methyl-1-pyridin-2-yl-4,5,6,7-tetrahydro-1H-[1,2,3]triazolo[4,5-c]pyridine

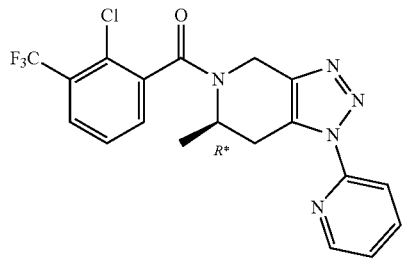

Example 118 and Example 119 were prepared by separation of the enantiomers of Example 117 using a (Chiralcel OD-H column). MS (ESI) mass calcd. C$_{19}$H$_{15}$ClF$_3$N$_5$O, 421.09; m/z found, 422.1 [M+H]$^+$.

Example 120: 5-[(2,3-Dichlorophenyl)carbonyl]-6-methyl-1-pyridin-2-yl-4,5,6,7-tetrahydro-1H-[1,2,3]triazolo[4,5-c]pyridine

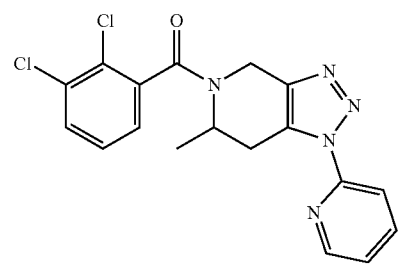

Example 120 was prepared from 6-methyl-1-(pyridin-2-yl)-4,5,6,7-tetrahydro-1H-[1,2,3]triazolo[4,5-c]pyridine and 2,3 dichlorobenzoic acid using the conditions described in Example 65. MS (ESI) mass calcd. $C_{18}H_{15}Cl_2N_5O$, 387.07; m/z found, 388.1 $[M+H]^+$.

Example 121: 5-[(2,3-Dichloro-4-fluorophenyl)carbonyl]-6-methyl-1-pyridin-2-yl-4,5,6,7-tetrahydro-1H-[1,2,3]triazolo[4,5-c]pyridine

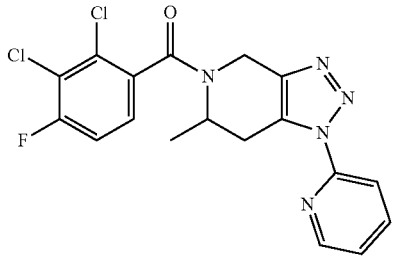

Example 121 was prepared from 6-methyl-1-(pyridin-2-yl)-4,5,6,7-tetrahydro-1H-[1,2,3]triazolo[4,5-c]pyridine and 2,3-dichloro-4-fluorobenzoic acid using the conditions described in Example 65. MS (ESI) mass calcd. $C_{18}H_{14}Cl_2FN_5O$, 405.06; m/z found, 406.1 $[M+H]^+$.

Example 122: 5-{[2-Chloro-3-(trifluoromethyl)phenyl]carbonyl}-1-(3-fluoropyridin-2-yl)-6-methyl-4,5,6,7-tetrahydro-1H-[1,2,3]triazolo[4,5-c]pyridine

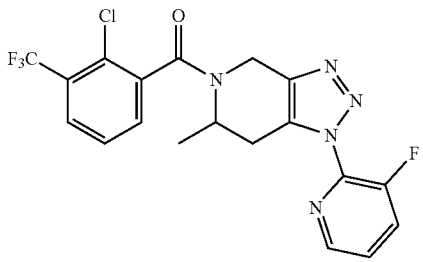

Example 122 was prepared via the route described for Example 116 beginning from 2-amino-3-fluoropyridine instead of 2-aminopyridine (in step A). Subsequent steps were carried out analogous to those described in steps B-D. MS (ESI) mass calcd. $C_{19}H_{14}ClF_4N_5O$, 439.08; m/z found, 440.1 $[M+H]^+$.

Example 123: (2-Fluoro-3-(trifluoromethyl)phenyl)(1-(pyridin-2-yl)-6,7-dihydro-1H-[1,2,3]triazolo[4,5-c]pyridin-5(4H)-yl)methanone

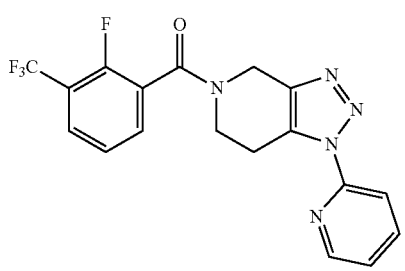

The title compound was prepared in a manner analogous to Example 61 substituting Intermediate 20 for 1-phenyl-4, 5,6,7-tetrahydro-1H-[1,2,3]triazolo[4,5-c]pyridine and 2-fluoro-3-(trifluoromethyl)benzoic acid for 2-chloro-3-(trifluoromethyl)benzoic acid. MS (ESI) mass calcd. $C_{18}H_{13}F_4N_5O$, 391.1; m/z found, 392.1 $[M+H]^+$.

Example 124: (2-Fluoro-3-(trifluoromethyl)phenyl)(1-(2-methoxyphenyl)-6,7-dihydro-1H-[1,2,3]triazolo[4,5-c]pyridin-5(4H)-yl)methanone

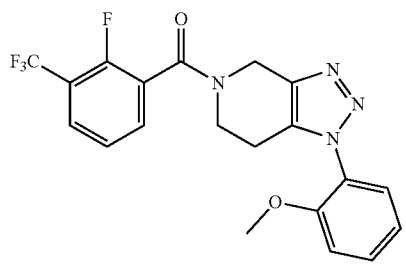

The title compound was prepared in a manner analgous to Example 61 substituting 2-fluoro-3-(trifluoromethyl)benzoic acid for 2-chloro-3-(trifluoromethyl)benzoic acid. The starting material was obtained following the procedure used to obtain Intermediate 20 where in Step 1, Intermediate 17 o-anisidine was substituted for 2-aminopyridine. MS (ESI) mass calcd. $C_{20}H_{16}F_4N_4O_2$, 420.1; m/z found, 421.2 $[M+H]^+$.

Example 125: (2-Chloro-3-(trifluoromethyl)phenyl)(1-(2-methoxyphenyl)-6,7-dihydro-1H-[1,2,3]triazolo[4,5-c]pyridin-5(4H)-yl)methanone

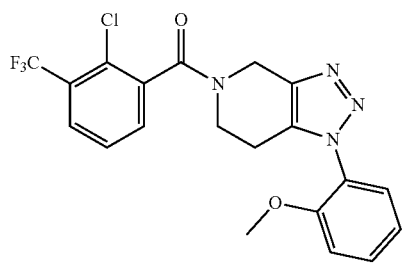

The title compound was prepared in a manner analgous to Example 61. The starting material was obtained following the procedure used to obtain Intermediate 20 where in Step 1, Intermediate 17 o-anisidine was substituted for 2-aminopyridine. MS (ESI) mass calcd. $C_{20}H_{16}ClF_3N_4O_2$, 436.1; m/z found, 437.1 $[M+H]^+$.

Example 126: (2-Chloro-3-(trifluoromethyl)phenyl)(1-(2-(2-fluoroethoxy)phenyl)-6,7-dihydro-1H-[1,2,3]triazolo[4,5-c]pyridin-5(4H)-yl)methanone Step 1: 1-bromo-2-(2-fluoroethoxy)benzene

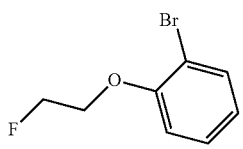 [SMILES: FCCOc1ccccc1Br]

To a solution of 2-bromophenol (1.0 g, 5.8 mmol) in THF (20 mL) was add NaH (60%) (462 mg, 11.6 mmol). The reaction mixture was stirred at room temperature for 10 min and then 1-bromo-2-fluoroethane (1.5 g, 11.6 mmol) was added and the mixture was irradiated in a microwave reactor at 130° C. for 40 min. The crude mixture was quenched with H$_2$O and the water layer was extracted with EtOAc. The combined organic layers were dried (Na$_2$SO$_4$), filtered and concentrated. The residue was purified by chromatography on silica gel (0-20% DCM in Heptane) to provide the desired compound as a colorless oil (800 mg, 63%).

Step 2: 2-(2-fluoroethoxy)aniline

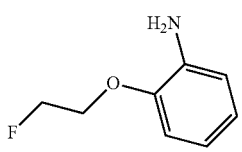 [SMILES: Nc1ccccc1OCCF]

To a solution of the product of Example 126, Step 1 (800 mg, 3.65, mmol) in deoxygenated toluene (15 mL) was added NaOtBu (498 mg, 5.2 mmol), BINAP (364 mg, 0.58 mmol) Pd$_2$(dba)$_3$ (217 mg, 0.24 mmol) and benzophenone imine (0.8 mL, 4.7 mmol). The reaction mixture was heated at 120° C. for 3 h. The crude mixture was then washed with DCM and the aqueous layer was made basic with sat. NaHCO$_3$. The aqueous layer was extracted with DCM and the combined organic extracts were dried (Na$_2$SO$_4$), filtered and concentrated. The residue was purified by chromatography on silica gel (0-5% MeOH in DCM) to afford the title compound (566 mg, 90%). MS (ESI) mass calcd. C$_8$H$_{10}$FNO, 155.1; m/z found, 156.1 [M+H]$^+$.

Step 3: N-(2-(2-fluoroethoxy)phenyl)-3-nitropyridin-4-amine

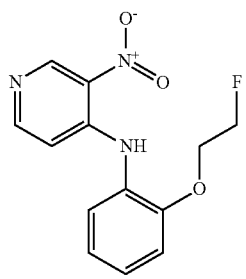 [SMILES: O=[N+]([O-])c1cnccc1Nc1ccccc1OCCF]

The title compound was prepared in a manner analogous to Intermediate 17, Step 1 substituting the product of Example 126, Step 2 for 2-aminopyridine. MS (ESI) mass calcd. C$_{13}$H$_{12}$FN$_3$O$_3$, 277.1; m/z found, 278.2 [M+H]$^+$.

Step 4: N$^4$-(2-(2-fluoroethoxy)phenyl)pyridine-3,4-diamine

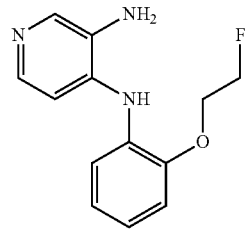 [SMILES: Nc1cnccc1Nc1ccccc1OCCF]

The title compound was prepared in a manner analogous to Intermediate 18, Step 2 substituting the product of Example 126, Step 3 for N-(3-Nitropyridin-4-yl)pyridin-2-amine. MS (ESI) mass calcd. C$_{13}$H$_{14}$FN$_3$O, 247.1; m/z found, 248.1 [M+H]$^+$.

Step 5: 1-(2-(2-fluoroethoxy)phenyl)-1H-[1,2,3]triazolo[4,5-c]pyridine

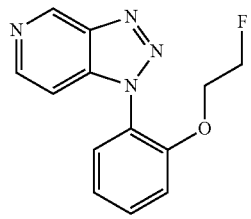 [SMILES: FCCOc1ccccc1-n1nnc2cnccc21]

The title compound was prepared in a manner analogous to Intermediate 19, Step 3 substituting the product of Example 126, Step 4 for N-4-Pyridin-2-ylpyridine-3,4-diamine. MS (ESI) mass calcd. C$_{13}$H$_{11}$FN$_4$O, 258.1; m/z found, 259.2 [M+H]$^+$.

Step 6: 1-(2-(2-fluoroethoxy)phenyl)-4,5,6,7-tetrahydro-1H-[1,2,3]triazolo[4,5-c]pyridine

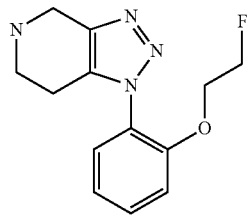 [SMILES: FCCOc1ccccc1-n1nnc2c1CCNC2]

The title compound was prepared in a manner analogous to Intermediate 20, Step 4 substituting the product of Example 126, Step 5 for 1-Pyridin-2-yl-1H-[1,2,3]-triazolo[4,5-c]pyridine. MS (ESI) mass calcd. C$_{13}$H$_{15}$FN$_4$O, 262.1; m/z found, 263.2 [M+H]$^+$.

Step 7: (2-Chloro-3-(trifluoromethyl)phenyl)(1-(2-methoxyphenyl)-6,7-dihydro-1H-[1,2,3]triazolo[4,5-c]pyridin-5(4H)-yl)methanone

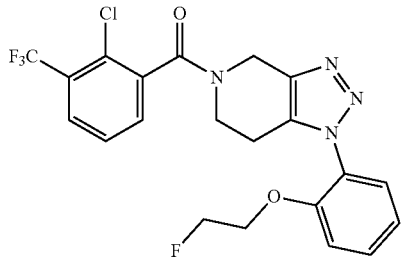

The title compound was prepared in a manner analogous to Example 61 substituting the product of Example 126, Step 6 for 1-phenyl-4,5,6,7-tetrahydro-1H-[1,2,3]triazolo[4,5-c]pyridine. MS (ESI) mass calcd. $C_{21}H_{17}ClF_4N_4O_2$, 468.1; m/z found, 469.2 $[M+H]^+$.

Example 127: (2-Chloro-3-(trifluoromethyl)phenyl)(1-(1-methyl-1H-pyrazol-3-yl)-6,7-dihydro-1H-[1,2,3]triazolo[4,5-c]pyridin-5(4H)-yl)methanone

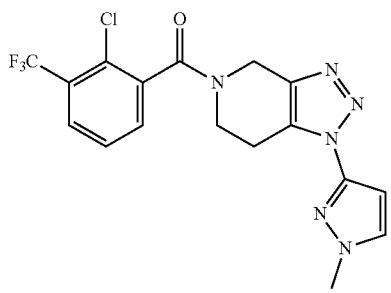 [SMILES: Cn1ccc(-n2nnc3c2CCN(C(=O)c2cccc(C(F)(F)F)c2Cl)C3)n1]

Step 1: N-(1-methyl-1H-pyrazol-3-yl)-3-nitropyridin-4-amine

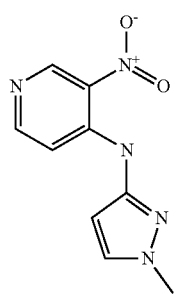

The title compound was prepared in a manner analogous to Intermediate 17, Step 1 substituting 1-methyl-1H-pyrazol-3-amine for 2-aminopyridine. MS (ESI) mass calcd. $C_9H_9N_5O_2$, 219.1; m/z found, 220.2 $[M+H]^+$.

Step 2: $N^4$-(1-methyl-1H-pyrazol-3-yl)pyridine-3,4-diamine

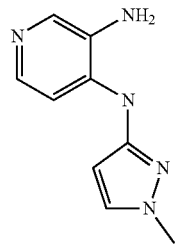

The title compound was prepared in a manner analogous to Intermediate 18, Step 2 substituting the product of Example 127, Step 1 for N-(3-Nitropyridin-4-yl)pyridin-2-amine. MS (ESI) mass calcd. $C_9H_{11}N_5$, 189.1; m/z found, 190.2 $[M+H]^+$.

Step 3: 1-(1-methyl-1H-pyrazol-3-yl)-1H-[1,2,3]triazolo[4,5-c]pyridine

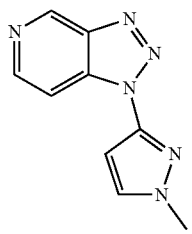

The title compound was prepared in a manner analogous to Intermediate 19, Step 3 substituting the product of Example 127, Step 2 for N-4-Pyridin-2-ylpyridine-3,4-diamine. MS (ESI) mass calcd. $C_9H_8N_6$, 200.1; m/z found, 201.2 $[M+H]^+$.

Step 4: 1-(1-methyl-1H-pyrazol-3-yl)-4,5,6,7-tetrahydro-1H-[1,2,3]triazolo[4,5-c]pyridine

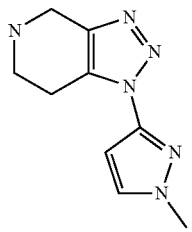

The title compound was prepared in a manner analogous to Intermediate 20, Step 4 substituting the product of Example 127, Step 3 for 1-Pyridin-2-yl-1H-[1,2,3]-triazolo[4,5-c]pyridine. MS (ESI) mass calcd. $C_9H_{12}N_6$, 204.1.1; m/z found, 205.2 $[M+H]^+$.

Step 5: (2-chloro-3-(trifluoromethyl)phenyl)(1-(1-methyl-1H-pyrazol-3-yl)-6,7-dihydro-1H-[1,2,3]triazolo[4,5-c]pyridin-5(4H)-yl)methanone

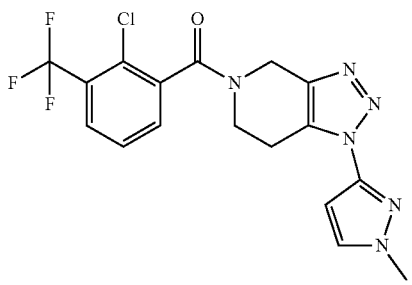 [SMILES: Cn1ccc(-n2nnc3c2CCN(C(=O)c2cccc(C(F)(F)F)c2Cl)C3)n1]

The title compound was prepared in a manner analogous to Example 61 substituting the product of Example 126, Step 4 for 1-phenyl-4,5,6,7-tetrahydro-1H-[1,2,3]triazolo[4,5-c]pyridine. MS (ESI) mass calcd. $C_{17}H_{14}ClF_3N_6O$, 410.1; m/z found, 411.2 [M+H]$^+$.

Example 128: (2-Chloro-3-(trifluoromethyl)phenyl)(1-(1-methyl-1H-pyrazol-5-yl)-6,7-dihydro-1H-[1,2,3]triazolo[4,5-c]pyridin-5(4H)-yl)methanone

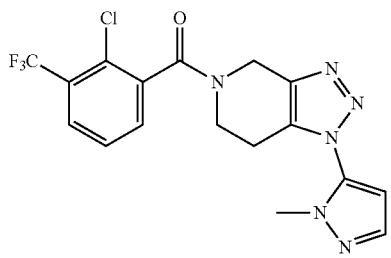 [SMILES: Cn1nccc1-n1nnc2c1CCN(C(=O)c1cccc(C(F)(F)F)c1Cl)C2]

The title compound was prepared in a manner analogous to Example 127 substituting 1-methyl-1H-pyrazol-5-ylamine for 1-methyl-1H-pyrazol-3-amine in Example 127, Step 1. MS (ESI) mass calcd. $C_{17}H_{14}ClF_3N_6O$, 410.1; m/z found, 411.2 [M+H]$^+$.

Example 129: (4-Chloro-2-fluorophenyl)(1-(pyridin-2-yl)-6,7-dihydro-1H-[1,2,3]triazolo[4,5-c]pyridin-5(4H)-yl)methanone

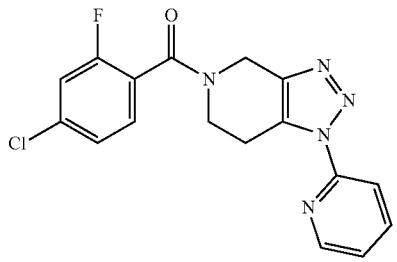 [SMILES: O=C(c1ccc(Cl)cc1F)N1CCc2c(nnn2-c2ccccn2)C1]

The title compound was prepared in a manner analogous to Example 61 substituting Intermediate 20 for 1-phenyl-4,5,6,7-tetrahydro-1H-[1,2,3]triazolo[4,5-c]pyridine and 4-chloro-2-fluorobenzoic acid for 2,3-dichlorobenzoic acid. MS (ESI) mass calcd. $C_{17}H_{13}ClFN_5O$, 357.1; m/z found, 358.2 [M+H]$^+$.

Example 130: (2,3-Dichloro-4-fluorophenyl)(1-(pyridin-2-yl)-6,7-dihydro-1H-[1,2,3]triazolo[4,5-c]pyridin-5(4H)-yl)methanone

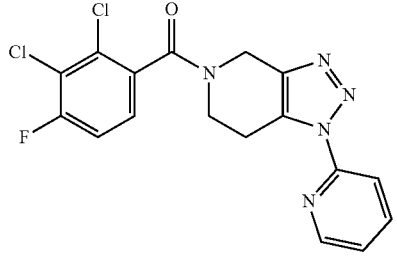 [SMILES: O=C(c1ccc(F)c(Cl)c1Cl)N1CCc2c(nnn2-c2ccccn2)C1]

The title compound was prepared in a manner analogous to Example 61 substituting Intermediate 20 for 1-phenyl-4,5,6,7-tetrahydro-1H-[1,2,3]triazolo[4,5-c]pyridine and 2,3-dichloro-4-fluorobenzoic acid for 2,3-dichlorobenzoic acid. MS (ESI) mass calcd. $C_{17}H_{12}Cl_2FN_5O$, 391.0; m/z found, 392.2 [M+H]$^+$.

Example 131: (2-Chloro-3-(trifluoromethyl)phenyl)(1-(4-fluoropyridin-2-yl)-6,7-dihydro-1H-[1,2,3]triazolo[4,5-c]pyridin-5(4H)-yl)methanone

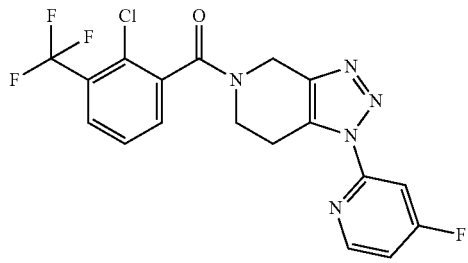

The title compound was prepared in a manner analogous to Example 127 substituting 4-fluoropyridin-2-amine for 1-methyl-1H-pyrazol-3-amine in Example 127, Step 1. MS (ESI) mass calcd. $C_{18}H_{12}ClF_4N_5O$, 425.1; m/z found, 426.2 [M+H]$^+$.

Example 132: (3,4-Difluoro-2-methylphenyl)(1-(pyridin-2-yl)-6,7-dihydro-1H-[1,2,3]triazolo-[4,5-c]pyridin-5(4H)-yl)methanone

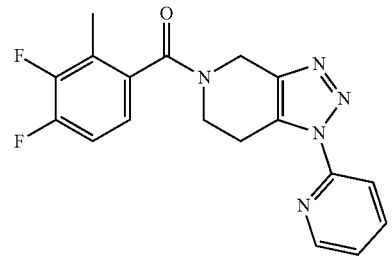 [SMILES: Cc1c(C(=O)N2CCc3c(nnn3-c3ccccn3)C2)ccc(F)c1F]

The title compound was prepared in a manner analogous to Example 61 substituting Intermediate 20 for 1-phenyl-4,5,6,7-tetrahydro-1H-[1,2,3]triazolo[4,5-c]pyridine and 3,4-difluoro-2-methylbenzoic acid for 2,3-dichlorobenzoic acid. MS (ESI) mass calcd. $C_{18}H_{15}F_2N_5O$, 355.1; m/z found, 356.2 [M+H]$^+$.

Example 133: (R*)-(2-Chloro-3-(trifluoromethyl)phenyl)(4-methyl-1-(1H-pyrazol-5-yl)-6,7-dihydro-1H-[1,2,3]triazolo[4,5-c]pyridin-5(4H)-yl)methanone

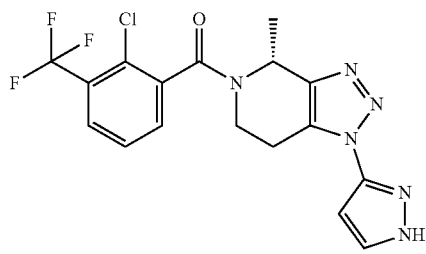 [SMILES: C[C@@H]1c2nnn(-c3cc[nH]n3)c2CCN1C(=O)c1cccc(C(F)(F)F)c1Cl]

Example 85 was purified by chiral SFC on (Chiralpak AD-H 5 μm 250×20 mm) using a mobile phase of 70% $CO_2$ and 30% EtOH to obtain the title compound as a single enantiomer, absolute configuration unknown. MS (ESI) mass calcd. $C_{17}H_{14}ClF_3N_6O$, 410.09; m/z found, 411.1 [M+H]$^+$.

Example 134: (S*)-(2-Chloro-3-(trifluoromethyl)phenyl)(4-methyl-1-(1H-pyrazol-5-yl)-6,7-dihydro-1H-[1,2,3]triazolo[4,5-c]pyridin-5(4H)-yl)methanone

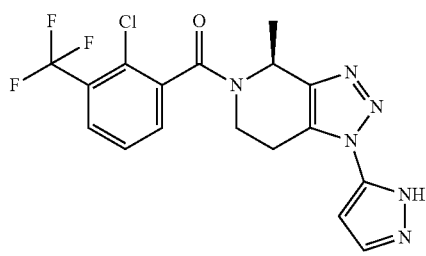 [SMILES: C[C@H]1c2nnn(-c3ccn[nH]3)c2CCN1C(=O)c1cccc(C(F)(F)F)c1Cl]

Example 85 was purified by chiral SFC on (Chiralpak AD-H 5 μm 250×20 mm) using a mobile phase of 70% $CO_2$ and 30% EtOH to obtain the title compound as a single enantiomer, absolute configuration unknown. The enantiomeric purity was confirmed by analytical SFC using a CHIRALPAK AD-H (250×4.6 mm) and a mobile phase of 70% $CO_2$, 30% EtOH containing 0.3% iPrNH$_2$ over 7 minutes. (100% single enantiomer, 1.99 min retention time). MS (ESI) mass calcd. $C_{17}H_{14}ClF_3N_6O$, 410.09; m/z found, 411.1 [M+H]$^+$.

Example 135: (2-Chloro-3-(trifluoromethyl)phenyl)(1-(6-fluoropyridin-2-yl)-6,7-dihydro-1H-[1,2,3]triazolo[4,5-c]pyridin-5(4H)-yl)methanone

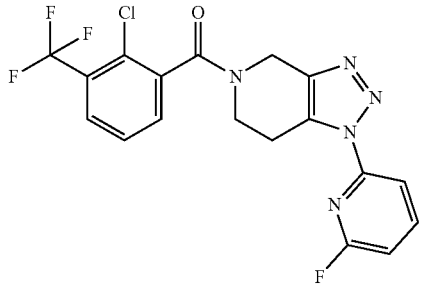 [SMILES: O=C(c1cccc(C(F)(F)F)c1Cl)N1CCc2c(nnn2-c2cccc(F)n2)C1]

The title compound was prepared in a manner analogous to Example 127 substituting 6-fluoropyridin-2-amine for 1-methyl-1H-pyrazol-3-amine in Example 127, Step 1. MS (ESI) mass calcd. $C_{18}H_{12}CF_4N_5O$, 425.1; m/z found, 426.1 [M+H]$^+$.

Example 136: (2-Chloro-3-(trifluoromethyl)phenyl)(1-(4-methoxypyridin-2-yl)-6,7-dihydro-1H-[1,2,3]triazolo[4,5-c]pyridin-5(4H)-yl)methanone

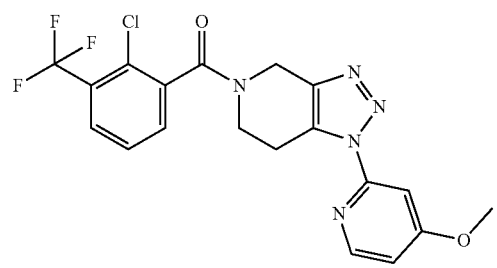 [SMILES: COc1ccnc(-n2nnc3c2CCN(C(=O)c2cccc(C(F)(F)F)c2Cl)C3)c1]

The title compound was prepared in a manner analogous to Example 127 substituting 2-amino-4-methoxypyridine for 1-methyl-1H-pyrazol-3-amine in Example 127, Step 1.

Example 137: (2-Chloro-3-(trifluoromethyl)phenyl)(1-(6-fluoropyridin-2-yl)-4-methyl-6,7-dihydro-1H-[1,2,3]triazolo[4,5-c]pyridin-5(4H)-yl)methanone Step 1: 1-(6-fluoropyridin-2-yl)-1H-[1,2,3]triazolo[4,5-c]pyridine

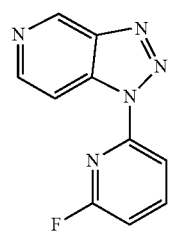 [SMILES: Fc1cccc(-n2nnc3cnccc32)n1]

The title compound was prepared in a manner analogous to Intermediate 19 (Intermediate 17, Step 1-Intermediate 19, Step 3) substituting 6-fluoropyridin-2-amine for 2-aminopyridine in the synthesis of Intermediate 17. The product was used crude in Step 2 below.

Step 2: (2-chloro-3-(trifluoromethyl)phenyl)(1-(6-fluoropyridin-2-yl)-4-methyl-1H-[1,2,3]triazolo[4,5-c]pyridin-5(4H)-yl)methanone

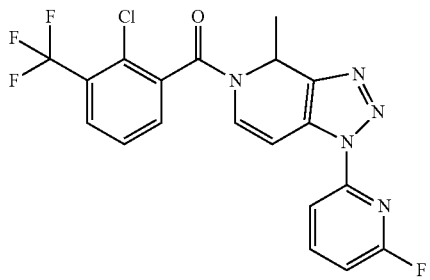 [SMILES: CC1c2nnn(-c3cccc(F)n3)c2C=CN1C(=O)c1cccc(C(F)(F)F)c1Cl]

The title compound was prepared in a manner analogous to Example 72 substituting the product of Example 126, Step 5 for 1-pyrazin-2-yl-1H-[1,2,3]triazolo[4,5-c]pyridine. MS (ESI) mass calcd. $C_{19}H_{12}ClF_4N_5O$, 437.1; m/z found, 438.0 [M+H]$^+$.

Step 3: (2-chloro-3-(trifluoromethyl)phenyl)(1-(6-fluoropyridin-2-yl)-4-methyl-6,7-dihydro-1H-[1,2,3]triazolo[4,5-c]pyridin-5(4H)-yl)methanone

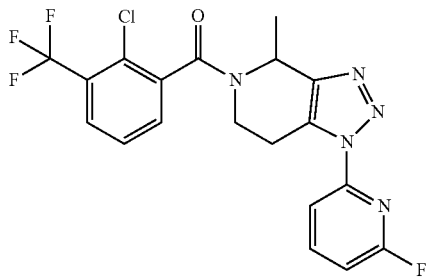 [SMILES: CC1c2nnn(-c3cccc(F)n3)c2CCN1C(=O)c1cccc(C(F)(F)F)c1Cl]

The title compound was prepared in a manner analogous to Example 11, Step A substituting the product of Example 137 Step 2, Step 6 for Intermediate 2. MS (ESI) mass calcd. $C_{19}H_{14}ClF_4N_5O$, 439.1; m/z found, 440.1 [M+H]$^+$.

Example 138: (2-Chloro-3-(trifluoromethyl)phenyl)(1-(4-fluoropyridin-2-yl)-4-methyl-6,7-dihydro-1H-[1,2,3]triazolo[4,5-c]pyridin-5(4H)-yl)methanone

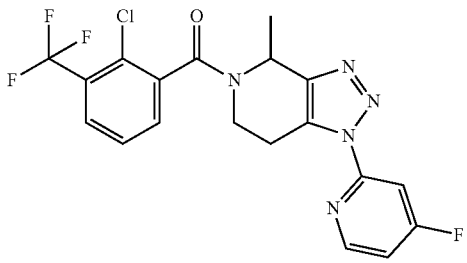 [SMILES: CC1c2nnn(-c3cc(F)ccn3)c2CCN1C(=O)c1cccc(C(F)(F)F)c1Cl]

The title compound was prepared in a manner analogous to Example 137 substituting 4-fluoropyridin-2-amine for 6-fluoropyridin-2-amine in Step 1. MS (ESI) mass calcd. $C_{19}H_{14}ClF_4N_5O$, 439.1; m/z found, 440.1 [M+H]$^+$.

Example 139: (2,3-dichloro-4-fluorophenyl)(4-methyl-1-(pyridin-2-yl)-6,7-dihydro-1H-[1,2,3]triazolo[4,5-c]pyridin-5(4H)-yl)methanone Step 1: 2,3-dichloro-4-fluorobenzoyl Chloride

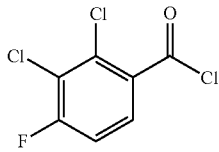 [SMILES: O=C(Cl)c1ccc(F)c(Cl)c1Cl]

The title compound was prepared in a manner analogous to Intermediate 12 substituting 2,3-dichloro-4-fluorobenzoic acid for 2-chloro-3-(trifluoromethyl)benzoic acid.

Step 2: (2,3-dichloro-4-fluorophenyl)(4-methyl-1-(pyridin-2-yl)-1H-[1,2,3]triazolo[4,5-c]pyridin-5(4H)-yl)methanone

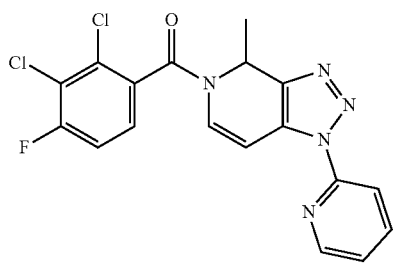 [SMILES: CC1c2nnn(-c3ccccn3)c2C=CN1C(=O)c1ccc(F)c(Cl)c1Cl]

The title compound was prepared in a manner analogous to Example 72 substituting the product of Example 139, Step 1 for 2-chloro-3-(trifluoromethyl)benzoyl chloride and Intermediate 19 for 1-pyrazin-2-yl-1H-[1,2,3]triazolo[4,5-c]pyridine. MS (ESI) mass calcd. $CH_{12}Cl_2FN_5O$, 403.0; m/z found, 403.9 [M+H]$^+$.

Step 3: (2,3-dichloro-4-fluorophenyl)(4-methyl-1-(pyridin-2-yl)-6,7-dihydro-1H-[1,2,3]triazolo[4,5-c]pyridin-5(4H)-yl)methanone

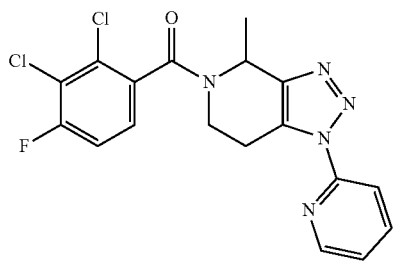 [SMILES: CC1c2nnn(-c3ccccn3)c2CCN1C(=O)c1ccc(F)c(Cl)c1Cl]

The title compound was prepared in a manner analogous to Example 11, Step A substituting the product of Example 139 Step 2, Step 6 for Intermediate 2. MS (ESI) mass calcd. $C_{18}H_{14}Cl_2FN_5O$, 405.1; m/z found, 406.0 [M+H]⁺.

Example 140: (2,3-dichloro-4-fluorophenyl)(4-methyl-1-(pyrazin-2-yl)-6,7-dihydro-1H-[1,2,3]triazolo[4,5-c]pyridin-5(4H)-yl)methanone Step 1: (2,3-dichloro-4-fluorophenyl)(4-methyl-1-(pyrazin-2-yl)-1H-[1,2,3]triazolo[4,5-c]pyridin-5(4H)-yl)methanone

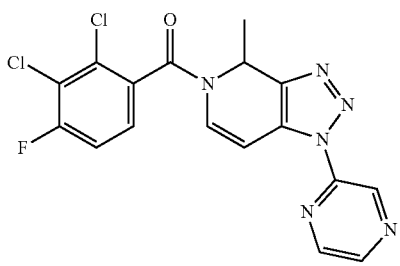 [SMILES: CC1c2nnn(-c3cnccn3)c2C=CN1C(=O)c1ccc(F)c(Cl)c1Cl]

The title compound was prepared in a manner analogous to Example 72 substituting the product of Example 139, Step 1 for 2-chloro-3-(trifluoromethyl)benzoyl chloride. MS (ESI) mass calcd. $C_{17}H_{11}Cl_2FN_6O$, 404.0; m/z found, 405.0 [M+H]⁺.

Step 2: 2,3-dichloro-4-fluorophenyl)(4-methyl-1-(pyrazin-2-yl)-6,7-dihydro-1H-[1,2,3]triazolo[4,5-c]pyridin-5(4H)-yl)methanone

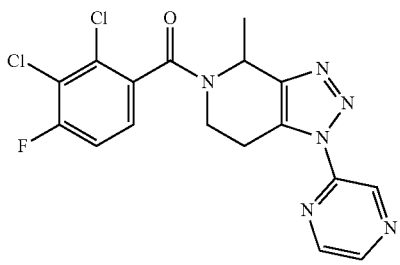 [SMILES: CC1c2nnn(-c3cnccn3)c2CCN1C(=O)c1ccc(F)c(Cl)c1Cl]

To a solution of the product of Example 140, Step 1 (350 mg, 0.864 mmol) in TFA (2 mL) was added triethylsilane (0.35 mL, 2.16 mmol). The reaction was sealed and heated at 80° C. for 2 h. The reaction was diluted with $CH_2Cl_2$ and the organic portion washed with $NaHCO_3$. The organic portion was then dried over $Na_2SO_4$, concentrated and purified by chromatography on silica gel eluted with heptane/EtOAc to afford the title compound (140 mg, 40%) MS (ESI) mass calcd. $C_{17}H_{13}Cl_2FN_6O$, 406.1; m/z found, 407.0 [M+H]⁺.

Example 141: (R*)-(2,3-Dichloro-4-fluorophenyl)(4-methyl-1-(pyridin-2-yl)-6,7-dihydro-1H-[1,2,3]triazolo[4,5-c]pyridin-5(4H)-yl)methanone

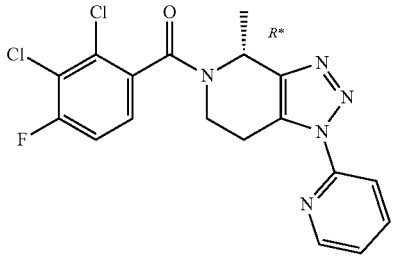 [SMILES: C[C@@H]1c2nnn(-c3ccccn3)c2CCN1C(=O)c1ccc(F)c(Cl)c1Cl]

The title compound, absolute configuration unknown, was obtained as a single enantiomer by Chiral SFC purification of Example 139 performed using CHIRALPAK AD-H (5 μm, 250×20 mm) and a mobile phase of 60% $CO_2$, 40% EtOH containing 0.3% iPrNH$_2$. The enantiomeric purity was confirmed by analytical SFC using a CHIRALPAK AD-H (250×4.6 mm) and a mobile phase of 60% $CO_2$, 40% EtOH containing 0.3% iPrNH$_2$ over 7 minutes. (100% single enantiomer, 3.13 min retention time). MS (ESI): mass calculated for $C_{18}H_{14}Cl_2FN_5O$, 405.1; m/z found, 405.8 [M+H]⁺.

Example 142: (S*)-(2,3-Dichloro-4-fluorophenyl)(4-methyl-1-(pyridin-2-yl)-6,7-dihydro-1H-[1,2,3]triazolo[4,5-c]pyridin-5(4H)-yl)methanone

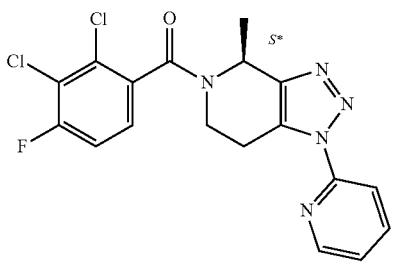 [SMILES: C[C@H]1c2nnn(-c3ccccn3)c2CCN1C(=O)c1ccc(F)c(Cl)c1Cl]

The title compound, absolute configuration unknown, was obtained as a single enantiomer by Chiral SFC purification of Example 139 performed using CHIRALPAK AD-H (5 μm, 250×20 mm) and a mobile phase of 60% $CO_2$, 40% EtOH containing 0.3% iPrNH$_2$. The enantiomeric purity was confirmed by analytical SFC using a CHIRALPAK AD-H (250×4.6 mm) and a mobile phase of 60% $CO_2$, 40% EtOH containing 0.3% iPrNH$_2$ over 7 minutes. (100% single enantiomer, 4.18 min retention time). MS (ESI): mass calculated for $C_{18}H_{14}Cl_2FN_5O$, 405.1; m/z found, 405.6 [M+H]⁺.

Example 143: (R*)-(2,3-Dichloro-4-fluorophenyl)(4-methyl-1-(pyrazin-2-yl)-6,7-dihydro-1H-[1,2,3]triazolo[4,5-c]pyridin-5(4H)-yl)methanone

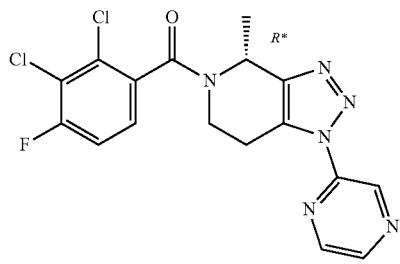 [SMILES: C[C@@H]1c2nnn(-c3cnccn3)c2CCN1C(=O)c1ccc(F)c(Cl)c1Cl]

The title compound, absolute configuration unknown, was obtained as a single enantiomer by Chiral SFC purification of Example 140 performed using CHIRALPAK AD-H (5 μm, 250×20 mm) and a mobile phase of 60% $CO_2$, 40% EtOH containing 0.3% $iPrNH_2$. The enantiomeric purity was confirmed by analytical SFC using a CHIRALPAK AD-H (250×4.6 mm) and a mobile phase of 60% $CO_2$, 40% EtOH containing 0.3% $iPrNH_2$ over 7 minutes. (100% single enantiomer, 3.21 min retention time). MS (ESI): mass calculated for $C_{17}H_{13}Cl_2FN_6O$, 406.1; m/z found, 406.8 $[M+H]^+$.

Example 144: (S*)-(2,3-Dichloro-4-fluorophenyl)(4-methyl-1-(pyrazin-2-yl)-6,7-dihydro-1H-[1,2,3]triazolo[4,5-c]pyridin-5(4H)-yl)methanone

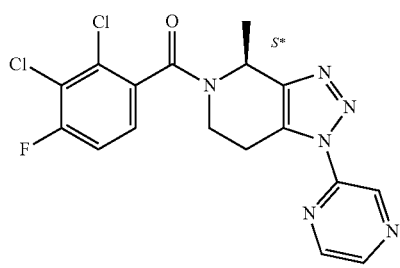 [SMILES: C[C@H]1c2nnn(-c3cnccn3)c2CCN1C(=O)c1ccc(F)c(Cl)c1Cl]

The title compound, absolute configuration unknown, was obtained as a single enantiomer by Chiral SFC purification of Example 140 performed using CHIRALPAK AD-H (5 μm, 250×20 mm) and a mobile phase of 60% $CO_2$, 40% EtOH containing 0.3% $iPrNH_2$. The enantiomeric purity was confirmed by analytical SFC using a CHIRALPAK AD-H (250×4.6 mm) and a mobile phase of 60% $CO_2$, 40% EtOH containing 0.3% $iPrNH_2$ over 7 minutes. (100% single enantiomer, 4.53 min retention time). MS (ESI): mass calculated for $C_{17}H_{13}Cl_2FN_6O$, 406.1; m/z found, 406.6 $[M+H]^+$.

Example 145: (2-Chloro-3-(trifluoromethyl)phenyl)(1-(5-methoxypyridin-2-yl)-4-methyl-6,7-dihydro-1H-[1,2,3]triazolo[4,5-c]pyridin-5(4H)-yl)methanone

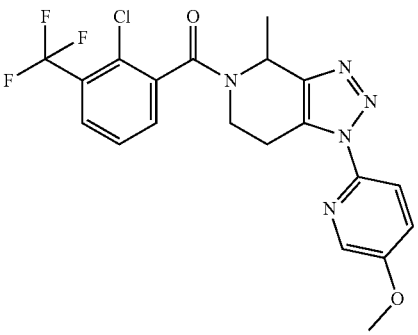 [SMILES: COc1ccc(-n2nnc3c2CCN(C(=O)c2cccc(C(F)(F)F)c2Cl)C3C)nc1]

The title compound was prepared in a manner analogous to Example 140. The starting material was prepared following the route described to synthesize Intermediate 19 substituting 5-methoxy-pyridin-2-ylamine for 2-aminopyridine in Step 1, Intermediate 17. MS (ESI): mass calculated for $C_{20}H_{17}CF_3N_5O_2$, 451.1; m/z found, 452.1 $[M+H]^+$.

Example 146: (R*)-(2-chloro-3-(trifluoromethyl)phenyl)(1-(6-fluoropyridin-2-yl)-4-methyl-6,7-dihydro-1H-[1,2,3]triazolo[4,5-c]pyridin-5(4H)-yl)methanone

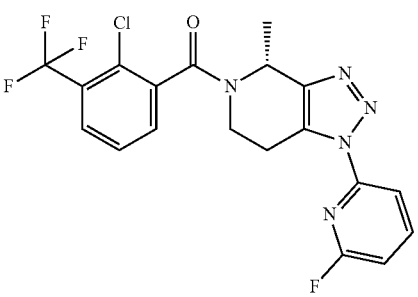 [SMILES: C[C@@H]1c2nnn(-c3cccc(F)n3)c2CCN1C(=O)c1cccc(C(F)(F)F)c1Cl]

Example 137 was purified by chiral SFC on (Chiralpak AD-H 5 μm 250×20 mm) using a mobile phase of 80% $CO_2$ and 20% EtOH containing 0.3% $iPrNH_2$ to obtain the title compound as a single enantiomer of unknown configuration. The enantiomeric purity was confirmed by analytical SFC using a CHIRALPAK AD-H (250×4.6 mm) and a mobile phase of 80% $CO_2$, 20% EtOH containing 0.3% $iPrNH_2$ over 7 minutes. (100% single enantiomer, 3.42 min retention time). $[\alpha]=+21.2°$ (c 0.52 w/v %, DMF,). MS (ESI): mass calculated for $C_{19}H_{14}CF_4N_5O$, 439.1; m/z found, 439.9 $[M+H]^+$.

Example 147: (S*)-(2-Chloro-3-(trifluoromethyl)phenyl)(1-(6-fluoropyridin-2-yl)-4-methyl-6,7-dihydro-1H-[1,2,3]triazolo[4,5-c]pyridin-5(4H)-yl)methanone

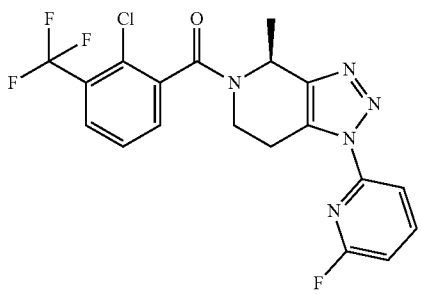 [SMILES: C[C@H]1c2nnn(-c3cccc(F)n3)c2CCN1C(=O)c1cccc(C(F)(F)F)c1Cl]

Example 137 was purified by chiral SFC on (Chiralpak AD-H 5 μm 250×20 mm) using a mobile phase of 80% CO$_2$ and 20% EtOH containing 0.3% iPrNH$_2$ to obtain the title compound as a single enantiomer of unknown configuration. The enantiomeric purity was confirmed by analytical SFC using a CHIRALPAK AD-H (250×4.6 mm) and a mobile phase of 80% CO$_2$, 20% EtOH containing 0.3% iPrNH$_2$ over 7 minutes. (100% single enantiomer, 4.06 min retention time). [α]=−22.4 (0.58 w/v %, DMF). MS (ESI): mass calculated for C$_{19}$H$_{14}$CF$_4$N$_5$O, 439.1; m/z found, 439.8 [M+H]$^+$.

Example 148: (R*)-(2-Chloro-3-(trifluoromethyl)phenyl)(1-(4-fluoropyridin-2-yl)-4-methyl-6,7-dihydro-1H-[1,2,3]triazolo[4,5-c]pyridin-5(4H)-yl)methanone

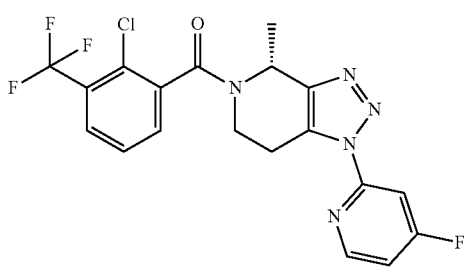

Example 138 was purified by chiral SFC on (Chiralcel OD-H 5 μm 250×20 mm) using a mobile phase of 80% CO$_2$ and 20% EtOH containing 0.3% iPrNH$_2$ to obtain the title compound as a single enantiomer of unknown configuration. The enantiomeric purity was confirmed by analytical SFC using a CHIRALCEL OD-H (250×4.6 mm) and a mobile phase of 80% CO$_2$, 20% EtOH containing 0.3% iPrNH$_2$ over 7 minutes. (100% single enantiomer, 3.43 min retention time). [α]=−23.2 (0.56 w/v %, DMF). MS (ESI): mass calculated for C$_{19}$H$_{14}$CF$_4$N$_5$O, 439.1; m/z found, 439.9 [M+H]$^+$.

Example 149: (S*)-(2-Chloro-3-(trifluoromethyl)phenyl)(1-(4-fluoropyridin-2-yl)-4-methyl-6,7-dihydro-1H-[1,2,3]triazolo[4,5-c]pyridin-5(4H)-yl)methanone

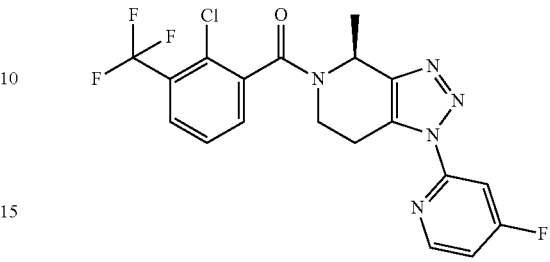

Example 138 was purified by chiral SFC on (Chiralcel OD-H 5 μm 250×20 mm) using a mobile phase of 80% CO$_2$ and 20% EtOH containing 0.3% iPrNH$_2$ to obtain the title compound as a single enantiomer of unknown configuration. The enantiomeric purity was confirmed by analytical SFC using a CHIRALCEL OD-H (250×4.6 mm) and a mobile phase of 80% CO$_2$, 20% EtOH containing 0.3% iPrNH$_2$ over 7 minutes. (100% single enantiomer, 4.48 min retention time). [α]=+23.1 (0.53 w/v %, DMF). MS (ESI): mass calculated for C$_{19}$H$_{14}$CF$_4$N$_5$O, 439.1; m/z found, 439.9 [M+H]$^+$.

Example 150: (2-Chloro-3-(trifluoromethyl)phenyl)(1-(4-methoxypyridin-2-yl)-4-methyl-6,7-dihydro-1H-[1,2,3]triazolo[4,5-c]pyridin-5(4H)-yl)methanone

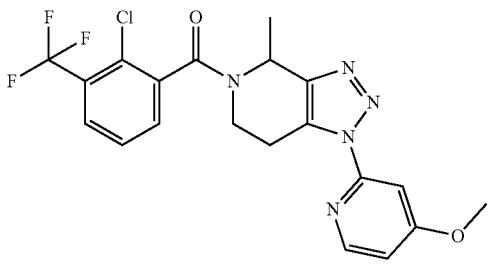 [SMILES: COc1ccnc(-n2nnc3c2CCN(C(=O)c2cccc(C(F)(F)F)c2Cl)C3C)c1]

The title compound was prepared in a manner analogous to Example 137 substituting 2-amino-4-methoxypyridine for 2-aminopyridine in the synthesis of Intermediate 17. MS (ESI): mass calculated for C$_{20}$H$_{17}$CF$_3$N$_5$O$_2$, 451.1; m/z found, 452.0 [M+H]$^+$.

Example 151: (R*)-(2-Chloro-3-(trifluoromethyl)phenyl)(1-(4-methoxypyridin-2-yl)-4-methyl-6,7-dihydro-1H-[1,2,3]triazolo[4,5-c]pyridin-5(4H)-yl)methanone

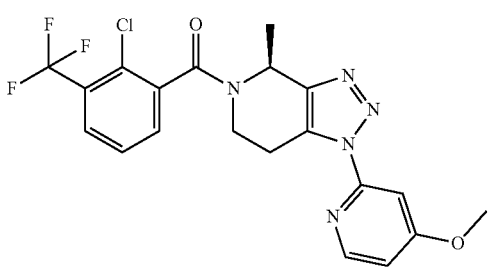 [SMILES: COc1ccnc(-n2nnc3c2CCN(C(=O)c2cccc(C(F)(F)F)c2Cl)[C@H]3C)c1]

The title compound, absolute configuration unknown, was obtained as a single enantiomer by Chiral SFC purification of Example 150 performed using CHIRALCEL OD-H (5 µm, 250×20 mm) and a mobile phase of 85% CO$_2$, 15% EtOH. The enantiomeric purity was confirmed by analytical SFC using a CHIRALCEL OD-H (250×4.6 mm) and a mobile phase of 80% CO$_2$, 20% EtOH containing 0.3% iPrNH$_2$ over 7 minutes. (100% single enantiomer, 4.40 min retention time). MS (ESI): mass calculated for C$_{20}$H$_{17}$CF$_3$N$_5$O$_2$, 451.1; m/z found, 451.8 [M+H]$^+$.

Example 152: (S*)-(2-Chloro-3-(trifluoromethyl) phenyl)(1-(4-methoxypyridin-2-yl)-4-methyl-6,7-dihydro-1H-[1,2,3]triazolo[4,5-c]pyridin-5(4H)-yl) methanone

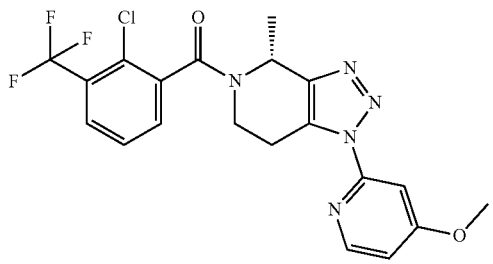 [SMILES: COc1ccnc(-n2nnc3c2CCN(C(=O)c2cccc(C(F)(F)F)c2Cl)[C@@H]3C)c1]

The title compound, absolute configuration unknown, was obtained as a single enantiomer by Chiral SFC purification of Example 150 performed using CHIRALCEL OD-H (5 µm, 250×20 mm) and a mobile phase of 85% CO$_2$, 15% EtOH. The enantiomeric purity was confirmed by analytical SFC using a CHIRALCEL OD-H (250×4.6 mm) and a mobile phase of 80% CO$_2$, 20% EtOH containing 0.3% iPrNH$_2$ over 7 minutes. (100% single enantiomer, 5.46 min retention time). [α]=+31.6 (0.51 w/v %, DMF). MS (ESI): mass calculated for C$_{20}$H$_{17}$CF$_3$N$_5$O$_2$, 451.1; m/z found, 451.9 [M+H]$^+$.

Example 153: (2-Chloro-3-(trifluoromethyl)phenyl) (1-(5-fluoropyrimidin-2-yl)-4-methyl-6,7-dihydro-1H-[1,2,3]triazolo[4,5-c]pyridin-5(4H)-yl)methanone

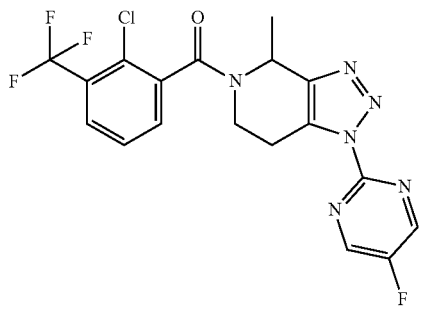

Step A: 5-Fluoro-N-(2-methyl-3-nitropyridin-4-yl) pyrimidin-2-amine

A solution of Pd(OAc)$_2$ (0.15 g, 0.68 mmol) and BINAP (0.42 g, 0.68 mmol) were stirred in toluene (2 ml) at rt for 10 minutes. This mixture was then added to a microwave vial which contained 4-chloro-2-methyl-3-nitropyridine (3.00 g, 16.8 mmol), 2-amino-4-fluoropyridine (2.20 g, 18.5 mmol), and K$_2$CO$_3$ (2.6 g, 18.6 mmol) in toluene (10 ml). The reaction was irradiated in a microwave apparatus at 110° C. for 1 h. The reaction was diluted with DCM, filtered through Celite©, washed, and concentrated. Chromatography of the resulting residue (SiO$_2$; EtOAc:Hex) gave the desired compound (1.60 g, 38%). MS (ESI): mass calculated for C$_{10}$H$_8$ClFN$_5$O$_2$, 249.07; m/z found 250.0 [M+H]$^+$.

Step B: N-(5-Fluoropyrimidin-2-yl)-2-methylpyridine-3,4-diamine

To a solution of 5-fluoro-N-(2-methyl-3-nitropyridin-4-yl)pyrimidin-2-amine (4.0 g, 16.0 mmol) in degassed EtOH (100 mL) and AcOH (2 mL) was added 10% Pd/C (1.70 g, 1.61 mmol) in EtOH (10 mL). The reaction was placed under a balloon of hydrogen at atmospheric pressure and let stir for 12 h. The reaction was filtered through Celite© and washed with DCM. The organic solvent was concentrated to give the title compound (3.10 g, 88%). MS (ESI): mass calculated for C$_{10}$H$_{10}$ClFN$_5$, 219.09; m/z found 220.1 [M+H]$^+$.

Step C: 1-(5-Fluoropyrimidin-2-yl)-4-methyl-1H-imidazo[4,5-c]pyridine

A solution of N-(5-fluoropyrimidin-2-yl)-2-methylpyridine-3,4-diamine (0.50 g, 2.28 mmol) in THF (15 ml) and HOAc (0.14 ml, 2.51 mmol) was treated with t-butyl nitrite (0.45 ml, 3.42 mmol) and heated to 100° C. for 90 min. The reaction was concentrated, diluted with 1N NaHCO$_3$, and extracted with DCM (50 mL×3). The organic layers were combined, dried (Na$_2$SO$_4$), and concentrated. Chromatography of the resulting residue (SiO$_2$; EtOAc:Hex) gave the title compound (0.40 g, 77%). MS (ESI): mass calcd. for C$_{10}$H$_7$FN$_6$, 230.07; m/z found, 231.1 [M+H]$^+$.

Step D: 1-(5-Fluoropyrimidin-2-yl)-4-methyl-4,5,6,7-tetrahydro-1H-imidazo[4,5-c]pyridine A solution of 1-(5-fluoropyrimidin-2-yl)-4-methyl-1H-imidazo[4,5-c]pyridine (0.90 g, 3.91 mmol) in AcOH (50 ml) was passed through a 10% Pt/C catalyst cartridge on an H-Cube© hydrogenation apparatus at a pressure of 60 bar, a temperature of 60° C., and a flow rate of 1 ml/min. The reaction was concentrated, diluted with 1N NaOH, and extracted with DCM (100 mL×3). The organic layers were combined, dried (Na$_2$SO$_4$), and concentrated. Chromatography of the resulting residue (SiO$_2$; MeOH (NH$_3$):DCM) gave the title compound (0.47 g, 51%). MS (ESI): mass calcd. for C$_{10}$H$_{11}$FN$_6$, 234.10; m/z found, 235.0 [M+H]$^+$.

Step E: (2-Chloro-3-(trifluoromethyl)phenyl)(1-(5-fluoropyrimidin-2-yl)-4-methyl-6,7-dihydro-1H-[1,2,3]triazolo[4,5-c]pyridin-5(4H)-yl)methanone A solution of 1-(5-fluoropyrimidin-2-yl)-4-methyl-4,5,6,7-tetrahydro-1H-imidazo[4,5-c]pyridine (0.30 g, 1.28 mmol), 2-chloro-3-(trifluoromethyl)benzoic acid (0.34 g, 1.54 mmol), HATU (0.38 g, 1.28 mmol), and Et$_3$N (0.18 mL, 1.28 mmol) in DMF (5 mL) was stirred for 30 min. The reaction was diluted with EtOAc (30 mL) and washed with H$_2$O (3×20 mL). The organic layers were combined, dried (Na$_2$SO$_4$), and concentrated. Chromatography of the resulting residue (SiO$_2$; MeOH (NH$_3$):DCM) gave the title compound (0.51 g, 90%). ¹H NMR (500 MHz, CDCl₃) δ 8.80-8.43 (m, 2H), 7.82-7.44 (m, 1H), 7.27-7.15 (m, 2H), 6.66-6.60 (m, 1H), 5.95-4.92 (m, 1H), 3.77-2.54 (m, 3H), 1.74-1.53 (m, 3H). MS (ESI): mass calculated for $C_{18}H_{13}CF_4N_6O$, 440.08; m/z found, 441.0 [M+H]⁺.

Example 154 (6-methyl-1-(1H-pyrazol-3-yl)-6,7-dihydro-1H-[1,2,3]triazolo[4,5-c]pyridin-5(4H)-yl) (2-methyl-3-(trifluoromethyl)phenyl)methanone

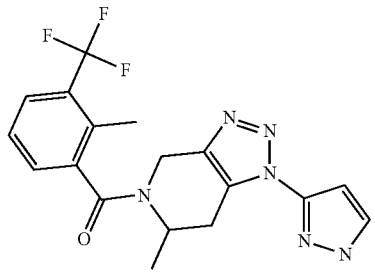 [SMILES: Cc1c(C(=O)N2Cc3nnn(-c4cc[nH]n4)c3CC2C)cccc1C(F)(F)F]

MS (ESI) mass calcd $C_{18}H_{17}F_3N_6O$, 390.1 m/z found, 391.1 [M+H]⁺.

Example 155 (S*)-(4-chloro-2-fluorophenyl)(1-(5-fluoropyrimidin-2-yl)-6-methyl-6,7-dihydro-1H-[1,2,3]triazolo[4,5-c]pyridin-5(4H)-yl)methanone

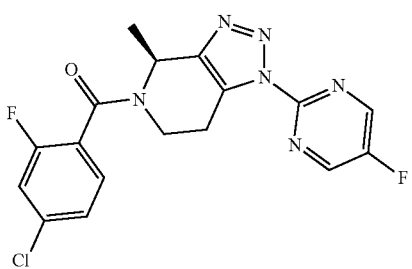 [SMILES: C[C@H]1c2nnn(-c3ncc(F)cn3)c2CCN1C(=O)c1ccc(Cl)cc1F]

MS (ESI) mass calcd $C_{17}H_{13}ClF_2N_6O$, 390.1 m/z found, 391.1 [M+H]⁺.

Example 156 (S)-(4-chloro-2-fluorophenyl)(1-(5-fluoropyrimidin-2-yl)-6-methyl-6,7-dihydro-1H-[1,2,3]triazolo[4,5-c]pyridin-5(4H)-yl)methanone

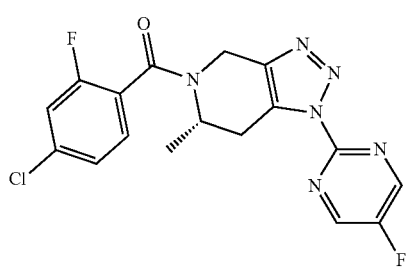 [SMILES: C[C@H]1Cc2c(nnn2-c2ncc(F)cn2)CN1C(=O)c1ccc(Cl)cc1F]

MS (ESI) mass calcd $C_{17}H_{13}ClF_2N_6O$, 390.1 m/z found, 391.1 [M+H]⁺.

Example 157: (S*)-(2-Chloro-3-(trifluoromethyl)phenyl)(1-(5-fluoropyrimidin-2-yl)-4-methyl-6,7-dihydro-1H-[1,2,3]triazolo[4,5-c]pyridin-5(4H)-yl)methanone

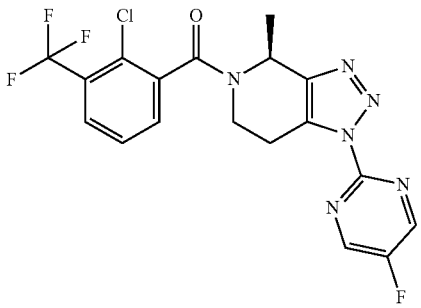

The title compound, absolute configuration unknown, was obtained as a single enantiomer by Chiral SFC purification of Example 153 performed using CHIRALPAK AD-H (5 μm, 250×20 mm) and a mobile phase of 70% CO₂, 30% EtOH. The enantiomeric purity was confirmed by analytical SFC using a CHIRALPAK AD (250×4.6 mm) and a mobile phase of 75% CO₂, 25% EtOH containing 0.3% iPrNH₂ over 7 minutes. (100% single enantiomer, 4.07 min retention time). MS (ESI): mass calculated for $C_{18}H_{13}ClF_4N_6O$, 440.08; m/z found, 441.0 [M+H]⁺.

Example 158: (R*)-(2-Chloro-3-(trifluoromethyl)phenyl)(1-(5-fluoropyrimidin-2-yl)-4-methyl-6,7-dihydro-1H-[1,2,3]triazolo[4,5-c]pyridin-5(4H)-yl)methanone

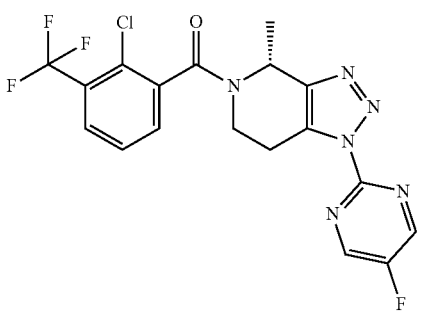

The title compound, absolute configuration unknown, was obtained as a single enantiomer by Chiral SFC purification of Example 153 performed using CHIRALPAK AD-H (5 μm, 250×20 mm) and a mobile phase of 70% CO₂, 30% EtOH containing 0.3% iPrNH₂. The enantiomeric purity was confirmed by analytical SFC using a CHIRALPAK AD (250×4.6 mm) and a mobile phase of 75% CO₂, 25% EtOH containing 0.3% iPrNH₂ over 7 minutes. (100% single enantiomer, 4.77 min retention time). MS (ESI): mass calculated for $C_{18}H_{13}CF_4N_6O$, 440.08; m/z found, 441.0 [M+H]⁺.

Example 159 (2-chloro-3-(trifluoromethyl)phenyl)(1-(3,5-dimethylpyridin-2-yl)-4-methyl-6,7-dihydro-1H-[1,2,3]triazolo[4,5-c]pyridin-5(4H)-yl)methanone

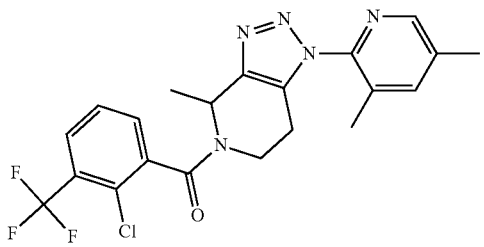 [SMILES: Cc1cnc(-n2nnc3c2CCN(C(=O)c2cccc(C(F)(F)F)c2Cl)C3C)c(C)c1]

MS (ESI) mass calcd C$_{21}$H$_{19}$ClF$_3$N$_5$O, 449.1 m/z found, 450.2 [M+H]$^+$.

Example 160 (2,3-dichlorophenyl)(1-(3,5-dimethylpyridin-2-yl)-4-methyl-6,7-dihydro-1H-[1,2,3]triazolo[4,5-c]pyridin-5(4H)-yl)methanone

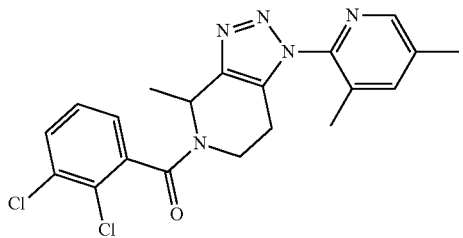 [SMILES: Cc1cnc(-n2nnc3c2CCN(C(=O)c2cccc(Cl)c2Cl)C3C)c(C)c1]

MS (ESI) mass calcd C$_{20}$H$_{19}$C$_2$N$_5$O, 415.1 m/z found, 416.1 [M+H]$^+$. $^1$H NMR (500 MHz, CDCl$_3$) δ 8.33-8.08 (m, 1H), 7.71-7.46 (m, 2H), 7.40-6.98 (m, 2H), 6.22-5.92 (m, 0.6H), 5.13-5.02 (m, 0.4H), 5.00-4.74 (m, 0.4H), 3.69-2.70 (m, 3.6H), 2.51-2.27 (m, 6H), 1.86-1.43 (m, 3H).

Example 161: (2,3-Dichlorophenyl)(1-(3-fluoropyridin-2-yl)-6-methyl-6,7-dihydro-1H-[1,2,3]triazolo[4,5-c]pyridin-5(4H)-yl)methanone

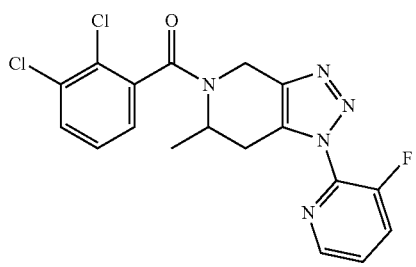 [SMILES: CC1Cc2c(nnn2-c2ncccc2F)CN1C(=O)c1cccc(Cl)c1Cl]

Example 161 was prepared from 6-methyl-1-(3-fluoropyridin-2-yl)-4,5,6,7-tetrahydro-1H-[1,2,3]triazolo[4,5-c]pyridine using the conditions described in Example 63 Step 5 substituting 2,3-dichlorobenzoyl chloride for 2-chloro-3-(trifluoromethyl)benzoyl chloride. 6-Methyl-1-(3-fluoropyridin-2-yl)-4,5,6,7-tetrahydro-1H-[1,2,3]triazolo[4,5-c]pyridine was made using the route described in Example 116 beginning from 2-amino-3-fluoropyridine instead of 2-aminopyridine in step A. Subsequent steps were carried out analogous to those described in Example 116 steps B-D. MS (ESI) mass calcd. C$_{18}$H$_{14}$Cl$_2$FN$_5$O, 405.06; m/z found, 406.1 [M+H]$^+$.

Example 162: (2-Chloro-3-(trifluoromethyl)phenyl)(1-(1-(2-fluoroethyl)-1H-pyrazol-3-yl)-4-methyl-6,7-dihydro-1H-[1,2,3]triazolo[4,5-c]pyridin-5(4H)-yl)methanone

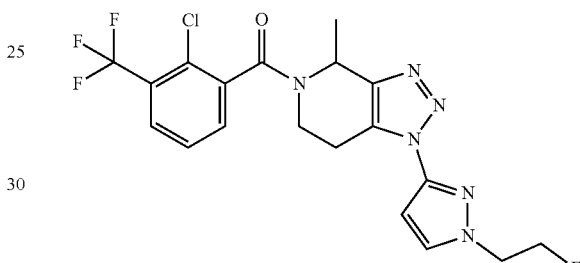

Intermediate 48

Step 1: 1-(1-(2-fluoroethyl)-1H-pyrazol-3-yl)-1H-[1,2,3]triazolo[4,5-c]pyridine

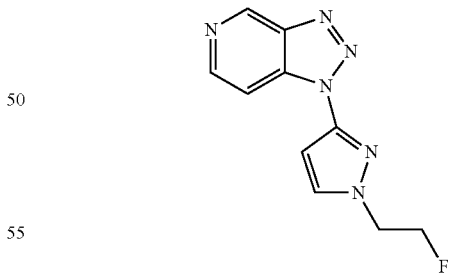

To a solution of Intermediate 48 (50 mg, 0.269 mmol) in DMF (1 mL) was added 1-bromo-2-fluoroethane (41 mg, 0.322 mmol) and Cs$_2$CO$_3$ (263 mg, 0.806 mmol). The reaction was irradiated in a microwave apparatus for 10 min at 120° C. The resulting mixture was filtered, concentrated and purified by chromatography on silica gel eluted with 100% EtOAc to obtain the title compound (62 mg, 88%). MS (ESI) mass calcd. C$_{10}$H$_9$FN$_6$, 232.1; m/z found, 233.0 [M+H]$^+$.

Step 2: (2-chloro-3-(trifluoromethyl)phenyl)(1-(1-(2-fluoroethyl)-1H-pyrazol-3-yl)-4-methyl-1H-[1,2,3]triazolo[4,5-c]pyridin-5(4H)-yl)methanone

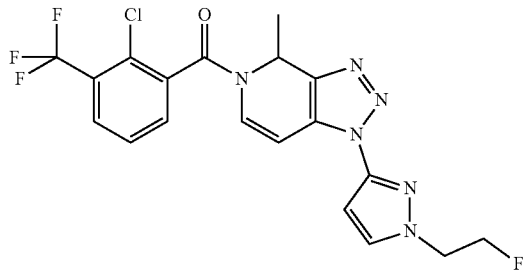

The title compound was prepared in a manner analogous to Example 72 substituting the product of Example 162, Step 1 for 1-pyrazin-2-yl-1H-[1,2,3]triazolo[4,5-c]pyridine. MS (ESI) mass calcd. $C_{19}H_{15}ClF_4N_6O$, 454.1; m/z found, 455.1 [M+H]$^+$.

Step 3: (2-chloro-3-(trifluoromethyl)phenyl)(1-(1-(2-fluoroethyl)-1H-pyrazol-3-yl)-4-methyl-6,7-dihydro-1H-[1,2,3]triazolo[4,5-c]pyridin-5(4H)-yl)methanone

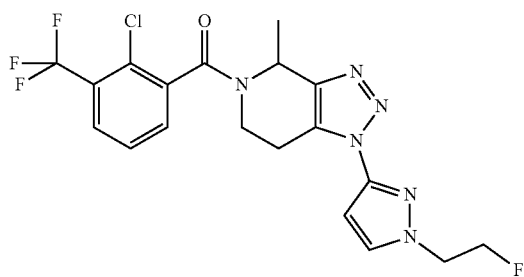

The title compound was prepared in a manner analogous to Example 73 substituting the product of Example 162 Step 2, for 5-{[2-chloro-3-(trifluoromethyl)phenyl]carbonyl}-4-methyl-1-pyrazin-2-yl-4,5-dihydro-1H-[1,2,3]triazolo[4,5-c]pyridine. MS (ESI) mass calcd. $C_{19}H_{17}ClF_4N_6O$, 456.1; m/z found, 457.0 [M+H]$^+$.

Example 163: (2-Chloro-3-(trifluoromethyl)phenyl)(4-methyl-1-(1-methyl-1H-pyrazol-3-yl)-6,7-dihydro-1H-[1,2,3]triazolo[4,5-c]pyridin-5(4H)-yl)methanone

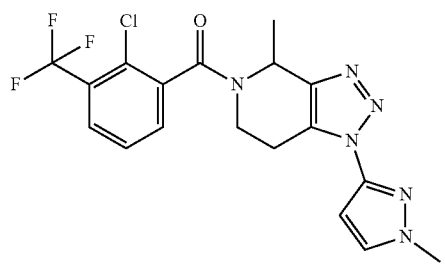

The title compound was obtained in a manner analogous to Example 162, Step 2 and 3. The starting material was obtained using the route described for Intermediate 19 substituting 1-methyl-1H-pyrazol-3-amine for 2-aminopyridine in the synthesis of Intermediate 17, Step 1. MS (ESI) mass calcd. $C_{18}H_{16}ClF_3N_6O$, 424.1; m/z found, 425.1 [M+H]$^+$.

Example 164 (S*)-(3-chloro-2-(trifluoromethyl)pyridin-4-yl)(1-(5-fluoropyrimidin-2-yl)-4-methyl-6,7-dihydro-1H-[1,2,3]triazolo[4,5-c]pyridin-5(4H)-yl)methanone

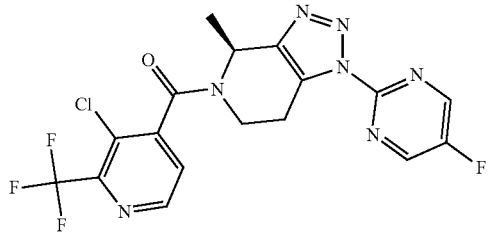 [SMILES: C[C@H]1c2nnn(-c3ncc(F)cn3)c2CCN1C(=O)c1ccnc(C(F)(F)F)c1Cl]

MS (ESI) mass calcd $C_{17}H_{12}ClF_4N_7O$, 441.1 m/z found, 442.1 [M+H]$^+$.

Example 165: (6R*)-5-[(2,3-Dichlorophenyl)carbonyl]-1-(3-fluoropyridin-2-yl)-6-methyl-4,5,6,7-tetrahydro-1H-[1,2,3]triazolo[4,5-c]pyridine

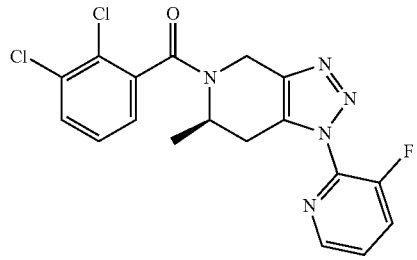

The title compound, absolute configuration unknown, was obtained as a single enantiomer by Chiral SFC purification of Example 161 performed using CHIRALPAK IA (5 μm, 250×20 mm) and a mobile phase of 65% $CO_2$, 35% iPrOH. The enantiomeric purity was confirmed by analytical SFC using a CHIRALPAK AD (250×4.6 mm) and a mobile phase of 70% $CO_2$, 30% iPrOH containing 0.3% iPrNH$_2$ over 7 minutes. (100% single enantiomer, 4.72 min retention time). MS (ESI) mass calcd. $C_{18}H_{14}Cl_2FN_5O$, 405.1; m/z found, 405.8 [M+H]$^+$.

Example 166: (6S*)-5-[(2,3-Dichlorophenyl)carbonyl]-1-(3-fluoropyridin-2-yl)-6-methyl-4,5,6,7-tetrahydro-1H-[1,2,3]triazolo[4,5-c]pyridine

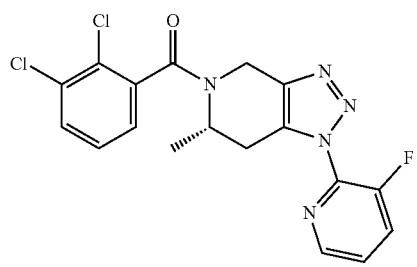

The title compound, absolute configuration unknown, was obtained as a single enantiomer by Chiral SFC purification of Example 161 performed using CHIRALPAK IA (5 μm, 250×20 mm) and a mobile phase of 65% CO$_2$, 35% iPrOH. The enantiomeric purity was confirmed by analytical SFC using a CHIRALPAK AD (250×4.6 mm) and a mobile phase of 70% CO$_2$, 30% iPrOH containing 0.3% iPrNH$_2$ over 7 minutes. (98% single enantiomer, 5.55 min retention time). MS (ESI) mass calcd. C$_{18}$H$_{14}$Cl$_2$FN$_5$O, 405.1; m/z found, 405.8 [M+H]$^+$.

Example 167: (6R*)-5-{[2-Chloro-3-(trifluoromethyl)phenyl]carbonyl}-1-(3-fluoropyridin-2-yl)-6-methyl-4,5,6,7-tetrahydro-1H-[1,2,3]triazolo[4,5-c]pyridine

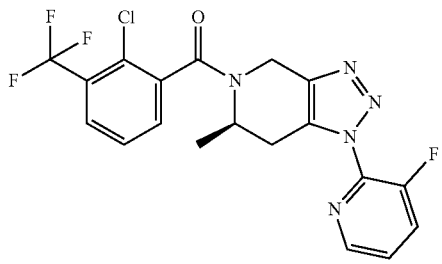

The title compound, absolute configuration unknown, was obtained as a single enantiomer by Chiral SFC purification of Example 122 performed using CHIRALPAK IA (5 μm, 250×20 mm) and a mobile phase of 72% CO$_2$, 28% iPrOH. The enantiomeric purity was confirmed by analytical SFC using a CHIRALPAK IA (250×4.6 mm) and a mobile phase of 70% CO$_2$, 30% iPrOH containing 0.3% iPrNH$_2$ over 7 minutes. (100% single enantiomer, 2.76 min retention time). MS (ESI) mass calcd. C$_{19}$H$_{14}$ClF$_4$N$_5$O, 439.1; m/z found, 439.8 [M+H]$^+$.

Example 168: (6S*)-5-{[2-Chloro-3-(trifluoromethyl)phenyl]carbonyl}-1-(3-fluoropyridin-2-yl)-6-methyl-4,5,6,7-tetrahydro-1H-[1,2,3]triazolo[4,5-c]pyridine

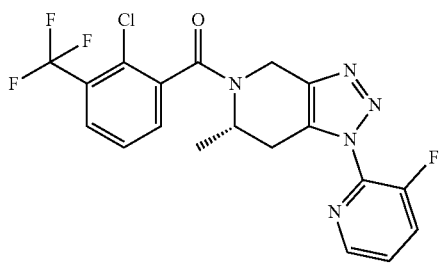

The title compound, absolute configuration unknown, was obtained as a single enantiomer by Chiral SFC purification of Example 122 performed using CHIRALPAK IA (5 μm, 250×20 mm) and a mobile phase of 72% CO$_2$, 28% iPrOH. The enantiomeric purity was confirmed by analytical SFC using a CHIRALPAK IA (250×4.6 mm) and a mobile phase of 70% CO$_2$, 30% iPrOH containing 0.3% iPrNH$_2$ over 7 minutes. (99% single enantiomer, 3.18 min retention time). MS (ESI) mass calcd. C$_{19}$H$_{14}$ClF$_4$N$_5$O, 439.1; m/z found, 439.8 [M+H]$^+$.

Example 169: (R*)-(2-Chloro-3-(trifluoromethyl)phenyl)(4-methyl-1-(1-methyl-1H-pyrazol-3-yl)-6,7-dihydro-1H-[1,2,3]triazolo[4,5-c]pyridin-5(4H)-yl)methanone

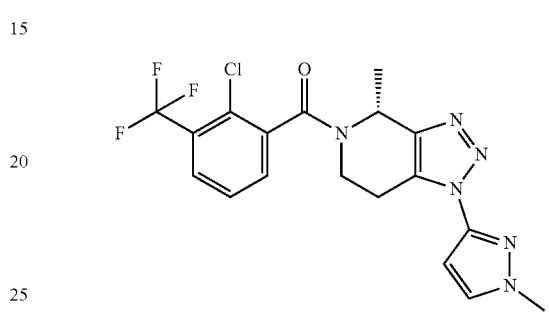

The title compound, absolute configuration unknown, was obtained as a single enantiomer by Chiral SFC purification of Example 163 performed using CHIRALPAK AD-H (5 μm, 250×20 mm) and a mobile phase of 75% CO$_2$, 25% EtOH. The enantiomeric purity was confirmed by analytical SFC using a CHIRALPAK AD (250×4.6 mm) and a mobile phase of 75% CO$_2$, 25% iPrOH containing 0.3% iPrNH$_2$ over 7 minutes. (100% single enantiomer, 2.80 min retention time). [α]=+13.7° (0.58 w/v %, DMF). MS (ESI) mass calcd. C$_{18}$H$_{16}$ClF$_3$N$_6$O, 424.1; m/z found, 424.8 [M+H]$^+$.

Example 170: (S*)-(2-Chloro-3-(trifluoromethyl)phenyl)(4-methyl-1-(1-methyl-1H-pyrazol-3-yl)-6,7-dihydro-1H-[1,2,3]triazolo[4,5-c]pyridin-5(4H)-yl)methanone

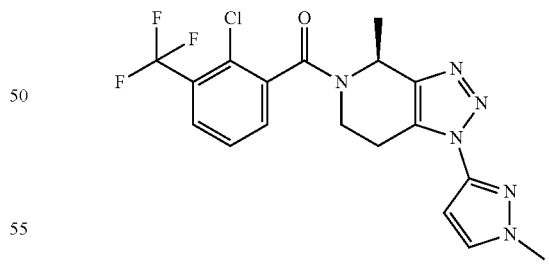

The title compound, absolute configuration unknown, was obtained as a single enantiomer by Chiral SFC purification of Example 163 performed using CHIRALPAK AD-H (5 μm, 250×20 mm) and a mobile phase of 75% CO$_2$, 25% EtOH. The enantiomeric purity was confirmed by analytical SFC using a CHIRALPAK AD (250×4.6 mm) and a mobile phase of 75% CO$_2$, 25% iPrOH containing 0.3% iPrNH$_2$ over 7 minutes. (100% single enantiomer, 4.02 min retention time). [α]=−14.0° (0.59 w/v %, DMF). MS (ESI) mass calcd. C$_{18}$H$_{16}$ClF$_3$N$_6$O, 424.1; m/z found, 424.8 [M+H]$^+$.

Example 171: (R*)-(2-Chloro-3-(trifluoromethyl)phenyl)(1-(1-(2-fluoroethyl)-1H-pyrazol-3-yl)-4-methyl-6,7-dihydro-1H-[1,2,3]triazolo[4,5-c]pyridin-5(4H)-yl)methanone

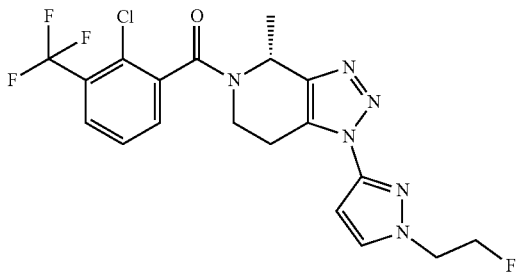

The title compound, absolute configuration unknown, was obtained as a single enantiomer by Chiral SFC purification of Example 162 performed using CHIRALPAK AD-H (5 μm, 250×20 mm) and a mobile phase of 75% $CO_2$, 25% EtOH. The enantiomeric purity was confirmed by analytical SFC using a CHIRALPAK AD (250×4.6 mm) and a mobile phase of 75% $CO_2$, 25% iPrOH containing 0.3% $iPrNH_2$ over 7 minutes. (100% single enantiomer, 2.64 min retention time). [α]=+11.7° (0.55 w/v %, DMF). MS (ESI) mass calcd. $C_{19}H_{17}CF_4N_6O$, 456.1; m/z found, 456.8 [M+H]$^+$.

Example 172: (S*)-(2-Chloro-3-(trifluoromethyl)phenyl)(1-(1-(2-fluoroethyl)-1H-pyrazol-3-yl)-4-methyl-6,7-dihydro-1H-[1,2,3]triazolo[4,5-c]pyridin-5(4H)-yl)methanone

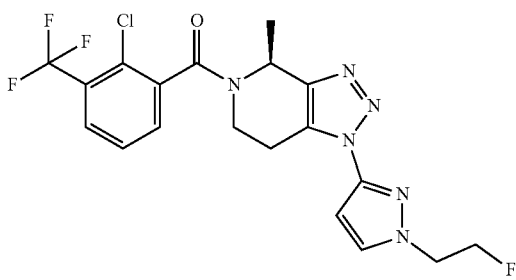

The title compound, absolute configuration unknown, was obtained as a single enantiomer by Chiral SFC purification of Example 162 performed using CHIRALPAK AD-H (5 μm, 250×20 mm) and a mobile phase of 75% $CO_2$, 25% EtOH. The enantiomeric purity was confirmed by analytical SFC using a CHIRALPAK AD (250×4.6 mm) and a mobile phase of 75% $CO_2$, 25% iPrOH containing 0.3% $iPrNH_2$ over 7 minutes. (100% single enantiomer, 3.72 min retention time). [α]=−12.8° (0.58 w/v %, DMF). MS (ESI) mass calcd. $C_{19}H_{17}CF_4N_6O$, 456.1; m/z found, 456.8 [M+H]$^+$.

Example 173: 5-[(2,3-Dichlorophenyl)carbonyl]-1-(4-fluoropyridin-2-yl)-6-methyl-4,5,6,7-tetrahydro-1H-[1,2,3]triazolo[4,5-c]pyridine

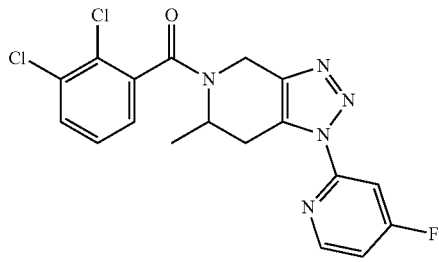

The title compound was prepared in a manner analogous to Example 116. In Intermediate 62, Step A, 4-fluoro-2-aminopyrazine was substituted for 2-aminopyridine, NaOtBu was substituted for NaH and DMSO was substituted for THF. In Intermediate 62b, Step B Pd/C in $NH_3$/MeOH was used in place of zinc powder in acetic acid. In Intermediate 63, Step C, isoamyl nitrite was substituted for tert-butyl nitrite. Step E was carried out using the conditions described for Example 63, Step 5 substituting Intermediate 14 for 2-chloro-3-(trifluoromethyl)benzoyl chloride. MS (ESI) mass calcd. $C_{18}H_{14}Cl_2FN_5O$, 405.1; m/z found, 406.0 [M+H]$^+$. $^1$H NMR (500 MHz, CDCl$_3$) δ 8.52-8.37 (m, 1H), 7.99-7.89 (m, 1H), 7.57-7.50 (m, 1H), 7.37-7.04 (m, 3H), 5.88-5.57 (m, 1H), 4.63-4.06 (m, 2H), 3.60-3.20 (m, 2H), 1.38-1.17 (m, 3H).

Example 174: (2,3-Dichlorophenyl)(1-(5-fluoropyrimidin-2-yl)-4-methyl-6,7-dihydro-1H-[1,2,3]triazolo[4,5-c]pyridin-5(4H)-yl)methanone

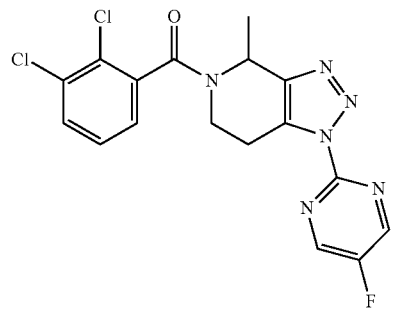 [SMILES: CC1c2nnn(-c3ncc(F)cn3)c2CCN1C(=O)c1cccc(Cl)c1Cl]

Example 174 was prepared in a manner analogous to Example 153 substituting 2,3-dichlorobenzoic acid. $^1$H NMR (600 MHz, CDCl$_3$) δ 8.81-8.68 (m, 1H), 8.01 (s, 1H), 7.57-7.50 (m, 1H), 7.38-7.19 (m, 2H), 6.16-5.91, 5.18-4.73 (m, 1H), 3.78-2.99 (m, 3H), 1.78-1.62 (m, 3H). [M+H]$^+$. MS (ESI): mass calculated for $C_{17}H_{13}Cl_2FN_6O$, 406.05; m/z found, 407.1.

Example 175: (2-fluoro-3-(trifluoromethyl)phenyl)(1-(5-fluoropyrimidin-2-yl)-4-methyl-6,7-dihydro-1H-[1,2,3]triazolo[4,5-c]pyridin-5(4H)-yl)methanone

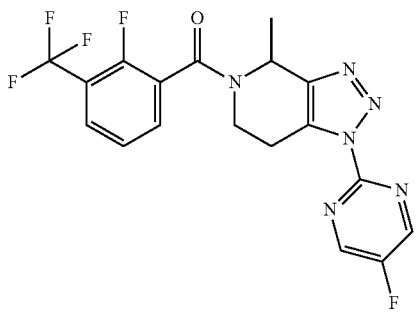 [SMILES: CC1c2nnn(-c3ncc(F)cn3)c2CCN1C(=O)c1cccc(C(F)(F)F)c1F]

Example 175 was prepared in a manner analogous to Example 153 substituting 2-fluoro-3-(trifluoromethyl)benzoic acid for 2-chloro-3-(trifluoromethyl)benzoic acid. $^1$H NMR (600 MHz, CDCl$_3$) δ 8.91-8.61 (m, 1H), 8.02 (s, 1H), 7.88-7.31 (m, 2H), 6.04 (s, 1H), 5.21-4.85 (m, 1H), 3.82-3.09 (m, 3H), 1.87-1.47 (m, 3H). MS (ESI): mass calculated for C$_{18}$H$_{13}$F$_5$N$_6$O, 424.11; m/z found, 425.1 [M+H]$^+$.

Example 176: (2-Chloro-3-(trifluoromethyl)phenyl)(1-(4-fluoropyridin-2-yl)-6-methyl-6,7-dihydro-1H-[1,2,3]triazolo[4,5-c]pyridin-5(4H)-yl)methanone

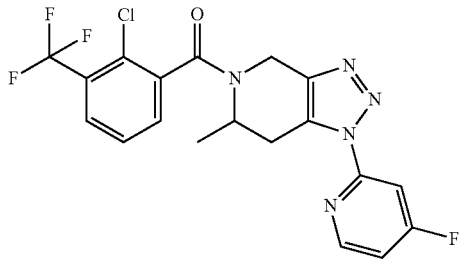 [SMILES: CC1Cc2c(nnn2-c2cc(F)ccn2)CN1C(=O)c1cccc(C(F)(F)F)c1Cl]

The title compound was prepared in a manner analogous to Example 173 substituting 2-chloro-3-(trifluoromethyl)benzoyl chloride for Intermediate 14. MS (ESI) mass calcd. C$_{19}$H$_{14}$ClF$_4$N$_5$O, 439.1; m/z found, 440.0 [M+H]$^+$. $^1$H NMR (500 MHz, CDCl$_3$) δ 8.53-8.38 (m, 1H), 8.00-7.89 (m, 1H), 7.82-7.76 (m, 1H), 7.57-7.40 (m, 2H), 7.14-7.04 (m, 1H), 5.90-5.59 (m, 1H), 4.68-4.02 (m, 2H), 3.57-3.19 (m, 2H), 1.41-1.16 (m, 3H).

Example 177: (2-Chloro-3-(trifluoromethyl)phenyl)(4-methyl-1-(pyrimidin-5-yl)-6,7-dihydro-1H-[1,2,3]triazolo[4,5-c]pyridin-5(4H)-yl)methanone

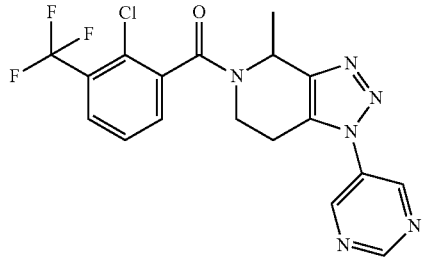 [SMILES: CC1c2nnn(-c3cncnc3)c2CCN1C(=O)c1cccc(C(F)(F)F)c1Cl]

A solution of (2-chloro-3-(trifluoromethyl)phenyl)(4-methyl-1-(pyrimidin-5-yl)-1H-[1,2,3]triazolo[4,5-c]pyridin-5(4H)-yl)methanone (237 mg, 0.56 mmol) in MeOH (12 ml) was treated with ammonium formate (147 mg, 2.3 mmol) and Pd/carbon (10 wt %, 20 mg) and the reaction was refluxed for 90 min. The reaction was filtered through celite and the filter cake washed with MeOH and concentrated to a crude solid which was re-suspended with CHCl$_3$ and filtered to remove in-organic salts then purified on 40 g SiO$_2$ with 0-60% EtOAc/hexanes to provide 243 mg (22%) of desired product. MS (ESI) mass calcd. C$_{18}$H$_{14}$ClF$_3$N$_6$O, 422.09; m/z found, 423.1 [M+H]$^+$. The enantiomers were separated by chiral SFC on (CHIRALPAK AD-H 5 μm 250×20 mm). Mobile phase (70% CO$_2$, 30% EtOH).

Intermediate 236: 2-ethyl-1-phenyl-1H-imidazo[4,5-c]pyridine

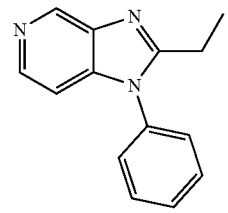 [SMILES: CCc1nc2cnccc2n1-c1ccccc1]

Step 1: 3-nitro-N-phenylpyridin-4-amine. To a mixture of 2-chloro-3-nitropyridine (15.8 g, 100 mmol) and aniline (11.1 g, 120 mmol) in dioxane (150 mL) was added was added K$_2$CO$_3$ (39 g, 120 mmol). The reaction was heated to reflux for 10 h and then purified by silica gel chromatography using petroleum ether/ethyl acetate to provide the product as a yellow solid (20 g, 93%).

Step 2: N$^4$-phenylpyridine-3,4-diamine. To a solution of 3-nitro-N-phenylpyridin-4-amine (20 g, 93 mmol) in MeOH (500 mL) was added 10% Pd/C. The reaction was stirred under a hydrogen atmosphere for 10 h. The reaction was filtered and the filtrate was concentrated to afford the product (17.2 g, 100%).

Step 3: 2-ethyl-1-phenyl-1H-imidazo[4,5-c]pyridine. A mixture of N$^4$-phenylpyridine-3,4-diamine (8.0 g, 37.2 mmol), propionic acid (2.7 g, 37.2 mmol) and phosphorous oxychloride (50 mL) was stirred at reflux for 10 h. The reaction was purified by silica gel chromatography using ethyl acetate to afford the product as a solid (1.6 g, 19%). MS (ESI) mass calcd. C$_{14}$H$_{13}$N$_3$, 223.1; m/z found, 224.1 [M+H]$^+$. $^1$H NMR (400 MHz, DMSO) δ 9.12 (s, 1H), 8.38 (d, J=5.8 Hz, 1H), 7.71-7.57 (m, 5H), 7.32 (d, J=5.5 Hz, 1H), 2.81 (q, J=7.5 Hz, 2H), 1.27 (t, J=7.4 Hz, 3H).

Example 178 (S*)-(2-fluoro-3-(trifluoromethyl)phenyl)(1-(5-fluoropyrimidin-2-yl)-4-methyl-6,7-dihydro-1H-[1,2,3]triazolo[4,5-c]pyridin-5(4H)-yl)methanone

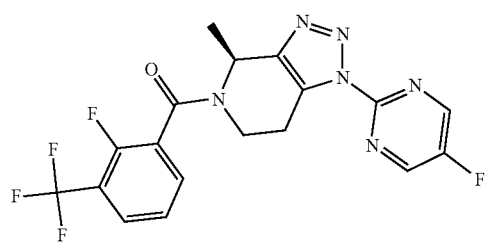 [SMILES: C[C@H]1c2nnn(-c3ncc(F)cn3)c2CCN1C(=O)c1cccc(C(F)(F)F)c1F]

MS (ESI) mass calcd $C_{18}H_{13}F_5N_6O$, 424.1 m/z found, 425.1 [M+H]$^+$.

Example 179 (2,3-dichlorophenyl)(1-(4,6-dimethylpyrimidin-2-yl)-4-methyl-6,7-dihydro-1H-[1,2,3]triazolo[4,5-c]pyridin-5(4H)-yl)methanone

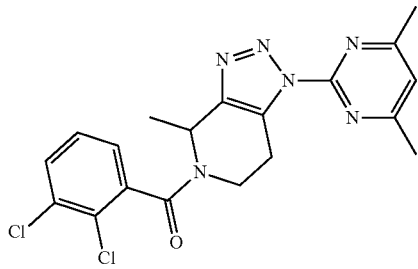 [SMILES: Cc1cc(C)nc(-n2nnc3c2CCN(C(=O)c2cccc(Cl)c2Cl)C3C)n1]

MS (ESI) mass calcd $C_{19}H_{1}Cl_2N_6O$, 416.1 m/z found, 417.1 [M+H]$^+$. $^1$H NMR (400 MHz, CDCl$_3$) δ 7.58-7.48 (m, 1H), 7.36-7.18 (m, 2H), 7.14-6.97 (m, 1H), 6.15-5.95 (m, 0.5H), 5.20-5.06 (m, 0.5H), 5.02-4.72 (m, 0.5H), 3.78-2.92 (m, 3.5H), 2.71-2.48 (m, 6H), 1.81-1.32 (m, 3H).

Example 180 (2,3-dichlorophenyl)(4-methyl-1-(6-methylpyrazin-2-yl)-6,7-dihydro-1H-[1,2,3]triazolo[4,5-c]pyridin-5(4H)-yl)methanone

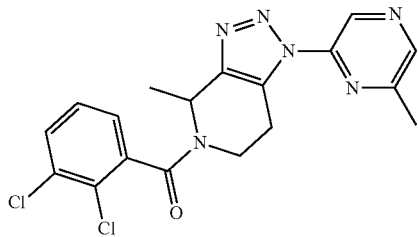 [SMILES: Cc1cncc(-n2nnc3c2CCN(C(=O)c2cccc(Cl)c2Cl)C3C)n1]

MS (ESI) mass calcd $C_{18}H_{16}Cl_2N_6O$, 402.1 m/z found, 403.1 [M+H]$^+$. $^1$H NMR (500 MHz, CDCl$_3$) δ 9.60-9.11 (m, 1H), 8.88-8.37 (m, 1H), 7.82-6.86 (m, 3H), 6.34-5.86 (m, 0.6H), 5.39-5.04 (m, 0.4H), 5.03-4.60 (m, 0.4H), 3.92-2.92 (m, 3.6H), 2.78-2.45 (m, 3H), 1.85-1.40 (m, 3H).

Example 181 (R*)-(2-chloro-3-(trifluoromethyl)phenyl)(1-(4,6-dimethylpyrimidin-2-yl)-4-methyl-6,7-dihydro-1H-[1,2,3]triazolo[4,5-c]pyridin-5(4H)-yl)methanone

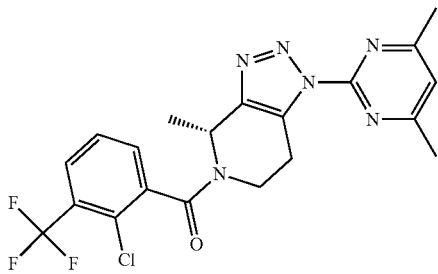 [SMILES: Cc1cc(C)nc(-n2nnc3c2CCN(C(=O)c2cccc(C(F)(F)F)c2Cl)[C@@H]3C)n1]

MS (ESI) mass calcd $C_{20}H_{18}ClF_3N_6O$, 450.1 m/z found, 451.1 [M+H]. $^1$H NMR (400 MHz, CDCl$_3$) δ 7.83-7.73 (m, 1H), 7.59-7.25 (m, 2H), 7.17-7.03 (m, 1H), 6.16-5.98 (m, 0.6H), 5.21-5.05 (m, 0.4H), 4.96-4.70 (m, 0.4H), 3.73-2.89 (m, 3.6H), 2.73-2.46 (m, 6H), 1.79-1.44 (m, 3H).

Example 182 (S*)-(2-chloro-3-(trifluoromethyl)phenyl)(1-(4,6-dimethylpyrimidin-2-yl)-4-methyl-6,7-dihydro-1H-[1,2,3]triazolo[4,5-c]pyridin-5(4H)-yl)methanone

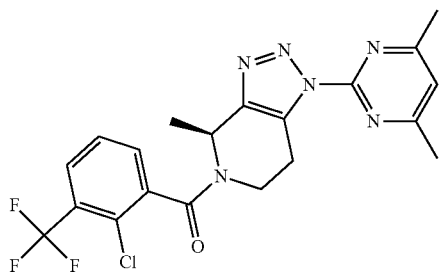 [SMILES: Cc1cc(C)nc(-n2nnc3c2CCN(C(=O)c2cccc(C(F)(F)F)c2Cl)[C@H]3C)n1]

MS (ESI) mass calcd $C_{20}H_{18}ClF_3N_6O$, 450.1 m/z found, 451.1 [M+H]$^+$. $^1$H NMR (400 MHz, CDCl$_3$) δ 7.83-7.73 (m, 1H), 7.59-7.25 (m, 2H), 7.17-7.03 (m, 1H), 6.16-5.98 (m, 0.6H), 5.21-5.05 (m, 0.4H), 4.96-4.70 (m, 0.4H), 3.73-2.89 (m, 3.6H), 2.73-2.46 (m, 6H), 1.79-1.44 (m, 3H).

Example 183 (R*)-(3-chloro-2-(trifluoromethyl)pyridin-4-yl)(1-(5-fluoropyrimidin-2-yl)-6-methyl-6,7-dihydro-1H-[1,2,3]triazolo[4,5-c]pyridin-5(4H)-yl)methanone

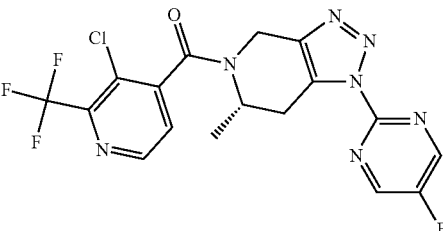

MS (ESI) mass calcd $C_{17}H_{12}ClF_4N_7O$, 441.1 m/z found, 442.1 [M+H]$^+$.

Example 184: (2-Chloro-3-(trifluoromethyl)phenyl)(2-ethyl-4-methyl-1-phenyl-6,7-dihydro-1H-imidazo[4,5-c]pyridin-5(4H)-yl)methanone

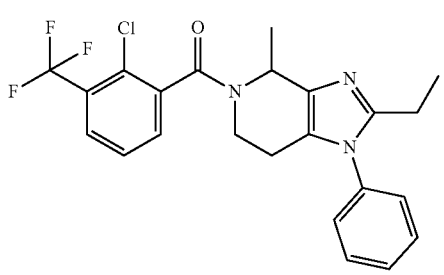 [SMILES: CCc1nc2c(n1-c1ccccc1)CCN(C(=O)c1cccc(C(F)(F)F)c1Cl)C2C]

The title compound was prepared in a manner analogous to Example 11 substituting Intermediate 236 for Intermediate 1. 1H NMR (500 MHz, CDCl3) δ 7.77-7.67 (m, 1H), 7.57-7.35 (m, 5H), 7.27-7.17 (m, 2H), 5.91-5.71 (m, 1H), 5.32-5.28 (s, 1H), 5.11-4.78 (m, 1H), 4.74-4.39 (m, 1H), 3.61-3.27 (m, 1H), 3.27-3.05 (m, 1H), 2.93-2.04 (m, 5H), 1.30-1.08 (m, 3H). MS (ESI) mass calcd. $C_{23}H_{21}ClF_3N_3O$, 447.1; m/z found, 448.2 $[M+H]^+$.

Too many Hs

Example 185 (R*)-(2-chloro-3-(trifluoromethyl)phenyl)(4-methyl-1-(4-methylpyridin-2-yl)-6,7-dihydro-1H-[1,2,3]triazolo[4,5-c]pyridin-5(4H)-yl)methanone

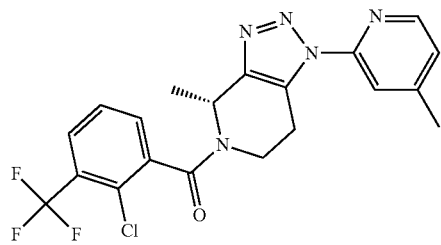 [SMILES: Cc1ccnc(-n2nnc3c2CCN(C(=O)c2cccc(C(F)(F)F)c2Cl)[C@@H]3C)c1]

MS (ESI) mass calcd $C_{20}H_{17}ClF_3N_5O$, 435.1 m/z found, 436.1 $[M+H]^+$. $^1$H NMR (400 MHz, CDCl$_3$) δ 8.41-8.24 (m, 1H), 8.03-7.91 (m, 1H), 7.82-7.72 (m, 1H), 7.61-7.29 (m, 2H), 7.21-7.11 (m, 1H), 6.18-5.90 (m, 0.6H), 5.18-5.02 (m, 0.4H), 4.96-4.66 (m, 0.4H), 3.72-2.92 (m, 3.6H), 2.50 (s, 3H), 1.87-1.40 (m, 3H).

Example 186 (S*)-(2-chloro-3-(trifluoromethyl)phenyl)(4-methyl-1-(4-methylpyridin-2-yl)-6,7-dihydro-1H-[1,2,3]triazolo[4,5-c]pyridin-5(4H)-yl)methanone

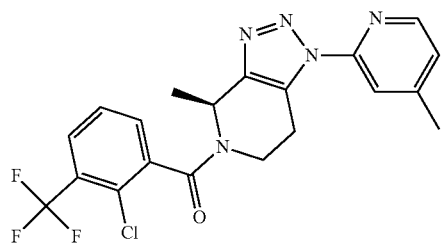 [SMILES: Cc1ccnc(-n2nnc3c2CCN(C(=O)c2cccc(C(F)(F)F)c2Cl)[C@H]3C)c1]

MS (ESI) mass calcd $C_{20}H_{17}ClF_3N_5O$, 435.1 m/z found, 436.1 $[M+H]^+$. $^1$H NMR (400 MHz, CDCl$_3$) δ 8.41-8.24 (m, 1H), 8.03-7.91 (m, 1H), 7.82-7.72 (m, 1H), 7.61-7.29 (m, 2H), 7.21-7.11 (m, 1H), 6.18-5.90 (m, 0.6H), 5.18-5.02 (m, 0.4H), 4.96-4.66 (m, 0.4H), 3.72-2.92 (m, 3.6H), 2.50 (s, 3H), 1.87-1.40 (m, 3H).

Example 187 (S*)-(1-(5-fluoropyrimidin-2-yl)-6-methyl-6,7-dihydro-1H-[1,2,3]triazolo[4,5-c]pyridin-5(4H)-yl)(3-methyl-2-(trifluoromethyl)pyridin-4-yl)methanone

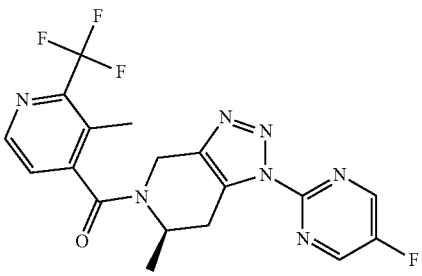 [SMILES: Cc1c(C(=O)N2Cc3nnn(-c4ncc(F)cn4)c3C[C@H]2C)ccnc1C(F)(F)F]

MS (ESI) mass calcd $C_{18}H_{15}F_4N_7O$, 421.1 m/z found, 422.1 $[M+H]^+$.

Example 188 (R*)-(4-methyl-1-(pyrimidin-2-yl)-6,7-dihydro-1H-[1,2,3]triazolo[4,5-c]pyridin-5(4H)-yl)(2-methyl-3-(trifluoromethyl)phenyl)methanone

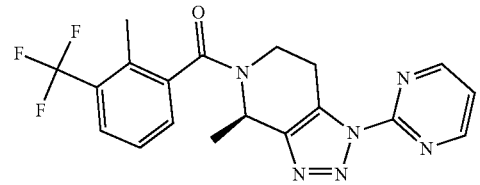 [SMILES: Cc1c(C(=O)N2CCc3c(nnn3-c3ncccn3)[C@H]2C)cccc1C(F)(F)F]

MS (ESI) mass calcd $C_{19}H_{17}F_3N_6O$, 402.1 m/z found, 403.2 $[M+H]^+$.

Example 189 (2-fluoro-3-(trifluoromethyl)phenyl)(6-methyl-1-(1H-pyrazol-3-yl)-6,7-dihydro-1H-[1,2,3]triazolo[4,5-c]pyridin-5(4H)-yl)methanone

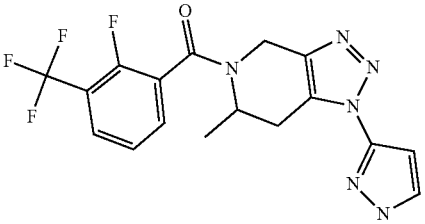

MS (ESI) mass calcd $C_{17}H_{14}F_4N_6O$, 394.1 m/z found, 395.1 $[M+H]^+$.

Example 190 (R*)-(2-fluoro-3-(trifluoromethyl)phenyl)(1-(5-fluoropyrimidin-2-yl)-4-methyl-6,7-dihydro-1H-[1,2,3]triazolo[4,5-c]pyridin-5(4H)-yl)methanone

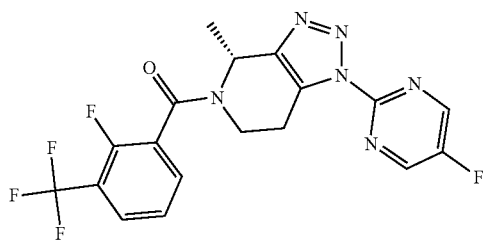 [SMILES: C[C@@H]1c2nnn(-c3ncc(F)cn3)c2CCN1C(=O)c1cccc(C(F)(F)F)c1F]

MS (ESI) mass calcd C$_{18}$H$_{13}$F$_5$N$_6$O, 424.1 m/z found, 425.1 [M+H]$^+$.

Example 191: (S*)-(2,3-Dichlorophenyl)(4-methyl-1-(pyridin-2-yl)-6,7-dihydro-1H-imidazo[4,5-c]pyridin-5(4H)-yl)methanone

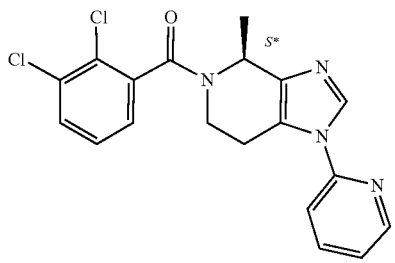 [SMILES: C[C@H]1c2ncn(-c3ccccn3)c2CCN1C(=O)c1cccc(Cl)c1Cl]

Step 1: (S*)-5-benzyl-4-methyl-4,5,6,7-tetrahydro-1H-imidazo[4,5-c]pyridine

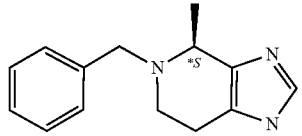

(S*)-5-benzyl-4-methyl-4,5,6,7-tetrahydro-1H-imidazo[4,5-c]pyridine was obtained, absolute configuration unknown, as a single enantiomer by Chiral SFC purification of Example 11 performed using CHIRALPAK IC (5 μm, 250×20 mm) and a mobile phase of 70% CO$_2$, 30% isopropanol (0.3% NEt$_3$). Step 2: (S*)-5-benzyl-4-methyl-1-(pyridin-2-yl)-4,5,6,7-tetrahydro-1H-imidazo[4,5-c]pyridine

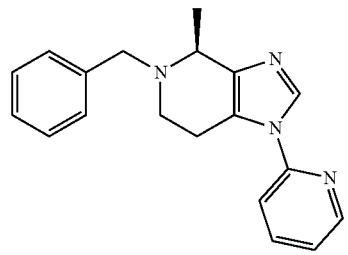 [SMILES: C[C@H]1c2ncn(-c3ccccn3)c2CCN1Cc1ccccc1]

The title compound was prepared in a manner analogous to Example 24, Step B substituting the product from Example 191, Step 1 for 5-tert-butyl 4-ethyl 6,7-dihydro-1H-imidazo[4,5-c]pyridine-4,5(4H)-dicarboxylate. MS (ESI) mass calcd. C$_{19}$H$_2$N$_4$, 304.2; m/z found, 305.2 [M+H]$^+$.

Step 3: (S*)-4-methyl-1-(pyridin-2-yl)-4,5,6,7-tetrahydro-1H-imidazo[4,5-c]pyridine

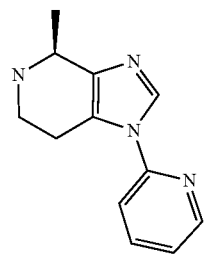 [SMILES: C[C@@H]1NCCc2c1ncn2-c1ccccn1]

The title compound was prepared in a manner analogous to Example 153, Step D substituting the product from Example 191, Step 2 for 1-(5-fluoropyrimidin-2-yl)-4-methyl-1H-imidazo[4,5-c]pyridine, Pd/C for Pt/C and MeOH for AcOH. MS (ESI) mass calcd. C$_{12}$H$_{14}$N$_4$, 214.1; m/z found, 215.1 [M+H]$^+$.

Step 4: (S*)-(2,3-dichlorophenyl)(4-methyl-1-(pyridin-2-yl)-6,7-dihydro-1H-imidazo[4,5-c]pyridin-5(4H)-yl)methanone

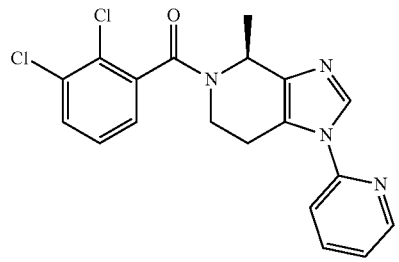 [SMILES: C[C@H]1c2ncn(-c3ccccn3)c2CCN1C(=O)c1cccc(Cl)c1Cl]

The title compound was prepared in a manner analogous to Example 1, Step C substituting the product from Example 191, Step 3 for 1-(pyridin-2-yl)-4,5,6,7-tetrahydro-1H-imidazo[4,5-c]pyridine and 2,3 dichlorobenzoic acid for 2-chloro-3-(trifluoromethyl) benzoic acid. MS (ESI) mass calcd. C$_{19}$H$_{16}$Cl$_2$N$_4$O, 386.1; m/z found, 387.1 [M+H]$^+$. $^1$H NMR (400 MHz, CDCl$_3$) δ 8.62-8.40 (m, 1H), 8.13-7.96 (m, 1H), 7.96-7.77 (m, 1H), 7.57-7.42 (m, 2H), 7.41-7.27 (m, 2H), 5.80 (t, J=8.0 Hz, 1H), 5.12-4.49 (m, 1H), 3.69-2.85 (m, 4H), 1.68-1.28 (m, 3H).

Example 192: (R*)-(2,3-Dichlorophenyl)(4-methyl-1-(pyridin-2-yl)-6,7-dihydro-1H-imidazo[4,5-c]pyridin-5(4H)-yl)methanone

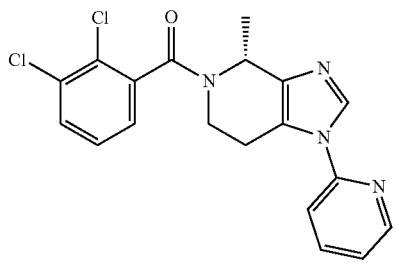 [SMILES: C[C@@H]1c2ncn(-c3ccccn3)c2CCN1C(=O)c1cccc(Cl)c1Cl]

The title compound was prepared in a manner analogous to Example 191 substituting (R*)-5-benzyl-4-methyl-4,5,6,7-tetrahydro-1H-imidazo[4,5-c]pyridine for (S*)-5-benzyl-4-methyl-4,5,6,7-tetrahydro-1H-imidazo[4,5-c]pyridine in Step 1. $^1$H NMR (400 MHz, CDCl$_3$) δ 8.62-8.40 (m, 1H), 8.13-7.96 (m, 1H), 7.96-7.77 (m, 1H), 7.57-7.42 (m, 2H), 7.41-7.27 (m, 2H), 5.90-5.71 (t, J=8.0 Hz, 1H), 5.12-4.49 (m, 1H), 3.69-2.85 (m, 4H), 1.68-1.28 (m, 3H). MS (ESI) mass calcd. C$_{19}$H$_{16}$Cl$_2$N$_4$O, 386.1; m/z found, 387.1 [M+H]$^+$.

Example 193: (R*)-(2-Chloro-3-(trifluoromethyl)phenyl)(1-(5-fluoropyrimidin-2-yl)-4-methyl-6,7-dihydro-1H-imidazo[4,5-c]pyridin-5(4H)-yl)methanone

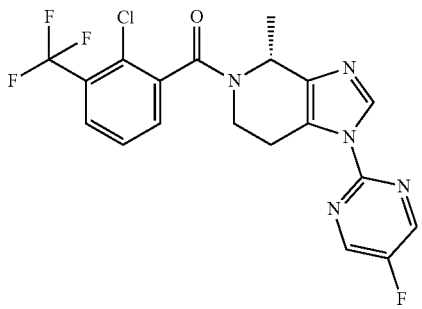 [SMILES: C[C@@H]1c2ncn(-c3ncc(F)cn3)c2CCN1C(=O)c1cccc(C(F)(F)F)c1Cl]

The title compound, absolute configuration unknown, was obtained as a single enantiomer by Chiral SFC purification of Example 22 performed using CHIRALCEL OD-H (5 μm, 250×20 mm) and a mobile phase of 72% CO$_2$, 28% 1:1 EtOH:iPrOH. The enantiomeric purity was confirmed by analytical SFC using Whelk-ol (S,S) (250×4.6 mm) and a mobile phase of 60% CO$_2$, 40% MeOH over 7 minutes. (100% single enantiomer, 2.98 min retention time). MS (ESI) mass calcd. C$_{19}$H$_{14}$ClF$_4$N$_5$O, 439.1; m/z found, 439.8 [M+H]$^+$.

Example 194: (S*)-(2-Chloro-3-(trifluoromethyl)phenyl)(1-(5-fluoropyrimidin-2-yl)-4-methyl-6,7-dihydro-1H-imidazo[4,5-c]pyridin-5(4H)-yl)methanone

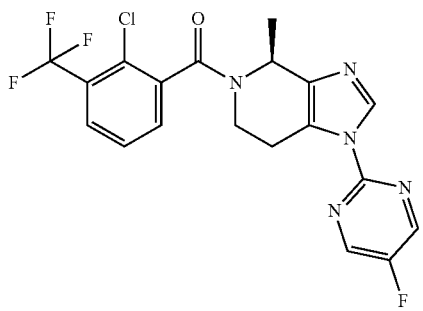 [SMILES: C[C@H]1c2ncn(-c3ncc(F)cn3)c2CCN1C(=O)c1cccc(C(F)(F)F)c1Cl]

The title compound, absolute configuration unknown, was obtained as a single enantiomer by Chiral SFC purification of Example 22 performed using CHIRALCEL OD-H (5 μm, 250×20 mm) and a mobile phase of 72% CO$_2$, 28% 1:1 EtOH:iPrOH. The enantiomeric purity was confirmed by analytical SFC using Whelk-ol (S,S) (250×4.6 mm) and a mobile phase of 60% CO$_2$, 40% MeOH over 7 minutes. (100% single enantiomer, 4.03 min retention time). MS (ESI) mass calcd. C$_{19}$H$_{14}$ClF$_4$N$_5$O, 439.1; m/z found, 439.8 [M+H]$^+$.

Example 195: (6R*)-5-[(2,3-Dichlorophenyl)carbonyl]-1-(4-fluoropyridin-2-yl)-6-methyl-4,5,6,7-tetrahydro-1H-[1,2,3]triazolo[4,5-c]pyridine

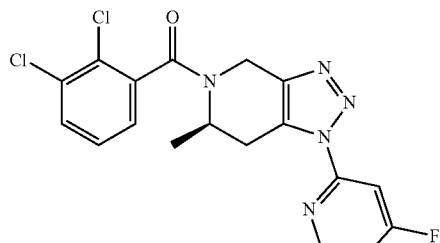

The title compound, absolute configuration unknown, was obtained as a single enantiomer by Chiral SFC purification of Example 173 performed using CHIRALCEL OJ-H (5 μm, 250×20 mm) and a mobile phase of 80% CO$_2$, 20% iPrOH. The enantiomeric purity was confirmed by analytical SFC using Chiralcel (250×4.6 mm) and a mobile phase of 80% CO$_2$, 20% iPrOH containing 0.3% iPrNH$_2$ over 7 minutes. (100% single enantiomer, 4.17 min retention time). MS (ESI) mass calcd. C$_{18}$H$_{14}$Cl$_2$FN$_5$O, 405.1; m/z found, 406.0 [M+H]$^+$.

Example 196: (6S*)-5-[(2,3-Dichlorophenyl)carbonyl]-1-(4-fluoropyridin-2-yl)-6-methyl-4,5,67-tetrahydro-1H-[1,2,3]triazolo[4,5-c]pyridine

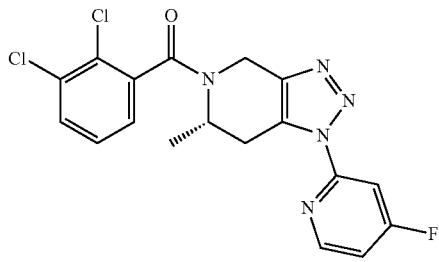 [SMILES: C[C@H]1Cc2c(nnn2-c2cc(F)ccn2)CN1C(=O)c1cccc(Cl)c1Cl]

The title compound, absolute configuration unknown, was obtained as a single enantiomer by Chiral SFC purification of Example 173 performed using CHIRALCEL OJ-H (5 μm, 250×20 mm) and a mobile phase of 80% $CO_2$, 20% iPrOH. The enantiomeric purity was confirmed by analytical SFC using Chiralcel (250×4.6 mm) and a mobile phase of 80% $CO_2$, 20% iPrOH containing 0.3% $iPrNH_2$ over 7 minutes. (100% single enantiomer, 5.35 min retention time). MS (ESI) mass calcd. $C_{18}H_{14}Cl_2FN_5O$, 405.1; m/z found, 406.0 [M+H]+.

Example 197 (S*)-(4-methyl-1-(pyrimidin-2-yl)-6,7-dihydro-1H-[1,2,3]triazolo[4,5-c]pyridin-5(4H)-yl)(2-methyl-3-(trifluoromethyl)phenyl)methanone

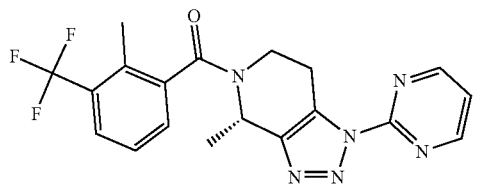 [SMILES: Cc1c(C(=O)N2CCc3c(nnn3-c3ncccn3)[C@@H]2C)cccc1C(F)(F)F]

MS (ESI) mass calcd $C_{19}H_{17}F_3N_6O$, 402.1 m/z found, 403.2 [M+H]+.

Example 198: (6R*)-5-{[2-Chloro-3-(trifluoromethyl)phenyl]carbonyl}-1-(4-fluoropyridin-2-yl)-6-methyl-4,5,6,7-tetrahydro-1H-[1,2,3]triazolo[4,5-c]pyridine

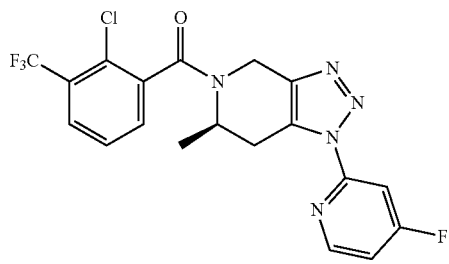 [SMILES: C[C@@H]1Cc2c(nnn2-c2cc(F)ccn2)CN1C(=O)c1cccc(C(F)(F)F)c1Cl]

The title compound, absolute configuration unknown, was obtained as a single enantiomer by Chiral SFC purification of Example 176 performed using CHIRALPAK IA (5 μm, 250×20 mm) and a mobile phase of 85% $CO_2$, 15% iPrOH. The enantiomeric purity was confirmed by analytical SFC using Chiralpak IA (250×4.6 mm) and a mobile phase of 85% $CO_2$, 15% iPrOH containing 0.3% $iPrNH_2$ over 7 minutes. (100% single enantiomer, 7.86 min retention time). MS (ESI) mass calcd. $C_{19}H_{14}ClF_4N_5O$, 439.1; m/z found, 440.0 [M+H]+. $^1$H NMR (500 MHz, $CDCl_3$) δ 8.53-8.38 (m, 1H), 8.00-7.89 (m, 1H), 7.82-7.76 (m, 1H), 7.57-7.40 (m, 2H), 7.14-7.04 (m, 1H), 5.90-5.59 (m, 1H), 4.68-4.02 (m, 2H), 3.57-3.19 (m, 2H), 1.41-1.16 (m, 3H).

Example 199: (6S*)-5-{[2-Chloro-3-(trifluoromethyl)phenyl]carbonyl}-1-(4-fluoropyridin-2-yl)-6-methyl-4,5,6,7-tetrahydro-1H-[1,2,3]triazolo[4,5-c]pyridine

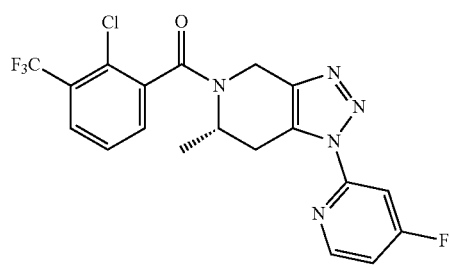 [SMILES: C[C@H]1Cc2c(nnn2-c2cc(F)ccn2)CN1C(=O)c1cccc(C(F)(F)F)c1Cl]

The title compound, absolute configuration unknown, was obtained as a single enantiomer by Chiral SFC purification of Example 176 performed using CHIRALPAK IA (5 μm, 250×20 mm) and a mobile phase of 85% $CO_2$, 15% iPrOH. The enantiomeric purity was confirmed by analytical SFC using Chiralpak IA (250×4.6 mm) and a mobile phase of 85% $CO_2$, 15% iPrOH containing 0.3% $iPrNH_2$ over 7 minutes. (100% single enantiomer, 8.55 min retention time). MS (ESI) mass calcd. $C_{19}H_{14}ClF_4N_5O$, 439.1; m/z found, 440.0 [M+H]+. $^1$H NMR (500 MHz, $CDCl_3$) δ 8.53-8.38 (m, 1H), 8.00-7.89 (m, 1H), 7.82-7.76 (m, 1H), 7.57-7.40 (m, 2H), 7.14-7.04 (m, 1H), 5.90-5.59 (m, 1H), 4.68-4.02 (m, 2H), 3.57-3.19 (m, 2H), 1.41-1.16 (m, 3H).

Example 200: 5-{[2-Chloro-3-(trifluoromethyl)phenyl]carbonyl}-1-(5-fluoropyrimidin-2-yl)-6-methyl-4,5,6,7-tetrahydro-1H-[1,2,3]triazolo[4,5-c]pyridine

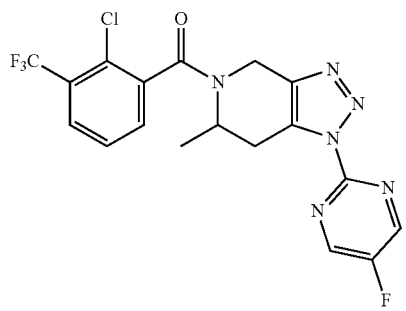

Step 1: N-(2-chloro-6-methyl-3-nitropyridin-4-yl)-5-fluoropyrimidin-2-amine

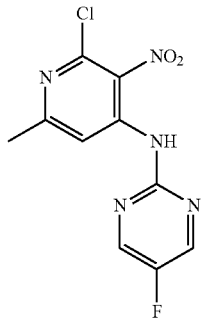 [SMILES: Cc1cc(Nc2ncc(F)cn2)c([N+](=O)[O-])c(Cl)n1]

To a mixture of 5-fluoropyrimidin-2-amine (8.2 g, 72.1 mmol) and sodium hydride (5.8 g, 144 mmol) in THF (100 mL) was added 2,4-dichloro-6-methyl-3-nitropyridine (15 g, 72.1 mmol). After stirring for 10 h, ethanol was added. Silica gel chromatography (5:1 Hexane:EtOAc) provided the product as a yellow solid (12.8 g, 63%).

Step 2: 1-(5-Fluoropyrimidin-2-yl)-6-methyl-1H-[1,2,3]triazolo[4,5-c]pyridine

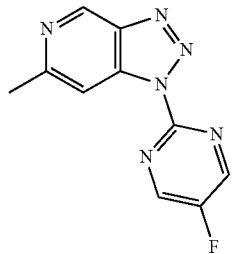 [SMILES: Cc1cc2c(cn1)nnn2-c1ncc(F)cn1]

To a slurry of N-(2-chloro-6-methyl-3-nitropyridin-4-yl)-5-fluoropyrimidin-2-amine (13 g, 45.8 mmol) in ethanol (300 mL) was added 10% Pd/C (100 mg). The reaction was stirred for 10 h under a hydrogen atmosphere after which time the reaction was filtered and the filtrate was concentrated. The residue was diluted with ethanol (200 mL) and cooled to 0° C. Isoamyl nitrite (4.0 g, 34.0 mmol) and HBF$_4$ (5.5 g, 34.0 mmol) were added and the reaction was stirred for 30 min at 0° C. followed by rt for 10 h. Evaporation of the solvents followed by recrystallization afforded the product as a white solid (3.2 g, 48%). MS (ESI) mass calcd. $C_{10}H_7FN_6$, 230.07; m/z found, 231.2 [M+H]$^+$. $^1$H NMR (400 MHz, DMSO-d$_6$) δ 9.44 (s, 1H), 9.17 (s, 2H), 8.14 (s, 1H), 2.70 (s, 3H).

Step 3: 1-(5-fluoropyrimidin-2-yl)-6-methyl-4,5,6,7-tetrahydro-1H-[1,2,3]triazolo[4,5-c]pyridine

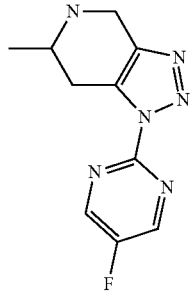 [SMILES: CC1Cc2c(nnn2-c2ncc(F)cn2)CN1]

The title compound was prepared in a manner analogous to Example 50, Step A substituting the product from Example 200, Step 1 for Intermediate 2. MS (ESI) mass calcd. $C_{10}H_{11}FN_6$, 234.1; m/z found, 235.1 [M+H]$^+$.

Step 4: (-{[2-Chloro-3-(trifluoromethyl)phenyl]carbonyl}-1-(5-fluoropyrimidin-2-yl)-6-methyl-4,5,6,7-tetrahydro-1H-[1,2,3]triazolo[4,5-c]pyridine

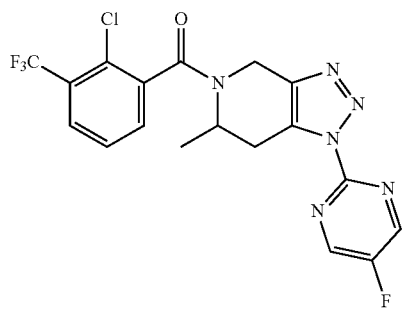

The title compound was prepared in a manner analogous to Example 63, Step 5 substituting the product from Example 200, Step 2 for 1-(pyridin-2-yl)-4,5,6,7-tetrahydro-1H-[1,2,3]triazolo[4,5-c]pyridine, and DCM for THF. MS (ESI) mass calcd. $CH_{13}CF_4N_6O$, 440.1; m/z found, 441.1 [M+H]$^+$.

Example 201: (6R*)-5-{[2-Chloro-3-(trifluoromethyl)phenyl]carbonyl}-1-(5-fluoropyrimidin-2-yl)-6-methyl-4,5,6,7-tetrahydro-1H-[1,2,3]triazolo[4,5-c]pyridine

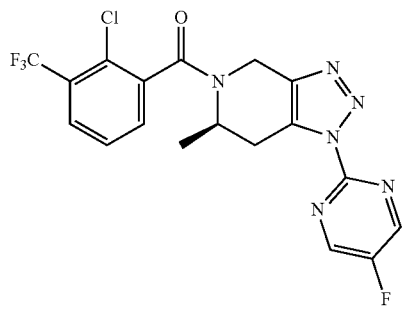

The title compound, absolute configuration unknown, was obtained as a single enantiomer by Chiral SFC purification of Example 200 performed using CHIRALPAK AD-H (5 μm, 250×20 mm) and a mobile phase of 70% CO$_2$, 30% 1:1 EtOH:iPrOH. The enantiomeric purity was confirmed by analytical SFC using Chiralpak AD-H (250×4.6 mm) and a mobile phase of 70% CO$_2$, 15% iPrOH, 15% EtOH containing 0.3% iPrNH$_2$ over 7 minutes. (100% single enantiomer, 2.93 min retention time). MS (ESI) mass calcd. $C_{18}H_{13}ClF_4N_6O$, 440.1; m/z found, 441.0 [M+H]$^+$. $^1$H NMR (500 MHz, CDCl$_3$) δ 8.80-8.68 (m, 2H), 7.86-7.73 (m, 1H), 7.61-7.38 (m, 2H), 5.92-5.60 (m, 1H), 4.69-4.04 (m, 2H), 3.56-3.06 (m, 2H), 1.43-1.16 (m, 3H).

Example 202: (6S*)-5-{[2-Chloro-3-(trifluoromethyl)phenyl]carbonyl}-1-(5-fluoropyrimidin-2-yl)-6-methyl-4,5,6,7-tetrahydro-1H-[1,2,3]triazolo[4,5-c]pyridine

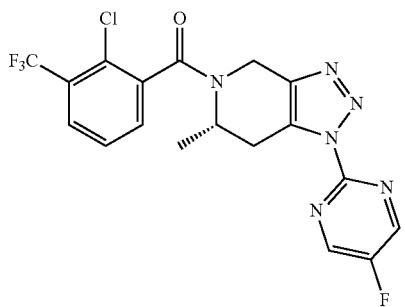

The title compound, absolute configuration unknown, was obtained as a single enantiomer by Chiral SFC purification of Example 200 performed using CHIRALPAK AD-H (5 μm, 250×20 mm) and a mobile phase of 70% $CO_2$, 30% 1:1 EtOH:iPrOH. The enantiomeric purity was confirmed by analytical SFC using Chiralpak AD-H (250×4.6 mm) and a mobile phase of 70% $CO_2$, 15% iPrOH, 15% EtOH containing 0.3% $iPrNH_2$ over 7 minutes. (100% single enantiomer, 3.37 min retention time). MS (ESI) mass calcd. $C_{18}H_{13}ClF_4N_6O$, 440.1; m/z found, 441.0 [M+H]$^+$.

Example 203: 5-[(2,3-Dichlorophenyl)carbonyl]-1-(5-fluoropyrimidin-2-yl)-6-methyl-4,5,6,7-tetrahydro-1H-[1,2,3]triazolo[4,5-c]pyridine

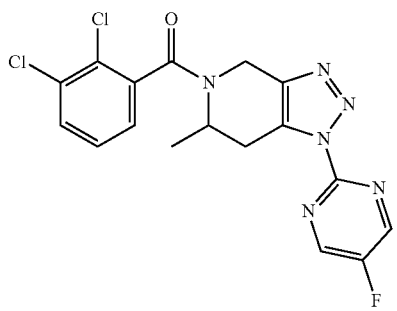 [SMILES: CC1Cc2c(nnn2-c2ncc(F)cn2)CN1C(=O)c1cccc(Cl)c1Cl]

The title compound was prepared in a manner analogous to Example 200 substituting Intermediate 14 for Intermediate 12. MS (ESI) mass calcd. $C_{17}H_{13}Cl_2FN_6O$, 406.1; m/z found, 407.1 [M+H]$^+$. $^1$H NMR (500 MHz, CDCl$_3$) δ 8.78-8.70 (m, 2H), 7.57-7.51 (m, 1H), 7.41-7.10 (m, 2H), 5.89-5.58 (m, 1H), 4.63-4.07 (m, 2H), 3.56-3.05 (m, 2H), 1.39-1.16 (m, 3H).

Example 204: (6R*)-5-[(2,3-Dichlorophenyl)carbonyl]-1-(5-fluoropyrimidin-2-yl)-6-methyl-4,5,6,7-tetrahydro-1H-[1,2,3]triazolo[4,5-c]pyridine

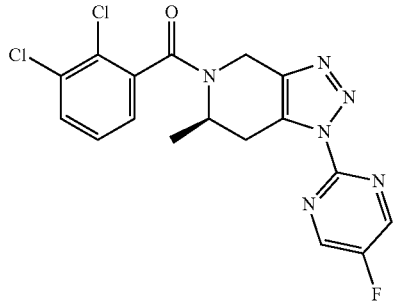 [SMILES: C[C@@H]1Cc2c(nnn2-c2ncc(F)cn2)CN1C(=O)c1cccc(Cl)c1Cl]

The title compound, absolute configuration unknown, was obtained as a single enantiomer by Chiral SFC purification of Example 203 performed using CHIRALPAK AD-H (5 μm, 250×20 mm) and a mobile phase of 60% $CO_2$, 40% 1:1 MeOH:iPrOH. The enantiomeric purity was confirmed by analytical SFC using Chiralpak AD-H (250×4.6 mm) and a mobile phase of 60% $CO_2$, 20% iPrOH, 20% EtOH containing 0.3% $iPrNH_2$ over 7 minutes. (100% single enantiomer, 3.49 min retention time). MS (ESI) mass calcd. $C_{17}H_{13}Cl_2FN_6O$, 406.05; m/z found, 406.9 [M+H]$^+$.

Example 205: (6S*)-5-[(2,3-Dichlorophenyl)carbonyl]-1-(5-fluoropyrimidin-2-yl)-6-methyl-4,5,6,7-tetrahydro-1H-[1,2,3]triazolo[4,5-c]pyridine

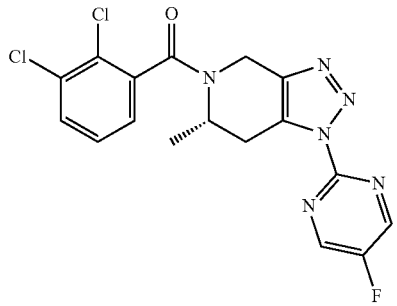 [SMILES: C[C@H]1Cc2c(nnn2-c2ncc(F)cn2)CN1C(=O)c1cccc(Cl)c1Cl]

The title compound, absolute configuration unknown, was obtained as a single enantiomer by Chiral SFC purification of Example 203 performed using CHIRALPAK AD-H (5 μm, 250×20 mm) and a mobile phase of 60% $CO_2$, 40% 1:1 MeOH:iPrOH. The enantiomeric purity was confirmed by analytical SFC using Chiralpak AD-H (250×4.6 mm) and a mobile phase of 60% $CO_2$, 20% iPrOH, 20% EtOH containing 0.3% $iPrNH_2$ over 7 minutes. (100% single enantiomer, 4.04 min retention time). MS (ESI) mass calcd. $C_{17}H_{13}Cl_2FN_6O$, 406.05; m/z found, 407.0 [M+H]$^+$.

Example 206: 1-(5-Fluoropyrimidin-2-yl)-6-methyl-5-{[2-methyl-3-(trifluoromethyl)phenyl]carbonyl}-4,5,6,7-tetrahydro-1H-[1,2,3]triazolo[4,5-c]pyridine Step 1: 2-methyl-3-(trifluoromethyl)benzoyl chloride

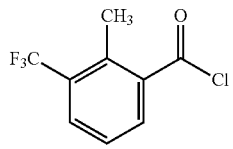

The title compound was prepared in a manner analogous to Intermediate 12 substituting 2-methyl-3-(trifluoromethyl)benzoic acid for 2-chloro-3-(trifluoromethyl)benzoic acid.

Step 2: 1-(5-Fluoropyrimidin-2-yl)-6-methyl-5-{[2-methyl-3-(trifluoromethyl)phenyl]carbonyl}-4,5,6,7-tetrahydro-1H-[1,2,3]triazolo[4,5-c]pyridine

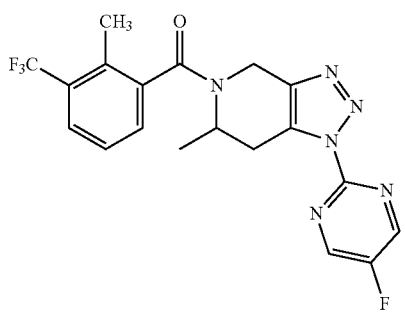

The title compound was prepared in a manner analogous to Example 200 substituting the product of Example 206, Step 1 for Intermediate 12. MS (ESI) mass calcd. $C_{19}H_{16}F_4N_6O$, 420.1; m/z found, 421.1 [M+H]$^+$. $^1$H NMR (500 MHz, CDCl$_3$) δ 8.82-8.67 (m, 2H), 7.77-7.64 (m, 1H), 7.50-7.21 (m, 2H), 5.94-5.62 (m, 1H), 4.58-4.07 (m, 2H), 3.55-3.03 (m, 2H), 2.60-2.17 (m, 3H), 1.43-1.16 (m, 3H).

Example 207: (6R*)-1-(5-Fluoropyrimidin-2-yl)-6-methyl-5-{[2-methyl-3-(trifluoromethyl)phenyl]carbonyl}-4,5,6,7-tetrahydro-1H-[1,2,3]triazolo[4,5-c]pyridine

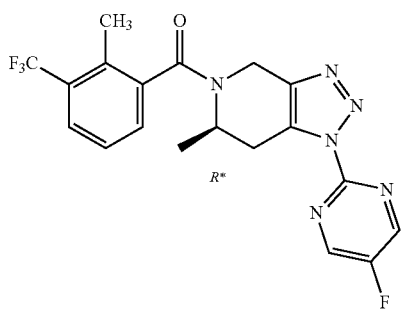 [SMILES: Cc1c(C(=O)N2Cc3nnn(-c4ncc(F)cn4)c3C[C@H]2C)cccc1C(F)(F)F]

The title compound, absolute configuration unknown, was obtained as a single enantiomer by Chiral SFC purification of Example 206 performed using CHIRALPAK AD-H (5 μm, 250×20 mm) and a mobile phase of 75% CO$_2$, 25% EtOH. The enantiomeric purity was confirmed by analytical SFC using a CHIRALPAK AD-H (250×4.6 mm) and a mobile phase of 75% CO$_2$, 25% EtOH containing 0.3% iPrNH$_2$ over 7 minutes. (100% single enantiomer, 2.91 min retention time). MS (ESI) mass calcd. $C_{19}H_{16}F_4N_6O$, 420.1; m/z found, 421.1 [M+H]$^+$.

Example 208: (6S*)-1-(5-Fluoropyrimidin-2-yl)-6-methyl-5-{[2-methyl-3-(trifluoromethyl)phenyl]carbonyl}-4,5,6,7-tetrahydro-1H-[1,2,3]triazolo[4,5-c]pyridine

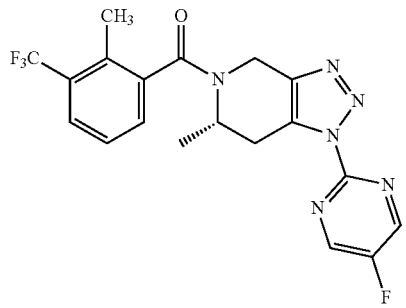

The title compound, absolute configuration unknown, was obtained as a single enantiomer by Chiral SFC purification of Example 206 performed using CHIRALPAK AD-H (5 μm, 250×20 mm) and a mobile phase of 75% CO$_2$, 25% EtOH. The enantiomeric purity was confirmed by analytical SFC using a CHIRALPAK AD-H (250×4.6 mm) and a mobile phase of 75% CO$_2$, 25% EtOH containing 0.3% iPrNH$_2$ over 7 minutes. (100% single enantiomer, 3.30 min retention time). $C_{19}H_{16}F_4N_6O$, 420.1; m/z found, 421.1 [M+H]$^+$.

Example 209: 5-{[2-Chloro-3-(trifluoromethyl)phenyl]carbonyl}-6-methyl-1-pyrazin-2-yl-4,5,6,7-tetrahydro-1H-[1,2,3]triazolo[4,5-c]pyridine

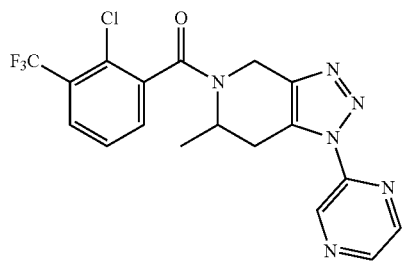 [SMILES: CC1Cc2c(nnn2-c2cnccn2)CN1C(=O)c1cccc(C(F)(F)F)c1Cl]

Intermediate 65: N-(2-Chloro-6-methyl-3-nitropyridin-4-yl)pyrazin-2-amine

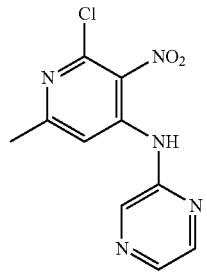

Step A: N-(2-chloro-6-methyl-3-nitropyridin-4-yl)pyrazin-2-amine

To a solution of 2-aminopyrazine (0.900 g, 9.47 mmol) in DMSO (40 mL) was added potassium tert-butoxide (2.13 g, 18.9 mmol) followed by 2,4-dichloro-6-methyl-3-nitropyridine (2.00 g, 9.47 mmol). After stirring for 30 min at rt, sat. $NH_4C_1$ solution was added. The organic layer was separated and the water layer was extracted with $CH_2Cl_2$ three times. The combined organic layers were dried over anhydrous $Na_2SO_4$, filtered and concentrated. Chromatography on silica gel (0-70% ethyl acetate/hexanes) provided the desired product (567 mg, 23%). MS (ESI) mass calcd. $C_{10}H_8ClN_5O_2$, 265.04; m/z found, 266.0 $[M+H]^+$. $^1H$ NMR (500 MHz, $CDCl_3$) δ 8.69-8.62 (br s, 1H), 8.38-8.34 (m, 2H), 8.34-8.29 (m, 2H), 2.59-2.56 (m, 3H).

Intermediate 66: 6-Methyl-$N^4$-(pyrazin-2-yl)pyridine-3,4-diamine

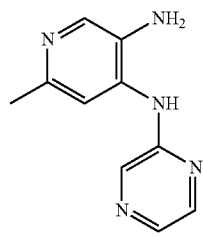

Step B: 6-Methyl-$N^4$-(pyrazin-2-yl)pyridine-3,4-diamine

A solution of N-(2-chloro-6-methyl-3-nitropyridin-4-yl)pryazin-2-amine (903 mg, 3.40 mmol) in 2M ammonia in methanol:THF (7:5, 120 mL) was passed through a 20% $Pd(OH)_2$ cartridge using an HCube® hydrogenation apparatus in a continuous loop overnight at 1 bar, 90° C. and 1 mL/min. The solvents were evaporated and the residue was purified by chromatography on silica gel (0-10% [2M $NH_3$ in MeOH]/$CH_2Cl_2$) to provide the desired product (285 mg, 42%). MS (ESI) mass calcd. $C_{10}H_{11}N_5$, 201.10; m/z found, 202.1 $[M+H]^+$.

Intermediate 67: 6-Methyl-1-(pyrazin-2-yl)-1H-[1,2,3]triazolo[4,5-c]pyridine

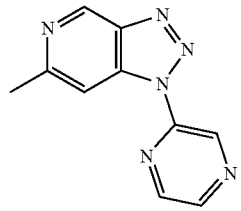 [SMILES: Cc1cc2c(cn1)nnn2-c1cnccn1]

Step C: 6-Methyl-1-(pyrazin-2-yl)-1H-[1,2,3]triazolo[4,5-c]pyridine

To a solution of 6-methyl-$N^4$-(pyrazin-2-yl)pyridine-3,4-diamine (520 mg, 2.58 mmol) in THF (30 mL) was added acetic acid (0.44 mL, 7.75 mmol) and tert-butyl nitrite (0.51 mL, 3.88 mmol). The reaction was heated to reflux. After 30 min the reaction was cooled and filtered. The filtrate was concentrated and the residue was purified by chromatography on silica gel (0-7% [2M $NH_3$ in MeOH]/$CH_2Cl_2$) to give the desired product (127 mg, 25%). MS (ESI) mass calcd. $C_{11}H_9N_5$, 212.08; m/z found, 213.1 $[M+H]^+$.

Intermediate 68: 6-Methyl-1-(pyrazin-2-yl)-4,5,6,7-tetrahydro-1H-[1,2,3]triazolo[4,5-c]pyridine

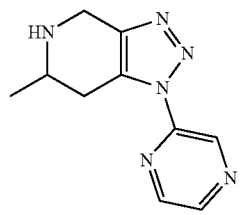 [SMILES: CC1Cc2c(nnn2-c2cnccn2)CN1]

Step D: 6-Methyl-1-(pyrazin-2-yl)-4,5,6,7-tetrahydro-1H-[1,2,3]triazolo[4,5-c]pyridine To a solution of 6-methyl-1-(pyrazin-2-yl)-1H-[1,2,3]triazolo[4,5-c]pyridine (245 mg, 1.15 mmol) in formic acid (0.70 mL, 18.5 mmol) was added dropwise triethylamine (1.28 mL, 9.24 mmol). The resulting mixture was heated to 140° C. for 24 h. The reaction was cooled and 1M NaOH was added until the pH was 7-9. The water layer was extracted with $CH_2Cl_2$ three times. The organic layers were combined, dried over anhydrous $MgSO_4$, filtered and concentrated. The residue was dissolved in 3:1 isopropanol/concentrated HCl (4 mL) and stirred at 50° C. for 16 h. The reaction was cooled and 1M NaOH was added until pH 12 was reached. The water layer was extracted with 1:4 isopropanol/$CH_2Cl_2$ three times. The organic layers were combined, dried over anhydrous $MgSO_4$, filtered and concentrated to a yellow solid (230 mg, 92%). MS (ESI) mass calcd. $C_{10}H_{12}N_6$, 216.11; m/z found, 217.0 $[M+H]^+$. $^1H$ NMR (500 MHz, $CDCl_3$) δ 9.51-9.47 (m, 1H), 8.64-8.60 (m, 1H), 8.49-8.46 (m, 1H), 4.26-4.08 (m, 2H), 3.37-3.28 (m, 1H), 3.14-3.04 (m, 1H), 2.85-2.74 (m, 1H), 2.23-2.02 (br s, 1H), 1.36 (d, J=6.3 Hz, 3H).

Example 209: 5-{[2-Chloro-3-(trifluoromethyl)phenyl]carbonyl}-6-methyl-1-pyrazin-2-yl-4,5,6,7-tetrahydro-1H-[1,2,3]triazolo[4,5-c]pyridine

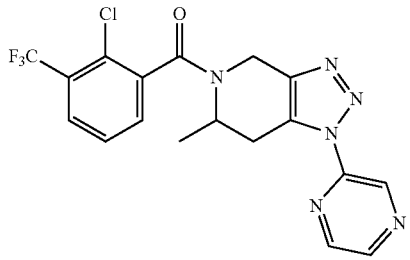 [SMILES: CC1Cc2c(nnn2-c2cnccn2)CN1C(=O)c1cccc(C(F)(F)F)c1Cl]

Step E: 5-{[2-Chloro-3-(trifluoromethyl)phenyl]carbonyl}-6-methyl-1-pyrazin-2-yl-4,5,6,7-tetrahydro-1H-[1,2,3]triazolo[4,5-c]pyridine To a solution of 6-methyl-1-(pyrizin-2-yl)-4,5,6,7-tetrahydro-1H-[1,2,3]triazolo[4,5-c]pyridine (207 mg, 0.96 mmol) in $CH_2Cl_2$ (8 mL) was added triethylamine (0.40 mL, 2.88 mmol) followed by 2-chloro-3-(trifluoromethyl)-benzoic acid (279 mg, 1.15 mmol). The resulting mixture was stirred for 10 min at rt and 5% $Na_2CO_3$ was added. The water layer was extracted with $CH_2Cl_2$ three times. The organic layers were combined, dried over anhydrous $MgSO_4$, filtered and concentrated. The residue was purified by preparative basic HPLC to give the product as a white solid (200 mg, 57%). MS (ESI) mass calcd. $C_{18}H_{14}ClF_3N_6O$, 422.09; m/z found, 423.0 $[M+H]^+$.

Example 210 (2-chloro-3-(trifluoromethyl)phenyl)(6-methyl-1-(1H-pyrazol-3-yl)-6,7-dihydro-1H-[1,2,3]triazolo[4,5-c]pyridin-5(4H)-yl)methanone

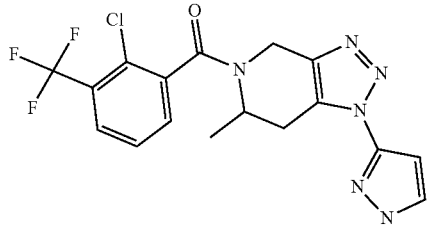

MS (ESI) mass calcd $C_{17}H_{14}ClF_3N_6O$, 410.1 m/z found, 411.1 $[M+H]^+$.

Example 211: (6R*)-5-{[2-Chloro-3-(trifluoromethyl)phenyl]carbonyl}-6-methyl-1-pyrazin-2-yl-4,5,6,7-tetrahydro-1H-[1,2,3]triazolo[4,5-c]pyridine

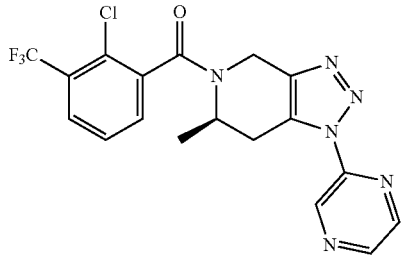 [SMILES: C[C@@H]1Cc2c(nnn2-c2cnccn2)CN1C(=O)c1cccc(C(F)(F)F)c1Cl]

The title compound, absolute configuration unknown, was obtained as a single enantiomer by Chiral SFC purification of Example 209 performed using CHIRALPAK IA (5 µm, 250×20 mm) and a mobile phase of 75% $CO_2$, 25% iPrOH. The enantiomeric purity was confirmed by analytical SFC using a CHIRALPAK IA (250×4.6 mm) and a mobile phase of 75% $CO_2$, 25% iPrOH containing 0.3% $iPrNH_2$ over 7 minutes. (100% single enantiomer, 4.33 min retention time). MS (ESI) mass calcd. $C_{18}H_{14}ClF_3N_6O$, 422.1; m/z found, 423.1 $[M+H]^+$.

Example 212: (6S*)-5-{[2-Chloro-3-(trifluoromethyl)phenyl]carbonyl}-6-methyl-1-pyrazin-2-yl-4,5,6,7-tetrahydro-1H-[1,2,3]triazolo[4,5-c]pyridine

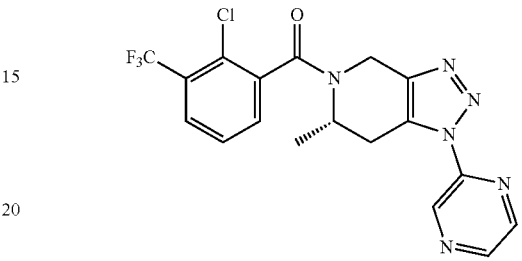

The title compound, absolute configuration unknown, was obtained as a single enantiomer by Chiral SFC purification of Example 209 performed using CHIRALPAK IA (5 µm, 250×20 mm) and a mobile phase of 75% $CO_2$, 25% iPrOH. The enantiomeric purity was confirmed by analytical SFC using a CHIRALPAK IA (250×4.6 mm) and a mobile phase of 75% $CO_2$, 25% iPrOH containing 0.3% $iPrNH_2$ over 7 minutes. (100% single enantiomer, 4.92 min retention time). MS (ESI) mass calcd. $C_{18}H_{14}ClF_3N_6O$, 422.1; m/z found, 423.1 $[M+H]^+$.

Example 213: 5-[(2,3-Dichloro-4-fluorophenyl)carbonyl]-1-(5-fluoropyrimidin-2-yl)-6-methyl-4,5,6,7-tetrahydro-1H-[1,2,3]triazolo[4,5-c]pyridine

Step 1: 2,3-dichloro-4-fluorobenzoyl Chloride

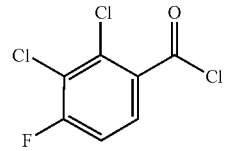 [SMILES: O=C(Cl)c1ccc(F)c(Cl)c1Cl]

The title compound was prepared in a manner analogous to Intermediate 12 substituting 2,3-dichloro-4-fluorobenzoic acid for 2-chloro-3-(trifluoromethyl)benzoic acid.

Step 2: -[(2,3-Dichloro-4-fluorophenyl)carbonyl]-1-(5-fluoropyrimidin-2-yl)-6-methyl-4,5,6,7-tetrahydro-1H-[1,2,3]triazolo[4,5-c]pyridine

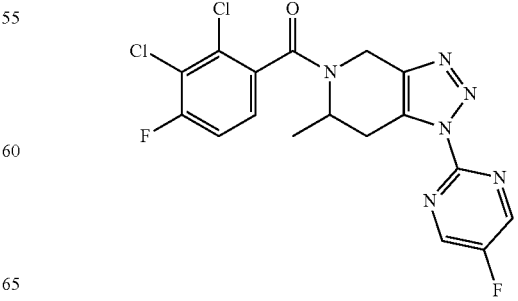

The title compound was prepared in a manner analogous to Example 200 substituting the product of Example 213, Step 1 for Intermediate 12. MS (ESI) mass calcd. $C_{17}H_{12}C_2F_2N_6O$, 424.0; m/z found, 424.9 [M+H]$^+$. $^1$H NMR (400 MHz, CDCl$_3$) δ 8.81-8.68 (m, 2H), 7.35-7.10 (m, 2H), 5.91-5.55 (m, 1H), 4.69-4.05 (m, 2H), 3.58-3.04 (m, 2H), 1.41-1.14 (m, 3H).

Example 214: (6R*)-5-[(2,3-Dichloro-4-fluorophenyl)carbonyl]-1-(5-fluoropyrimidin-2-yl)-6-methyl-4,5,6,7-tetrahydro-1H-[1,2,3]triazolo[4,5-c]pyridine

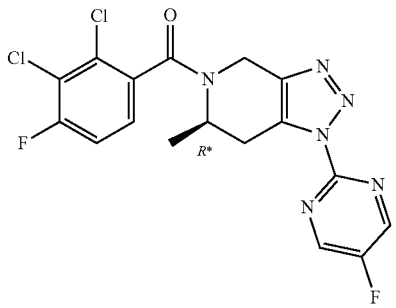

The title compound, absolute configuration unknown, was obtained as a single enantiomer by Chiral SFC purification of Example 213 performed using CHIRALPAK AD-H (5 μm, 250×20 mm) and a mobile phase of 60% CO$_2$, 40% MeOH. The enantiomeric purity was confirmed by analytical SFC using a CHIRALPAK AD (250×4.6 mm) and a mobile phase of 60% CO$_2$, 40% MeOH containing 0.3% iPrNH$_2$ over 7 minutes. (100% single enantiomer, 3.36 min retention time). MS (ESI) mass calcd. $C_{17}H_{12}C_{12}F_2N_6O$, 424.0; m/z found, 425.0 [M+H]$^+$. $^1$H NMR (500 MHz, CDCl$_3$) δ 8.78-8.69 (m, 2H), 7.28-7.12 (m, 2H), 5.87-5.56 (m, 1H), 4.65-4.07 (m, 2H), 3.54-3.06 (m, 2H), 1.42-1.12 (m, 3H).

Example 215: (6S*)-5-[(2,3-Dichloro-4-fluorophenyl)carbonyl]-1-(5-fluoropyrimidin-2-yl)-6-methyl-4,5,6,7-tetrahydro-1H-[1,2,3]triazolo[4,5-c]pyridine

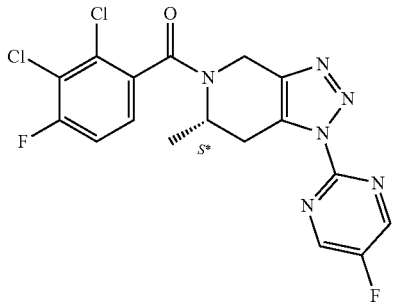

The title compound, absolute configuration unknown, was obtained as a single enantiomer by Chiral SFC purification of Example 213 performed using CHIRALPAK AD-H (5 μm, 250×20 mm) and a mobile phase of 60% CO$_2$, 40% MeOH. The enantiomeric purity was confirmed by analytical SFC using a CHIRALPAK AD (250×4.6 mm) and a mobile phase of 60% CO$_2$, 40% MeOH containing 0.3% iPrNH$_2$ over 7 minutes. (100% single enantiomer, 4.45 min retention time). MS (ESI) mass calcd. $C_{17}H_{12}C_{12}F_2N_6O$, 424.0; m/z found, 425.0 [M+H]$^+$. $^1$H NMR (500 MHz, CDCl$_3$) δ 8.78-8.69 (m, 2H), 7.28-7.12 (m, 2H), 5.87-5.56 (m, 1H), 4.65-4.07 (m, 2H), 3.54-3.06 (m, 2H), 1.42-1.12 (m, 3H).

Example 216: 5-[(2,4-Dichloro-3-fluorophenyl)carbonyl]-1-(5-fluoropyrimidin-2-yl)-6-methyl-4,5,6,7-tetrahydro-1H-[1,2,3]triazolo[4,5-c]pyridine

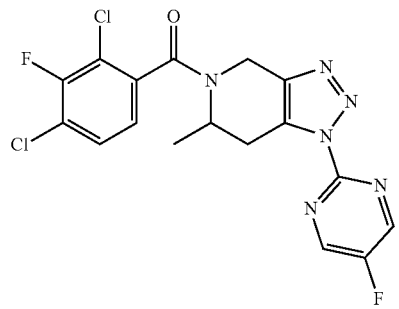

The title compound was prepared in manner analogous to Example 213 substituting 2,3-dichloro-4-fluorobenzoic acid for 2,3-dichloro-4-fluorobenzoic acid. MS (ESI) mass calcd. $C_{17}H_2C_2F_2N_6O$, 424.0; m/z found, 424.9 [M+H]$^+$. $^1$H NMR (400 MHz, CDCl$_3$) δ 8.82-8.69 (m, 2H), 7.53-7.34 (m, 1H), 7.18-6.96 (m, 1H), 5.89-5.55 (m, 1H), 4.68-4.07 (m, 2H), 3.58-3.05 (m, 2H), 1.43-1.15 (m, 3H).

Example 217: (6R*)-5-[(2,4-Dichloro-3-fluorophenyl)carbonyl]-1-(5-fluoropyrimidin-2-yl)-6-methyl-4,5,6,7-tetrahydro-1H-[1,2,3]triazolo[4,5-c]pyridine

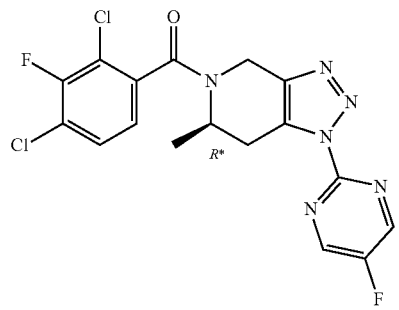

The title compound, absolute configuration unknown, was obtained as a single enantiomer by Chiral SFC purification of Example 216 performed using CHIRALPAK AD-H (5 μm, 250×20 mm) and a mobile phase of 60% CO$_2$, 40% MeOH. The enantiomeric purity was confirmed by analytical SFC using a CHIRALPAK AD (250×4.6 mm) and a mobile phase of 60% CO$_2$, 40% MeOH containing 0.3% iPrNH$_2$ over 7 minutes. (100% single enantiomer, 3.63 min retention time). MS (ESI) mass calcd. $C_{17}H_2Cl_2F_2N_6O$, 424.0; m/z found, 425.0 [M+H]$^+$. $^1$H NMR (500 MHz, CDCl$_3$) δ 8.79-8.69 (m, 2H), 7.52-7.33 (m, 1H), 7.17-6.97 (m, 1H), 5.91-5.56 (m, 1H), 4.68-4.07 (m, 2H), 3.57-3.05 (m, 2H), 1.42-1.14 (m, 3H).

Example 218: (6S*)-5-[(2,4-Dichloro-3-fluorophenyl)carbonyl]-1-(5-fluoropyrimidin-2-yl)-6-methyl-4,5,6,7-tetrahydro-1H-[1,2,3]triazolo[4,5-c]pyridine

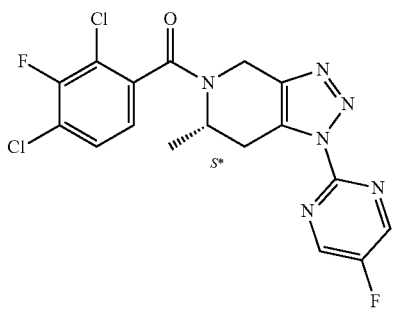

The title compound, absolute configuration unknown, was obtained as a single enantiomer by Chiral SFC purification of Example 216 performed using CHIRALPAK AD-H (5 μm, 250×20 mm) and a mobile phase of 60% $CO_2$, 40% MeOH. The enantiomeric purity was confirmed by analytical SFC using a CHIRALPAK AD (250×4.6 mm) and a mobile phase of 60% $CO_2$, 40% MeOH containing 0.3% $iPrNH_2$ over 7 minutes. (100% single enantiomer, 5.34 min retention time). MS (ESI) mass calcd. $C_{17}H_2Cl_2F_2N_6O$, 424.0; m/z found, 424.9 [M+H]$^+$. $^1$H NMR (500 MHz, CDCl$_3$) δ 8.79-8.69 (m, 2H), 7.52-7.33 (m, 1H), 7.17-6.97 (m, 1H), 5.91-5.56 (m, 1H), 4.68-4.07 (m, 2H), 3.57-3.05 (m, 2H), 1.42-1.14 (m, 3H).

Example 219: (6R)-1-(5-Fluoropyrimidin-2-yl)-5-{[2-fluoro-3-(trifluoromethyl)phenyl]carbonyl}-6-methyl-4,5,6,7-tetrahydro-1H-[1,2,3]triazolo[4,5-c]pyridine

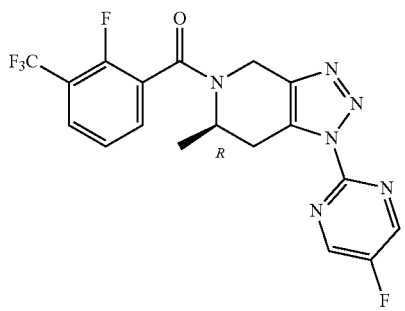

The title compound was prepared in a manner analogous to Example 213 substituting 2-fluoro-3-(trifluoromethyl)benzoic acid for 2,3-dichloro-4-fluorobenzoic acid. The racemate was purified by chiral SFC on (Chiralpak AD 5 μm 250×20 mm) using a mobile phase of 80% $CO_2$ and 20% EtOH to obtain the title compound. The enantiomeric purity was confirmed by analytical SFC using a CHIRALPAK AD (250×4.6 mm) and a mobile phase of 80% $CO_2$, 20% EtOH containing 0.3% $iPrNH_2$ over 7 minutes. (100% single enantiomer, 4.49 min retention time). The absolute configuration was determined by co-injecting Example 219 with the product of Method II synthesis of Example 220 in the SFC analytical method to obtain differentiated peaks. MS (ESI) mass calcd. $C_{18}H_{13}F_5N_6O$, 424.1; m/z found, 424.8 [M+H]$^+$. $^1$H NMR (500 MHz, CDCl$_3$) δ 8.79-8.68 (m, 2H), 7.79-7.54 (m, 2H), 7.46-7.30 (m, 1H), 5.97-5.55 (m, 1H), 4.77-4.19 (m, 2H), 3.58-3.11 (m, 2H), 1.43-1.14 (m, 3H).

Example 220: (6S)-1-(5-Fluoropyrimidin-2-yl)-5-{[2-fluoro-3-(trifluoromethyl)phenyl]carbonyl}-6-methyl-4,5,6,7-tetrahydro-1H-[1,2,3]triazolo[4,5-c]pyridine

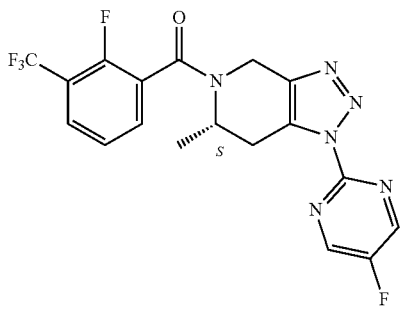

Method I

The title compound was prepared in a manner analogous to Example 213 substituting 2-fluoro-3-(trifluoromethyl)benzoic acid for 2,3-dichloro-4-fluorobenzoic acid. The racemate was purified by chiral SFC on (Chiralpak AD 5 μm 250×20 mm) using a mobile phase of 80% $CO_2$ and 20% EtOH to obtain the title compound. The enantiomeric purity was confirmed by analytical SFC using a CHIRALPAK AD (250×4.6 mm) and a mobile phase of 80% $CO_2$, 20% EtOH containing 0.3% $iPrNH_2$ over 7 minutes. (100% single enantiomer, 5.43 min retention time). The absolute configuration was determined by co-injecting the products from Method I synthesis and Method II synthesis of Example 220 in the SFC analytical method to obtain a single peak. MS (ESI) mass calcd. $C_{18}H_{13}F_5N_6O$, 424.1; m/z found, 424.8 [M+H]$^+$. $^1$H NMR (500 MHz, CDCl$_3$) δ 8.79-8.68 (m, 2H), 7.79-7.54 (m, 2H), 7.46-7.30 (m, 1H), 5.97-5.55 (m, 1H), 4.77-4.19 (m, 2H), 3.58-3.11 (m, 2H), 1.43-1.14 (m, 3H).

Method II

Step 1: (S)-tert-butyl 1-(5-fluoropyrimidin-2-yl)-6-methyl-6,7-dihydro-1H-[1,2,3]triazolo[4,5-c]pyridine-5(4H)-carboxylate

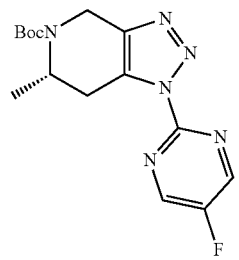

(S)-tert-butyl 1-(5-fluoropyrimidin-2-yl)-6-methyl-6,7-dihydro-1H-[1,2,3]triazolo[4,5-c]pyridine-5(4H)-carboxylate To a solution of (S)-tert-butyl 2-methyl-4-oxopiperidine-1-carboxylate (2.76 g, 12.9 mmol) in toluene (100 mL) at 100° C. was added 2-azido-5-fluoropyrimidine (2.34 g, 16.8 mmol) as a solution in toluene (15 mL) followed by pyrrolidine (1.06 mL, 12.9 mmol). After stirring for 3 h at rt, the reaction was cooled to 0° C. and CH$_2$Cl$_2$ (100 mL) was added followed by NaHCO$_3$ (2.17 g, 25.9 mmol) and mCPBA (4.47 g, 25.9 mmol). The reaction was allowed to warm to rt over 30 min followed by the addition of 1N NaOH (100 mL). The organic layer was separated and the water layer was extracted with CH$_2$Cl$_2$ two times. The combined organic layers were dried over anhydrous MgSO$_4$, filtered and concentrated. Chromatography on silica gel (0-100% ethyl acetate/hexanes) provided the desired product as a 9:1 mixture of regioisomers (9:1=(S)-tert-butyl 1-(5-fluoropyrimidin-2-yl)-6-methyl-6,7-dihydro-1H-[1,2,3]triazolo[4,5-c]pyridine-5(4H)-carboxylate: (S)-tert-butyl 1-(5-fluoropyrimidin-2-yl)-4-methyl-6,7-dihydro-1H-[1,2,3]triazolo[4,5-c]pyridine-5(4H)-carboxylate (2.85 g, 66%). The minor regioisomer was separated by SFC (Chiralpak IC 5 μm 250*21 mm, mobile phase 70% CO$_2$, 30% iPrOH) to provide the product as a white solid. MS (ESI) mass calcd. C$_{15}$H$_{19}$FN$_6$O$_2$, 334.16; m/z found, 335.2 [M+H]$^+$. $^1$H NMR (500 MHz, CDCl$_3$) δ 8.73 (s, 2H), 5.16 (d, J=16.1 Hz, 1H), 4.96 (br s, 1H), 4.25 (d, J=16.4 Hz, 1H), 3.38-3.28 (m, 1H), 3.19-3.10 (m, 1H), 1.50 (s, 9H), 1.16 (d, J=7.0 Hz, 3H).

Step 2: (S)-1-(5-fluoropyrimidin-2-yl)-6-methyl-4,5,6,7-tetrahydro-H-[1,2,3]triazolo[4,5-c]pyridine-hydrochloride salt

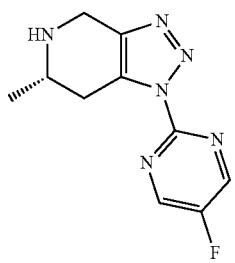

(S)-1-(5-fluoropyrimidin-2-yl)-6-methyl-4,5,6,7-tetrahydro-1H-[1,2,3]triazolo[4,5-c]pyridine-hydrochloride salt To a solution of (S)-tert-butyl 1-(5-fluoropyrimidin-2-yl)-6-methyl-6,7-dihydro-1H-[1,2,3]triazolo[4,5-c]pyridine-5(4H)-carboxylate (0.711 g, 2.13 mmol) in CH$_2$Cl$_2$ (10 mL) was added 4M HCl in dioxane (2.66 mL, 10.6 mmol). After stirring overnight at rt, the reaction was concentrated in vacuo to give the desired product as a light yellow solid (0.580 mg, 100%). MS (ESI) mass calcd. C$_{10}$H$_{11}$FN$_6$, 234.23; m/z found, 235.1 [M+H]$^+$. $^1$H NMR (400 MHz, DMSO) δ 9.97-9.69 (m, 1H), 9.15 (s, 2H), 4.58-4.35 (m, 2H), 3.80-3.47 (m, 2H), 3.21-3.03 (m, 1H), 1.46 (d, J=6.5 Hz, 3H).

Step 3: (6S)-1-(5-Fluoropyrimidin-2-yl)-5-{[2-fluoro-3-(trifluoromethyl)phenyl]carbonyl}-6-methyl-4,5,6,7-tetrahydro-1H-[1,2,3]triazolo[4,5-c]pyridine

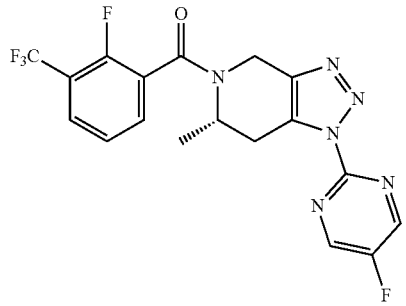 [SMILES: C[C@H]1Cc2c(nnn2-c2ncc(F)cn2)CN1C(=O)c1cccc(C(F)(F)F)c1F]

To a solution of (S)-1-(5-fluoropyrimidin-2-yl)-6-methyl-4,5,6,7-tetrahydro-1H-[1,2,3]triazolo[4,5-c]pyridinium chloride (0.575 g, 2.12 mmol) in CH$_2$Cl$_2$ (10 mL) was added triethylamine (1.18 mL, 8.50 mmol) followed by 2-fluoro-3-(trifluoromethyl)benzoyl chloride (0.625 g, 2.76 mmol). After stirring for 30 min at rt, sat NaHCO$_3$ (20 mL) was added. The organic layer was separated and the water layer was extracted with CH$_2$Cl$_2$ two times. The combined organic layers were dried over anhydrous MgSO$_4$, filtered and concentrated. Chromatography on silica gel (0-100% ethyl acetate/hexanes) provided the desired product as a white solid (0.837 g, 93%). MS (ESI) mass calcd. CH$_{13}$F$_5$N$_6$O, 424.11; m/z found, 425.1 [M+H]$^+$. $^1$H NMR (500 MHz, CDCl$_3$) δ 8.75 (s, 2H), 7.81-7.49 (m, 2H), 7.46-7.30 (m, 1H), 5.92-5.66 (m, 0.5H), 5.68-5.55 (m, 0.5H), 4.81-4.54 (m, 1H), 4.37 (d, J=16.9 Hz, 0.5H), 4.30-4.18 (m, 0.5H), 3.58-3.40 (m, 0.8H), 3.34-3.12 (m, 1.2H), 1.43-1.12 (m, 3H).

Example 221: (6R*)-5-{[2-Chloro-3-(trifluoromethyl)phenyl]carbonyl}-6-methyl-1-pyrimidin-2-yl-4,5,6,7-tetrahydro-1H-[1,2,3]triazolo[4,5-c]pyridine

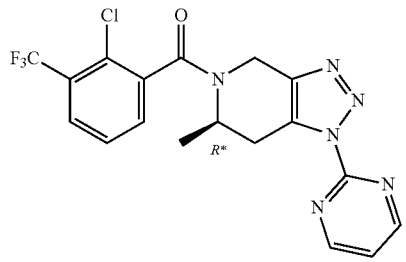 [SMILES: C[C@@H]1Cc2c(nnn2-c2ncccn2)CN1C(=O)c1cccc(C(F)(F)F)c1Cl]

The title compound was prepared using the conditions described in Example 209 Steps A-E beginning from 2-aminopyrimidine instead of 2-aminopyrazine in step A Intermediate 65. Chiral separation of the product of Step E by SFC (CHIRALPAK AD-H 5 μm 250×20 mm, mobile phase 80% CO$_2$/20% EtOH) provided the title compound. The enantiomeric purity was confirmed by analytical SFC using a CHIRALPAK AD (250×4.6 mm) and a mobile phase of 80% CO$_2$, 20% EtOH containing 0.3% iPrNH$_2$ over 7 minutes.

(100% single enantiomer, 5.98 min retention time). MS (ESI) mass calcd. $C_{18}H_{14}ClF_3N_6O$, 422.09; m/z found, 422.9 $[M+H]^+$.

Example 222: (6S*)-5-{[2-Chloro-3-(trifluoromethyl)phenyl]carbonyl}-6-methyl-1-pyrimidin-2-yl-4,5,6,7-tetrahydro-1H-[1,2,3]triazolo[4,5-c]pyridine

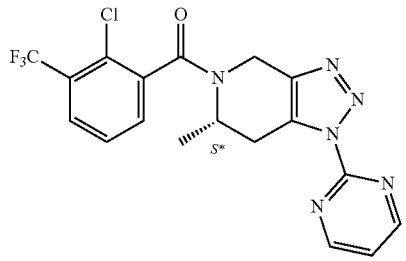 [SMILES: C[C@H]1Cc2c(nnn2-c2ncccn2)CN1C(=O)c1cccc(C(F)(F)F)c1Cl]

The title compound was prepared using the conditions described in Example 209 Steps A-E beginning from 2-aminopyrimidine instead of 2-aminopyrazine in step A Intermediate 65. Chiral separation of the product of Step E by SFC (CHIRALPAK AD-H 5 μm 250×20 mm, mobile phase 80% $CO_2$/20% EtOH) provided the title compound. The enantiomeric purity was confirmed by analytical SFC using a CHIRALPAK AD (250×4.6 mm) and a mobile phase of 80% $CO_2$, 20% EtOH containing 0.3% $iPrNH_2$ over 7 minutes. (100% single enantiomer, 6.74 min retention time). MS (ESI) mass calcd. $C_{18}H_{14}ClF_3N_6O$, 422.09; m/z found, 422.9 $[M+H]^+$.

Intermediate 69: 3-(Pyridin-2-yl)-3H-imidazo[4,5-c]pyridine

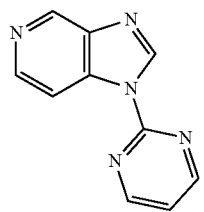 [SMILES: c1cnc(-n2cnc3cnccc32)nc1]

Intermediate 69 was prepared in a manner analogous to Intermediate 1, substituting 2-bromopyrimidine for 2-bromo-fluoropyridine. MS (ESI): mass calculated for $C_{11}H_8N_4$, 196.07; m/z found 197.1 $[M+H]^+$.

Example 223 (R*)-(2-chloro-3-(trifluoromethyl)phenyl)(3-(5-fluoropyrimidin-2-yl)-7-methyl-4,5-dihydro-2H-pyrazolo[3,4-c]pyridin-6(7H)-yl)methanone

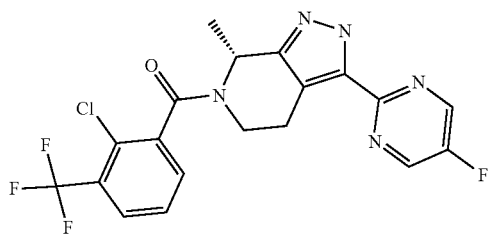

Example 224 (S*)-(2-chloro-3-(trifluoromethyl)phenyl)(3-(5-fluoropyrimidin-2-yl)-7-methyl-4,5-dihydro-2H-pyrazolo[3,4-c]pyridin-6(7H)-yl)methanone

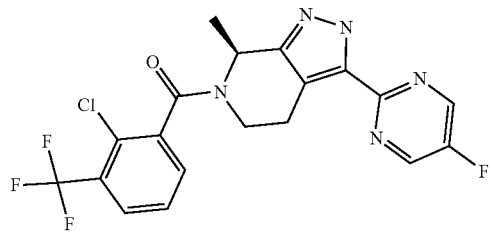

Example 225 (2,3-dichlorophenyl)(4-methyl-1-(4-methylpyrimidin-2-yl)-6,7-dihydro-1H-[1,2,3]triazolo[4,5-c]pyridin-5(4H)-4-)methanone

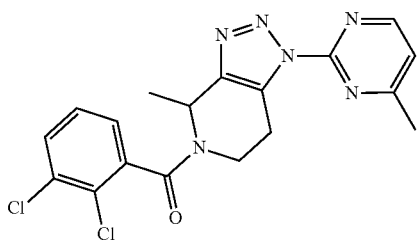 [SMILES: Cc1ccnc(-n2nnc3c2CCN(C(=O)c2cccc(Cl)c2Cl)C3C)n1]

MS (ESI) mass calcd $C_{18}H_{16}C_2N_6$, 402.1 m/z found, 403.1 [M+H. $^1$H NMR (400 MHz, $CDCl_3$) δ 8.82-8.57 (m, 1H), 7.58-7.48 (m, 1H), 7.39-6.97 (m, 3H), 6.16-5.98 (m, 0.6H), 5.20-5.05 (m, 0.4H), 5.02-4.74 (m, 0.4H), 3.79-2.93 (m, 3.6H), 2.75-2.57 (m, 3H), 1.77-1.44 (m, 3H).

Example 226 (R*)-(2-chloro-3-(trifluoromethyl)phenyl)(4-methyl-1-(6-methylpyridin-2-yl)-6,7-dihydro-1H-[1.2.3]triazolo[4,5-c]pyridin-5(4H)-yl)methanone

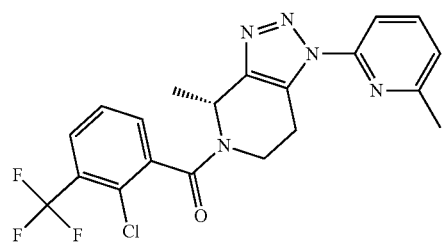 [SMILES: Cc1cccc(-n2nnc3c2CCN(C(=O)c2cccc(C(F)(F)F)c2Cl)[C@@H]3C)n1]

MS (ESI) mass calcd $C_{20}H_{17}CF_3N_5O$, 435.1 m/z found, 436.1 $[M+H]^+$.

Example 227 (S*)-(2-chloro-3-(trifluoromethyl)phenyl)(4-methyl-1-(6-methylpyridin-2-yl)-6,7-dihydro-1H-[1,2,3]triazolo[4,5-c]pyridin-5(4H)-yl)methanone

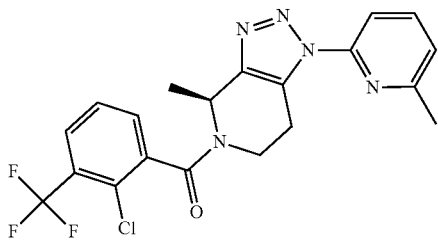 [SMILES: Cc1cccc(-n2nnc3c2CCN(C(=O)c2cccc(C(F)(F)F)c2Cl)[C@H]3C)n1]

MS (ESI) mass calcd $C_{20}H_{17}ClF_3N_5O$, 435.1 m/z found, 436.1 [M+H]$^+$.

Example 228 (S*)-(3-fluoro-2-(trifluoromethyl)pyridin-4-yl)(1-(5-fluoropyrimidin-2-yl)-6-methyl-6,7-dihydro-1H-[1,2,3]triazolo[4,5-c]pyridin-5(4H)-yl)methanone

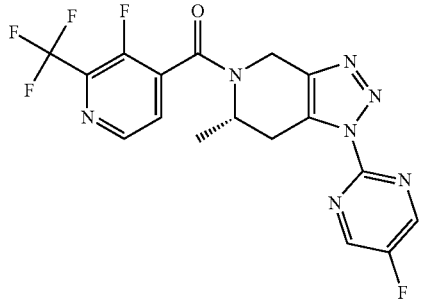

MS (ESI) mass calcd $C_{17}H_{12}F_5N_7O$, 425.1 m/z found, 426.1 [M+H]$^+$.

Example 229 (S*)-(3-fluoro-2-(trifluoromethyl)pyridin-4-yl)(1-(5-fluoropyrimidin-2-yl)-4-methyl-6,7-dihydro-1H-[1,2,3]triazolo[4,5-c]pyridin-5(4H)-yl)methanone

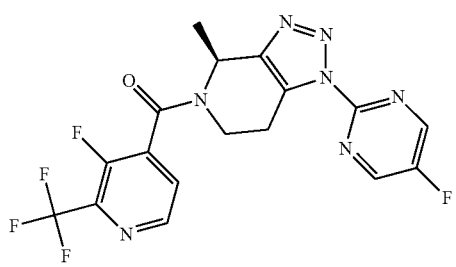 [SMILES: C[C@H]1c2nnn(-c3ncc(F)cn3)c2CCN1C(=O)c1ccnc(C(F)(F)F)c1F]

MS (ESI) mass calcd $C_{17}H_{12}FN_7O$, 425.1 m/z found, 426.1 [M+H]$^+$.

Example 230: (2-chloro-3-(trifluoromethyl)phenyl)(1-(5-fluoro-4-methylpyrimidin-2-yl)-4-methyl-6,7-dihydro-1H-[1,2,3]triazolo[4,5-c]pyridin-5(4H)-yl)methanone

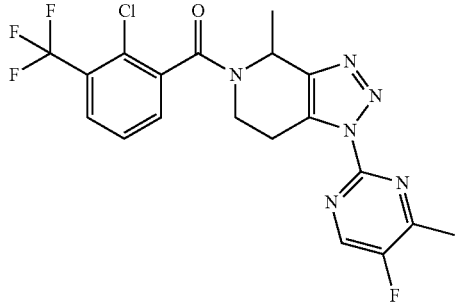 [SMILES: Cc1nc(-n2nnc3c2CCN(C(=O)c2cccc(C(F)(F)F)c2Cl)C3C)ncc1F]

Example 230 was prepared in a manner analogous to Example 11 substituting Intermediate 51 and excess MeMgBr in Step A. MS (ESI): mass calculated for $C_{19}H_{15}ClF_4N_6O$, 454.09; m/z found, 455.1 [M+H]$^+$.

Intermediate 231: tert-butyl 3-(5-(2-chloro-3-(trifluoromethyl)benzoyl)-4-methyl-4,5-dihydro-1H-[1,2,3]triazolo[4,5-c]pyridin-1-yl)-1H-pyrazole-1-carboxylate

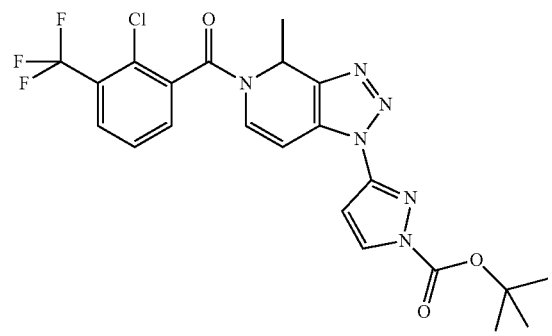 [SMILES: CC1c2nnn(-c3ccn(C(=O)OC(C)(C)C)n3)c2C=CN1C(=O)c1cccc(C(F)(F)F)c1Cl]

Was made in a fashion analogous to compound Example 11, Step A substituting Intermediate 49 for Intermediate 1. MS (ESI) mass calcd. $C_{22}H_{20}ClF_3N_6O_3$, 508.88; m/z found, 509.2 [M+H]$^+$. $^1$H NMR (400 MHz, CDCl$_3$); 8.14 (t, J=2.6 Hz, 1H), 7.89-7.77 (m, 1H), 7.68-7.40 (m, 2H), 7.01-6.92 (m, 1H), 6.59-6.47 (m, 1H), 6.39-6.23 (m, 1H), 4.12 (q, J=7.1 Hz, 1H), 1.73-1.55 (m, 12H).

Intermediate 232: tert-Butyl 3-(5-(2-chloro-3-(trifluoromethyl)benzoyl)-4-methyl-4,5,6,7-tetrahydro-1H-[1,2,3]triazolo[4,5-c]pyridin-1-yl)-1H-pyrazole-1-carboxylate

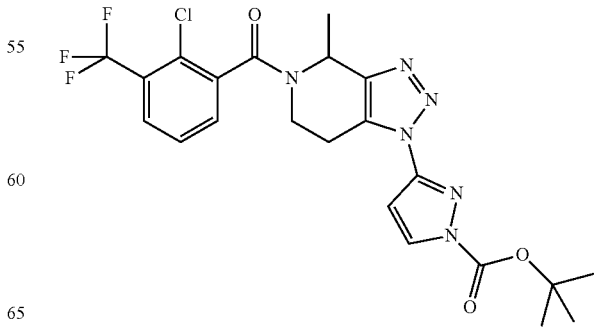

A solution of tert-butyl 3-(5-(2-chloro-3-(trifluoromethyl)benzoyl)-4-methyl-4,5,6,7-tetrahydro-1H-[1,2,3]triazolo[4,5-c]pyridin-1-yl)-1H-pyrazole-1-carboxylate (34 mg, 0.07 mmol) in MeOH 92.5 ml) was treated with Pd/carbon (5 wt %, 14 mg) and put under 1 atmosphere of $H_2$ and reaction stirred for 16 h. Reaction filtered, and concentrated and the crude product was purified on 16 g $SiO_2$ with 0-40% EtOAc/hexanes. MS (ESI) mass calcd. $C_{22}H_{22}CF_3N_6O_3$, 510.90; m/z found, 511.2 $[M+H]^+$.

Example 231 (2,3-dichlorophenyl)(1-(4,6-dimethylpyridin-2-yl)-4-methyl-6,7-dihydro-1H-[1,2,3]triazolo[4,5-c]pyridin-5(4H)-yl)methanone

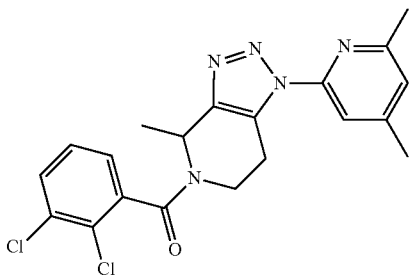 [SMILES: Cc1cc(C)nc(-n2nnc3c2CCN(C(=O)c2cccc(Cl)c2Cl)C3C)c1]

MS (ESI) mass calcd $C_{20}H_{19}C_2N_5O$, 415.1 m/z found, 416.1 $[M+H]^+$. $^1$H NMR (500 MHz, CDCl$_3$) δ 7.81-7.67 (m, 1H), 7.60-7.47 (m, 1H), 7.38-7.19 (m, 2H), 7.06-6.96 (m, 1H), 6.11-5.96 (m, 0.6H), 5.21-5.04 (m, 0.4H), 4.98-4.70 (m, 0.4H), 3.69-2.94 (m, 3.6H), 2.59-2.39 (m, 6H), 1.77-1.40 (m, 3H).

Example 232 (S*)-(2-fluoro-5-(trifluoromethyl)phenyl)(1-(5-fluoropyrimidin-2-yl)-6-methyl-6,7-dihydro-1H-[1,2,3]triazolo[4,5-c]pyridin-5(4H)-yl)methanone

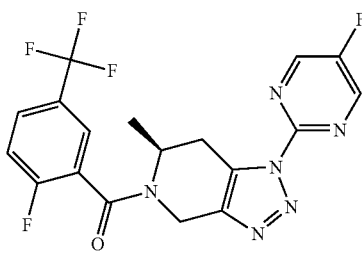

MS (ESI) mass calcd $C_{18}H_{13}F_5N_6O$, 424.1 m/z found, 425.1 $[M+H]^+$.

Example 233 (2,3-dichlorophenyl)(4-methyl-1-(6-methylpyridin-2-yl)-6,7-dihydro-1H-[1,2,3]triazolo[4,5-c]pyridin-5(4H)-yl)methanone

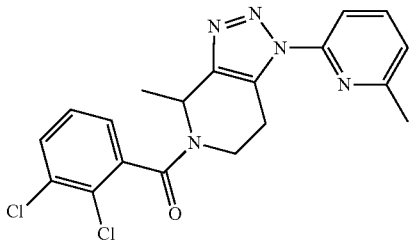 [SMILES: Cc1cccc(-n2nnc3c2CCN(C(=O)c2cccc(Cl)c2Cl)C3C)n1]

MS (ESI) mass calcd $C_{19}H_{17}Cl_2N_5O$, 401.1 m/z found, 402.1 $[M+H]^+$. $^1$H NMR (400 MHz, CDCl$_3$) δ 7.99-7.87 (m, 1H), 7.85-7.71 (m, 1H), 7.62-7.49 (m, 1H), 7.39-6.99 (m, 3H), 6.17-5.95 (m, 0.6H), 5.17-5.04 (m, 0.4H), 5.00-4.67 (m, 0.4H), 3.79-2.94 (m, 3.6H), 2.70-2.42 (m, 3H), 1.83-1.41 (m, 3H).

Example 234: (4R*)-(2-Chloro-3-(trifluoromethyl)phenyl)((4R)-4-methyl-1-(6-methyl-1,6-dihydropyrimidin-2-yl)-6,7-dihydro-1H-[1,2,3]triazolo[4,5-c]pyridin-5(4H)-yl)methanone

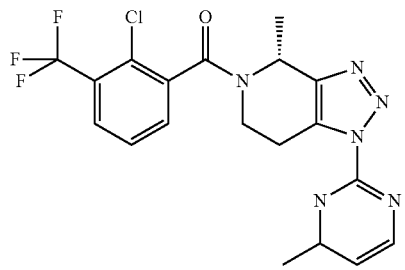 [SMILES: CC1C=CN=C(n2nnc3c2CCN(C(=O)c2cccc(C(F)(F)F)c2Cl)[C@@H]3C)N1]

A solution of 4R-5-{[2-2hloro-3-(trifluoromethyl)phenyl]carbonyl}-4-methyl-1-pyrimidin-2-yl-4,5,6,7-tetrahydro-1H-[1,2,3]triazolo[4,5-c]pyridine (45 mg, 0.11 mmol) in THF was cooled to −30° C. and treated with 2.0 MeMgBr in THF (0.04 ml, 0.12 ml) and the reaction was warmed to 0° C. and diluted with EtOAc and washed with water. The EtOAc solution was dried and concentrated and purified on 4 g $SiO_2$ with 0-40% EtOAc/DCM. MS (ESI) mass calcd. $C_{19}H_1ClF_3N_6O$, 438.12; m/z found, 439.2 $[M+H]^+$.

Example 235: (4R)-(2-Chloro-3-(trifluoromethyl)phenyl)(4-methyl-1-(4-methylpyrimidin-2-yl)-6,7-dihydro-1H-[1,2,3]triazolo[4,5-c]pyridin-5(4H)-yl)methanone

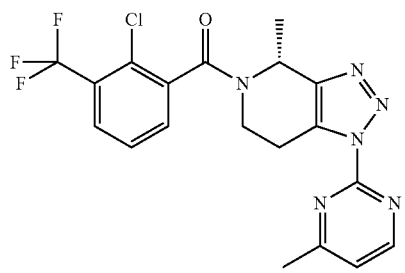 [SMILES: Cc1ccnc(-n2nnc3c2CCN(C(=O)c2cccc(C(F)(F)F)c2Cl)[C@@H]3C)n1]

A solution of (4R*)-(2-chloro-3-(trifluoromethyl)phenyl)((4R)-4-methyl-1-(6-methyl-1,6-dihydropyrimidin-2-yl)-6,7-dihydro-1H-[1,2,3]triazolo[4,5-c]pyridin-5(4H)-yl)methanone (41 mg, 0.9 mmol) in DCM was treated with DDQ (50 mg, 0.21 mmol).

After 2 min, the reaction was complete and the crude reaction was applied directly to a 12 g $SiO_2$ column and eluted with 0-4% NH3 MeOH/DCM to provide desired product (24 mg, 59%) MS (ESI) mass calcd. $C_{19}H_{16}ClF_3N_6O$, 436.10; m/z found, 437.2 $[M+H]^+$. $^1$H NMR (400 MHz, CDCl$_3$) δ 8.71 (dd, J=5.0, 2.5 Hz, 0.5H), 8.69-8.64 (m, 0.5H), 7.81-7.73 (m, 1H), 7.58-7.36 (m, 2H), 7.31-7.27 (m, 0.3H), 7.25-7.20 (m, 0.7H), 6.13-6.02 (m, 0.5H), 5.16-5.10 (m, 0.4H), 4.92-4.85 (m, 0.1H), 4.80-4.75 (m, 0.3H), 3.67-3.11 (m, 3.3H), 3.07-2.95 (m, 0.4H), 2.68-

2.67 (m, 1.3H), 2.65 (s, 0.6H), 2.63 (s, 1H), 1.72 (d, J=6.9 Hz, 0.9H), 1.70 (d, J=7.0 Hz, 0.6H), 1.58 (d, J=7.1 Hz, 0.5H), 1.50 (d, J=6.7 Hz, 0.9H).

Example 236: (2-Chloro-3-(trifluoromethyl)phenyl)(4-methyl-1-(pyrimidin-5-yl)-1H-[1,2,3]triazolo[4,5-c]pyridin-5(4H)-yl)methanone

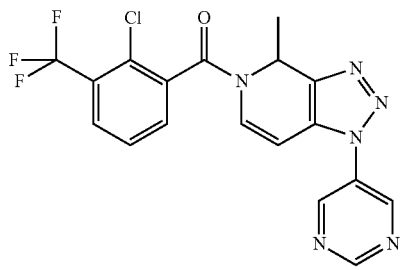 [SMILES: CC1c2nnn(-c3cncnc3)c2C=CN1C(=O)c1cccc(C(F)(F)F)c1Cl]

The title compound was prepared in a manner analogous to Example 72 substituting 5-aminopyrimidine for 2-aminopyrazine in the synthesis of 1-pyrazin-2-yl-1H-[1,2,3]triazolo[4,5-c]pyridine. MS (ESI) mass calcd. $C_{18}H_{12}ClF_3N_6O$, 420.07; m/z found, 421.1 [M+H]$^+$. $^1$H NMR (400 MHz, CDCl$_3$) δ 9.34 (s, 1H), 9.16-9.02 (m, 2H), 7.85 (ddd, J=7.7, 3.5, 1.6 Hz, 1H), 7.70-7.44 (m, 2H), 6.43-6.30 (m, 2H), 5.85-5.74 (m, 1H), 1.66 (d, J=1.8 Hz, 3H).

Example 237 (2,3-dichlorophenyl)(4-methyl-1-(4-methylpyridin-2-yl)-6,7-dihydro-1H-[1,2,3]triazolo[4,5-c]pyridin-5(4H)-yl)methanone

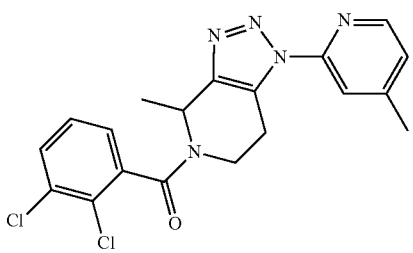 [SMILES: Cc1ccnc(-n2nnc3c2CCN(C(=O)c2cccc(Cl)c2Cl)C3C)c1]

MS (ESI) mass calcd $C_{19}H_{17}Cl_2N_5O$, 401.1 m/z found, 402.1 [M+H]$^+$. $^1$H NMR (400 MHz, CDCl$_3$) δ 8.47-8.19 (m, 1H), 8.05-7.88 (m, 1H), 7.62-7.47 (m, 1H), 7.40-6.98 (m, 3H), 6.17-5.92 (m, 0.611), 5.15-5.04 (m, 0.411), 5.00-4.74 (m, 0.411), 3.75-2.92 (m, 3.611), 2.58-2.37 (m, 3H), 1.82-1.39 (m, 3H).

Example 238: (2-Chloro-3-(trifluoromethyl)phenyl)(1-(4-fluorophenyl)-4,7-dimethyl-6,7-dihydro-H-[0,1,2,3]triazolo[4,5-c]pyridin-5(4H)-yl)methanone Step 1: 1-(4-fluorophenyl)-7-methyl-1H-[1,2,3]triazolo[4,5-c]pyridine

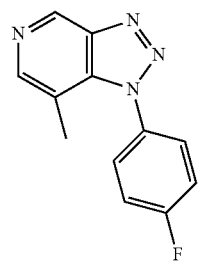 [SMILES: Cc1cncc2nnn(-c3ccc(F)cc3)c12]

The title compound was prepared in a manner analogous to Intermediate 17, Step 1 through Intermediate 19, Step 3 substituting 4-chloro-3-methyl-5-nitro-pyridine for 4-chloro-3-nitropyridine and 4-fluoroaniline for 2-aminopyridine in the synthesis of Intermediate 17, Step 1. MS (ESI) mass calcd. $C_{12}H_9FN_4$, 228.1; m/z found, 229.1 [M+H]$^+$.

Step 2: 1-(1-(4-fluorophenyl)-4,7-dimethyl-1H-[1,2,3]triazolo[4,5-c]pyridin-5(4H)-yl)-2-(4-methoxyphenyl)propan-2-ol

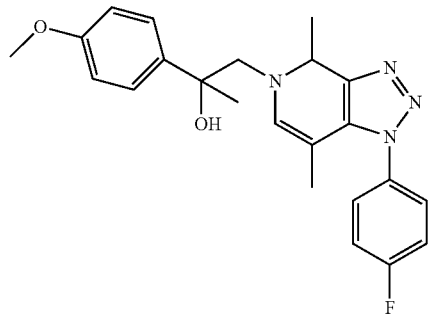 [SMILES: COc1ccc(C(C)(O)CN2C=C(C)c3c(nnn3-c3ccc(F)cc3)C2C)cc1]

The title compound was prepared in a manner analogous to Example 72 substituting 2-bromo-4'-methoxyacetophenone for 2-chloro-3-(trifluoromethyl)benzoyl chloride. MS (ESI) mass calcd. $C_{23}H_{25}FN_4O_2$, 408.2; m/z found 409.18 [M+H]$^+$.

Step 3: 1-(1-(4-fluorophenyl)-4,7-dimethyl-6,7-dihydro-1H-[1,2,3]triazolo[4,5-c]pyridin-5(4H)-yl)-2-(4-methoxyphenyl)propan-2-ol

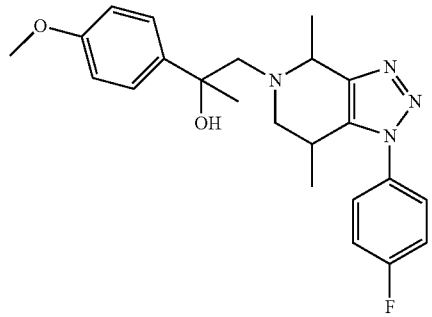 [SMILES: COc1ccc(C(C)(O)CN2CC(C)c3c(nnn3-c3ccc(F)cc3)C2C)cc1]

To a solution of the product of Example 238, Step 2 (200 mg, 0.49 mmol) in MeOH (2 mL) was added Pd/C (52 mg, 0.049 mmol) and ammonium formate (93 mg, 1.45 mmol). The reaction vessel was sealed and heated 80° C. for 16 h. The reaction mixture was then filtered through Celite, concentrated and purified on silica gel with 0-2% NH$_3$ MeOH/CH$_2$Cl$_2$ to afford the title compound (93 mg, 46%). MS (ESI) mass calcd. $C_{23}H_{27}FN_4O_2$, 410.2; m/z found, 411.20 [M+H]$^+$.

Step 4: 1-(4-fluorophenyl)-4,7-dimethyl-4,5,6,7-tetrahydro-1H-[1,2,3]triazolo[4,5-c]pyridine

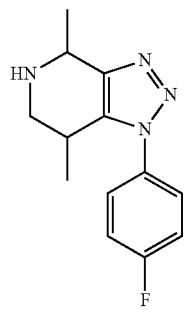 [SMILES: CC1CNC(C)c2nnn(-c3ccc(F)cc3)c21]

The product of Example 238, Step 3 (90 mg, 0.22 mmol) was dissolved in a solution of HCl in dioxane (4M, 2 mL). The reaction was heated at 90° C. for 16 h. The solvent was removed in vacuo to afford the title compound (50 mg, 92%). MS (ESI) mass calcd. $C_{13}H_{15}FN_4$, 246.10; m/z found, 247.16 [M+H]$^+$.

Step 5: (2-Chloro-3-(trifluoromethyl)phenyl)(1-(4-fluorophenyl)-4,7-dimethyl-6,7-dihydro-1H-[1,2,3]triazolo[4,5-c]pyridin-5(4H)-yl)methanone

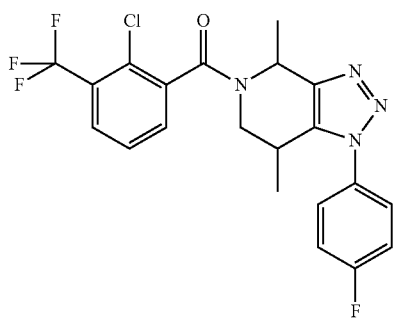

The title compound was prepared in a manner analogous to Example 63, Step 5 substituting the product of Example 238, Step 4 for 1-(pyridin-2-yl)-4,5,6,7-tetrahydro-1H-[1,2,3]triazolo[4,5-c]pyridine and DIPEA for TEA. MS (ESI) mass calcd. $C_{21}H_{17}ClF_4N_4O$, 452.1; m/z found, 453.1 [M+H]$^+$.

Example 239 (S*)-(2-chloro-3-(trifluoromethyl)phenyl)(4-methyl-1-(5-methylpyridin-2-yl)-6,7-dihydro-1H-[1,2,3]triazolo[4,5-c]pyridin-5(4H)-yl)methanone

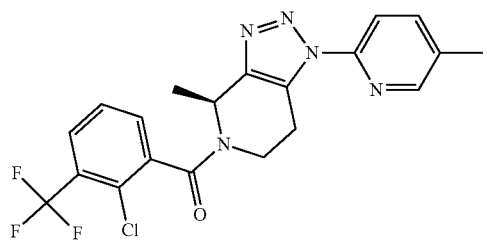 [SMILES: Cc1ccc(-n2nnc3c2CCN(C(=O)c2cccc(C(F)(F)F)c2Cl)[C@H]3C)nc1]

MS (ESI) mass calcd $C_{20}H_{17}CF_3N_5O$, 435.1 m/z found, 435.7 [M+H]$^+$. $^1$H NMR (500 MHz, CDCl$_3$) δ 8.41-8.16 (m, 1H), 8.12-7.94 (m, 1H), 7.85-7.64 (m, 2H), 7.63-7.28 (m, 2H), 6.16-5.96 (m, 0.6H), 5.20-5.05 (m, 0.4H), 4.93-4.68 (m, 0.4H), 3.66-2.96 (m, 3.6H), 2.59-2.28 (m, 3H), 1.82-1.44 (m, 3H).

Example 240: (2-Chloro-3-(trifluoromethyl)phenyl)(4,6-dimethyl-1-phenyl-6,7-dihydro-1H-[1,2,3]triazolo[4,5-c]pyridin-5(4H)-yl)methanone Step 1: 4,6-dimethyl-1-phenyl-1H-[1,2,3]triazolo[4,5-c]pyridine

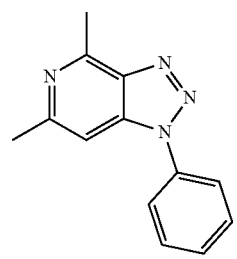 [SMILES: Cc1cc2c(nnn2-c2ccccc2)c(C)n1]

The title compound was prepared in a manner analogous to Intermediate 17, Step 1 through Intermediate 19, Step 3. In the synthesis of Intermediate 17, Step 1 Pd(OAc)$_2$ and BINAP were eliminated and these substitutions were made: 4-chloro-2,6-dimethyl-3-nitropyridine for 4-chloro-3-nitropyridine, aniline for 2-aminopyridine, NaH for K$_2$CO$_3$, and THF for toluene, and the reaction was carried out for 24 h at room temperature. MS (ESI) mass calcd. $C_{13}H_{12}N_4$, 224.1; m/z found, 225.1 [M+H]$^+$.

Step 2: 4,6-dimethyl-1-phenyl-4,5,6,7-tetrahydro-1H-[1,2,3]triazolo[4,5-c]pyridine

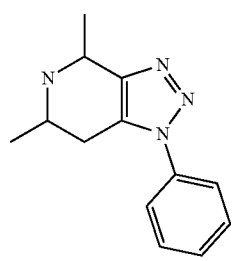 [SMILES: CC1Cc2c(nnn2-c2ccccc2)C(C)N1]

The title compound was prepared in a manner analogous to Intermediate 68, Step D Substituting the product of Example 240, Step 1 for 6-methyl-1-(pyrazin-2-yl)-1H-[1,2,3]triazolo[4,5-c]pyridine. MS (ESI) mass calcd. $C_{13}H_{16}N_4$, 228.1; m/z found, 229.1 [M+H]$^+$.

Step 3: 2-Chloro-3-(trifluoromethyl)phenyl)(4,6-dimethyl-1-phenyl-6,7-dihydro-1H-[1,2,3]triazolo[4,5-c]pyridin-5(4H)-yl)methanone

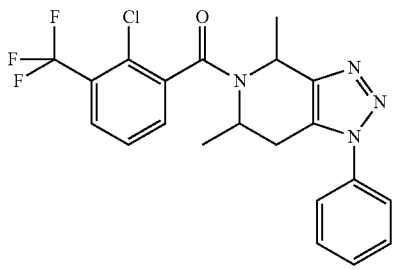

The title compound was prepared in a manner analogous to Example 63, Step 5 substituting the product of Example 238, Step 4 for 1-(pyridin-2-yl)-4,5,6,7-tetrahydro-1H-[1,2,3]triazolo[4,5-c]pyridine. MS (ESI) mass calcd. $C_{21}H_{18}ClF_3N_4O$, 434.1; m/z found, 435.1 [M+H]$^+$.

Example 241: (2-Chloro-3-(trifluoromethyl)phenyl)(4,7-dimethyl-1-phenyl-6,7-dihydro-1H-[1,2,3]triazolo[4,5-c]pyridin-5(4H)-yl)methanone

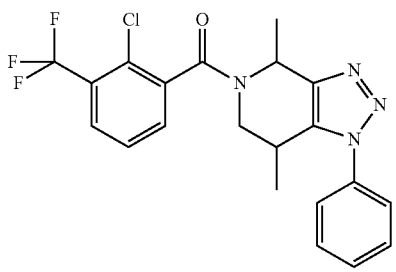

The title compound was prepared in a manner analogous to Example 238 substituting aniline for 4-fluoroaniline in Step 1, acetyl chloride for 2-bromo-4'-methoxyacetophenone in Step 2 and HCl (12N) in MeOH/H$_2$O (3:1) for HCl (4N in dioxane) in MeOH in Step 4. MS (ESI) mass calcd. $C_{21}H_{18}ClF_3N_4O$, 434.1; m/z found, 435.1 [M+H]$^+$.

Example 242: (2,3-Dichlorophenyl)(1-(4-fluorophenyl)-4,6-dimethyl-6,7-dihydro-1H-[1,2,3]triazolo[4,5-c]pyridin-5(4H)-yl)methanone

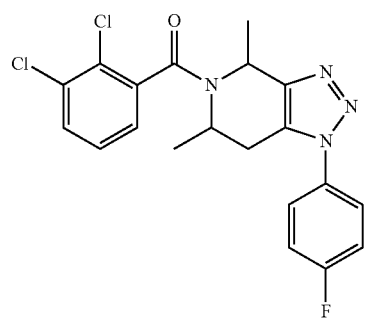

The title compound was prepared in a manner analogous to Example 240 substituting 4-fluoroaniline for aniline in the synthesis of example 240, step 1 and substituting 2,3-dichlorobenzoyl chloride for 2-chloro-3-(trifluoromethyl)benzoyl chloride in the synthesis of Example 240, Step 3. MS (ESI) mass calcd. $C_{20}H_{17}Cl_2FN_4O$, 418.1; m/z found, 419.0 [M+H]$^+$.

Example 243: (2-Chloro-3-(trifluoromethyl)phenyl)(1-(4-fluorophenyl)-4,6-dimethyl-6,7-dihydro-1H-[1,2,3]triazolo[4,5-c]pyridin-5(4H)-yl)methanone

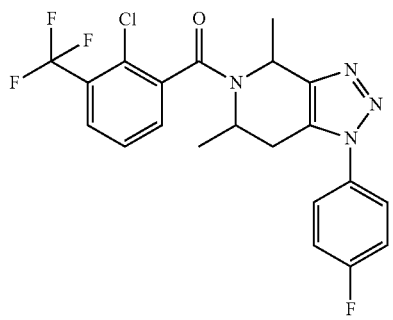

The title compound was prepared in a manner analogous to Example 240 substituting 4-fluoroaniline for aniline in the synthesis of example 240, step 1. MS (ESI) mass calcd. $C_{21}H_{17}ClF_4N_4O$, 452.1; m/z found, 453.2 [M+H]$^+$.

Example 244: (2,3-Dichlorophenyl)(7-methyl-1-phenyl-6,7-dihydro-1H-[1,2,3]triazolo[4,5-c]pyridin-5(4H)-yl)methanone Step 1: 7-methyl-1-phenyl-1H-[1,2,3]triazolo[4,5-c]pyridine

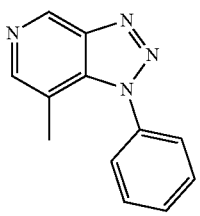 [SMILES: Cc1cncc2nnn(-c3ccccc3)c12]

The title compound was prepared in a manner analogous to Intermediate 17, Step 1 through Intermediate 19, Step 3 substituting 4-chloro-3-methyl-5-nitro-pyridine for 4-chloro-3-nitropyridine, and aniline for 2-aminopyridine. MS (ESI) mass calcd. $C_{12}H_{10}N_4$, 210.1; m/z found, 225.1 [M+H]$^+$.

Step 2: 7-methyl-1-phenyl-4,5,6,7-tetrahydro-1H-[1,2,3]triazolo[4,5-c]pyridine

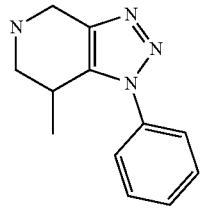 [SMILES: CC1CNCc2nnn(-c3ccccc3)c21]

The title compound was prepared in a manner analogous to Intermediate 68, Step D Substituting the product of Example 244, Step 1 for 6-methyl-1-(pyrazin-2-yl)-1H-[1,2,3]triazolo[4,5-c]pyridine. MS (ESI) mass calcd. $C_{12}H_{14}N$, 214.1; m/z found, 215.1 $[M+H]^+$.

Step 3: (2,3-Dichlorophenyl)(7-methyl-1-phenyl-6,7-dihydro-1H-[1,2,3]triazolo[4,5-c]pyridin-5(4H)-yl)methanone

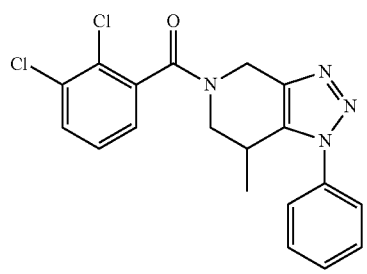

The title compound was prepared in a manner analogous to Example 63, Step 5 substituting the product of Example 244, Step 2 for 1-(pyridin-2-yl)-4,5,6,7-tetrahydro-1H-[1,2,3]triazolo[4,5-c]pyridine, 2,3-dichlorobenzoyl chloride for 2-chloro-3-(trifluoromethyl)benzoyl chloride and DIPEA for TEA. MS (ESI) mass calcd. $C_{19}H_{16}Cl_2N_4O$, 386.1; m/z found, 387.1 $[M+H]^+$.

Example 245: (2-Chloro-3-(trifluoromethyl)phenyl)(7-methyl-1-phenyl-6,7-dihydro-1H-[1,2,3]triazolo[4,5-c]pyridin-5(4H)-yl)methanone

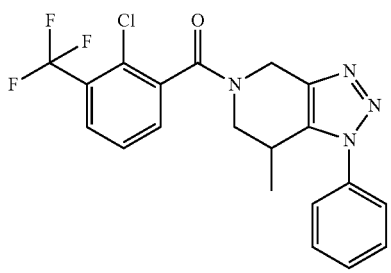

The title compound was prepared in a manner analogous to Example 244 substituting 2-chloro-3-(trifluoromethyl)benzoyl chloride for 2,3-dichlorobenzoyl chloride in the final step. MS (ESI) mass calcd. $C_{20}H_{16}ClF_3N_4O$, 420.1; m/z found, 421.2 $[M+H]^+$.

Example 246: (2-Chloro-3-(trifluoromethyl)phenyl)(1-(4-fluorophenyl)-7-methyl-6,7-dihydro-1H-[1,2,3]triazolo[4,5-c]pyridin-5(4H)-yl)methanone

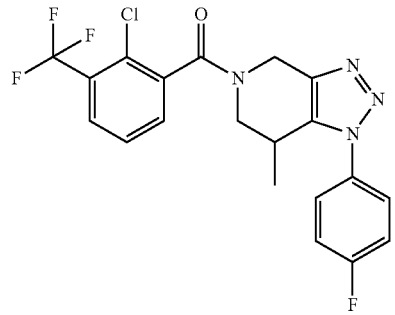

The title compound was prepared in a manner analogous to Example 244 substituting 4-fluoroaniline for aniline in Example 244, Step 1 and 2-chloro-3-(trifluoromethyl)benzoyl chloride for 2, 3-dichlorobenzoyl chloride in Step 3. MS (ESI) mass calcd. $C_{20}H_{15}CF_4N_4O$, 438.1; m/z found, 439.1 $[M+H]^+$.

Example 247: (2,3-Dichlorophenyl)(1-(4-fluorophenyl)-7-methyl-6,7-dihydro-1H-[1,2,3]triazolo[4,5-c]pyridin-5(4H)-yl)methanone

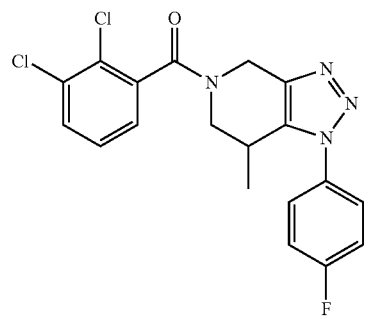

The title compound was prepared in a manner analogous to Example 244 substituting 4-fluoroaniline for aniline in Example 244, Step 1. MS (ESI) mass calcd. $C_{19}H_5Cl_2FN_4O$, 404.1; m/z found, 405.2 $[M+H]^+$.

Example 248: (R*)-(2-Chloro-3-(trifluoromethyl)phenyl)(1-(1-(2-methoxyethyl)-1H-pyrazol-3-yl)-4-methyl-6,7-dihydro-1H-[1,2,3]triazolo[4,5-c]pyridin-5(4H)-yl)methanone

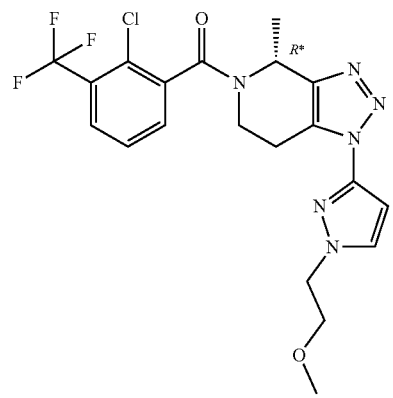

The racemic mixture of the title compound was prepared in a manner analogous to Example 162 substituting 2-bromoethyl methyl ether for 1-bromo-2-fluoroethane in Example 162, Step 2. The title compound was obtain by chiral SFC purification of the racemic mixture (Chiralpak AD-H 5 µm 250×20 mm) using a mobile phase of 80% $CO_2$ and 20% EtOH to obtain the title compound. The enantiomeric purity was confirmed by analytical SFC using a CHIRALPAK AD (250×4.6 mm) and a mobile phase of 80% $CO_2$, 20% EtOH containing 0.3% $iPrNH_2$ over 7 minutes. (100% single enantiomer, 4.66 min retention time). MS (ESI) mass calcd. $C_{20}H_{20}CF_3N_6O_2$, 468.1; m/z found, 469.1 $[M+H]^+$.

Example 249: (S*)-(2-Chloro-3-(trifluoromethyl)phenyl)(1-(1-(2-methoxyethyl)-1H-pyrazol-3-yl)-4-methyl-6,7-dihydro-1H-[1,2,3]triazolo[4,5-c]pyridin-5(4H)-yl)methanone

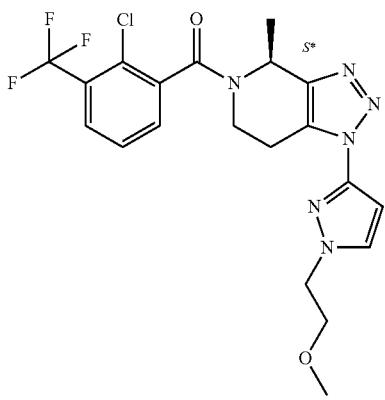 [SMILES: COCCn1ccc(-n2nnc3c2CCN(C(=O)c2cccc(C(F)(F)F)c2Cl)[C@H]3C)n1]

The racemic mixture of the title compound was prepared in a manner analogous to Example 162 substituting 2-bromoethyl methyl ether for 1-bromo-2-fluoroethane in Example 162, Step 2. The title compound was obtain by chiral SFC purification of the racemic mixture (Chirapak AD-H 5 µm 250×20 mm) using a mobile phase of 80% $CO_2$ and 20% EtOH to obtain the title compound. The enantiomeric purity was confirmed by analytical SFC using a CHIRALPAK AD (250×4.6 mm) and a mobile phase of 80% $CO_2$, 20% EtOH containing 0.3% $iPrNH_2$ over 7 minutes. (100% single enantiomer, 6.61 min retention time). MS (ESI) mass calcd. $C_{20}H_{20}ClF_3N_6O_2$, 468.1; m/z found, 469.1 $[M+H]^+$.

Example 250: (2-Chloro-3-(trifluoromethyl)phenyl)(4-methyl-1-(oxazol-2-yl)-6,7-dihydro-1H-[1,2,3]triazolo[4,5-c]pyridin-5(4H)-yl)methanone Step 1: 2-(1H-[1,2,3]triazolo[4,5-c]pyridin-1-yl)oxazole

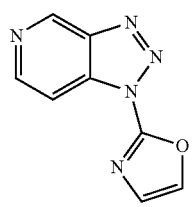

The title compound was prepared in a manner analogous to Intermediate 17, Step 1 through Intermediate 19, Step 3. In the synthesis of Intermediate 17, Step 1 $Pd(OAc)_2$ and BINAP were eliminated and these substitutions were made: 2-aminooxazole for 2-aminopyridine, NaOtBu for $K_2CO_3$, and tert-amyl alcohol for toluene, reaction carried out for 0.5 h at room temperature. MS (ESI) mass calcd. $C_8H_5N_5O$, 187.0; m/z found, 188.1 $[M+H]^+$.

Step 2: (2-Chloro-3-(trifluoromethyl)phenyl)(4-methyl-1-(oxazol-2-yl)-6,7-dihydro-1H-[1,2,3]triazolo[4,5-c]pyridin-5(4H)-yl)methanone

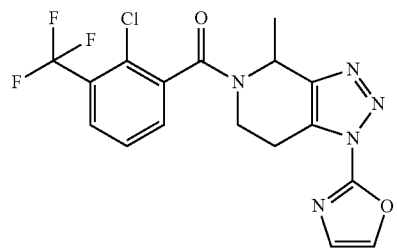 [SMILES: CC1c2nnn(-c3ncco3)c2CCN1C(=O)c1cccc(C(F)(F)F)c1Cl]

The title compound was prepared following the route to prepare Example 73 using the product of Example 250, Step 1 as starting material. MS (ESI) mass calcd $C_{17}H_{13}CF_3N_5O_2$, 411.1; m/z found, 412.1 $[M+H]^+$.

Example 251: (2-Chloro-3-(trifluoromethyl)phenyl)(4-methyl-1-(6-methylpyrazin-2-yl)-6,7-dihydro-1H-[1,2,3]triazolo[4,5-c]pyridin-5(4H)-yl)methanone

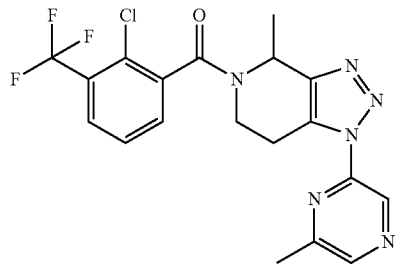 [SMILES: Cc1cncc(-n2nnc3c2CCN(C(=O)c2cccc(C(F)(F)F)c2Cl)C3C)n1]

The title compound was obtained using the route described to synthesize Example 73. The starting material was obtained in a manner analogous to Intermediate 20, Step 4 substituting 2-amino-6-methylpyrazine for 2-aminopyridine, Xantphos for BINAP, $Cs_2CO_3$ for $K_2CO_3$ and dioxane for toluene in the synthesis of Intermediate 17, Step 1. MS (ESI) mass calcd $C_{19}H_{16}ClF_3N_6O$, 436.1; m/z found, 437.1 $[M+H]^+$.

Example 252: (2-Chloro-3-(trifluoromethyl)phenyl)(4-methyl-1-(4-methylpyrimidin-2-yl)-6,7-dihydro-1H-[1,2,3]triazolo[4,5-c]pyridin-5(4H)-yl)methanone

Step 1: 1-(4-methylpyrimidin-2-yl)-1H-[1,2,3]triazolo[4,5-c]pyridine

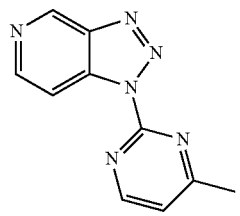 [SMILES: Cc1ccnc(-n2nnc3cnccc32)n1]

The title compound was prepared in a manner analogous to Intermediate 17, Step 1 through Intermediate 19, Step 3. In the synthesis of Intermediate 17, Step 1 these substitutions were made: 4-methylpyrimidin-2-amine for 2-aminopyridine, $Cs_2CO_3$ for $K_2CO_3$, and dioxane for toluene, reaction carried out for 0.5 h at room temperature. MS (ESI) mass calcd. $C_{10}H_8N_6$, 212.1; m/z found, 213.1 $[M+H]^+$.

Step 2: (2-chloro-3-(trifluoromethyl)phenyl)(4-methyl-1-(4-methylpyrimidin-2-yl)-1H-[1,2,3]triazolo[4,5-c]pyridin-5(4H)-yl)methanone

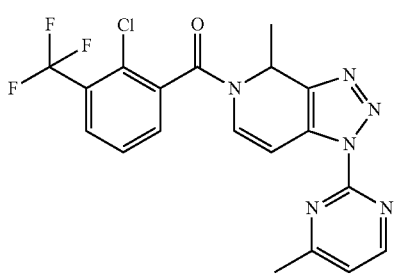 [SMILES: Cc1ccnc(-n2nnc3c2C=CN(C(=O)c2cccc(C(F)(F)F)c2Cl)C3C)n1]

To a suspension of the product of Example 252, Step 1 (200 mg, 0.94 mmol) in THF (30 mL) cooled to −78° C. was added Intermediate 12 (251 mg, 1.04 mmol). Trimethylsilyl trifluoromethanesulfonate (0.188 mL, 1.04 mmol) was then added and the reaction was stirred at −78° C. for 30 min. The resulting mixture was treated with MeMgBr (3.0 M solution in $Et_2O$, 0.94 mL, 2.83 mmol) and stirred for 1 h. The reaction was quenched with $NH_4C_1$ and extracted with EtOAc, dried over $MgSO_4$ and concentrated. The residue was purified by chromatography on silica gel (0-5% MeOH/DCM) to provide the desired product (66 mg, 16%). MS (ESI) mass calcd. $C_{19}H_{14}ClF_3N_6O$, 434.1; m/z found, 435.1 $[M+H]^+$.

Step 3: (2-Chloro-3-(trifluoromethyl)phenyl)(4-methyl-1-(4-methylpyrimidin-2-yl)-6,7-dihydro-1H-[1,2,3]triazolo[4,5-c]pyridin-5(4H)-yl)methanone

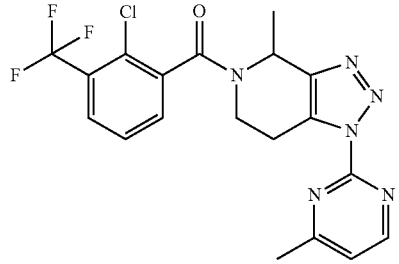 [SMILES: Cc1ccnc(-n2nnc3c2CCN(C(=O)c2cccc(C(F)(F)F)c2Cl)C3C)n1]

The title compound was prepared in a manner analogous to Example 73 substituting the product of Example 252, Step 2 for the 5-{[2-chloro-3-(trifluoromethyl)phenyl]carbonyl}-4-methyl-1-pyrazin-2-yl-4,5-dihydro-1H-[1,2,3]triazolo[4,5-c]pyridine. MS (ESI) mass calcd. $C_{19}H_{16}ClF_3N_6O$, 436.1; m/z found, 437.1 $[M+H]^+$.

Example 253: (2-Chloro-3-(trifluoromethyl)phenyl)(1-(4,6-dimethylpyrimidin-2-yl)-4-methyl-6,7-dihydro-1H-[1,2,3]triazolo[4,5-c]pyridin-5(4H)-yl)methanone

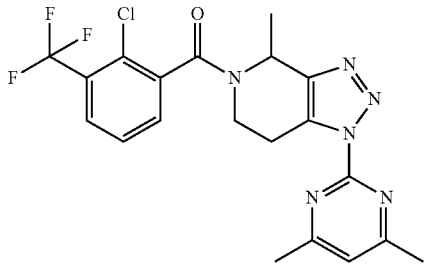 [SMILES: Cc1cc(C)nc(-n2nnc3c2CCN(C(=O)c2cccc(C(F)(F)F)c2Cl)C3C)n1]

The title compound was prepared in a manner analogous to Example 252 substituting 4,6-dimethylpyrimidin-2-amine for 4-methylpyrimidin-2-amine in Step 1. MS (ESI) mass calcd. $C_{20}H_{18}ClF_3N_6O$, 450.1; m/z found, 451.2 $[M+H]^+$.

Example 254: (2-Chloro-3-(trifluoromethyl)phenyl)(1-(3-ethylpyridin-2-yl)-4-methyl-6,7-dihydro-1H-[1,2,3]triazolo[4,5-c]pyridin-5(4H)-yl)methanone

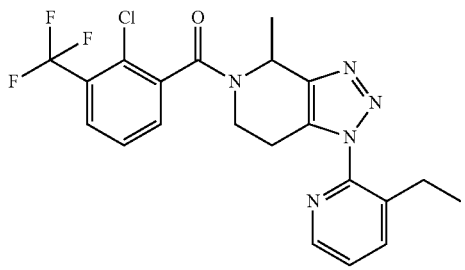

The title compound was prepared in a manner analogous to Example 252 substituting 3-ethylpyridin-2-amine for 4-methylpyrimidin-2-amine in Step 1 and triisopropylsilyl trifluoromethanesulfonate for trimethylsilyl trifluoromethanesulfonate in Step 2. MS (ESI) mass calcd. $C_{21}H_{19}ClF_3N_5O$, 449.1; m/z found, 450.0 [M+H]$^+$. $^1$H NMR (400 MHz, CDCl$_3$) δ 8.50-8.34 (m, 1H), 7.89-7.68 (m, 2H), 7.63-7.34 (m, 3H), 6.18-6.04 (m, 0.5H), 5.18-5.04 (m, 0.4H), 5.00-4.71 (m, 0.4H), 3.64-2.65 (m, 4.7H), 1.76-1.68 (m, 2H), 1.51 (d, J=6.8 Hz, 1H), 1.25-1.11 (m, 4H).

Intermediate 234: 2-chloro-4-fluorobenzoyl Chloride

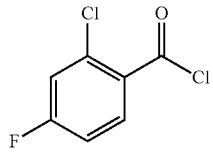

The title compound was prepared in a manner analogous to Intermediate 12 substituting 2-chloro-4-fluorobenzoic acid for 2-chloro-3-(trifluoromethyl)benzoic acid.

Example 255 (R*)-(2-chloro-3-(trifluoromethyl) phenyl)(4-methyl-1-(5-methylpyridin-2-yl)-6,7-dihydro-1H-[1,2,3]triazolo[4,5-c]pyridin-5(4H)-yl) methanone

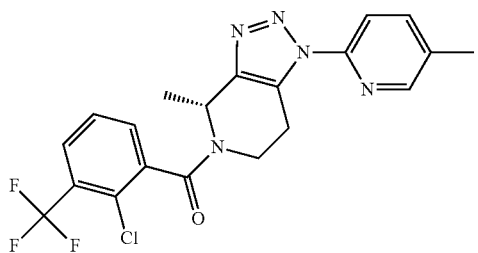 [SMILES: Cc1ccc(-n2nnc3c2CCN(C(=O)c2cccc(C(F)(F)F)c2Cl)[C@@H]3C)nc1]

MS (ESI) mass calcd $C_{20}H_{17}ClF_3N_5O$, 435.1 m/z found, 435.7 [M+H]$^+$. $^1$H NMR (500 MHz, CDCl$_3$) δ 8.41-8.16 (m, 1H), 8.12-7.94 (m, 1H), 7.85-7.64 (m, 2H), 7.63-7.28 (m, 2H), 6.16-5.96 (m, 0.6H), 5.20-5.05 (m, 0.4H), 4.93-4.68 (m, 0.4H), 3.66-2.96 (m, 3.6H), 2.59-2.28 (m, 3H), 1.82-1.44 (m, 3H).

Example 256: (2-chloro-4-fluorophenyl)(1-(5-fluoropyridin-2-yl)-4-methyl-6,7-dihydro-1H-imidazo[4,5-c]pyridin-5(4H)-yl)methanone

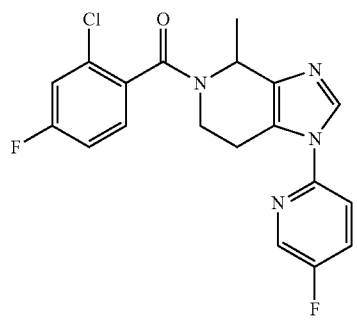 [SMILES: CC1c2ncn(-c3ccc(F)cn3)c2CCN1C(=O)c1ccc(F)cc1Cl]

The title compound was prepared in a manner analogous to Example 11 substituting Intermediate 234 for Intermediate 12 in Step A as well as the addition of triisopropylsilyl trifluoromethanesulfonate (1 eq) to Step A. $^1$H NMR (500 MHz, CDCl$_3$) δ 8.46-8.30 (m, 1H), 8.13-7.87 (m, 1H), 7.66-7.41 (m, 1H), 7.40-7.00 (m, 4H), 5.83-5.73 (q, J=6.7 Hz, 1H), 5.14-4.46 (m, 1H), 3.66-3.24 (m, 1H), 3.24-2.64 (m, 3H), 1.72-1.51 (m, 3H). MS (ESI) mass calcd. $C_{19}H_{15}ClF_2N_4O$, 388.1; m/z found, 389.1 [M+H]$^+$.

Intermediate 235: 2,4-dichlorobenzoyl Chloride

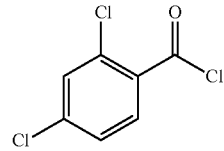 [SMILES: O=C(Cl)c1ccc(Cl)cc1Cl]

The title compound was prepared in a manner analogous to Intermediate 12 substituting 2,4-dichlorobenzoic acid for 2-chloro-3-(trifluoromethyl)benzoic acid.

Example 257: (2,4-dichlorophenyl)(1-(pyrimidin-2-yl)-6,7-dihydro-1H-[1,2,3]triazolo[4,5-c]pyridin-5(4H)-yl)methanone

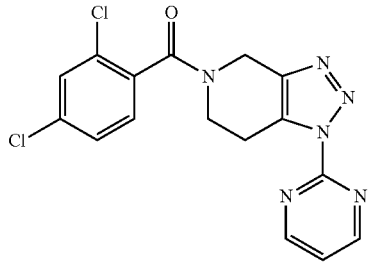 [SMILES: O=C(c1ccc(Cl)cc1Cl)N1CCc2c(nnn2-c2ncccn2)C1]

The title compound was prepared in a manner analogous to Example 63, Step 5 substituting Intermediate 50 for 1-(pyridin-2-yl)-4,5,6,7-tetrahydro-1H-[1,2,3]triazolo[4,5-c]pyridine and Intermediate 235 for 2-chloro-3-(trifluoromethyl)benzoyl chloride. MS (ESI) mass calcd. $C_{16}H_{12}Cl_2N_6O$, 374.0; m/z found, 375.1 [M+H]$^+$. $^1$H NMR (400 MHz, CDCl$_3$) δ 8.97-8.77 (dd, J=13.6, 4.8 Hz, 2H), 7.63-7.10 (m, 6H), 5.43-5.24 (s, 0.5H), 5.24-4.90 (m, 1H), 4.71-4.29 (m, 1H), 4.33-3.94 (m, 1H), 3.68-3.40 (m, 2H), 3.39-3.12 (m, 1H).

Example 258: (2-Chloro-3-(trifluoromethyl)phenyl)(1-(3-ethoxypyridin-2-yl)-4-methyl-6,7-dihydro-1H-[1,2,3]triazolo[4,5-c]pyridin-5(4H)-yl)methanone

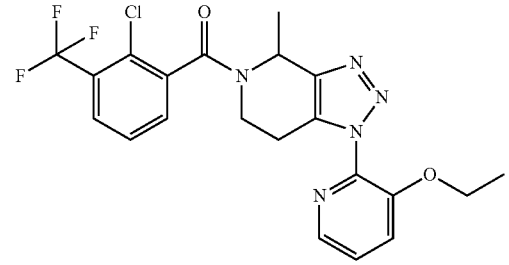 [SMILES: CCOc1cccnc1-n1nnc2c1CCN(C(=O)c1cccc(C(F)(F)F)c1Cl)C2C]

The title compound was prepared in a manner analogous to Example 252 substituting 3-ethoxypyridin-2-amine for 4-methylpyrimidin-2-amine in Step 1 and triisopropylsilyl trifluoromethanesulfonate for trimethylsilyl trifluoromethanesulfonate in Step 2. MS (ESI) mass calcd. $C_{21}H_{19}ClF_3N_5O_2$, 465.1; m/z found, 466.1 [M+H]$^+$. $^1$H NMR (400 MHz, CDCl$_3$) δ 8.27-8.13 (m, 1H), 7.82-7.68 (m, 1H), 7.64-7.39 (m, 4H), 6.24-6.01 (m, 0.5H), 5.16-4.98 (m, 0.5H), 4.96-4.71 (m, 0.5H), 4.22-4.00 (m, 2H), 3.64-3.45 (m, 0.7H), 3.40-2.96 (m, 1.5H), 2.82-2.59 (m, 1.3H), 1.75-1.66 (m, 1.5H), 1.59-1.47 (m, 1.5H), 1.44-1.29 (m, 3H).

Example 259: (2-Chloro-3-(trifluoromethyl)phenyl)(4-methyl-1-(3-methylpyridin-2-yl)-6,7-dihydro-1H-[1,2,3]triazolo[4,5-c]pyridin-5(4H)-yl)methanone

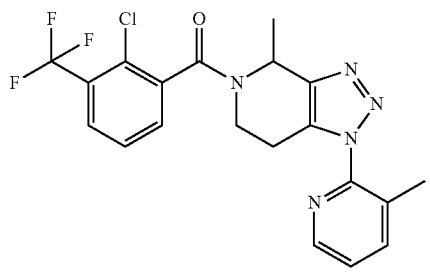 [SMILES: Cc1cccnc1-n1nnc2c1CCN(C(=O)c1cccc(C(F)(F)F)c1Cl)C2C]

The title compound was prepared in a manner analogous to Example 252 substituting 3-methylpyridin-2-amine for 4-methylpyrimidin-2-amine in Step 1 and triisopropylsilyl trifluoromethanesulfonate for trimethylsilyl trifluoromethanesulfonate in Step 2. MS (ESI) mass calcd. $C_{20}H_{17}CF_3N_5O$, 435.1; m/z found, 436.0 [M+H]$^+$. $^1$H NMR (400 MHz, CDCl$_3$) δ 8.49-8.28 (m, 1H), 7.84-7.70 (m, 2H), 7.59-7.40 (m, 2H), 7.41-7.29 (m, 1H), 6.16-6.01 (m, 0.6H), 5.15-5.04 (m, 0.4H), 4.95-4.72 (m, 0.4H), 3.64-3.33 (m, 1.2H), 3.29-2.81 (m, 2.4H), 2.54-2.39 (m, 3H), 1.78-1.67 (m, 2H), 1.62-1.43 (m, 1H).

Example 260: (2-Chloro-3-(trifluoromethyl)phenyl)(1-(3-methoxypyridin-2-yl)-4-methyl-6,7-dihydro-1H-[1,2,3]triazolo[4,5-c]pyridin-5(4H)-yl)methanone

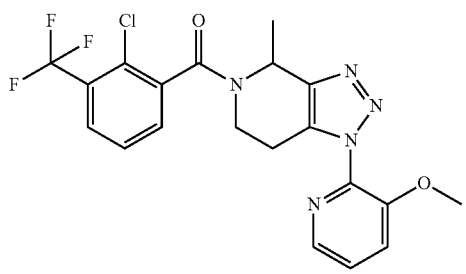

The title compound was prepared in a manner analogous to Example 252 substituting 3-methoxypyridin-2-amine for 4-methylpyrimidin-2-amine in Step 1 and triisopropylsilyl trifluoromethanesulfonate for trimethylsilyl trifluoromethanesulfonate in Step 2. MS (ESI) mass calcd. $C_{20}H_{17}ClF_3N_5O_2$, 451.1; m/z found, 436.0 [M+H]$^+$. $^1$H NMR (400 MHz, CDCl$_3$) δ 8.28-8.12 (m, 1H), 7.83-7.73 (m, 1H), 7.59-7.33 (m, 4H), 6.22-5.99 (m, 0.5H), 5.14-5.01 (m, 0.4H), 4.96-4.74 (m, 0.4H), 3.99-3.81 (m, 3H), 3.61-3.31 (m, 1.1H), 3.29-2.97 (m, 1.1H), 2.84-2.59 (m, 1.5H), 1.76-1.66 (m, 1.5H), 1.60-1.44 (m, 1.5H).

Example 261: (2,3-dichloro-4-fluorophenyl)(1-(5-fluoropyridin-2-yl)-4-methyl-6,7-dihydro-1H-imidazo[4,5-c]pyridin-5(4H)-yl)methanone

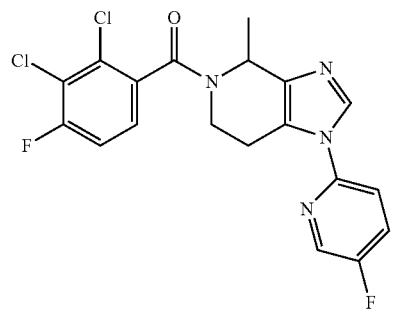 [SMILES: CC1c2ncn(-c3ccc(F)cn3)c2CCN1C(=O)c1ccc(F)c(Cl)c1Cl]

The title compound was prepared in a manner analogous to Example 252 substituting Intermediate 1 for the product of Example 252, Step 1, 2,3-dichloro-4-fluorobenzoyl chloride for Intermediate 12 and excluding trimethylsilyl trifluoromethanesulfonate in Step 2. MS (ESI) mass calcd. $C_{19}H_{14}Cl_2F_2N_4O$, 422.1; m/z found, 423.1 [M+H]$^+$. $^1$H NMR (600 MHz, CDCl$_3$) δ 8.42-8.29 (m, 1H), 8.00-7.89 (m, 1H), 7.67-7.55 (m, 1H), 7.37-7.30 (m, 1H), 7.25-7.05 (m, 2H), 5.87-5.40 (m, 1H), 5.08-3.80 (m, 2H), 3.71-2.69 (m, 3H), 1.83-1.29 (m, 3H)

Example 262: (2-fluoro-3-(trifluoromethyl)phenyl)(1-(5-fluoropyridin-2-yl)-4-methyl-6,7-dihydro-1H-imidazo[4,5-c]pyridin-5(4H)-yl)methanone

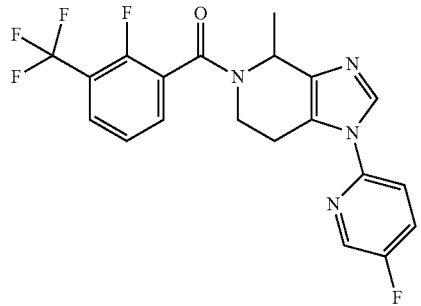 [SMILES: CC1c2ncn(-c3ccc(F)cn3)c2CCN1C(=O)c1cccc(C(F)(F)F)c1F]

The title compound was prepared in a manner analogous to Example 252 substituting Intermediate 1 for the product of Example 252, Step 1, 2-fluoro-3-(trifluoromethyl)benzoyl chloride for Intermediate 12 and excluding trimethylsilyl trifluoromethanesulfonate in Step 2. MS (ESI) mass calcd. $C_{20}H_{15}F_5N_4O$, 422.1; m/z found, 423.2 [M+H]$^+$. $^1$H NMR (600 MHz, CDCl$_3$) δ 8.43-8.32 (m, 1H), 7.98-7.83 (m, 1H), 7.74-7.54 (m, 3H), 7.40-7.30 (m, 2H), 5.87-5.48 (m, 1H), 5.09-4.55 (m, 1H), 4.41-3.57 (m, 1H), 3.29-2.69 (m, 2H), 2.16-1.35 (m, 3H).

Example 263: (1-(5-fluoropyridin-2-yl)-4-methyl-6,7-dihydro-1H-imidazo[4,5-c]pyridin-5(4H)-yl)(2-methyl-3-(trifluoromethyl)phenyl)methanone

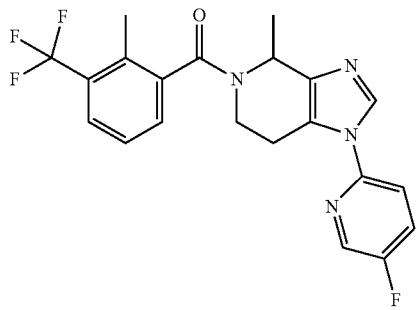 [SMILES: Cc1c(C(=O)N2CCc3c(ncn3-c3ccc(F)cn3)C2C)cccc1C(F)(F)F]

The title compound was prepared in a manner analogous to Example 252 substituting Intermediate 1 for the product of Example 252, Step 1, 2-methyl-3-(trifluoromethyl)benzoyl chloride for Intermediate 12 and excluding trimethylsilyl trifluoromethanesulfonate in Step 2. MS (ESI) mass calcd. $C_{21}H_{18}F_4N_4O$, 418.1; m/z found, 419.2 [M+H]$^+$. $^1$H NMR (600 MHz, CDCl$_3$) δ 8.48-8.26 (m, 1H), 8.07-7.77 (m, 1H), 7.77-7.50 (m, 2H), 7.50-7.32 (m, 3H), 5.17-4.03 (s, 1H), 3.74-2.66 (m, 3H), 2.33-1.89 (m, 2H), 1.63-1.09 (m, 5H).

Example 264: (2-fluorophenyl)(1-(5-fluoropyridin-2-yl)-4-methyl-6,7-dihydro-1H-imidazo[4,5-c]pyridin-5(4H)-yl)methanone Step 1

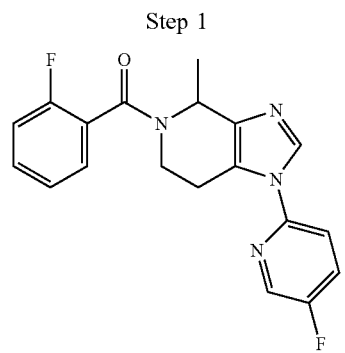

MS (ESI) mass calcd. $C_{19}H_{16}F_2N_4O$, 354.1; m/z found, 355.2 [M+H]$^+$.

Example 265: (4-(tert-butyl)phenyl)(1-(5-fluoropyridin-2-yl)-4-methyl-6,7-dihydro-1H-imidazo[4,5-c]pyridin-5(4H)-yl)methanone

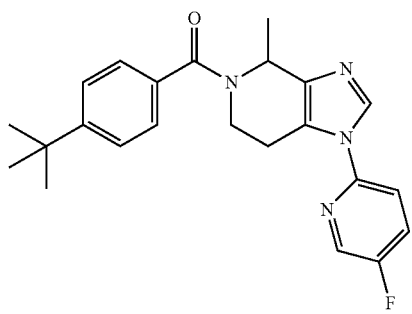 [SMILES: CC1c2ncn(-c3ccc(F)cn3)c2CCN1C(=O)c1ccc(C(C)(C)C)cc1]

The title compound was prepared in a manner analogous to Example 252 substituting Intermediate 1 for the product of Example 252, Step 1, 4-(tert-butyl)benzoyl chloride for Intermediate 12 and excluding trimethylsilyl trifluoromethanesulfonate in Step 2. MS (ESI) mass calcd. $C_{23}H_{25}FN_4O$, 392.2; m/z found, 393.3 [M+H]$^+$. $^1$H NMR (500 MHz, CDCl$_3$) δ 8.53-8.17 (s, 1H), 8.07-7.78 (s, 1H), 7.70-7.27 (m, 6H), 5.05-4.58 (s, 1H), 3.43-2.73 (m, 3H), 1.67-1.46 (s, 4H), 1.43-1.17 (m, 9H).

Example 266: (2-chloro-3-(trifluoromethyl)phenyl)(1,5-dimethyl-3-(1-methyl-1H-pyrazol-5-yl)-4,5-dihydro-1H-pyrazolo[3,4-c]pyridin-6(7H)-yl)methanone

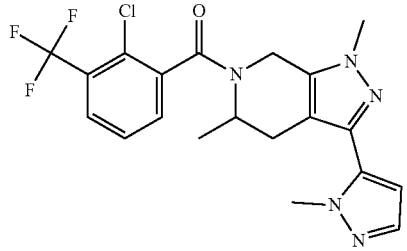 [SMILES: CC1Cc2c(-c3ccnn3C)nn(C)c2CN1C(=O)c1cccc(C(F)(F)F)c1Cl]

$^1$H NMR (400 MHz, CDCl$_3$) δ 7.81-7.73 (m, 1H), 7.54-7.39 (m, 1H), 7.35 (d, J=2.3 Hz, 1H), 6.53 (dd, J=2.3, 1.7 Hz, 1H), 5.61 (ddd, J=21.5, 16.8, 1.2 Hz, 1H), 4.21-4.10 (m, 1H), 3.97-3.85 (m, 5H), 3.73 (s, 6H), 2.89-2.71 (m, 1H), 1.29 (d, J=6.8 Hz, 2H), 1.15 (d, J=6.8 Hz, 1H). MS (ESI) mass calcd. $C_{20}H_{19}ClF_3N_5O$, 437.1; m/z found, 438.4 [M+H]$^+$.

Example 267: (2-chloro-3-(trifluoromethyl)phenyl)(5-methyl-3-(1H-pyrazol-5-yl)-4,5-dihydro-1H-pyrazolo[3,4-c]pyridin-6(7H)-yl)methanone

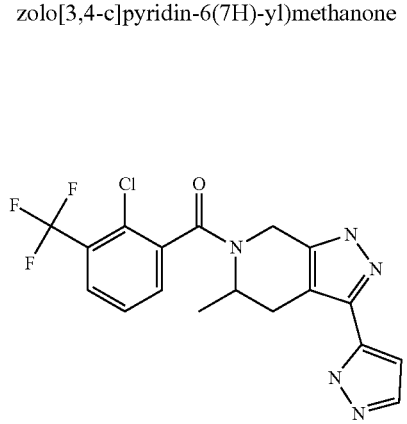

$^1$H NMR (400 MHz, CDCl$_3$) δ 7.85-7.72 (m, 1H), 7.71-7.62 (m, 1H), 7.55-7.42 (m, 3H), 6.58-6.34 (m, 1H), 6.09-5.83 (m, 1H), 5.59 (d, J=6.6 Hz, 1H), 4.30 (d, J=8.9 Hz, 0.29H), 4.04 (s, 2H), 3.21 (s, 2H), 2.89 (s, 0.36H), 2.82-2.55 (m, 3H), 1.35 (dd, J=6.8, 4.8 Hz, 3H). MS (ESI) mass calcd. $C_{18}H_{15}ClF_3N_5O$, 409.1; m/z found, 410.3 [M+H]$^+$.

Example 268: (2,4-dichlorophenyl)(5-methyl-3-(1H-pyrazol-5-yl)-4,5-dihydro-1H-pyrazolo[3,4-c]pyridin-6(7H)-yl)methanone

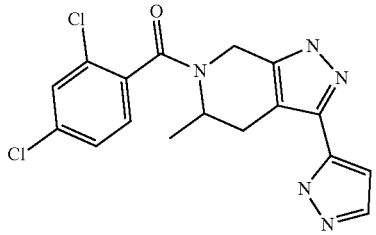 [SMILES: CC1Cc2c(-c3ccn[nH]3)n[nH]c2CN1C(=O)c1ccc(Cl)cc1Cl]

¹H NMR (400 MHz, CDCl₃) δ 7.65 (dd, J=7.8, 2.4 Hz, 1H), 7.50 (dd, J=9.5, 2.0 Hz, 1H), 7.46-7.38 (m, 1.6H), 7.38-7.28 (m, 1H), 7.23 (d, J=8.2 Hz, 1H), 6.51 (d, J=2.5 Hz, 0.5H), 6.44 (dd, J=8.9, 2.4 Hz, 0.82H), 6.05 (dd, J=39.7, 17.0 Hz, 1H), 5.56 (s, 0.5H), 4.41-4.21 (m, 1.5H), 4.13-3.99 (m, 1H), 3.22 (dd, J=15.1, 5.7 Hz, 1H), 2.79-2.45 (m, 0.5H), 1.38-1.25 (m, 3H). MS (ESI) mass calcd. $C_{17}H_{15}Cl_2N_5O$, 375.1; m/z found, 376.3 [M+H]⁺.

Example 269: (2-fluoro-3-(trifluoromethyl)phenyl)(4-methyl-1-(4-methylpyrimidin-2-yl)-6,7-dihydro-1H-[1,2,3]triazolo[4,5-c]pyridin-5(4H)-yl)methanone

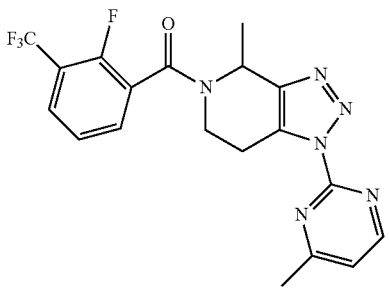 [SMILES: Cc1ccnc(-n2nnc3c2CCN(C(=O)c2cccc(C(F)(F)F)c2F)C3C)n1]

MS (ESI) mass calcd. $C_{19}H_{16}F_4N_6O$, 420.1; m/z found, 421.1 [M+H]⁺.

Example 270: (S*)-(2-fluoro-3-(trifluoromethyl)phenyl)(4-methyl-1-(pyrimidin-2-yl)-6,7-dihydro-1H-[1,2,3]triazolo[4,5-c]pyridin-5(4H)-yl)methanone

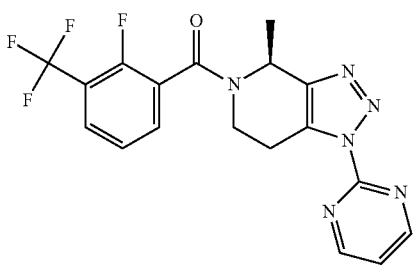

MS (ESI) mass calcd. $C_{18}H_{14}F_4N_6O$, 406.1; m/z found, 407.1 [M+H]⁺.

Example 271: (R*)-(2-fluoro-3-(trifluoromethyl)phenyl)(4-methyl-1-(pyrimidin-2-yl)-6,7-dihydro-1H-[1,2,3]triazolo[4,5-c]pyridin-5(4H)-yl)methanone

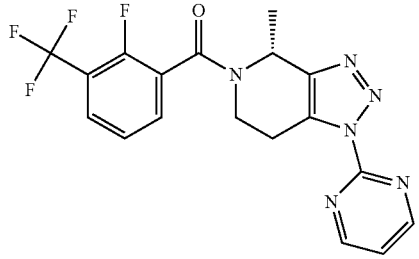 [SMILES: C[C@@H]1c2nnn(-c3ncccn3)c2CCN1C(=O)c1cccc(C(F)(F)F)c1F]

¹H NMR (400 MHz, CDCl₃) δ 8.88 (dd, J=11.2, 4.8 Hz, 2H), 7.82-7.46 (m, 2H), 7.47-7.29 (m, 2H), 5.09 (dd, J=13.0, 5.2 Hz, 0.59H), 4.92 (d, J=6.7 Hz, 0.60H), 3.73 (t, J=7.4 Hz, 0.73H), 3.60-3.04 (m, 3.46H), 1.70 (d, J=6.7 Hz, 1.82H), 1.26 (s, 1.55H).
MS (ESI) mass calcd. $C_{18}H_{14}F_4N_6O$, 406.1; m/z found, 407.1 [M+H]⁺.

Example 272: (4-chloro-2-fluorophenyl)(1-(pyrazin-2-yl)-6,7-dihydro-1H-[1,2,3]triazolo[4,5-c]pyridin-5(4H)-yl)methanone

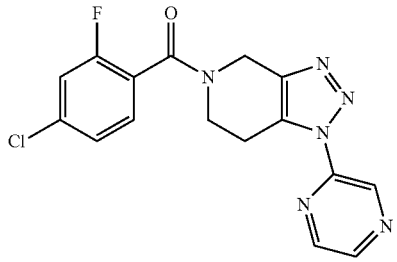 [SMILES: O=C(c1ccc(Cl)cc1F)N1CCc2c(nnn2-c2cnccn2)C1]

¹H NMR (400 MHz, CDCl₃) δ 9.52 (d, J=16.3 Hz, 1H), 8.65 (dd, J=6.0, 2.5 Hz, 1H), 8.56-8.37 (m, 1H), 7.39 (dt, J=15.8, 7.6 Hz, 1H), 7.20 (dd, J=9.3, 1.9 Hz, 1H), 5.06 (s, 1H), 4.66 (s, 1H), 3.66 (s, 1H), 3.48-3.13 (m, 3H). MS (ESI) mass calcd. $C_{16}H_{12}ClFN_6O$, 358.1; m/z found, 359.1 [M+H]⁺.

Example 273: (2-fluoro-3-(trifluoromethyl)phenyl)(4-methyl-1-(pyrazin-2-yl)-6,7-dihydro-1H-[1,2,3]triazolo[4,5-c]pyridin-5(4H)-yl)methanone

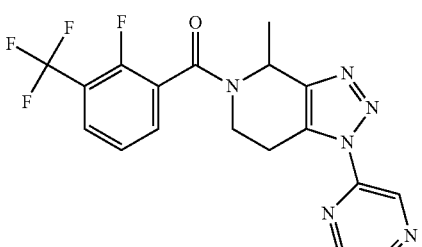

¹H NMR (400 MHz, CDCl₃) δ 9.63-9.39 (m, 1H), 8.73-8.60 (m, 1H), 8.55-8.39 (m, 1H), 7.81-7.31 (m, 3H), 6.05 (s,

1H), 5.17-4.84 (m, 1H), 3.74 (d, J=11.4 Hz, 1H), 3.60-3.03 (m, 3H), 1.70 (d, J=6.7 Hz, 2H). MS (ESI) mass calcd. $C_{18}H_{14}F_4N_6O$, 406.1; m/z found, 407.1 [M+H]$^+$.

Example 274: (4-chloro-2-fluorophenyl)(4-methyl-1-(pyrazin-2-yl)-6,7-dihydro-1H-[1,2,3]triazolo[4,5-c]pyridin-5(4H)-yl)methanone

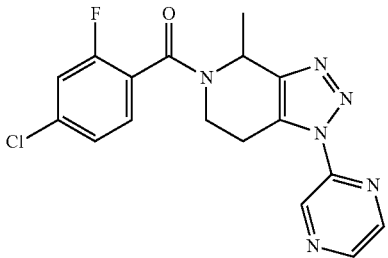 [SMILES: CC1c2nnn(-c3cnccn3)c2CCN1C(=O)c1ccc(Cl)cc1F]

$^1$H NMR (400 MHz, CDCl$_3$) 9.59-9.45. (m, 1H), 8.73-8.57 (m, 1H), 8.53-8.39 (m, 1H), 7.19 (dd, J=9.2, 1.9 Hz, 1H), 6.02 (d, J=7.1 Hz, 1H), 4.95 (d, J=7.0 Hz, 1H), 3.78 (d, J=11.4 Hz, 1H), 3.54-3.28 (m, 2H), 3.23 (q, J=7.3 Hz, 2H), 1.68 (d, J=6.7 Hz, 3H). MS (ESI) mass calcd. $C_{17}H_{14}ClFN_6O$, 372.1; m/z found, 373.1[M+H]$^+$.

Example 275: (4-chloro-2-fluorophenyl)(4-methyl-1-(pyrimidin-2-yl)-6,7-dihydro-1H-[1,2,3]triazolo[4,5-c]pyridin-5(4H)-yl)methanone

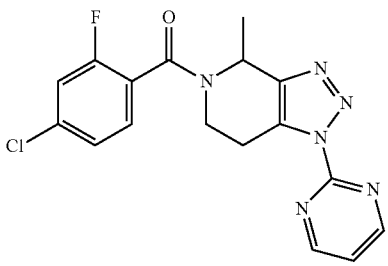

$^1$H NMR (400 MHz, CDCl$_3$) δ 8.87 (dd, J=11.3, 4.8 Hz, 2H), 7.39 (q, J=4.7 Hz, 1.66H), 7.25-7.10 (m, 1.6H), 6.02 (d, J=7.5 Hz, 1H), 5.15-4.90 (m, 1H), 3.78 (d, J=12.6 Hz, 1H), 3.58-3.05 (m, 3H), 1.68 (d, J=6.8 Hz, 1.6H). MS (ESI) mass calcd. $C_{17}H_{14}ClFN_6O$, 372.1; m/z found, 373.1 [M+H]$^+$.

Example 276: (2-methyl-3-(trifluoromethyl)phenyl)(1-(pyrazin-2-yl)-6,7-dihydro-1H-[1,2,3]triazolo[4,5-c]pyridin-5(4H)-yl)methanone

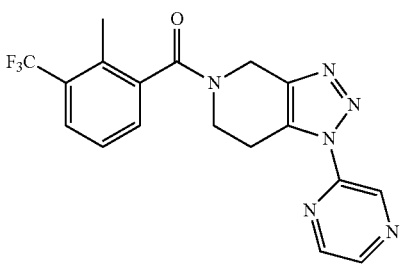 [SMILES: Cc1c(C(=O)N2CCc3c(nnn3-c3cnccn3)C2)cccc1C(F)(F)F]

$^1$H NMR (400 MHz, CDCl$_3$) δ 9.64-9.44 (m, 1H), 8.66 (ddd, J=11.5, 2.5, 0.5 Hz, 1H), 8.46 (ddd, J=33.8, 2.5, 1.4 Hz, 1H), 7.79-7.62 (m, 1H), 7.45-7.31 (m, 2H), 5.41-5.18 (m, 0.70H), 5.05-4.87 (m, 0.63H), 4.50 (d, J=1.4 Hz, 1.2H), 4.38-3.96 (m, 1H), 3.71-3.09 (m, 3H), 2.41 (dd, J=39.2, 1.7 Hz, 3H). MS (ESI) mass calcd. $C_{18}H_{15}F_3N_6O$, 388.1; m/z found, 389.2 [M+H]$^+$.

Example 277: (2,4-dichlorophenyl)(1-(pyrazin-2-yl)-6,7-dihydro-1H-[1,2,3]triazolo[4,5-c]pyridin-5(4H)-yl)methanone

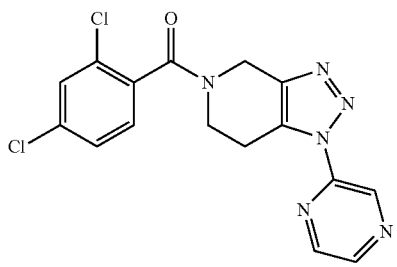 [SMILES: O=C(c1ccc(Cl)cc1Cl)N1CCc2c(nnn2-c2cnccn2)C1]

$^1$H NMR (400 MHz, CDCl$_3$) δ 9.69-9.38 (m, 1H), 8.65 (dd, J=9.1, 2.5 Hz, 1H), 8.46 (ddd, J=29.7, 2.6, 1.5 Hz, 1H), 7.57-7.43 (m, 1H), 7.34 (dd, J=8.4, 1.9 Hz, 2H), 5.24-4.91 (m, 1H), 4.71-4.39 (m, 1H), 4.37-3.96 (m, 1.3H), 3.59 (q, J=6.1 Hz, 1H), 3.51-3.08 (m, 1.86H). MS (ESI) mass calcd. $C_{16}H_{12}Cl_2N_6O$, 374.1; m/z found, 375.1 [M+H]$^+$.

Example 278: (4-methyl-1-(pyrazin-2-yl)-6,7-dihydro-1H-[1,2,3]triazolo[4,5-c]pyridin-5(4H)-yl)(2-methyl-3-(trifluoromethyl)phenyl)methanone

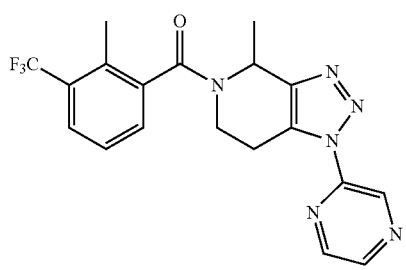 [SMILES: Cc1c(C(=O)N2CCc3c(nnn3-c3cnccn3)C2C)cccc1C(F)(F)F]

$^1$H NMR (400 MHz, CDCl$_3$) δ 9.58-9.46 (m, 1H), 8.74-8.58 (m, 1H), 8.54-8.36 (m, 1H), 7.77-7.65 (m, 1H), 7.51-7.32 (m, 2H), 6.19-6.03 (m, 0.71H), 5.23-4.71 (m, 1.49H), 3.75-2.94 (m, 3H), 2.58-2.38 (m, 2H), 2.21 (d, J=1.8 Hz, 1H), 1.79-1.63 (m, 1.66H), 1.53-1.43 (m, 1.32H). MS (ESI) mass calcd. $C_{19}H_{17}F_3N_6O$, 402.1; m/z found, 403.2 [M+H]$^+$.

Example 279: (2,4-dichlorophenyl)(4-methyl-1-(pyrazin-2-yl)-6,7-dihydro-1H-[1,2,3]triazolo[4,5-c]pyridin-5(4H)-yl)methanone

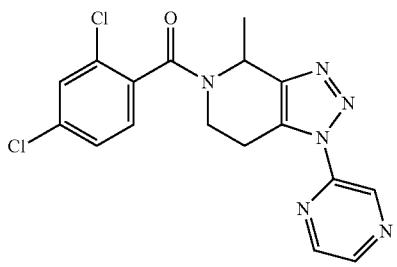 [SMILES: CC1c2nnn(-c3cnccn3)c2CCN1C(=O)c1ccc(Cl)cc1Cl]

$^1$H NMR (400 MHz, CDCl$_3$) δ 9.60-9.45 (m, 1H), 8.72-8.59 (m, 0.81H), 8.50 (s, 0.39H), 8.41 (dd, J=2.5, 1.5 Hz, 0.44H), 7.60-7.28 (m, 3H), 6.06 (d, J=6.8 Hz, 0.56H), 5.14-4.80 (m, 1.23H), 3.74-2.83 (m, 3.62H), 1.77-1.64 (m, 1.36H). MS (ESI) mass calcd. C$_{17}$H$_{14}$Cl$_2$N$_6$O, 388.1; m/z found, 389.1 [M+H]$^+$.

Example 280: (4-chloro-2-fluorophenyl)(1-(pyrimidin-2-yl)-6,7-dihydro-1H-[1,2,3]triazolo[4,5-c]pyridin-5(4H)-yl)methanone

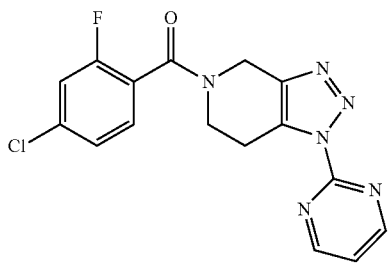 [SMILES: O=C(c1ccc(Cl)cc1F)N1CCc2c(nnn2-c2ncccn2)C1]

$^1$H NMR (400 MHz, CDCl$_3$) δ 9.06-8.74 (m, 2H), 7.57-7.30 (m, 2H), 7.25-7.11 (m, 2.5H), 5.47-4.95 (m, 0.881H), 4.66 (s, 1.31H), 3.66 (s, 1H), 3.51-3.19 (m, 2H). MS (ESI) mass calcd. C$_{16}$H$_{12}$ClFN$_6$O, 358.1; m/z found, 359.1 [M+H]$^+$.

Example 281: (2-methyl-3-(trifluoromethyl)phenyl)(1-(pyrimidin-2-yl)-6,7-dihydro-1H-[1,2,3]triazolo[4,5-c]pyridin-5(4H)-yl)methanone Duncan fix

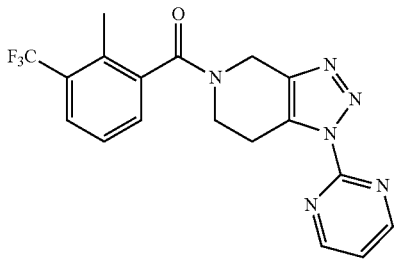 [SMILES: Cc1c(C(=O)N2CCc3c(nnn3-c3ncccn3)C2)cccc1C(F)(F)F]

$^1$H NMR (400 MHz, CDCl$_3$) δ 9.03-8.78 (m, 2H), 7.71 (td, J=6.4, 2.6 Hz, 1H), 7.48-7.32 (m, 3H), 5.29 (d, J=16.6 Hz, 0.57H), 4.97 (d, J=16.4 Hz, 0.58H), 4.50 (d, J=1.1 Hz, 1H), 4.37-4.21 (m, 0.48H), 4.09 (d, J=6.5 Hz, 0.63H), 3.71-3.48 (m, 1H), 3.45 (d, J=5.1 Hz, 1H), 3.22 (s, 0.88H), 2.41 (dd, J=41.9, 1.7 Hz, 3H).

MS (ESI) mass calcd. C$_{18}$H$_{15}$F$_3$N$_6$O, 388.1; m/z found, 389.1 [M+H]$^+$.

Example 282: (4-methyl-1-(pyrimidin-2-yl)-6,7-dihydro-1H-[1,2,3]triazolo[4,5-c]pyridin-5(4H)-yl)(2-methyl-3-(trifluoromethyl)phenyl)methanone

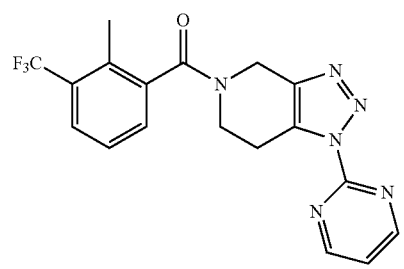 [SMILES: Cc1c(C(=O)N2CCc3c(nnn3-c3ncccn3)C2)cccc1C(F)(F)F]

$^1$H NMR (400 MHz, CDCl$_3$) δ 8.90 (d, J=4.8 Hz, 1H), 8.85 (d, J=4.8 Hz, 1H), 7.70 (d, J=6.6 Hz, 1H), 7.50-7.33 (m, 3H), 6.19-6.04 (m, 0.5H), 5.24-4.65 (m, 1.5H), 3.77-2.96 (m, 2H), 2.57-2.36 (m, 3H), 2.20 (d, J=1.8 Hz, 1H), 1.77-1.65 (m 1H), 1.53-1.43 (m, 2H).

MS (ESI) mass calcd. C$_{19}$H$_{17}$F$_3$N$_6$O, 402.1; m/z found, 403.2[M+H]$^+$.

Example 283: (2,4-dichlorophenyl)(4-methyl-1-(pyrimidin-2-yl)-6,7-dihydro-1H-[1,2,3]triazolo[4,5-c]pyridin-5(4H)-yl)methanone

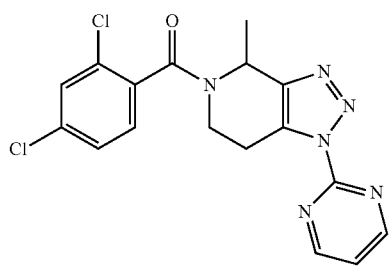 [SMILES: CC1c2nnn(-c3ncccn3)c2CCN1C(=O)c1ccc(Cl)cc1Cl]

$^1$H NMR (400 MHz, CDCl$_3$) δ 8.96-8.79 (m, 2H), 7.48 (d, J=2.0 Hz, 1H), 7.45-7.29 (m, 1H), 6.06 (q, J=6.8 Hz, 0.5H), 5.11 (dd, J=13.2, 5.4 Hz, 0.5H), 4.81 (d, J=6.9 Hz, 0.5H), 3.75-2.87 (m, 4H), 1.77-1.64 (m, 1.5H), 1.49 (d, J=6.8 Hz, 0.5H). MS (ESI) mass calcd. C$_{17}$H$_{14}$Cl$_2$N$_6$O, 388.1; m/z found, 389.1 [M+H]$^+$.

Example 284: (2-chloro-3-(trifluoromethyl)phenyl) ((4R,6R)-1-(4-fluorophenyl)-4,6-dimethyl-6,7-di-hydro-1H-[1,2,3]triazolo[4,5-c]pyridin-5(4H)-yl) methanone

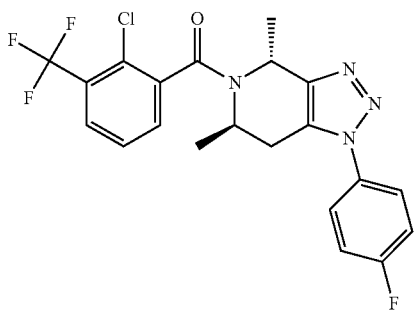 [SMILES: C[C@@H]1Cc2c(nnn2-c2ccc(F)cc2)[C@@H](C)N1C(=O)c1cccc(C(F)(F)F)c1Cl]

MS (ESI) mass calcd. $C_{21}H_{17}ClF_4N_4O$, 452.1; m/z found, 452.8 [M+H]$^+$.

Example 285: (2-chloro-3-(trifluoromethyl)phenyl) ((4S,6S)-1-(4-fluorophenyl)-4,6-dimethyl-6,7-di-hydro-1H-[1,2,3]triazolo[4,5-c]pyridin-5(4H)-yl) methanone

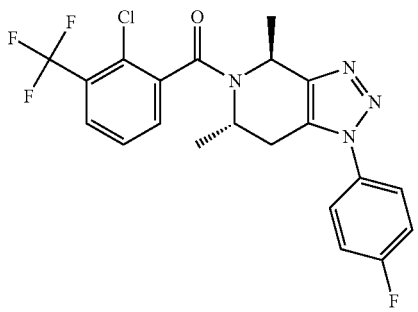 [SMILES: C[C@H]1Cc2c(nnn2-c2ccc(F)cc2)[C@H](C)N1C(=O)c1cccc(C(F)(F)F)c1Cl]

MS (ESI) mass calcd. $C_{21}H_{17}ClF_4N_4O$, 452.1; m/z found, 452.8 [M+H]$^+$.

Example 286: (2-chloro-3-(trifluoromethyl)phenyl) ((4S,6R)-1-(4-fluorophenyl)-4,6-dimethyl-6,7-di-hydro-1H-[1,2,3]triazolo[4,5-c]pyridin-5(4H)-yl) methanone

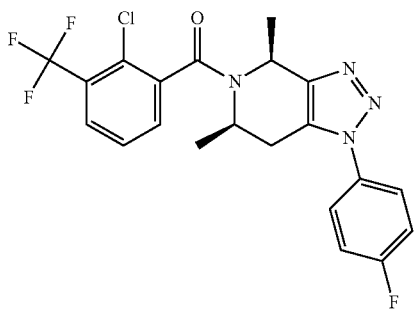 [SMILES: C[C@@H]1Cc2c(nnn2-c2ccc(F)cc2)[C@H](C)N1C(=O)c1cccc(C(F)(F)F)c1Cl]

MS (ESI) mass calcd. $C_{21}H_{17}ClF_4N_4O$, 452.1; m/z found, 452.8 [M+H]$^+$.

Example 287: (2-chloro-3-(trifluoromethyl)phenyl) ((4R,6S)-1-(4-fluorophenyl)-4,6-dimethyl-6,7-di-hydro-1H-[1,2,3]triazolo[4,5-c]pyridin-5(4H)-yl) methanone

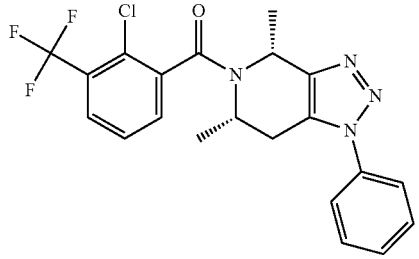 [SMILES: C[C@@H]1c2nnn(-c3ccccc3)c2C[C@H](C)N1C(=O)c1cccc(C(F)(F)F)c1Cl]

MS (ESI) mass calcd. $C_{21}H_{17}ClF_4N_4O$, 452.1; m/z found, 452.8 [M+H]$^+$.

288: (S)-(2-chloro-3-(trifluoromethyl)phenyl)(6-methyl-1-phenyl-6,7-dihydro-1H-[1,2,3]triazolo[4,5-c]pyridin-5(4H)-yl)methanone

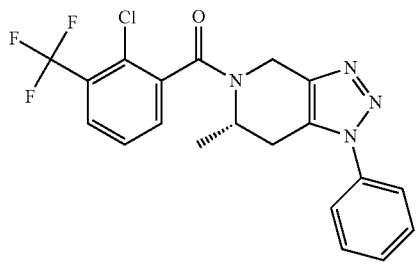 [SMILES: C[C@H]1Cc2c(nnn2-c2ccccc2)CN1C(=O)c1cccc(C(F)(F)F)c1Cl]

MS (ESI) mass calcd. $C_{20}H_{16}ClF_3N_4O$, 420.1; m/z found, 421.0 [M+H]$^+$.

Example 289: (2-chloro-3-(trifluoromethyl)phenyl) (4-methyl-3-phenyl-6,7-dihydro-3H-[1,2,3]triazolo [4,5-c]pyridin-5(4H)-yl)methanone

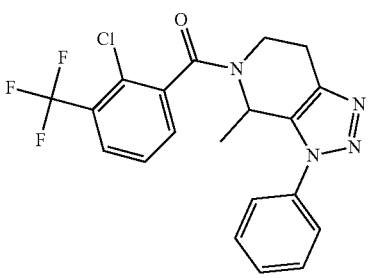 [SMILES: CC1c2c(nnn2-c2ccccc2)CCN1C(=O)c1cccc(C(F)(F)F)c1Cl]

MS (ESI) mass calcd. $C_{20}H_{16}ClF_3N_4O$, 420.1; m/z found, 421.0 [M+H]$^+$.

Example 290: (2-chloro-3-(trifluoromethyl)phenyl)(6-methyl-1-phenyl-6,7-dihydro-1H-[1,2,3]triazolo[4,5-c]pyridin-5(4H)-yl)methanone

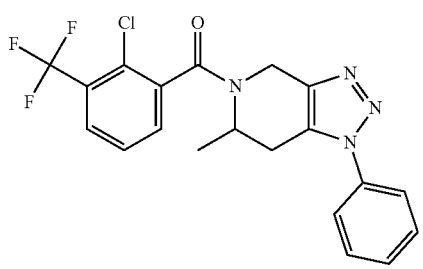 [SMILES: CC1Cc2c(nnn2-c2ccccc2)CN1C(=O)c1cccc(C(F)(F)F)c1Cl]

MS (ESI) mass calcd. C₂₀H₁₆ClF₃N₄O, 420.1; m/z found, 421.0 [M+H]⁺.

Example 291: (R*)-(2-chloro-3-(trifluoromethyl)phenyl)(4-methyl-1-(3-methylpyridin-2-yl)-6,7-dihydro-1H-[1,2,3]triazolo[4,5-c]pyridin-5(4H)-yl)methanone

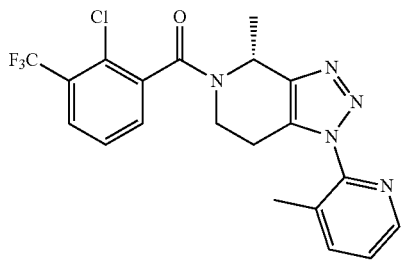 [SMILES: Cc1cccnc1-n1nnc2c1CCN(C(=O)c1cccc(C(F)(F)F)c1Cl)[C@@H]2C]

MS (ESI) mass calcd. C₂₀H₁₇ClF₃N₅O, 435.1; m/z found, 436.0 [M+H]⁺.

Example 292: (S*)-(2-chloro-3-(trifluoromethyl)phenyl)(4-methyl-1-(3-methylpyridin-2-yl)-6,7-dihydro-1H-[1,2,3]triazolo[4,5-c]pyridin-5(4H)-yl)methanone

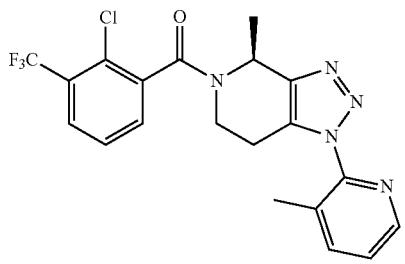 [SMILES: Cc1cccnc1-n1nnc2c1CCN(C(=O)c1cccc(C(F)(F)F)c1Cl)[C@H]2C]

MS (ESI) mass calcd. C₂₀H₁₇ClF₃N₅O, 435.1; m/z found, 436.0 [M+H]⁺.

Example 293: (2-chloro-3-(trifluoromethyl)phenyl)(4-methyl-1-(3-propoxypyridin-2-yl)-6,7-dihydro-1H-[1,2,3]triazolo[4,5-c]pyridin-5(4H)-yl)methanone

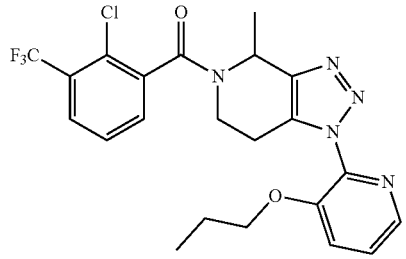 [SMILES: CCCOc1cccnc1-n1nnc2c1CCN(C(=O)c1cccc(C(F)(F)F)c1Cl)C2C]

MS (ESI) mass calcd. C₂₂H₂₁ClF₃N₅O₂, 479.1; m/z found, 480.0 [M+H]⁺.

Example 294: (R*)-(2-chloro-3-(trifluoromethyl)phenyl)(1-(4-ethylpyrimidin-2-yl)-4-methyl-6,7-dihydro-1H-[1,2,3]triazolo[4,5-c]pyridin-5(4H)-yl)methanone

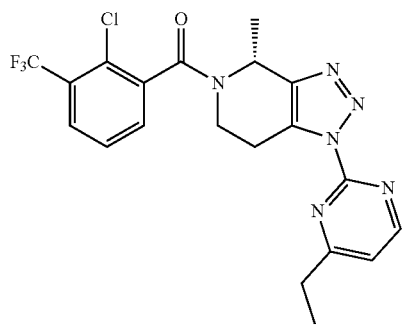 [SMILES: CCc1ccnc(-n2nnc3c2CCN(C(=O)c2cccc(C(F)(F)F)c2Cl)[C@@H]3C)n1]

MS (ESI) mass calcd. C₂₀H₁₈ClF₃N₆O, 450.1; m/z found, 451.0 [M+H]⁺.

Example 295: (1-(3-ethylpyridin-2-yl)-4-methyl-6,7-dihydro-1H-[1,2,3]triazolo[4,5-c]pyridin-5(4H)-yl)(3-(trifluoromethyl)phenyl)methanone

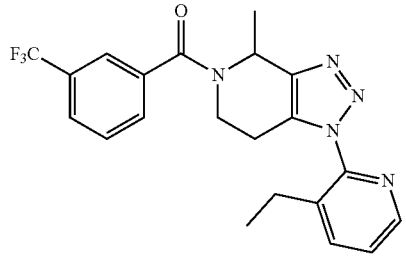 [SMILES: CCc1cccnc1-n1nnc2c1CCN(C(=O)c1cccc(C(F)(F)F)c1)C2C]

MS (ESI) mass calcd. C₂₁H₂₀F₃N₅O, 415.1; m/z found, 416.1 [M+H]⁺.

Example 296: (2-chloro-3-(trifluoromethyl)phenyl) ((4R,6R)-4,6-dimethyl-1-(1H-pyrazol-5-yl)-6,7-dihydro-1H-[1,2,3]triazolo[4,5-c]pyridin-5(4H)-yl)methanone

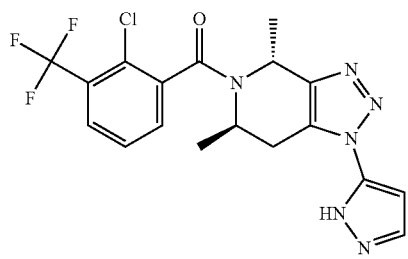 [SMILES: C[C@@H]1Cc2c(nnn2-c2ccn[nH]2)[C@@H](C)N1C(=O)c1cccc(C(F)(F)F)c1Cl]

MS (ESI) mass calcd. $C_{18}H_{16}ClF_3N_6O$, 424.1; m/z found, [M+H]$^+$.

Example 297: (2-chloro-3-(trifluoromethyl)phenyl) ((4S,6R)-4,6-dimethyl-1-(1H-pyrazol-5-yl)-6,7-dihydro-1H-[1,2,3]triazolo[4,5-c]pyridin-5(4H)-yl) methanone

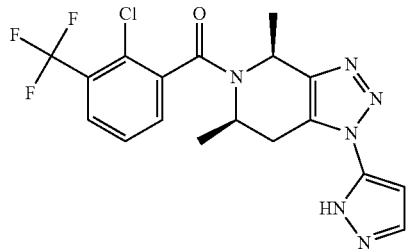 [SMILES: C[C@@H]1Cc2c(nnn2-c2ccn[nH]2)[C@H](C)N1C(=O)c1cccc(C(F)(F)F)c1Cl]

MS (ESI) mass calcd. $C_{18}H_{16}ClF_3N_6O$, 424.1; m/z found, 425.1 [M+H]$^+$.

Example 298: (2-chloro-3-(trifluoromethyl)phenyl) (4,6-dimethyl-1-(1H-pyrazol-5-yl)-6,7-dihydro-1H-[1,2,3]triazolo[4,5-c]pyridin-5(4H)-yl)methanone

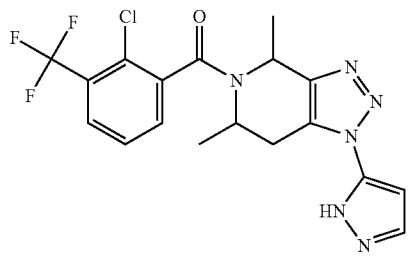 [SMILES: CC1Cc2c(nnn2-c2ccn[nH]2)C(C)N1C(=O)c1cccc(C(F)(F)F)c1Cl]

MS (ESI) mass calcd. $C_{18}H_{16}ClF_3N_6O$, 424.1; m/z found, 425.2 [M+H]$^+$.

Example 299: (2-chloro-3-(trifluoromethyl)phenyl) (4-methyl-1-(4-methylpyridin-2-yl)-6,7-dihydro-1H-[1,2,3]triazolo[4,5-c]pyridin-5(4H)-yl)methanone

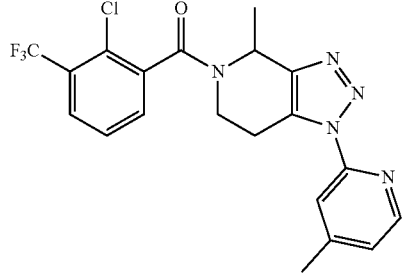 [SMILES: Cc1ccnc(-n2nnc3c2CCN(C(=O)c2cccc(C(F)(F)F)c2Cl)C3C)c1]

$^1$H NMR (400 MHz, CDCl$_3$) δ 8.41-8.24 (m, 1H), 8.03-7.91 (m, 1H), 7.82-7.72 (m, 1H), 7.61-7.29 (m, 2H), 7.21-7.11 (m, 1H), 6.18-5.90 (m, 0.6H), 5.18-5.02 (m, 0.4H), 4.96-4.66 (m, 0.4H), 3.72-2.92 (m, 3.6H), 2.63-2.37 (s, 3H), 1.87-1.40 (m, 3H). MS (ESI) mass calcd $C_{20}H_{17}ClF_3N_5O$, 435.1; m/z found, 436.1 [M+H]$^+$.

Example 300: (2-chloro-3-(trifluoromethyl)phenyl) (1-(4,6-dimethylpyridin-2-yl)-4-methyl-6,7-dihydro-1H-[1,2,3]triazolo[4,5-c]pyridin-5(4H)-yl)methanone

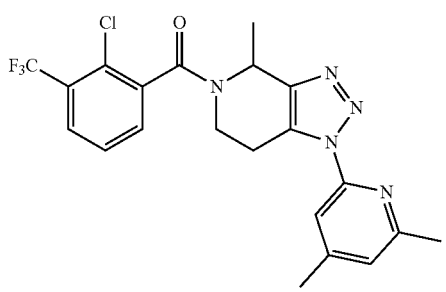 [SMILES: Cc1cc(C)nc(-n2nnc3c2CCN(C(=O)c2cccc(C(F)(F)F)c2Cl)C3C)c1]

$^1$H NMR (400 MHz, CDCl$_3$) δ 7.84-7.69 (m, 2H), 7.60-7.29 (m, 2H), 7.09-6.93 (m, 1H), 6.19-5.92 (m, 0.6H), 5.25-5.01 (m, 0.4H), 4.94-4.66 (m, 0.4H), 3.68-2.93 (m, 3.6H), 2.62-2.33 (m, 6H), 1.81-1.42 (m, 3H). MS (ESI) mass calcd $C_{21}H_{19}ClF_3N_5O$, 449.1; m/z found, 450.1 [M+H]$^+$.

Example 301: (2-chloro-3-(trifluoromethyl)phenyl) (4-methyl-1-(5-methylpyridin-2-yl)-6,7-dihydro-1H-[1,2,3]triazolo[4,5-c]pyridin-5(4H)-yl)methanone

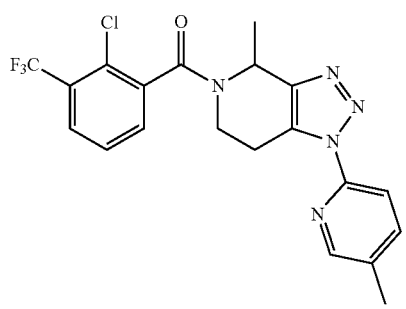 [SMILES: Cc1ccc(-n2nnc3c2CCN(C(=O)c2cccc(C(F)(F)F)c2Cl)C3C)nc1]

¹H NMR (400 MHz, CDCl₃) δ 8.36-8.19 (m, 1H), 8.10-7.95 (m, 1H), 7.85-7.66 (m, 2H), 7.61-7.29 (m, 2H), 6.14-5.95 (m, 0.6H), 5.19-5.05 (m, 0.4H), 4.93-4.69 (m, 0.4H), 3.67-2.89 (m, 3.6H), 2.54-2.26 (d, J=10.0 Hz, 3H), 1.82-1.41 (m, 3H). MS (ESI) mass calcd C₂₀H₁₇CF₃N₅O, 435.1; m/z found, 436.1 [M+H]⁺.

Example 302: (2-chloro-3-(trifluoromethyl)phenyl)(4-methyl-1-(6-methylpyridin-2-yl)-6,7-dihydro-1H-[1,2,3]triazolo[4,5-c]pyridin-5(4H)-yl)methanone

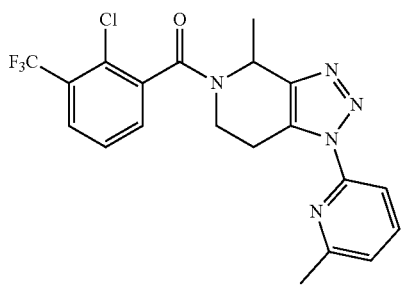 [SMILES: Cc1cccc(-n2nnc3c2CCN(C(=O)c2cccc(C(F)(F)F)c2Cl)C3C)n1]

¹H NMR (400 MHz, CDCl₃) δ 8.00-7.88 (m, 1H), 7.85-7.73 (m, 2H), 7.61-7.29 (m, 2H), 7.24-7.12 (m, 1H), 6.16-5.95 (m, 0.6H), 5.21-5.03 (m, 0.4H), 4.95-4.67 (m, 0.4H), 3.71-2.94 (m, 3.6H), 2.70-2.39 (m, 3H), 1.84-1.41 (m, 3H). MS (ESI) mass calcd C₂₀H₁₇CF₃N₅O, 435.1; m/z found, 436.1 [M+H]⁺.

Example 303: (2-chloro-3-(trifluoromethyl)phenyl)(3-(5-fluoropyrimidin-2-yl)-7-methyl-2-((2-(trimethylsilyl)ethoxy)methyl)-4,5-dihydro-2H-pyrazolo[3,4-c]pyridin-6(7H)-yl)methanone

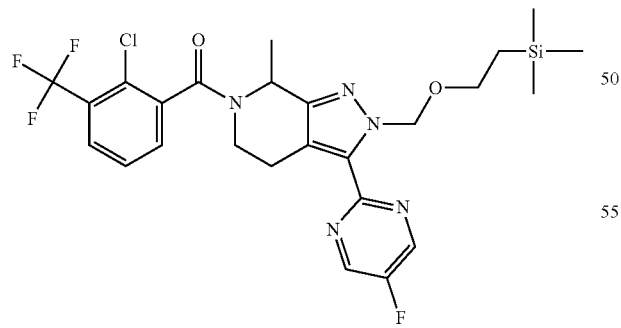

¹H NMR (400 MHz, CDCl₃) δ 8.73-8.60 (m, 2H), 7.75 (td, J=7.2, 6.8, 1.7 Hz, 1H), 7.60-7.28 (m, 2H), 6.23-5.86 (m, 2H), 5.08-4.56 (m, 1H), 3.67-3.26 (m, 3H), 3.26-2.61 (m, 2H), 1.70-1.41 (m, 4H), 0.91-0.73 (m, 2H), −0.04-0.19 (m, 9H). MS (ESI) mass calcd C₂₄H₃₂FN₅OSi, 569.2; m/z found, 570.1 [M+H]⁺.

Example 304: (S)-(1-(5-fluoropyrimidin-2-yl)-6-methyl-6,7-dihydro-1H-[1,2,3]triazolo[4,5-c]pyridin-5(4H)-yl)(3-(trifluoromethyl)phenyl)methanone

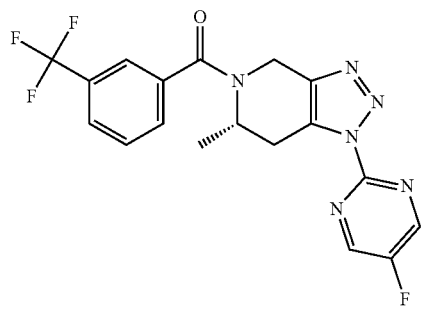 [SMILES: C[C@H]1Cc2c(nnn2-c2ncc(F)cn2)CN1C(=O)c1cccc(C(F)(F)F)c1]

MS (ESI) mass calcd C₁₈H₁₄F₄N₆O, 406.1; m/z found, 407.2 [M+H]⁺.

Example 305: (R*)-(2-chloro-3-(trifluoromethyl)phenyl)(1-(5-fluoro-4-methylpyrimidin-2-yl)-4-methyl-6,7-dihydro-1H-[1,2,3]triazolo[4,5-c]pyridin-5(4H)-yl)methanone

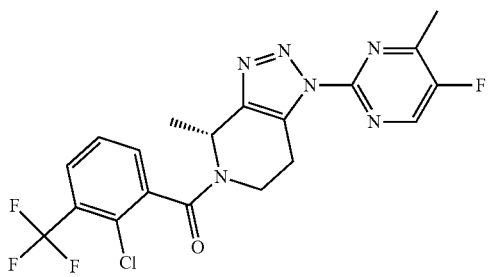 [SMILES: Cc1nc(-n2nnc3c2CCN(C(=O)c2cccc(C(F)(F)F)c2Cl)[C@@H]3C)ncc1F]

MS (ESI) mass calcd C₁₉H₁₅ClF₄N₆O, 454.1; m/z found, 454.8 [M+H]⁺.

306: (S*)-(2-chloro-3-(trifluoromethyl)phenyl)(1-(5-fluoro-4-methylpyrimidin-2-yl)-4-methyl-6,7-dihydro-1H-[1,2,3]triazolo[4,5-c]pyridin-5(4H)-yl)methanone

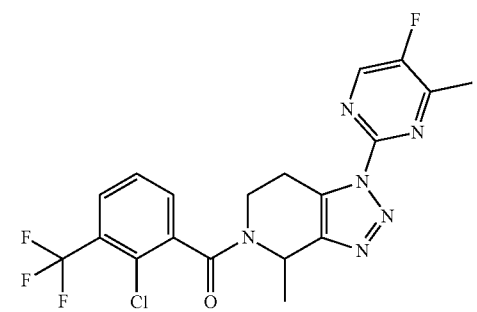 [SMILES: Cc1nc(-n2nnc3c2CCN(C(=O)c2cccc(C(F)(F)F)c2Cl)C3C)ncc1F]

MS (ESI) mass calcd C₁₉H₁₅ClF₄N₆O, 454.1; m/z found, 454.8 [M+H]⁺.

Example 307: (S)-(3-fluoro-5-(trifluoromethyl)phenyl)(1-(5-fluoropyrimidin-2-yl)-6-methyl-6,7-dihydro-1H-[1,2,3]triazolo[4,5-c]pyridin-5(4H)-yl)methanone

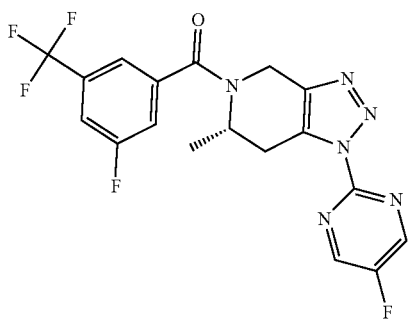 [SMILES: C[C@H]1Cc2c(nnn2-c2ncc(F)cn2)CN1C(=O)c1cc(F)cc(C(F)(F)F)c1]

MS (ESI) mass calcd $C_{18}H_{13}F_5N_6O$, 424.1; m/z found, 425.1 [M+H]$^+$.

Example 308: (2-chloro-3-(trifluoromethyl)phenyl)(7-methyl-3-(trifluoromethyl)-4,5-dihydro-1H-pyrazolo[3,4-c]pyridin-6(7H)-yl)methanone

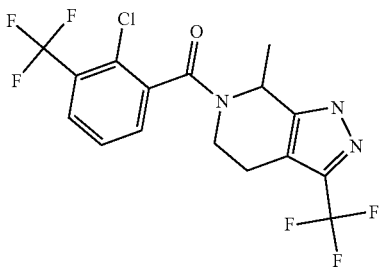 [SMILES: CC1c2[nH]nc(C(F)(F)F)c2CCN1C(=O)c1cccc(C(F)(F)F)c1Cl]

MS (ESI) mass calcd $C_{16}H_{12}ClF_6N_3O$, 411.1; m/z found, 412.0 [M+H]$^+$.

Example 309: (2-chloro-3-(trifluoromethyl)phenyl)((4S,6R)-4,6-dimethyl-1-(1H-pyrazol-5-yl)-6,7-dihydro-1H-[1,2,3]triazolo[4,5-c]pyridin-5(4H)-yl)methanone

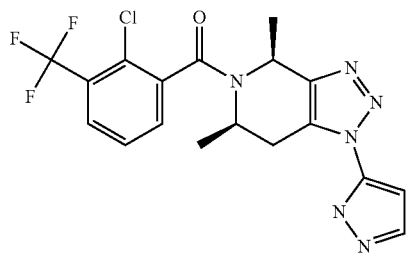

MS (ESI) mass calcd $C_{18}H_{16}ClF_3N_6O$, 424.1; m/z found, 424.7 [M+H]$^+$.

Example 310: (2-chloro-3-(trifluoromethyl)phenyl)((4R,6S)-4,6-dimethyl-1-(1H-pyrazol-5-yl)-6,7-dihydro-1H-[1,2,3]triazolo[4,5-c]pyridin-5(4H)-yl)methanone

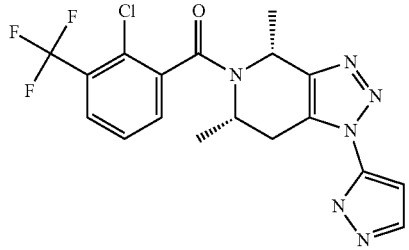

MS (ESI) mass calcd $C_{18}H_{16}ClF_3N_6O$, 424.1; m/z found, 424.7 [M+H]$^+$.

Example 311: (2-fluoro-3-(trifluoromethyl)phenyl)(1-(5-fluoropyrimidin-2-yl)-6-methyl-6,7-dihydro-1H-[1,2,3]triazolo[4,5-c]pyridin-5(4H)-yl)methanone

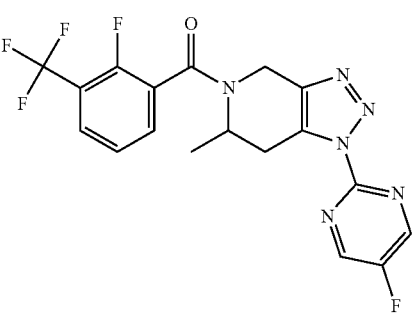 [SMILES: CC1Cc2c(nnn2-c2ncc(F)cn2)CN1C(=O)c1cccc(C(F)(F)F)c1F]

MS (ESI) mass calcd $C_{18}H_{13}F_5N_6O$, 424.1; m/z found, 425.1 [M+H]$^+$.

Example 312: (1-(5-fluoropyridin-2-yl)-6,7-dihydro-1H-imidazo[4,5-c]pyridin-5(4H)-yl)(2-methyl-3-(trifluoromethyl)phenyl)methanone

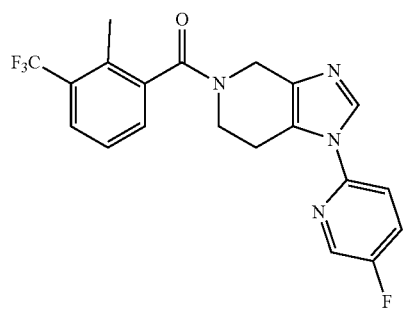 [SMILES: Cc1c(C(=O)N2CCc3c(ncn3-c3ccc(F)cn3)C2)cccc1C(F)(F)F]

$^1$H NMR (400 MHz, DMSO-d$_6$) δ 8.57 (d, J=3.0 Hz, 0.35H), 8.53 (d, J=3.0 Hz, 0.65H), 8.26 (s, 0.65H), 8.19 (s, 0.35H), 8.00 (tdd, J=8.7, 6.4, 3.1 Hz, 1H), 7.82-7.73 (m, 2H), 7.60 (d, J=7.5 Hz, 0.65H), 7.51 (p, J=4.5 Hz, 1.35H), 4.88 (d, J=15.9 Hz, 0.65H), 4.56 (d, J=16.0 Hz, 0.65H), 4.25-4.06 (m, 1H), 3.89 (dd, J=12.7, 6.3 Hz, 0.3H), 3.47-3.39 (m, 1.4H), 3.03 (t, J=5.8 Hz, 0.7H), 2.88 (d, J=6.9 Hz, 0.65H), 2.79 (d, J=16.1 Hz, 0.65H), 2.35 (d, J=1.9 Hz, 2H), 2.27 (q, J=1.7 Hz, 1H). MS (ESI) mass calcd $C_{20}H_{16}F_4N_4O$, 404.1; m/z found, 405.1 $[M+H]^+$.

Example 313: (2,4-dichlorophenyl)(1-(5-fluoropyridin-2-yl)-6,7-dihydro-1H-imidazo[4,5-c]pyridin-5(4H)-yl)methanone

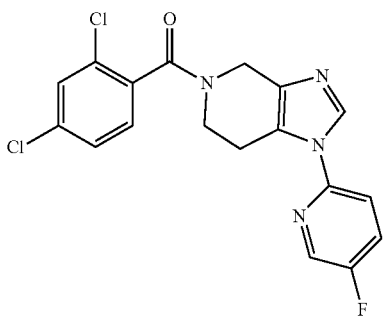 [SMILES: O=C(c1ccc(Cl)cc1Cl)N1CCc2c(ncn2-c2ccc(F)cn2)C1]

$^1$H NMR (400 MHz, DMSO-$d_6$) δ 8.57 (d, J=2.9 Hz, 0.35H), 8.53 (d, J=3.1 Hz, 0.65H), 8.26 (d, J=4.9 Hz, 0.65H), 8.19 (d, J=3.0 Hz, 0.35H), 8.04-7.96 (m, 1H), 7.82-7.73 (m, 2H), 7.58-7.42 (m, 2H), 4.78 (d, J=16.0 Hz, 0.5H), 4.58 (d, J=16.0 Hz, 0.5H), 4.30 (s, 0.2H), 4.18 (d, J=1.9 Hz, 0.5H), 4.07-3.87 (m, 0.6H), 3.59-3.40 (m, 1.4H), 3.01 (s, 0.8H), 2.88 (t, J=5.8 Hz, 1.5H). MS (ESI) mass calcd $C_{18}H_{13}Cl_2FN_4O$, 390.1; m/z found, 391.0 $[M+H]^+$.

Example 314: (2-fluoro-3-(trifluoromethyl)phenyl)(1-(5-fluoropyridin-2-yl)-6,7-dihydro-1H-imidazo[4,5-c]pyridin-5(4H)-yl)methanone

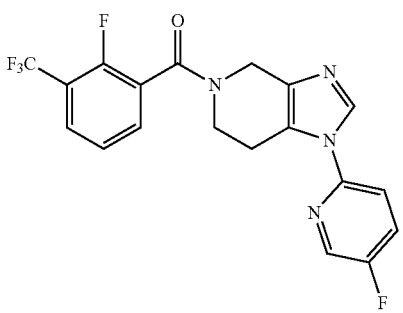 [SMILES: O=C(c1cccc(C(F)(F)F)c1F)N1CCc2c(ncn2-c2ccc(F)cn2)C1]

$^1$H NMR (400 MHz, DMSO-$d_6$) δ 8.57 (d, J=3.0 Hz, 0.35H), 8.54 (d, J=3.1 Hz, 0.65H), 8.27 (s, 0.65H), 8.20 (s, 0.35H), 8.00 (tt, J=8.3, 3.1 Hz, 1H), 7.95-7.89 (m, 1.3H), 7.86 (t, J=7.0 Hz, 0.7H), 7.80 (d, J=4.0 Hz, 0.65H), 7.77 (d, J=3.7 Hz, 0.35H), 7.54 (td, J=7.8, 4.7 Hz, 1H), 4.70 (s, 1H), 4.30 (s, 0.65H), 4.00 (t, J=5.8 Hz, 0.65H), 3.54 (t, J=5.7 Hz, 1.3H), 3.02 (s, 0.90H), 2.91 (s, 1.10H). MS (ESI) mass calcd $C_{19}H_{13}F_5N_4O$, 408.1; m/z found, 409.1 $[M+H]^+$.

Example 315: (2-chloro-3-(trifluoromethyl)phenyl)(1-(5-fluoropyridin-2-yl)-6,7-dihydro-1H-imidazo[4,5-c]pyridin-5(4H)-yl)methanone

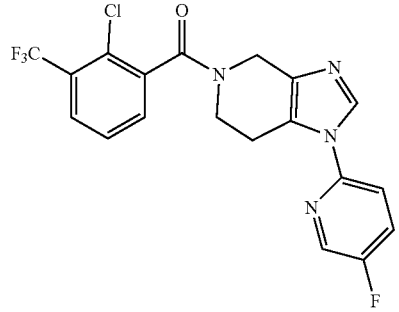 [SMILES: O=C(c1cccc(C(F)(F)F)c1Cl)N1CCc2c(ncn2-c2ccc(F)cn2)C1]

$^1$H NMR (400 MHz, DMSO-$d_6$) δ 8.57 (d, J=3.1 Hz, 0.35H), 8.53 (d, J=3.0 Hz, 0.652H), 8.27 (s, 0.65H), 8.19 (s, 0.35H), 8.05-7.93 (m, 2H), 7.84-7.72 (m, 2H), 7.67 (td, J=7.7, 3.8 Hz, 1H), 4.83 (d, J=16.0 Hz, 0.65H), 4.60 (d, J=16.1 Hz, 0.35H), 4.18 (d, J=3.0 Hz, 0.7H), 4.08-3.91 (m, 0.8H), 3.45 (q, J=5.9 Hz, 1.4H), 3.04 (d, J=6.2 Hz, 0.6H), 2.94-2.82 (m, 1.2H). MS (ESI) mass calcd $C_{19}H_{13}ClF_4N_4O$, 424.1; m/z found, 425.1 $[M+H]^+$.

316: (R*)-(2-chloro-3-(trifluoromethyl)phenyl)(1-(3-ethoxypyridin-2-yl)-4-methyl-6,7-dihydro-1H-[1,2,3]triazolo[4,5-c]pyridin-5(4H)-yl)methanone

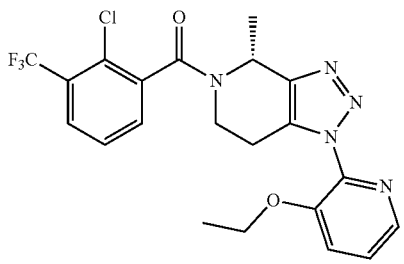 [SMILES: CCOc1cccnc1-n1nnc2c1CCN(C(=O)c1cccc(C(F)(F)F)c1Cl)[C@@H]2C]

MS (ESI) mass calcd $C_{21}H_{19}ClF_3N_5O_2$, 465.1; m/z found, 465.8 $[M+H]^+$.

Example 317: (S*)-(2-chloro-3-(trifluoromethyl)phenyl)(1-(3-ethoxypyridin-2-yl)-4-methyl-6,7-dihydro-1H-[1,2,3]triazolo[4,5-c]pyridin-5(4H)-yl)methanone

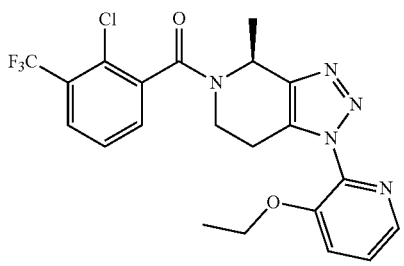 [SMILES: CCOc1cccnc1-n1nnc2c1CCN(C(=O)c1cccc(C(F)(F)F)c1Cl)[C@H]2C]

MS (ESI) mass calcd $C_{21}H_{19}ClF_3N_5O_2$, 465.1; m/z found, 465.8 $[M+H]^+$.

Example 318: (S*)-(2-chloro-3-(trifluoromethyl)phenyl)(1-(1-(2-hydroxyethyl)-1H-pyrazol-3-yl)-4-methyl-6,7-dihydro-1H-[1,2,3]triazolo[4,5-c]pyridin-5(4H)-yl)methanone

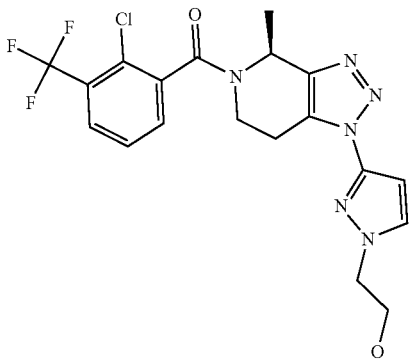 [SMILES: C[C@H]1c2nnn(-c3ccn(CCO)n3)c2CCN1C(=O)c1cccc(C(F)(F)F)c1Cl]

MS (ESI) mass calcd $C_{19}H_{18}ClF_3N_6O_2$, 454.1; m/z found, 455.1 [M+H]$^+$.

Example 319: (2-chloro-3-(trifluoromethyl)phenyl)((4S,6S)-4,6-dimethyl-1-(1H-pyrazol-5-yl)-6,7-dihydro-1H-[1,2,3]triazolo[4,5-c]pyridin-5(4H)-yl)methanone

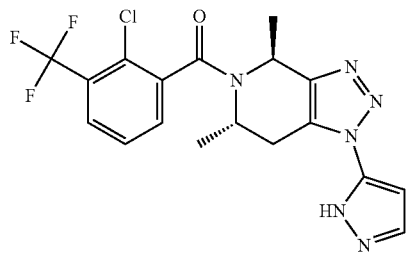 [SMILES: C[C@H]1Cc2c(nnn2-c2ccn[nH]2)[C@H](C)N1C(=O)c1cccc(C(F)(F)F)c1Cl]

MS (ESI) mass calcd $C_{18}H_{16}ClF_3N_6O$, 424.1; m/z found, 425.1 [M+H]$^+$.

Example 320: (2-chloro-3-(trifluoromethyl)phenyl)((4R,6R)-4,6-dimethyl-1-(1H-pyrazol-5-yl)-6,7-dihydro-1H-[1,2,3]triazolo[4,5-c]pyridin-5(4H)-yl)methanone

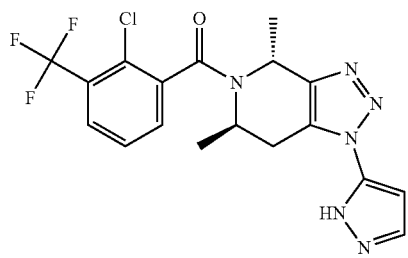 [SMILES: C[C@@H]1Cc2c(nnn2-c2ccn[nH]2)[C@@H](C)N1C(=O)c1cccc(C(F)(F)F)c1Cl]

MS (ESI) mass calcd $C_{18}H_{16}ClF_3N_6O$, 424.1; m/z found, 425.1 [M+H]$^+$.

Example 321: (2-chloro-3-(trifluoromethyl)phenyl)(1-(5-fluoropyridin-2-yl)-4-methyl-1H-imidazo[4,5-c]pyridin-5(4H)-yl)methanone

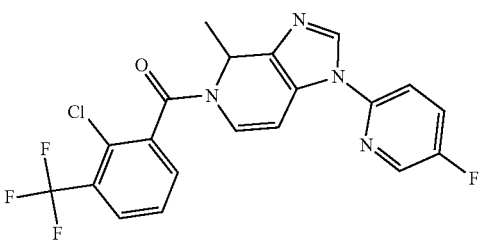 [SMILES: CC1c2ncn(-c3ccc(F)cn3)c2C=CN1C(=O)c1cccc(C(F)(F)F)c1Cl]

MS (ESI) mass calcd $C_{20}H_{13}ClF_4N_4O$, 436.1; m/z found, 437.1 [M+H]$^+$.

Example 322: (3-phenyl-4,5-dihydro-1H-pyrazolo[3,4-c]pyridin-6(7H)-yl)(2-(trifluoromethyl)pyridin-3-yl)methanone

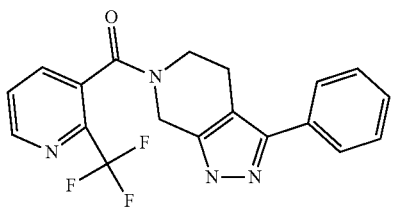 [SMILES: O=C(c1cccnc1C(F)(F)F)N1CCc2c(-c3ccccc3)n[nH]c2C1]

MS (ESI) mass calcd $C_{19}H_{15}F_3N_4O$, 372.1; m/z found, 373.1 [M+H]$^+$.

Example 323: (2-chloro-4-fluorophenyl)(3-phenyl-4,5-dihydro-1H-pyrazolo[3,4-c]pyridin-6(7H)-yl)methanone

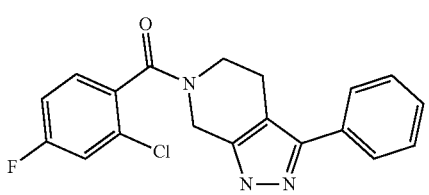 [SMILES: O=C(c1ccc(F)cc1Cl)N1CCc2c(-c3ccccc3)n[nH]c2C1]

MS (ESI) mass calcd $C_{19}H_{15}ClFN_3O$, 355.1; m/z found, 356.1 [M+H]$^+$.

Example 324: (2,6-dichlorophenyl)(3-phenyl-4,5-dihydro-1H-pyrazolo[3,4-c]pyridin-6(7H)-yl)methanone

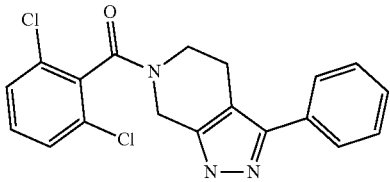 [SMILES: O=C(c1c(Cl)cccc1Cl)N1CCc2c(-c3ccccc3)n[nH]c2C1]

MS (ESI) mass calcd C$_{19}$H$_{15}$Cl$_2$N$_3$O, 371.1; m/z found, 372.1 [M+H]$^+$.

Example 325: (2-chloro-6-fluorophenyl)(3-phenyl-4,5-dihydro-1H-pyrazolo[3,4-c]pyridin-6(7H)-yl)methanone

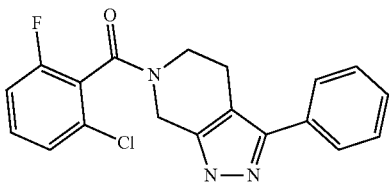 [SMILES: O=C(c1c(F)cccc1Cl)N1CCc2c(-c3ccccc3)n[nH]c2C1]

MS (ESI) mass calcd C$_{19}$H$_{15}$ClFN$_3$O, 355.1; m/z found, 356.1 [M+H]$^+$.

Example 326: (2,3-dichlorophenyl)(3-(4-fluorophenyl)-2-methyl-4,5-dihydro-2H-pyrazolo[3,4-c]pyridin-6(7H)-yl)methanone

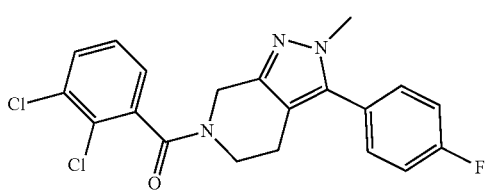 [SMILES: Cn1nc2c(c1-c1ccc(F)cc1)CCN(C(=O)c1cccc(Cl)c1Cl)C2]

MS (ESI) mass calcd C$_{20}$H$_{16}$Cl$_2$FN$_3$O, 403.1; m/z found, 404.1 [M+H]$^+$.

Example 327: (2-chloro-3-(trifluoromethyl)phenyl)(2-methyl-3-(pyridin-4-yl)-4,5-dihydro-2H-pyrazolo[3,4-c]pyridin-6(7H)-yl)methanone

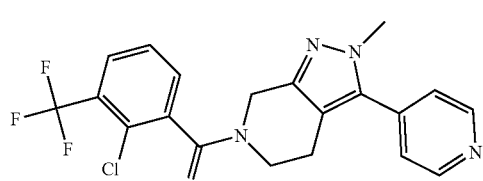

MS (ESI) mass calcd C$_{20}$H$_{16}$ClF$_3$N$_4$O, 420.1; m/z found, 421.1 [M+H]$^+$.

Example 328: (2,3-dichlorophenyl)(2-methyl-3-(pyridin-4-yl)-4,5-dihydro-2H-pyrazolo[3,4-c]pyridin-6(7H)-yl)methanone

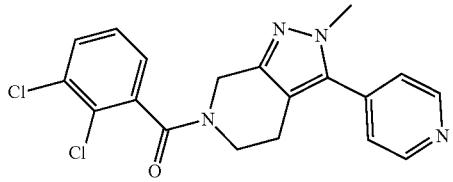 [SMILES: Cn1nc2c(c1-c1ccncc1)CCN(C(=O)c1cccc(Cl)c1Cl)C2]

MS (ESI) mass calcd C$_{19}$H$_{16}$Cl$_2$N$_4$O, 386.1; m/z found, 387.1 [M+H]$^+$.

Example 329: (2,3-dichlorophenyl)(2-methyl-3-(pyrimidin-5-yl)-4,5-dihydro-2H-pyrazolo[3,4-c]pyridin-6(7H)-yl)methanone

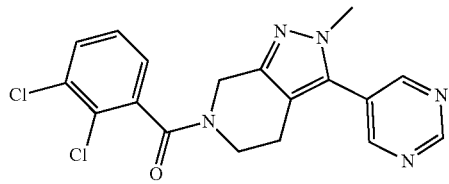 [SMILES: Cn1nc2c(c1-c1cncnc1)CCN(C(=O)c1cccc(Cl)c1Cl)C2]

MS (ESI) mass calcd C$_{18}$H$_{15}$Cl$_2$N$_5$O, 387.1; m/z found, [M+H]$^+$.

Example 330: (2,3-dichlorophenyl)(3-(pyrimidin-5-yl)-4,5-dihydro-2H-pyrazolo[3,4-c]pyridin-6(7H)-yl)methanone

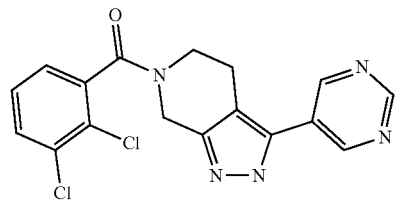 [SMILES: O=C(c1cccc(Cl)c1Cl)N1CCc2c(n[nH]c2-c2cncnc2)C1]

MS (ESI) mass calcd C$_{17}$H$_{13}$Cl$_2$N$_5$O, 373.0; m/z found, 374.1 [M+H]$^+$.

Example 331: (2,3-dichlorophenyl)(2-methyl-1-phenyl-6,7-dihydro-1H-imidazo[4,5-c]pyridin-5(4H)-yl)methanone

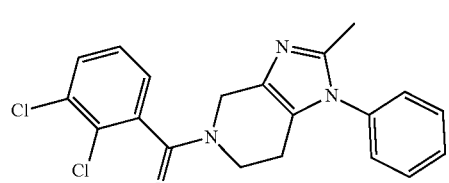

MS (ESI) mass calcd C$_{20}$H$_{17}$Cl$_2$NO, 385.1 m/z found, [M+H]$^+$.

Example 332 (2,3-dichlorophenyl)(2-ethyl-1-phenyl-6,7-dihydro-1H-imidazo[4,5-c]pyridin-5(4H)-yl)methanone

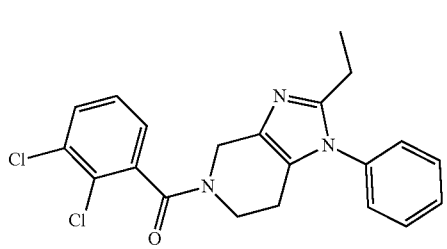 [SMILES: CCc1nc2c(n1-c1ccccc1)CCN(C(=O)c1cccc(Cl)c1Cl)C2]

MS (ESI) mass calcd $C_{21}H_{19}Cl_2N_3O$, 399.1 m/z found, [M+H]$^+$.

Example 333 (S)-(2-chloro-3-(trifluoromethyl)phenyl)(4-methyl-1-(pyrimidin-5-yl)-6,7-dihydro-1H-[1,2,3]triazolo[4,5-c]pyridin-5(4H)-yl)methanone

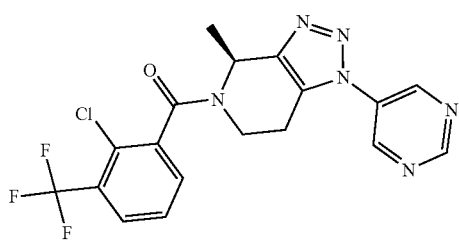 [SMILES: C[C@H]1c2nnn(-c3cncnc3)c2CCN1C(=O)c1cccc(C(F)(F)F)c1Cl]

MS (ESI) mass calcd $C_{18}H_{14}ClF_3N_6O$, 422.1 m/z found, 423.1 [M+H]$^+$.

Example 334 (R*)-(2-chloro-3-(trifluoromethyl)phenyl)(4-methyl-1-(pyrimidin-5-yl)-6,7-dihydro-1H-[1,2,3]triazolo[4,5-c]pyridin-5(4H)-yl)methanone

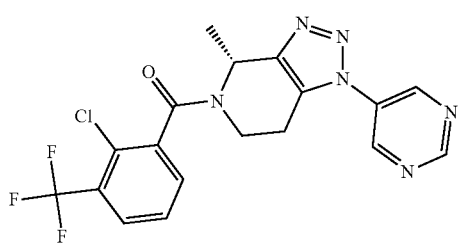 [SMILES: C[C@@H]1c2nnn(-c3cncnc3)c2CCN1C(=O)c1cccc(C(F)(F)F)c1Cl]

MS (ESI) mass calcd $C_{18}H_{14}ClF_3N_6O$, 422.1 m/z found, 423.1 [M+H]$^+$.

Example 336 (2,3-dichlorophenyl)(4-methyl-1-(5-methylpyridin-2-yl)-6,7-dihydro-1H-[1,2,3]triazolo[4,5-c]pyridin-5(4H)-yl)methanone

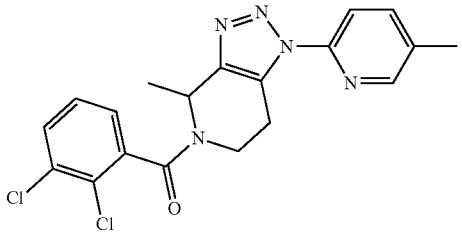 [SMILES: Cc1ccc(-n2nnc3c2CCN(C(=O)c2cccc(Cl)c2Cl)C3C)nc1]

MS (ESI) mass calcd $C_{19}H_{17}Cl_2N_5O$, 401.1 m/z found, 402.1 [M+H]$^+$. $^1$H NMR (400 MHz, CDCl$_3$) δ 8.38-8.19 (m, 1H), 8.09-7.94 (m, 1H), 7.79-7.64 (m, 1H), 7.59-7.46 (m, 1H), 7.42-6.98 (m, 2H), 6.20-5.92 (m, 0.6H), 5.17-5.04 (m, 0.4H), 4.99-4.69 (m, 0.4H), 3.82-2.90 (m, 3.6H), 2.57-2.24 (m, 3H), 2.12-1.25 (m, 3H).

Example 337 Alternative synthesis of Example 88: (2-chloro-3-(trifluoromethyl)phenyl)(4-methyl-1-(pyrimidin-2-yl)-6,7-dihydro-1H-[1,2,3]triazolo[4,5-c]pyridin-5(4H)-yl)methanone Intermediate 233: N-(but-3-yn-2-yl)-2-chloro-3-(trifluoromethyl)benzamide

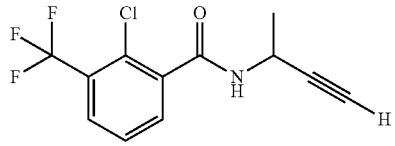 [SMILES: C#CC(C)NC(=O)c1cccc(C(F)(F)F)c1Cl]

To the suspension of but-3-yn-2-amine HCl salt (10 g, 94.7 mmol, 1.0 equiv.) in THF (150 mL), Et$_3$N (27.5 mL, 199 mmol, 2.1 equiv.) and (2-chloro-3-(trifluoromethyl)benzoyl chloride (23.1 g, 94.7 mmol, 1.0 equiv.) were added sequentially at 0° C. The reaction mixture was then stirred at room temperature for 16 hours. The precipitate was filtered off and washed with THF. The filtrate solution was concentrated and re-dissolved in EtOAc. The EtOAc solution was washed with saturated NaHCO$_3$ and brine, dried over Na$_2$SO$_4$, concentrated. Trituration of the crude product from EtOAc/hexanes afforded Intermediate 233: (23 g, 83.8 mmol, 88%) as a white solid. $^1$H NMR (600 MHz, CDCl$_3$) δ 7.82-7.75 (dd, J=7.9, 1.6 Hz, 1H), 7.73-7.66 (dd, J=7.7, 1.6 Hz, 1H), 7.48-7.41 (dd, J=8.2, 7.3 Hz, 1H), 6.35-6.02 (d, J=7.9 Hz, 1H), 5.09-4.90 (dqd, J=8.1, 6.9, 2.3 Hz, 1H), 2.47-2.20 (m, 1H), 1.58-1.54 (d, J=6.9 Hz, 3H). $^{13}$C NMR (151 MHz, CDCl$_3$) δ 164.7, 137.9, 132.5, 129.4 (q, $J_{C-F}$=31.5 Hz), 129.1, 129.0 (q, $J_{C-F}$=5.2 Hz), 127.1, 122.5 (q, $J_{C-F}$=273.4 Hz), 83.2, 71.2, 37.8, 22.1. HRMS-ESI (m/z): [M+H]$^+$ calcd for $C_{12}H_{10}ClF_3NO$, 276.0398; found, 276.0390.

Intermediate 235: N-(1-(5-allyl-1-(pyrimidin-2-yl)-1H-1,2,3-triazol-4-yl)ethyl)-2-chloro-3-(trifluoromethyl)benzamide

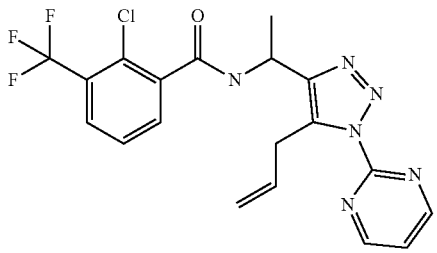 [SMILES: C=CCc1c(C(C)NC(=O)c2cccc(C(F)(F)F)c2Cl)nnn1-c1ncccn1]

Method 1: To the suspension of Intermediate 233 (138 mg, 0.5 mmol, 1.0 equiv), tetrazolo[1,5-a]pyrimidine (Intermediate 234) (67 mg, 0.55 mmol, 1.1 equiv.), allyl bromide (73 mg, 0.6 mmol, 1.2 equiv.) and $Cs_2CO_3$ (0.49 g, 1.5 mmol, 3.0 equiv.) in THF (2 mL), CuI (48 mg, 0.25 mmol, 0.5 equiv.) was added at room temperature in one portion under $N_2$. The reaction mixture was then stirred at room temperature under $N_2$ for 16 hours. Celite and EtOAc (5 mL) were added and the suspension was stirred for 20 minutes. The insoluble solid was filtered off and washed with EtOAc. The filtrate solution was washed with brine, dried over $Na_2SO_4$ and concentrated. The crude product was purified by column chromatography with EtOAc/hexanes as eluents to afford compound Intermediate 235 (146 mg, 0.34 mmol, 67% yield) as a white solid. Byproducts Intermediate 236 (30 mg, 0.075 mmol, 15% yield) and Intermediate 237 (2% yield) were also isolated.

Method 2: To the suspension of compound Intermediate 233 (138 mg, 0.5 mmol, 1.0 equiv), tetrazolo[1,5-a]pyrimidine (Intermediate 234) (67 mg, 0.55 mmol, 1.1 equiv.) and Hunig's base (0.3 mL, 1.75 mmol, 3.5 equiv.), (CuOTf)$_2$.Benzene (150 mg, 0.6 mmol, 1.2 equiv.) was added at room temperature in one portion under $N_2$. After 6 hours at room temperature, HPLC analysis indicated the complete consumption of Intermediate 233. Allyl bromide (242 mg, 2.0 mmol, 4.0 equiv.) was added and the reaction solution was stirred for another 2 hours. The same workup/purification procedure were followed to afford Intermediate 235 (113 mg, 0.26 mml, 52% yield) along with Intermediate 236 (49 mg, 0.12 mmol, 25% yield).

Intermediate 235: N-(1-(5-allyl-1-(pyrimidin-2-yl)-1H-1,2,3-triazol-4-yl)ethyl)-2-chloro-3-(trifluoromethyl)benzamide $^1$H NMR (600 MHz, CDCl$_3$) δ 8.95-8.85 (d, J=4.8 Hz, 2H), 7.78-7.72 (dd, J=7.8, 1.6 Hz, 1H), 7.67-7.61 (dd, J=7.7, 1.6 Hz, 1H), 7.46-7.43 (s, 1H), 7.43-7.38 (td, J=7.8, 0.9 Hz, 1H), 6.93-6.79 (d, J=8.3 Hz, 1H), 5.96-5.85 (dddd, J=16.7, 10.1, 6.4, 5.5 Hz, 1H), 5.57-5.47 (dq, J=8.3, 6.8 Hz, 1H), 5.08-4.92 (m, 2H), 4.15-4.05 (m, 1H), 4.04-3.95 (m, 1H), 1.76-1.71 (d, J=6.9 Hz, 3H). $^{13}$C NMR (151 MHz, CDCl$_3$) δ 165.1, 159.1, 155.7, 146.8, 138.3, 133.2, 132.6, 132.2, 129.3 (q, $J_{C-F}$=31.5 Hz), 129.3, 128.7 (q, $J_{C-F}$=5.2 Hz), 126.9, 122.5 (q, $J_{C-F}$=273.4 Hz), 120.8, 117.2, 41.3, 27.9, 21.5. HRMS-ESI (m/z): [M+H]$^+$ calcd for $C_{19}H_{17}ClF_3N_6O$, 437.1099; found, 437.1088.

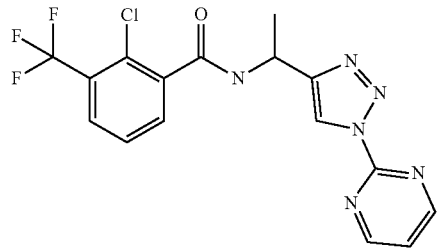 [SMILES: CC(NC(=O)c1cccc(C(F)(F)F)c1Cl)c1cn(-c2ncccn2)nn1]

Intermediate 236: 2-chloro-N-(1-(1-(pyrimidin-2-yl)-1H-1,2,3-triazol-4-yl)ethyl)-3-(trifluoromethyl)benzamide $^1$H NMR (600 MHz, CDCl$_3$) δ 8.91-8.84 (d, J=4.8 Hz, 2H), 8.65-8.57 (s, 1H), 7.81-7.74 (dd, J=7.8, 1.6 Hz, 1H), 7.72-7.64 (dd, J=7.7, 1.6 Hz, 1H), 7.51-7.38 (m, 2H), 6.80-6.64 (d, J=8.1 Hz, 1H), 5.71-5.49 (p, J=7.1 Hz, 1H), 1.87-1.69 (d, J=7.0 Hz, 3H). $^{13}$C NMR (151 MHz, CDCl$_3$) δ 165.3, 159.3, 154.4, 149.0, 138.2, 132.4, 129.3 (q, $J_{C-F}$=31.5 Hz), 129.2, 128.7 (q, $J_{C-F}$=5.2 Hz), 127.0, 122.5 (q, $J_{C-F}$=273.4 Hz), 120.8, 120.1, 42.5, 21.1. HRMS-ESI (m/z): [M+H]$^+$ calcd for $C_{16}H_{13}ClF_3N_6O$, 397.0786; found, 397.0780.

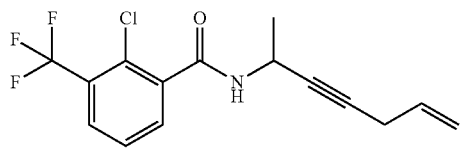 [SMILES: C=CCC#CC(C)NC(=O)c1cccc(C(F)(F)F)c1Cl]

Intermediate 237: 2-chloro-N-(hept-6-en-3-yn-2-yl)-3-(trifluoromethyl)benzamide $^1$H NMR (600 MHz, CDCl$_3$) δ 7.81-7.72 (dd, J=7.7, 1.7 Hz, 1H), 7.70-7.60 (dd, J=7.6, 1.7 Hz, 1H), 7.52-7.37 (t, J=7.8 Hz, 1H), 6.37-6.21 (d, J=8.2 Hz, 1H), 5.86-5.72 (ddt, J=17.1, 10.2, 5.2 Hz, 1H), 5.37-5.27 (m, 1H), 5.18-5.07 (dq, J=10.8, 1.9 Hz, 1H), 5.06-4.92 (ddt, J=8.4, 4.5, 2.3 Hz, 1H), 3.13-2.76 (dq, J=5.1, 2.0 Hz, 2H), 1.61-1.32 (d, J=6.8 Hz, 3H). $^{13}$C NMR (151 MHz, CDCl$_3$) δ 164.6, 138.2, 132.4, 132.1, 129.3 (q, $J_{C-F}$=31.5 Hz), 129.1, 128.8 (q, $J_{C-F}$=5.2 Hz), 127.0, 122.5 (q, $J_{C-F}$=273.4 Hz), 116.2, 81.9, 80.0, 38.3, 22.9, 22.5. HRMS-ESI (m/z): [M+H]$^+$ calcd for $C_{15}H_{14}ClF_3NO$, 316.0711; found, 316.0726.

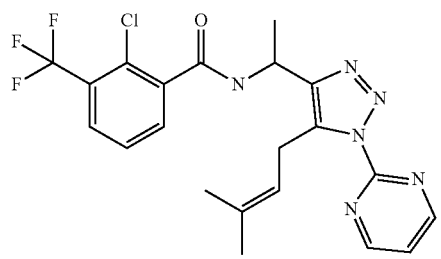 [SMILES: CC(C)=CCc1c(C(C)NC(=O)c2cccc(C(F)(F)F)c2Cl)nnn1-c1ncccn1]

Intermediate 238: 2-chloro-N-(1-(5-(3-methylbut-2-en-1-yl)-1-(pyrimidin-2-yl)-1H-1,2,3-triazol-4-yl)ethyl)-3-(trifluoromethyl)benzamide Following Method 1 described above for Intermediate 235 substituting dimethylallyl bromide for allyl bromide, the title compound was isolated in 77% yield. $^1$H NMR (600 MHz, CDCl$_3$) δ 8.94-8.87 (d, J=4.8 Hz, 2H), 7.77-7.70 (dd, J=7.8, 1.7 Hz, 1H), 7.67-7.61 (dd, J=7.7, 1.6 Hz, 1H), 7.47-7.43 (t, J=4.8 Hz, 1H), 7.43-7.36 (t, J=7.7 Hz, 1H), 7.04-6.91 (d, J=8.3 Hz, 1H), 5.58-5.48 (m, 1H), 5.10-5.02 (m, 1H), 3.98-3.90 (d, J=6.8 Hz, 2H), 1.76-1.72 (s, 3H), 1.72-1.68 (d, J=6.8 Hz, 3H), 1.65-1.60 (d, J=1.5 Hz, 3H). $^{13}$C NMR (151 MHz, CDCl$_3$) δ 165.0, 159.0, 155.8, 146.1, 138.4, 134.7, 134.3, 132.2, 129.3 (q, $J_{C-F}$=31.5 Hz), 129.3, 128.7 (q, $J_{C-F}$=5.2 Hz), 126.9, 122.5 (q, $J_{C-F}$=273.4 Hz), 120.7, 118.8, 41.4, 25.5, 23.1, 21.6, 18.1. HRMS-ESI (m/z): [M+H]$^+$ calcd for C$_{21}$H$_{21}$ClF$_3$N$_6$O, 465.1412; found, 465.1393.

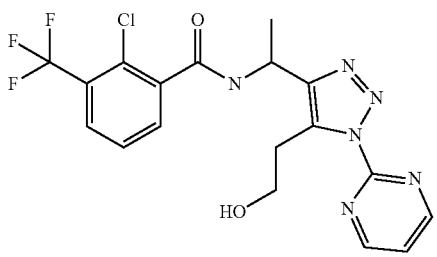 [SMILES: CC(NC(=O)c1cccc(C(F)(F)F)c1Cl)c1nnn(-c2ncccn2)c1CCO]

Intermediate 239: 2-chloro-N-(1-(5-(2-hydroxy-ethyl)-1-(pyrimidin-2-yl)-1H-1,2,3-triazol-4-yl)ethyl)-3-(trifluoromethyl)benzamide A stream of O$_3$ generated from an ozonator was passed through the solution of Intermediate 238 (200 mg, 0.43 mmol, 1.0 equiv.) in MeOH (30 mL) at −78° C. until the color of the reaction solution became blue (~10 min). NaBH$_4$ (49 mg, 1.3 mmol, 3.0 equiv.) was added at −78° C. The reaction solution was warmed to room temperature and partitioned between EtOAc and brine. The organic layer was separated, dried over Na$_2$SO$_4$ and concentrated. The crude product was purified by column chromatography with EtOAc/hexanes as eluents to afford the title compound (140 mg, 0.30 mmol, 70% yield) as a white solid. $^1$H NMR (500 MHz, CDCl$_3$) δ 8.95-8.88 (d, J=4.9 Hz, 2H), 7.81-7.73 (dd, J=7.8, 1.7 Hz, 1H), 7.67-7.58 (dd, J=7.7, 1.6 Hz, 1H), 7.50-7.44 (t, J=4.9 Hz, 1H), 7.43-7.36 (t, J=7.8 Hz, 1H), 6.95-6.83 (d, J=8.1 Hz, 1H), 5.62-5.44 (m, 1H), 4.06-3.89 (m, 2H), 3.66-3.56 (ddd, J=14.7, 6.1, 4.6 Hz, 1H), 3.44-3.34 (ddd, J=14.7, 7.7, 4.9 Hz, 1H), 3.20-3.14 (t, J=5.9 Hz, 1H), 1.88-1.71 (d, J=7.0 Hz, 3H). $^{13}$C NMR (151 MHz, CDCl$_3$) δ 165.5, 159.0, 155.5, 147.4, 138.3, 133.1, 132.2, 129.2, 129.1 (q, $J_{C-F}$=31.5 Hz), 128.5 (q, $J_{C-F}$=5.2 Hz), 126.8, 122.5 (q, $J_{C-F}$=273.4 Hz), 120.7, 61.1, 41.4, 27.3, 20.7. HRMS-ESI (m/z): [M+H]$^+$ calcd for C$_{18}$H$_{17}$ClF$_3$N$_6$O$_2$, 441.1048; found, 441.1038.

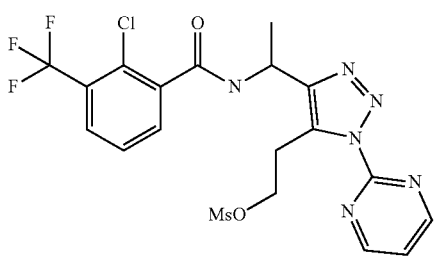 [SMILES: CC(NC(=O)c1cccc(C(F)(F)F)c1Cl)c1nnn(-c2ncccn2)c1CCOS(C)(=O)=O]

Intermediate 240: To the solution of Intermediate 239 (100 mg, 0.22 mmol, 1.0 equiv.) in THF (10 mL), Et$_3$N (37 uL, 0.27 mmol, 1.2 equiv.) and MsCl (29 mg, 0.24 mmol, 1.1 equiv.) was added sequentially. The reaction solution was stirred at room temperature for 16 hours. EtOAc and water were added. The organic layer was separated, dried over Na$_2$SO$_4$ and concentrated. The crude product (112 mg, 0.21 mmol, 95% yield) was used directly in the next reaction without further purification. $^1$H NMR (600 MHz, CDCl$_3$) δ 8.97-8.88 (d, J=4.8 Hz, 2H), 7.80-7.72 (dd, J=7.9, 1.6 Hz, 1H), 7.66-7.59 (dd, J=7.7, 1.6 Hz, 1H), 7.50-7.45 (t, J=4.8 Hz, 1H), 7.44-7.36 (t, J=7.8 Hz, 1H), 6.86-6.77 (d, J=8.3 Hz, 1H), 5.60-5.47 (dd, J=8.3, 7.0 Hz, 1H), 4.66-4.57 (ddd, J=7.5, 6.0, 3.9 Hz, 2H), 3.92-3.79 (m, 1H), 3.73-3.59 (d, J=14.6 Hz, 1H), 3.04-2.95 (s, 3H), 1.83-1.72 (d, J=7.0 Hz, 3H). $^{13}$C NMR (151 MHz, CDCl$_3$) δ 165.3, 159.3, 155.5, 148.2, 138.1, 132.2, 129.8, 129.4 (q, $J_{C-F}$=31.5 Hz), 129.2, 128.9 (q, $J_{C-F}$=5.2 Hz), 127.0, 122.5 (q, $J_{C-F}$=273.4 Hz), 120.9, 67.6, 41.1, 37.3, 24.4, 21.0. HRMS-ESI (m/z): [M+H]$^+$ calcd for C$_{19}$H$_{19}$CF$_3$N$_6$O$_4$S, 519.0824; found, 519.0805.

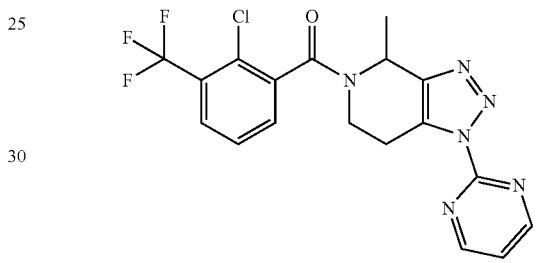

(2-Chloro-3-(trifluoromethyl)phenyl)(4-methyl-1-(pyrimidin-2-yl)-6,7-dihydro-1H-[1,2,3]triazolo[4,5-c]pyridin-5(4H)-yl)methanone To the solution of Intermediate 240 (112 mg, 0.21 mmol, 1.0 equiv.) in THF (20 mL), NaH (60 wt % in mineral oil, 30 mg, 0.74 mmol, 3.5 equiv.) was added in one portion. The reaction solution was heated to reflux temperature for 3 hours and then cooled to room temperature. The reaction solution was partitioned between EtOAc and brine. The organic layer was separated, dried over Na$_2$SO$_4$ and concentrated. The crude product was purified by column chromatography to afford (2-chloro-3-(trifluoromethyl)phenyl) (4-methyl-1-(pyrimidin-2-yl)-6,7-dihydro-1H-[1,2,3] triazolo[4,5-c]pyridin-5(4H)-yl)methanone (68 mg, 0.16 mmol, 75% yield) as a white solid. $^1$H NMR (600 MHz, MeOD) δ 8.97-8.86 (m, 2H), 7.98-7.88 (dd, J=7.8, 1.7 Hz, 1H), 7.83-7.52 (m, 3H), [6.05-5.78 (m), 4.87-4.82 (m), 4.72-4.66 (m), 1H] [5.04-4.98 (m), 3.94-2.86 (m), 4H], [1.72-1.66 (m), 1.59-1.48 (m), 3H]. $^{13}$C NMR (151 MHz, MeOD) δ 168.36, 168.27, 168.25, 160.68, 160.64, 160.63, 156.44, 156.42, 156.40, 146.71, 146.59, 146.46, 139.78, 139.59, 139.56, 139.37, 134.20, 133.93, 133.22, 132.96, 132.90, 132.61, 132.47, 130.47, 130.37, 130.27, 130.16, 130.06, 129.85, 129.82, 129.78, 129.76, 129.72, 129.69, 129.65, 129.59, 129.57, 129.48, 129.46, 129.33, 129.30, 129.13, 129.04, 126.83, 125.03, 124.91, 123.22, 123.10, 122.50, 122.47, 122.41, 121.41, 51.90, 51.40, 46.88, 46.66, 41.78, 41.01, 36.04, 35.83, 26.17, 25.75, 25.21, 25.17, 20.28, 20.13, 18.84, 18.51. HRMS-ESI (m/z): [M+H]$^+$ calcd for C$_{18}$H$_{15}$ClF$_3$N$_6$O, 423.0942; found, 423.0937.

Examples 338 to 343 are made in accordance with the synthetic schemes, and in light of the specific examples, provided above.

Example 338: (R*)-(3-chloro-4-(trifluoromethyl)pyridin-2-yl)(1-(5-fluoropyrimidin-2-yl)-4-methyl-6,7-dihydro-1H-[1,2,3]triazolo[4,5-c]pyridin-5(4H)-yl)methanone

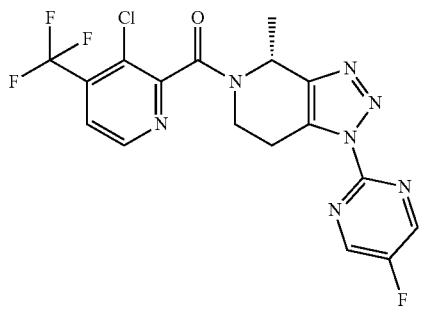 [SMILES: C[C@@H]1c2nnn(-c3ncc(F)cn3)c2CCN1C(=O)c1nccc(C(F)(F)F)c1Cl]

Example 339: (R*)-(4-chloro-5-(trifluoromethyl)pyridin-3-yl)(1-(5-fluoropyrimidin-2-yl)-4-methyl-6,7-dihydro-1H-[1,2,3]triazolo[4,5-c]pyridin-5(4H)-yl)methanone

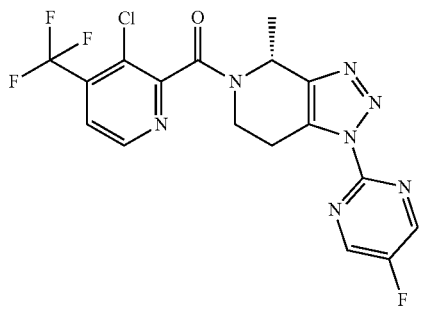 [SMILES: C[C@@H]1c2nnn(-c3ncc(F)cn3)c2CCN1C(=O)c1nccc(C(F)(F)F)c1Cl]

Example 340: (R*)-(3-chloro-2-(trifluoromethyl)pyridin-4-yl)(1-(5-fluoropyrimidin-2-yl)-4-methyl-6,7-dihydro-1H-[1,2,3]triazolo[4,5-c]pyridin-5(4H)-yl)methanone

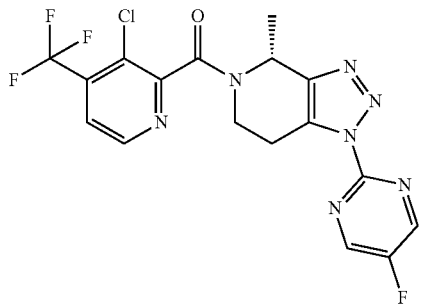 [SMILES: C[C@@H]1c2nnn(-c3ncc(F)cn3)c2CCN1C(=O)c1nccc(C(F)(F)F)c1Cl]

Example 341: (R*)-(3-chloro-4-(trifluoromethyl)pyridin-2-yl)(4-methyl-1-(pyrazin-2-yl)-6,7-dihydro-1H-[1,2,3]triazolo[4,5-c]pyridin-5(4H)-yl)methanone

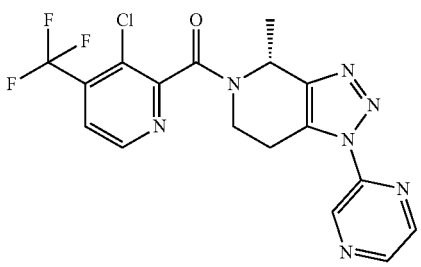 [SMILES: C[C@@H]1c2nnn(-c3cnccn3)c2CCN1C(=O)c1nccc(C(F)(F)F)c1Cl]

Example 342: (R*)-(4-chloro-5-(trifluoromethyl)pyridin-3-yl)(4-methyl-1-(pyrazin-2-yl)-6,7-dihydro-1H-[1,2,3]triazolo[4,5-c]pyridin-5(4H)-yl)methanone

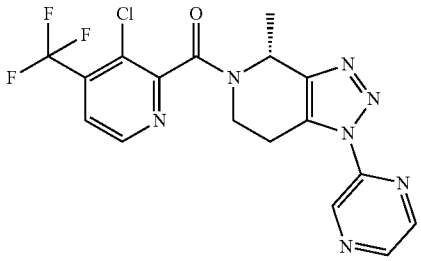 [SMILES: C[C@@H]1c2nnn(-c3cnccn3)c2CCN1C(=O)c1nccc(C(F)(F)F)c1Cl]

Example 343: (R*)-(3-chloro-2-(trifluoromethyl)pyridin-4-yl)(4-methyl-1-(pyrazin-2-yl)-6,7-dihydro-1H-[1.2.3]triazolo[4,5-c]pyridin-5(4H)-yl)methanone

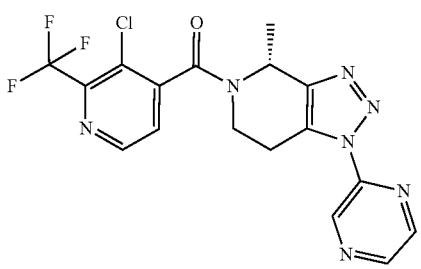

Example 344: (R)-(2-chloro-3-(trifluoromethyl)phenyl)(1-(5-fluoropyrimidin-2-yl)-4-methyl-6,7-dihydro-1H-[1,2,3]triazolo[4,5-c]pyridin-5(4H)-yl)methanone Intermediate 241: (R)—N-(but-3-yn-2-yl)-2-chloro-5-fluoro-3-(trifluoromethyl)benzamide

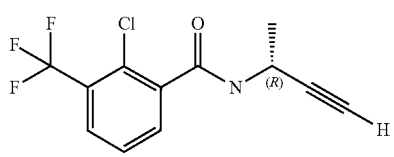

Intermediate 241: (R)—N-(but-3-yn-2-yl)-2-chloro-5-fluoro-3-(trifluoromethyl)benzamide: To the suspension of (R) but-3-yn-2-amine HCl salt (10 g, 94.7 mmol, 1.0 equiv.) in THF (150 mL), Et$_3$N (27.5 mL, 199 mmol, 2.1 equiv.) and (2-chloro-3-(trifluoromethyl)benzoyl chloride (23.1 g, 94.7 mmol, 1.0 equiv.) were added sequentially at 0° C. The reaction mixture was then stirred at room temperature for 16 hours. The precipitate was filtered off and washed with THF. The filtrate solution was concentrated and re-dissolved in EtOAc. The EtOAc solution was washed with saturated NaHCO$_3$ and brine, dried over Na$_2$SO$_4$, concentrated. Trituration of the crude product from EtOAc/hexanes afforded the title compound (23 g, 83.8 mmol, 88%) as a white solid. $^1$H NMR (600 MHz, CDCl$_3$) δ 7.82-7.75 (dd, J=7.9, 1.6 Hz, 1H), 7.73-7.66 (dd, J=7.7, 1.6 Hz, 1H), 7.48-7.41 (dd, J=8.2, 7.3 Hz, 1H), 6.35-6.02 (d, J=7.9 Hz, 1H), 5.09-4.90 (dqd, J=8.1, 6.9, 2.3 Hz, 1H), 2.47-2.20 (m, 1H), 1.58-1.54 (d, J=6.9 Hz, 3H). $^{13}$C NMR (151 MHz, CDCl$_3$) δ 164.7, 137.9, 132.5, 129.4 (q, $J_{C-F}$=31.5 Hz), 129.1, 129.0 (q, $J_{C-F}$=5.2 Hz), 127.1, 122.5 (q, $J_{C-F}$=273.4 Hz), 83.2, 71.2, 37.8, 22.1. HRMS-ESI (m/z): [M+H]$^+$ calcd for C$_{12}$H$_{10}$ClF$_3$NO, 276.0398; found, 276.0390.

Intermediate 242: (R)—N-(1-(5-allyl-1-(5-fluoropyrimidin-2-yl)-1H-1,2,3-triazol-4-yl)ethyl)-2-chloro-3-(trifluoromethyl)benzamide

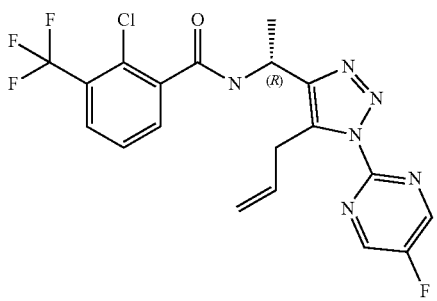

To the suspension of Intermediate 241 (41.93 g, 152.11 mmol, 1.0 equiv), tetrazolo[1,5-a]pyrimidine (Intermediate 234, 25.43 g, 182.85 mmol, 1.2 equiv.), allyl bromide (16.73 mL, 197.74 mmol, 1.3 equiv.) and Cs$_2$CO$_3$ (148.68 g, 456.33 mmol, 3.0 equiv.) in 2-methylTHF (1000 mL) was added CuI (28.97 g, 152.11 mmol, 1.0 equiv.) at room temperature in one portion under N$_2$. The reaction mixture was stirred at room temperature under N$_2$(g) for 16 hours. The insoluble solid was filtered off and the filtrate was washed with KOH (700 mL) and EtOAc (300 mL). The organic layer was extracted, dried over Na$_2$SO$_4$ and concentrated. The crude was slurried in 4/1 EtOAc/TMBE 400 mL/100 mL for 48 hours then filtered to recover Intermediate 242: (R)—N-(1-(5-allyl-1-(5-fluoropyrimidin-2-yl)-1H-1,2,3-triazol-4-yl)ethyl)-2-chloro-3-(trifluoromethyl)benzamide as a light yellow solid. (56.5 g, 124.27 mmol, 82%). MS-ESI (m/z): [M+H]$^+$ calcd for C$_{19}$H$_{15}$ClF$_4$N$_6$O, 454.81; found, 455.10.

Intermediate 243: (R)-2-chloro-N-(1-(1-(5-fluoropyrimidin-2-yl)-5-(2-hydroxyethyl)-1H-1,2,3-triazol-4-yl)ethyl)-3-(trifluoromethyl)benzamide

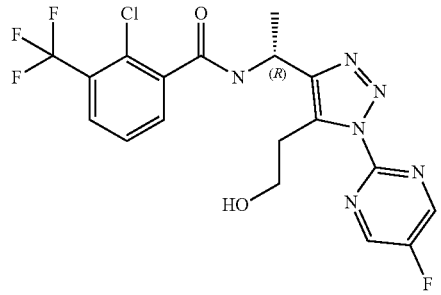

Intermediate 243: (R)-2-chloro-N-(1-(1-(5-fluoropyrimidin-2-yl)-5-(2-hydroxyethyl)-1H-1,2,3-triazol-4-yl)ethyl)-3-(trifluoromethyl)benzamide: A stream of O$_3$ generated from an ozonator was passed though the solution of Intermediate 242 (8 g, 17.59 mmol, 1.0 equiv.) in MeOH (350 mL) and CH$_2$Cl$_2$ at −78° C. until the color of the reaction solution became blue (45 min). Removed O$_3$(g) and bubbled in N$_2$(g) for 15 minutes. Slowly, NaBH$_4$ (2 g, 52.77 mmol, 3.0 equiv.) was added at −78° C. and stirred for 30 minutes. The reaction solution was warmed above 0° C. by quenching with ice and CH$_2$Cl$_2$. The organic layer was separated, dried over Na$_2$SO$_4$ and concentrated. The crude product was purified by column chromatography with 9/1 EtOAc/hexanes as eluents to afford the title compound (Intermediate 243: (R)-2-chloro-N-(1-(1-(5-fluoropyrimidin-2-yl)-5-(2-hydroxyethyl)-1H-1,2,3-triazol-4-yl)ethyl)-3-(trifluoromethyl)benzamide) (5.7 g, 12.42 mmol, 71% yield) as a foam oil. MS-ESI (m/z): [M+H]$^+$ calcd for C$_{18}$H$_{15}$ClF$_4$N$_6$O$_2$, 458.80; found, 459.10.

Intermediate 244: (R)-2-(4-(1-(2-chloro-3-(trifluoromethyl)benzamido)ethyl)-1-(5-fluoropyrimidin-2-yl)-1H-1,2,3-triazol-5-yl)ethyl 4-methylbenzenesulfonate

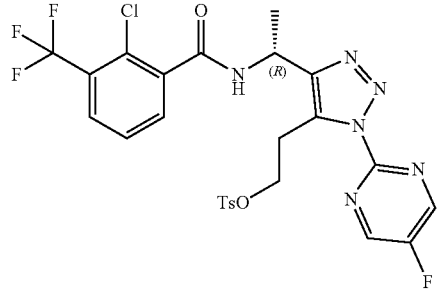

Intermediate 244: To the solution of Intermediate 243 (10 g, 21.80 mmol, 1.0 equiv.) in $CH_2Cl_2$ (80 mL) was added TsCl (5.0 g, 26.16 mmol, 1.2 equiv.), DMAP (0.27 g, 2.18 mmol, 0.1 equiv.) and trimethyl amine HCl (0.42 g, 4.36 mmol, 0.2 equiv.). Slowly, $Et_3N$ (3.9 mL, 28.33 mmol, 1.3 equiv.) was added drop wise. The reaction solution was stirred at room temperature for 16 hours then quenched with $H_2O$. The organic layer was separated, dried over $Na_2SO_4$ and concentrated.

The crude product was purified by column chromatography using 3/2 EtOAc/hexane to recover Intermediate 244 (12.90 g, 21.04 mmol, 96% yield). MS-ESI (m/z): $[M+H]^+$ calcd for $C_{25}H_{21}CF_4N_6O_4S$, 612.99; found, 613.

Example 344: (R)-(2-chloro-3-(trifluoromethyl)phenyl)(1-(5-fluoropyrimidin-2-yl)-4-methyl-6,7-dihydro-1H-[1,2,3]triazolo[4,5-c]pyridin-5(4H)-yl)methanone

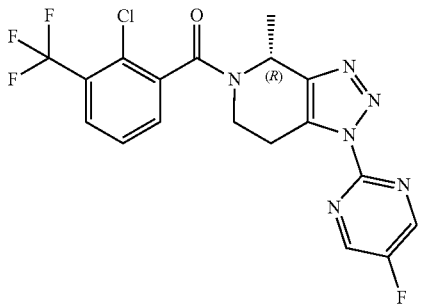

To the solution of Intermediate 244 (12.9 g, 21.04 mmol, 1.0 equiv.) in THF (150 mL) was added NaH (60 wt % in mineral oil, 4.5 g, 112.38 mmol, 5.3 equiv.). The reaction solution was heated to 60° C. for 3 hours and then cooled to room temperature. The reaction was quenched with cold $H_2O$ and EtOAc. The organic layer was separated, dried over $Na_2SO_4$ and concentrated. The crude product was purified by column chromatography to afford Example 344: (R)-(2-chloro-3-(trifluoromethyl)phenyl)(1-(5-fluoropyrimidin-2-yl)-4-methyl-6,7-dihydro-1H-[1,2,3]triazolo[4,5-c]pyridin-5(4H)-yl)methanone (6.70 g, 15.20 mmol, 72% yield) as a white solid. MS-ESI (m/z): $[M+H]^+$ calcd for $CH_{13}CF_4N_6O$, 440.79; found, 440.90. CHN analysis calcd for $C_{18}H_{13}ClF_4N_6O$: 49.04% C, 2.98% H, 19.05 N; found, 48.93% C, 3.25% H, 19.02 N. Chiral HPLC analysis: Chiral Pak AD-H column, 0.4 mL/min, 80% EtOH/20% hexane, major isomer 12.56 min, minor isomer 11.28 min.

Example 345: (R)-(2-chloro-3-(trifluoromethyl)phenyl)(1-(5-fluoropyridin-2-yl)-4-methyl-6,7-dihydro-1H-imidazo[4,5-c]pyridin-5(4H)-yl)methanone

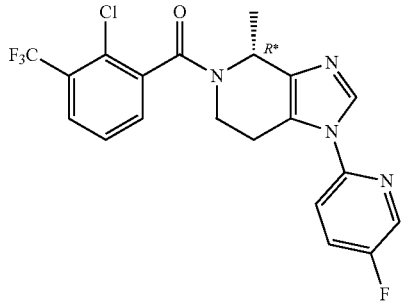

Intermediate 245: (2-chloro-3-(trifluoromethyl)phenyl)(1-(5-fluoropyridin-2-yl)-4-methyl-1H-imidazo[4,5-c]pyridin-5(4H)-yl)methanone

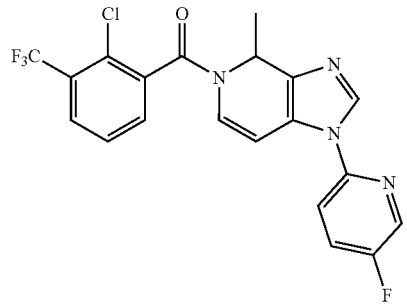

In a three-neck round-bottom flask equipped with a mechanic stirring, an internal thermal couple and an addition funnel, 1-(5-fluoropyridin-2-yl)-1H-imidazo[4,5-c]pyridine (70 g, 326 mmol) was suspended in THF (1.7 L) and then warmed to 50° C. to form a clear solution. The clear solution was cooled to −78° C. and a lot of solid precipitated out. Under $N_2$, MeMgBr (3.0 mol/L in THF, 109 mL, 326 mmol) was added over 30 min while the internal temperature was maintained at ←70° C. After 20 min, the solution of Intermediate 12 (87 g, 359 mmol) in THF (100 mL) was added over 30 min with the internal temperature maintained at ←70° C. The rest of MeMgBr (3.0 mol/L in THF, 130 mL, 390 mmol) was then added over 30 min. The reaction was stirred at −78° C. for 1 hour. The cold bath was removed and the reaction solution was warmed to 0° C. With an ice/water bath, 2 mol/L HCl aqueous solution was slowly added to quench the reaction while the internal temperature was maintained at <5° C. Concentrated $NH_4C_1$ aqueous solution was then added until clear phase separation was obtained. The aqueous layer was extracted with EtOAc twice (300 mL). The organic layers were combined, dried over $Na_2SO_4$, and concentrated. The crude product was recrystallized from hot EtOAc (250 mL)/MTBE (500 mL). The precipitated solid was collected by filtration, washed with cold MTBE (500 mL) to afford Intermediate 245 as a white solid (117 g, 82%). MS-EI (m/z): $[M+H]^+$ observed: 437.0.

Alternative Synthesis of Example 11. (2-Chloro-3-(trifluoromethyl)phenyl)(1-(5-fluoropyridin-2-yl)-4-methyl-6,7-dihydro-1H-imidazo[4,5-c]pyridin-5(4H)-yl)methanone

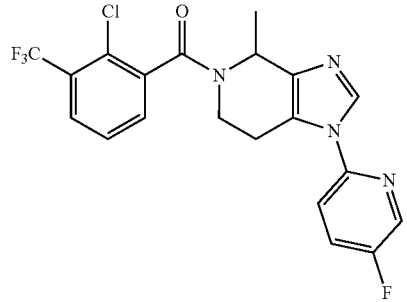

Intermediate 245 (80 g, 183 mmol) was dissolved in the mixed solvent of THF (450 mL), EtOH (600 mL), AcOH (80 mL) at 50° C. The solution was poured into Pd/C (23 g, 10 wt % dry base, 1:1 with water). The hydrogenation was performed on a Parr shaker at 55° C., 30 PSI overnight. After the reaction was complete, Pd/C was filtered off under $N_2$ and washed with EtOH. The filtrate solution was concentrated and repartitioned between EtOAc/saturated aqueous $NaHCO_3$ solution. The EtOAc layer was washed with brine, dried on $Na_2SO_4$ and concentrated. The residue was recrystallized from hot EtOAc (200 mL)/TBME (400 mL) to afford a white, free-flowing solid. Recrystallization from hot EtOAc (700 mL) afforded pure Example 11 as a white solid (54.3 g, 124 mmol, 67%). MS-EI (m/z): $[M+H]^+$ observed: 439.0.

Alternative Chiral Separation of Example 11: (R)-(2-chloro-3-(trifluoromethyl)phenyl)(1-(5-fluoropyridin-2-yl)-4-methyl-6,7-dihydro-1H-imidazo[4,5-c]pyridin-5(4H)-yl)methanone

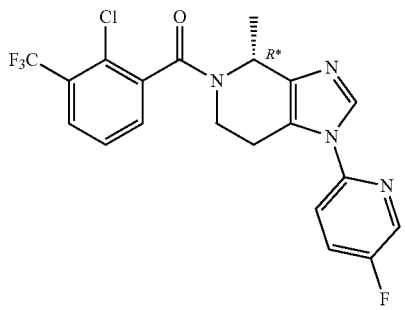

Chiral separation of Example 11 (54.3 g) was performed on chiral SFC (Stationary phase: CHIRALCEL OD-H 5 µm 250×20 mm), Mobile phase: 85% $CO_2$, 15% EtOH). 26.7 grams of enantiopure compound was obtained. $^1$H NMR (600 MHz, $CDCl_3$) δ 8.45-8.29 (m, H), 7.99-7.86 (m, H), 7.81-7.70 (m, 1H), 7.64-7.29 (m, 4H), 5.87-5.75 (m, 0.7H), 5.15-5.01 (m, 0.6H), 4.71-4.58 (m, 0.3H), 4.57-4.46 (m, 0.4H), 3.61-3.46 (m, 1H), 3.44-3.33 (m, 0.3H), 3.27-3.09 (m, 1.2H), 3.00-2.72 (m, 1.5H), 1.67-1.59 (m, 1.7H), 1.51-1.46 (d, J=6.8 Hz, 0.8H), 1.44-1.39 (d, J=6.9 Hz, 0.5H).

Pharmacological Examples

P2X7 Antagonism in Human Peripheral Blood Mononuclear Cells (PBMCs) and Mouse/Human Whole Blood.

Human blood was collected using a blood donor program. PBMCs were isolated from blood using a Ficoll density gradient technique. Briefly, blood was laid on Ficoll solution and centrifuged at RT for 20 minutes at 2000 rpm. The buffy layer (between red blood cells and plasma) was carefully collected by aspiration, washed with PBS and centrifuged again at 1500 rpm for 15 minutes. The resulting cell pellet was washed and plated on 96 well-plates for experiments. For the Mouse/Human Whole Blood experiments, 150 µl of either mouse or human blood was platted on 96 well-plates. Lipopolysaccharide (LPS) (30 ng/ml) was added to each well and incubated for 1 hour. Test compounds were then added and incubated for 30 minutes. The P2X7 agonist, 2'(3')-O-(4-benzoylbenzoyl) adenosine 5'-triphosphate (Bz-ATP) was then added at a final concentration of 0.5 mM (PBMC) or 1 mM (blood). Cells were incubated for an additional 1.5 hours. At that point, supernatant was collected and stored for IL-1β assay using manufacturer's protocol for enzyme-linked immunosorbent assay (ELISA). Data was expressed as percent control, where control is defined as the difference in IL-1β release in LPS+Bz-ATP samples and LPS only samples. Data was plotted as response (% control) versus concentration to generate $IC_{50}$ values. In Table 2, this data is represented by PBMC P2X7 and blood P2X7 $IC_{50}$. In Table 2, when the data cell has been left blank, it is intended to mean that the compound was not tested in that assay.

P2X7 Antagonism in Recombinant hP2X7 Cells: (a) $Ca^{2+}$ Flux (b) Radioligand Binding (A) $Ca^{2+}$ flux: 1321N1 cells expressing the recombinant human, rat or mouse P2X7 channel was cultured in HyQ DME/(HyClone/Dulbecco's Modified Eagle Medium) high glucose supplemented with 10% Fetal Bovine Serum (FBS) and appropriate selection marker. Cells were seeded at a density of 25000 cells/well (96-well clear bottom black walled plates) in 100 µl volume/well. On the day of the experiment, cell plates were washed with assay buffer, containing (in mM): 130 NaCl, 2 KCl, 1 $CaCl_2$), 1 $MgCl_2$, 10 HEPES, 5 glucose; pH 7.40 and 300 mOs. After the wash, cells were loaded with the Calcium-4 dye (Molecular Device) and incubated in the dark for 60 minutes. Test compounds were prepared at 250× the test concentration in neat DMSO. Intermediate 96-well compound plates were prepared by transferring 1.2 µL of the compound into 300 µL of assay buffer. A further 3× dilution occurred when transferring 50 µL/well of the compound plate to 100 µL/well in the cell plate. Cells were incubated with test compounds and dye for 30 minutes. Calcium dye fluorescence was monitored in FLIPR as the cells were challenged by adding 50 µL/well of BzATP (final concentration is 250 µM BzATP (human and rat) or 600 M (mouse)). The fluorescence change was measured 180 seconds after adding the agonist. Peak fluorescence was plotted as a function of test concentration and the resultant $IC_{50}$ is shown in Table 2

(B) Radioligand binding: human or rat P2X7-1321N1 cells were collected and frozen @ −80° C. On the day of the experiment, cell membrane preparations were made according to standard published methods. The total assay volume was 100 µl:10 µl compound (10×)+(b) 40 µl tracer (2.5×)+50 µl membrane (2×). The tracer used for the assay was tritiated A-804598. The compound can be prepared as described in the literature. (Donnelly-Roberts, D. Neuropharmacology 2008, 56 (1), 223-229.) Compounds, tracer and membranes were incubated for 1 hour @ 4° C. The assay was terminated by filtration (GF/B filters pre-soaked with 0.3% PEI) and washed with washing buffer (Tris-HCl 50 mM). The $IC_{50}$ generated in the binding assay was corrected for tracer concentration and affinity of the tracer to derive at the affinity ($K_i$) of the test compounds.

TABLE 2

P2X7 activity of the compounds of Formula (I, IIa and IIb) in a panel of in-vitro assays

| Example | PBMC 1 μM (% control) | PBMC 10 μM (% control) | P2X7 human Ki (μM) | P2X7 rat Ki (μM) | FLIPR (human) IC$_{50}$ (μM) | FLIPR (rat) IC$_{50}$ (μM) | Human whole blood IC$_{50}$ (μM) |
|---|---|---|---|---|---|---|---|
| 1 | 11.5 | | 0.0759 | | 0.0061 | 1.2078 | |
| 2 | 7.9 | | 0.0871 | | 0.0184 | 1.9409 | |
| 3 | 23.0 | | 0.0603 | | 0.0811 | 4.4771 | |
| 4 | | −3.7 | 0.0251 | | 0.0465 | 2.5704 | |
| 5 | | 11.6 | 0.0316 | | 0.0124 | 0.3236 | |
| 6 | 14.3 | | 0.0427 | | 0.0094 | 1.7824 | |
| 7 | 98.7 | | | | | | |
| 8 | 83.1 | | | | | | |
| 9 | 83.7 | | | | | | |
| 10 | 76.5 | | | | | | |
| 11 | | 25.2 | 0.1259 | | 0.0223 | 0.6714 | 1.585 |
| 12 | 11.2 | | 0.0851 | 0.1349 | 0.0061 | 1.3213 | 0.631 |
| 13 | 27.9 | | 0.0794 | | 0.0126 | 0.1259 | |
| 14 | 12.8 | | 0.0794 | | 0.0830 | 0.1409 | |
| 15 | 9.1 | | 0.1585 | | 0.0875 | 0.1791 | |
| 16 | 8.5 | | 0.2512 | | 0.1038 | 0.4560 | |
| 17 | 6.5 | | 0.0501 | | 0.0259 | 0.1560 | |
| 18 | 5.3 | | 0.1000 | | 0.0773 | 0.9162 | |
| 19 | | 11.6 | 0.1000 | | 0.0352 | 0.4539 | |
| 20 | | 8.6 | 0.5012 | | 0.9311 | 2.3714 | |
| 21 | | 1.6 | 0.1259 | | 0.0785 | 1.6069 | |
| 22 | | −15.9 | 0.1259 | | 0.0131 | 1.6256 | |
| 23 | | 6.4 | 0.0398 | | 0.0344 | 0.0906 | |
| 24 | 2.9 | | 0.0912 | | 0.0350 | 0.0342 | |
| 25 | 9.7 | | 0.0741 | | 0.1114 | 3.2659 | |
| 26 | 14.0 | | 0.0851 | | 0.0098 | 0.0710 | |
| 27 | 39.2 | | 1.3804 | | 0.1799 | 1.8923 | |
| 28 | 4.8 | | 0.0794 | | 0.0138 | 0.0165 | |
| 29 | 34.7 | | 0.0380 | | 0.0798 | 2.0701 | |
| 30 | 87.0 | | 0.3981 | | 1.3677 | 6.1376 | |
| 31 | 50.8 | | 0.3162 | | 0.1563 | 0.1074 | |
| 32 | | 1.9 | 0.0372 | | 0.0105 | 0.0655 | 0.251 |
| 33 | 100.7 | | | | | | |
| 34 | 29.8 | | 0.6310 | | 0.1585 | 0.1585 | |
| 35 | 31.6 | | 0.3162 | | 0.3162 | 0.3162 | |
| 36 | 16.6 | | | | 3.0832 | 10.0693 | |
| 37 | | −9.1 | 0.0794 | | 0.0993 | 1.5311 | |
| 38 | | −0.3 | 0.2512 | | 0.0143 | 0.1265 | |
| 39 | | 112.0 | | | | | |
| 40 | | 36.5 | 0.0071 | 0.0078 | 0.0040 | 0.1152 | 0.092 |
| 41 | | 40.5 | | | 1.6118 | 10.0000 | |
| 42 | | 5.8 | 0.0398 | 0.0141 | 0.0557 | 0.0883 | 2.512 |
| 43 | | 77.8 | | 1.9953 | 5.2360 | >10 | |
| 44 | | 44.7 | 0.0316 | | 0.0150 | 0.1164 | |
| 45 | | 29.4 | | | 1.6106 | 14.9969 | |
| 46 | | 2.1 | 0.0398 | | 0.0603 | 0.4721 | 3.981 |
| 47 | | −1.1 | 0.3162 | | 0.1486 | 2.0417 | |
| 48 | 90.1 | | | | | | |
| 49 | 93.5 | | | | | | |
| 50 | 96.0 | | | | | | |
| 51 | 97.6 | | | | | | |
| 52 | 98.9 | | | | | | |
| 53 | 99.0 | | 0.7413 | | 0.9750 | 4.9545 | |
| 54 | 8.6 | | 0.0437 | | 0.1984 | 4.1115 | |
| 55 | 11.3 | | 0.1259 | | 0.0167 | 0.2594 | |
| 56 | 10.1 | | 0.0794 | | 0.0251 | 0.3981 | |
| 57 | | 46.7 | 0.7943 | | 0.7178 | 0.2198 | |
| 58 | | −2.0 | 0.1259 | | 0.0107 | 0.7656 | |
| 59 | | 10.2 | 0.5012 | | 0.3784 | 0.5272 | |
| 60 | | 8.4 | 0.1000 | | 0.0557 | 1.6482 | |
| 61 | −0.1 | | 0.0389 | | 0.0047 | 1.3996 | |
| 62 | 5.2 | | 0.0437 | | 0.0762 | 4.2756 | |
| 63 | 12.6 | | 0.0117 | | 0.0033 | 1.0864 | |
| 64 | | −9.2 | 0.0316 | 0.0263 | 0.0143 | 2.4434 | 0.251 |
| 65 | | 5.8 | 0.0158 | | 0.0063 | 0.0087 | 0.079 |
| 66 | | 2.7 | 0.0158 | | 0.0174 | 0.2065 | 0.363 |
| 67 | | 6.5 | 0.0079 | | 0.0030 | 0.0789 | 0.158 |
| 68 | | 12.9 | 0.0182 | | 0.0169 | 0.1845 | |
| 69 | | 6.8 | 0.0141 | | 0.1058 | 1.4571 | |
| 70 | | 10.6 | 0.0126 | | 0.0075 | 1.3274 | 0.501 |
| 71 | | 11.1 | 0.2512 | | 0.0490 | 0.3972 | |
| 72 | | −5.7 | 0.0295 | | 0.0042 | 0.1687 | 0.126 |
| 73 | 4.3 | | 0.2512 | 0.0191 | 0.0145 | 0.0408 | 0.016 |

TABLE 2-continued

P2X7 activity of the compounds of Formula (I, IIa and IIb) in a panel of in-vitro assays

| Example | PBMC 1 μM (% control) | PBMC 10 μM (% control) | P2X7 human Ki (μM) | P2X7 rat Ki (μM) | FLIPR (human) IC$_{50}$ (μM) | FLIPR (rat) IC$_{50}$ (μM) | Human whole blood IC$_{50}$ (μM) |
|---|---|---|---|---|---|---|---|
| 74 | 102.6 | | 13.1826 | 2.2387 | 13.3660 | 19.2309 | 5.012 |
| 75 | 5.2 | −0.3 | 0.0447 | 0.0062 | 0.0034 | 0.0091 | 0.013 |
| 76 | 1.6 | | 0.3631 | | 0.0244 | 0.0324 | |
| 77 | 31.7 | | 0.3981 | | 0.1259 | 0.0063 | |
| 78 | 57.7 | | 0.1000 | | 0.0631 | 0.5012 | |
| 79 | 23.2 | | 0.0316 | | 0.0062 | 0.0865 | |
| 80 | | 4.6 | 0.0398 | | 0.0207 | 0.0187 | 0.016 |
| 81 | | 5.9 | 0.0631 | | 0.0735 | 0.1076 | |
| 82 | | 7.9 | 0.0575 | | 0.0173 | 0.1545 | |
| 83 | | 4.5 | 0.1585 | | 0.0169 | 0.3972 | |
| 84 | | 8.5 | 0.0398 | | 0.0177 | 0.1871 | 0.200 |
| 85 | | 24.7 | 0.0398 | | 0.0141 | 0.0146 | |
| 86 | | 13.0 | 0.0398 | | 0.0129 | 0.1361 | |
| 87 | | 21.7 | 1.2589 | 0.7943 | 2.5050 | 5.2180 | 3.311 |
| 88 | | 13.3 | 0.0126 | 0.0022 | 0.0022 | 0.0020 | 0.002 |
| 89 | −1.5 | | 0.0158 | | 0.0055 | 0.9078 | |
| 90 | 13.3 | | 0.0295 | | 0.0103 | 0.9727 | |
| 91 | 6.1 | | 0.0234 | 0.0162 | 0.0029 | 1.4928 | 0.316 |
| 92 | 2.8 | | 0.0263 | | 0.0054 | 0.4395 | |
| 93 | 9.0 | | 0.0398 | | 0.0079 | 0.2512 | |
| 94 | | 10.8 | 0.0316 | | 0.0124 | 0.1230 | |
| 95 | | 14.4 | 0.3162 | | 0.2042 | >10 | |
| 96 | | 3.6 | 0.0148 | | 0.0025 | 0.1786 | |
| 97 | | 12.7 | 0.0200 | | 0.0045 | 2.2909 | |
| 98 | | 32.5 | 0.0141 | | 0.0066 | 0.5483 | |
| 99 | 7.0 | | 0.0813 | 0.7413 | 0.0115 | 0.1948 | |
| 100 | 9.2 | | 0.0759 | | 0.0062 | 1.6387 | |
| 101 | 7.6 | | 0.0851 | | 0.1285 | 3.4594 | |
| 102 | 18.0 | | 0.1096 | | 0.2299 | 5.9361 | |
| 103 | 56.0 | | 0.2754 | | 0.3917 | 8.3560 | |
| 104 | 8.9 | | 0.0501 | | 0.2046 | 1.6088 | |
| 105 | 51.0 | | 0.1995 | | 0.0794 | 1.2589 | |
| 106 | 64.4 | | 0.2512 | | 0.1585 | 1.5849 | |
| 107 | 24.7 | | 0.0794 | | 0.0158 | 0.7943 | |
| 108 | 1.1 | | 0.1000 | | 0.0126 | 0.7943 | |
| 109 | 94.1 | | | | 0.2512 | 3.1623 | |
| 110 | −15.1 | | 0.1820 | | 0.0100 | 1.2589 | |
| 111 | 15.7 | | 0.0794 | | 0.1585 | 1.5849 | |
| 112 | 51.9 | | 0.2512 | | 0.1259 | 3.9811 | |
| 113 | | 42.6 | 0.3981 | | 0.8551 | >10 | |
| 114 | 20.4 | | 0.2512 | | 0.0631 | 1.2589 | |
| 115 | | −3.3 | | | 1.0691 | >10 | |
| 116 | | 45.3 | 0.0063 | | 0.0088 | 0.0041 | |
| 117 | | 4.3 | | | 2.2182 | >10 | |
| 118 | | 12.6 | 0.7943 | | 1.1858 | 1.7378 | |
| 119 | | 20.0 | 0.0063 | 0.0025 | 0.0013 | 0.0015 | 0.013 |
| 120 | | −3.8 | 0.0063 | | 0.0059 | 0.0556 | |
| 121 | | −0.2 | 0.0112 | | 0.0032 | 0.0065 | |
| 122 | | 0.2 | 0.0200 | | 0.0048 | 0.0120 | |
| 123 | 22.0 | | 0.0631 | | 0.0501 | 1.0000 | |
| 124 | 94.7 | | | | | | |
| 125 | 83.4 | | 0.2512 | | 0.1585 | 1.2589 | |
| 126 | 71.7 | | 0.0933 | | 0.0855 | 1.4109 | |
| 127 | | 9.2 | 0.0398 | | 0.0221 | 0.0891 | |
| 128 | | 23.1 | | | 2.1086 | >10 | |
| 129 | | 8.4 | | | 0.3664 | 3.3497 | |
| 130 | | 3.7 | 0.0501 | | 0.0036 | 0.1545 | 0.501 |
| 131 | | 8.3 | 0.0501 | | 0.0029 | 0.0515 | 0.316 |
| 132 | | 3.8 | 0.0501 | | 0.0783 | 4.4259 | |
| 133 | | −0.2 | 0.0100 | 0.0016 | 0.0022 | 0.0093 | |
| 134 | | 12.3 | 3.9811 | | 6.6989 | 10.8643 | |
| 135 | | 1.7 | 0.1000 | | 0.0482 | 1.3804 | |
| 136 | | 5.3 | 0.0158 | | 0.0093 | 0.1327 | 0.063 |
| 137 | | | | | | | |
| 138 | | | | | | | |
| 139 | | | | | | | |
| 140 | | | | | | | |
| 141 | | 40.5 | | | 9.5940 | >10 | |
| 142 | | 33.8 | 0.0100 | | 0.0020 | 0.1432 | |
| 143 | | 58.0 | | | >10 | >10 | |
| 144 | | 19.6 | 0.0032 | | 0.0097 | 0.0552 | |
| 145 | | 15.2 | | | 2.3068 | 13.7721 | |
| 146 | | 30.9 | | | 2.7040 | >10 | |

TABLE 2-continued

P2X7 activity of the compounds of Formula (I, IIa and IIb) in a panel of in-vitro assays

| Example | PBMC 1 μM (% control) | PBMC 10 μM (% control) | P2X7 human Ki (μM) | P2X7 rat Ki (μM) | FLIPR (human) IC$_{50}$ (μM) | FLIPR (rat) IC$_{50}$ (μM) | Human whole blood IC$_{50}$ (μM) |
|---|---|---|---|---|---|---|---|
| 147 | | −8.9 | 0.0398 | | 0.0113 | 0.5070 | |
| 148 | | −9.6 | 0.0316 | | 0.0085 | 0.0118 | |
| 149 | | 3.5 | | | 2.4917 | 17.2783 | |
| 150 | | | | | | | |
| 151 | | 19.5 | 0.0501 | | 0.0057 | 0.0216 | |
| 152 | | 15.4 | | | 0.9795 | 1.9770 | |
| 153 | | 28.9 | 0.0631 | | 0.0051 | 0.0303 | |
| 154 | | −0.6 | | | 0.0165 | 0.0102 | |
| 155 | | 111.6 | | | | | |
| 156 | | 1.8 | | | 0.0144 | 0.6039 | |
| 157 | | −1.4 | 3.1623 | | 1.5346 | 3.2961 | |
| 158 | | 1.1 | 0.0094 | 0.0055 | 0.0030 | 0.0188 | 0.008 |
| 159 | | 54.1 | | | >10 | >10 | |
| 160 | | 101.5 | | | >10 | >10 | |
| 161 | | −0.9 | 0.0158 | | 0.0181 | 0.1791 | |
| 162 | | | | | | | |
| 163 | | | | | | | |
| 164 | | 98.1 | | | | | |
| 165 | | 60.7 | | | 9.7949 | >10 | |
| 166 | | 0.6 | 0.0025 | | 0.0024 | 0.0185 | |
| 167 | | 4.2 | | | 10.4713 | >10 | |
| 168 | | −4.2 | 0.0032 | | 0.0036 | 0.0049 | |
| 169 | | 95.0 | | | | | |
| 170 | | −5.7 | 0.0200 | 0.0032 | 0.0089 | 0.0102 | |
| 171 | | 28.7 | | | 2.0277 | >10 | |
| 172 | | −6.0 | 0.0316 | 0.0050 | 0.0117 | 0.0054 | |
| 173 | | 8.8 | 0.0158 | | 0.0089 | 0.0102 | |
| 174 | | 4.2 | 0.0501 | | 0.0033 | 1.6827 | |
| 175 | | 4.5 | 0.0398 | | 0.0181 | 2.8774 | |
| 176 | | 7.3 | 0.0316 | | 0.0080 | 0.0072 | |
| 177 | | 8.6 | 0.0794 | | 0.2270 | >10 | |
| 178 | | −4.7 | | | 0.0051 | 0.1180 | |
| 179 | | −4.3 | | | 1.0568 | >10 | |
| 180 | | −3.7 | | | 0.5916 | >10 | |
| 181 | | −0.1 | | | 0.0944 | >10 | |
| 182 | | 62.5 | | | | | |
| 183 | | −1.2 | | | 0.0204 | 0.0083 | |
| 184 | | −0.7 | 0.3715 | | 0.1059 | 1.6406 | |
| 185 | | −3.7 | | | 0.0052 | 0.0195 | |
| 186 | | −0.5 | | | 9.0365 | 11.6950 | |
| 187 | | −0.6 | | | 0.0446 | 6.4714 | |
| 188 | | −0.7 | 0.0079 | | 0.0027 | 0.0085 | |
| 189 | | 0.5 | 0.0135 | | 0.0039 | 0.0063 | |
| 190 | | 7.1 | | | 1.5560 | 1.2912 | |
| 191 | | 5.2 | 0.0251 | | 0.0122 | 1.3002 | |
| 192 | | −6.3 | | | 2.5119 | 10.0000 | |
| 193 | | 1.4 | 0.0224 | | 0.0532 | 0.2382 | |
| 194 | | −12.8 | 1.3804 | | 3.9811 | >10 | |
| 195 | | 14.4 | 0.0100 | | 0.0034 | 0.0108 | |
| 196 | | −3.1 | 0.5012 | | 0.3908 | 2.6182 | |
| 197 | | 2.1 | | | 0.6622 | 0.6714 | |
| 198 | | 1.3 | 0.6310 | | 0.1803 | 4.9774 | |
| 199 | | 0.0 | 0.0398 | | 0.0086 | 0.0025 | |
| 200 | | 3.2 | 0.0251 | | 0.0370 | 0.0173 | |
| 201 | | 20.4 | | | 1.2503 | 7.6208 | |
| 202 | | 24.1 | 0.0100 | 0.0025 | 0.0017 | 0.0037 | |
| 203 | | 0.6 | 0.0079 | | 0.0105 | 0.1132 | |
| 204 | | 180.6 | | | | | |
| 205 | | 17.1 | 0.0040 | | 0.0010 | 0.1084 | |
| 206 | | −1.0 | 0.0282 | | 0.0159 | 0.0800 | |
| 207 | | 45.0 | | | 8.5507 | >10 | |
| 208 | | 20.9 | 0.0100 | 0.0020 | 0.0126 | 0.0200 | 0.015 |
| 209 | | −1.0 | 0.0158 | | 0.0142 | 0.0021 | |
| 210 | | 0.8 | 0.0050 | | 0.0102 | 0.0077 | |
| 211 | | 28.5 | | | 6.3096 | 5.0119 | |
| 212 | | 17.4 | 0.0050 | | 0.0050 | 0.0016 | |
| 213 | | 0.3 | 0.0251 | | 0.0133 | 0.0106 | |
| 214 | | 8.2 | | | 8.4918 | 46.2381 | |
| 215 | | 2.7 | 0.0100 | | 0.0020 | 0.0019 | |
| 216 | | 0.6 | 0.0126 | | 0.0126 | 0.0834 | |
| 217 | | 60.8 | | | | | |
| 218 | | 6.1 | 0.0025 | | 0.0124 | 0.0180 | |
| 219 | | 76.5 | | | 7.4131 | >10 | |

TABLE 2-continued

P2X7 activity of the compounds of Formula (I, IIa and IIb) in a panel of in-vitro assays

| Example | PBMC 1 μM (% control) | PBMC 10 μM (% control) | P2X7 human Ki (μM) | P2X7 rat Ki (μM) | FLIPR (human) IC$_{50}$ (μM) | FLIPR (rat) IC$_{50}$ (μM) | Human whole blood IC$_{50}$ (μM) |
|---|---|---|---|---|---|---|---|
| 220 | | 15.1 | 0.0056 | 0.0012 | 0.0048 | 0.0059 | 0.063 |
| 221 | | 17.8 | | | 0.5058 | 6.6834 | |
| 222 | | 11.8 | 0.0251 | | 0.0011 | 0.0010 | |
| 223 | | 1.8 | 0.0447 | | 0.0250 | 0.5636 | |
| 224 | | 103.3 | | | | | |
| 225 | | −1.0 | 0.0091 | | 0.0062 | 0.0423 | |
| 226 | | 58.0 | | | | | |
| 227 | | −0.4 | 0.0200 | | 0.0072 | 0.0102 | |
| 228 | | 0.1 | 0.0048 | | 0.0051 | 0.0082 | |
| 229 | | 116.4 | | | | | |
| 230 | | 2.9 | 0.0589 | | 0.0139 | 0.0895 | |
| 231 | | −4.8 | | | 0.4989 | 38.1944 | |
| 232 | | 7.5 | | | 5.5976 | >10 | |
| 233 | | −0.1 | 0.1000 | | 0.0060 | 0.1324 | |
| 234 | | −40.9 | 0.0794 | | 0.1995 | 1.9953 | |
| 235 | | −3.7 | 0.0141 | 0.0031 | 0.0054 | 0.0066 | 0.017 |
| 236 | | 9.3 | | | 1.1858 | >10 | |
| 237 | | −5.1 | 0.0363 | | 0.0032 | 0.1276 | |
| 238 | | −4.1 | 0.0794 | | 0.0271 | 0.7244 | |
| 239 | | 86.9 | | | | | |
| 240 | | −8.9 | 2.5119 | | 0.1002 | 0.0226 | |
| 241 | | 6.5 | 1.9953 | | 2.5823 | >10 | |
| 242 | | −3.4 | 0.0251 | | 0.0815 | 0.0604 | |
| 243 | | 1.0 | 0.0631 | | 0.0160 | 0.0150 | |
| 244 | | −2.3 | | | 1.1429 | 13.5207 | |
| 245 | | −7.3 | 0.1000 | | 0.1607 | 2.0701 | |
| 246 | | −3.1 | 0.1738 | | 0.2296 | 6.5313 | |
| 247 | | −0.8 | | | 2.3281 | 8.2035 | |
| 248 | | 74.3 | | | | | |
| 249 | | 5.1 | 0.0200 | 0.0022 | 0.0127 | 0.0038 | |
| 250 | | −1.3 | 0.0398 | | 0.0086 | 0.6699 | |
| 251 | | 11.6 | 0.1445 | | 0.1237 | 9.1096 | |
| 252 | | −0.8 | 0.0282 | | 0.0188 | 0.0223 | |
| 253 | | −2.6 | 0.1950 | | 0.1849 | 12.6911 | |
| 254 | | 0.9 | 0.0447 | | 0.0223 | 4.2560 | |
| 255 | | −5.5 | 0.0724 | | 0.0160 | 0.2113 | |
| 256 | | 7.1 | | | 2.3878 | >10 | |
| 257 | | 7.1 | 0.0158 | | 0.6516 | 6.1660 | |
| 258 | | −3.2 | 0.0631 | | 0.0855 | 4.8417 | |
| 259 | | −3.5 | 0.0575 | | 0.0406 | 10.0925 | |
| 260 | | 1.4 | 0.0355 | | 0.0270 | 6.9343 | |
| 261 | | −3.1 | 0.0363 | | 0.0194 | 1.2331 | |
| 262 | | −3.6 | 0.0398 | | 0.1276 | 1.5453 | |
| 263 | | −1.6 | 0.0550 | | 0.0161 | 1.2531 | |
| 264 | | 89.5 | | | >10 | >10 | |
| 265 | | 76.5 | | | | | |
| 266 | | 5.8 | 0.0200 | | 0.0127 | 0.0126 | |
| 267 | | −50.8 | 0.0100 | | 0.0081 | 0.0095 | |
| 268 | | −59.9 | | | 0.5998 | 1.2190 | |
| 269 | | 16.3 | 0.0200 | | 0.0131 | 0.0206 | |
| 270 | | 98.5 | | | | | |
| 271 | | −3.7 | 0.0059 | | 0.0033 | 0.0111 | |
| 272 | | −7.6 | 0.1000 | | 0.6223 | 3.0200 | |
| 273 | | −2.1 | 0.0182 | | 0.0076 | 0.0832 | |
| 274 | | −4.8 | 0.0417 | | 0.0745 | 1.8793 | |
| 275 | | −8.3 | 0.0245 | | 0.0469 | 0.6730 | |
| 276 | | −0.9 | 0.0058 | | 0.0064 | 0.8690 | |
| 277 | | −3.7 | 0.0234 | | 0.0946 | 1.9187 | |
| 278 | | −19.5 | 0.0126 | | 0.0072 | 0.0923 | |
| 279 | | −16.9 | 0.0115 | | 0.0086 | 0.4385 | |
| 280 | | 3.4 | 0.0631 | | 0.5675 | 1.2331 | |
| 281 | | −1.9 | 0.0023 | | 0.0031 | 0.1633 | |
| 282 | | −5.5 | 0.0158 | | 0.0029 | 0.0191 | |
| 283 | | −6.3 | 0.0063 | | 0.0047 | 0.1923 | |
| 284 | | 18.2 | 0.3162 | | 0.2404 | 0.6730 | |
| 285 | | −2.6 | | | 0.6714 | 1.6827 | |
| 286 | | 5.8 | | | 6.9024 | 0.1442 | |
| 287 | | −4.1 | 0.0141 | | 0.0070 | 0.0028 | |
| 288 | | 4.4 | 0.0059 | | 0.0068 | 0.0063 | |
| 289 | | −27.6 | | | 1.1885 | 2.4099 | |
| 290 | | −11.2 | 0.0079 | | 0.0130 | 0.0067 | |
| 291 | | −7.1 | 0.0219 | | 0.0991 | 1.6218 | |
| 292 | | 36.7 | | | 10.4472 | >10 | |

TABLE 2-continued

P2X7 activity of the compounds of Formula (I, IIa and IIb) in a panel of in-vitro assays

| Example | PBMC 1 μM (% control) | PBMC 10 μM (% control) | P2X7 human Ki (μM) | P2X7 rat Ki (μM) | FLIPR (human) IC$_{50}$ (μM) | FLIPR (rat) IC$_{50}$ (μM) | Human whole blood IC$_{50}$ (μM) |
|---|---|---|---|---|---|---|---|
| 293 | | −11.3 | 0.0437 | | 0.1791 | 0.4285 | |
| 294 | | −8.1 | 0.0126 | | 0.0108 | 0.0028 | |
| 295 | | 10.1 | | | >10 | >10 | |
| 296 | | 3.6 | 0.1000 | | 0.0624 | 0.0923 | |
| 297 | | 2.6 | 0.0100 | | 0.0050 | 0.0056 | |
| 298 | | | | | | | |
| 299 | | 1.5 | 0.0200 | | 0.0081 | 0.0127 | |
| 300 | | −1.8 | 0.3981 | | 0.1710 | 20.2302 | |
| 301 | | −2.2 | 0.1000 | | 0.0776 | 0.1629 | |
| 302 | | −2.8 | 0.0316 | | 0.0116 | 0.0143 | |
| 303 | | −1.6 | | | 6.9183 | 5.1880 | |
| 304 | | 3.2 | 0.0224 | | 0.1127 | 5.6494 | |
| 305 | | 0.9 | 0.0457 | | 0.0155 | 0.0197 | |
| 306 | | 2.5 | | | 6.8707 | 5.9841 | |
| 307 | | 2.2 | | | >10 | 10.6660 | |
| 308 | | 22.9 | | | >10 | >10 | |
| 309 | | 1.4 | | | 1.3062 | 1.2647 | |
| 310 | | 12.2 | 0.0050 | | 0.0092 | 0.0026 | |
| 311 | | 63.6 | 0.0158 | | 0.0179 | 0.0352 | |
| 312 | | 9.5 | 0.0398 | | 0.1574 | 8.6696 | |
| 313 | | −5.4 | | | 1.1117 | 24.7172 | |
| 314 | | 18.7 | | | 2.8314 | >10 | |
| 315 | | 8.8 | 0.0158 | | 0.0398 | 2.4889 | |
| 316 | | −9.6 | 0.0316 | | 0.0723 | 2.2080 | |
| 317 | | 4.8 | | | >10 | >10 | |
| 318 | | | | | | | |
| 319 | | −6.8 | | | 10.0000 | 4.5709 | |
| 320 | | −19.7 | | | 0.6324 | 0.8337 | |
| 321 | | 14.1 | 0.1000 | | 0.0374 | 0.5888 | |
| 322 | 100.4 | | | | | | |
| 323 | 102.4 | | | | | | |
| 324 | 100.4 | | | | | | |
| 325 | 99.7 | | | | | | |
| 326 | 92.0 | | | | | | |
| 327 | 93.1 | | | | >10 | >10 | |
| 328 | 88.0 | | | | >10 | >10 | |
| 329 | 99.5 | | | | >10 | >10 | |
| 330 | | 33.8 | | | >10 | >10 | |
| 331 | | −11.0 | 0.1778 | | 0.1479 | 4.2954 | |
| 332 | | −9.5 | 0.6310 | | 0.2168 | 3.7239 | |
| 333 | | 6.9 | 0.0631 | | 0.1014 | >10 | |
| 334 | | 101.8 | | | >10 | >10 | |
| 336 | | −0.5 | 0.3715 | | 0.2891 | 2.1627 | |

What is claimed:

1. A method of treating a disease, disorder, or medical condition mediated by P2X7 receptor activity in a subject, comprising administering to the subject in need of such treatment a therapeutically effective amount of a compound selected from compounds of Formula (I):

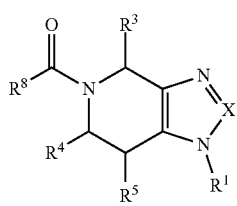

Formula (I)

wherein;
R$^1$ is (a) phenyl, optionally substituted with zero to four groups selected from the group consisting of: halo, C$_1$-C$_4$alkyl, alkoxy, perhaloalkyl and perhaloalkoxy; and (b) heteroaryl, selected from the group consisting of:

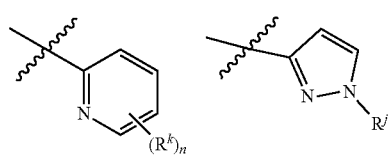

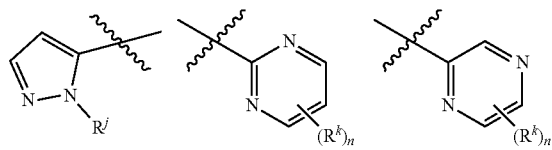

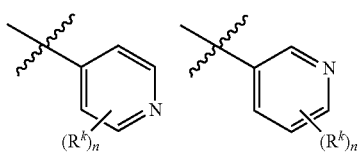

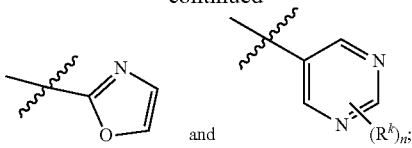

wherein $R^k$ is selected from the group consisting of:
H, halo, $C_1$-$C_3$alkyl and alkoxy;
$R^j$ is selected from H or $C_1$-$C_3$alkyl; wherein $C_1$-$C_3$alkyl is optionally substituted with halo, OH or alkoxy; and
n is an integer from 0-3;
X is N or $CR^2$;
$R^2$ is H, perhaloalkyl or $C_1$-$C_3$ lower alkyl;
$R^3$ is H, perhaloalkyl, $C_1$-$C_4$ alkyl, alkalkoxy, $CH_2R^i$, —$C(O)R^e$ or phenyl; wherein phenyl is optionally substituted with zero to two groups selected from the group consisting of: halo, $C_1$-$C_3$alkyl, alkoxy, perhaloalkyl and perhaloalkoxy;
$R^i$ is OH, $OC_1$-$C_3$ alkyl, $NC_3H_6$, $N(C_1$-$C_3$alkyl$)_2$ or halo;
$R^e$ is OH, $OC_1$-$C_3$ alkyl, $N(C_1$-$C_3$alkyl$)_2$, $NC_3H_6$;
$R^4$ and $R^5$ are independently H or $C_1$-$C_3$ alkyl; and
$R^8$ is phenyl or pyridyl, optionally substituted with zero to four $R^m$ substituents wherein $R^m$ is selected from the group consisting of: halo, $C_1$-$C_3$alkyl, alkoxy, perhaloalkyl and perhaloalkoxy; or
$R^8$ is selected from the group consisting of:

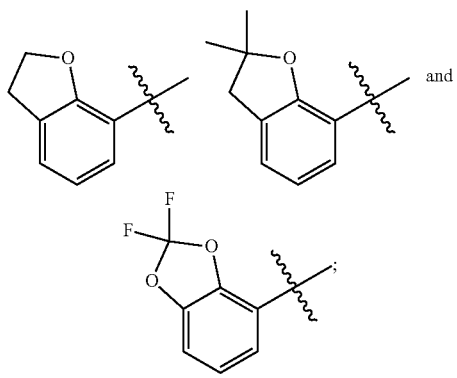

and
pharmaceutically acceptable salts thereof.

2. A method of treating a subject suffering from or diagnosed with a disease, disorder, or medical condition mediated by P2X7 receptor activity, comprising administering to a subject in need of such treatment a therapeutically effective amount of at least one compound selected from compounds of Formula (IIa and IIb):

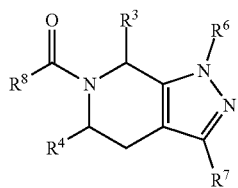

Formula (IIa)

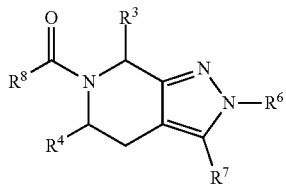

Formula (IIb)

wherein:
$R^3$, $R^4$ and $R^6$ are independently H or $C_1$-$C_3$ alkyl;
$R^8$ is phenyl or pyridyl, optionally substituted with zero to three $R^m$ substituents wherein $R^m$ is selected from the group consisting of: halo, $C_1$-$C_3$alkyl and perhaloalkyl;
$R^7$ is (a) phenyl, optionally substituted with zero to two groups selected from: halo or $C_1$-$C_3$alkyl; and
(b) heteroaryl, selected from the group consisting of:

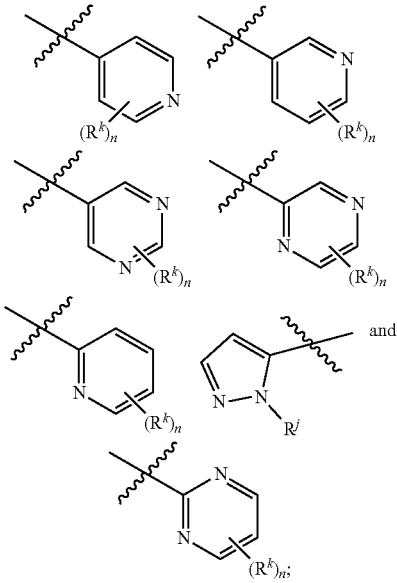

wherein $R^k$ is selected from: halo or $C_1$-$C_3$alkyl;
$R^j$ is selected from H or $C_1$-$C_3$alkyl wherein $C_1$-$C_3$alkyl is optionally substituted with halo or alkoxy; and
n is an integer from 0-3; and
pharmaceutically acceptable salts of compounds of Formula (IIa and IIb).

3. The method according to claim 1, wherein the disease, disorder, or medical condition is selected from the group consisting of:
rheumatoid arthritis, osteoarthritis, psoriasis, septic shock, allergic dermatitis, asthma, allergic asthma, mild to severe asthma, steroid resistant asthma, idiopathic pulmonary fibrosis, allergic rhinitis, chronic obstructive pulmonary disease, and airway hyper-responsiveness.

4. The method according to claim 2, wherein the disease, disorder, or medical condition is selected from the group consisting of:
rheumatoid arthritis, osteoarthritis, psoriasis, septic shock, allergic dermatitis, asthma, allergic asthma, mild to severe asthma, steroid resistant asthma, idiopathic pulmonary fibrosis, allergic rhinitis, chronic obstructive pulmonary disease, and airway hyper-responsiveness.

5. The method of claim 1, wherein the compound is:

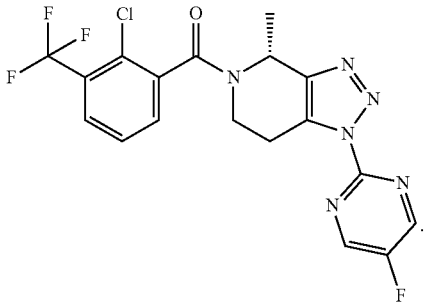 [SMILES: C[C@@H]1c2nnn(-c3ncc(F)cn3)c2CCN1C(=O)c1cccc(C(F)(F)F)c1Cl]

, or a pharmaceutically acceptable salt thereof.

6. The method of claim 1, wherein the compound is:

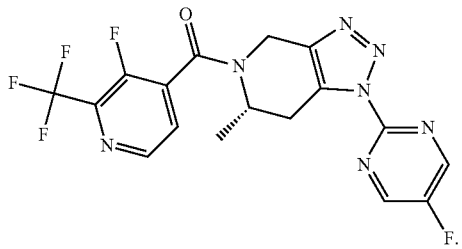 [SMILES: C[C@H]1Cc2c(nnn2-c2ncc(F)cn2)CN1C(=O)c1ccnc(C(F)(F)F)c1F]

, or a pharmaceutically acceptable salt thereof.

7. The method of claim 5, wherein the compound is:
(R)-(2-Chloro-3-(trifluoromethyl)phenyl)(1-(5-fluoropyrimidin-2-yl)-4-methyl-6,7-dihydro-1H-[1,2,3]triazolo[4,5-c]pyridin-5(4H)-yl)methanone.

8. The method of claim 6, wherein the compound is:
(S)-(3-fluoro-2-(trifluoromethyl)pyridin-4-yl)(1-(5-fluoropyrimidin-2-yl)-6-methyl-6,7-dihydro-1H-[1,2,3]triazolo[4,5-c]pyridin-5(4H)-yl)methanone.

9. The method of claim 1, wherein the compound is selected from the compounds of Formula (I),
wherein:
$R^1$ is

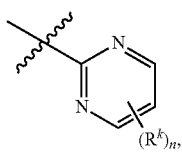

wherein $R^k$ is F, and n is 1;
X is N;
$R^3$ is methyl;
$R^4$ is H;
$R^5$ is H; and
$R^8$ is phenyl, substituted with two $R^m$ substituents, wherein the two $R^m$ substituents are Cl and perfluoromethyl; and
pharmaceutically acceptable salts thereof.

10. The method of claim 1, wherein the compound is selected from the compounds of Formula (I),
wherein:
$R^1$ is

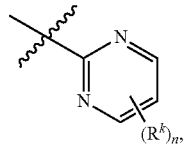

wherein $R^k$ is F, and n is 1;
X is N;
$R^3$ is H;
$R^4$ is methyl;
$R^5$ is H; and
$R^8$ is pyridyl, substituted with two $R^m$ substituents, wherein the two $R^m$ substituents are F and perfluoromethyl; and
pharmaceutically acceptable salts thereof.

11. The method of claim 5, wherein the disease, disorder or medical condition is depression.

12. The method of claim 6, wherein the disease, disorder or medical condition is depression.

13. The method of claim 7, wherein the disease, disorder or medical condition is depression.

14. The method of claim 8, wherein the disease, disorder or medical condition is depression.

15. The method of claim 5, wherein the disease, disorder or medical condition is major depressive disorder.

16. The method of claim 6, wherein the disease, disorder or medical condition is major depressive disorder.

17. The method of claim 7, wherein the disease, disorder or medical condition is major depressive disorder.

18. The method of claim 8, wherein the disease, disorder or medical condition is major depressive disorder.

19. The method of claim 5, wherein the disease, disorder or medical condition is treatment resistant depression.

20. The method of claim 6, wherein the disease, disorder or medical condition is treatment resistant depression.

21. The method of claim 7, wherein the disease, disorder or medical condition is treatment resistant depression.

22. The method of claim 8, wherein the disease, disorder or medical condition is treatment resistant depression.

23. The method of claim 5, wherein the disease, disorder, or medical condition is bipolar disorder.

24. The method of claim 6, wherein the disease, disorder, or medical condition is bipolar disorder.

25. The method of claim 7, wherein the disease, disorder, or medical condition is bipolar disorder.

26. The method of claim 8, wherein the disease, disorder, or medical condition is bipolar disorder.

27. The method of claim 5, wherein the disease, disorder, or medical condition is anxious depression.

28. The method of claim 6, wherein the disease, disorder, or medical condition is anxious depression.

29. The method of claim 7, wherein the disease, disorder, or medical condition is anxious depression.

30. The method of claim 8, wherein the disease, disorder, or medical condition is anxious depression.

31. The method of claim 5, wherein the disease, disorder, or medical condition is anxiety.

32. The method of claim 6, wherein the disease, disorder, or medical condition is anxiety.

33. The method of claim 7, wherein the disease, disorder, or medical condition is anxiety.

34. The method of claim 8, wherein the disease, disorder, or medical condition is anxiety.

35. The method of claim 5, wherein the disease, disorder, or medical condition is epileptic seizures.

36. The method of claim 6, wherein the disease, disorder, or medical condition is epileptic seizures.

37. The method of claim 7, wherein the disease, disorder, or medical condition is epileptic seizures.

38. The method of claim 8, wherein the disease, disorder, or medical condition is epileptic seizures.

39. The method of claim 5, wherein the disease, disorder, or medical condition is traumatic brain injury.

40. The method of claim 6, wherein the disease, disorder, or medical condition is traumatic brain injury.

41. The method of claim 7, wherein the disease, disorder, or medical condition is traumatic brain injury.

42. The method of claim 8, wherein the disease, disorder, or medical condition is traumatic brain injury.

43. The method of claim 5, wherein the disease, disorder, or medical condition is Alzheimer's disease.

44. The method of claim 6, wherein the disease, disorder, or medical condition is Alzheimer's disease.

45. The method of claim 7, wherein the disease, disorder, or medical condition is Alzheimer's disease.

46. The method of claim 8, wherein the disease, disorder, or medical condition is Alzheimer's disease.

\* \* \* \* \*